US010687542B2

(12) United States Patent
Raab et al.

(10) Patent No.: US 10,687,542 B2
(45) Date of Patent: Jun. 23, 2020

(54) ENGINEERED PHYTASES AND METHODS OF USING THE SAME

(71) Applicant: AGRIVIDA, INC., Woburn, MA (US)

(72) Inventors: R. Michael Raab, Arlington, MA (US); Gabor Lazar, Belmont, MA (US); Binzhang Shen, Boston, MA (US)

(73) Assignee: AGRIVIDA, INC., Woburn, MA (US)

( * ) Notice: Subject to any disclaimer, the term of this patent is extended or adjusted under 35 U.S.C. 154(b) by 0 days.

(21) Appl. No.: 15/756,231

(22) PCT Filed: Sep. 16, 2016

(86) PCT No.: PCT/US2016/052147
§ 371 (c)(1),
(2) Date: Feb. 28, 2018

(87) PCT Pub. No.: WO2017/049094
PCT Pub. Date: Mar. 23, 2017

(65) Prior Publication Data

US 2018/0255804 A1 Sep. 13, 2018

Related U.S. Application Data

(60) Provisional application No. 62/220,688, filed on Sep. 18, 2015.

(51) Int. Cl.

| | |
|---|---|
| ***C12Q 1/42*** | (2006.01) |
| ***A23K 10/14*** | (2016.01) |
| ***C07K 14/245*** | (2006.01) |
| ***C07K 14/38*** | (2006.01) |
| ***C07K 14/39*** | (2006.01) |
| ***C12N 9/16*** | (2006.01) |
| ***C12N 15/80*** | (2006.01) |
| ***A23K 20/189*** | (2016.01) |
| ***C12N 15/82*** | (2006.01) |
| ***C07K 14/00*** | (2006.01) |

(52) U.S. Cl.
CPC ............ *A23K 10/14* (2016.05); *A23K 20/189* (2016.05); *C07K 14/00* (2013.01); *C07K 14/245* (2013.01); *C07K 14/38* (2013.01); *C07K 14/39* (2013.01); *C12N 9/16* (2013.01); *C12N 15/80* (2013.01); *C12N 15/8257* (2013.01); *C12Y 301/03* (2013.01)

(58) Field of Classification Search
None
See application file for complete search history.

(56) References Cited

U.S. PATENT DOCUMENTS

| | | | |
|---|---|---|---|
| 7,629,139 | B2 | 12/2009 | Basu |
| 2003/0224494 | A1 | 12/2003 | Nomoto |
| 2005/0125860 | A1 | 6/2005 | Raab |
| 2005/0208635 | A1 | 9/2005 | Nomoto |
| 2010/0273198 | A1 | 10/2010 | Basu |
| 2011/0111442 | A1 | 5/2011 | Shen |
| 2012/0190609 | A1 | 7/2012 | Bader |
| 2013/0007919 | A1 | 1/2013 | Shen |
| 2013/0036517 | A1 | 2/2013 | Apgar |
| 2015/0056656 | A1 | 2/2015 | Grossmann |

FOREIGN PATENT DOCUMENTS

| | | | |
|---|---|---|---|
| CN | 101638642 | A | 2/2010 |
| EP | 2617823 | B1 | 7/2013 |
| WO | 2005115433 | A2 | 12/2005 |
| WO | 2008143679 | A8 | 11/2008 |
| WO | 2009110933 | A2 | 9/2009 |
| WO | 2011057163 | A3 | 5/2011 |
| WO | 2013119468 | A2 | 8/2013 |

OTHER PUBLICATIONS

Apgar, et al. (2012), A predictive model of intein insertion site for use in the engineering of molecular switches. PloS one, 7(5), e37355.

Arakawa, et al. (1998), Efficacy of a food plant-based oral cholera toxin B subunit vaccine. Nature Biotechnology, 16 (3), 292-297. doi:10.1038/nbt0398-292.

Beare, et al. Feb. 2009, Comparative Genomics Reveal Extensive Transposozon-Mediated Genomic Plasticity and Diversity among Potential Effector Proteins within Genus Coxiell; Infection and Immunity, vol. 77, No. 2, pp. 642-656; DOI: 10.1128/IAJ.01141-08.

Cervelli, et al. (2004), A novel C-terminal sequence from barley polyamine oxidase is a vacuolar sorting signal. Plant Journal, 40(3), 410-418. doi:10.1111/j.1365-313X.2004.02221.X.

Engelen, et al. (2001), Determination of phytase activity in feed by a colorimetric enzymatic method: collaborative interlaboratory study. Journal of AOAC International, 84(3), 629-633.

English, et al. Nov. 21, 2012, Mind the Gap: Upgrading Genomes with Pacific Biosciences RS Long-Read Sequencing Technology. PLoS One, vol. 7, No. 11, e477768 Genbank Supplement , pp. 1-3; DOI:10.1371/journal.pone. 0047768.

Fu. (2002), Digestion stability as a criterion for protein allergenicity assessment. Annals of the New York Academy of Sciences, 964(1), 99-110.

Gogarten, et al. (2002), Inteins: structure, function, and evolution. Annual Reviews in Microbiology, 56(1), 263-287.

Haq, et al. (1995), Oral immunization with a recombinant bacterial antigen produced in transgenic plants. Science (New York, N.Y.), 268(5211), 714-716. doi:10.1126/science.7732379.

(Continued)

*Primary Examiner* — Hope A Robinson
(74) *Attorney, Agent, or Firm* — Volpe and Koenig, P.C.

(57) ABSTRACT

Methods for enhancing phytase thermal stability by fusing binding elements to target phytases are provided. Engineered phytases that include binding elements fused to target phytases to cause cyclization of the engineered phytases and enhance thermal stability of the target phytases are described. Engineered nucleic acids encoding engineered phytases and hosts engineered to express engineered nucleic acids are also provided. Methods for incorporating engineered phytases in animal feed and animal feed including the same are described.

3 Claims, 27 Drawing Sheets

Specification includes a Sequence Listing.

(56) References Cited

Heidelberg Team: Heidelberg/Project/Background—Explore the world of inteins. Webpage [online] 2014 [retrieved on Jan. 9, 2017] Retrieved from the Internet: <URL: http://2014.igem.org/Team:Heidelberg/Project/Background> p. 2, 5th paragraph; Figure 1.
Korban. (2002), Targeting and expression of antigenic proteins in transgenic plants for production of edible oral vaccines. In Vitro Cellular & Developmental Biology—Plant, 38(3), 231-236. doi:10.1079/IVP2002292.
Lau et al. (1984), Synthesis of a model protein of defined secondary and quaternary structure. Effect of chain length on the stabilization and formation of two-stranded αhelical coiled-coils. J. Biol. Chem. 259 (21), 13253-61.
Munro, et al. (1987), A C-terminal signal prevents secretion of luminal ER proteins. Cell, 48(5), 899-907. doi:10.1016/0092-8674(87)90086-9.
Parry, et al. (2008), Fifty years of coiled-coils and alpha-helical bundles: a close relationship between sequence and structure. J Struct Biol. 163(3), 258-69.
Paul, et al. Feb. 13, 2014, Genome Sequence of the Oleaginous Yeast Rhodotorula glutinis ATCC 204091; Journal of the American Society of Microbiology, vol. 2, No. 1, e00046-14; Genbank Supplement, pp. 1-2; DOI:10.1128/genomeA.00046-14.
Perler, et al. (1994), Protein splicing elements: inteins and exteins—a definition of terms and recommended nomenclature. Nucleic acids research, 22(7), 1125.
Perler. (2002), InBase: the intein database. Nucleic acids research, 30(1), 383-384.
Schoene, et al. (2014), SpyTag/SpyCatcher cyclization confers resilience to boiling on a mesophilic enzyme. Angewandte Chemie International Edition, 53(24), 6101-6104.
Selgrade, et al. May 22, 2013, Protein Scaffold-Activated Protein Trans-Splicing in Mammalian Cells., Journal of the American Chemical Society, vol. 136, No. 20, pp. 7713-7719.
Thomas, et al. (2004), A multi-laboratory evaluation of a common in vitro pepsin digestion assay protocol used in assessing the safety of novel proteins. Regulatory Toxicology and Pharmacology, 39(2), 87-98.
Veggiani et al. Oct. 2014, Supeglue from bacteria: unbreakable bridges for protein nanotechnologu. Trends in Biotechnology, vol. 32, No. 32, pp. 506-512.
Woolfson. (2005), The design of coiled-coil structures and assemblies. Adv. Protein Chem.70, 79-f112.
Xu, et al. (1996), The mechanism of protein splicing and its modulation by mutation. The EMBO journal, 15(19), 5146.
Zakeri, et al.(2012), Peptide tag forming a rapid covalent bond to a protein, through engineering a bacterial adhesin. Proceedings of the National Academy of Sciences, 109(12), E690-E697.
Zhou et al. 2014, Genome Sequence of Anopheles sinensis provides insight into genetics basis of mosquito competence for malaria parasites. BioMed Central Genomics, vol. 15, No. 42; Genbank supplement, pp. 1-2.
International Search Report issued for PCT Application No. PCT/US16/52147 dated Feb. 6, 2017.
International Preliminary Report on Patentability dated Mar. 20, 2018 for PCT/US2016/1052147, consisting of 18 pp.
European Search Report dated Apr. 8, 2019 for EP 16847392.4.
Zhang et al., 2013, Controlling Macromolecular Topology With Genetically Encoded SpyTag-SpyCatcher Chemistry, J Am Chem Soc, 135, 13988-13997.

ZmZ27P:xGZein27ss:Gp41-1C:Phy02opt:Gp41-1N:DPNGSEKDEL:NosT as KpnI-EcoRI
3370 bp ZmZ27P:Ssp DnaE-C:Phy02opt:Ssp DnaE-N:NosT as KpnI-EcoRI
3385 bp ZmZ27P:xGZein27ss:Ssp DnaE-C:PhyO2opt:Ssp DnaE-N:DPNGSEKDEL:NosT as KpnI-EcoRI 3472 bp ZmZ27P:Ssp DnaE-C:L33-1:PhyO2opt:L33-2:Ssp DnaE-N: NosT as KpnI-EcoRI
3463 bp

SEQUENCE LISTING

```
<160> NUMBER OF SEQ ID NOS: 219

<210> SEQ ID NO 1
<211> LENGTH: 94
<212> TYPE: PRT
<213> ORGANISM: Artificial Sequence
<220> FEATURE:
<223> OTHER INFORMATION: Synthetic construct, Cbu_DnaB-N (#12-N)

<400> SEQUENCE: 1

Cys Val Thr Gly Asp Thr Leu Ile Cys Leu Ala Asp Gly Arg Arg Val
1               5                   10                  15

Pro Ile Gln Asp Leu Val Gly His Ser Pro Glu Val Ile Ala Val Asp
            20                  25                  30

Asp Lys Gly Arg Leu Val Cys Ala Lys Ser Glu Val Ile Trp Lys Val
        35                  40                  45

Gly Glu Arg Ser Val Phe Glu Ile Lys Leu Ala Ser Gly Arg Ser Ile
    50                  55                  60

Lys Ala Thr Ala Glu His Arg Leu Leu Ala Phe Lys Gly Trp Arg His
65                  70                  75                  80

Val Lys Asp Phe Lys Val Gly Asp Arg Leu Ala Ile Ala His
                85                  90


<210> SEQ ID NO 2
<211> LENGTH: 40
<212> TYPE: PRT
<213> ORGANISM: Artificial Sequence
<220> FEATURE:
<223> OTHER INFORMATION: Synthetic cionstruct, Cbu_DnaB-C (#12-C)

<400> SEQUENCE: 2

Met Ser Asp Leu Phe Trp Asp Arg Ile Val Ser Ile Glu Glu Lys Gly
1               5                   10                  15

Ser Glu Glu Val Tyr Asp Leu Thr Val Pro Lys Tyr Ala Ser Trp Leu
            20                  25                  30

Ala Asp Gly Val Val Ser His Asn
        35                  40
```

<210> SEQ ID NO 3
<211> LENGTH: 96
<212> TYPE: PRT
<213> ORGANISM: Artificial Sequence
<220> FEATURE:
<223> OTHER INFORMATION: Synthetic construct, Mja_GF6P-N (#44-N)

<400> SEQUENCE: 3

```
Cys Leu His Pro Asp Thr Tyr Val Ile Leu Pro Asp Gly Arg Met Lys
1               5                   10                  15

Lys Ile Ser Glu Ile Asp Glu Asp Glu Val Leu Ser Val Asn Phe Glu
            20                  25                  30

Asp Leu Lys Leu Tyr Asn Lys Lys Ile Lys Lys Phe Lys His Lys Ala
        35                  40                  45

Pro Lys Ile Leu Tyr Lys Ile Lys Thr Ala Phe Ser Glu Leu Ile Thr
    50                  55                  60

Thr Gly Glu His Lys Leu Phe Val Val Glu Asn Gly Lys Ile Val Glu
65                  70                  75                  80

Lys Cys Val Lys Asp Leu Asn Gly Ser Glu Leu Ile Gly Val Val Arg
                85                  90                  95
```

<210> SEQ ID NO 4
<211> LENGTH: 41
<212> TYPE: PRT
<213> ORGANISM: Artificial Sequence
<220> FEATURE:
<223> OTHER INFORMATION: Synthetic construct, Mja_GF6P-C (#44-C)

<400> SEQUENCE: 4

```
Met Ala Asp Ile Val Trp Thr Lys Phe Lys Ile Glu Glu Val Glu Ser
1               5                   10                  15

Asp Val Glu Tyr Val Tyr Asp Leu Glu Val Glu Asp Tyr His Asn Phe
            20                  25                  30

Ile Gly Asn Leu Ile Ile Asn His Asn
        35                  40
```

<210> SEQ ID NO 5
<211> LENGTH: 126
<212> TYPE: PRT
<213> ORGANISM: Artificial Sequence
<220> FEATURE:
<223> OTHER INFORMATION: Synthetic construct, Mja_Hyp1-N (#46-N)

<400> SEQUENCE: 5

```
Cys Val Pro Pro Asp Thr Leu Leu Ile Leu Glu Asn Gly Phe Lys Arg
1               5                   10                  15

Ile Val Asp Ile Lys Val Gly Asp Lys Val Leu Thr His Glu Asn Arg
            20                  25                  30

Phe Lys Lys Val Glu Lys Val Tyr Lys Arg Arg Tyr Ile Gly Asp Ile
        35                  40                  45

Ile Lys Ile Lys Val Arg Tyr Phe Pro Glu Glu Ile Ile Leu Thr Pro
    50                  55                  60

Glu His Pro Val Tyr Ala Ile Lys Thr Glu Lys Arg Cys Asp Gly Ser
65                  70                  75                  80

His Gly Ile Cys Lys Phe Asn Cys Leu Thr Gln Tyr Thr Asn Pro Ser
                85                  90                  95

Cys Lys Lys Arg Tyr Arg Lys Tyr Lys Arg Glu Trp Ile Ile Ala Lys
            100                 105                 110

Asp Leu Lys Val Gly Asp Val Ile Val Tyr Pro Ile Pro Asn
        115                 120                 125
```

<210> SEQ ID NO 6
<211> LENGTH: 41
<212> TYPE: PRT
<213> ORGANISM: Artificial Sequence
<220> FEATURE:
<223> OTHER INFORMATION: Synthetic construct, Mja_Hyp1-C (#46-C)

<400> SEQUENCE: 6

```
Met Gly Asn Tyr Leu Tyr Ala Pro Ile Ile Arg Ile Gly Arg Glu Tyr
1               5                   10                  15

Tyr Asp Gly Phe Val Tyr Asn Leu Glu Val Glu Asp Asp Ser Ser Tyr
            20                  25                  30

Val Thr Val Ser Gly Thr Leu His Asn
        35                  40
```

<210> SEQ ID NO 7
<211> LENGTH: 110
<212> TYPE: PRT
<213> ORGANISM: Artificial Sequence
<220> FEATURE:
<223> OTHER INFORMATION: Synthetic construct, Mja_IF2-N (#47-N)

<400> SEQUENCE: 7

```
Cys Leu Met Pro His Glu Lys Val Leu Thr Glu Tyr Gly Glu Ile Lys
1               5                   10                  15

Ile Glu Asp Leu Phe Lys Ile Gly Lys Glu Ile Val Glu Lys Asp Glu
            20                  25                  30

Leu Lys Glu Ile Arg Lys Leu Asn Ile Lys Val His Thr Leu Asn Glu
        35                  40                  45

Asn Gly Glu Ile Lys Ile Ile Asn Ala Pro Tyr Val Trp Lys Leu Lys
    50                  55                  60

His Lys Gly Lys Met Ile Lys Val Lys Leu Lys Asn Trp His Ser Ile
65                  70                  75                  80

Thr Thr Thr Pro Glu His Pro Phe Leu Thr Asn Asn Gly Trp Ile Lys
                85                  90                  95

Ala Glu Asn Ile Lys Lys Gly Met Tyr Val Ala Ile Pro Arg
            100                 105                 110
```

<210> SEQ ID NO 8
<211> LENGTH: 39
<212> TYPE: PRT
<213> ORGANISM: Artificial Sequence
<220> FEATURE:
<223> OTHER INFORMATION: Synthetic construct, Mja_IF2-C (#47-C)

<400> SEQUENCE: 8

```
Met Asn Ile Ala Phe Val Glu Val Glu Asp Val Glu Ile Ile Asp Tyr
1               5                   10                  15

Asp Gly Tyr Val Tyr Asp Leu Thr Thr Glu Thr His Asn Phe Ile Ala
            20                  25                  30

Asn Gly Ile Val Val His Asn
        35
```

<210> SEQ ID NO 9
<211> LENGTH: 102
<212> TYPE: PRT
<213> ORGANISM: Artificial Sequence
<220> FEATURE:
<223> OTHER INFORMATION: Synthetic construct, Mja_Pol1-N (#50-N)

<400> SEQUENCE: 9

```
Cys His Pro Lys Gly Thr Lys Val Val Val Lys Gly Lys Gly Ile Val
1               5                   10                  15

Asn Ile Glu Asp Val Lys Glu Gly Asn Tyr Val Leu Gly Ile Asp Gly
            20                  25                  30

Trp Gln Lys Val Lys Lys Val Trp Lys Tyr Glu Tyr Glu Gly Glu Leu
        35                  40                  45

Ile Asn Val Asn Gly Leu Lys Cys Thr Pro Asn His Lys Ile Pro Leu
    50                  55                  60

Arg Tyr Lys Ile Lys His Lys Lys Ile Asn Lys Asn Asp Tyr Leu Val
65                  70                  75                  80

Arg Asp Ile Tyr Ala Lys Ser Leu Leu Thr Lys Phe Lys Gly Glu Gly
                85                  90                  95

Lys Leu Ile Leu Cys Lys
            100
```

<210> SEQ ID NO 10
<211> LENGTH: 41
<212> TYPE: PRT
<213> ORGANISM: Artificial Sequence
<220> FEATURE:
<223> OTHER INFORMATION: Synthetic construct, Pab_CDC211-C (#79-C)

<400> SEQUENCE: 10

```
Met Ser Val Ser Trp Asp Glu Val Ala Glu Ile Leu Glu Tyr Glu Pro
1               5                   10                  15

Lys Asp Pro Trp Val Tyr Asp Leu Gln Val Pro Gly Tyr His Asn Phe
            20                  25                  30

Leu Ala Asn Gly Ile Phe Val His Asn
        35                  40
```

<210> SEQ ID NO 11
<211> LENGTH: 122
<212> TYPE: PRT
<213> ORGANISM: Artificial Sequence
<220> FEATURE:
<223> OTHER INFORMATION: Synthetic construct, Pab_CDC211-N (#79-N)

<400> SEQUENCE: 11

```
Cys Val Asp Tyr Glu Thr Glu Val Val Leu Gly Asn Gly Glu Arg Lys
1               5                   10                  15

Lys Ile Gly Glu Ile Val Glu Arg Ala Ile Glu Glu Ala Glu Lys Asn
            20                  25                  30

Gly Lys Leu Gly Arg Val Asp Asp Gly Phe Tyr Ala Pro Ile Asp Ile
        35                  40                  45

Glu Val Tyr Ser Leu Asp Leu Glu Thr Leu Lys Val Arg Lys Ala Arg
    50                  55                  60

Ala Asn Ile Ala Trp Lys Arg Thr Ala Pro Lys Lys Met Met Leu Val
65                  70                  75                  80

Lys Thr Arg Gly Gly Lys Arg Ile Arg Val Thr Pro Thr His Pro Phe
                85                  90                  95

Phe Val Leu Glu Glu Gly Lys Val Ala Met Arg Lys Ala Arg Asp Leu
            100                 105                 110

Glu Glu Gly Asn Lys Ile Ala Thr Ile Glu
        115                 120
```

<210> SEQ ID NO 12
<211> LENGTH: 41
<212> TYPE: PRT

<213> ORGANISM: Artificial Sequence
<220> FEATURE:
<223> OTHER INFORMATION: Synthetic construct, Pab_CDC211-C (#79-C)

<400> SEQUENCE: 12

Met Ser Val Ser Trp Asp Glu Val Ala Glu Ile Leu Glu Tyr Glu Pro
1 5 10 15

Lys Asp Pro Trp Val Tyr Asp Leu Gln Val Pro Gly Tyr His Asn Phe
20 25 30

Leu Ala Asn Gly Ile Phe Val His Asn
35 40

<210> SEQ ID NO 13
<211> LENGTH: 111
<212> TYPE: PRT
<213> ORGANISM: Artificial Sequence
<220> FEATURE:
<223> OTHER INFORMATION: Synthetic construct, Pab_IF2-N (#81-N)

<400> SEQUENCE: 13

Cys Leu Leu Pro Asp Glu Lys Val Val Val Pro Ser Val Gly Phe Val
1 5 10 15

Thr Leu Lys Glu Leu Phe Glu Thr Ala Ser Lys Val Val Glu Arg Asp
20 25 30

Asp Glu Lys Glu Ile Arg Glu Leu Asp Glu Arg Ile Thr Ser Val Asn
35 40 45

Gly Asp Gly Lys Thr Gly Leu Val Lys Ala Ser Tyr Val Trp Lys Val
50 55 60

Arg His Lys Gly Lys Val Ile Arg Val Lys Leu Lys Asn Trp His Gly
65 70 75 80

Val Thr Val Thr Pro Glu His Pro Phe Leu Thr Thr Lys Gly Trp Lys
85 90 95

Arg Ala Asp Gln Leu Arg Pro Gly Asp Tyr Val Ala Val Pro Arg
100 105 110

<210> SEQ ID NO 14
<211> LENGTH: 39
<212> TYPE: PRT
<213> ORGANISM: Artificial Sequence
<220> FEATURE:
<223> OTHER INFORMATION: Synthetic construct, Pab_IF2-C (#81-C)

<400> SEQUENCE: 14

Met Thr Leu Val Phe Ile Pro Val Glu Asn Val Glu Glu Glu Glu Tyr
1 5 10 15

Asp Gly Tyr Val Tyr Asp Leu Thr Thr Glu Thr His Asn Phe Ile Ala
20 25 30

Asn Gly Ile Leu Val His Asn
35

<210> SEQ ID NO 15
<211> LENGTH: 121
<212> TYPE: PRT
<213> ORGANISM: Artificial Sequence
<220> FEATURE:
<223> OTHER INFORMATION: Synthetic construct, Pab_VMA-N (#92-N)

<400> SEQUENCE: 15

Cys Val Asp Gly Asp Thr Leu Val Leu Thr Lys Glu Phe Gly Leu Ile
1 5 10 15

Lys Ile Lys Asp Leu Tyr Lys Ile Leu Asp Gly Lys Gly Lys Lys Thr

```
            20                  25                  30

Val Asn Gly Asn Glu Glu Trp Thr Glu Leu Glu Arg Pro Ile Thr Leu
        35                  40                  45

Tyr Gly Tyr Lys Asp Gly Lys Ile Val Glu Ile Lys Ala Thr His Val
    50                  55                  60

Tyr Lys Gly Phe Ser Ala Gly Met Ile Glu Ile Arg Thr Arg Thr Gly
65                  70                  75                  80

Arg Lys Ile Lys Val Thr Pro Ile His Lys Leu Phe Thr Gly Arg Val
                85                  90                  95

Thr Lys Asn Gly Leu Glu Ile Arg Glu Val Met Ala Lys Asp Leu Lys
            100                 105                 110

Lys Gly Asp Arg Ile Ile Val Ala Lys
        115                 120


<210> SEQ ID NO 16
<211> LENGTH: 42
<212> TYPE: PRT
<213> ORGANISM: Artificial Sequence
<220> FEATURE:
<223> OTHER INFORMATION: Synthetic construct, Pab_VMA-C (#92-C)

<400> SEQUENCE: 16

Met Thr His Val Leu Phe Asp Glu Ile Val Glu Ile Arg Tyr Ile Ser
1               5                   10                  15

Glu Gly Gln Glu Val Tyr Asp Val Thr Thr Glu Thr His Asn Phe Ile
            20                  25                  30

Gly Gly Asn Met Pro Thr Leu Leu His Asn
        35                  40


<210> SEQ ID NO 17
<211> LENGTH: 111
<212> TYPE: PRT
<213> ORGANISM: Artificial Sequence
<220> FEATURE:
<223> OTHER INFORMATION: Synthetic construct, Pho_IF2-N (#103-N)

<400> SEQUENCE: 17

Cys Leu Leu Pro Glu Glu Arg Val Ile Leu Pro Asp Tyr Gly Pro Ile
1               5                   10                  15

Thr Leu Glu Glu Leu Phe Asn Met Thr Lys Glu Thr Val Phe Lys Asp
            20                  25                  30

Glu Glu Lys Glu Val Arg Lys Leu Gly Ile Arg Met Pro Val Ala Gly
        35                  40                  45

Val Asp Gly Arg Val Arg Leu Leu Glu Gly Pro Tyr Val Trp Lys Val
    50                  55                  60

Arg Tyr Lys Gly Lys Met Leu Arg Val Lys Leu Lys Asp Trp His Ser
65                  70                  75                  80

Val Ala Val Thr Pro Glu His Pro Phe Leu Thr Thr Arg Gly Trp Val
                85                  90                  95

Arg Ala Asp Gln Leu Lys Pro Gly Asp Tyr Val Ala Val Pro Lys
            100                 105                 110


<210> SEQ ID NO 18
<211> LENGTH: 39
<212> TYPE: PRT
<213> ORGANISM: Artificial Sequence
<220> FEATURE:
<223> OTHER INFORMATION: Synthetic construct, Pho_IF2-C (#103-C)

<400> SEQUENCE: 18
```

-continued

Met Asn Phe Val Phe Leu Pro Val Glu Lys Ile Glu Glu Phe Glu Tyr
1 5 10 15

Asp Gly Tyr Val Tyr Asp Val Thr Thr Glu Thr His Asn Phe Ile Ala
20 25 30

Asn Gly Ile Leu Val His Asn
35

<210> SEQ ID NO 19
<211> LENGTH: 121
<212> TYPE: PRT
<213> ORGANISM: Artificial Sequence
<220> FEATURE:
<223> OTHER INFORMATION: Synthetic construct, Pho_VMA-N (#110-N)

<400> SEQUENCE: 19

Cys Val Asp Gly Asp Thr Leu Val Leu Thr Lys Glu Phe Gly Leu Ile
1 5 10 15

Lys Ile Lys Glu Leu Tyr Glu Lys Leu Asp Gly Lys Gly Arg Lys Ile
20 25 30

Val Glu Gly Asn Glu Glu Trp Thr Glu Leu Glu Lys Pro Ile Thr Val
35 40 45

Tyr Gly Tyr Lys Asp Gly Lys Ile Val Glu Ile Lys Ala Thr His Val
50 55 60

Tyr Lys Gly Val Ser Ser Gly Met Val Glu Ile Arg Thr Arg Thr Gly
65 70 75 80

Arg Lys Ile Lys Val Thr Pro Ile His Arg Leu Phe Thr Gly Arg Val
85 90 95

Thr Lys Asp Gly Leu Ile Leu Lys Glu Val Met Ala Met His Val Lys
100 105 110

Pro Gly Asp Arg Ile Ala Val Val Lys
115 120

<210> SEQ ID NO 20
<211> LENGTH: 42
<212> TYPE: PRT
<213> ORGANISM: Artificial Sequence
<220> FEATURE:
<223> OTHER INFORMATION: Synthetic construct, Pho_VMA-C (#110-C)

<400> SEQUENCE: 20

Met Gln His Ile Ile Phe Asp Glu Val Ile Asp Val Arg Tyr Ile Pro
1 5 10 15

Glu Pro Gln Glu Val Tyr Asp Val Thr Thr Glu Thr His Asn Phe Val
20 25 30

Gly Gly Asn Met Pro Thr Leu Leu His Asn
35 40

<210> SEQ ID NO 21
<211> LENGTH: 96
<212> TYPE: PRT
<213> ORGANISM: Artificial Sequence
<220> FEATURE:
<223> OTHER INFORMATION: Synthetic construct, Rma_DnaB-N (#116-N)

<400> SEQUENCE: 21

Cys Leu Ala Gly Asp Thr Leu Ile Thr Leu Ala Asp Gly Arg Arg Val
1 5 10 15

Pro Ile Arg Glu Leu Val Ser Gln Gln Asn Phe Ser Val Trp Ala Leu
20 25 30

Asn Pro Gln Thr Tyr Arg Leu Glu Arg Ala Arg Val Ser Arg Ala Phe
35 40 45

Cys Thr Gly Ile Lys Pro Val Tyr Arg Leu Thr Thr Arg Leu Gly Arg
50 55 60

Ser Ile Arg Ala Thr Ala Asn His Arg Phe Leu Thr Pro Gln Gly Trp
65 70 75 80

Lys Arg Val Asp Glu Leu Gln Pro Gly Asp Tyr Leu Ala Leu Pro Arg
85 90 95

<210> SEQ ID NO 22
<211> LENGTH: 40
<212> TYPE: PRT
<213> ORGANISM: Artificial Sequence
<220> FEATURE:
<223> OTHER INFORMATION: Synthetic construct, Rma_DnaB-C (#116-C)

<400> SEQUENCE: 22

Met Ser Asp Val Tyr Trp Asp Pro Ile Val Ser Ile Glu Pro Asp Gly
1 5 10 15

Val Glu Glu Val Phe Asp Leu Thr Val Pro Gly Pro His Asn Phe Val
20 25 30

Ala Asn Asp Ile Ile Ala His Asn
35 40

<210> SEQ ID NO 23
<211> LENGTH: 89
<212> TYPE: PRT
<213> ORGANISM: Artificial Sequence
<220> FEATURE:
<223> OTHER INFORMATION: Synthetic construct, Sru_DnaB-N (#123-N)

<400> SEQUENCE: 23

Cys Leu Gly Lys Gly Thr Pro Val Met Met Tyr Asp Gly Arg Thr Lys
1 5 10 15

Pro Val Glu Lys Val Glu Val Gly Asp Arg Leu Met Gly Asp Asp Gly
20 25 30

Ser Pro Arg Thr Val Gln Ser Leu Ala Arg Gly Arg Glu Gln Met Tyr
35 40 45

Trp Val Arg Gln Lys Arg Gly Met Asp Tyr Arg Val Asn Glu Ser His
50 55 60

Ile Leu Ser Leu Lys Lys Ser Arg Arg Glu Gly Ala Arg Asp Arg Gly
65 70 75 80

Ser Ile Ala Asp Ile Ser Val Arg Asp
85

<210> SEQ ID NO 24
<211> LENGTH: 38
<212> TYPE: PRT
<213> ORGANISM: Artificial Sequence
<220> FEATURE:
<223> OTHER INFORMATION: Synthetic construct, Sru_DnaB-C (#123-C)

<400> SEQUENCE: 24

Met Trp Arg Met Thr Gly Ile Asp Val Glu Pro Asp Gly Val Gly Asp
1 5 10 15

Tyr Phe Gly Phe Thr Leu Asp Gly Asn Gly Arg Phe Leu Leu Gly Asp
20 25 30

Gly Thr Val Thr His Asn
35

```
<210> SEQ ID NO 25
<211> LENGTH: 95
<212> TYPE: PRT
<213> ORGANISM: Artificial Sequence
<220> FEATURE:
<223> OTHER INFORMATION: Synthetic construct, Tag_Pol1Tsp-TYPol1-N
      (#128-N)

<400> SEQUENCE: 25

Cys His Pro Ala Asp Thr Lys Val Ile Val Lys Gly Lys Gly Ile Val
1               5                   10                  15

Asn Ile Ser Asp Val Lys Glu Gly Asp Tyr Ile Leu Gly Ile Asp Gly
            20                  25                  30

Trp Gln Arg Val Lys Lys Val Trp Lys Tyr His Tyr Glu Gly Lys Leu
        35                  40                  45

Ile Asn Ile Asn Gly Leu Lys Cys Thr Pro Asn His Lys Val Pro Val
    50                  55                  60

Val Thr Glu Asn Asp Arg Gln Thr Arg Ile Arg Asp Ser Leu Ala Lys
65                  70                  75                  80

Ser Phe Leu Ser Gly Lys Val Lys Gly Lys Ile Ile Thr Thr Lys
                85                  90                  95


<210> SEQ ID NO 26
<211> LENGTH: 41
<212> TYPE: PRT
<213> ORGANISM: Artificial Sequence
<220> FEATURE:
<223> OTHER INFORMATION: Synthetic construct, Tag_Pol1Tsp-TYPol1-C
      (#128-C)

<400> SEQUENCE: 26

Met Asn Ser Phe Tyr Asn Leu Ser Thr Phe Glu Val Ser Ser Glu Tyr
1               5                   10                  15

Tyr Lys Gly Glu Val Tyr Asp Leu Thr Leu Glu Gly Asn Pro Tyr Tyr
            20                  25                  30

Phe Ala Asn Gly Ile Leu Thr His Asn
        35                  40


<210> SEQ ID NO 27
<211> LENGTH: 107
<212> TYPE: PRT
<213> ORGANISM: Artificial Sequence
<220> FEATURE:
<223> OTHER INFORMATION: Synthetic construct, Ter_RIR14-N (#135-N)

<400> SEQUENCE: 27

Cys Leu Asp Lys Thr Ala Leu Arg Ile Phe Asn Gln Gly Leu Leu Tyr
1               5                   10                  15

Ala Asp Glu Val Val Thr Pro Gly Ser Gly Glu Thr Val Gly Leu Gly
            20                  25                  30

Leu Thr Val Arg Asn Gly Ile Gly Ala Ser Thr Ala Ile Ala Asn Gln
        35                  40                  45

Pro Met Glu Leu Val Glu Ile Lys Leu Ala Asn Gly Arg Lys Leu Arg
    50                  55                  60

Met Thr Pro Asn His Arg Met Ser Val Lys Gly Lys Trp Ile His Ala
65                  70                  75                  80

Cys Asn Leu Lys Pro Gly Met Leu Leu Asp Tyr Ser Ile Gly Glu Tyr
                85                  90                  95

Gln Lys Arg Glu Asp Thr Leu Leu Ile Pro Leu
            100                 105
```

<210> SEQ ID NO 28
<211> LENGTH: 49
<212> TYPE: PRT
<213> ORGANISM: Artificial Sequence
<220> FEATURE:
<223> OTHER INFORMATION: Synthetic construct, Ter_RIR14-C (#135-C)

<400> SEQUENCE: 28

```
Met Ser Lys Cys Val Leu Asn Tyr Ser Pro Tyr Lys Ile Glu Ser Val
1               5                   10                  15

Asn Ile Gly Ala Val Cys Asp Tyr Ser Tyr Asp Phe Ala Ile Glu Gly
            20                  25                  30

Ile Asn Asp Asn Asp Ser Trp Tyr Trp Gln Gly Ala Leu Lys Ser His
        35                  40                  45

Asn
```

<210> SEQ ID NO 29
<211> LENGTH: 111
<212> TYPE: PRT
<213> ORGANISM: Artificial Sequence
<220> FEATURE:
<223> OTHER INFORMATION: Synthetic construct, Tko_IF2-N (#143-N)

<400> SEQUENCE: 29

```
Cys Leu Leu Pro Asp Glu Lys Val Ile Leu Pro Glu His Gly Pro Ile
1               5                   10                  15

Thr Leu Lys Gly Leu Phe Asp Leu Ala Lys Glu Thr Val Val Ala Asp
            20                  25                  30

Asn Glu Lys Glu Ile Arg Lys Leu Gly Ala Lys Leu Thr Ile Val Gly
        35                  40                  45

Glu Asp Gly Arg Leu Arg Val Leu Glu Ser Pro Tyr Val Trp Lys Val
    50                  55                  60

Arg His Arg Gly Lys Met Leu Arg Val Lys Leu Lys Asn Trp His Ser
65                  70                  75                  80

Val Ser Val Thr Pro Glu His Pro Phe Leu Thr Thr Arg Gly Trp Val
                85                  90                  95

Arg Ala Asp Gln Leu Lys Pro Gly Asp Tyr Val Ala Val Pro Arg
            100                 105                 110
```

<210> SEQ ID NO 30
<211> LENGTH: 39
<212> TYPE: PRT
<213> ORGANISM: Artificial Sequence
<220> FEATURE:
<223> OTHER INFORMATION: Synthetic construct, Tko_IF2-C (#143-C)

<400> SEQUENCE: 30

```
Met Asn Leu Val Phe Ile Pro Val Glu Asp Ile Glu Glu Phe Glu Tyr
1               5                   10                  15

Glu Gly Tyr Val Tyr Asp Val Thr Thr Glu Thr His Asn Phe Val Ala
            20                  25                  30

Asn Gly Ile Leu Val His Asn
        35
```

<210> SEQ ID NO 31
<211> LENGTH: 99
<212> TYPE: PRT
<213> ORGANISM: Artificial Sequence
<220> FEATURE:
<223> OTHER INFORMATION: Synthetic construct, Tth-HB27DnaE2-N (#150-N)

<400> SEQUENCE: 31

```
Cys Leu Pro Ala Arg Ala Arg Val Val Asp Trp Cys Thr Gly Arg Val
1               5                   10                  15

Val Arg Val Gly Glu Ile Val Arg Gly Glu Ala Lys Gly Val Trp Val
            20                  25                  30

Val Ser Leu Asp Glu Ala Arg Leu Arg Leu Val Pro Arg Pro Val Val
        35                  40                  45

Ala Ala Phe Pro Ser Gly Lys Ala Gln Val Tyr Ala Leu Arg Thr Ala
    50                  55                  60

Thr Gly Arg Val Leu Glu Ala Thr Ala Asn His Pro Val Tyr Thr Pro
65                  70                  75                  80

Glu Gly Trp Arg Pro Leu Gly Thr Leu Ala Pro Gly Asp Tyr Val Ala
                85                  90                  95

Leu Pro Arg
```

<210> SEQ ID NO 32
<211> LENGTH: 40
<212> TYPE: PRT
<213> ORGANISM: Artificial Sequence
<220> FEATURE:
<223> OTHER INFORMATION: Synthetic construct, Tth-HB27DnaE2-C (#150-C)

<400> SEQUENCE: 32

```
Met Ala Glu Val Tyr Trp Asp Arg Val Glu Ala Val Glu Pro Leu Gly
1               5                   10                  15

Glu Glu Glu Val Phe Asp Leu Thr Val Glu Gly Thr His Thr Phe Val
            20                  25                  30

Ala Glu Asp Val Ile Val His Asn
        35                  40
```

<210> SEQ ID NO 33
<211> LENGTH: 14
<212> TYPE: PRT
<213> ORGANISM: Artificial Sequence
<220> FEATURE:
<223> OTHER INFORMATION: Synthetic construct, Phy_tag1-N

<400> SEQUENCE: 33

```
Met Ala His Ile Val Met Val Asp Ala Tyr Lys Pro Thr Lys
1               5                   10
```

<210> SEQ ID NO 34
<211> LENGTH: 13
<212> TYPE: PRT
<213> ORGANISM: Artificial Sequence
<220> FEATURE:
<223> OTHER INFORMATION: Synthetic construct, Phy_tag1-C

<400> SEQUENCE: 34

```
Ala His Ile Val Met Val Asp Ala Tyr Lys Pro Thr Lys
1               5                   10
```

<210> SEQ ID NO 35
<211> LENGTH: 117
<212> TYPE: PRT
<213> ORGANISM: Artificial Sequence
<220> FEATURE:
<223> OTHER INFORMATION: Synthetic construct, Phy_catcher1-N

<400> SEQUENCE: 35

```
Met Gly Ala Met Val Asp Thr Leu Ser Gly Leu Ser Ser Glu Gln Gly
1               5                   10                  15
```

```
Gln Ser Gly Asp Met Thr Ile Glu Glu Asp Ser Ala Thr His Ile Lys
            20                  25                  30

Phe Ser Lys Arg Asp Glu Asp Gly Lys Glu Leu Ala Gly Ala Thr Met
        35                  40                  45

Glu Leu Arg Asp Ser Ser Gly Lys Thr Ile Ser Thr Trp Ile Ser Asp
    50                  55                  60

Gly Gln Val Lys Asp Phe Tyr Leu Tyr Pro Gly Lys Tyr Thr Phe Val
65                  70                  75                  80

Glu Thr Ala Ala Pro Asp Gly Tyr Glu Val Ala Thr Ala Ile Thr Phe
                85                  90                  95

Thr Val Asn Glu Gln Gly Gln Val Thr Val Asn Gly Lys Ala Thr Lys
            100                 105                 110

Gly Asp Ala His Ile
        115
```

<210> SEQ ID NO 36
<211> LENGTH: 116
<212> TYPE: PRT
<213> ORGANISM: Artificial Sequence
<220> FEATURE:
<223> OTHER INFORMATION: Synthetic construct, Phy_catcher1-C

<400> SEQUENCE: 36

```
Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile
        115
```

<210> SEQ ID NO 37
<211> LENGTH: 34
<212> TYPE: PRT
<213> ORGANISM: Artificial Sequence
<220> FEATURE:
<223> OTHER INFORMATION: Synthetic construct, cc17 N

<400> SEQUENCE: 37

```
Met Arg Ala Lys Gln Leu Glu Asp Lys Ile Glu Glu Leu Leu Ser Lys
1               5                   10                  15

Ile Tyr His Leu Glu Asn Glu Ile Ala Arg Leu Lys Lys Leu Ile Gly
            20                  25                  30

Glu Arg
```

<210> SEQ ID NO 38
<211> LENGTH: 28
<212> TYPE: PRT
<213> ORGANISM: Artificial Sequence -continued
<220> FEATURE:
<223> OTHER INFORMATION: Synthetic construct, cc17 C

<400> SEQUENCE: 38

Gln Leu Glu Asp Lys Ile Glu Glu Leu Leu Ser Lys Ile Tyr His Leu
1 5 10 15

Glu Asn Glu Ile Ala Arg Leu Lys Lys Leu Ile Gly
20 25

<210> SEQ ID NO 39
<211> LENGTH: 34
<212> TYPE: PRT
<213> ORGANISM: Artificial Sequence
<220> FEATURE:
<223> OTHER INFORMATION: Synthetic construct, cc30 N

<400> SEQUENCE: 39

Met Arg Ala Lys Gln Leu Glu Asp Lys Val Glu Glu Leu Leu Ser Lys
1 5 10 15

Asn Tyr His Leu Glu Asn Glu Val Ala Arg Leu Lys Lys Leu Val Gly
20 25 30

Thr Arg

<210> SEQ ID NO 40
<211> LENGTH: 28
<212> TYPE: PRT
<213> ORGANISM: Artificial Sequence
<220> FEATURE:
<223> OTHER INFORMATION: Synthetic construct, cc30 C

<400> SEQUENCE: 40

Gln Leu Glu Asp Lys Val Glu Glu Leu Leu Ser Lys Asn Tyr His Leu
1 5 10 15

Glu Asn Glu Val Ala Arg Leu Lys Lys Leu Val Gly
20 25

<210> SEQ ID NO 41
<211> LENGTH: 16
<212> TYPE: PRT
<213> ORGANISM: Artificial Sequence
<220> FEATURE:
<223> OTHER INFORMATION: Synthetic construct, L 33-1 linker

<400> SEQUENCE: 41

Ser Gly Gly Gly Ser Gly Gly Gly Ser Thr Pro Gln Ser Ala Phe Ala
1 5 10 15

<210> SEQ ID NO 42
<211> LENGTH: 11
<212> TYPE: PRT
<213> ORGANISM: Artificial Sequence
<220> FEATURE:
<223> OTHER INFORMATION: Synthetic construct, L33-2 linker

<400> SEQUENCE: 42

Gly Gly Gly Ser Gly Gly Gly Ser Gly Gly Gly
1 5 10

<210> SEQ ID NO 43
<211> LENGTH: 20
<212> TYPE: PRT
<213> ORGANISM: Artificial Sequence
<220> FEATURE:
<223> OTHER INFORMATION: Synthetic construct, L38-1 linker

<400> SEQUENCE: 43

Ser Gly Gly Ser Ser Gly Ser Thr Thr Thr Thr Arg Ile Thr Pro Gln
1 5 10 15

Ser Ala Phe Ala
20

<210> SEQ ID NO 44
<211> LENGTH: 12
<212> TYPE: PRT
<213> ORGANISM: Artificial Sequence
<220> FEATURE:
<223> OTHER INFORMATION: Synthetic construct, L38-2 linker

<400> SEQUENCE: 44

Gln Asn Thr Phe Ser Gln Gly Ser Ser Ser Gly Ser
1 5 10

<210> SEQ ID NO 45
<211> LENGTH: 4
<212> TYPE: PRT
<213> ORGANISM: Artificial Sequence
<220> FEATURE:
<223> OTHER INFORMATION: Synthetic construct, L46-1 linker

<400> SEQUENCE: 45

Ser Ala Phe Ala
1

<210> SEQ ID NO 46
<211> LENGTH: 36
<212> TYPE: PRT
<213> ORGANISM: Artificial Sequence
<220> FEATURE:
<223> OTHER INFORMATION: Synthetic construct, L46-2 linker

<400> SEQUENCE: 46

Gly Ala Ala Pro Ala Ala Ala Pro Ala Lys Gln Glu Ala Ala Ala Pro
1 5 10 15

Ala Pro Ala Ala Lys Ala Glu Ala Pro Ala Ala Ala Pro Ala Ala Lys
20 25 30

Ala Thr Pro Gln
35

<210> SEQ ID NO 47
<211> LENGTH: 33
<212> TYPE: PRT
<213> ORGANISM: Artificial Sequence
<220> FEATURE:
<223> OTHER INFORMATION: Synthetic construct, L55-1.1 linker

<400> SEQUENCE: 47

Ser Ala Ala Glu Ala Ala Ala Lys Glu Ala Ala Ala Lys Glu Ala Ala
1 5 10 15

Ala Lys Glu Ala Ala Ala Lys Ala Val Asn Thr Pro Gln Ser Ala Phe
20 25 30

Ala

<210> SEQ ID NO 48
<211> LENGTH: 33
<212> TYPE: PRT
<213> ORGANISM: Artificial Sequence
<220> FEATURE:
<223> OTHER INFORMATION: Synthetic construct, L55-1 linker

<400> SEQUENCE: 48

Ser Ala Ala Glu Ala Ala Ala Lys Glu Ala Ala Ala Lys Glu Ala Ala
1 5 10 15

Ala Lys Glu Ala Ala Ala Lys Ala Leu Asn Thr Pro Gln Ser Ala Phe
20 25 30

Ala

<210> SEQ ID NO 49
<211> LENGTH: 16
<212> TYPE: PRT
<213> ORGANISM: Artificial Sequence
<220> FEATURE:
<223> OTHER INFORMATION: Synthetic construct, L55-2 linker

<400> SEQUENCE: 49

Gly Gly Ala Glu Ala Ala Ala Lys Glu Ala Ala Ala Lys Val Asn Leu
1 5 10 15

<210> SEQ ID NO 50
<211> LENGTH: 6
<212> TYPE: PRT
<213> ORGANISM: Artificial Sequence
<220> FEATURE:
<223> OTHER INFORMATION: Synthetic construct, Phy_taglink

<400> SEQUENCE: 50

Gly Ser Gly Gly Ser Gly
1 5

<210> SEQ ID NO 51
<211> LENGTH: 6
<212> TYPE: PRT
<213> ORGANISM: Artificial Sequence
<220> FEATURE:
<223> OTHER INFORMATION: Synthetic construct, Phy_catcherlink

<400> SEQUENCE: 51

Gly Ser Gly Gly Ser Gly
1 5

<210> SEQ ID NO 52
<211> LENGTH: 1233
<212> TYPE: DNA
<213> ORGANISM: Artificial Sequence
<220> FEATURE:
<223> OTHER INFORMATION: Synthetic construct, Phy02 coding seq

<400> SEQUENCE: 52
gcccaatcgg aaccggaact gaaactggaa agtgtggtta ttgtgtctcg tcatggcgtt 60
cgcgctccga ccaaatttac gcagctgatg caagatgtca ccccggacgc cttctatacg 120
tggccggtga agctgggtga actgaccccg cgtggcggtg aactgatcgc ctatctgggt 180
cactactggc gtcagcgcct ggtggcagat ggtctgctgc cgaaaaaggg ctgcccgcag 240
agcggtcaag ttgcaattat cgctgatgtc gacgaacgta cccgcaaaac gggtgaagca 300
tttgcggccg gtctggcacc ggattgcgcc attaccgttc atacgcaggc agataccagc 360
tctccggacc cgctgttcaa cccgctgaaa accggcgtct gtcagctgga tgtcgcgcaa 420
gtgacggacg ccattctgga acgtgcaggc ggttccatcg ctgattttac cggtcactac 480
cagacggcat tccgtgaact ggaacgcgtt ctgaactttc cgcagtcaaa tctggcgctg 540
aaacgcgaaa agcaggatga aagtgcgtcc ctgacccaag ccctgccgag tgaactgaaa 600

```
gtctccgccg acaatgtgtc actgaccggc gcatggtcac tggcttcgat gctgacggaa    660

atttttctgc tgcagcaagc acagggtatg ccggaaccgg gttggggtcg tatcaccgat    720

tcgcatcagt ggaacacgct gctgagcctg cacaatgcgc agttcgacct gctgcaacgt    780

accccggaag tggcacgttc gcgcgccacg ccgctgctgg atctgattaa aaccgctctg    840

acgccgcatc cgccgcagaa gcaagcgtat ggcgtgaccc tgccgacgag cgttctgttt    900

atcgcgggtc acgacaccaa cctggcaaat ctgggcggtg ctctggaact gcagtggacc    960

ctgccgggtc aaccggataa cacgccgccg ggcggtgaac tggttttcga acgttggcgt   1020

cgcctgagcg acaattctca gtggatccaa gttagcctgg tctttcagac cctgcagcaa   1080

atgcgcgata aaaccccgct gttcctgaac acgccgccgg gcgaagtgaa gctgaccctg   1140

gcgggttgcg aagaacgtaa cgcccagggc atgtgttctc tggcaggttt tacccagatt   1200

gttaatgaag cacgcatccc ggcttgtagt ctg                                1233
```

<210> SEQ ID NO 53
<211> LENGTH: 411
<212> TYPE: PRT
<213> ORGANISM: Artificial Sequence
<220> FEATURE:
<223> OTHER INFORMATION: Synthetic construct, Phy02 protein

<400> SEQUENCE: 53

```
Ala Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Phe Tyr Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Gln Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Ala Leu Lys Arg Glu Lys Gln Asp Glu Ser Ala Ser Leu Thr
            180                 185                 190

Gln Ala Leu Pro Ser Glu Leu Lys Val Ser Ala Asp Asn Val Ser Leu
        195                 200                 205

Thr Gly Ala Trp Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255
```

-continued

```
Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Gln Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Phe
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410


<210> SEQ ID NO 54
<211> LENGTH: 411
<212> TYPE: PRT
<213> ORGANISM: Artificial Sequence
<220> FEATURE:
<223> OTHER INFORMATION: Synthetic construct, Nov9X protein

<400> SEQUENCE: 54

Ala Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205
```

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 55
<211> LENGTH: 1254
<212> TYPE: DNA
<213> ORGANISM: Artificial Sequence
<220> FEATURE:
<223> OTHER INFORMATION: Synthetic construct, CQBscks coding seq

<400> SEQUENCE: 55
gcccagtcgg agcctgagct gaagctggag tcggtcgtca tcgtttcccg gcacggcgtt 60
agggccccaa ccaagttcac acagctgatg caggacgtga cccccgatgc ttggccaacc 120
tggcctgtca agctcggcga gctgaccccc aggggcgggg agctcatcgc gtacctgggg 180
cactactggc gccagcggct ggtcgctgac ggcctcctgc caaaggaagg ctgccctcag 240
tctgggcagg tggctatcat tgccgacgtc gatgagcgca ccaggaagac gggcgaggcc 300
ttcgccgcgg ggctcgcccc agactgcgct atcaccgtgc accatcaggc ggacacgtcc 360
agcccagatc ctctcttcaa cccgctgaag accggcgtct gccagctgga cgtggcgaat 420
gtccgcaggg ctatcctgga gagggccggc gggtccattg ccgatttcac aaggcattac 480
cagactgcgt tcagggagct ggagcgggtg ctgaacttcc cgcagagcaa tctctgcctg 540
aagcgcgaga agcaggacga gtcgtgctct ctcacgcagg ccctgccctc tgagctcaag 600
gtctcagcgg acgatgtttc cctgacaggc gcctggtcac tggcgtccat gctcactgag 660
attttcctcc tgcagcaggc tcaggggatg ccggagccag gctgggggcg gattacagac 720
agccaccagt ggaacactct cctgtcgctc cataatgcgg ttttcgatct cctgcagagg 780
acccccgagg tggctcggtc gcgcgccacg cccctcctgg acctgatcaa gacagctctc 840
actccacacc cgccccagaa gcaggcctac ggcgttaccc tgcctacgtc cgtgctcttc 900

```
attgccggcc atgataccaa cctcgctaat ctgggcgggg ccctggagct gaactggacc    960

ctgccgggcc agcccgacaa ttacccacct ggcggggagc tggtgttcga gaggtggagg   1020

cgcctcagcg ataactcgca gtggattcag gtgtccctcg tgttccagac actccagcag   1080

atgcgggaca agacaccgct ctcactgaac actccgcccg gcgaggtcaa gctcacgctg   1140

gccgggtgcg aggagaggaa cgctcagggc atgtgctccc tggctgggtt cacacagatt   1200

gtcaacgagg cccgcatccc cgcttgctct ctctccgaga aggacgagct gtaa         1254
```

<210> SEQ ID NO 56
<211> LENGTH: 411
<212> TYPE: PRT
<213> ORGANISM: Artificial Sequence
<220> FEATURE:
<223> OTHER INFORMATION: Synthetic construct, CQBscks Phytase

<400> SEQUENCE: 56

```
Ala Gln Ser Glu Pro Glu Leu Lys Leu Glu Ser Val Val Ile Val Ser
1               5                   10                  15

Arg His Gly Val Arg Ala Pro Thr Lys Phe Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Glu Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Glu Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asp Val Ser Leu
        195                 200                 205

Thr Gly Ala Trp Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300
```

```
Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410
```

<210> SEQ ID NO 57
<211> LENGTH: 1641
<212> TYPE: DNA
<213> ORGANISM: Artificial Sequence
<220> FEATURE:
<223> OTHER INFORMATION: Synthetic construct, Cbu_DnaB-C:Phy02:Cbu_DnaB-N coding seq

<400> SEQUENCE: 57

```
atgtcggacc tgttctggga taggatcgtg tcgattgagg agaaggggtc tgaggaggtc     60

tacgatctca cagttccaaa gtacgcttct tggctcgcgg atggggttgt ttcacataat    120

agcgcccaat cggaaccgga actgaaactg gaaagtgtgg ttattgtgtc tcgtcatggc    180

gttcgcgctc cgaccaaatt tacgcagctg atgcaagatg tcaccccgga cgccttctat    240

acgtggccgg tgaagctggg tgaactgacc ccgcgtggcg gtgaactgat cgcctatctg    300

ggtcactact ggcgtcagcg cctggtggca gatggtctgc tgccgaaaaa gggctgcccg    360

cagagcggtc aagttgcaat tatcgctgat gtcgacgaac gtacccgcaa aacgggtgaa    420

gcatttgcgg ccggtctggc accggattgc gccattaccg ttcatacgca ggcagatacc    480

agctctccgg acccgctgtt caacccgctg aaaaccggcg tctgtcagct ggatgtcgcg    540

caagtgacgg acgccattct ggaacgtgca ggcggttcca tcgctgattt taccggtcac    600

taccagacgg cattccgtga actggaacgc gttctgaact ttccgcagtc aaatctggcg    660

ctgaaacgcg aaaagcagga tgaaagtgcg tccctgaccc aagccctgcc gagtgaactg    720

aaagtctccg ccgacaatgt gtcactgacc ggcgcatggt cactggcttc gatgctgacg    780

gaaatttttc tgctgcagca agcacagggt atgccggaac cgggttgggg tcgtatcacc    840

gattcgcatc agtggaacac gctgctgagc ctgcacaatg cgcagttcga cctgctgcaa    900

cgtaccccgg aagtggcacg ttcgcgcgcc acgccgctgc tggatctgat taaaaccgct    960

ctgacgccgc atccgccgca gaagcaagcg tatggcgtga ccctgccgac gagcgttctg   1020

tttatcgcgg gtcacgacac caacctggca aatctgggcg gtgctctgga actgcagtgg   1080

accctgccgg gtcaaccgga taacacgccg ccgggcggtg aactggtttt cgaacgttgg   1140

cgtcgcctga gcgacaattc tcagtggatc caagttagcc tggtctttca gaccctgcag   1200

caaatgcgcg ataaaacccc gctgttcctg aacacgccgc cgggcgaagt gaagctgacc   1260

ctggcgggtt gcgaagaacg taacgcccag ggcatgtgtt ctctggcagg ttttacccag   1320

attgttaatg aagcacgcat cccggcttgt agtctgtgcg tgacagggga cactctcatc   1380
```

-continued

```
tgcctcgctg acgggcgccg cgttcctatt caggatctcg tggggcattc gccggaggtt   1440

attgcggtcg acgataaggg ccgcctcgtt tgcgctaagt cagaggtcat ctggaaggtc   1500

ggcgagcggt ccgttttcga gatcaagctg gcttccggga ggagcattaa ggctaccgct   1560

gagcacaggc tcctggcgtt caagggctgg aggcatgtta aggacttcaa agtgggggat   1620

aggctcgcta ttgctcacta a                                             1641
```

```
<210> SEQ ID NO 58
<211> LENGTH: 546
<212> TYPE: PRT
<213> ORGANISM: Artificial Sequence
<220> FEATURE:
<223> OTHER INFORMATION: Synthetic construt, #12 Phy02C

<400> SEQUENCE: 58

Met Ser Asp Leu Phe Trp Asp Arg Ile Val Ser Ile Glu Glu Lys Gly
1               5                   10                  15

Ser Glu Glu Val Tyr Asp Leu Thr Val Pro Lys Tyr Ala Ser Trp Leu
            20                  25                  30

Ala Asp Gly Val Val Ser His Asn Ser Ala Gln Ser Glu Pro Glu Leu
        35                  40                  45

Lys Leu Glu Ser Val Val Ile Val Ser Arg His Gly Val Arg Ala Pro
    50                  55                  60

Thr Lys Phe Thr Gln Leu Met Gln Asp Val Thr Pro Asp Ala Phe Tyr
65                  70                  75                  80

Thr Trp Pro Val Lys Leu Gly Glu Leu Thr Pro Arg Gly Gly Glu Leu
                85                  90                  95

Ile Ala Tyr Leu Gly His Tyr Trp Arg Gln Arg Leu Val Ala Asp Gly
            100                 105                 110

Leu Leu Pro Lys Lys Gly Cys Pro Gln Ser Gly Gln Val Ala Ile Ile
        115                 120                 125

Ala Asp Val Asp Glu Arg Thr Arg Lys Thr Gly Glu Ala Phe Ala Ala
    130                 135                 140

Gly Leu Ala Pro Asp Cys Ala Ile Thr Val His Thr Gln Ala Asp Thr
145                 150                 155                 160

Ser Ser Pro Asp Pro Leu Phe Asn Pro Leu Lys Thr Gly Val Cys Gln
                165                 170                 175

Leu Asp Val Ala Gln Val Thr Asp Ala Ile Leu Glu Arg Ala Gly Gly
            180                 185                 190

Ser Ile Ala Asp Phe Thr Gly His Tyr Gln Thr Ala Phe Arg Glu Leu
        195                 200                 205

Glu Arg Val Leu Asn Phe Pro Gln Ser Asn Leu Ala Leu Lys Arg Glu
    210                 215                 220

Lys Gln Asp Glu Ser Ala Ser Leu Thr Gln Ala Leu Pro Ser Glu Leu
225                 230                 235                 240

Lys Val Ser Ala Asp Asn Val Ser Leu Thr Gly Ala Trp Ser Leu Ala
                245                 250                 255

Ser Met Leu Thr Glu Ile Phe Leu Leu Gln Gln Ala Gln Gly Met Pro
            260                 265                 270

Glu Pro Gly Trp Gly Arg Ile Thr Asp Ser His Gln Trp Asn Thr Leu
        275                 280                 285

Leu Ser Leu His Asn Ala Gln Phe Asp Leu Leu Gln Arg Thr Pro Glu
    290                 295                 300

Val Ala Arg Ser Arg Ala Thr Pro Leu Leu Asp Leu Ile Lys Thr Ala
305                 310                 315                 320
```

-continued

```
Leu Thr Pro His Pro Pro Gln Lys Gln Ala Tyr Gly Val Thr Leu Pro
                325                 330                 335

Thr Ser Val Leu Phe Ile Ala Gly His Asp Thr Asn Leu Ala Asn Leu
            340                 345                 350

Gly Gly Ala Leu Glu Leu Gln Trp Thr Leu Pro Gly Gln Pro Asp Asn
        355                 360                 365

Thr Pro Pro Gly Gly Glu Leu Val Phe Glu Arg Trp Arg Arg Leu Ser
    370                 375                 380

Asp Asn Ser Gln Trp Ile Gln Val Ser Leu Val Phe Gln Thr Leu Gln
385                 390                 395                 400

Gln Met Arg Asp Lys Thr Pro Leu Phe Leu Asn Thr Pro Pro Gly Glu
                405                 410                 415

Val Lys Leu Thr Leu Ala Gly Cys Glu Glu Arg Asn Ala Gln Gly Met
            420                 425                 430

Cys Ser Leu Ala Gly Phe Thr Gln Ile Val Asn Glu Ala Arg Ile Pro
        435                 440                 445

Ala Cys Ser Leu Cys Val Thr Gly Asp Thr Leu Ile Cys Leu Ala Asp
    450                 455                 460

Gly Arg Arg Val Pro Ile Gln Asp Leu Val Gly His Ser Pro Glu Val
465                 470                 475                 480

Ile Ala Val Asp Asp Lys Gly Arg Leu Val Cys Ala Lys Ser Glu Val
                485                 490                 495

Ile Trp Lys Val Gly Glu Arg Ser Val Phe Glu Ile Lys Leu Ala Ser
            500                 505                 510

Gly Arg Ser Ile Lys Ala Thr Ala Glu His Arg Leu Leu Ala Phe Lys
        515                 520                 525

Gly Trp Arg His Val Lys Asp Phe Lys Val Gly Asp Arg Leu Ala Ile
    530                 535                 540

Ala His
545
```

<210> SEQ ID NO 59
<211> LENGTH: 1650
<212> TYPE: DNA
<213> ORGANISM: Artificial Sequence
<220> FEATURE:
<223> OTHER INFORMATION: Synthetic construct, #44 Phy02C coding seq

<400> SEQUENCE: 59

```
atggcggata tcgtttggac gaagttcaag attgaggagg tggagagcga tgttgagtat      60

gtgtacgatc tggaggtgga ggactaccac aacttcattg gcaatctcat catcaaccac     120

aacagcgccc aatcggaacc ggaactgaaa ctggaaagtg tggttattgt gtctcgtcat     180

ggcgttcgcg ctccgaccaa atttacgcag ctgatgcaag atgtcacccc ggacgccttc     240

tatacgtggc cggtgaagct gggtgaactg accccgcgtg gcggtgaact gatcgcctat     300

ctgggtcact actggcgtca gcgcctggtg gcagatggtc tgctgccgaa aaagggctgc     360

ccgcagagcg gtcaagttgc aattatcgct gatgtcgacg aacgtacccg caaaacgggt     420

gaagcatttg cggccggtct ggcaccggat tgcgccatta ccgttcatac gcaggcagat     480

accagctctc cggacccgct gttcaacccg ctgaaaaccg gcgtctgtca gctggatgtc     540

gcgcaagtga cggacgccat tctggaacgt gcaggcggtt ccatcgctga ttttaccggt     600

cactaccaga cggcattccg tgaactggaa cgcgttctga actttccgca gtcaaatctg     660

gcgctgaaac gcgaaaagca ggatgaaagt gcgtccctga cccaagccct gccgagtgaa     720
```

-continued

```
ctgaaagtct ccgccgacaa tgtgtcactg accggcgcat ggtcactggc ttcgatgctg    780

acggaaattt ttctgctgca gcaagcacag ggtatgccgg aaccgggttg ggtcgtatc     840

accgattcgc atcagtggaa cacgctgctg agcctgcaca atgcgcagtt cgacctgctg    900

caacgtaccc cggaagtggc acgttcgcgc gccacgccgc tgctggatct gattaaaacc    960

gctctgacgc cgcatccgcc gcagaagcaa gcgtatggcg tgaccctgcc gacgagcgtt   1020

ctgtttatcg cgggtcacga caccaacctg gcaaatctgg gcggtgctct ggaactgcag   1080

tggaccctgc cgggtcaacc ggataacacg ccgccgggcg gtgaactggt tttcgaacgt   1140

tggcgtcgcc tgagcgacaa ttctcagtgg atccaagtta gcctggtctt tcagaccctg   1200

cagcaaatgc gcgataaaac cccgctgttc ctgaacacgc cgccgggcga agtgaagctg   1260

accctggcgg gttgcgaaga acgtaacgcc cagggcatgt gttctctggc aggttttacc   1320

cagattgtta atgaagcacg catcccggct tgtagtctgt gcctgcaccc tgacacatac   1380

gttattctcc ctgacgggcg catgaagaag atttcggaga ttgatgagga tgaggttctc   1440

tcagtcaact tcgaggacct gaagctctac aataagaaga tcaagaagtt caagcacaag   1500

gctccgaaga tcctctacaa gattaagacc gcgttctccg agctcatcac cacgggcgag   1560

cataagctgt tcgtggtcga gaacgggaag atcgtcgaga agtgcgttaa ggacctcaat   1620

ggcagcgagc tgatcggggt tgtgaggtaa                                    1650
```

<210> SEQ ID NO 60
<211> LENGTH: 549
<212> TYPE: PRT
<213> ORGANISM: Artificial Sequence
<220> FEATURE:
<223> OTHER INFORMATION: Synthetic construct, #44 Phy02C

<400> SEQUENCE: 60

```
Met Ala Asp Ile Val Trp Thr Lys Phe Lys Ile Glu Glu Val Glu Ser
1               5                   10                  15

Asp Val Glu Tyr Val Tyr Asp Leu Glu Val Glu Asp Tyr His Asn Phe
            20                  25                  30

Ile Gly Asn Leu Ile Ile Asn His Asn Ser Ala Gln Ser Glu Pro Glu
        35                  40                  45

Leu Lys Leu Glu Ser Val Val Ile Val Ser Arg His Gly Val Arg Ala
    50                  55                  60

Pro Thr Lys Phe Thr Gln Leu Met Gln Asp Val Thr Pro Asp Ala Phe
65                  70                  75                  80

Tyr Thr Trp Pro Val Lys Leu Gly Glu Leu Thr Pro Arg Gly Gly Glu
                85                  90                  95

Leu Ile Ala Tyr Leu Gly His Tyr Trp Arg Gln Arg Leu Val Ala Asp
            100                 105                 110

Gly Leu Leu Pro Lys Lys Gly Cys Pro Gln Ser Gly Gln Val Ala Ile
        115                 120                 125

Ile Ala Asp Val Asp Glu Arg Thr Arg Lys Thr Gly Glu Ala Phe Ala
    130                 135                 140

Ala Gly Leu Ala Pro Asp Cys Ala Ile Thr Val His Thr Gln Ala Asp
145                 150                 155                 160

Thr Ser Ser Pro Asp Pro Leu Phe Asn Pro Leu Lys Thr Gly Val Cys
                165                 170                 175

Gln Leu Asp Val Ala Gln Val Thr Asp Ala Ile Leu Glu Arg Ala Gly
            180                 185                 190
```

-continued

```
Gly Ser Ile Ala Asp Phe Thr Gly His Tyr Gln Thr Ala Phe Arg Glu
        195                 200                 205

Leu Glu Arg Val Leu Asn Phe Pro Gln Ser Asn Leu Ala Leu Lys Arg
    210                 215                 220

Glu Lys Gln Asp Glu Ser Ala Ser Leu Thr Gln Ala Leu Pro Ser Glu
225                 230                 235                 240

Leu Lys Val Ser Ala Asp Asn Val Ser Leu Thr Gly Ala Trp Ser Leu
                245                 250                 255

Ala Ser Met Leu Thr Glu Ile Phe Leu Leu Gln Gln Ala Gln Gly Met
            260                 265                 270

Pro Glu Pro Gly Trp Gly Arg Ile Thr Asp Ser His Gln Trp Asn Thr
        275                 280                 285

Leu Leu Ser Leu His Asn Ala Gln Phe Asp Leu Leu Gln Arg Thr Pro
    290                 295                 300

Glu Val Ala Arg Ser Arg Ala Thr Pro Leu Leu Asp Leu Ile Lys Thr
305                 310                 315                 320

Ala Leu Thr Pro His Pro Pro Gln Lys Gln Ala Tyr Gly Val Thr Leu
                325                 330                 335

Pro Thr Ser Val Leu Phe Ile Ala Gly His Asp Thr Asn Leu Ala Asn
            340                 345                 350

Leu Gly Gly Ala Leu Glu Leu Gln Trp Thr Leu Pro Gly Gln Pro Asp
        355                 360                 365

Asn Thr Pro Pro Gly Gly Glu Leu Val Phe Glu Arg Trp Arg Arg Leu
    370                 375                 380

Ser Asp Asn Ser Gln Trp Ile Gln Val Ser Leu Val Phe Gln Thr Leu
385                 390                 395                 400

Gln Gln Met Arg Asp Lys Thr Pro Leu Phe Leu Asn Thr Pro Pro Gly
                405                 410                 415

Glu Val Lys Leu Thr Leu Ala Gly Cys Glu Glu Arg Asn Ala Gln Gly
            420                 425                 430

Met Cys Ser Leu Ala Gly Phe Thr Gln Ile Val Asn Glu Ala Arg Ile
        435                 440                 445

Pro Ala Cys Ser Leu Cys Leu His Pro Asp Thr Tyr Val Ile Leu Pro
    450                 455                 460

Asp Gly Arg Met Lys Lys Ile Ser Glu Ile Asp Glu Asp Glu Val Leu
465                 470                 475                 480

Ser Val Asn Phe Glu Asp Leu Lys Leu Tyr Asn Lys Lys Ile Lys Lys
                485                 490                 495

Phe Lys His Lys Ala Pro Lys Ile Leu Tyr Lys Ile Lys Thr Ala Phe
            500                 505                 510

Ser Glu Leu Ile Thr Thr Gly Glu His Lys Leu Phe Val Val Glu Asn
        515                 520                 525

Gly Lys Ile Val Glu Lys Cys Val Lys Asp Leu Asn Gly Ser Glu Leu
    530                 535                 540

Ile Gly Val Val Arg
545
```

<210> SEQ ID NO 61
<211> LENGTH: 1740
<212> TYPE: DNA
<213> ORGANISM: Artificial Sequence
<220> FEATURE:
<223> OTHER INFORMATION: Synthetic construct, #46 Phy02C coding seq

<400> SEQUENCE: 61

-continued

```
atggggaatt acctgtacgc tcccatcatt aggatcggcc gggagtacta cgacgggttc     60
gtctacaatc tggaggtgga ggatgactct tcatacgtta cagtctcagg cactctgcac    120
aacagcgccc aatcggaacc ggaactgaaa ctggaaagtg tggttattgt gtctcgtcat    180
ggcgttcgcg ctccgaccaa atttacgcag ctgatgcaag atgtcacccc ggacgccttc    240
tatacgtggc cggtgaagct gggtgaactg accccgcgtg gcggtgaact gatcgcctat    300
ctgggtcact actggcgtca gcgcctggtg gcagatggtc tgctgccgaa aaagggctgc    360
ccgcagagcg gtcaagttgc aattatcgct gatgtcgacg aacgtacccg caaaacgggt    420
gaagcatttg cggccggtct ggcaccggat tgcgccatta ccgttcatac gcaggcagat    480
accagctctc cggacccgct gttcaacccg ctgaaaaccg gcgtctgtca gctggatgtc    540
gcgcaagtga cggacgccat tctggaacgt gcaggcggtt ccatcgctga ttttaccggt    600
cactaccaga cggcattccg tgaactggaa cgcgttctga actttccgca gtcaaatctg    660
gcgctgaaac gcgaaaagca ggatgaaagt gcgtccctga cccaagccct gccgagtgaa    720
ctgaaagtct ccgccgacaa tgtgtcactg accggcgcat ggtcactggc ttcgatgctg    780
acggaaattt ttctgctgca gcaagcacag ggtatgccgg aaccgggttg ggtcgtatc    840
accgattcgc atcagtggaa cacgctgctg agcctgcaca atgcgcagtt cgacctgctg    900
caacgtaccc cggaagtggc acgttcgcgc gccacgccgc tgctggatct gattaaaacc    960
gctctgacgc cgcatccgcc gcagaagcaa gcgtatggcg tgaccctgcc gacgagcgtt   1020
ctgtttatcg cgggtcacga caccaacctg gcaaatctgg gcggtgctct ggaactgcag   1080
tggaccctgc cgggtcaacc ggataacacg ccgccgggcg gtgaactggt tttcgaacgt   1140
tggcgtcgcc tgagcgacaa ttctcagtgg atccaagtta gcctggtctt tcagaccctg   1200
cagcaaatgc gcgataaaac cccgctgttc ctgaacacgc cgccgggcga agtgaagctg   1260
accctggcgg gttgcgaaga acgtaacgcc cagggcatgt gttctctggc aggttttacc   1320
cagattgtta atgaagcacg catcccggct tgtagtctgt gcgttccgcc tgacactctg   1380
ctcatcctgg agaatgggtt caagcgcatc gtggacatta aggtcgggga caaggtcctg   1440
acgcacgaga accggttcaa gaaggttgag aaggtgtaca agcgcaggta catcggcgac   1500
atcattaaga ttaaggtgcg ctacttccca gaggagatca ttctcacccc agagcaccct   1560
gtctacgcta tcaagacgga gaagaggtgc gatggctctc atgggatctg caagttcaac   1620
tgcctcacac agtacactaa tccttcatgc aagaagcggt accgcaagta caagagggag   1680
tggatcattg ccaaggacct gaaggtcggc gatgtgatcg tctacccgat tcccaactaa   1740
```

<210> SEQ ID NO 62
<211> LENGTH: 579
<212> TYPE: PRT
<213> ORGANISM: Artificial Sequence
<220> FEATURE:
<223> OTHER INFORMATION: Synthetic construct, #46 Phy02C

<400> SEQUENCE: 62

```
Met Gly Asn Tyr Leu Tyr Ala Pro Ile Ile Arg Ile Gly Arg Glu Tyr
1               5                   10                  15

Tyr Asp Gly Phe Val Tyr Asn Leu Glu Val Glu Asp Asp Ser Ser Tyr
            20                  25                  30

Val Thr Val Ser Gly Thr Leu His Asn Ser Ala Gln Ser Glu Pro Glu
        35                  40                  45

Leu Lys Leu Glu Ser Val Val Ile Val Ser Arg His Gly Val Arg Ala
    50                  55                  60
```

```
Pro Thr Lys Phe Thr Gln Leu Met Gln Asp Val Thr Pro Asp Ala Phe
65                  70                  75                  80

Tyr Thr Trp Pro Val Lys Leu Gly Glu Leu Thr Pro Arg Gly Gly Glu
                85                  90                  95

Leu Ile Ala Tyr Leu Gly His Tyr Trp Arg Gln Arg Leu Val Ala Asp
            100                 105                 110

Gly Leu Leu Pro Lys Lys Gly Cys Pro Gln Ser Gly Gln Val Ala Ile
        115                 120                 125

Ile Ala Asp Val Asp Glu Arg Thr Arg Lys Thr Gly Glu Ala Phe Ala
    130                 135                 140

Ala Gly Leu Ala Pro Asp Cys Ala Ile Thr Val His Thr Gln Ala Asp
145                 150                 155                 160

Thr Ser Ser Pro Asp Pro Leu Phe Asn Pro Leu Lys Thr Gly Val Cys
                165                 170                 175

Gln Leu Asp Val Ala Gln Val Thr Asp Ala Ile Leu Glu Arg Ala Gly
            180                 185                 190

Gly Ser Ile Ala Asp Phe Thr Gly His Tyr Gln Thr Ala Phe Arg Glu
        195                 200                 205

Leu Glu Arg Val Leu Asn Phe Pro Gln Ser Asn Leu Ala Leu Lys Arg
    210                 215                 220

Glu Lys Gln Asp Glu Ser Ala Ser Leu Thr Gln Ala Leu Pro Ser Glu
225                 230                 235                 240

Leu Lys Val Ser Ala Asp Asn Val Ser Leu Thr Gly Ala Trp Ser Leu
                245                 250                 255

Ala Ser Met Leu Thr Glu Ile Phe Leu Leu Gln Gln Ala Gln Gly Met
            260                 265                 270

Pro Glu Pro Gly Trp Gly Arg Ile Thr Asp Ser His Gln Trp Asn Thr
        275                 280                 285

Leu Leu Ser Leu His Asn Ala Gln Phe Asp Leu Leu Gln Arg Thr Pro
    290                 295                 300

Glu Val Ala Arg Ser Arg Ala Thr Pro Leu Leu Asp Leu Ile Lys Thr
305                 310                 315                 320

Ala Leu Thr Pro His Pro Pro Gln Lys Gln Ala Tyr Gly Val Thr Leu
                325                 330                 335

Pro Thr Ser Val Leu Phe Ile Ala Gly His Asp Thr Asn Leu Ala Asn
            340                 345                 350

Leu Gly Gly Ala Leu Glu Leu Gln Trp Thr Leu Pro Gly Gln Pro Asp
        355                 360                 365

Asn Thr Pro Pro Gly Gly Glu Leu Val Phe Glu Arg Trp Arg Arg Leu
    370                 375                 380

Ser Asp Asn Ser Gln Trp Ile Gln Val Ser Leu Val Phe Gln Thr Leu
385                 390                 395                 400

Gln Gln Met Arg Asp Lys Thr Pro Leu Phe Leu Asn Thr Pro Pro Gly
                405                 410                 415

Glu Val Lys Leu Thr Leu Ala Gly Cys Glu Glu Arg Asn Ala Gln Gly
            420                 425                 430

Met Cys Ser Leu Ala Gly Phe Thr Gln Ile Val Asn Glu Ala Arg Ile
        435                 440                 445

Pro Ala Cys Ser Leu Cys Val Pro Pro Asp Thr Leu Leu Ile Leu Glu
    450                 455                 460

Asn Gly Phe Lys Arg Ile Val Asp Ile Lys Val Gly Asp Lys Val Leu
465                 470                 475                 480
```

-continued

```
Thr His Glu Asn Arg Phe Lys Lys Val Glu Lys Val Tyr Lys Arg Arg
                485                 490                 495

Tyr Ile Gly Asp Ile Ile Lys Ile Lys Val Arg Tyr Phe Pro Glu Glu
            500                 505                 510

Ile Ile Leu Thr Pro Glu His Pro Val Tyr Ala Ile Lys Thr Glu Lys
        515                 520                 525

Arg Cys Asp Gly Ser His Gly Ile Cys Lys Phe Asn Cys Leu Thr Gln
    530                 535                 540

Tyr Thr Asn Pro Ser Cys Lys Lys Arg Tyr Arg Lys Tyr Lys Arg Glu
545                 550                 555                 560

Trp Ile Ile Ala Lys Asp Leu Lys Val Gly Asp Val Ile Val Tyr Pro
                565                 570                 575

Ile Pro Asn


<210> SEQ ID NO 63
<211> LENGTH: 1686
<212> TYPE: DNA
<213> ORGANISM: Artificial Sequence
<220> FEATURE:
<223> OTHER INFORMATION: Synthetic construct, #47 Phy02C coding seq

<400> SEQUENCE: 63

atgaacattg cgttcgtcga ggttgaggat gtcgagatca ttgactacga tggctacgtt     60

tacgatctca caacagagac tcataacttc attgctaatg gcatcgtggt tcataatagc    120

gcccaatcgg aaccggaact gaaactggaa agtgtggtta ttgtgtctcg tcatggcgtt    180

cgcgctccga ccaaatttac gcagctgatg caagatgtca ccccggacgc cttctatacg    240

tggccggtga agctgggtga actgaccccg cgtggcggtg aactgatcgc ctatctgggt    300

cactactggc gtcagcgcct ggtggcagat ggtctgctgc cgaaaaaggg ctgcccgcag    360

agcggtcaag ttgcaattat cgctgatgtc gacgaacgta cccgcaaaac gggtgaagca    420

tttgcggccg gtctggcacc ggattgcgcc attaccgttc atacgcaggc agataccagc    480

tctccggacc cgctgttcaa cccgctgaaa accggcgtct gtcagctgga tgtcgcgcaa    540

gtgacggacg ccattctgga acgtgcaggc ggttccatcg ctgattttac cggtcactac    600

cagacggcat tccgtgaact ggaacgcgtt ctgaactttc cgcagtcaaa tctggcgctg    660

aaacgcgaaa agcaggatga aagtgcgtcc ctgacccaag ccctgccgag tgaactgaaa    720

gtctccgccg acaatgtgtc actgaccggc gcatggtcac tggcttcgat gctgacggaa    780

atttttctgc tgcagcaagc acagggtatg ccggaaccgg gttggggtcg tatcaccgat    840

tcgcatcagt ggaacacgct gctgagcctg cacaatgcgc agttcgacct gctgcaacgt    900

accccggaag tggcacgttc gcgcgccacg ccgctgctgg atctgattaa aaccgctctg    960

acgccgcatc cgccgcagaa gcaagcgtat ggcgtgaccc tgccgacgag cgttctgttt   1020

atcgcgggtc acgacaccaa cctggcaaat ctgggcggtg ctctggaact gcagtggacc   1080

ctgccgggtc aaccggataa cacgccgccg ggcggtgaac tggttttcga acgttggcgt   1140

cgcctgagcg acaattctca gtggatccaa gttagcctgg tctttcagac cctgcagcaa   1200

atgcgcgata aaaccccgct gttcctgaac acgccgccgg gcgaagtgaa gctgaccctg   1260

gcgggttgcg aagaacgtaa cgcccagggc atgtgttctc tggcaggttt tacccagatt   1320

gttaatgaag cacgcatccc ggcttgtagt ctgtgcctga tgccgcatga gaaggtgctg   1380

acggagtacg gggagattaa gattgaggac ctgttcaaga tcgggaagga gatcgtggag   1440

aaggacgagc tcaaggagat caggaagctg aatattaagg tgcacactct caacgagaat   1500
```

ggcgagatca agatcattaa cgccccatac gtgtggaagc tcaagcataa ggggaagatg 1560
atcaaggtca agctgaagaa ctggcactcg atcaccacga caccggagca tcccttcctg 1620
accaacaatg gctggatcaa ggcggagaat attaagaagg ggatgtatgt ggctatccct 1680
cgctaa 1686

<210> SEQ ID NO 64
<211> LENGTH: 561
<212> TYPE: PRT
<213> ORGANISM: Artificial Sequence
<220> FEATURE:
<223> OTHER INFORMATION: Synthetic construct, #47 Phy02C

<400> SEQUENCE: 64

Met Asn Ile Ala Phe Val Glu Val Glu Asp Val Glu Ile Ile Asp Tyr
1 5 10 15

Asp Gly Tyr Val Tyr Asp Leu Thr Thr Glu Thr His Asn Phe Ile Ala
20 25 30

Asn Gly Ile Val Val His Asn Ser Ala Gln Ser Glu Pro Glu Leu Lys
35 40 45

Leu Glu Ser Val Val Ile Val Ser Arg His Gly Val Arg Ala Pro Thr
50 55 60

Lys Phe Thr Gln Leu Met Gln Asp Val Thr Pro Asp Ala Phe Tyr Thr
65 70 75 80

Trp Pro Val Lys Leu Gly Glu Leu Thr Pro Arg Gly Gly Glu Leu Ile
85 90 95

Ala Tyr Leu Gly His Tyr Trp Arg Gln Arg Leu Val Ala Asp Gly Leu
100 105 110

Leu Pro Lys Lys Gly Cys Pro Gln Ser Gly Gln Val Ala Ile Ile Ala
115 120 125

Asp Val Asp Glu Arg Thr Arg Lys Thr Gly Glu Ala Phe Ala Ala Gly
130 135 140

Leu Ala Pro Asp Cys Ala Ile Thr Val His Thr Gln Ala Asp Thr Ser
145 150 155 160

Ser Pro Asp Pro Leu Phe Asn Pro Leu Lys Thr Gly Val Cys Gln Leu
165 170 175

Asp Val Ala Gln Val Thr Asp Ala Ile Leu Glu Arg Ala Gly Gly Ser
180 185 190

Ile Ala Asp Phe Thr Gly His Tyr Gln Thr Ala Phe Arg Glu Leu Glu
195 200 205

Arg Val Leu Asn Phe Pro Gln Ser Asn Leu Ala Leu Lys Arg Glu Lys
210 215 220

Gln Asp Glu Ser Ala Ser Leu Thr Gln Ala Leu Pro Ser Glu Leu Lys
225 230 235 240

Val Ser Ala Asp Asn Val Ser Leu Thr Gly Ala Trp Ser Leu Ala Ser
245 250 255

Met Leu Thr Glu Ile Phe Leu Leu Gln Gln Ala Gln Gly Met Pro Glu
260 265 270

Pro Gly Trp Gly Arg Ile Thr Asp Ser His Gln Trp Asn Thr Leu Leu
275 280 285

Ser Leu His Asn Ala Gln Phe Asp Leu Leu Gln Arg Thr Pro Glu Val
290 295 300

Ala Arg Ser Arg Ala Thr Pro Leu Leu Asp Leu Ile Lys Thr Ala Leu
305 310 315 320

-continued

```
Thr Pro His Pro Pro Gln Lys Gln Ala Tyr Gly Val Thr Leu Pro Thr
                325                 330                 335

Ser Val Leu Phe Ile Ala Gly His Asp Thr Asn Leu Ala Asn Leu Gly
            340                 345                 350

Gly Ala Leu Glu Leu Gln Trp Thr Leu Pro Gly Gln Pro Asp Asn Thr
        355                 360                 365

Pro Pro Gly Gly Glu Leu Val Phe Glu Arg Trp Arg Arg Leu Ser Asp
    370                 375                 380

Asn Ser Gln Trp Ile Gln Val Ser Leu Val Phe Gln Thr Leu Gln Gln
385                 390                 395                 400

Met Arg Asp Lys Thr Pro Leu Phe Leu Asn Thr Pro Pro Gly Glu Val
                405                 410                 415

Lys Leu Thr Leu Ala Gly Cys Glu Glu Arg Asn Ala Gln Gly Met Cys
            420                 425                 430

Ser Leu Ala Gly Phe Thr Gln Ile Val Asn Glu Ala Arg Ile Pro Ala
        435                 440                 445

Cys Ser Leu Cys Leu Met Pro His Glu Lys Val Leu Thr Glu Tyr Gly
    450                 455                 460

Glu Ile Lys Ile Glu Asp Leu Phe Lys Ile Gly Lys Glu Ile Val Glu
465                 470                 475                 480

Lys Asp Glu Leu Lys Glu Ile Arg Lys Leu Asn Ile Lys Val His Thr
                485                 490                 495

Leu Asn Glu Asn Gly Glu Ile Lys Ile Ile Asn Ala Pro Tyr Val Trp
            500                 505                 510

Lys Leu Lys His Lys Gly Lys Met Ile Lys Val Lys Leu Lys Asn Trp
        515                 520                 525

His Ser Ile Thr Thr Thr Pro Glu His Pro Phe Leu Thr Asn Asn Gly
    530                 535                 540

Trp Ile Lys Ala Glu Asn Ile Lys Lys Gly Met Tyr Val Ala Ile Pro
545                 550                 555                 560

Arg
```

<210> SEQ ID NO 65
<211> LENGTH: 1668
<212> TYPE: DNA
<213> ORGANISM: Artificial Sequence
<220> FEATURE:
<223> OTHER INFORMATION: Synthetic construct, #50 Phy02C coding seq

<400> SEQUENCE: 65

```
atgtacgggt tctacgacct cgacgatgtg tgcgtctcac tggagtccta caagggcgag     60

gtgtacgatc tcactctgga gggcaggcct tactacttcg ccaatggcat cctcactcat    120

aatagcgccc aatcggaacc ggaactgaaa ctggaaagtg tggttattgt gtctcgtcat    180

ggcgttcgcg ctccgaccaa atttacgcag ctgatgcaag atgtcacccc ggacgccttc    240

tatacgtggc cggtgaagct gggtgaactg accccgcgtg gcggtgaact gatcgcctat    300

ctgggtcact actggcgtca gcgcctggtg gcagatggtc tgctgccgaa aaagggctgc    360

ccgcagagcg gtcaagttgc aattatcgct gatgtcgacg aacgtacccg caaaacgggt    420

gaagcatttg cggccggtct ggcaccggat tgcgccatta ccgttcatac gcaggcagat    480

accagctctc cggacccgct gttcaacccg ctgaaaaccg gcgtctgtca gctggatgtc    540

gcgcaagtga cggacgccat tctggaacgt gcaggcggtt ccatcgctga ttttaccggt    600

cactaccaga cggcattccg tgaactggaa cgcgttctga actttccgca gtcaaatctg    660
```

-continued gcgctgaaac gcgaaaagca ggatgaaagt gcgtccctga cccaagccct gccgagtgaa 720
ctgaaagtct ccgccgacaa tgtgtcactg accggcgcat ggtcactggc ttcgatgctg 780
acggaaattt ttctgctgca gcaagcacag ggtatgccgg aaccgggttg ggtcgtatc 840 accgattcgc atcagtggaa cacgctgctg agcctgcaca atgcgcagtt cgacctgctg 900
caacgtaccc cggaagtggc acgttcgcgc gccacgccgc tgctggatct gattaaaacc 960
gctctgacgc cgcatccgcc gcagaagcaa gcgtatggcg tgaccctgcc gacgagcgtt 1020
ctgtttatcg cgggtcacga caccaacctg gcaaatctgg gcggtgctct ggaactgcag 1080
tggaccctgc cgggtcaacc ggataacacg ccgccgggcg gtgaactggt tttcgaacgt 1140
tggcgtcgcc tgagcgacaa ttctcagtgg atccaagtta gcctggtctt tcagaccctg 1200
cagcaaatgc gcgataaaac cccgctgttc ctgaacacgc cgccgggcga agtgaagctg 1260
accctggcgg gttgcgaaga acgtaacgcc cagggcatgt gttctctggc aggttttacc 1320
cagattgtta atgaagcacg catcccggct tgtagtctgt gccatccaaa ggggacaaag 1380
gtcgtggtca agggcaaggg catcgtgaat attgaggacg ttaaggaggg gaattacgtt 1440
ctcggcatcg acggctggca gaaggttaag aaggtctgga agtacgagta cgagggcgag 1500
ctcattaacg ttaatgggct gaagtgcaca ccgaaccaca agatccccct ccgctacaag 1560
attaagcata agaagatcaa caagaacgat tacctggtga gggacatcta cgcgaagtcg 1620
ctcctgacca agttcaaggg cgaggggaag ctcatcctgt gcaagtaa 1668

<210> SEQ ID NO 66
<211> LENGTH: 555
<212> TYPE: PRT
<213> ORGANISM: Artificial Sequence
<220> FEATURE:
<223> OTHER INFORMATION: Synthetic construct, #50 Phy02C

<400> SEQUENCE: 66

Met Tyr Gly Phe Tyr Asp Leu Asp Asp Val Cys Val Ser Leu Glu Ser
1 5 10 15

Tyr Lys Gly Glu Val Tyr Asp Leu Thr Leu Glu Gly Arg Pro Tyr Tyr
20 25 30

Phe Ala Asn Gly Ile Leu Thr His Asn Ser Ala Gln Ser Glu Pro Glu
35 40 45

Leu Lys Leu Glu Ser Val Val Ile Val Ser Arg His Gly Val Arg Ala
50 55 60

Pro Thr Lys Phe Thr Gln Leu Met Gln Asp Val Thr Pro Asp Ala Phe
65 70 75 80

Tyr Thr Trp Pro Val Lys Leu Gly Glu Leu Thr Pro Arg Gly Gly Glu
85 90 95

Leu Ile Ala Tyr Leu Gly His Tyr Trp Arg Gln Arg Leu Val Ala Asp
100 105 110

Gly Leu Leu Pro Lys Lys Gly Cys Pro Gln Ser Gly Gln Val Ala Ile
115 120 125

Ile Ala Asp Val Asp Glu Arg Thr Arg Lys Thr Gly Glu Ala Phe Ala
130 135 140

Ala Gly Leu Ala Pro Asp Cys Ala Ile Thr Val His Thr Gln Ala Asp
145 150 155 160

Thr Ser Ser Pro Asp Pro Leu Phe Asn Pro Leu Lys Thr Gly Val Cys
165 170 175

Gln Leu Asp Val Ala Gln Val Thr Asp Ala Ile Leu Glu Arg Ala Gly
180 185 190

Gly Ser Ile Ala Asp Phe Thr Gly His Tyr Gln Thr Ala Phe Arg Glu
195 200 205

Leu Glu Arg Val Leu Asn Phe Pro Gln Ser Asn Leu Ala Leu Lys Arg
210 215 220

Glu Lys Gln Asp Glu Ser Ala Ser Leu Thr Gln Ala Leu Pro Ser Glu
225 230 235 240

Leu Lys Val Ser Ala Asp Asn Val Ser Leu Thr Gly Ala Trp Ser Leu
245 250 255

Ala Ser Met Leu Thr Glu Ile Phe Leu Leu Gln Gln Ala Gln Gly Met
260 265 270

Pro Glu Pro Gly Trp Gly Arg Ile Thr Asp Ser His Gln Trp Asn Thr
275 280 285

Leu Leu Ser Leu His Asn Ala Gln Phe Asp Leu Leu Gln Arg Thr Pro
290 295 300

Glu Val Ala Arg Ser Arg Ala Thr Pro Leu Leu Asp Leu Ile Lys Thr
305 310 315 320

Ala Leu Thr Pro His Pro Pro Gln Lys Gln Ala Tyr Gly Val Thr Leu
325 330 335

Pro Thr Ser Val Leu Phe Ile Ala Gly His Asp Thr Asn Leu Ala Asn
340 345 350

Leu Gly Gly Ala Leu Glu Leu Gln Trp Thr Leu Pro Gly Gln Pro Asp
355 360 365

Asn Thr Pro Pro Gly Gly Glu Leu Val Phe Glu Arg Trp Arg Arg Leu
370 375 380

Ser Asp Asn Ser Gln Trp Ile Gln Val Ser Leu Val Phe Gln Thr Leu
385 390 395 400

Gln Gln Met Arg Asp Lys Thr Pro Leu Phe Leu Asn Thr Pro Pro Gly
405 410 415

Glu Val Lys Leu Thr Leu Ala Gly Cys Glu Glu Arg Asn Ala Gln Gly
420 425 430

Met Cys Ser Leu Ala Gly Phe Thr Gln Ile Val Asn Glu Ala Arg Ile
435 440 445

Pro Ala Cys Ser Leu Cys His Pro Lys Gly Thr Lys Val Val Val Lys
450 455 460

Gly Lys Gly Ile Val Asn Ile Glu Asp Val Lys Glu Gly Asn Tyr Val
465 470 475 480

Leu Gly Ile Asp Gly Trp Gln Lys Val Lys Lys Val Trp Lys Tyr Glu
485 490 495

Tyr Glu Gly Glu Leu Ile Asn Val Asn Gly Leu Lys Cys Thr Pro Asn
500 505 510

His Lys Ile Pro Leu Arg Tyr Lys Ile Lys His Lys Lys Ile Asn Lys
515 520 525

Asn Asp Tyr Leu Val Arg Asp Ile Tyr Ala Lys Ser Leu Leu Thr Lys
530 535 540

Phe Lys Gly Glu Gly Lys Leu Ile Leu Cys Lys
545 550 555

<210> SEQ ID NO 67
<211> LENGTH: 1728
<212> TYPE: DNA
<213> ORGANISM: Artificial Sequence
<220> FEATURE:
<223> OTHER INFORMATION: Synthetic construct, #79 Phy02C coding seq

<400> SEQUENCE: 67
atgtccgtga gctgggacga ggtcgcggag atcctggagt acgagccaaa ggatccttgg 60
gtctacgatc tgcaggttcc aggctaccac aacttcctcg ctaatggcat cttcgttcat 120
aatagcgccc aatcggaacc ggaactgaaa ctggaaagtg tggttattgt gtctcgtcat 180
ggcgttcgcg ctccgaccaa atttacgcag ctgatgcaag atgtcacccc ggacgccttc 240
tatacgtggc cggtgaagct gggtgaactg accccgcgtg gcggtgaact gatcgcctat 300
ctgggtcact actggcgtca gcgcctggtg gcagatggtc tgctgccgaa aaagggctgc 360
ccgcagagcg gtcaagttgc aattatcgct gatgtcgacg aacgtacccg caaaacgggt 420
gaagcatttg cggccggtct ggcaccggat tgcgccatta ccgttcatac gcaggcagat 480
accagctctc cggacccgct gttcaacccg ctgaaaaccg gcgtctgtca gctggatgtc 540
gcgcaagtga cggacgccat tctggaacgt gcaggcggtt ccatcgctga ttttaccggt 600
cactaccaga cggcattccg tgaactggaa cgcgttctga actttccgca gtcaaatctg 660
gcgctgaaac gcgaaaagca ggatgaaagt gcgtccctga cccaagccct gccgagtgaa 720
ctgaaagtct ccgccgacaa tgtgtcactg accggcgcat ggtcactggc ttcgatgctg 780
acggaaattt ttctgctgca gcaagcacag ggtatgccgg aaccgggttg ggtcgtatc 840 accgattcgc atcagtggaa cacgctgctg agcctgcaca atgcgcagtt cgacctgctg 900
caacgtaccc cggaagtggc acgttcgcgc gccacgccgc tgctggatct gattaaaacc 960
gctctgacgc cgcatccgcc gcagaagcaa gcgtatggcg tgaccctgcc gacgagcgtt 1020
ctgtttatcg cgggtcacga caccaacctg gcaaatctgg gcggtgctct ggaactgcag 1080
tggaccctgc cgggtcaacc ggataacacg ccgccgggcg gtgaactggt tttcgaacgt 1140
tggcgtcgcc tgagcgacaa ttctcagtgg atccaagtta gcctggtctt tcagaccctg 1200
cagcaaatgc gcgataaaac cccgctgttc ctgaacacgc cgccgggcga agtgaagctg 1260
accctggcgg gttgcgaaga acgtaacgcc cagggcatgt gttctctggc aggttttacc 1320
cagattgtta atgaagcacg catcccggct tgtagtctgt gcgtggatta cgagactgag 1380
gtcgtgctgg ggaatgggga gcggaagaag atcggggaga tcgtggagcg ggctattgag 1440
gaggctgaga agaacggcaa gctcgggcgg gttgacgatg gcttctacgc tccgatcgac 1500
attgaggtct actcgctcga tctggagacc ctcaaggttc ggaaggcgcg ggcaaatatc 1560
gcgtggaagc gcacagctcc aaagaagatg atgctggtga agactagggg cgggaagcgc 1620
attagggtca ccccgacgca ccccttcttc gttctggagg agggcaaggt ggctatgagg 1680
aaggcccggg acctggagga gggcaacaag atcgccacga ttgagtaa 1728

<210> SEQ ID NO 68
<211> LENGTH: 575
<212> TYPE: PRT
<213> ORGANISM: Artificial Sequence
<220> FEATURE:
<223> OTHER INFORMATION: Synthetic construct, #79 Phy02C

<400> SEQUENCE: 68

Met Ser Val Ser Trp Asp Glu Val Ala Glu Ile Leu Glu Tyr Glu Pro
1 5 10 15

Lys Asp Pro Trp Val Tyr Asp Leu Gln Val Pro Gly Tyr His Asn Phe
20 25 30

Leu Ala Asn Gly Ile Phe Val His Asn Ser Ala Gln Ser Glu Pro Glu
35 40 45

Leu Lys Leu Glu Ser Val Val Ile Val Ser Arg His Gly Val Arg Ala

-continued

```
    50                  55                  60

Pro Thr Lys Phe Thr Gln Leu Met Gln Asp Val Thr Pro Asp Ala Phe
65                  70                  75                  80

Tyr Thr Trp Pro Val Lys Leu Gly Glu Leu Thr Pro Arg Gly Gly Glu
                85                  90                  95

Leu Ile Ala Tyr Leu Gly His Tyr Trp Arg Gln Arg Leu Val Ala Asp
            100                 105                 110

Gly Leu Leu Pro Lys Lys Gly Cys Pro Gln Ser Gly Gln Val Ala Ile
        115                 120                 125

Ile Ala Asp Val Asp Glu Arg Thr Arg Lys Thr Gly Glu Ala Phe Ala
    130                 135                 140

Ala Gly Leu Ala Pro Asp Cys Ala Ile Thr Val His Thr Gln Ala Asp
145                 150                 155                 160

Thr Ser Ser Pro Asp Pro Leu Phe Asn Pro Leu Lys Thr Gly Val Cys
                165                 170                 175

Gln Leu Asp Val Ala Gln Val Thr Asp Ala Ile Leu Glu Arg Ala Gly
            180                 185                 190

Gly Ser Ile Ala Asp Phe Thr Gly His Tyr Gln Thr Ala Phe Arg Glu
        195                 200                 205

Leu Glu Arg Val Leu Asn Phe Pro Gln Ser Asn Leu Ala Leu Lys Arg
    210                 215                 220

Glu Lys Gln Asp Glu Ser Ala Ser Leu Thr Gln Ala Leu Pro Ser Glu
225                 230                 235                 240

Leu Lys Val Ser Ala Asp Asn Val Ser Leu Thr Gly Ala Trp Ser Leu
                245                 250                 255

Ala Ser Met Leu Thr Glu Ile Phe Leu Leu Gln Gln Ala Gln Gly Met
            260                 265                 270

Pro Glu Pro Gly Trp Gly Arg Ile Thr Asp Ser His Gln Trp Asn Thr
        275                 280                 285

Leu Leu Ser Leu His Asn Ala Gln Phe Asp Leu Leu Gln Arg Thr Pro
    290                 295                 300

Glu Val Ala Arg Ser Arg Ala Thr Pro Leu Leu Asp Leu Ile Lys Thr
305                 310                 315                 320

Ala Leu Thr Pro His Pro Pro Gln Lys Gln Ala Tyr Gly Val Thr Leu
                325                 330                 335

Pro Thr Ser Val Leu Phe Ile Ala Gly His Asp Thr Asn Leu Ala Asn
            340                 345                 350

Leu Gly Gly Ala Leu Glu Leu Gln Trp Thr Leu Pro Gly Gln Pro Asp
        355                 360                 365

Asn Thr Pro Pro Gly Gly Glu Leu Val Phe Glu Arg Trp Arg Arg Leu
    370                 375                 380

Ser Asp Asn Ser Gln Trp Ile Gln Val Ser Leu Val Phe Gln Thr Leu
385                 390                 395                 400

Gln Gln Met Arg Asp Lys Thr Pro Leu Phe Leu Asn Thr Pro Pro Gly
                405                 410                 415

Glu Val Lys Leu Thr Leu Ala Gly Cys Glu Glu Arg Asn Ala Gln Gly
            420                 425                 430

Met Cys Ser Leu Ala Gly Phe Thr Gln Ile Val Asn Glu Ala Arg Ile
        435                 440                 445

Pro Ala Cys Ser Leu Cys Val Asp Tyr Glu Thr Glu Val Val Leu Gly
    450                 455                 460

Asn Gly Glu Arg Lys Lys Ile Gly Glu Ile Val Glu Arg Ala Ile Glu
465                 470                 475                 480
```

```
Glu Ala Glu Lys Asn Gly Lys Leu Gly Arg Val Asp Asp Gly Phe Tyr
                485                 490                 495

Ala Pro Ile Asp Ile Glu Val Tyr Ser Leu Asp Leu Glu Thr Leu Lys
            500                 505                 510

Val Arg Lys Ala Arg Ala Asn Ile Ala Trp Lys Arg Thr Ala Pro Lys
        515                 520                 525

Lys Met Met Leu Val Lys Thr Arg Gly Gly Lys Arg Ile Arg Val Thr
    530                 535                 540

Pro Thr His Pro Phe Phe Val Leu Glu Glu Gly Lys Val Ala Met Arg
545                 550                 555                 560

Lys Ala Arg Asp Leu Glu Glu Gly Asn Lys Ile Ala Thr Ile Glu
                565                 570                 575


<210> SEQ ID NO 69
<211> LENGTH: 1689
<212> TYPE: DNA
<213> ORGANISM: Artificial Sequence
<220> FEATURE:
<223> OTHER INFORMATION: Synthetic construct, #81 Phy02C coding seq

<400> SEQUENCE: 69

atgacgctgg tgttcatccc cgttgagaat gtggaggagg aggagtacga cggctacgtt     60

tacgatctca ctacggagac tcataacttc attgctaatg gcatcctcgt tcataatagc    120

gcccaatcgg aaccggaact gaaactggaa agtgtggtta ttgtgtctcg tcatggcgtt    180

cgcgctccga ccaaatttac gcagctgatg caagatgtca ccccggacgc cttctatacg    240

tggccggtga agctgggtga actgaccccg cgtggcggtg aactgatcgc ctatctgggt    300

cactactggc gtcagcgcct ggtggcagat ggtctgctgc cgaaaaaggg ctgcccgcag    360

agcggtcaag ttgcaattat cgctgatgtc gacgaacgta cccgcaaaac gggtgaagca    420

tttgcggccg gtctggcacc ggattgcgcc attaccgttc atacgcaggc agataccagc    480

tctccggacc cgctgttcaa cccgctgaaa accggcgtct gtcagctgga tgtcgcgcaa    540

gtgacggacg ccattctgga acgtgcaggc ggttccatcg ctgattttac cggtcactac    600

cagacggcat tccgtgaact ggaacgcgtt ctgaactttc cgcagtcaaa tctggcgctg    660

aaacgcgaaa agcaggatga aagtgcgtcc ctgacccaag ccctgccgag tgaactgaaa    720

gtctccgccg acaatgtgtc actgaccggc gcatggtcac tggcttcgat gctgacggaa    780

atttttctgc tgcagcaagc acagggtatg ccggaaccgg gttggggtcg tatcaccgat    840

tcgcatcagt ggaacacgct gctgagcctg cacaatgcgc agttcgacct gctgcaacgt    900

accccggaag tggcacgttc gcgcgccacg ccgctgctgg atctgattaa aaccgctctg    960

acgccgcatc cgccgcagaa gcaagcgtat ggcgtgaccc tgccgacgag cgttctgttt   1020

atcgcgggtc acgacaccaa cctggcaaat ctgggcggtg ctctggaact gcagtggacc   1080

ctgccgggtc aaccggataa cacgccgccg ggcggtgaac tggttttcga acgttggcgt   1140

cgcctgagcg acaattctca gtggatccaa gttagcctgg tctttcagac cctgcagcaa   1200

atgcgcgata aaaccccgct gttcctgaac acgccgccgg gcgaagtgaa gctgaccctg   1260

gcgggttgcg aagaacgtaa cgcccagggc atgtgttctc tggcaggttt tacccagatt   1320

gttaatgaag cacgcatccc ggcttgtagt ctgtgcctcc tccctgatga gaaggtcgtg   1380

gttccctcgg tcgggttcgt gacactcaag gagctgttcg agacggcttc caaggtcgtg   1440

gagcgcgacg atgagaagga gatcagggag ctcgacgagc ggattaccag cgttaacggc   1500
```

gatgggaaga cgggcctggt caaggcctcc tacgtgtgga aggttaggca caagggcaag 1560
gtcatccggg tcaagctcaa gaattggcac ggcgttacag tgactccgga gcatcccttc 1620
ctcaccacga aggggtggaa gagggctgac cagctgaggc caggcgatta cgtcgcggtt 1680
cctaggtaa 1689

<210> SEQ ID NO 70
<211> LENGTH: 562
<212> TYPE: PRT
<213> ORGANISM: Artificial Sequence
<220> FEATURE:
<223> OTHER INFORMATION: Synthetic construct, #81 Phy02C

<400> SEQUENCE: 70

Met Thr Leu Val Phe Ile Pro Val Glu Asn Val Glu Glu Glu Glu Tyr
1               5                   10                  15

Asp Gly Tyr Val Tyr Asp Leu Thr Thr Glu Thr His Asn Phe Ile Ala
            20                  25                  30

Asn Gly Ile Leu Val His Asn Ser Ala Gln Ser Glu Pro Glu Leu Lys
        35                  40                  45

Leu Glu Ser Val Val Ile Val Ser Arg His Gly Val Arg Ala Pro Thr
    50                  55                  60

Lys Phe Thr Gln Leu Met Gln Asp Val Thr Pro Asp Ala Phe Tyr Thr
65                  70                  75                  80

Trp Pro Val Lys Leu Gly Glu Leu Thr Pro Arg Gly Gly Glu Leu Ile
                85                  90                  95

Ala Tyr Leu Gly His Tyr Trp Arg Gln Arg Leu Val Ala Asp Gly Leu
            100                 105                 110

Leu Pro Lys Lys Gly Cys Pro Gln Ser Gly Gln Val Ala Ile Ile Ala
        115                 120                 125

Asp Val Asp Glu Arg Thr Arg Lys Thr Gly Glu Ala Phe Ala Ala Gly
    130                 135                 140

Leu Ala Pro Asp Cys Ala Ile Thr Val His Thr Gln Ala Asp Thr Ser
145                 150                 155                 160

Ser Pro Asp Pro Leu Phe Asn Pro Leu Lys Thr Gly Val Cys Gln Leu
                165                 170                 175

Asp Val Ala Gln Val Thr Asp Ala Ile Leu Glu Arg Ala Gly Gly Ser
            180                 185                 190

Ile Ala Asp Phe Thr Gly His Tyr Gln Thr Ala Phe Arg Glu Leu Glu
        195                 200                 205

Arg Val Leu Asn Phe Pro Gln Ser Asn Leu Ala Leu Lys Arg Glu Lys
    210                 215                 220

Gln Asp Glu Ser Ala Ser Leu Thr Gln Ala Leu Pro Ser Glu Leu Lys
225                 230                 235                 240

Val Ser Ala Asp Asn Val Ser Leu Thr Gly Ala Trp Ser Leu Ala Ser
                245                 250                 255

Met Leu Thr Glu Ile Phe Leu Leu Gln Gln Ala Gln Gly Met Pro Glu
            260                 265                 270

Pro Gly Trp Gly Arg Ile Thr Asp Ser His Gln Trp Asn Thr Leu Leu
        275                 280                 285

Ser Leu His Asn Ala Gln Phe Asp Leu Leu Gln Arg Thr Pro Glu Val
    290                 295                 300

Ala Arg Ser Arg Ala Thr Pro Leu Leu Asp Leu Ile Lys Thr Ala Leu
305                 310                 315                 320

Thr Pro His Pro Pro Gln Lys Gln Ala Tyr Gly Val Thr Leu Pro Thr

-continued

```
                325                 330                 335

Ser Val Leu Phe Ile Ala Gly His Asp Thr Asn Leu Ala Asn Leu Gly
            340                 345                 350

Gly Ala Leu Glu Leu Gln Trp Thr Leu Pro Gly Gln Pro Asp Asn Thr
        355                 360                 365

Pro Pro Gly Gly Glu Leu Val Phe Glu Arg Trp Arg Arg Leu Ser Asp
    370                 375                 380

Asn Ser Gln Trp Ile Gln Val Ser Leu Val Phe Gln Thr Leu Gln Gln
385                 390                 395                 400

Met Arg Asp Lys Thr Pro Leu Phe Leu Asn Thr Pro Pro Gly Glu Val
                405                 410                 415

Lys Leu Thr Leu Ala Gly Cys Glu Glu Arg Asn Ala Gln Gly Met Cys
            420                 425                 430

Ser Leu Ala Gly Phe Thr Gln Ile Val Asn Glu Ala Arg Ile Pro Ala
        435                 440                 445

Cys Ser Leu Cys Leu Leu Pro Asp Glu Lys Val Val Val Pro Ser Val
    450                 455                 460

Gly Phe Val Thr Leu Lys Glu Leu Phe Glu Thr Ala Ser Lys Val Val
465                 470                 475                 480

Glu Arg Asp Asp Glu Lys Glu Ile Arg Glu Leu Asp Glu Arg Ile Thr
                485                 490                 495

Ser Val Asn Gly Asp Gly Lys Thr Gly Leu Val Lys Ala Ser Tyr Val
            500                 505                 510

Trp Lys Val Arg His Lys Gly Lys Val Ile Arg Val Lys Leu Lys Asn
        515                 520                 525

Trp His Gly Val Thr Val Thr Pro Glu His Pro Phe Leu Thr Thr Lys
    530                 535                 540

Gly Trp Lys Arg Ala Asp Gln Leu Arg Pro Gly Asp Tyr Val Ala Val
545                 550                 555                 560

Pro Arg
```

<210> SEQ ID NO 71
<211> LENGTH: 1728
<212> TYPE: DNA
<213> ORGANISM: Artificial Sequence
<220> FEATURE:
<223> OTHER INFORMATION: Synthetic construct, #92 Phy02C coding seq

<400> SEQUENCE: 71

```
atgacccatg ttctgttcga cgagatcgtg gagattcggt acatctccga gggccaggag     60

gtgtacgacg ttactacgga gactcataat ttcattgggg gcaacatgcc tactctgctc    120

cacaacagcg cccaatcgga accggaactg aaactggaaa gtgtggttat tgtgtctcgt    180

catggcgttc gcgctccgac caaatttacg cagctgatgc aagatgtcac cccggacgcc    240

ttctatacgt ggccggtgaa gctgggtgaa ctgaccccgc gtggcggtga actgatcgcc    300

tatctgggtc actactggcg tcagcgcctg gtggcagatg gtctgctgcc gaaaaagggc    360

tgcccgcaga gcggtcaagt tgcaattatc gctgatgtcg acgaacgtac ccgcaaaacg    420

ggtgaagcat ttgcggccgg tctggcaccg gattgcgcca ttaccgttca tacgcaggca    480

gataccagct ctccggaccc gctgttcaac ccgctgaaaa ccggcgtctg tcagctggat    540

gtcgcgcaag tgacggacgc cattctggaa cgtgcaggcg gttccatcgc tgattttacc    600

ggtcactacc agacggcatt ccgtgaactg gaacgcgttc tgaactttcc gcagtcaaat    660

ctggcgctga aacgcgaaaa gcaggatgaa agtgcgtccc tgacccaagc cctgccgagt    720
```

gaactgaaag tctccgccga caatgtgtca ctgaccggcg catggtcact ggcttcgatg 780
ctgacggaaa tttttctgct gcagcaagca cagggtatgc cggaaccggg ttggggtcgt 840
atcaccgatt cgcatcagtg gaacacgctg ctgagcctgc acaatgcgca gttcgacctg 900
ctgcaacgta ccccggaagt ggcacgttcg cgcgccacgc cgctgctgga tctgattaaa 960
accgctctga cgccgcatcc gccgcagaag caagcgtatg gcgtgaccct gccgacgagc 1020
gttctgttta tcgcgggtca cgacaccaac ctggcaaatc tgggcggtgc tctggaactg 1080
cagtggaccc tgccgggtca accggataac acgccgccgg gcggtgaact ggttttcgaa 1140
cgttggcgtc gcctgagcga caattctcag tggatccaag ttagcctggt ctttcagacc 1200
ctgcagcaaa tgcgcgataa aaccccgctg ttcctgaaca cgccgccggg cgaagtgaag 1260
ctgaccctgg cgggttgcga agaacgtaac gcccagggca tgtgttctct ggcaggtttt 1320
acccagattg ttaatgaagc acgcatcccg gcttgtagtc tgtgcgtgga cggggacact 1380
ctcgtgctga caaaggagtt cggctcatc aagatcaagg acctctacaa gattctggac 1440
ggcaagggga agaagacagt gaacggcaat gaggagtgga cagagctgga gaggccaatc 1500
actctgtacg gctacaagga cggaagatc gtcgagatta aggctaccca cgtttacaag 1560
ggcttctccg ccgggatgat cgagattcgg acccgcacgg gccgcaagat taaggtcacg 1620
cccatccata agctcttcac aggcagggtt actaagaatg ggctggagat ccgggaggtc 1680
atggccaagg acctcaagaa gggcgatcgg atcattgtgg cgaagtaa 1728

<210> SEQ ID NO 72
<211> LENGTH: 575
<212> TYPE: PRT
<213> ORGANISM: Artificial Sequence
<220> FEATURE:
<223> OTHER INFORMATION: Syntehtic construct, #92 Phy02C

<400> SEQUENCE: 72

Met Thr His Val Leu Phe Asp Glu Ile Val Glu Ile Arg Tyr Ile Ser
1 5 10 15

Glu Gly Gln Glu Val Tyr Asp Val Thr Thr Glu Thr His Asn Phe Ile
20 25 30

Gly Gly Asn Met Pro Thr Leu Leu His Asn Ser Ala Gln Ser Glu Pro
35 40 45

Glu Leu Lys Leu Glu Ser Val Val Ile Val Ser Arg His Gly Val Arg
50 55 60

Ala Pro Thr Lys Phe Thr Gln Leu Met Gln Asp Val Thr Pro Asp Ala
65 70 75 80

Phe Tyr Thr Trp Pro Val Lys Leu Gly Glu Leu Thr Pro Arg Gly Gly
85 90 95

Glu Leu Ile Ala Tyr Leu Gly His Tyr Trp Arg Gln Arg Leu Val Ala
100 105 110

Asp Gly Leu Leu Pro Lys Lys Gly Cys Pro Gln Ser Gly Gln Val Ala
115 120 125

Ile Ile Ala Asp Val Asp Glu Arg Thr Arg Lys Thr Gly Glu Ala Phe
130 135 140

Ala Ala Gly Leu Ala Pro Asp Cys Ala Ile Thr Val His Thr Gln Ala
145 150 155 160

Asp Thr Ser Ser Pro Asp Pro Leu Phe Asn Pro Leu Lys Thr Gly Val
165 170 175

Cys Gln Leu Asp Val Ala Gln Val Thr Asp Ala Ile Leu Glu Arg Ala

-continued

```
            180                 185                 190

Gly Gly Ser Ile Ala Asp Phe Thr Gly His Tyr Gln Thr Ala Phe Arg
        195                 200                 205

Glu Leu Glu Arg Val Leu Asn Phe Pro Gln Ser Asn Leu Ala Leu Lys
    210                 215                 220

Arg Glu Lys Gln Asp Glu Ser Ala Ser Leu Thr Gln Ala Leu Pro Ser
225                 230                 235                 240

Glu Leu Lys Val Ser Ala Asp Asn Val Ser Leu Thr Gly Ala Trp Ser
                245                 250                 255

Leu Ala Ser Met Leu Thr Glu Ile Phe Leu Leu Gln Gln Ala Gln Gly
            260                 265                 270

Met Pro Glu Pro Gly Trp Gly Arg Ile Thr Asp Ser His Gln Trp Asn
        275                 280                 285

Thr Leu Leu Ser Leu His Asn Ala Gln Phe Asp Leu Leu Gln Arg Thr
    290                 295                 300

Pro Glu Val Ala Arg Ser Arg Ala Thr Pro Leu Leu Asp Leu Ile Lys
305                 310                 315                 320

Thr Ala Leu Thr Pro His Pro Pro Gln Lys Gln Ala Tyr Gly Val Thr
                325                 330                 335

Leu Pro Thr Ser Val Leu Phe Ile Ala Gly His Asp Thr Asn Leu Ala
            340                 345                 350

Asn Leu Gly Gly Ala Leu Glu Leu Gln Trp Thr Leu Pro Gly Gln Pro
        355                 360                 365

Asp Asn Thr Pro Pro Gly Gly Glu Leu Val Phe Glu Arg Trp Arg Arg
    370                 375                 380

Leu Ser Asp Asn Ser Gln Trp Ile Gln Val Ser Leu Val Phe Gln Thr
385                 390                 395                 400

Leu Gln Gln Met Arg Asp Lys Thr Pro Leu Phe Leu Asn Thr Pro Pro
                405                 410                 415

Gly Glu Val Lys Leu Thr Leu Ala Gly Cys Glu Glu Arg Asn Ala Gln
            420                 425                 430

Gly Met Cys Ser Leu Ala Gly Phe Thr Gln Ile Val Asn Glu Ala Arg
        435                 440                 445

Ile Pro Ala Cys Ser Leu Cys Val Asp Gly Asp Thr Leu Val Leu Thr
    450                 455                 460

Lys Glu Phe Gly Leu Ile Lys Ile Lys Asp Leu Tyr Lys Ile Leu Asp
465                 470                 475                 480

Gly Lys Gly Lys Lys Thr Val Asn Gly Asn Glu Glu Trp Thr Glu Leu
                485                 490                 495

Glu Arg Pro Ile Thr Leu Tyr Gly Tyr Lys Asp Gly Lys Ile Val Glu
            500                 505                 510

Ile Lys Ala Thr His Val Tyr Lys Gly Phe Ser Ala Gly Met Ile Glu
        515                 520                 525

Ile Arg Thr Arg Thr Gly Arg Lys Ile Lys Val Thr Pro Ile His Lys
    530                 535                 540

Leu Phe Thr Gly Arg Val Thr Lys Asn Gly Leu Glu Ile Arg Glu Val
545                 550                 555                 560

Met Ala Lys Asp Leu Lys Lys Gly Asp Arg Ile Ile Val Ala Lys
                565                 570                 575
```

<210> SEQ ID NO 73
<211> LENGTH: 1689
<212> TYPE: DNA
<213> ORGANISM: Artificial Sequence
<220> FEATURE:
<223> OTHER INFORMATION: Synthetic construct, #103 Phy02C coding seq

<400> SEQUENCE: 73

```
atgaacttcg ttttcctgcc ggtggagaag atcgaggagt tcgagtacga tggctacgtc     60

tacgacgtta ctacagagac tcataatttc attgctaatg gcatcctcgt tcataatagc    120

gcccaatcgg aaccggaact gaaactggaa agtgtggtta ttgtgtctcg tcatggcgtt    180

cgcgctccga ccaaatttac gcagctgatg caagatgtca ccccggacgc cttctatacg    240

tggccggtga agctgggtga actgaccccg cgtggcggtg aactgatcgc ctatctgggt    300

cactactggc gtcagcgcct ggtggcagat ggtctgctgc cgaaaaaggg ctgcccgcag    360

agcggtcaag ttgcaattat cgctgatgtc gacgaacgta cccgcaaaac gggtgaagca    420

tttgcggccg gtctggcacc ggattgcgcc attaccgttc atacgcaggc agataccagc    480

tctccggacc cgctgttcaa cccgctgaaa accggcgtct gtcagctgga tgtcgcgcaa    540

gtgacggacg ccattctgga acgtgcaggc ggttccatcg ctgattttac cggtcactac    600

cagacggcat tccgtgaact ggaacgcgtt ctgaactttc cgcagtcaaa tctggcgctg    660

aaacgcgaaa agcaggatga aagtgcgtcc ctgacccaag ccctgccgag tgaactgaaa    720

gtctccgccg acaatgtgtc actgaccggc gcatggtcac tggcttcgat gctgacggaa    780

atttttctgc tgcagcaagc acagggtatg ccggaaccgg gttggggtcg tatcaccgat    840

tcgcatcagt ggaacacgct gctgagcctg cacaatgcgc agttcgacct gctgcaacgt    900

accccggaag tggcacgttc gcgcgccacg ccgctgctgg atctgattaa aaccgctctg    960

acgccgcatc cgccgcagaa gcaagcgtat ggcgtgaccc tgccgacgag cgttctgttt   1020

atcgcgggtc acgacaccaa cctggcaaat ctgggcggtg ctctggaact gcagtggacc   1080

ctgccgggtc aaccggataa cacgccgccg ggcggtgaac tggttttcga acgttggcgt   1140

cgcctgagcg acaattctca gtggatccaa gttagcctgg tctttcagac cctgcagcaa   1200

atgcgcgata aaaccccgct gttcctgaac acgccgccgg gcgaagtgaa gctgaccctg   1260

gcgggttgcg aagaacgtaa cgcccagggc atgtgttctc tggcaggttt tacccagatt   1320

gttaatgaag cacgcatccc ggcttgtagt ctgtgcctgc tgccggagga gcgggttatt   1380

ctgcctgact acgggcctat tactctggag gagctcttca atatgacaaa ggagacagtg   1440

ttcaaggacg aggagaagga ggtccggaag ctcggcatcc gcatgccagt ggctggcgtc   1500

gatgggcggg tgcgcctgct ggagggcccc tacgtttgga aggtgcgcta caaggggaag   1560

atgctcaggg tcaagctgaa ggactggcac agcgtggctg tcacaccaga gcatcccttc   1620

ctcaccacgc ggggctgggt gcgcgctgac cagctgaagc ccggggatta cgttgccgtg   1680

ccaaagtaa                                                           1689
```

<210> SEQ ID NO 74
<211> LENGTH: 562
<212> TYPE: PRT
<213> ORGANISM: Artificial Sequence
<220> FEATURE:
<223> OTHER INFORMATION: Synthetic construct, #103 Phy02C

<400> SEQUENCE: 74

```
Met Asn Phe Val Phe Leu Pro Val Glu Lys Ile Glu Glu Phe Glu Tyr
1               5                   10                  15

Asp Gly Tyr Val Tyr Asp Val Thr Thr Glu Thr His Asn Phe Ile Ala
            20                  25                  30
```

```
Asn Gly Ile Leu Val His Asn Ser Ala Gln Ser Glu Pro Glu Leu Lys
        35                  40                  45

Leu Glu Ser Val Val Ile Val Ser Arg His Gly Val Arg Ala Pro Thr
    50                  55                  60

Lys Phe Thr Gln Leu Met Gln Asp Val Thr Pro Asp Ala Phe Tyr Thr
65                  70                  75                  80

Trp Pro Val Lys Leu Gly Glu Leu Thr Pro Arg Gly Gly Glu Leu Ile
                85                  90                  95

Ala Tyr Leu Gly His Tyr Trp Arg Gln Arg Leu Val Ala Asp Gly Leu
            100                 105                 110

Leu Pro Lys Lys Gly Cys Pro Gln Ser Gly Gln Val Ala Ile Ile Ala
        115                 120                 125

Asp Val Asp Glu Arg Thr Arg Lys Thr Gly Glu Ala Phe Ala Ala Gly
    130                 135                 140

Leu Ala Pro Asp Cys Ala Ile Thr Val His Thr Gln Ala Asp Thr Ser
145                 150                 155                 160

Ser Pro Asp Pro Leu Phe Asn Pro Leu Lys Thr Gly Val Cys Gln Leu
                165                 170                 175

Asp Val Ala Gln Val Thr Asp Ala Ile Leu Glu Arg Ala Gly Gly Ser
            180                 185                 190

Ile Ala Asp Phe Thr Gly His Tyr Gln Thr Ala Phe Arg Glu Leu Glu
        195                 200                 205

Arg Val Leu Asn Phe Pro Gln Ser Asn Leu Ala Leu Lys Arg Glu Lys
    210                 215                 220

Gln Asp Glu Ser Ala Ser Leu Thr Gln Ala Leu Pro Ser Glu Leu Lys
225                 230                 235                 240

Val Ser Ala Asp Asn Val Ser Leu Thr Gly Ala Trp Ser Leu Ala Ser
                245                 250                 255

Met Leu Thr Glu Ile Phe Leu Leu Gln Gln Ala Gln Gly Met Pro Glu
            260                 265                 270

Pro Gly Trp Gly Arg Ile Thr Asp Ser His Gln Trp Asn Thr Leu Leu
        275                 280                 285

Ser Leu His Asn Ala Gln Phe Asp Leu Leu Gln Arg Thr Pro Glu Val
    290                 295                 300

Ala Arg Ser Arg Ala Thr Pro Leu Leu Asp Leu Ile Lys Thr Ala Leu
305                 310                 315                 320

Thr Pro His Pro Pro Gln Lys Gln Ala Tyr Gly Val Thr Leu Pro Thr
                325                 330                 335

Ser Val Leu Phe Ile Ala Gly His Asp Thr Asn Leu Ala Asn Leu Gly
            340                 345                 350

Gly Ala Leu Glu Leu Gln Trp Thr Leu Pro Gly Gln Pro Asp Asn Thr
        355                 360                 365

Pro Pro Gly Gly Glu Leu Val Phe Glu Arg Trp Arg Arg Leu Ser Asp
    370                 375                 380

Asn Ser Gln Trp Ile Gln Val Ser Leu Val Phe Gln Thr Leu Gln Gln
385                 390                 395                 400

Met Arg Asp Lys Thr Pro Leu Phe Leu Asn Thr Pro Pro Gly Glu Val
                405                 410                 415

Lys Leu Thr Leu Ala Gly Cys Glu Glu Arg Asn Ala Gln Gly Met Cys
            420                 425                 430

Ser Leu Ala Gly Phe Thr Gln Ile Val Asn Glu Ala Arg Ile Pro Ala
        435                 440                 445

Cys Ser Leu Cys Leu Leu Pro Glu Glu Arg Val Ile Leu Pro Asp Tyr
```

```
    450                 455                 460

Gly Pro Ile Thr Leu Glu Glu Leu Phe Asn Met Thr Lys Glu Thr Val
465                 470                 475                 480

Phe Lys Asp Glu Glu Lys Glu Val Arg Lys Leu Gly Ile Arg Met Pro
                485                 490                 495

Val Ala Gly Val Asp Gly Arg Val Arg Leu Leu Glu Gly Pro Tyr Val
            500                 505                 510

Trp Lys Val Arg Tyr Lys Gly Lys Met Leu Arg Val Lys Leu Lys Asp
        515                 520                 525

Trp His Ser Val Ala Val Thr Pro Glu His Pro Phe Leu Thr Thr Arg
    530                 535                 540

Gly Trp Val Arg Ala Asp Gln Leu Lys Pro Gly Asp Tyr Val Ala Val
545                 550                 555                 560

Pro Lys


<210> SEQ ID NO 75
<211> LENGTH: 1728
<212> TYPE: DNA
<213> ORGANISM: Artificial Sequence
<220> FEATURE:
<223> OTHER INFORMATION: Synthetic construct, #110 Phy02C coding seq

<400> SEQUENCE: 75

atgcagcata tcattttcga cgaggtcatc gatgtcaggt acattccgga gccccaggag     60

gtgtacgatg ttactacaga gactcataat ttcgtggggg gcaacatgcc aactctgctc    120

cacaatagcg cccaatcgga accggaactg aaactggaaa gtgtggttat tgtgtctcgt    180

catggcgttc gcgctccgac caaatttacg cagctgatgc aagatgtcac cccggacgcc    240

ttctatacgt ggccggtgaa gctgggtgaa ctgaccccgc gtggcggtga actgatcgcc    300

tatctgggtc actactggcg tcagcgcctg gtggcagatg gtctgctgcc gaaaaagggc    360

tgcccgcaga gcggtcaagt tgcaattatc gctgatgtcg acgaacgtac ccgcaaaacg    420

ggtgaagcat ttgcggccgg tctggcaccg gattgcgcca ttaccgttca tacgcaggca    480

gataccagct ctccggaccc gctgttcaac ccgctgaaaa ccggcgtctg tcagctggat    540

gtcgcgcaag tgacggacgc cattctggaa cgtgcaggcg gttccatcgc tgattttacc    600

ggtcactacc agacggcatt ccgtgaactg gaacgcgttc tgaactttcc gcagtcaaat    660

ctggcgctga aacgcgaaaa gcaggatgaa agtgcgtccc tgacccaagc cctgccgagt    720

gaactgaaag tctccgccga caatgtgtca ctgaccggcg catggtcact ggcttcgatg    780

ctgacggaaa tttttctgct gcagcaagca cagggtatgc cggaaccggg ttggggtcgt    840

atcaccgatt cgcatcagtg gaacacgctg ctgagcctgc acaatgcgca gttcgacctg    900

ctgcaacgta ccccggaagt ggcacgttcg cgcgccacgc cgctgctgga tctgattaaa    960

accgctctga cgccgcatcc gccgcagaag caagcgtatg gcgtgaccct gccgacgagc   1020

gttctgttta tcgcgggtca cgacaccaac ctggcaaatc tgggcggtgc tctggaactg   1080

cagtggaccc tgccgggtca accggataac acgccgccgg gcggtgaact ggttttcgaa   1140

cgttggcgtc gcctgagcga caattctcag tggatccaag ttagcctggt ctttcagacc   1200

ctgcagcaaa tgcgcgataa aacccccgctg ttcctgaaca cgccgccggg cgaagtgaag   1260

ctgaccctgg cgggttgcga agaacgtaac gcccagggca tgtgttctct ggcaggtttt   1320

acccagattg ttaatgaagc acgcatcccg gcttgtagtc tgtgcgtgga cggggacaca   1380

ctggtgctga caaaggagtt cgggctcatc aagatcaagg agctctacga gaagctggac   1440
```

```
ggcaaggggc gcaagattgt ggagggcaac gaggagtgga ccgagctgga gaagccaatc   1500

acggtctacg gctacaagga cgggaagatc gttgagatta aggccaccca cgtttacaag   1560

ggcgtgtcca gcgggatggt cgagatcagg acccggacgg gccggaagat caaggtgacg   1620

ccgattcacc gcctgttcac aggcagggtc actaaggacg ggctgatcct caaggaggtc   1680

atggctatgc atgttaagcc cggcgatagg atcgccgtgg tcaagtaa                1728


<210> SEQ ID NO 76
<211> LENGTH: 575
<212> TYPE: PRT
<213> ORGANISM: Artificial Sequence
<220> FEATURE:
<223> OTHER INFORMATION: Syntehtic construct, #110 Phy02C

<400> SEQUENCE: 76

Met Gln His Ile Ile Phe Asp Glu Val Ile Asp Val Arg Tyr Ile Pro
1               5                   10                  15

Glu Pro Gln Glu Val Tyr Asp Val Thr Thr Glu Thr His Asn Phe Val
            20                  25                  30

Gly Gly Asn Met Pro Thr Leu Leu His Asn Ser Ala Gln Ser Glu Pro
        35                  40                  45

Glu Leu Lys Leu Glu Ser Val Val Ile Val Ser Arg His Gly Val Arg
    50                  55                  60

Ala Pro Thr Lys Phe Thr Gln Leu Met Gln Asp Val Thr Pro Asp Ala
65                  70                  75                  80

Phe Tyr Thr Trp Pro Val Lys Leu Gly Glu Leu Thr Pro Arg Gly Gly
                85                  90                  95

Glu Leu Ile Ala Tyr Leu Gly His Tyr Trp Arg Gln Arg Leu Val Ala
            100                 105                 110

Asp Gly Leu Leu Pro Lys Lys Gly Cys Pro Gln Ser Gly Gln Val Ala
        115                 120                 125

Ile Ile Ala Asp Val Asp Glu Arg Thr Arg Lys Thr Gly Glu Ala Phe
    130                 135                 140

Ala Ala Gly Leu Ala Pro Asp Cys Ala Ile Thr Val His Thr Gln Ala
145                 150                 155                 160

Asp Thr Ser Ser Pro Asp Pro Leu Phe Asn Pro Leu Lys Thr Gly Val
                165                 170                 175

Cys Gln Leu Asp Val Ala Gln Val Thr Asp Ala Ile Leu Glu Arg Ala
            180                 185                 190

Gly Gly Ser Ile Ala Asp Phe Thr Gly His Tyr Gln Thr Ala Phe Arg
        195                 200                 205

Glu Leu Glu Arg Val Leu Asn Phe Pro Gln Ser Asn Leu Ala Leu Lys
    210                 215                 220

Arg Glu Lys Gln Asp Glu Ser Ala Ser Leu Thr Gln Ala Leu Pro Ser
225                 230                 235                 240

Glu Leu Lys Val Ser Ala Asp Asn Val Ser Leu Thr Gly Ala Trp Ser
                245                 250                 255

Leu Ala Ser Met Leu Thr Glu Ile Phe Leu Leu Gln Gln Ala Gln Gly
            260                 265                 270

Met Pro Glu Pro Gly Trp Gly Arg Ile Thr Asp Ser His Gln Trp Asn
        275                 280                 285

Thr Leu Leu Ser Leu His Asn Ala Gln Phe Asp Leu Leu Gln Arg Thr
    290                 295                 300

Pro Glu Val Ala Arg Ser Arg Ala Thr Pro Leu Leu Asp Leu Ile Lys
```

305 310 315 320

Thr Ala Leu Thr Pro His Pro Pro Gln Lys Gln Ala Tyr Gly Val Thr
325 330 335

Leu Pro Thr Ser Val Leu Phe Ile Ala Gly His Asp Thr Asn Leu Ala
340 345 350

Asn Leu Gly Gly Ala Leu Glu Leu Gln Trp Thr Leu Pro Gly Gln Pro
355 360 365

Asp Asn Thr Pro Pro Gly Gly Glu Leu Val Phe Glu Arg Trp Arg Arg
370 375 380

Leu Ser Asp Asn Ser Gln Trp Ile Gln Val Ser Leu Val Phe Gln Thr
385 390 395 400

Leu Gln Gln Met Arg Asp Lys Thr Pro Leu Phe Leu Asn Thr Pro Pro
405 410 415

Gly Glu Val Lys Leu Thr Leu Ala Gly Cys Glu Glu Arg Asn Ala Gln
420 425 430

Gly Met Cys Ser Leu Ala Gly Phe Thr Gln Ile Val Asn Glu Ala Arg
435 440 445

Ile Pro Ala Cys Ser Leu Cys Val Asp Gly Asp Thr Leu Val Leu Thr
450 455 460

Lys Glu Phe Gly Leu Ile Lys Ile Lys Glu Leu Tyr Glu Lys Leu Asp
465 470 475 480

Gly Lys Gly Arg Lys Ile Val Glu Gly Asn Glu Glu Trp Thr Glu Leu
485 490 495

Glu Lys Pro Ile Thr Val Tyr Gly Tyr Lys Asp Gly Lys Ile Val Glu
500 505 510

Ile Lys Ala Thr His Val Tyr Lys Gly Val Ser Ser Gly Met Val Glu
515 520 525

Ile Arg Thr Arg Thr Gly Arg Lys Ile Lys Val Thr Pro Ile His Arg
530 535 540

Leu Phe Thr Gly Arg Val Thr Lys Asp Gly Leu Ile Leu Lys Glu Val
545 550 555 560

Met Ala Met His Val Lys Pro Gly Asp Arg Ile Ala Val Val Lys
565 570 575

<210> SEQ ID NO 77
<211> LENGTH: 1647
<212> TYPE: DNA
<213> ORGANISM: Artificial Sequence
<220> FEATURE:
<223> OTHER INFORMATION: Synthetic construct, #116 Phy02C coding seq

<400> SEQUENCE: 77
atgtcagacg tctactggga tccgatcgtt tccattgagc ccgacggcgt tgaggaggtg 60
ttcgatctca ctgttccagg gccacataac ttcgttgcta atgacatcat tgctcataat 120
agcgcccaat cggaaccgga actgaaactg gaaagtgtgg ttattgtgtc tcgtcatggc 180
gttcgcgctc cgaccaaatt tacgcagctg atgcaagatg tcaccccgga cgccttctat 240
acgtggccgg tgaagctggg tgaactgacc ccgcgtggcg gtgaactgat cgcctatctg 300
ggtcactact ggcgtcagcg cctggtggca gatggtctgc tgccgaaaaa gggctgcccg 360
cagagcggtc aagttgcaat tatcgctgat gtcgacgaac gtacccgcaa aacgggtgaa 420
gcatttgcgg ccggtctggc accggattgc gccattaccg ttcatacgca ggcagatacc 480
agctctccgg acccgctgtt caacccgctg aaaaccggcg tctgtcagct ggatgtcgcg 540
caagtgacgg acgccattct ggaacgtgca ggcggttcca tcgctgattt taccggtcac 600
taccagacgg cattccgtga actggaacgc gttctgaact ttccgcagtc aaatctggcg 660
ctgaaacgcg aaaagcagga tgaaagtgcg tccctgaccc aagccctgcc gagtgaactg 720
aaagtctccg ccgacaatgt gtcactgacc ggcgcatggt cactggcttc gatgctgacg 780
gaaatttttc tgctgcagca agcacagggt atgccggaac cgggttgggg tcgtatcacc 840
gattcgcatc agtggaacac gctgctgagc ctgcacaatg cgcagttcga cctgctgcaa 900
cgtaccccgg aagtggcacg ttcgcgcgcc acgccgctgc tggatctgat taaaaccgct 960
ctgacgccgc atccgccgca gaagcaagcg tatggcgtga ccctgccgac gagcgttctg 1020
tttatcgcgg gtcacgacac caacctggca aatctgggcg gtgctctgga actgcagtgg 1080
accctgccgg gtcaaccgga taacacgccg ccgggcggtg aactggtttt cgaacgttgg 1140
cgtcgcctga gcgacaattc tcagtggatc caagttagcc tggtctttca gaccctgcag 1200
caaatgcgcg ataaaacccc gctgttcctg aacacgccgc cgggcgaagt gaagctgacc 1260
ctggcgggtt gcgaagaacg taacgcccag ggcatgtgtt ctctggcagg ttttacccag 1320
attgttaatg aagcacgcat cccggcttgt agtctgtgcc tcgcggggga cactctcatt 1380
acactggctg acgggcggcg ggttcctatt cgggagctgg tctcgcagca gaatttctcg 1440
gtctgggcgc tgaacccgca gacgtacagg ctggagaggg ctcgggtctc ccgggccttc 1500
tgcacaggca tcaagcccgt ttacaggctg accacgaggc tcgggaggag cattagggct 1560
actgctaatc accgcttcct gaccccacag ggctggaaga gggtggacga gctccagcct 1620
ggggattacc tggctctccc aaggtaa 1647

<210> SEQ ID NO 78
<211> LENGTH: 548
<212> TYPE: PRT
<213> ORGANISM: Artificial Sequence
<220> FEATURE:
<223> OTHER INFORMATION: Synthetic construct, #116 Phy02C

<400> SEQUENCE: 78

Met Ser Asp Val Tyr Trp Asp Pro Ile Val Ser Ile Glu Pro Asp Gly
1 5 10 15

Val Glu Glu Val Phe Asp Leu Thr Val Pro Gly Pro His Asn Phe Val
20 25 30

Ala Asn Asp Ile Ile Ala His Asn Ser Ala Gln Ser Glu Pro Glu Leu
35 40 45

Lys Leu Glu Ser Val Val Ile Val Ser Arg His Gly Val Arg Ala Pro
50 55 60

Thr Lys Phe Thr Gln Leu Met Gln Asp Val Thr Pro Asp Ala Phe Tyr
65 70 75 80

Thr Trp Pro Val Lys Leu Gly Glu Leu Thr Pro Arg Gly Gly Glu Leu
85 90 95

Ile Ala Tyr Leu Gly His Tyr Trp Arg Gln Arg Leu Val Ala Asp Gly
100 105 110

Leu Leu Pro Lys Lys Gly Cys Pro Gln Ser Gly Gln Val Ala Ile Ile
115 120 125

Ala Asp Val Asp Glu Arg Thr Arg Lys Thr Gly Glu Ala Phe Ala Ala
130 135 140

Gly Leu Ala Pro Asp Cys Ala Ile Thr Val His Thr Gln Ala Asp Thr
145 150 155 160

Ser Ser Pro Asp Pro Leu Phe Asn Pro Leu Lys Thr Gly Val Cys Gln
165 170 175

```
Leu Asp Val Ala Gln Val Thr Asp Ala Ile Leu Glu Arg Ala Gly Gly
            180                 185                 190

Ser Ile Ala Asp Phe Thr Gly His Tyr Gln Thr Ala Phe Arg Glu Leu
        195                 200                 205

Glu Arg Val Leu Asn Phe Pro Gln Ser Asn Leu Ala Leu Lys Arg Glu
    210                 215                 220

Lys Gln Asp Glu Ser Ala Ser Leu Thr Gln Ala Leu Pro Ser Glu Leu
225                 230                 235                 240

Lys Val Ser Ala Asp Asn Val Ser Leu Thr Gly Ala Trp Ser Leu Ala
                245                 250                 255

Ser Met Leu Thr Glu Ile Phe Leu Leu Gln Gln Ala Gln Gly Met Pro
            260                 265                 270

Glu Pro Gly Trp Gly Arg Ile Thr Asp Ser His Gln Trp Asn Thr Leu
        275                 280                 285

Leu Ser Leu His Asn Ala Gln Phe Asp Leu Leu Gln Arg Thr Pro Glu
    290                 295                 300

Val Ala Arg Ser Arg Ala Thr Pro Leu Leu Asp Leu Ile Lys Thr Ala
305                 310                 315                 320

Leu Thr Pro His Pro Pro Gln Lys Gln Ala Tyr Gly Val Thr Leu Pro
                325                 330                 335

Thr Ser Val Leu Phe Ile Ala Gly His Asp Thr Asn Leu Ala Asn Leu
            340                 345                 350

Gly Gly Ala Leu Glu Leu Gln Trp Thr Leu Pro Gly Gln Pro Asp Asn
        355                 360                 365

Thr Pro Pro Gly Gly Glu Leu Val Phe Glu Arg Trp Arg Arg Leu Ser
    370                 375                 380

Asp Asn Ser Gln Trp Ile Gln Val Ser Leu Val Phe Gln Thr Leu Gln
385                 390                 395                 400

Gln Met Arg Asp Lys Thr Pro Leu Phe Leu Asn Thr Pro Pro Gly Glu
                405                 410                 415

Val Lys Leu Thr Leu Ala Gly Cys Glu Glu Arg Asn Ala Gln Gly Met
            420                 425                 430

Cys Ser Leu Ala Gly Phe Thr Gln Ile Val Asn Glu Ala Arg Ile Pro
        435                 440                 445

Ala Cys Ser Leu Cys Leu Ala Gly Asp Thr Leu Ile Thr Leu Ala Asp
    450                 455                 460

Gly Arg Arg Val Pro Ile Arg Glu Leu Val Ser Gln Gln Asn Phe Ser
465                 470                 475                 480

Val Trp Ala Leu Asn Pro Gln Thr Tyr Arg Leu Glu Arg Ala Arg Val
                485                 490                 495

Ser Arg Ala Phe Cys Thr Gly Ile Lys Pro Val Tyr Arg Leu Thr Thr
            500                 505                 510

Arg Leu Gly Arg Ser Ile Arg Ala Thr Ala Asn His Arg Phe Leu Thr
        515                 520                 525

Pro Gln Gly Trp Lys Arg Val Asp Glu Leu Gln Pro Gly Asp Tyr Leu
    530                 535                 540

Ala Leu Pro Arg
545
```

<210> SEQ ID NO 79
<211> LENGTH: 1620
<212> TYPE: DNA
<213> ORGANISM: Artificial Sequence
<220> FEATURE:

<223> OTHER INFORMATION: Synthetic construct, #123 Phy02C coding seq

<400> SEQUENCE: 79
atgtggcgga tgaccggcat cgatgtcgag cccgacggcg ttggggatta cttcggcttc 60
actctggatg gcaatgggcg cttcctcctc ggggatggca ctgttactca taatagcgcc 120
caatcggaac cggaactgaa actggaaagt gtggttattg tgtctcgtca tggcgttcgc 180
gctccgacca aatttacgca gctgatgcaa gatgtcaccc cggacgcctt ctatacgtgg 240
ccggtgaagc tgggtgaact gaccccgcgt ggcggtgaac tgatcgccta tctgggtcac 300
tactggcgtc agcgcctggt ggcagatggt ctgctgccga aaaagggctg cccgcagagc 360
ggtcaagttg caattatcgc tgatgtcgac gaacgtaccc gcaaaacggg tgaagcattt 420
gcggccggtc tggcaccgga ttgcgccatt accgttcata cgcaggcaga taccagctct 480
ccggacccgc tgttcaaccc gctgaaaacc ggcgtctgtc agctggatgt cgcgcaagtg 540
acggacgcca ttctggaacg tgcaggcggt tccatcgctg attttaccgg tcactaccag 600
acggcattcc gtgaactgga acgcgttctg aactttccgc agtcaaatct ggcgctgaaa 660
cgcgaaaagc aggatgaaag tgcgtccctg acccaagccc tgccgagtga actgaaagtc 720
tccgccgaca atgtgtcact gaccggcgca tggtcactgg cttcgatgct gacggaaatt 780
tttctgctgc agcaagcaca gggtatgccg gaaccgggtt ggggtcgtat caccgattcg 840
catcagtgga acacgctgct gagcctgcac aatgcgcagt tcgacctgct gcaacgtacc 900
ccggaagtgg cacgttcgcg cgccacgccg ctgctggatc tgattaaaac cgctctgacg 960
ccgcatccgc cgcagaagca agcgtatggc gtgaccctgc cgacgagcgt tctgtttatc 1020
gcgggtcacg acaccaacct ggcaaatctg ggcggtgctc tggaactgca gtggaccctg 1080
ccgggtcaac cggataacac gccgccgggc ggtgaactgg ttttcgaacg ttggcgtcgc 1140
ctgagcgaca attctcagtg gatccaagtt agcctggtct ttcagaccct gcagcaaatg 1200
cgcgataaaa ccccgctgtt cctgaacacg ccgccgggcg aagtgaagct gaccctggcg 1260
ggttgcgaag aacgtaacgc ccagggcatg tgttctctgg caggttttac ccagattgtt 1320
aatgaagcac gcatcccggc ttgtagtctg tgcctcggga aggggacacc ggttatgatg 1380
tacgatgggc ggacaaagcc agtggagaag gtggaggtcg gggacaggct catgggggac 1440
gatggcagcc caaggacggt gcagtcgctg gccaggggga gggagcagat gtactgggtc 1500
cgccagaaga ggggcatgga ctacagggtt aacgagagcc acatcctctc gctgaagaag 1560
tctaggaggg agggcgcccg cgacaggggg tcaatcgcgg atatttccgt ccgcgactaa 1620

<210> SEQ ID NO 80
<211> LENGTH: 539
<212> TYPE: PRT
<213> ORGANISM: Artificial Sequence
<220> FEATURE:
<223> OTHER INFORMATION: Synthetic construct, #123 Phy02C

<400> SEQUENCE: 80

Met Trp Arg Met Thr Gly Ile Asp Val Glu Pro Asp Gly Val Gly Asp
1 5 10 15

Tyr Phe Gly Phe Thr Leu Asp Gly Asn Gly Arg Phe Leu Leu Gly Asp
20 25 30

Gly Thr Val Thr His Asn Ser Ala Gln Ser Glu Pro Glu Leu Lys Leu
35 40 45

Glu Ser Val Val Ile Val Ser Arg His Gly Val Arg Ala Pro Thr Lys
50 55 60

```
Phe Thr Gln Leu Met Gln Asp Val Thr Pro Asp Ala Phe Tyr Thr Trp
65                  70                  75                  80

Pro Val Lys Leu Gly Glu Leu Thr Pro Arg Gly Gly Glu Leu Ile Ala
                85                  90                  95

Tyr Leu Gly His Tyr Trp Arg Gln Arg Leu Val Ala Asp Gly Leu Leu
            100                 105                 110

Pro Lys Lys Gly Cys Pro Gln Ser Gly Gln Val Ala Ile Ile Ala Asp
        115                 120                 125

Val Asp Glu Arg Thr Arg Lys Thr Gly Glu Ala Phe Ala Ala Gly Leu
    130                 135                 140

Ala Pro Asp Cys Ala Ile Thr Val His Thr Gln Ala Asp Thr Ser Ser
145                 150                 155                 160

Pro Asp Pro Leu Phe Asn Pro Leu Lys Thr Gly Val Cys Gln Leu Asp
                165                 170                 175

Val Ala Gln Val Thr Asp Ala Ile Leu Glu Arg Ala Gly Gly Ser Ile
            180                 185                 190

Ala Asp Phe Thr Gly His Tyr Gln Thr Ala Phe Arg Glu Leu Glu Arg
        195                 200                 205

Val Leu Asn Phe Pro Gln Ser Asn Leu Ala Leu Lys Arg Glu Lys Gln
    210                 215                 220

Asp Glu Ser Ala Ser Leu Thr Gln Ala Leu Pro Ser Glu Leu Lys Val
225                 230                 235                 240

Ser Ala Asp Asn Val Ser Leu Thr Gly Ala Trp Ser Leu Ala Ser Met
                245                 250                 255

Leu Thr Glu Ile Phe Leu Leu Gln Gln Ala Gln Gly Met Pro Glu Pro
            260                 265                 270

Gly Trp Gly Arg Ile Thr Asp Ser His Gln Trp Asn Thr Leu Leu Ser
        275                 280                 285

Leu His Asn Ala Gln Phe Asp Leu Leu Gln Arg Thr Pro Glu Val Ala
    290                 295                 300

Arg Ser Arg Ala Thr Pro Leu Leu Asp Leu Ile Lys Thr Ala Leu Thr
305                 310                 315                 320

Pro His Pro Pro Gln Lys Gln Ala Tyr Gly Val Thr Leu Pro Thr Ser
                325                 330                 335

Val Leu Phe Ile Ala Gly His Asp Thr Asn Leu Ala Asn Leu Gly Gly
            340                 345                 350

Ala Leu Glu Leu Gln Trp Thr Leu Pro Gly Gln Pro Asp Asn Thr Pro
        355                 360                 365

Pro Gly Gly Glu Leu Val Phe Glu Arg Trp Arg Arg Leu Ser Asp Asn
    370                 375                 380

Ser Gln Trp Ile Gln Val Ser Leu Val Phe Gln Thr Leu Gln Gln Met
385                 390                 395                 400

Arg Asp Lys Thr Pro Leu Phe Leu Asn Thr Pro Pro Gly Glu Val Lys
                405                 410                 415

Leu Thr Leu Ala Gly Cys Glu Glu Arg Asn Ala Gln Gly Met Cys Ser
            420                 425                 430

Leu Ala Gly Phe Thr Gln Ile Val Asn Glu Ala Arg Ile Pro Ala Cys
        435                 440                 445

Ser Leu Cys Leu Gly Lys Gly Thr Pro Val Met Met Tyr Asp Gly Arg
    450                 455                 460

Thr Lys Pro Val Glu Lys Val Glu Val Gly Asp Arg Leu Met Gly Asp
465                 470                 475                 480
```

```
Asp Gly Ser Pro Arg Thr Val Gln Ser Leu Ala Arg Gly Arg Glu Gln
                485                 490                 495

Met Tyr Trp Val Arg Gln Lys Arg Gly Met Asp Tyr Arg Val Asn Glu
            500                 505                 510

Ser His Ile Leu Ser Leu Lys Lys Ser Arg Arg Glu Gly Ala Arg Asp
        515                 520                 525

Arg Gly Ser Ile Ala Asp Ile Ser Val Arg Asp
    530                 535


<210> SEQ ID NO 81
<211> LENGTH: 1647
<212> TYPE: DNA
<213> ORGANISM: Artificial Sequence
<220> FEATURE:
<223> OTHER INFORMATION: Synthetic construct, #128 Phy02C coding seq

<400> SEQUENCE: 81

atgaattctt tctacaatct gtcaaccttc gaggtgtcat ccgagtacta caagggcgag     60

gtctacgatc tcactctgga gggcaatcct tactacttcg ccaatggcat cctcacacat    120

aatagcgccc aatcggaacc ggaactgaaa ctggaaagtg tggttattgt gtctcgtcat    180

ggcgttcgcg ctccgaccaa atttacgcag ctgatgcaag atgtcacccc ggacgccttc    240

tatacgtggc cggtgaagct gggtgaactg accccgcgtg gcggtgaact gatcgcctat    300

ctgggtcact actggcgtca gcgcctggtg gcagatggtc tgctgccgaa aaagggctgc    360

ccgcagagcg gtcaagttgc aattatcgct gatgtcgacg aacgtacccg caaaacgggt    420

gaagcatttg cggccggtct ggcaccggat tgcgccatta ccgttcatac gcaggcagat    480

accagctctc cggacccgct gttcaacccg ctgaaaaccg gcgtctgtca gctggatgtc    540

gcgcaagtga cggacgccat tctggaacgt gcaggcggtt ccatcgctga ttttaccggt    600

cactaccaga cggcattccg tgaactggaa cgcgttctga actttccgca gtcaaatctg    660

gcgctgaaac gcgaaaagca ggatgaaagt gcgtccctga cccaagccct gccgagtgaa    720

ctgaaagtct ccgccgacaa tgtgtcactg accggcgcat ggtcactggc ttcgatgctg    780

acggaaattt ttctgctgca gcaagcacag ggtatgccgg aaccgggttg ggtcgtatc     840

accgattcgc atcagtggaa cacgctgctg agcctgcaca atgcgcagtt cgacctgctg    900

caacgtaccc cggaagtggc acgttcgcgc gccacgccgc tgctggatct gattaaaacc    960

gctctgacgc cgcatccgcc gcagaagcaa gcgtatggcg tgaccctgcc gacgagcgtt   1020

ctgtttatcg cgggtcacga caccaacctg gcaaatctgg gcggtgctct ggaactgcag   1080

tggaccctgc cgggtcaacc ggataacacg ccgccgggcg gtgaactggt tttcgaacgt   1140

tggcgtcgcc tgagcgacaa ttctcagtgg atccaagtta gcctggtctt tcagaccctg   1200

cagcaaatgc gcgataaaac cccgctgttc ctgaacacgc cgccgggcga agtgaagctg   1260

accctggcgg gttgcgaaga acgtaacgcc cagggcatgt gttctctggc aggttttacc   1320

cagattgtta atgaagcacg catcccggct tgtagtctgt gccatcctgc ggacactaag   1380

gtcatcgtga agggcaaggg catcgttaat atctcggacg tgaaggaggg ggactacatt   1440

ctcggcatcg acggctggca gcgggtcaag aaggtttgga agtaccacta cgagggcaag   1500

ctcatcaaca ttaatgggct gaagtgcacg ccgaaccata aggttcccgt ggtcacagag   1560

aatgacaggc agactcgcat cagggattcc ctcgccaaga gcttcctgtc gggcaaggtc   1620

aaggggaaga tcattaccac gaagtaa                                       1647
```

<210> SEQ ID NO 82
<211> LENGTH: 548
<212> TYPE: PRT
<213> ORGANISM: Artificial Sequence
<220> FEATURE:
<223> OTHER INFORMATION: Synthetic construct, #128 Phy02C

<400> SEQUENCE: 82

```
Met Asn Ser Phe Tyr Asn Leu Ser Thr Phe Glu Val Ser Ser Glu Tyr
1               5                   10                  15

Tyr Lys Gly Glu Val Tyr Asp Leu Thr Leu Glu Gly Asn Pro Tyr Tyr
            20                  25                  30

Phe Ala Asn Gly Ile Leu Thr His Asn Ser Ala Gln Ser Glu Pro Glu
        35                  40                  45

Leu Lys Leu Glu Ser Val Val Ile Val Ser Arg His Gly Val Arg Ala
    50                  55                  60

Pro Thr Lys Phe Thr Gln Leu Met Gln Asp Val Thr Pro Asp Ala Phe
65                  70                  75                  80

Tyr Thr Trp Pro Val Lys Leu Gly Glu Leu Thr Pro Arg Gly Gly Glu
                85                  90                  95

Leu Ile Ala Tyr Leu Gly His Tyr Trp Arg Gln Arg Leu Val Ala Asp
            100                 105                 110

Gly Leu Leu Pro Lys Lys Gly Cys Pro Gln Ser Gly Gln Val Ala Ile
        115                 120                 125

Ile Ala Asp Val Asp Glu Arg Thr Arg Lys Thr Gly Glu Ala Phe Ala
    130                 135                 140

Ala Gly Leu Ala Pro Asp Cys Ala Ile Thr Val His Thr Gln Ala Asp
145                 150                 155                 160

Thr Ser Ser Pro Asp Pro Leu Phe Asn Pro Leu Lys Thr Gly Val Cys
                165                 170                 175

Gln Leu Asp Val Ala Gln Val Thr Asp Ala Ile Leu Glu Arg Ala Gly
            180                 185                 190

Gly Ser Ile Ala Asp Phe Thr Gly His Tyr Gln Thr Ala Phe Arg Glu
        195                 200                 205

Leu Glu Arg Val Leu Asn Phe Pro Gln Ser Asn Leu Ala Leu Lys Arg
    210                 215                 220

Glu Lys Gln Asp Glu Ser Ala Ser Leu Thr Gln Ala Leu Pro Ser Glu
225                 230                 235                 240

Leu Lys Val Ser Ala Asp Asn Val Ser Leu Thr Gly Ala Trp Ser Leu
                245                 250                 255

Ala Ser Met Leu Thr Glu Ile Phe Leu Leu Gln Gln Ala Gln Gly Met
            260                 265                 270

Pro Glu Pro Gly Trp Gly Arg Ile Thr Asp Ser His Gln Trp Asn Thr
        275                 280                 285

Leu Leu Ser Leu His Asn Ala Gln Phe Asp Leu Leu Gln Arg Thr Pro
    290                 295                 300

Glu Val Ala Arg Ser Arg Ala Thr Pro Leu Leu Asp Leu Ile Lys Thr
305                 310                 315                 320

Ala Leu Thr Pro His Pro Pro Gln Lys Gln Ala Tyr Gly Val Thr Leu
                325                 330                 335

Pro Thr Ser Val Leu Phe Ile Ala Gly His Asp Thr Asn Leu Ala Asn
            340                 345                 350

Leu Gly Gly Ala Leu Glu Leu Gln Trp Thr Leu Pro Gly Gln Pro Asp
        355                 360                 365

Asn Thr Pro Pro Gly Gly Glu Leu Val Phe Glu Arg Trp Arg Arg Leu
```

370 375 380

Ser Asp Asn Ser Gln Trp Ile Gln Val Ser Leu Val Phe Gln Thr Leu
385 390 395 400

Gln Gln Met Arg Asp Lys Thr Pro Leu Phe Leu Asn Thr Pro Pro Gly
405 410 415

Glu Val Lys Leu Thr Leu Ala Gly Cys Glu Glu Arg Asn Ala Gln Gly
420 425 430

Met Cys Ser Leu Ala Gly Phe Thr Gln Ile Val Asn Glu Ala Arg Ile
435 440 445

Pro Ala Cys Ser Leu Cys His Pro Ala Asp Thr Lys Val Ile Val Lys
450 455 460

Gly Lys Gly Ile Val Asn Ile Ser Asp Val Lys Glu Gly Asp Tyr Ile
465 470 475 480

Leu Gly Ile Asp Gly Trp Gln Arg Val Lys Lys Val Trp Lys Tyr His
485 490 495

Tyr Glu Gly Lys Leu Ile Asn Ile Asn Gly Leu Lys Cys Thr Pro Asn
500 505 510

His Lys Val Pro Val Val Thr Glu Asn Asp Arg Gln Thr Arg Ile Arg
515 520 525

Asp Ser Leu Ala Lys Ser Phe Leu Ser Gly Lys Val Lys Gly Lys Ile
530 535 540

Ile Thr Thr Lys
545

<210> SEQ ID NO 83
<211> LENGTH: 1707
<212> TYPE: DNA
<213> ORGANISM: Artificial Sequence
<220> FEATURE:
<223> OTHER INFORMATION: Synthetic construct, #135 Phy02C coding seq

<400> SEQUENCE: 83
atgtcgaagt gcgtcctcaa ctactcgccc tacaagatcg agtctgttaa tattggcgct 60
gtgtgcgact acagctacga tttcgccatc gagggcatca atgataatga ctcttggtac 120
tggcaggggg ctctcaagtc tcacaacagc gcccaatcgg aaccggaact gaaactggaa 180
agtgtggtta ttgtgtctcg tcatggcgtt cgcgctccga ccaaatttac gcagctgatg 240
caagatgtca ccccggacgc cttctatacg tggccggtga agctgggtga actgaccccg 300
cgtggcggtg aactgatcgc ctatctgggt cactactggc gtcagcgcct ggtggcagat 360
ggtctgctgc cgaaaaaggg ctgcccgcag agcggtcaag ttgcaattat cgctgatgtc 420
gacgaacgta cccgcaaaac gggtgaagca tttgcggccg gtctggcacc ggattgcgcc 480
attaccgttc atacgcaggc agataccagc tctccggacc cgctgttcaa cccgctgaaa 540
accggcgtct gtcagctgga tgtcgcgcaa gtgacggacg ccattctgga acgtgcaggc 600
ggttccatcg ctgattttac cggtcactac cagacggcat tccgtgaact ggaacgcgtt 660
ctgaactttc cgcagtcaaa tctggcgctg aaacgcgaaa agcaggatga aagtgcgtcc 720
ctgacccaag ccctgccgag tgaactgaaa gtctccgccg acaatgtgtc actgaccggc 780
gcatggtcac tggcttcgat gctgacggaa atttttctgc tgcagcaagc acagggtatg 840
ccggaaccgg gttggggtcg tatcaccgat tcgcatcagt ggaacacgct gctgagcctg 900
cacaatgcgc agttcgacct gctgcaacgt accccggaag tggcacgttc gcgcgccacg 960
ccgctgctgg atctgattaa aaccgctctg acgccgcatc cgccgcagaa gcaagcgtat 1020

-continued ggcgtgaccc tgccgacgag cgttctgttt atcgcgggtc acgacaccaa cctggcaaat 1080
ctgggcggtg ctctggaact gcagtggacc ctgccgggtc aaccggataa cacgccgccg 1140
ggcggtgaac tggttttcga acgttggcgt cgcctgagcg acaattctca gtggatccaa 1200
gttagcctgg tctttcagac cctgcagcaa atgcgcgata aaaccccgct gttcctgaac 1260
acgccgccgg gcgaagtgaa gctgaccctg gcgggttgcg aagaacgtaa cgcccagggc 1320
atgtgttctc tggcaggttt tacccagatt gttaatgaag cacgcatccc ggcttgtagt 1380
ctgtgcctgg acaagacggc tctgcggatt ttcaatcagg ggctgctcta cgcggatgag 1440
gtcgtgacac cgggctcggg ggagacagtc ggcctcgggc tgacggtcag gaacggcatc 1500
ggggcgtcca cagccattgc gaatcagccg atggagctgg ttgagatcaa gctcgctaac 1560
ggccggaagc tgcgcatgac ccctaatcac cggatgtccg tgaagggcaa gtggattcat 1620
gcctgcaacc tcaagccggg gatgctcctg gactacagca tcggcgagta ccagaagcgc 1680
gaggacaccc tcctgattcc tctctaa 1707

<210> SEQ ID NO 84
<211> LENGTH: 568
<212> TYPE: PRT
<213> ORGANISM: Artificial Sequence
<220> FEATURE:
<223> OTHER INFORMATION: Synthetic construct, #135 Phy02C

<400> SEQUENCE: 84

Met Ser Lys Cys Val Leu Asn Tyr Ser Pro Tyr Lys Ile Glu Ser Val
1 5 10 15

Asn Ile Gly Ala Val Cys Asp Tyr Ser Tyr Asp Phe Ala Ile Glu Gly
20 25 30

Ile Asn Asp Asn Asp Ser Trp Tyr Trp Gln Gly Ala Leu Lys Ser His
35 40 45

Asn Ser Ala Gln Ser Glu Pro Glu Leu Lys Leu Glu Ser Val Val Ile
50 55 60

Val Ser Arg His Gly Val Arg Ala Pro Thr Lys Phe Thr Gln Leu Met
65 70 75 80

Gln Asp Val Thr Pro Asp Ala Phe Tyr Thr Trp Pro Val Lys Leu Gly
85 90 95

Glu Leu Thr Pro Arg Gly Gly Glu Leu Ile Ala Tyr Leu Gly His Tyr
100 105 110

Trp Arg Gln Arg Leu Val Ala Asp Gly Leu Leu Pro Lys Lys Gly Cys
115 120 125

Pro Gln Ser Gly Gln Val Ala Ile Ile Ala Asp Val Asp Glu Arg Thr
130 135 140

Arg Lys Thr Gly Glu Ala Phe Ala Ala Gly Leu Ala Pro Asp Cys Ala
145 150 155 160

Ile Thr Val His Thr Gln Ala Asp Thr Ser Ser Pro Asp Pro Leu Phe
165 170 175

Asn Pro Leu Lys Thr Gly Val Cys Gln Leu Asp Val Ala Gln Val Thr
180 185 190

Asp Ala Ile Leu Glu Arg Ala Gly Gly Ser Ile Ala Asp Phe Thr Gly
195 200 205

His Tyr Gln Thr Ala Phe Arg Glu Leu Glu Arg Val Leu Asn Phe Pro
210 215 220

Gln Ser Asn Leu Ala Leu Lys Arg Glu Lys Gln Asp Glu Ser Ala Ser
225 230 235 240

-continued

```
Leu Thr Gln Ala Leu Pro Ser Glu Leu Lys Val Ser Ala Asp Asn Val
                245                 250                 255

Ser Leu Thr Gly Ala Trp Ser Leu Ala Ser Met Leu Thr Glu Ile Phe
            260                 265                 270

Leu Leu Gln Gln Ala Gln Gly Met Pro Glu Pro Gly Trp Gly Arg Ile
        275                 280                 285

Thr Asp Ser His Gln Trp Asn Thr Leu Leu Ser Leu His Asn Ala Gln
    290                 295                 300

Phe Asp Leu Leu Gln Arg Thr Pro Glu Val Ala Arg Ser Arg Ala Thr
305                 310                 315                 320

Pro Leu Leu Asp Leu Ile Lys Thr Ala Leu Thr Pro His Pro Pro Gln
                325                 330                 335

Lys Gln Ala Tyr Gly Val Thr Leu Pro Thr Ser Val Leu Phe Ile Ala
            340                 345                 350

Gly His Asp Thr Asn Leu Ala Asn Leu Gly Gly Ala Leu Glu Leu Gln
        355                 360                 365

Trp Thr Leu Pro Gly Gln Pro Asp Asn Thr Pro Pro Gly Gly Glu Leu
    370                 375                 380

Val Phe Glu Arg Trp Arg Arg Leu Ser Asp Asn Ser Gln Trp Ile Gln
385                 390                 395                 400

Val Ser Leu Val Phe Gln Thr Leu Gln Gln Met Arg Asp Lys Thr Pro
                405                 410                 415

Leu Phe Leu Asn Thr Pro Pro Gly Glu Val Lys Leu Thr Leu Ala Gly
            420                 425                 430

Cys Glu Glu Arg Asn Ala Gln Gly Met Cys Ser Leu Ala Gly Phe Thr
        435                 440                 445

Gln Ile Val Asn Glu Ala Arg Ile Pro Ala Cys Ser Leu Cys Leu Asp
    450                 455                 460

Lys Thr Ala Leu Arg Ile Phe Asn Gln Gly Leu Leu Tyr Ala Asp Glu
465                 470                 475                 480

Val Val Thr Pro Gly Ser Gly Glu Thr Val Gly Leu Gly Leu Thr Val
                485                 490                 495

Arg Asn Gly Ile Gly Ala Ser Thr Ala Ile Ala Asn Gln Pro Met Glu
            500                 505                 510

Leu Val Glu Ile Lys Leu Ala Asn Gly Arg Lys Leu Arg Met Thr Pro
        515                 520                 525

Asn His Arg Met Ser Val Lys Gly Lys Trp Ile His Ala Cys Asn Leu
    530                 535                 540

Lys Pro Gly Met Leu Leu Asp Tyr Ser Ile Gly Glu Tyr Gln Lys Arg
545                 550                 555                 560

Glu Asp Thr Leu Leu Ile Pro Leu
                565
```

<210> SEQ ID NO 85
<211> LENGTH: 1689
<212> TYPE: DNA
<213> ORGANISM: Artificial Sequence
<220> FEATURE:
<223> OTHER INFORMATION: Synthetic construct, #143 Phy02C coding seq

<400> SEQUENCE: 85

```
atgaatctcg tcttcatccc ggttgaggac attgaggagt tcgagtacga gggctacgtt      60

tacgacgtta ctacagagac tcataatttc gttgctaatg gcatcctcgt tcataatagc     120

gcccaatcgg aaccggaact gaaactggaa agtgtggtta ttgtgtctcg tcatggcgtt     180
```

cgcgctccga ccaaatttac gcagctgatg caagatgtca ccccggacgc cttctatacg 240
tggccggtga agctgggtga actgaccccg cgtggcggtg aactgatcgc ctatctgggt 300
cactactggc gtcagcgcct ggtggcagat ggtctgctgc cgaaaaaggg ctgcccgcag 360
agcggtcaag ttgcaattat cgctgatgtc gacgaacgta cccgcaaaac gggtgaagca 420
tttgcggccg gtctggcacc ggattgcgcc attaccgttc atacgcaggc agataccagc 480
tctccggacc cgctgttcaa cccgctgaaa accggcgtct gtcagctgga tgtcgcgcaa 540
gtgacggacg ccattctgga acgtgcaggc ggttccatcg ctgattttac cggtcactac 600
cagacggcat tccgtgaact ggaacgcgtt ctgaactttc cgcagtcaaa tctggcgctg 660
aaacgcgaaa agcaggatga aagtgcgtcc ctgacccaag ccctgccgag tgaactgaaa 720
gtctccgccg acaatgtgtc actgaccggc gcatggtcac tggcttcgat gctgacggaa 780
atttttctgc tgcagcaagc acagggtatg ccggaaccgg gttggggtcg tatcaccgat 840
tcgcatcagt ggaacacgct gctgagcctg cacaatgcgc agttcgacct gctgcaacgt 900
accccggaag tggcacgttc gcgcgccacg ccgctgctgg atctgattaa aaccgctctg 960
acgccgcatc cgccgcagaa gcaagcgtat ggcgtgaccc tgccgacgag cgttctgttt 1020
atcgcgggtc acgacaccaa cctggcaaat ctgggcggtg ctctggaact gcagtggacc 1080
ctgccgggtc aaccggataa cacgccgccg ggcggtgaac tggttttcga acgttggcgt 1140
cgcctgagcg acaattctca gtggatccaa gttagcctgg tctttcagac cctgcagcaa 1200
atgcgcgata aaaccccgct gttcctgaac acgccgccgg gcgaagtgaa gctgaccctg 1260
gcgggttgcg aagaacgtaa cgcccagggc atgtgttctc tggcaggttt tacccagatt 1320
gttaatgaag cacgcatccc ggcttgtagt ctgtgcctgc tgccggatga gaaggttatt 1380
ctccctgagc atgggcctat tacactcaag ggctcttcg atctcgctaa ggagacagtc 1440
gtggctgaca acgagaagga gatccgcaag ctgggcgcca agctcaccat tgtgggcgag 1500
gatgggaggc tcagggtcct ggagagccca tacgtttgga aggtgcggca ccgcggcaag 1560
atgctgaggg tcaagctcaa gaactggcac tcagtgtccg tcacgccaga gcatcccttc 1620
ctgaccacgc ggggctgggt gcgcgctgac cagctcaagc cgggggatta cgttgcggtg 1680
cccaggtaa 1689

<210> SEQ ID NO 86
<211> LENGTH: 562
<212> TYPE: PRT
<213> ORGANISM: Artificial Sequence
<220> FEATURE:
<223> OTHER INFORMATION: Synthetic construct, #143 Phy02C

<400> SEQUENCE: 86

Met Asn Leu Val Phe Ile Pro Val Glu Asp Ile Glu Glu Phe Glu Tyr
1               5                   10                  15

Glu Gly Tyr Val Tyr Asp Val Thr Thr Glu Thr His Asn Phe Val Ala
            20                  25                  30

Asn Gly Ile Leu Val His Asn Ser Ala Gln Ser Glu Pro Glu Leu Lys
        35                  40                  45

Leu Glu Ser Val Val Ile Val Ser Arg His Gly Val Arg Ala Pro Thr
    50                  55                  60

Lys Phe Thr Gln Leu Met Gln Asp Val Thr Pro Asp Ala Phe Tyr Thr
65                  70                  75                  80

Trp Pro Val Lys Leu Gly Glu Leu Thr Pro Arg Gly Gly Glu Leu Ile
                85                  90                  95

```
Ala Tyr Leu Gly His Tyr Trp Arg Gln Arg Leu Val Ala Asp Gly Leu
            100                 105                 110

Leu Pro Lys Lys Gly Cys Pro Gln Ser Gly Gln Val Ala Ile Ile Ala
        115                 120                 125

Asp Val Asp Glu Arg Thr Arg Lys Thr Gly Glu Ala Phe Ala Ala Gly
    130                 135                 140

Leu Ala Pro Asp Cys Ala Ile Thr Val His Thr Gln Ala Asp Thr Ser
145                 150                 155                 160

Ser Pro Asp Pro Leu Phe Asn Pro Leu Lys Thr Gly Val Cys Gln Leu
                165                 170                 175

Asp Val Ala Gln Val Thr Asp Ala Ile Leu Glu Arg Ala Gly Gly Ser
            180                 185                 190

Ile Ala Asp Phe Thr Gly His Tyr Gln Thr Ala Phe Arg Glu Leu Glu
        195                 200                 205

Arg Val Leu Asn Phe Pro Gln Ser Asn Leu Ala Leu Lys Arg Glu Lys
    210                 215                 220

Gln Asp Glu Ser Ala Ser Leu Thr Gln Ala Leu Pro Ser Glu Leu Lys
225                 230                 235                 240

Val Ser Ala Asp Asn Val Ser Leu Thr Gly Ala Trp Ser Leu Ala Ser
                245                 250                 255

Met Leu Thr Glu Ile Phe Leu Leu Gln Gln Ala Gln Gly Met Pro Glu
            260                 265                 270

Pro Gly Trp Gly Arg Ile Thr Asp Ser His Gln Trp Asn Thr Leu Leu
        275                 280                 285

Ser Leu His Asn Ala Gln Phe Asp Leu Leu Gln Arg Thr Pro Glu Val
    290                 295                 300

Ala Arg Ser Arg Ala Thr Pro Leu Leu Asp Leu Ile Lys Thr Ala Leu
305                 310                 315                 320

Thr Pro His Pro Pro Gln Lys Gln Ala Tyr Gly Val Thr Leu Pro Thr
                325                 330                 335

Ser Val Leu Phe Ile Ala Gly His Asp Thr Asn Leu Ala Asn Leu Gly
            340                 345                 350

Gly Ala Leu Glu Leu Gln Trp Thr Leu Pro Gly Gln Pro Asp Asn Thr
        355                 360                 365

Pro Pro Gly Gly Glu Leu Val Phe Glu Arg Trp Arg Arg Leu Ser Asp
    370                 375                 380

Asn Ser Gln Trp Ile Gln Val Ser Leu Val Phe Gln Thr Leu Gln Gln
385                 390                 395                 400

Met Arg Asp Lys Thr Pro Leu Phe Leu Asn Thr Pro Pro Gly Glu Val
                405                 410                 415

Lys Leu Thr Leu Ala Gly Cys Glu Glu Arg Asn Ala Gln Gly Met Cys
            420                 425                 430

Ser Leu Ala Gly Phe Thr Gln Ile Val Asn Glu Ala Arg Ile Pro Ala
        435                 440                 445

Cys Ser Leu Cys Leu Leu Pro Asp Glu Lys Val Ile Leu Pro Glu His
    450                 455                 460

Gly Pro Ile Thr Leu Lys Gly Leu Phe Asp Leu Ala Lys Glu Thr Val
465                 470                 475                 480

Val Ala Asp Asn Glu Lys Glu Ile Arg Lys Leu Gly Ala Lys Leu Thr
                485                 490                 495

Ile Val Gly Glu Asp Gly Arg Leu Arg Val Leu Glu Ser Pro Tyr Val
            500                 505                 510
```

-continued

Trp Lys Val Arg His Arg Gly Lys Met Leu Arg Val Lys Leu Lys Asn
515 520 525

Trp His Ser Val Ser Val Thr Pro Glu His Pro Phe Leu Thr Thr Arg
530 535 540

Gly Trp Val Arg Ala Asp Gln Leu Lys Pro Gly Asp Tyr Val Ala Val
545 550 555 560

Pro Arg

<210> SEQ ID NO 87
<211> LENGTH: 1656
<212> TYPE: DNA
<213> ORGANISM: Artificial Sequence
<220> FEATURE:
<223> OTHER INFORMATION: Synthetic construct, #150 Phy02C coding seq

<400> SEQUENCE: 87
atggctgagg tttactggga tcgcgtcgag gcggttgagc cgctcggcga ggaggaggtc 60
ttcgatctca ctgtggaggg cactcatact ttcgttgcgg aggatgttat cgttcataat 120
agcgcccaat cggaaccgga actgaaactg gaaagtgtgg ttattgtgtc tcgtcatggc 180
gttcgcgctc cgaccaaatt tacgcagctg atgcaagatg tcaccccgga cgccttctat 240
acgtggccgg tgaagctggg tgaactgacc ccgcgtggcg gtgaactgat cgcctatctg 300
ggtcactact ggcgtcagcg cctggtggca gatggtctgc tgccgaaaaa gggctgcccg 360
cagagcggtc aagttgcaat tatcgctgat gtcgacgaac gtacccgcaa aacgggtgaa 420
gcatttgcgg ccggtctggc accggattgc gccattaccg ttcatacgca ggcagatacc 480
agctctccgg acccgctgtt caacccgctg aaaaccggcg tctgtcagct ggatgtcgcg 540
caagtgacgg acgccattct ggaacgtgca ggcggttcca tcgctgattt taccggtcac 600
taccagacgg cattccgtga actggaacgc gttctgaact ttccgcagtc aaatctggcg 660
ctgaaacgcg aaaagcagga tgaaagtgcg tccctgaccc aagccctgcc gagtgaactg 720
aaagtctccg ccgacaatgt gtcactgacc ggcgcatggt cactggcttc gatgctgacg 780
gaaatttttc tgctgcagca agcacagggt atgccggaac cgggttgggg tcgtatcacc 840
gattcgcatc agtggaacac gctgctgagc ctgcacaatg cgcagttcga cctgctgcaa 900
cgtaccccgg aagtggcacg ttcgcgcgcc acgccgctgc tggatctgat taaaaccgct 960
ctgacgccgc atccgccgca gaagcaagcg tatggcgtga ccctgccgac gagcgttctg 1020
tttatcgcgg gtcacgacac caacctggca aatctgggcg gtgctctgga actgcagtgg 1080
accctgccgg gtcaaccgga taacacgccg ccgggcggtg aactggtttt cgaacgttgg 1140
cgtcgcctga gcgacaattc tcagtggatc caagttagcc tggtctttca gaccctgcag 1200
caaatgcgcg ataaaacccc gctgttcctg aacacgccgc cgggcgaagt gaagctgacc 1260
ctggcgggtt gcgaagaacg taacgcccag ggcatgtgtt ctctggcagg ttttacccag 1320
attgttaatg aagcacgcat cccggcttgt agtctgtgcc tgcctgcgcg ggctagggtc 1380
gtggattggt gcacagggcg ggtcgttcgg gtcggggaga tcgttagggg ggaggctaag 1440
ggcgtctggg tggtctccct ggacgaggct aggctgaggc tcgttccaag gcctgttgtg 1500
gctgctttcc caagcggcaa ggctcaggtg tacgctctga ggaccgctac gggcagggtg 1560
ctggaggcga cagctaacca cccagtctac actccagagg gctggaggcc actggggacc 1620
ctcgctcctg gcgactacgt cgctctgcca aggtaa 1656

<210> SEQ ID NO 88

<211> LENGTH: 551
<212> TYPE: PRT
<213> ORGANISM: Artificial Sequence
<220> FEATURE:
<223> OTHER INFORMATION: Synthetic construct, #150 Phy02C

<400> SEQUENCE: 88

```
Met Ala Glu Val Tyr Trp Asp Arg Val Glu Ala Val Glu Pro Leu Gly
1               5                   10                  15

Glu Glu Glu Val Phe Asp Leu Thr Val Glu Gly Thr His Thr Phe Val
            20                  25                  30

Ala Glu Asp Val Ile Val His Asn Ser Ala Gln Ser Glu Pro Glu Leu
        35                  40                  45

Lys Leu Glu Ser Val Val Ile Val Ser Arg His Gly Val Arg Ala Pro
    50                  55                  60

Thr Lys Phe Thr Gln Leu Met Gln Asp Val Thr Pro Asp Ala Phe Tyr
65                  70                  75                  80

Thr Trp Pro Val Lys Leu Gly Glu Leu Thr Pro Arg Gly Gly Glu Leu
                85                  90                  95

Ile Ala Tyr Leu Gly His Tyr Trp Arg Gln Arg Leu Val Ala Asp Gly
            100                 105                 110

Leu Leu Pro Lys Lys Gly Cys Pro Gln Ser Gly Gln Val Ala Ile Ile
        115                 120                 125

Ala Asp Val Asp Glu Arg Thr Arg Lys Thr Gly Glu Ala Phe Ala Ala
    130                 135                 140

Gly Leu Ala Pro Asp Cys Ala Ile Thr Val His Thr Gln Ala Asp Thr
145                 150                 155                 160

Ser Ser Pro Asp Pro Leu Phe Asn Pro Leu Lys Thr Gly Val Cys Gln
                165                 170                 175

Leu Asp Val Ala Gln Val Thr Asp Ala Ile Leu Glu Arg Ala Gly Gly
            180                 185                 190

Ser Ile Ala Asp Phe Thr Gly His Tyr Gln Thr Ala Phe Arg Glu Leu
        195                 200                 205

Glu Arg Val Leu Asn Phe Pro Gln Ser Asn Leu Ala Leu Lys Arg Glu
    210                 215                 220

Lys Gln Asp Glu Ser Ala Ser Leu Thr Gln Ala Leu Pro Ser Glu Leu
225                 230                 235                 240

Lys Val Ser Ala Asp Asn Val Ser Leu Thr Gly Ala Trp Ser Leu Ala
                245                 250                 255

Ser Met Leu Thr Glu Ile Phe Leu Leu Gln Gln Ala Gln Gly Met Pro
            260                 265                 270

Glu Pro Gly Trp Gly Arg Ile Thr Asp Ser His Gln Trp Asn Thr Leu
        275                 280                 285

Leu Ser Leu His Asn Ala Gln Phe Asp Leu Leu Gln Arg Thr Pro Glu
    290                 295                 300

Val Ala Arg Ser Arg Ala Thr Pro Leu Leu Asp Leu Ile Lys Thr Ala
305                 310                 315                 320

Leu Thr Pro His Pro Pro Gln Lys Gln Ala Tyr Gly Val Thr Leu Pro
                325                 330                 335

Thr Ser Val Leu Phe Ile Ala Gly His Asp Thr Asn Leu Ala Asn Leu
            340                 345                 350

Gly Gly Ala Leu Glu Leu Gln Trp Thr Leu Pro Gly Gln Pro Asp Asn
        355                 360                 365

Thr Pro Pro Gly Gly Glu Leu Val Phe Glu Arg Trp Arg Arg Leu Ser
    370                 375                 380
```

```
Asp Asn Ser Gln Trp Ile Gln Val Ser Leu Val Phe Gln Thr Leu Gln
385                 390                 395                 400

Gln Met Arg Asp Lys Thr Pro Leu Phe Leu Asn Thr Pro Pro Gly Glu
                405                 410                 415

Val Lys Leu Thr Leu Ala Gly Cys Glu Glu Arg Asn Ala Gln Gly Met
            420                 425                 430

Cys Ser Leu Ala Gly Phe Thr Gln Ile Val Asn Glu Ala Arg Ile Pro
        435                 440                 445

Ala Cys Ser Leu Cys Leu Pro Ala Arg Ala Arg Val Val Asp Trp Cys
    450                 455                 460

Thr Gly Arg Val Val Arg Val Gly Glu Ile Val Arg Gly Glu Ala Lys
465                 470                 475                 480

Gly Val Trp Val Val Ser Leu Asp Glu Ala Arg Leu Arg Leu Val Pro
                485                 490                 495

Arg Pro Val Val Ala Ala Phe Pro Ser Gly Lys Ala Gln Val Tyr Ala
            500                 505                 510

Leu Arg Thr Ala Thr Gly Arg Val Leu Glu Ala Thr Ala Asn His Pro
        515                 520                 525

Val Tyr Thr Pro Glu Gly Trp Arg Pro Leu Gly Thr Leu Ala Pro Gly
    530                 535                 540

Asp Tyr Val Ala Leu Pro Arg
545                 550


<210> SEQ ID NO 89
<211> LENGTH: 1716
<212> TYPE: DNA
<213> ORGANISM: Artificial Sequence
<220> FEATURE:
<223> OTHER INFORMATION: Synthetic costruct, #225 Phy02C coding seq

<400> SEQUENCE: 89

atggttaagg tgattggaag acgttctctt ggtgttcaaa ggatcttcga tatcggattg     60

ccacaagacc acaactttct tctcgctaat ggtgccatcg ctgccaatag cgcccaatcg    120

gaaccggaac tgaaactgga aagtgtggtt attgtgtctc gtcatggcgt tcgcgctccg    180

accaaattta cgcagctgat gcaagatgtc accccggacg ccttctatac gtggccggtg    240

aagctgggtg aactgacccc gcgtggcggt gaactgatcg cctatctggg tcactactgg    300

cgtcagcgcc tggtggcaga tggtctgctg ccgaaaaagg gctgcccgca gagcggtcaa    360

gttgcaatta tcgctgatgt cgacgaacgt acccgcaaaa cgggtgaagc atttgcggcc    420

ggtctggcac cggattgcgc cattaccgtt catacgcagg cagataccag ctctccggac    480

ccgctgttca acccgctgaa aaccggcgtc tgtcagctgg atgtcgcgca agtgacggac    540

gccattctgg aacgtgcagg cggttccatc gctgatttta ccggtcacta ccagacggca    600

ttccgtgaac tggaacgcgt tctgaacttt ccgcagtcaa atctggcgct gaaacgcgaa    660

aagcaggatg aaagtgcgtc cctgacccaa gccctgccga gtgaactgaa agtctccgcc    720

gacaatgtgt cactgaccgg cgcatggtca ctggcttcga tgctgacgga aatttttctg    780

ctgcagcaag cacagggtat gccggaaccg ggttggggtc gtatcaccga ttcgcatcag    840

tggaacacgc tgctgagcct gcacaatgcg cagttcgacc tgctgcaacg taccccggaa    900

gtggcacgtt cgcgcgccac gccgctgctg gatctgatta aaaccgctct gacgccgcat    960

ccgccgcaga agcaagcgta tggcgtgacc ctgccgacga gcgttctgtt tatcgcgggt   1020

cacgacacca acctggcaaa tctgggcggt gctctggaac tgcagtggac cctgccgggt   1080
```

```
caaccggata acacgccgcc gggcggtgaa ctggttttcg aacgttggcg tcgcctgagc   1140

gacaattctc agtggatcca agttagcctg gtctttcaga ccctgcagca aatgcgcgat   1200

aaaaccccgc tgttcctgaa cacgccgccg ggcgaagtga agctgaccct ggcgggttgc   1260

gaagaacgta acgcccaggg catgtgttct ctggcaggtt ttacccagat tgttaatgaa   1320

gcacgcatcc cggcttgtag tctgtgcctt tctttcggaa ctgagatcct taccgttgag   1380

tacggaccac ttcctattgg taagatcgtt tctgaggaaa ttaactgctc agtgtactct   1440

gttgatccag aaggaagagt ttacactcag gctatcgcac aatggcacga taggggtgaa   1500

caagaggttc tggagtacga gcttgaagat ggatccgtta ttcgtgctac ctctgaccat   1560

agattcttga ctacagatta tcagcttctc gctatcgagg aaatctttgc taggcaactt   1620

gatctcctta ctttggagaa catcaagcag acagaagagg ctcttgacaa ccacagactt   1680

ccattccctt tgctcgatgc tggaaccatc aagtaa                              1716
```

<210> SEQ ID NO 90
<211> LENGTH: 571
<212> TYPE: PRT
<213> ORGANISM: Artificial Sequence
<220> FEATURE:
<223> OTHER INFORMATION: Synthetic construct, #225 Phy02C

<400> SEQUENCE: 90

```
Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn Ser Ala Gln Ser Glu Pro Glu Leu Lys Leu Glu Ser
        35                  40                  45

Val Val Ile Val Ser Arg His Gly Val Arg Ala Pro Thr Lys Phe Thr
    50                  55                  60

Gln Leu Met Gln Asp Val Thr Pro Asp Ala Phe Tyr Thr Trp Pro Val
65                  70                  75                  80

Lys Leu Gly Glu Leu Thr Pro Arg Gly Gly Glu Leu Ile Ala Tyr Leu
                85                  90                  95

Gly His Tyr Trp Arg Gln Arg Leu Val Ala Asp Gly Leu Leu Pro Lys
            100                 105                 110

Lys Gly Cys Pro Gln Ser Gly Gln Val Ala Ile Ile Ala Asp Val Asp
        115                 120                 125

Glu Arg Thr Arg Lys Thr Gly Glu Ala Phe Ala Ala Gly Leu Ala Pro
    130                 135                 140

Asp Cys Ala Ile Thr Val His Thr Gln Ala Asp Thr Ser Ser Pro Asp
145                 150                 155                 160

Pro Leu Phe Asn Pro Leu Lys Thr Gly Val Cys Gln Leu Asp Val Ala
                165                 170                 175

Gln Val Thr Asp Ala Ile Leu Glu Arg Ala Gly Gly Ser Ile Ala Asp
            180                 185                 190

Phe Thr Gly His Tyr Gln Thr Ala Phe Arg Glu Leu Glu Arg Val Leu
        195                 200                 205

Asn Phe Pro Gln Ser Asn Leu Ala Leu Lys Arg Glu Lys Gln Asp Glu
    210                 215                 220

Ser Ala Ser Leu Thr Gln Ala Leu Pro Ser Glu Leu Lys Val Ser Ala
225                 230                 235                 240

Asp Asn Val Ser Leu Thr Gly Ala Trp Ser Leu Ala Ser Met Leu Thr
```

-continued

```
                245                 250                 255

Glu Ile Phe Leu Leu Gln Gln Ala Gln Gly Met Pro Glu Pro Gly Trp
            260                 265                 270

Gly Arg Ile Thr Asp Ser His Gln Trp Asn Thr Leu Leu Ser Leu His
        275                 280                 285

Asn Ala Gln Phe Asp Leu Leu Gln Arg Thr Pro Glu Val Ala Arg Ser
    290                 295                 300

Arg Ala Thr Pro Leu Leu Asp Leu Ile Lys Thr Ala Leu Thr Pro His
305                 310                 315                 320

Pro Pro Gln Lys Gln Ala Tyr Gly Val Thr Leu Pro Thr Ser Val Leu
                325                 330                 335

Phe Ile Ala Gly His Asp Thr Asn Leu Ala Asn Leu Gly Gly Ala Leu
            340                 345                 350

Glu Leu Gln Trp Thr Leu Pro Gly Gln Pro Asp Asn Thr Pro Pro Gly
        355                 360                 365

Gly Glu Leu Val Phe Glu Arg Trp Arg Arg Leu Ser Asp Asn Ser Gln
    370                 375                 380

Trp Ile Gln Val Ser Leu Val Phe Gln Thr Leu Gln Gln Met Arg Asp
385                 390                 395                 400

Lys Thr Pro Leu Phe Leu Asn Thr Pro Pro Gly Glu Val Lys Leu Thr
                405                 410                 415

Leu Ala Gly Cys Glu Glu Arg Asn Ala Gln Gly Met Cys Ser Leu Ala
            420                 425                 430

Gly Phe Thr Gln Ile Val Asn Glu Ala Arg Ile Pro Ala Cys Ser Leu
        435                 440                 445

Cys Leu Ser Phe Gly Thr Glu Ile Leu Thr Val Glu Tyr Gly Pro Leu
    450                 455                 460

Pro Ile Gly Lys Ile Val Ser Glu Glu Ile Asn Cys Ser Val Tyr Ser
465                 470                 475                 480

Val Asp Pro Glu Gly Arg Val Tyr Thr Gln Ala Ile Ala Gln Trp His
                485                 490                 495

Asp Arg Gly Glu Gln Glu Val Leu Glu Tyr Glu Leu Glu Asp Gly Ser
            500                 505                 510

Val Ile Arg Ala Thr Ser Asp His Arg Phe Leu Thr Thr Asp Tyr Gln
        515                 520                 525

Leu Leu Ala Ile Glu Glu Ile Phe Ala Arg Gln Leu Asp Leu Leu Thr
    530                 535                 540

Leu Glu Asn Ile Lys Gln Thr Glu Glu Ala Leu Asp Asn His Arg Leu
545                 550                 555                 560

Pro Phe Pro Leu Leu Asp Ala Gly Thr Ile Lys
                565                 570
```

<210> SEQ ID NO 91
<211> LENGTH: 1614
<212> TYPE: DNA
<213> ORGANISM: Artificial Sequence
<220> FEATURE:
<223> OTHER INFORMATION: Synthetic construct, #230 Phy02C coding seq

<400> SEQUENCE: 91

```
atgatgctga agaaaattct gaagatcgaa gaactggatg aacgtgaact gattgacatc      60

gaagttagcg gcaaccatct gttttacgcg aatgacattc tgacccacaa cagcgcccaa     120

tcggaaccgg aactgaaact ggaaagtgtg gttattgtgt ctcgtcatgg cgttcgcgct     180

ccgaccaaat ttacgcagct gatgcaagat gtcaccccgg acgccttcta tacgtggccg     240
```

```
gtgaagctgg gtgaactgac ccgcgtggc ggtgaactga tcgcctatct gggtcactac     300
tggcgtcagc gcctggtggc agatggtctg ctgccgaaaa agggctgccc gcagagcggt     360
caagttgcaa ttatcgctga tgtcgacgaa cgtacccgca aaacgggtga agcatttgcg     420
gccggtctgg caccggattg cgccattacc gttcatacgc aggcagatac cagctctccg     480
gacccgctgt tcaacccgct gaaaaccggc gtctgtcagc tggatgtcgc gcaagtgacg     540
gacgccattc tggaacgtgc aggcggttcc atcgctgatt ttaccggtca ctaccagacg     600
gcattccgtg aactggaacg cgttctgaac tttccgcagt caaatctggc gctgaaacgc     660
gaaaagcagg atgaaagtgc gtccctgacc caagccctgc cgagtgaact gaaagtctcc     720
gccgacaatg tgtcactgac cggcgcatgg tcactggctt cgatgctgac ggaaattttt     780
ctgctgcagc aagcacaggg tatgccggaa ccgggttggg gtcgtatcac cgattcgcat     840
cagtggaaca cgctgctgag cctgcacaat gcgcagttcg acctgctgca acgtaccccg     900
gaagtggcac gttcgcgcgc cacgccgctg ctggatctga ttaaaaccgc tctgacgccg     960
catccgccgc agaagcaagc gtatggcgtg accctgccga cgagcgttct gtttatcgcg    1020
ggtcacgaca ccaacctggc aaatctgggc ggtgctctgg aactgcagtg gaccctgccg    1080
ggtcaaccgg ataacacgcc gccgggcggt gaactggttt tcgaacgttg gcgtcgcctg    1140
agcgacaatt ctcagtggat ccaagttagc ctggtctttc agaccctgca gcaaatgcgc    1200
gataaaaccc cgctgttcct gaacacgccg ccgggcgaag tgaagctgac cctggcgggt    1260
tgcgaagaac gtaacgccca gggcatgtgt tctctggcag gttttaccca gattgttaat    1320
gaagcacgca tcccggcttg tagtctgtgt ctggacctga aaacgcaagt gcaaaccccg    1380
caaggcatga aggaaatctc aaacatccaa gtcggtgacc tggtgctgtc gaataccggc    1440
tataacgaag tgctgaatgt ttttccgaag agcaaaaaga aatcttacaa gatcacgctg    1500
gaagatggca aggaaattat ttgcagcgaa gaacatctgt tcccgaccca gacgggcgaa    1560
atgaatatct ccggcggtct gaaagaaggc atgtgtctgt acgtcaagga ataa          1614
```

<210> SEQ ID NO 92
<211> LENGTH: 537
<212> TYPE: PRT
<213> ORGANISM: Artificial Sequence
<220> FEATURE:
<223> OTHER INFORMATION: Synthetic construct, #230 Phy02C

<400> SEQUENCE: 92

```
Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Asp
            20                  25                  30

Ile Leu Thr His Asn Ser Ala Gln Ser Glu Pro Glu Leu Lys Leu Glu
        35                  40                  45

Ser Val Val Ile Val Ser Arg His Gly Val Arg Ala Pro Thr Lys Phe
    50                  55                  60

Thr Gln Leu Met Gln Asp Val Thr Pro Asp Ala Phe Tyr Thr Trp Pro
65                  70                  75                  80

Val Lys Leu Gly Glu Leu Thr Pro Arg Gly Gly Glu Leu Ile Ala Tyr
                85                  90                  95

Leu Gly His Tyr Trp Arg Gln Arg Leu Val Ala Asp Gly Leu Leu Pro
            100                 105                 110

Lys Lys Gly Cys Pro Gln Ser Gly Gln Val Ala Ile Ile Ala Asp Val
```

-continued

```
        115                 120                 125

Asp Glu Arg Thr Arg Lys Thr Gly Glu Ala Phe Ala Ala Gly Leu Ala
    130                 135                 140

Pro Asp Cys Ala Ile Thr Val His Thr Gln Ala Asp Thr Ser Ser Pro
145                 150                 155                 160

Asp Pro Leu Phe Asn Pro Leu Lys Thr Gly Val Cys Gln Leu Asp Val
                165                 170                 175

Ala Gln Val Thr Asp Ala Ile Leu Glu Arg Ala Gly Gly Ser Ile Ala
            180                 185                 190

Asp Phe Thr Gly His Tyr Gln Thr Ala Phe Arg Glu Leu Glu Arg Val
        195                 200                 205

Leu Asn Phe Pro Gln Ser Asn Leu Ala Leu Lys Arg Glu Lys Gln Asp
    210                 215                 220

Glu Ser Ala Ser Leu Thr Gln Ala Leu Pro Ser Glu Leu Lys Val Ser
225                 230                 235                 240

Ala Asp Asn Val Ser Leu Thr Gly Ala Trp Ser Leu Ala Ser Met Leu
                245                 250                 255

Thr Glu Ile Phe Leu Leu Gln Gln Ala Gln Gly Met Pro Glu Pro Gly
            260                 265                 270

Trp Gly Arg Ile Thr Asp Ser His Gln Trp Asn Thr Leu Leu Ser Leu
        275                 280                 285

His Asn Ala Gln Phe Asp Leu Leu Gln Arg Thr Pro Glu Val Ala Arg
    290                 295                 300

Ser Arg Ala Thr Pro Leu Leu Asp Leu Ile Lys Thr Ala Leu Thr Pro
305                 310                 315                 320

His Pro Pro Gln Lys Gln Ala Tyr Gly Val Thr Leu Pro Thr Ser Val
                325                 330                 335

Leu Phe Ile Ala Gly His Asp Thr Asn Leu Ala Asn Leu Gly Gly Ala
            340                 345                 350

Leu Glu Leu Gln Trp Thr Leu Pro Gly Gln Pro Asp Asn Thr Pro Pro
        355                 360                 365

Gly Gly Glu Leu Val Phe Glu Arg Trp Arg Arg Leu Ser Asp Asn Ser
    370                 375                 380

Gln Trp Ile Gln Val Ser Leu Val Phe Gln Thr Leu Gln Gln Met Arg
385                 390                 395                 400

Asp Lys Thr Pro Leu Phe Leu Asn Thr Pro Pro Gly Glu Val Lys Leu
                405                 410                 415

Thr Leu Ala Gly Cys Glu Glu Arg Asn Ala Gln Gly Met Cys Ser Leu
            420                 425                 430

Ala Gly Phe Thr Gln Ile Val Asn Glu Ala Arg Ile Pro Ala Cys Ser
        435                 440                 445

Leu Cys Leu Asp Leu Lys Thr Gln Val Gln Thr Pro Gln Gly Met Lys
    450                 455                 460

Glu Ile Ser Asn Ile Gln Val Gly Asp Leu Val Leu Ser Asn Thr Gly
465                 470                 475                 480

Tyr Asn Glu Val Leu Asn Val Phe Pro Lys Ser Lys Lys Lys Ser Tyr
                485                 490                 495

Lys Ile Thr Leu Glu Asp Gly Lys Glu Ile Ile Cys Ser Glu Glu His
            500                 505                 510

Leu Phe Pro Thr Gln Thr Gly Glu Met Asn Ile Ser Gly Gly Leu Lys
        515                 520                 525

Glu Gly Met Cys Leu Tyr Val Lys Glu
    530                 535
```

<210> SEQ ID NO 93
<211> LENGTH: 536
<212> TYPE: PRT
<213> ORGANISM: Artificial Sequence
<220> FEATURE:
<223> OTHER INFORMATION: Synthetic construct, Gp411-C:Phy02r14:Gp411-N

<400> SEQUENCE: 93

```
Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Asp
            20                  25                  30

Ile Leu Thr His Asn Ser Arg His Gly Val Arg Ala Pro Thr Lys Phe
        35                  40                  45

Thr Gln Leu Met Gln Asp Val Thr Pro Asp Ala Phe Tyr Thr Trp Pro
    50                  55                  60

Val Lys Leu Gly Glu Leu Thr Pro Arg Gly Gly Glu Leu Ile Ala Tyr
65                  70                  75                  80

Leu Gly His Tyr Trp Arg Gln Arg Leu Val Ala Asp Gly Leu Leu Pro
                85                  90                  95

Lys Lys Gly Cys Pro Gln Ser Gly Gln Val Ala Ile Ile Ala Asp Val
            100                 105                 110

Asp Glu Arg Thr Arg Lys Thr Gly Glu Ala Phe Ala Ala Gly Leu Ala
        115                 120                 125

Pro Asp Cys Ala Ile Thr Val His Thr Gln Ala Asp Thr Ser Ser Pro
    130                 135                 140

Asp Pro Leu Phe Asn Pro Leu Lys Thr Gly Val Cys Gln Leu Asp Val
145                 150                 155                 160

Ala Gln Val Thr Asp Ala Ile Leu Glu Arg Ala Gly Gly Ser Ile Ala
                165                 170                 175

Asp Phe Thr Gly His Tyr Gln Thr Ala Phe Arg Glu Leu Glu Arg Val
            180                 185                 190

Leu Asn Phe Pro Gln Ser Asn Leu Ala Leu Lys Arg Glu Lys Gln Asp
        195                 200                 205

Glu Ser Ala Ser Leu Thr Gln Ala Leu Pro Ser Glu Leu Lys Val Ser
    210                 215                 220

Ala Asp Asn Val Ser Leu Thr Gly Ala Trp Ser Leu Ala Ser Met Leu
225                 230                 235                 240

Thr Glu Ile Phe Leu Leu Gln Gln Ala Gln Gly Met Pro Glu Pro Gly
                245                 250                 255

Trp Gly Arg Ile Thr Asp Ser His Gln Trp Asn Thr Leu Leu Ser Leu
            260                 265                 270

His Asn Ala Gln Phe Asp Leu Leu Gln Arg Thr Pro Glu Val Ala Arg
        275                 280                 285

Ser Arg Ala Thr Pro Leu Leu Asp Leu Ile Lys Thr Ala Leu Thr Pro
    290                 295                 300

His Pro Pro Gln Lys Gln Ala Tyr Gly Val Thr Leu Pro Thr Ser Val
305                 310                 315                 320

Leu Phe Ile Ala Gly His Asp Thr Asn Leu Ala Asn Leu Gly Gly Ala
                325                 330                 335

Leu Glu Leu Gln Trp Thr Leu Pro Gly Gln Pro Asp Asn Thr Pro Pro
            340                 345                 350

Gly Gly Glu Leu Val Phe Glu Arg Trp Arg Arg Leu Ser Asp Asn Ser
        355                 360                 365
```

```
Gln Trp Ile Gln Val Ser Leu Val Phe Gln Thr Leu Gln Gln Met Arg
    370                 375                 380

Asp Lys Thr Pro Leu Phe Leu Asn Thr Pro Pro Gly Glu Val Lys Leu
385                 390                 395                 400

Thr Leu Ala Gly Cys Glu Glu Arg Asn Ala Gln Gly Met Cys Ser Leu
                405                 410                 415

Ala Gly Phe Thr Gln Ile Val Asn Glu Ala Arg Ile Pro Ala Cys Ser
            420                 425                 430

Leu Ala Gln Ser Glu Pro Glu Leu Lys Leu Glu Ser Val Val Ile Val
        435                 440                 445

Cys Leu Asp Leu Lys Thr Gln Val Gln Thr Pro Gln Gly Met Lys Glu
    450                 455                 460

Ile Ser Asn Ile Gln Val Gly Asp Leu Val Leu Ser Asn Thr Gly Tyr
465                 470                 475                 480

Asn Glu Val Leu Asn Val Phe Pro Lys Ser Lys Lys Lys Ser Tyr Lys
                485                 490                 495

Ile Thr Leu Glu Asp Gly Lys Glu Ile Ile Cys Ser Glu Glu His Leu
            500                 505                 510

Phe Pro Thr Gln Thr Gly Glu Met Asn Ile Ser Gly Gly Leu Lys Glu
        515                 520                 525

Gly Met Cys Leu Tyr Val Lys Glu
    530                 535
```

<210> SEQ ID NO 94
<211> LENGTH: 1794
<212> TYPE: DNA
<213> ORGANISM: Artificial Sequence
<220> FEATURE:
<223> OTHER INFORMATION: Synthetic construct, Phy02C-27:SspDnaE coding seq

<400> SEQUENCE: 94

```
atggttaagg tgattggaag acgttctctt ggtgttcaaa ggatcttcga tatcggattg     60

ccacaagacc acaactttct tctcgctaat ggtgccatcg ctgccaatag cgggggtggc    120

agtggaggcg gttcgacccc gcagtccgca tttgccgccc aatcggaacc ggaactgaaa    180

ctggaaagtg tggttattgt gtctcgtcat ggcgttcgcg ctccgaccaa atttacgcag    240

ctgatgcaag atgtcacccc ggacgccttc tatacgtggc cggtgaagct gggtgaactg    300

accccgcgtg gcggtgaact gatcgcctat ctgggtcact actggcgtca gcgcctggtg    360

gcagatggtc tgctgccgaa aaagggctgc ccgcagagcg gtcaagttgc aattatcgct    420

gatgtcgacg aacgtacccg caaaacgggt gaagcatttg cggccggtct ggcaccggat    480

tgcgccatta ccgttcatac gcaggcagat accagctctc cggacccgct gttcaacccg    540

ctgaaaaccg gcgtctgtca gctggatgtc gcgcaagtga cggacgccat tctggaacgt    600

gcaggcggtt ccatcgctga ttttaccggt cactaccaga cggcattccg tgaactggaa    660

cgcgttctga actttccgca gtcaaatctg gcgctgaaac gcgaaaagca ggatgaaagt    720

gcgtccctga cccaagccct gccgagtgaa ctgaaagtct ccgccgacaa tgtgtcactg    780

accggcgcat ggtcactggc ttcgatgctg acggaaattt ttctgctgca gcaagcacag    840

ggtatgccgg aaccgggttg ggtcgtatc accgattcgc atcagtggaa cacgctgctg    900

agcctgcaca atgcgcagtt cgacctgctg caacgtaccc cggaagtggc acgttcgcgc    960

gccacgccgc tgctggatct gattaaaacc gctctgacgc cgcatccgcc gcagaagcaa   1020
```

-continued

```
gcgtatggcg tgaccctgcc gacgagcgtt ctgtttatcg cgggtcacga caccaacctg   1080

gcaaatctgg gcggtgctct ggaactgcag tggaccctgc cgggtcaacc ggataacacg   1140

ccgccgggcg gtgaactggt tttcgaacgt tggcgtcgcc tgagcgacaa ttctcagtgg   1200

atccaagtta gcctggtctt tcagaccctg cagcaaatgc gcgataaaac cccgctgttc   1260

ctgaacacgc cgccgggcga agtgaagctg accctggcgg gttgcgaaga acgtaacgcc   1320

cagggcatgt gttctctggc aggttttacc cagattgtta atgaagcacg catcccggct   1380

tgtagtctgg gtggcgggag cggtggaggg agtgggggcg gttgcctttc tttcggaact   1440

gagatcctta ccgttgagta cggaccactt cctattggta agatcgtttc tgaggaaatt   1500

aactgctcag tgtactctgt tgatccagaa ggaagagttt acactcaggc tatcgcacaa   1560

tggcacgata ggggtgaaca agaggttctg gagtacgagc ttgaagatgg atccgttatt   1620

cgtgctacct ctgaccatag attcttgact acagattatc agcttctcgc tatcgaggaa   1680

atctttgcta ggcaacttga tctccttact ttggagaaca tcaagcagac agaagaggct   1740

cttgacaacc acagacttcc attccctttg ctcgatgctg gaaccatcaa gtaa         1794
```

<210> SEQ ID NO 95
<211> LENGTH: 597
<212> TYPE: PRT
<213> ORGANISM: Artificial Sequence
<220> FEATURE:
<223> OTHER INFORMATION: Synthetic construct, Phy02C-27:SspDnaE

<400> SEQUENCE: 95

```
Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn Ser Gly Gly Gly Ser Gly Gly Gly Ser Thr Pro Gln
        35                  40                  45

Ser Ala Phe Ala Ala Gln Ser Glu Pro Glu Leu Lys Leu Glu Ser Val
    50                  55                  60

Val Ile Val Ser Arg His Gly Val Arg Ala Pro Thr Lys Phe Thr Gln
65                  70                  75                  80

Leu Met Gln Asp Val Thr Pro Asp Ala Phe Tyr Thr Trp Pro Val Lys
                85                  90                  95

Leu Gly Glu Leu Thr Pro Arg Gly Gly Glu Leu Ile Ala Tyr Leu Gly
            100                 105                 110

His Tyr Trp Arg Gln Arg Leu Val Ala Asp Gly Leu Leu Pro Lys Lys
        115                 120                 125

Gly Cys Pro Gln Ser Gly Gln Val Ala Ile Ile Ala Asp Val Asp Glu
    130                 135                 140

Arg Thr Arg Lys Thr Gly Glu Ala Phe Ala Ala Gly Leu Ala Pro Asp
145                 150                 155                 160

Cys Ala Ile Thr Val His Thr Gln Ala Asp Thr Ser Ser Pro Asp Pro
                165                 170                 175

Leu Phe Asn Pro Leu Lys Thr Gly Val Cys Gln Leu Asp Val Ala Gln
            180                 185                 190

Val Thr Asp Ala Ile Leu Glu Arg Ala Gly Gly Ser Ile Ala Asp Phe
        195                 200                 205

Thr Gly His Tyr Gln Thr Ala Phe Arg Glu Leu Glu Arg Val Leu Asn
    210                 215                 220

Phe Pro Gln Ser Asn Leu Ala Leu Lys Arg Glu Lys Gln Asp Glu Ser
```

```
225                 230                 235                 240

Ala Ser Leu Thr Gln Ala Leu Pro Ser Glu Leu Lys Val Ser Ala Asp
                245                 250                 255

Asn Val Ser Leu Thr Gly Ala Trp Ser Leu Ala Ser Met Leu Thr Glu
            260                 265                 270

Ile Phe Leu Leu Gln Gln Ala Gln Gly Met Pro Glu Pro Gly Trp Gly
        275                 280                 285

Arg Ile Thr Asp Ser His Gln Trp Asn Thr Leu Leu Ser Leu His Asn
    290                 295                 300

Ala Gln Phe Asp Leu Leu Gln Arg Thr Pro Glu Val Ala Arg Ser Arg
305                 310                 315                 320

Ala Thr Pro Leu Leu Asp Leu Ile Lys Thr Ala Leu Thr Pro His Pro
                325                 330                 335

Pro Gln Lys Gln Ala Tyr Gly Val Thr Leu Pro Thr Ser Val Leu Phe
            340                 345                 350

Ile Ala Gly His Asp Thr Asn Leu Ala Asn Leu Gly Gly Ala Leu Glu
        355                 360                 365

Leu Gln Trp Thr Leu Pro Gly Gln Pro Asp Asn Thr Pro Pro Gly Gly
    370                 375                 380

Glu Leu Val Phe Glu Arg Trp Arg Arg Leu Ser Asp Asn Ser Gln Trp
385                 390                 395                 400

Ile Gln Val Ser Leu Val Phe Gln Thr Leu Gln Gln Met Arg Asp Lys
                405                 410                 415

Thr Pro Leu Phe Leu Asn Thr Pro Pro Gly Glu Val Lys Leu Thr Leu
            420                 425                 430

Ala Gly Cys Glu Glu Arg Asn Ala Gln Gly Met Cys Ser Leu Ala Gly
        435                 440                 445

Phe Thr Gln Ile Val Asn Glu Ala Arg Ile Pro Ala Cys Ser Leu Gly
    450                 455                 460

Gly Gly Ser Gly Gly Gly Ser Gly Gly Gly Cys Leu Ser Phe Gly Thr
465                 470                 475                 480

Glu Ile Leu Thr Val Glu Tyr Gly Pro Leu Pro Ile Gly Lys Ile Val
                485                 490                 495

Ser Glu Glu Ile Asn Cys Ser Val Tyr Ser Val Asp Pro Glu Gly Arg
            500                 505                 510

Val Tyr Thr Gln Ala Ile Ala Gln Trp His Asp Arg Gly Glu Gln Glu
        515                 520                 525

Val Leu Glu Tyr Glu Leu Glu Asp Gly Ser Val Ile Arg Ala Thr Ser
    530                 535                 540

Asp His Arg Phe Leu Thr Thr Asp Tyr Gln Leu Leu Ala Ile Glu Glu
545                 550                 555                 560

Ile Phe Ala Arg Gln Leu Asp Leu Leu Thr Leu Glu Asn Ile Lys Gln
                565                 570                 575

Thr Glu Glu Ala Leu Asp Asn His Arg Leu Pro Phe Pro Leu Leu Asp
            580                 585                 590

Ala Gly Thr Ile Lys
        595
```

<210> SEQ ID NO 96
<211> LENGTH: 1809
<212> TYPE: DNA
<213> ORGANISM: Artificial Sequence
<220> FEATURE:
<223> OTHER INFORMATION: Synthetc construct, Phy02C-32:SspDnaE coding
seq

<400> SEQUENCE: 96
atggttaagg tgattggaag acgttctctt ggtgttcaaa ggatcttcga tatcggattg 60
ccacaagacc acaactttct tctcgctaat ggtgccatcg ctgccaatag cggtggctcg 120
tcagggagta cgacaaccac gcgtatcacc ccgcaatctg cgttcgctgc ccaatcggaa 180
ccggaactga aactggaaag tgtggttatt gtgtctcgtc atggcgttcg cgctccgacc 240
aaatttacgc agctgatgca agatgtcacc ccggacgcct tctatacgtg gccggtgaag 300
ctgggtgaac tgaccccgcg tggcggtgaa ctgatcgcct atctgggtca ctactggcgt 360
cagcgcctgg tggcagatgg tctgctgccg aaaaagggct gcccgcagag cggtcaagtt 420
gcaattatcg ctgatgtcga cgaacgtacc cgcaaaacgg gtgaagcatt tgcggccggt 480
ctggcaccgg attgcgccat taccgttcat acgcaggcag ataccagctc tccggacccg 540
ctgttcaacc cgctgaaaac cggcgtctgt cagctggatg tcgcgcaagt gacggacgcc 600
attctggaac gtgcaggcgg ttccatcgct gattttaccg gtcactacca gacggcattc 660
cgtgaactgg aacgcgttct gaactttccg cagtcaaatc tggcgctgaa acgcgaaaag 720
caggatgaaa gtgcgtccct gacccaagcc ctgccgagtg aactgaaagt ctccgccgac 780
aatgtgtcac tgaccggcgc atggtcactg gcttcgatgc tgacggaaat tttctgctg 840
cagcaagcac agggtatgcc ggaaccgggt tggggtcgta tcaccgattc gcatcagtgg 900
aacacgctgc tgagcctgca caatgcgcag ttcgacctgc tgcaacgtac cccggaagtg 960
gcacgttcgc gcgccacgcc gctgctggat ctgattaaaa ccgctctgac gccgcatccg 1020
ccgcagaagc aagcgtatgg cgtgaccctg ccgacgagcg ttctgtttat cgcgggtcac 1080
gacaccaacc tggcaaatct gggcggtgct ctggaactgc agtggaccct gccgggtcaa 1140
ccggataaca cgccgccggg cggtgaactg gttttcgaac gttggcgtcg cctgagcgac 1200
aattctcagt ggatccaagt tagcctggtc tttcagaccc tgcagcaaat gcgcgataaa 1260
accccgctgt tcctgaacac gccgccgggc gaagtgaagc tgaccctggc gggttgcgaa 1320
gaacgtaacg cccagggcat gtgttctctg gcaggtttta cccagattgt taatgaagca 1380
cgcatcccgg cttgtagtct gcaaaacacg tttagccagg ggagtagctc gggatcctgc 1440
ctttctttcg gaactgagat ccttaccgtt gagtacggac cacttcctat tggtaagatc 1500
gtttctgagg aaattaactg ctcagtgtac tctgttgatc cagaaggaag agtttacact 1560
caggctatcg cacaatggca cgataggggt gaacaagagg ttctggagta cgagcttgaa 1620
gatggatccg ttattcgtgc tacctctgac catagattct tgactacaga ttatcagctt 1680
ctcgctatcg aggaaatctt tgctaggcaa cttgatctcc ttactttgga gaacatcaag 1740
cagacagaag aggctcttga caaccacaga cttccattcc ctttgctcga tgctggaacc 1800
atcaagtaa 1809

<210> SEQ ID NO 97

<400> SEQUENCE: 97

000

<210> SEQ ID NO 98
<211> LENGTH: 1833
<212> TYPE: DNA
<213> ORGANISM: Artificial Sequence
<220> FEATURE:
<223> OTHER INFORMATION: Synthetic construct, Phy02C-40: SspDnaE coding seq

<400> SEQUENCE: 98

```
atggttaagg tgattggaag acgttctctt ggtgttcaaa ggatcttcga tatcggattg     60
ccacaagacc acaactttct tctcgctaat ggtgccatcg ctgccaatag cgcctttgca    120
gcccaatcgg aaccggaact gaaactggaa agtgtggtta ttgtgtctcg tcatggcgtt    180
cgcgctccga ccaaatttac gcagctgatg caagatgtca ccccggacgc cttctatacg    240
tggccggtga agctgggtga actgaccccg cgtggcggtg aactgatcgc ctatctgggt    300
cactactggc gtcagcgcct ggtggcagat ggtctgctgc cgaaaaaggg ctgcccgcag    360
agcggtcaag ttgcaattat cgctgatgtc gacgaacgta cccgcaaaac gggtgaagca    420
tttgcggccg gtctggcacc ggattgcgcc attaccgttc atacgcaggc agataccagc    480
tctccggacc cgctgttcaa cccgctgaaa accggcgtct gtcagctgga tgtcgcgcaa    540
gtgacggacg ccattctgga acgtgcaggc ggttccatcg ctgattttac cggtcactac    600
cagacggcat tccgtgaact ggaacgcgtt ctgaactttc cgcagtcaaa tctggcgctg    660
aaacgcgaaa agcaggatga aagtgcgtcc ctgacccaag ccctgccgag tgaactgaaa    720
gtctccgccg acaatgtgtc actgaccggc gcatggtcac tggcttcgat gctgacggaa    780
atttttctgc tgcagcaagc acagggtatg ccggaaccgg gttggggtcg tatcaccgat    840
tcgcatcagt ggaacacgct gctgagcctg cacaatgcgc agttcgacct gctgcaacgt    900
accccggaag tggcacgttc gcgcgccacg ccgctgctgg atctgattaa aaccgctctg    960
acgccgcatc cgccgcagaa gcaagcgtat ggcgtgaccc tgccgacgag cgttctgttt   1020
atcgcgggtc acgacaccaa cctggcaaat ctgggcggtg ctctggaact gcagtggacc   1080
ctgccgggtc aaccggataa cacgccgccg ggcggtgaac tggttttcga acgttggcgt   1140
cgcctgagcg acaattctca gtggatccaa gttagcctgg tctttcagac cctgcagcaa   1200
atgcgcgata aaaccccgct gttcctgaac acgccgccgg gcgaagtgaa gctgaccctg   1260
gcgggttgcg aagaacgtaa cgcccagggc atgtgttctc tggcaggttt tacccagatt   1320
gttaatgaag cacgcatccc ggcttgtagt ctgggtgcag ctccagcggc cgcaccggct   1380
aaacaggaag cggcagctcc ggctcctgca gcgaaggcgg aagcaccggc cgcagctcct   1440
gcggcaaaag cgaccccgca gtgcctttct ttcggaactg agatccttac cgttgagtac   1500
ggaccacttc ctattggtaa gatcgtttct gaggaaatta actgctcagt gtactctgtt   1560
gatccagaag gaagagttta cactcaggct atcgcacaat ggcacgatag gggtgaacaa   1620
gaggttctgg agtacgagct tgaagatgga tccgttattc gtgctacctc tgaccataga   1680
ttcttgacta cagattatca gcttctcgct atcgaggaaa tctttgctag gcaacttgat   1740
ctccttactt tggagaacat caagcagaca gaagaggctc ttgacaacca cagacttcca   1800
ttccctttgc tcgatgctgg aaccatcaag taa                                1833
```

<210> SEQ ID NO 99
<211> LENGTH: 610
<212> TYPE: PRT
<213> ORGANISM: Artificial Sequence
<220> FEATURE:
<223> OTHER INFORMATION: Synthetic construct, Phy02C-40: SspDnaE

<400> SEQUENCE: 99

```
Met Val Lys Val Ile Gly Arg Arg Ser Leu Gly Val Gln Arg Ile Phe
1               5                   10                  15
```

-continued

```
Asp Ile Gly Leu Pro Gln Asp His Asn Phe Leu Leu Ala Asn Gly Ala
            20                  25                  30

Ile Ala Ala Asn Ser Ala Phe Ala Ala Gln Ser Glu Pro Glu Leu Lys
        35                  40                  45

Leu Glu Ser Val Val Ile Val Ser Arg His Gly Val Arg Ala Pro Thr
    50                  55                  60

Lys Phe Thr Gln Leu Met Gln Asp Val Thr Pro Asp Ala Phe Tyr Thr
65                  70                  75                  80

Trp Pro Val Lys Leu Gly Glu Leu Thr Pro Arg Gly Gly Glu Leu Ile
                85                  90                  95

Ala Tyr Leu Gly His Tyr Trp Arg Gln Arg Leu Val Ala Asp Gly Leu
            100                 105                 110

Leu Pro Lys Lys Gly Cys Pro Gln Ser Gly Gln Val Ala Ile Ile Ala
        115                 120                 125

Asp Val Asp Glu Arg Thr Arg Lys Thr Gly Glu Ala Phe Ala Ala Gly
    130                 135                 140

Leu Ala Pro Asp Cys Ala Ile Thr Val His Thr Gln Ala Asp Thr Ser
145                 150                 155                 160

Ser Pro Asp Pro Leu Phe Asn Pro Leu Lys Thr Gly Val Cys Gln Leu
                165                 170                 175

Asp Val Ala Gln Val Thr Asp Ala Ile Leu Glu Arg Ala Gly Gly Ser
            180                 185                 190

Ile Ala Asp Phe Thr Gly His Tyr Gln Thr Ala Phe Arg Glu Leu Glu
        195                 200                 205

Arg Val Leu Asn Phe Pro Gln Ser Asn Leu Ala Leu Lys Arg Glu Lys
    210                 215                 220

Gln Asp Glu Ser Ala Ser Leu Thr Gln Ala Leu Pro Ser Glu Leu Lys
225                 230                 235                 240

Val Ser Ala Asp Asn Val Ser Leu Thr Gly Ala Trp Ser Leu Ala Ser
                245                 250                 255

Met Leu Thr Glu Ile Phe Leu Leu Gln Gln Ala Gln Gly Met Pro Glu
            260                 265                 270

Pro Gly Trp Gly Arg Ile Thr Asp Ser His Gln Trp Asn Thr Leu Leu
        275                 280                 285

Ser Leu His Asn Ala Gln Phe Asp Leu Leu Gln Arg Thr Pro Glu Val
    290                 295                 300

Ala Arg Ser Arg Ala Thr Pro Leu Leu Asp Leu Ile Lys Thr Ala Leu
305                 310                 315                 320

Thr Pro His Pro Pro Gln Lys Gln Ala Tyr Gly Val Thr Leu Pro Thr
                325                 330                 335

Ser Val Leu Phe Ile Ala Gly His Asp Thr Asn Leu Ala Asn Leu Gly
            340                 345                 350

Gly Ala Leu Glu Leu Gln Trp Thr Leu Pro Gly Gln Pro Asp Asn Thr
        355                 360                 365

Pro Pro Gly Gly Glu Leu Val Phe Glu Arg Trp Arg Arg Leu Ser Asp
    370                 375                 380

Asn Ser Gln Trp Ile Gln Val Ser Leu Val Phe Gln Thr Leu Gln Gln
385                 390                 395                 400

Met Arg Asp Lys Thr Pro Leu Phe Leu Asn Thr Pro Pro Gly Glu Val
                405                 410                 415

Lys Leu Thr Leu Ala Gly Cys Glu Glu Arg Asn Ala Gln Gly Met Cys
            420                 425                 430

Ser Leu Ala Gly Phe Thr Gln Ile Val Asn Glu Ala Arg Ile Pro Ala
```

```
        435                 440                 445

Cys Ser Leu Gly Ala Ala Pro Ala Ala Ala Pro Ala Lys Gln Glu Ala
    450                 455                 460

Ala Ala Pro Ala Pro Ala Ala Lys Ala Glu Ala Pro Ala Ala Ala Pro
465                 470                 475                 480

Ala Ala Lys Ala Thr Pro Gln Cys Leu Ser Phe Gly Thr Glu Ile Leu
                485                 490                 495

Thr Val Glu Tyr Gly Pro Leu Pro Ile Gly Lys Ile Val Ser Glu Glu
            500                 505                 510

Ile Asn Cys Ser Val Tyr Ser Val Asp Pro Glu Gly Arg Val Tyr Thr
        515                 520                 525

Gln Ala Ile Ala Gln Trp His Asp Arg Gly Glu Gln Glu Val Leu Glu
    530                 535                 540

Tyr Glu Leu Glu Asp Gly Ser Val Ile Arg Ala Thr Ser Asp His Arg
545                 550                 555                 560

Phe Leu Thr Thr Asp Tyr Gln Leu Leu Ala Ile Glu Glu Ile Phe Ala
                565                 570                 575

Arg Gln Leu Asp Leu Leu Thr Leu Glu Asn Ile Lys Gln Thr Glu Glu
            580                 585                 590

Ala Leu Asp Asn His Arg Leu Pro Phe Pro Leu Leu Asp Ala Gly Thr
        595                 600                 605

Ile Lys
    610
```

<210> SEQ ID NO 100
<211> LENGTH: 1860
<212> TYPE: DNA
<213> ORGANISM: Artificial Sequence
<220> FEATURE:
<223> OTHER INFORMATION: Synthetic construct, Phy02C-49:SspDnaE coding seq

<400> SEQUENCE: 100

```
atggttaagg tgattggaag acgttctctt ggtgttcaaa ggatcttcga tatcggattg     60

ccacaagacc acaactttct tctcgctaat ggtgccatcg ctgccaatag cgcagccgaa    120

gccgctgcga aggaggcagc tgcgaaagaa gcggctgcaa aagaagcggc agctaaggct    180

ttgaataccc cgcaatcggc tttcgctgcc caatcggaac cggaactgaa actggaaagt    240

gtggttattg tgtctcgtca tggcgttcgc gctccgacca aatttacgca gctgatgcaa    300

gatgtcaccc cggacgcctt ctatacgtgg ccggtgaagc tgggtgaact gaccccgcgt    360

ggcggtgaac tgatcgccta tctgggtcac tactggcgtc agcgcctggt ggcagatggt    420

ctgctgccga aaaagggctg cccgcagagc ggtcaagttg caattatcgc tgatgtcgac    480

gaacgtaccc gcaaaacggg tgaagcattt gcggccggtc tggcaccgga ttgcgccatt    540

accgttcata cgcaggcaga taccagctct ccggacccgc tgttcaaccc gctgaaaacc    600

ggcgtctgtc agctggatgt cgcgcaagtg acggacgcca ttctggaacg tgcaggcggt    660

tccatcgctg attttaccgg tcactaccag acggcattcc gtgaactgga acgcgttctg    720

aactttccgc agtcaaatct ggcgctgaaa cgcgaaaagc aggatgaaag tgcgtccctg    780

acccaagccc tgccgagtga actgaaagtc tccgccgaca atgtgtcact gaccggcgca    840

tggtcactgg cttcgatgct gacggaaatt tttctgctgc agcaagcaca gggtatgccg    900

gaaccgggtt ggggtcgtat caccgattcg catcagtgga acacgctgct gagcctgcac    960

aatgcgcagt tcgacctgct gcaacgtacc ccggaagtgg cacgttcgcg cgccacgccg   1020
```

ctgctggatc tgattaaaac cgctctgacg ccgcatccgc cgcagaagca agcgtatggc 1080
gtgaccctgc cgacgagcgt tctgtttatc gcgggtcacg acaccaacct ggcaaatctg 1140
ggcggtgctc tggaactgca gtggaccctg ccgggtcaac cggataacac gccgccgggc 1200
ggtgaactgg ttttcgaacg ttggcgtcgc ctgagcgaca attctcagtg gatccaagtt 1260
agcctggtct ttcagaccct gcagcaaatg cgcgataaaa ccccgctgtt cctgaacacg 1320
ccgccgggcg aagtgaagct gaccctggcg ggttgcgaag aacgtaacgc ccagggcatg 1380
tgttctctgg caggttttac ccagattgtt aatgaagcac gcatcccggc ttgtagtctg 1440
gggggcgcag aagcagctgc caaagaggcg gccgcaaagg tcaatctgtg cctttctttc 1500
ggaactgaga tccttaccgt tgagtacgga ccacttccta ttggtaagat cgtttctgag 1560
gaaattaact gctcagtgta ctctgttgat ccagaaggaa gagtttacac tcaggctatc 1620
gcacaatggc acgatagggg tgaacaagag gttctggagt acgagcttga agatggatcc 1680
gttattcgtg ctacctctga ccatagattc ttgactacag attatcagct tctcgctatc 1740
gaggaaatct ttgctaggca acttgatctc cttactttgg agaacatcaa gcagacagaa 1800
gaggctcttg acaaccacag acttccattc cctttgctcg atgctggaac catcaagtaa 1860

<210> SEQ ID NO 101
<211> LENGTH: 619
<212> TYPE: PRT
<213> ORGANISM: Artificial Sequence
<220> FEATURE:
<223> OTHER INFORMATION: Synthetic construct, Phy02C-49:SspDnaE

<400> SEQUENCE: 101

Met Val Lys Val Ile Gly Arg Arg Ser Leu Gly Val Gln Arg Ile Phe
1 5 10 15

Asp Ile Gly Leu Pro Gln Asp His Asn Phe Leu Leu Ala Asn Gly Ala
20 25 30

Ile Ala Ala Asn Ser Ala Ala Glu Ala Ala Ala Lys Glu Ala Ala Ala
35 40 45

Lys Glu Ala Ala Ala Lys Glu Ala Ala Ala Lys Ala Leu Asn Thr Pro
50 55 60

Gln Ser Ala Phe Ala Ala Gln Ser Glu Pro Glu Leu Lys Leu Glu Ser
65 70 75 80

Val Val Ile Val Ser Arg His Gly Val Arg Ala Pro Thr Lys Phe Thr
85 90 95

Gln Leu Met Gln Asp Val Thr Pro Asp Ala Phe Tyr Thr Trp Pro Val
100 105 110

Lys Leu Gly Glu Leu Thr Pro Arg Gly Gly Glu Leu Ile Ala Tyr Leu
115 120 125

Gly His Tyr Trp Arg Gln Arg Leu Val Ala Asp Gly Leu Leu Pro Lys
130 135 140

Lys Gly Cys Pro Gln Ser Gly Gln Val Ala Ile Ile Ala Asp Val Asp
145 150 155 160

Glu Arg Thr Arg Lys Thr Gly Glu Ala Phe Ala Ala Gly Leu Ala Pro
165 170 175

Asp Cys Ala Ile Thr Val His Thr Gln Ala Asp Thr Ser Ser Pro Asp
180 185 190

Pro Leu Phe Asn Pro Leu Lys Thr Gly Val Cys Gln Leu Asp Val Ala
195 200 205

Gln Val Thr Asp Ala Ile Leu Glu Arg Ala Gly Gly Ser Ile Ala Asp

```
    210                 215                 220

Phe Thr Gly His Tyr Gln Thr Ala Phe Arg Glu Leu Glu Arg Val Leu
225                 230                 235                 240

Asn Phe Pro Gln Ser Asn Leu Ala Leu Lys Arg Glu Lys Gln Asp Glu
                245                 250                 255

Ser Ala Ser Leu Thr Gln Ala Leu Pro Ser Glu Leu Lys Val Ser Ala
            260                 265                 270

Asp Asn Val Ser Leu Thr Gly Ala Trp Ser Leu Ala Ser Met Leu Thr
        275                 280                 285

Glu Ile Phe Leu Leu Gln Gln Ala Gln Gly Met Pro Glu Pro Gly Trp
    290                 295                 300

Gly Arg Ile Thr Asp Ser His Gln Trp Asn Thr Leu Leu Ser Leu His
305                 310                 315                 320

Asn Ala Gln Phe Asp Leu Leu Gln Arg Thr Pro Glu Val Ala Arg Ser
                325                 330                 335

Arg Ala Thr Pro Leu Leu Asp Leu Ile Lys Thr Ala Leu Thr Pro His
            340                 345                 350

Pro Pro Gln Lys Gln Ala Tyr Gly Val Thr Leu Pro Thr Ser Val Leu
        355                 360                 365

Phe Ile Ala Gly His Asp Thr Asn Leu Ala Asn Leu Gly Gly Ala Leu
    370                 375                 380

Glu Leu Gln Trp Thr Leu Pro Gly Gln Pro Asp Asn Thr Pro Pro Gly
385                 390                 395                 400

Gly Glu Leu Val Phe Glu Arg Trp Arg Arg Leu Ser Asp Asn Ser Gln
                405                 410                 415

Trp Ile Gln Val Ser Leu Val Phe Gln Thr Leu Gln Gln Met Arg Asp
            420                 425                 430

Lys Thr Pro Leu Phe Leu Asn Thr Pro Pro Gly Glu Val Lys Leu Thr
        435                 440                 445

Leu Ala Gly Cys Glu Glu Arg Asn Ala Gln Gly Met Cys Ser Leu Ala
    450                 455                 460

Gly Phe Thr Gln Ile Val Asn Glu Ala Arg Ile Pro Ala Cys Ser Leu
465                 470                 475                 480

Gly Gly Ala Glu Ala Ala Ala Lys Glu Ala Ala Ala Lys Val Asn Leu
                485                 490                 495

Cys Leu Ser Phe Gly Thr Glu Ile Leu Thr Val Glu Tyr Gly Pro Leu
            500                 505                 510

Pro Ile Gly Lys Ile Val Ser Glu Glu Ile Asn Cys Ser Val Tyr Ser
        515                 520                 525

Val Asp Pro Glu Gly Arg Val Tyr Thr Gln Ala Ile Ala Gln Trp His
    530                 535                 540

Asp Arg Gly Glu Gln Glu Val Leu Glu Tyr Glu Leu Glu Asp Gly Ser
545                 550                 555                 560

Val Ile Arg Ala Thr Ser Asp His Arg Phe Leu Thr Thr Asp Tyr Gln
                565                 570                 575

Leu Leu Ala Ile Glu Glu Ile Phe Ala Arg Gln Leu Asp Leu Leu Thr
            580                 585                 590

Leu Glu Asn Ile Lys Gln Thr Glu Glu Ala Leu Asp Asn His Arg Leu
        595                 600                 605

Pro Phe Pro Leu Leu Asp Ala Gly Thr Ile Lys
    610                 615
```

<210> SEQ ID NO 102

<211> LENGTH: 1503
<212> TYPE: DNA
<213> ORGANISM: Artificial Sequence
<220> FEATURE:
<223> OTHER INFORMATION: Synthetic construct, Phy02-33:cc17 coding seq

<400> SEQUENCE: 102

```
atgagggcca agcagctgga ggacaagatt gaggagctgc tgagcaagat ctaccacctg     60

gagaacgaga tagcccgcct gaagaagctg attggcgagc gcagcggggg tggcagtgga    120

ggcggttcga ccccgcagtc cgcatttgcc gcccaatcgg aaccggaact gaaactggaa    180

agtgtggtta ttgtgtctcg tcatggcgtt cgcgctccga ccaaatttac gcagctgatg    240

caagatgtca ccccggacgc cttctatacg tggccggtga agctgggtga actgaccccg    300

cgtggcggtg aactgatcgc ctatctgggt cactactggc gtcagcgcct ggtggcagat    360

ggtctgctgc cgaaaaaggg ctgcccgcag agcggtcaag ttgcaattat cgctgatgtc    420

gacgaacgta cccgcaaaac gggtgaagca tttgcggccg gtctggcacc ggattgcgcc    480

attaccgttc atacgcaggc agataccagc tctccggacc cgctgttcaa cccgctgaaa    540

accggcgtct gtcagctgga tgtcgcgcaa gtgacggacg ccattctgga acgtgcaggc    600

ggttccatcg ctgattttac cggtcactac cagacggcat tccgtgaact ggaacgcgtt    660

ctgaactttc cgcagtcaaa tctggcgctg aaacgcgaaa agcaggatga aagtgcgtcc    720

ctgacccaag ccctgccgag tgaactgaaa gtctccgccg acaatgtgtc actgaccggc    780

gcatggtcac tggcttcgat gctgacggaa atttttctgc tgcagcaagc acagggtatg    840

ccggaaccgg gttggggtcg tatcaccgat tcgcatcagt ggaacacgct gctgagcctg    900

cacaatgcgc agttcgacct gctgcaacgt accccggaag tggcacgttc gcgcgccacg    960

ccgctgctgg atctgattaa aaccgctctg acgccgcatc cgccgcagaa gcaagcgtat   1020

ggcgtgaccc tgccgacgag cgttctgttt atcgcgggtc acgacaccaa cctggcaaat   1080

ctgggcggtg ctctggaact gcagtggacc ctgccgggtc aaccggataa cacgccgccg   1140

ggcggtgaac tggttttcga acgttggcgt cgcctgagcg acaattctca gtggatccaa   1200

gttagcctgg tctttcagac cctgcagcaa atgcgcgata aaaccccgct gttcctgaac   1260

acgccgccgg gcgaagtgaa gctgaccctg gcgggttgcg aagaacgtaa cgcccagggc   1320

atgtgttctc tggcaggttt tacccagatt gttaatgaag cacgcatccc ggcttgtagt   1380

ctgggtggcg ggagcggtgg agggagtggg ggcggtcagc tggaggacaa gattgaggag   1440

ctgctgagca agatctacca cctggagaac gagatagcga ggctgaagaa gctgattggc   1500

taa                                                                 1503
```

<210> SEQ ID NO 103
<211> LENGTH: 500
<212> TYPE: PRT
<213> ORGANISM: Artificial Sequence
<220> FEATURE:
<223> OTHER INFORMATION: Synthetic construct, Phy02-33:cc17

<400> SEQUENCE: 103

```
Met Arg Ala Lys Gln Leu Glu Asp Lys Ile Glu Glu Leu Leu Ser Lys
1               5                   10                  15

Ile Tyr His Leu Glu Asn Glu Ile Ala Arg Leu Lys Lys Leu Ile Gly
            20                  25                  30

Glu Arg Ser Gly Gly Gly Ser Gly Gly Gly Ser Thr Pro Gln Ser Ala
        35                  40                  45
```

-continued

```
Phe Ala Ala Gln Ser Glu Pro Glu Leu Lys Leu Glu Ser Val Val Ile
    50                  55                  60

Val Ser Arg His Gly Val Arg Ala Pro Thr Lys Phe Thr Gln Leu Met
65                  70                  75                  80

Gln Asp Val Thr Pro Asp Ala Phe Tyr Thr Trp Pro Val Lys Leu Gly
                85                  90                  95

Glu Leu Thr Pro Arg Gly Gly Glu Leu Ile Ala Tyr Leu Gly His Tyr
            100                 105                 110

Trp Arg Gln Arg Leu Val Ala Asp Gly Leu Leu Pro Lys Lys Gly Cys
        115                 120                 125

Pro Gln Ser Gly Gln Val Ala Ile Ile Ala Asp Val Asp Glu Arg Thr
    130                 135                 140

Arg Lys Thr Gly Glu Ala Phe Ala Ala Gly Leu Ala Pro Asp Cys Ala
145                 150                 155                 160

Ile Thr Val His Thr Gln Ala Asp Thr Ser Ser Pro Asp Pro Leu Phe
                165                 170                 175

Asn Pro Leu Lys Thr Gly Val Cys Gln Leu Asp Val Ala Gln Val Thr
            180                 185                 190

Asp Ala Ile Leu Glu Arg Ala Gly Gly Ser Ile Ala Asp Phe Thr Gly
        195                 200                 205

His Tyr Gln Thr Ala Phe Arg Glu Leu Glu Arg Val Leu Asn Phe Pro
    210                 215                 220

Gln Ser Asn Leu Ala Leu Lys Arg Glu Lys Gln Asp Glu Ser Ala Ser
225                 230                 235                 240

Leu Thr Gln Ala Leu Pro Ser Glu Leu Lys Val Ser Ala Asp Asn Val
                245                 250                 255

Ser Leu Thr Gly Ala Trp Ser Leu Ala Ser Met Leu Thr Glu Ile Phe
            260                 265                 270

Leu Leu Gln Gln Ala Gln Gly Met Pro Glu Pro Gly Trp Gly Arg Ile
        275                 280                 285

Thr Asp Ser His Gln Trp Asn Thr Leu Leu Ser Leu His Asn Ala Gln
    290                 295                 300

Phe Asp Leu Leu Gln Arg Thr Pro Glu Val Ala Arg Ser Arg Ala Thr
305                 310                 315                 320

Pro Leu Leu Asp Leu Ile Lys Thr Ala Leu Thr Pro His Pro Pro Gln
                325                 330                 335

Lys Gln Ala Tyr Gly Val Thr Leu Pro Thr Ser Val Leu Phe Ile Ala
            340                 345                 350

Gly His Asp Thr Asn Leu Ala Asn Leu Gly Gly Ala Leu Glu Leu Gln
        355                 360                 365

Trp Thr Leu Pro Gly Gln Pro Asp Asn Thr Pro Pro Gly Gly Glu Leu
    370                 375                 380

Val Phe Glu Arg Trp Arg Arg Leu Ser Asp Asn Ser Gln Trp Ile Gln
385                 390                 395                 400

Val Ser Leu Val Phe Gln Thr Leu Gln Gln Met Arg Asp Lys Thr Pro
                405                 410                 415

Leu Phe Leu Asn Thr Pro Pro Gly Glu Val Lys Leu Thr Leu Ala Gly
            420                 425                 430

Cys Glu Glu Arg Asn Ala Gln Gly Met Cys Ser Leu Ala Gly Phe Thr
        435                 440                 445

Gln Ile Val Asn Glu Ala Arg Ile Pro Ala Cys Ser Leu Gly Gly Gly
    450                 455                 460

Ser Gly Gly Gly Ser Gly Gly Gly Gln Leu Glu Asp Lys Ile Glu Glu
```

-continued 465 470 475 480

Leu Leu Ser Lys Ile Tyr His Leu Glu Asn Glu Ile Ala Arg Leu Lys
485 490 495

Lys Leu Ile Gly
500

<210> SEQ ID NO 104
<211> LENGTH: 1518
<212> TYPE: DNA
<213> ORGANISM: Artificial Sequence
<220> FEATURE:
<223> OTHER INFORMATION: Synthetic construct, Phy02-38: cc17 coding seq

<400> SEQUENCE: 104
atgagggcca agcagctgga ggacaagatt gaggagctgc tgagcaagat ctaccacctg 60
gagaacgaga tagcccgcct gaagaagctg attggcgagc gcagcggtgg ctcgtcaggg 120
agtacgacaa ccacgcgtat caccccgcaa tctgcgttcg ctgcccaatc ggaaccggaa 180
ctgaaactgg aaagtgtggt tattgtgtct cgtcatggcg ttcgcgctcc gaccaaattt 240
acgcagctga tgcaagatgt caccccggac gccttctata cgtggccggt gaagctgggt 300
gaactgaccc cgcgtggcgg tgaactgatc gcctatctgg gtcactactg gcgtcagcgc 360
ctggtggcag atggtctgct gccgaaaaag ggctgcccgc agagcggtca agttgcaatt 420
atcgctgatg tcgacgaacg tacccgcaaa acgggtgaag catttgcggc cggtctggca 480
ccggattgcg ccattaccgt tcatacgcag gcagatacca gctctccgga cccgctgttc 540
aacccgctga aaaccggcgt ctgtcagctg gatgtcgcgc aagtgacgga cgccattctg 600
gaacgtgcag gcggttccat cgctgatttt accggtcact accagacggc attccgtgaa 660
ctggaacgcg ttctgaactt tccgcagtca aatctggcgc tgaaacgcga aaagcaggat 720
gaaagtgcgt ccctgaccca agccctgccg agtgaactga aagtctccgc cgacaatgtg 780
tcactgaccg gcgcatggtc actggcttcg atgctgacgg aaatttttct gctgcagcaa 840
gcacagggta tgccggaacc gggttggggt cgtatcaccg attcgcatca gtggaacacg 900
ctgctgagcc tgcacaatgc gcagttcgac ctgctgcaac gtaccccgga agtggcacgt 960
tcgcgcgcca cgccgctgct ggatctgatt aaaaccgctc tgacgccgca tccgccgcag 1020
aagcaagcgt atggcgtgac cctgccgacg agcgttctgt ttatcgcggg tcacgacacc 1080
aacctggcaa atctgggcgg tgctctggaa ctgcagtgga ccctgccggg tcaaccggat 1140
aacacgccgc cgggcggtga actggttttc gaacgttggc gtcgcctgag cgacaattct 1200
cagtggatcc aagttagcct ggtctttcag accctgcagc aaatgcgcga taaaaccccg 1260
ctgttcctga acacgccgcc gggcgaagtg aagctgaccc tggcgggttg cgaagaacgt 1320
aacgcccagg gcatgtgttc tctggcaggt tttacccaga ttgttaatga agcacgcatc 1380
ccggcttgta gtctgcaaaa cacgtttagc caggggagta gctcgggatc ccagctggag 1440
gacaagattg aggagctgct gagcaagatc taccacctgg agaacgagat agcgaggctg 1500
aagaagctga ttggctaa 1518

<210> SEQ ID NO 105
<211> LENGTH: 505
<212> TYPE: PRT
<213> ORGANISM: Artificial Sequence
<220> FEATURE:
<223> OTHER INFORMATION: Synthetic construct, Phy02-38: cc17

<400> SEQUENCE: 105

-continued

```
Met Arg Ala Lys Gln Leu Glu Asp Lys Ile Glu Glu Leu Leu Ser Lys
1               5                   10                  15

Ile Tyr His Leu Glu Asn Glu Ile Ala Arg Leu Lys Lys Leu Ile Gly
            20                  25                  30

Glu Arg Ser Gly Gly Ser Ser Gly Ser Thr Thr Thr Thr Arg Ile Thr
        35                  40                  45

Pro Gln Ser Ala Phe Ala Ala Gln Ser Glu Pro Glu Leu Lys Leu Glu
    50                  55                  60

Ser Val Val Ile Val Ser Arg His Gly Val Arg Ala Pro Thr Lys Phe
65                  70                  75                  80

Thr Gln Leu Met Gln Asp Val Thr Pro Asp Ala Phe Tyr Thr Trp Pro
                85                  90                  95

Val Lys Leu Gly Glu Leu Thr Pro Arg Gly Gly Glu Leu Ile Ala Tyr
            100                 105                 110

Leu Gly His Tyr Trp Arg Gln Arg Leu Val Ala Asp Gly Leu Leu Pro
        115                 120                 125

Lys Lys Gly Cys Pro Gln Ser Gly Gln Val Ala Ile Ile Ala Asp Val
    130                 135                 140

Asp Glu Arg Thr Arg Lys Thr Gly Glu Ala Phe Ala Ala Gly Leu Ala
145                 150                 155                 160

Pro Asp Cys Ala Ile Thr Val His Thr Gln Ala Asp Thr Ser Ser Pro
                165                 170                 175

Asp Pro Leu Phe Asn Pro Leu Lys Thr Gly Val Cys Gln Leu Asp Val
            180                 185                 190

Ala Gln Val Thr Asp Ala Ile Leu Glu Arg Ala Gly Gly Ser Ile Ala
        195                 200                 205

Asp Phe Thr Gly His Tyr Gln Thr Ala Phe Arg Glu Leu Glu Arg Val
    210                 215                 220

Leu Asn Phe Pro Gln Ser Asn Leu Ala Leu Lys Arg Glu Lys Gln Asp
225                 230                 235                 240

Glu Ser Ala Ser Leu Thr Gln Ala Leu Pro Ser Glu Leu Lys Val Ser
                245                 250                 255

Ala Asp Asn Val Ser Leu Thr Gly Ala Trp Ser Leu Ala Ser Met Leu
            260                 265                 270

Thr Glu Ile Phe Leu Leu Gln Gln Ala Gln Gly Met Pro Glu Pro Gly
        275                 280                 285

Trp Gly Arg Ile Thr Asp Ser His Gln Trp Asn Thr Leu Leu Ser Leu
    290                 295                 300

His Asn Ala Gln Phe Asp Leu Leu Gln Arg Thr Pro Glu Val Ala Arg
305                 310                 315                 320

Ser Arg Ala Thr Pro Leu Leu Asp Leu Ile Lys Thr Ala Leu Thr Pro
                325                 330                 335

His Pro Pro Gln Lys Gln Ala Tyr Gly Val Thr Leu Pro Thr Ser Val
            340                 345                 350

Leu Phe Ile Ala Gly His Asp Thr Asn Leu Ala Asn Leu Gly Gly Ala
        355                 360                 365

Leu Glu Leu Gln Trp Thr Leu Pro Gly Gln Pro Asp Asn Thr Pro Pro
    370                 375                 380

Gly Gly Glu Leu Val Phe Glu Arg Trp Arg Arg Leu Ser Asp Asn Ser
385                 390                 395                 400

Gln Trp Ile Gln Val Ser Leu Val Phe Gln Thr Leu Gln Gln Met Arg
                405                 410                 415
```

```
Asp Lys Thr Pro Leu Phe Leu Asn Thr Pro Pro Gly Glu Val Lys Leu
            420                 425                 430

Thr Leu Ala Gly Cys Glu Glu Arg Asn Ala Gln Gly Met Cys Ser Leu
        435                 440                 445

Ala Gly Phe Thr Gln Ile Val Asn Glu Ala Arg Ile Pro Ala Cys Ser
    450                 455                 460

Leu Gln Asn Thr Phe Ser Gln Gly Ser Ser Ser Gly Ser Gln Leu Glu
465                 470                 475                 480

Asp Lys Ile Glu Glu Leu Leu Ser Lys Ile Tyr His Leu Glu Asn Glu
                485                 490                 495

Ile Ala Arg Leu Lys Lys Leu Ile Gly
            500                 505


<210> SEQ ID NO 106
<211> LENGTH: 1542
<212> TYPE: DNA
<213> ORGANISM: Artificial Sequence
<220> FEATURE:
<223> OTHER INFORMATION: Synthetic construct, Phy02-46: cc17 coding seq

<400> SEQUENCE: 106

atgagggcca agcagctgga ggacaagatt gaggagctgc tgagcaagat ctaccacctg      60

gagaacgaga tagcccgcct gaagaagctg attggcgagc gcagcgcctt tgcagcccaa     120

tcggaaccgg aactgaaact ggaaagtgtg gttattgtgt ctcgtcatgg cgttcgcgct     180

ccgaccaaat ttacgcagct gatgcaagat gtcaccccgg acgccttcta tacgtggccg     240

gtgaagctgg gtgaactgac ccgcgtggc ggtgaactga tcgcctatct gggtcactac     300

tggcgtcagc gcctggtggc agatggtctg ctgccgaaaa agggctgccc gcagagcggt     360

caagttgcaa ttatcgctga tgtcgacgaa cgtacccgca aaacgggtga agcatttgcg     420

gccggtctgg caccggattg cgccattacc gttcatacgc aggcagatac cagctctccg     480

gacccgctgt tcaacccgct gaaaaccggc gtctgtcagc tggatgtcgc gcaagtgacg     540

gacgccattc tggaacgtgc aggcggttcc atcgctgatt ttaccggtca ctaccagacg     600

gcattccgtg aactggaacg cgttctgaac tttccgcagt caaatctggc gctgaaacgc     660

gaaaagcagg atgaaagtgc gtccctgacc caagccctgc cgagtgaact gaaagtctcc     720

gccgacaatg tgtcactgac cggcgcatgg tcactggctt cgatgctgac ggaaattttt     780

ctgctgcagc aagcacaggg tatgccggaa ccgggttggg gtcgtatcac cgattcgcat     840

cagtggaaca cgctgctgag cctgcacaat gcgcagttcg acctgctgca acgtaccccg     900

gaagtggcac gttcgcgcgc cacgccgctg ctggatctga ttaaaaccgc tctgacgccg     960

catccgccgc agaagcaagc gtatggcgtg accctgccga cgagcgttct gtttatcgcg    1020

ggtcacgaca ccaacctggc aaatctgggc ggtgctctgg aactgcagtg gaccctgccg    1080

ggtcaaccgg ataacacgcc gccgggcggt gaactggttt tcgaacgttg gcgtcgcctg    1140

agcgacaatt ctcagtggat ccaagttagc ctggtctttc agaccctgca gcaaatgcgc    1200

gataaaaccc cgctgttcct gaacacgccg ccgggcgaag tgaagctgac cctggcgggt    1260

tgcgaagaac gtaacgccca gggcatgtgt tctctggcag gttttaccca gattgttaat    1320

gaagcacgca tcccggcttg tagtctgggt gcagctccag cggccgcacc ggctaaacag    1380

gaagcggcag ctccggctcc tgcagcgaag gcggaagcac cggccgcagc tcctgcggca    1440

aaagcgaccc cgcagcagct ggaggacaag attgaggagc tgctgagcaa gatctaccac    1500

ctggagaacg agatagcgag gctgaagaag ctgattggct aa                       1542
```

<210> SEQ ID NO 107
<211> LENGTH: 513
<212> TYPE: PRT
<213> ORGANISM: Artificial Sequence
<220> FEATURE:
<223> OTHER INFORMATION: Synthetic construct, Phy02-46: cc17

<400> SEQUENCE: 107

```
Met Arg Ala Lys Gln Leu Glu Asp Lys Ile Glu Glu Leu Leu Ser Lys
1               5                   10                  15

Ile Tyr His Leu Glu Asn Glu Ile Ala Arg Leu Lys Lys Leu Ile Gly
            20                  25                  30

Glu Arg Ser Ala Phe Ala Ala Gln Ser Glu Pro Glu Leu Lys Leu Glu
        35                  40                  45

Ser Val Val Ile Val Ser Arg His Gly Val Arg Ala Pro Thr Lys Phe
    50                  55                  60

Thr Gln Leu Met Gln Asp Val Thr Pro Asp Ala Phe Tyr Thr Trp Pro
65                  70                  75                  80

Val Lys Leu Gly Glu Leu Thr Pro Arg Gly Gly Glu Leu Ile Ala Tyr
                85                  90                  95

Leu Gly His Tyr Trp Arg Gln Arg Leu Val Ala Asp Gly Leu Leu Pro
            100                 105                 110

Lys Lys Gly Cys Pro Gln Ser Gly Gln Val Ala Ile Ile Ala Asp Val
        115                 120                 125

Asp Glu Arg Thr Arg Lys Thr Gly Glu Ala Phe Ala Ala Gly Leu Ala
    130                 135                 140

Pro Asp Cys Ala Ile Thr Val His Thr Gln Ala Asp Thr Ser Ser Pro
145                 150                 155                 160

Asp Pro Leu Phe Asn Pro Leu Lys Thr Gly Val Cys Gln Leu Asp Val
                165                 170                 175

Ala Gln Val Thr Asp Ala Ile Leu Glu Arg Ala Gly Gly Ser Ile Ala
            180                 185                 190

Asp Phe Thr Gly His Tyr Gln Thr Ala Phe Arg Glu Leu Glu Arg Val
        195                 200                 205

Leu Asn Phe Pro Gln Ser Asn Leu Ala Leu Lys Arg Glu Lys Gln Asp
    210                 215                 220

Glu Ser Ala Ser Leu Thr Gln Ala Leu Pro Ser Glu Leu Lys Val Ser
225                 230                 235                 240

Ala Asp Asn Val Ser Leu Thr Gly Ala Trp Ser Leu Ala Ser Met Leu
                245                 250                 255

Thr Glu Ile Phe Leu Leu Gln Gln Ala Gln Gly Met Pro Glu Pro Gly
            260                 265                 270

Trp Gly Arg Ile Thr Asp Ser His Gln Trp Asn Thr Leu Leu Ser Leu
        275                 280                 285

His Asn Ala Gln Phe Asp Leu Leu Gln Arg Thr Pro Glu Val Ala Arg
    290                 295                 300

Ser Arg Ala Thr Pro Leu Leu Asp Leu Ile Lys Thr Ala Leu Thr Pro
305                 310                 315                 320

His Pro Pro Gln Lys Gln Ala Tyr Gly Val Thr Leu Pro Thr Ser Val
                325                 330                 335

Leu Phe Ile Ala Gly His Asp Thr Asn Leu Ala Asn Leu Gly Gly Ala
            340                 345                 350

Leu Glu Leu Gln Trp Thr Leu Pro Gly Gln Pro Asp Asn Thr Pro Pro
        355                 360                 365
```

-continued

```
Gly Gly Glu Leu Val Phe Glu Arg Trp Arg Arg Leu Ser Asp Asn Ser
    370                 375                 380

Gln Trp Ile Gln Val Ser Leu Val Phe Gln Thr Leu Gln Gln Met Arg
385                 390                 395                 400

Asp Lys Thr Pro Leu Phe Leu Asn Thr Pro Pro Gly Glu Val Lys Leu
                405                 410                 415

Thr Leu Ala Gly Cys Glu Glu Arg Asn Ala Gln Gly Met Cys Ser Leu
            420                 425                 430

Ala Gly Phe Thr Gln Ile Val Asn Glu Ala Arg Ile Pro Ala Cys Ser
        435                 440                 445

Leu Gly Ala Ala Pro Ala Ala Ala Pro Ala Lys Gln Glu Ala Ala Ala
    450                 455                 460

Pro Ala Pro Ala Ala Lys Ala Glu Ala Pro Ala Ala Ala Pro Ala Ala
465                 470                 475                 480

Lys Ala Thr Pro Gln Gln Leu Glu Asp Lys Ile Glu Glu Leu Leu Ser
                485                 490                 495

Lys Ile Tyr His Leu Glu Asn Glu Ile Ala Arg Leu Lys Lys Leu Ile
            500                 505                 510

Gly
```

<210> SEQ ID NO 108
<211> LENGTH: 1569
<212> TYPE: DNA
<213> ORGANISM: Artificial Sequence
<220> FEATURE:
<223> OTHER INFORMATION: Synthetic construct, Phy02-55: cc17 coding seq

<400> SEQUENCE: 108

```
atgagggcca agcagctgga ggacaagatt gaggagctgc tgagcaagat ctaccacctg     60

gagaacgaga tagcccgcct gaagaagctg attggcgagc gcagcgcagc cgaagccgct    120

gcgaaggagg cagctgcgaa agaagcggct gcaaaagaag cggcagctaa ggctttgaat    180

accccgcaat cggctttcgc tgcccaatcg gaaccggaac tgaaactgga aagtgtggtt    240

attgtgtctc gtcatggcgt tcgcgctccg accaaattta cgcagctgat gcaagatgtc    300

accccggacg ccttctatac gtggccggtg aagctgggtg aactgacccc gcgtggcggt    360

gaactgatcg cctatctggg tcactactgg cgtcagcgcc tggtggcaga tggtctgctg    420

ccgaaaaagg gctgcccgca gagcggtcaa gttgcaatta tcgctgatgt cgacgaacgt    480

acccgcaaaa cgggtgaagc atttgcggcc ggtctggcac cggattgcgc cattaccgtt    540

catacgcagg cagataccag ctctccggac ccgctgttca acccgctgaa aaccggcgtc    600

tgtcagctgg atgtcgcgca agtgacggac gccattctgg aacgtgcagg cggttccatc    660

gctgatttta ccggtcacta ccagacggca ttccgtgaac tggaacgcgt tctgaacttt    720

ccgcagtcaa atctggcgct gaaacgcgaa aagcaggatg aaagtgcgtc cctgacccaa    780

gccctgccga gtgaactgaa agtctccgcc gacaatgtgt cactgaccgg cgcatggtca    840

ctggcttcga tgctgacgga aatttttctg ctgcagcaag cacagggtat gccggaaccg    900

ggttggggtc gtatcaccga ttcgcatcag tggaacacgc tgctgagcct gcacaatgcg    960

cagttcgacc tgctgcaacg taccccggaa gtggcacgtt cgcgcgccac gccgctgctg   1020

gatctgatta aaaccgctct gacgccgcat ccgccgcaga agcaagcgta tggcgtgacc   1080

ctgccgacga gcgttctgtt tatcgcgggt cacgacacca acctggcaaa tctgggcggt   1140

gctctggaac tgcagtggac cctgccgggt caaccggata acacgccgcc gggcggtgaa   1200
```

```
ctggttttcg aacgttggcg tcgcctgagc gacaattctc agtggatcca agttagcctg   1260

gtctttcaga ccctgcagca aatgcgcgat aaaaccccgc tgttcctgaa cacgccgccg   1320

ggcgaagtga agctgaccct ggcgggttgc gaagaacgta acgcccaggg catgtgttct   1380

ctggcaggtt ttacccagat tgttaatgaa gcacgcatcc cggcttgtag tctgggggc   1440

gcagaagcag ctgccaaaga ggcggccgca aaggtcaatc tgcagctgga ggacaagatt   1500

gaggagctgc tgagcaagat ctaccacctg gagaacgaga tagcgaggct gaagaagctg   1560

attggctaa                                                           1569
```

<210> SEQ ID NO 109
<211> LENGTH: 522
<212> TYPE: PRT
<213> ORGANISM: Artificial Sequence
<220> FEATURE:
<223> OTHER INFORMATION: Synthetic construct, Phy02-55: cc17

<400> SEQUENCE: 109

```
Met Arg Ala Lys Gln Leu Glu Asp Lys Ile Glu Glu Leu Leu Ser Lys
1               5                   10                  15

Ile Tyr His Leu Glu Asn Glu Ile Ala Arg Leu Lys Lys Leu Ile Gly
            20                  25                  30

Glu Arg Ser Ala Ala Glu Ala Ala Ala Lys Glu Ala Ala Ala Lys Glu
        35                  40                  45

Ala Ala Ala Lys Glu Ala Ala Ala Lys Ala Leu Asn Thr Pro Gln Ser
    50                  55                  60

Ala Phe Ala Ala Gln Ser Glu Pro Glu Leu Lys Leu Glu Ser Val Val
65                  70                  75                  80

Ile Val Ser Arg His Gly Val Arg Ala Pro Thr Lys Phe Thr Gln Leu
                85                  90                  95

Met Gln Asp Val Thr Pro Asp Ala Phe Tyr Thr Trp Pro Val Lys Leu
            100                 105                 110

Gly Glu Leu Thr Pro Arg Gly Gly Glu Leu Ile Ala Tyr Leu Gly His
        115                 120                 125

Tyr Trp Arg Gln Arg Leu Val Ala Asp Gly Leu Leu Pro Lys Lys Gly
    130                 135                 140

Cys Pro Gln Ser Gly Gln Val Ala Ile Ile Ala Asp Val Asp Glu Arg
145                 150                 155                 160

Thr Arg Lys Thr Gly Glu Ala Phe Ala Ala Gly Leu Ala Pro Asp Cys
                165                 170                 175

Ala Ile Thr Val His Thr Gln Ala Asp Thr Ser Ser Pro Asp Pro Leu
            180                 185                 190

Phe Asn Pro Leu Lys Thr Gly Val Cys Gln Leu Asp Val Ala Gln Val
        195                 200                 205

Thr Asp Ala Ile Leu Glu Arg Ala Gly Gly Ser Ile Ala Asp Phe Thr
    210                 215                 220

Gly His Tyr Gln Thr Ala Phe Arg Glu Leu Glu Arg Val Leu Asn Phe
225                 230                 235                 240

Pro Gln Ser Asn Leu Ala Leu Lys Arg Glu Lys Gln Asp Glu Ser Ala
                245                 250                 255

Ser Leu Thr Gln Ala Leu Pro Ser Glu Leu Lys Val Ser Ala Asp Asn
            260                 265                 270

Val Ser Leu Thr Gly Ala Trp Ser Leu Ala Ser Met Leu Thr Glu Ile
        275                 280                 285
```

-continued

```
Phe Leu Leu Gln Gln Ala Gln Gly Met Pro Glu Pro Gly Trp Gly Arg
    290                 295                 300

Ile Thr Asp Ser His Gln Trp Asn Thr Leu Leu Ser Leu His Asn Ala
305                 310                 315                 320

Gln Phe Asp Leu Leu Gln Arg Thr Pro Glu Val Ala Arg Ser Arg Ala
                325                 330                 335

Thr Pro Leu Leu Asp Leu Ile Lys Thr Ala Leu Thr Pro His Pro Pro
            340                 345                 350

Gln Lys Gln Ala Tyr Gly Val Thr Leu Pro Thr Ser Val Leu Phe Ile
        355                 360                 365

Ala Gly His Asp Thr Asn Leu Ala Asn Leu Gly Gly Ala Leu Glu Leu
    370                 375                 380

Gln Trp Thr Leu Pro Gly Gln Pro Asp Asn Thr Pro Pro Gly Gly Glu
385                 390                 395                 400

Leu Val Phe Glu Arg Trp Arg Arg Leu Ser Asp Asn Ser Gln Trp Ile
                405                 410                 415

Gln Val Ser Leu Val Phe Gln Thr Leu Gln Gln Met Arg Asp Lys Thr
            420                 425                 430

Pro Leu Phe Leu Asn Thr Pro Pro Gly Glu Val Lys Leu Thr Leu Ala
        435                 440                 445

Gly Cys Glu Glu Arg Asn Ala Gln Gly Met Cys Ser Leu Ala Gly Phe
    450                 455                 460

Thr Gln Ile Val Asn Glu Ala Arg Ile Pro Ala Cys Ser Leu Gly Gly
465                 470                 475                 480

Ala Glu Ala Ala Ala Lys Glu Ala Ala Ala Lys Val Asn Leu Gln Leu
                485                 490                 495

Glu Asp Lys Ile Glu Glu Leu Leu Ser Lys Ile Tyr His Leu Glu Asn
            500                 505                 510

Glu Ile Ala Arg Leu Lys Lys Leu Ile Gly
        515                 520
```

<210> SEQ ID NO 110
<211> LENGTH: 1503
<212> TYPE: DNA
<213> ORGANISM: Artificial Sequence
<220> FEATURE:
<223> OTHER INFORMATION: Synthetic construct, Phy02-33:cc30 coding seq

<400> SEQUENCE: 110

```
atgagggcca agcagctgga ggacaaggtc gaggagctgc tgagcaagaa ctaccacctg      60

gagaacgagg tcgcccgcct gaagaagctg gtgggcaccc gcagcggggg tggcagtgga     120

ggcggttcga ccccgcagtc cgcatttgcc gcccaatcgg aaccggaact gaaactggaa     180

agtgtggtta ttgtgtctcg tcatggcgtt cgcgctccga ccaaatttac gcagctgatg     240

caagatgtca ccccggacgc cttctatacg tggccggtga agctgggtga actgaccccg     300

cgtggcggtg aactgatcgc ctatctgggt cactactggc gtcagcgcct ggtggcagat     360

ggtctgctgc cgaaaaaggg ctgcccgcag agcggtcaag ttgcaattat cgctgatgtc     420

gacgaacgta cccgcaaaac gggtgaagca tttgcggccg gtctggcacc ggattgcgcc     480

attaccgttc atacgcaggc agataccagc tctccggacc cgctgttcaa cccgctgaaa     540

accggcgtct gtcagctgga tgtcgcgcaa gtgacggacg ccattctgga acgtgcaggc     600

ggttccatcg ctgattttac cggtcactac cagacggcat tccgtgaact ggaacgcgtt     660

ctgaactttc cgcagtcaaa tctggcgctg aaacgcgaaa agcaggatga aagtgcgtcc     720
```

```
ctgacccaag ccctgccgag tgaactgaaa gtctccgccg acaatgtgtc actgaccggc    780

gcatggtcac tggcttcgat gctgacggaa atttttctgc tgcagcaagc acagggtatg    840

ccggaaccgg gttggggtcg tatcaccgat tcgcatcagt ggaacacgct gctgagcctg    900

cacaatgcgc agttcgacct gctgcaacgt accccggaag tggcacgttc gcgcgccacg    960

ccgctgctgg atctgattaa aaccgctctg acgccgcatc cgccgcagaa gcaagcgtat   1020

ggcgtgaccc tgccgacgag cgttctgttt atcgcgggtc acgacaccaa cctggcaaat   1080

ctgggcggtg ctctggaact gcagtggacc ctgccgggtc aaccggataa cacgccgccg   1140

ggcggtgaac tggttttcga acgttggcgt cgcctgagcg acaattctca gtggatccaa   1200

gttagcctgg tctttcagac cctgcagcaa atgcgcgata aaaccccgct gttcctgaac   1260

acgccgccgg gcgaagtgaa gctgaccctg gcgggttgcg aagaacgtaa cgcccagggc   1320

atgtgttctc tggcaggttt tacccagatt gttaatgaag cacgcatccc ggcttgtagt   1380

ctgggtggcg ggagcggtgg agggagtggg ggcggtcaat tggaagataa agtggaagag   1440

ctcctgtcca aaaattatca tctggaaaat gaggtggccc gcttgaagaa actcgtggga   1500

taa                                                                  1503
```

```
<210> SEQ ID NO 111
<211> LENGTH: 500
<212> TYPE: PRT
<213> ORGANISM: Artificial Sequence
<220> FEATURE:
<223> OTHER INFORMATION: Synthetic construct, Phy02-33:cc30

<400> SEQUENCE: 111

Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Thr Arg Ser Gly Gly Gly Ser Gly Gly Gly Ser Thr Pro Gln Ser Ala
        35                  40                  45

Phe Ala Ala Gln Ser Glu Pro Glu Leu Lys Leu Glu Ser Val Val Ile
    50                  55                  60

Val Ser Arg His Gly Val Arg Ala Pro Thr Lys Phe Thr Gln Leu Met
65                  70                  75                  80

Gln Asp Val Thr Pro Asp Ala Phe Tyr Thr Trp Pro Val Lys Leu Gly
                85                  90                  95

Glu Leu Thr Pro Arg Gly Gly Glu Leu Ile Ala Tyr Leu Gly His Tyr
            100                 105                 110

Trp Arg Gln Arg Leu Val Ala Asp Gly Leu Leu Pro Lys Lys Gly Cys
        115                 120                 125

Pro Gln Ser Gly Gln Val Ala Ile Ile Ala Asp Val Asp Glu Arg Thr
    130                 135                 140

Arg Lys Thr Gly Glu Ala Phe Ala Ala Gly Leu Ala Pro Asp Cys Ala
145                 150                 155                 160

Ile Thr Val His Thr Gln Ala Asp Thr Ser Ser Pro Asp Pro Leu Phe
                165                 170                 175

Asn Pro Leu Lys Thr Gly Val Cys Gln Leu Asp Val Ala Gln Val Thr
            180                 185                 190

Asp Ala Ile Leu Glu Arg Ala Gly Gly Ser Ile Ala Asp Phe Thr Gly
        195                 200                 205

His Tyr Gln Thr Ala Phe Arg Glu Leu Glu Arg Val Leu Asn Phe Pro
    210                 215                 220
```

```
Gln Ser Asn Leu Ala Leu Lys Arg Glu Lys Gln Asp Glu Ser Ala Ser
225                 230                 235                 240

Leu Thr Gln Ala Leu Pro Ser Glu Leu Lys Val Ser Ala Asp Asn Val
                245                 250                 255

Ser Leu Thr Gly Ala Trp Ser Leu Ala Ser Met Leu Thr Glu Ile Phe
            260                 265                 270

Leu Leu Gln Gln Ala Gln Gly Met Pro Glu Pro Gly Trp Gly Arg Ile
        275                 280                 285

Thr Asp Ser His Gln Trp Asn Thr Leu Leu Ser Leu His Asn Ala Gln
    290                 295                 300

Phe Asp Leu Leu Gln Arg Thr Pro Glu Val Ala Arg Ser Arg Ala Thr
305                 310                 315                 320

Pro Leu Leu Asp Leu Ile Lys Thr Ala Leu Thr Pro His Pro Pro Gln
                325                 330                 335

Lys Gln Ala Tyr Gly Val Thr Leu Pro Thr Ser Val Leu Phe Ile Ala
            340                 345                 350

Gly His Asp Thr Asn Leu Ala Asn Leu Gly Gly Ala Leu Glu Leu Gln
        355                 360                 365

Trp Thr Leu Pro Gly Gln Pro Asp Asn Thr Pro Pro Gly Gly Glu Leu
    370                 375                 380

Val Phe Glu Arg Trp Arg Arg Leu Ser Asp Asn Ser Gln Trp Ile Gln
385                 390                 395                 400

Val Ser Leu Val Phe Gln Thr Leu Gln Gln Met Arg Asp Lys Thr Pro
                405                 410                 415

Leu Phe Leu Asn Thr Pro Pro Gly Glu Val Lys Leu Thr Leu Ala Gly
            420                 425                 430

Cys Glu Glu Arg Asn Ala Gln Gly Met Cys Ser Leu Ala Gly Phe Thr
        435                 440                 445

Gln Ile Val Asn Glu Ala Arg Ile Pro Ala Cys Ser Leu Gly Gly Gly
    450                 455                 460

Ser Gly Gly Gly Ser Gly Gly Gly Gln Leu Glu Asp Lys Val Glu Glu
465                 470                 475                 480

Leu Leu Ser Lys Asn Tyr His Leu Glu Asn Glu Val Ala Arg Leu Lys
                485                 490                 495

Lys Leu Val Gly
            500
```

<210> SEQ ID NO 112
<211> LENGTH: 1518
<212> TYPE: DNA
<213> ORGANISM: Artificial Sequence
<220> FEATURE:
<223> OTHER INFORMATION: Synthetic construct, Phy02-38: cc30coding seq

<400> SEQUENCE: 112

```
atgagggcca agcagctgga ggacaaggtc gaggagctgc tgagcaagaa ctaccacctg      60

gagaacgagg tcgcccgcct gaagaagctg gtgggcaccc gcagcggtgg ctcgtcaggg     120

agtacgacaa ccacgcgtat caccccgcaa tctgcgttcg ctgcccaatc ggaaccggaa     180

ctgaaactgg aaagtgtggt tattgtgtct cgtcatggcg ttcgcgctcc gaccaaattt     240

acgcagctga tgcaagatgt caccccggac gccttctata cgtggccggt gaagctgggt     300

gaactgaccc cgcgtggcgg tgaactgatc gcctatctgg gtcactactg gcgtcagcgc     360

ctggtggcag atggtctgct gccgaaaaag ggctgcccgc agagcggtca agttgcaatt     420
```

```
atcgctgatg tcgacgaacg tacccgcaaa acgggtgaag catttgcggc cggtctggca    480

ccggattgcg ccattaccgt tcatacgcag gcagatacca gctctccgga cccgctgttc    540

aacccgctga aaaccggcgt ctgtcagctg gatgtcgcgc aagtgacgga cgccattctg    600

gaacgtgcag gcggttccat cgctgatttt accggtcact accagacggc attccgtgaa    660

ctggaacgcg ttctgaactt tccgcagtca aatctggcgc tgaaacgcga aaagcaggat    720

gaaagtgcgt ccctgaccca agccctgccg agtgaactga aagtctccgc cgacaatgtg    780

tcactgaccg gcgcatggtc actggcttcg atgctgacgg aaatttttct gctgcagcaa    840

gcacagggta tgccggaacc gggttggggt cgtatcaccg attcgcatca gtggaacacg    900

ctgctgagcc tgcacaatgc gcagttcgac ctgctgcaac gtaccccgga agtggcacgt    960

tcgcgcgcca cgccgctgct ggatctgatt aaaaccgctc tgacgccgca tccgccgcag   1020

aagcaagcgt atggcgtgac cctgccgacg agcgttctgt ttatcgcggg tcacgacacc   1080

aacctggcaa atctgggcgg tgctctggaa ctgcagtgga ccctgccggg tcaaccggat   1140

aacacgccgc cgggcggtga actggttttc gaacgttggc gtcgcctgag cgacaattct   1200

cagtggatcc aagttagcct ggtctttcag accctgcagc aaatgcgcga taaaaccccg   1260

ctgttcctga acacgccgcc gggcgaagtg aagctgaccc tggcgggttg cgaagaacgt   1320

aacgcccagg gcatgtgttc tctggcaggt tttacccaga ttgttaatga agcacgcatc   1380

ccggcttgta gtctgcaaaa cacgtttagc caggggagta gctcgggatc ccaattggaa   1440

gataaagtgg aagagctcct gtccaaaaat tatcatctgg aaaatgaggt ggcccgcttg   1500

aagaaactcg tgggataa                                                 1518
```

```
<210> SEQ ID NO 113
<211> LENGTH: 505
<212> TYPE: PRT
<213> ORGANISM: Artificial Sequence
<220> FEATURE:
<223> OTHER INFORMATION: Synthetic construct, Phy02-38: cc30

<400> SEQUENCE: 113

Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Thr Arg Ser Gly Gly Ser Ser Gly Ser Thr Thr Thr Thr Arg Ile Thr
        35                  40                  45

Pro Gln Ser Ala Phe Ala Ala Gln Ser Glu Pro Glu Leu Lys Leu Glu
    50                  55                  60

Ser Val Val Ile Val Ser Arg His Gly Val Arg Ala Pro Thr Lys Phe
65                  70                  75                  80

Thr Gln Leu Met Gln Asp Val Thr Pro Asp Ala Phe Tyr Thr Trp Pro
                85                  90                  95

Val Lys Leu Gly Glu Leu Thr Pro Arg Gly Gly Glu Leu Ile Ala Tyr
            100                 105                 110

Leu Gly His Tyr Trp Arg Gln Arg Leu Val Ala Asp Gly Leu Leu Pro
        115                 120                 125

Lys Lys Gly Cys Pro Gln Ser Gly Gln Val Ala Ile Ile Ala Asp Val
    130                 135                 140

Asp Glu Arg Thr Arg Lys Thr Gly Glu Ala Phe Ala Ala Gly Leu Ala
145                 150                 155                 160

Pro Asp Cys Ala Ile Thr Val His Thr Gln Ala Asp Thr Ser Ser Pro
```

-continued

```
                165                 170                 175

Asp Pro Leu Phe Asn Pro Leu Lys Thr Gly Val Cys Gln Leu Asp Val
            180                 185                 190

Ala Gln Val Thr Asp Ala Ile Leu Glu Arg Ala Gly Gly Ser Ile Ala
        195                 200                 205

Asp Phe Thr Gly His Tyr Gln Thr Ala Phe Arg Glu Leu Glu Arg Val
    210                 215                 220

Leu Asn Phe Pro Gln Ser Asn Leu Ala Leu Lys Arg Glu Lys Gln Asp
225                 230                 235                 240

Glu Ser Ala Ser Leu Thr Gln Ala Leu Pro Ser Glu Leu Lys Val Ser
                245                 250                 255

Ala Asp Asn Val Ser Leu Thr Gly Ala Trp Ser Leu Ala Ser Met Leu
            260                 265                 270

Thr Glu Ile Phe Leu Leu Gln Gln Ala Gln Gly Met Pro Glu Pro Gly
        275                 280                 285

Trp Gly Arg Ile Thr Asp Ser His Gln Trp Asn Thr Leu Leu Ser Leu
    290                 295                 300

His Asn Ala Gln Phe Asp Leu Leu Gln Arg Thr Pro Glu Val Ala Arg
305                 310                 315                 320

Ser Arg Ala Thr Pro Leu Leu Asp Leu Ile Lys Thr Ala Leu Thr Pro
                325                 330                 335

His Pro Pro Gln Lys Gln Ala Tyr Gly Val Thr Leu Pro Thr Ser Val
            340                 345                 350

Leu Phe Ile Ala Gly His Asp Thr Asn Leu Ala Asn Leu Gly Gly Ala
        355                 360                 365

Leu Glu Leu Gln Trp Thr Leu Pro Gly Gln Pro Asp Asn Thr Pro Pro
    370                 375                 380

Gly Gly Glu Leu Val Phe Glu Arg Trp Arg Arg Leu Ser Asp Asn Ser
385                 390                 395                 400

Gln Trp Ile Gln Val Ser Leu Val Phe Gln Thr Leu Gln Gln Met Arg
                405                 410                 415

Asp Lys Thr Pro Leu Phe Leu Asn Thr Pro Pro Gly Glu Val Lys Leu
            420                 425                 430

Thr Leu Ala Gly Cys Glu Glu Arg Asn Ala Gln Gly Met Cys Ser Leu
        435                 440                 445

Ala Gly Phe Thr Gln Ile Val Asn Glu Ala Arg Ile Pro Ala Cys Ser
    450                 455                 460

Leu Gln Asn Thr Phe Ser Gln Gly Ser Ser Ser Gly Ser Gln Leu Glu
465                 470                 475                 480

Asp Lys Val Glu Glu Leu Leu Ser Lys Asn Tyr His Leu Glu Asn Glu
                485                 490                 495

Val Ala Arg Leu Lys Lys Leu Val Gly
            500                 505
```

<210> SEQ ID NO 114
<211> LENGTH: 1542
<212> TYPE: DNA
<213> ORGANISM: Artificial Sequence
<220> FEATURE:
<223> OTHER INFORMATION: Synthetic construct, Phy02-46: cc30

<400> SEQUENCE: 114

```
atgagggcca agcagctgga ggacaaggtc gaggagctgc tgagcaagaa ctaccacctg      60

gagaacgagg tcgcccgcct gaagaagctg gtgggcaccc gcagcgcctt tgcagcccaa     120
```

```
tcggaaccgg aactgaaact ggaaagtgtg gttattgtgt ctcgtcatgg cgttcgcgct    180

ccgaccaaat ttacgcagct gatgcaagat gtcaccccgg acgccttcta tacgtggccg    240

gtgaagctgg gtgaactgac ccgcgtggc ggtgaactga tcgcctatct gggtcactac    300

tggcgtcagc gcctggtggc agatggtctg ctgccgaaaa agggctgccc gcagagcggt    360

caagttgcaa ttatcgctga tgtcgacgaa cgtacccgca aaacgggtga agcatttgcg    420

gccggtctgg caccggattg cgccattacc gttcatacgc aggcagatac cagctctccg    480

gacccgctgt tcaacccgct gaaaaccggc gtctgtcagc tggatgtcgc gcaagtgacg    540

gacgccattc tggaacgtgc aggcggttcc atcgctgatt ttaccggtca ctaccagacg    600

gcattccgtg aactggaacg cgttctgaac tttccgcagt caaatctggc gctgaaacgc    660

gaaaagcagg atgaaagtgc gtccctgacc caagccctgc cgagtgaact gaaagtctcc    720

gccgacaatg tgtcactgac cggcgcatgg tcactggctt cgatgctgac ggaaattttt    780

ctgctgcagc aagcacaggg tatgccggaa ccgggttggg gtcgtatcac cgattcgcat    840

cagtggaaca cgctgctgag cctgcacaat gcgcagttcg acctgctgca acgtaccccg    900

gaagtggcac gttcgcgcgc cacgccgctg ctggatctga ttaaaaccgc tctgacgccg    960

catccgccgc agaagcaagc gtatggcgtg accctgccga cgagcgttct gtttatcgcg   1020

ggtcacgaca ccaacctggc aaatctgggc ggtgctctgg aactgcagtg gaccctgccg   1080

ggtcaaccgg ataacacgcc gccgggcggt gaactggttt tcgaacgttg gcgtcgcctg   1140

agcgacaatt ctcagtggat ccaagttagc ctggtctttc agaccctgca gcaaatgcgc   1200

gataaaaccc cgctgttcct gaacacgccg ccgggcgaag tgaagctgac cctggcgggt   1260

tgcgaagaac gtaacgccca gggcatgtgt tctctggcag gttttaccca gattgttaat   1320

gaagcacgca tcccggcttg tagtctgggt gcagctccag cggccgcacc ggctaaacag   1380

gaagcggcag ctccggctcc tgcagcgaag gcggaagcac cggccgcagc tcctgcggca   1440

aaagcgaccc cgcagcaatt ggaagataaa gtggaagagc tcctgtccaa aaattatcat   1500

ctggaaaatg aggtggcccg cttgaagaaa ctcgtgggat aa                      1542
```

<210> SEQ ID NO 115
<211> LENGTH: 513
<212> TYPE: PRT
<213> ORGANISM: Artificial Sequence
<220> FEATURE:
<223> OTHER INFORMATION: Synthetic construct, Phy02-46: cc30

<400> SEQUENCE: 115

```
Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Thr Arg Ser Ala Phe Ala Ala Gln Ser Glu Pro Glu Leu Lys Leu Glu
        35                  40                  45

Ser Val Val Ile Val Ser Arg His Gly Val Arg Ala Pro Thr Lys Phe
    50                  55                  60

Thr Gln Leu Met Gln Asp Val Thr Pro Asp Ala Phe Tyr Thr Trp Pro
65                  70                  75                  80

Val Lys Leu Gly Glu Leu Thr Pro Arg Gly Gly Glu Leu Ile Ala Tyr
                85                  90                  95

Leu Gly His Tyr Trp Arg Gln Arg Leu Val Ala Asp Gly Leu Leu Pro
            100                 105                 110
```

-continued

```
Lys Lys Gly Cys Pro Gln Ser Gly Gln Val Ala Ile Ile Ala Asp Val
        115                 120                 125

Asp Glu Arg Thr Arg Lys Thr Gly Glu Ala Phe Ala Ala Gly Leu Ala
    130                 135                 140

Pro Asp Cys Ala Ile Thr Val His Thr Gln Ala Asp Thr Ser Ser Pro
145                 150                 155                 160

Asp Pro Leu Phe Asn Pro Leu Lys Thr Gly Val Cys Gln Leu Asp Val
                165                 170                 175

Ala Gln Val Thr Asp Ala Ile Leu Glu Arg Ala Gly Gly Ser Ile Ala
            180                 185                 190

Asp Phe Thr Gly His Tyr Gln Thr Ala Phe Arg Glu Leu Glu Arg Val
        195                 200                 205

Leu Asn Phe Pro Gln Ser Asn Leu Ala Leu Lys Arg Glu Lys Gln Asp
    210                 215                 220

Glu Ser Ala Ser Leu Thr Gln Ala Leu Pro Ser Glu Leu Lys Val Ser
225                 230                 235                 240

Ala Asp Asn Val Ser Leu Thr Gly Ala Trp Ser Leu Ala Ser Met Leu
                245                 250                 255

Thr Glu Ile Phe Leu Leu Gln Gln Ala Gln Gly Met Pro Glu Pro Gly
            260                 265                 270

Trp Gly Arg Ile Thr Asp Ser His Gln Trp Asn Thr Leu Leu Ser Leu
        275                 280                 285

His Asn Ala Gln Phe Asp Leu Leu Gln Arg Thr Pro Glu Val Ala Arg
    290                 295                 300

Ser Arg Ala Thr Pro Leu Leu Asp Leu Ile Lys Thr Ala Leu Thr Pro
305                 310                 315                 320

His Pro Pro Gln Lys Gln Ala Tyr Gly Val Thr Leu Pro Thr Ser Val
                325                 330                 335

Leu Phe Ile Ala Gly His Asp Thr Asn Leu Ala Asn Leu Gly Gly Ala
            340                 345                 350

Leu Glu Leu Gln Trp Thr Leu Pro Gly Gln Pro Asp Asn Thr Pro Pro
        355                 360                 365

Gly Gly Glu Leu Val Phe Glu Arg Trp Arg Arg Leu Ser Asp Asn Ser
    370                 375                 380

Gln Trp Ile Gln Val Ser Leu Val Phe Gln Thr Leu Gln Gln Met Arg
385                 390                 395                 400

Asp Lys Thr Pro Leu Phe Leu Asn Thr Pro Pro Gly Glu Val Lys Leu
                405                 410                 415

Thr Leu Ala Gly Cys Glu Glu Arg Asn Ala Gln Gly Met Cys Ser Leu
            420                 425                 430

Ala Gly Phe Thr Gln Ile Val Asn Glu Ala Arg Ile Pro Ala Cys Ser
        435                 440                 445

Leu Gly Ala Ala Pro Ala Ala Ala Pro Ala Lys Gln Glu Ala Ala Ala
    450                 455                 460

Pro Ala Pro Ala Ala Lys Ala Glu Ala Pro Ala Ala Ala Pro Ala Ala
465                 470                 475                 480

Lys Ala Thr Pro Gln Gln Leu Glu Asp Lys Val Glu Glu Leu Leu Ser
                485                 490                 495

Lys Asn Tyr His Leu Glu Asn Glu Val Ala Arg Leu Lys Lys Leu Val
            500                 505                 510

Gly
```

<210> SEQ ID NO 116

<211> LENGTH: 1569
<212> TYPE: DNA
<213> ORGANISM: Artificial Sequence
<220> FEATURE:
<223> OTHER INFORMATION: Synthetic construct, Phy02-55: cc30 coding seq

<400> SEQUENCE: 116

```
atgagggcca agcagctgga ggacaaggtc gaggagctgc tgagcaagaa ctaccacctg     60
gagaacgagg tcgcccgcct gaagaagctg gtgggcaccc gcagcgcagc cgaagccgct    120
gcgaaggagg cagctgcgaa agaagcggct gcaaaagaag cggcagctaa ggctttgaat    180
accccgcaat cggctttcgc tgcccaatcg gaaccggaac tgaaactgga aagtgtggtt    240
attgtgtctc gtcatggcgt tcgcgctccg accaaattta cgcagctgat gcaagatgtc    300
accccggacg ccttctatac gtggccggtg aagctgggtg aactgacccc gcgtggcggt    360
gaactgatcg cctatctggg tcactactgg cgtcagcgcc tggtggcaga tggtctgctg    420
ccgaaaaagg gctgcccgca gagcggtcaa gttgcaatta tcgctgatgt cgacgaacgt    480
acccgcaaaa cgggtgaagc atttgcggcc ggtctggcac cggattgcgc cattaccgtt    540
catacgcagg cagataccag ctctccggac ccgctgttca acccgctgaa aaccggcgtc    600
tgtcagctgg atgtcgcgca agtgacggac gccattctgg aacgtgcagg cggttccatc    660
gctgatttta ccggtcacta ccagacggca ttccgtgaac tggaacgcgt tctgaacttt    720
ccgcagtcaa atctggcgct gaaacgcgaa aagcaggatg aaagtgcgtc cctgacccaa    780
gccctgccga gtgaactgaa agtctccgcc gacaatgtgt cactgaccgg cgcatggtca    840
ctggcttcga tgctgacgga aatttttctg ctgcagcaag cacagggtat gccggaaccg    900
ggttggggtc gtatcaccga ttcgcatcag tggaacacgc tgctgagcct gcacaatgcg    960
cagttcgacc tgctgcaacg taccccggaa gtggcacgtt cgcgcgccac gccgctgctg   1020
gatctgatta aaaccgctct gacgccgcat ccgccgcaga agcaagcgta tggcgtgacc   1080
ctgccgacga gcgttctgtt tatcgcgggt cacgacacca acctggcaaa tctgggcggt   1140
gctctggaac tgcagtggac cctgccgggt caaccggata acacgccgcc gggcggtgaa   1200
ctggttttcg aacgttggcg tcgcctgagc gacaattctc agtggatcca agttagcctg   1260
gtctttcaga ccctgcagca aatgcgcgat aaaaccccgc tgttcctgaa cacgccgccg   1320
ggcgaagtga agctgaccct ggcgggttgc gaagaacgta acgcccaggg catgtgttct   1380
ctggcaggtt ttacccagat tgttaatgaa gcacgcatcc cggcttgtag tctgggggc    1440
gcagaagcag ctgccaaaga ggcggccgca aaggtcaatc tgcaattgga agataaagtg   1500
gaagagctcc tgtccaaaaa ttatcatctg gaaaatgagg tggcccgctt gaagaaactc   1560
gtgggataa                                                            1569
```

<210> SEQ ID NO 117
<211> LENGTH: 522
<212> TYPE: PRT
<213> ORGANISM: Artificial Sequence
<220> FEATURE:
<223> OTHER INFORMATION: Synthetic construct, Phy02-55: cc30

<400> SEQUENCE: 117

```
Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Thr Arg Ser Ala Ala Glu Ala Ala Ala Lys Glu Ala Ala Ala Lys Glu
```

-continued

```
        35                  40                  45

Ala Ala Ala Lys Glu Ala Ala Ala Lys Ala Leu Asn Thr Pro Gln Ser
    50                  55                  60

Ala Phe Ala Ala Gln Ser Glu Pro Glu Leu Lys Leu Glu Ser Val Val
65                  70                  75                  80

Ile Val Ser Arg His Gly Val Arg Ala Pro Thr Lys Phe Thr Gln Leu
                85                  90                  95

Met Gln Asp Val Thr Pro Asp Ala Phe Tyr Thr Trp Pro Val Lys Leu
            100                 105                 110

Gly Glu Leu Thr Pro Arg Gly Gly Glu Leu Ile Ala Tyr Leu Gly His
        115                 120                 125

Tyr Trp Arg Gln Arg Leu Val Ala Asp Gly Leu Leu Pro Lys Lys Gly
    130                 135                 140

Cys Pro Gln Ser Gly Gln Val Ala Ile Ile Ala Asp Val Asp Glu Arg
145                 150                 155                 160

Thr Arg Lys Thr Gly Glu Ala Phe Ala Ala Gly Leu Ala Pro Asp Cys
                165                 170                 175

Ala Ile Thr Val His Thr Gln Ala Asp Thr Ser Ser Pro Asp Pro Leu
            180                 185                 190

Phe Asn Pro Leu Lys Thr Gly Val Cys Gln Leu Asp Val Ala Gln Val
        195                 200                 205

Thr Asp Ala Ile Leu Glu Arg Ala Gly Gly Ser Ile Ala Asp Phe Thr
    210                 215                 220

Gly His Tyr Gln Thr Ala Phe Arg Glu Leu Glu Arg Val Leu Asn Phe
225                 230                 235                 240

Pro Gln Ser Asn Leu Ala Leu Lys Arg Glu Lys Gln Asp Glu Ser Ala
                245                 250                 255

Ser Leu Thr Gln Ala Leu Pro Ser Glu Leu Lys Val Ser Ala Asp Asn
            260                 265                 270

Val Ser Leu Thr Gly Ala Trp Ser Leu Ala Ser Met Leu Thr Glu Ile
        275                 280                 285

Phe Leu Leu Gln Gln Ala Gln Gly Met Pro Glu Pro Gly Trp Gly Arg
    290                 295                 300

Ile Thr Asp Ser His Gln Trp Asn Thr Leu Leu Ser Leu His Asn Ala
305                 310                 315                 320

Gln Phe Asp Leu Leu Gln Arg Thr Pro Glu Val Ala Arg Ser Arg Ala
                325                 330                 335

Thr Pro Leu Leu Asp Leu Ile Lys Thr Ala Leu Thr Pro His Pro Pro
            340                 345                 350

Gln Lys Gln Ala Tyr Gly Val Thr Leu Pro Thr Ser Val Leu Phe Ile
        355                 360                 365

Ala Gly His Asp Thr Asn Leu Ala Asn Leu Gly Gly Ala Leu Glu Leu
    370                 375                 380

Gln Trp Thr Leu Pro Gly Gln Pro Asp Asn Thr Pro Pro Gly Gly Glu
385                 390                 395                 400

Leu Val Phe Glu Arg Trp Arg Arg Leu Ser Asp Asn Ser Gln Trp Ile
                405                 410                 415

Gln Val Ser Leu Val Phe Gln Thr Leu Gln Gln Met Arg Asp Lys Thr
            420                 425                 430

Pro Leu Phe Leu Asn Thr Pro Pro Gly Glu Val Lys Leu Thr Leu Ala
        435                 440                 445

Gly Cys Glu Glu Arg Asn Ala Gln Gly Met Cys Ser Leu Ala Gly Phe
    450                 455                 460
```

```
Thr Gln Ile Val Asn Glu Ala Arg Ile Pro Ala Cys Ser Leu Gly Gly
465                 470                 475                 480

Ala Glu Ala Ala Ala Lys Glu Ala Ala Ala Lys Val Asn Leu Gln Leu
                485                 490                 495

Glu Asp Lys Val Glu Glu Leu Leu Ser Lys Asn Tyr His Leu Glu Asn
            500                 505                 510

Glu Val Ala Arg Leu Lys Lys Leu Val Gly
        515                 520


<210> SEQ ID NO 118
<211> LENGTH: 1659
<212> TYPE: DNA
<213> ORGANISM: Artificial Sequence
<220> FEATURE:
<223> OTHER INFORMATION: Synthetic construct, Tag:Tlinker1:Phy02:Clink1:
      Catcher coding seq

<400> SEQUENCE: 118

atggcccaca tcgtgatggt ggacgcctac aagccgacga agggttcagg ggttccggt     60

gcccaatcgg aaccggaact gaaactggaa agtgtggtta ttgtgtctcg tcatggcgtt    120

cgcgctccga ccaaatttac gcagctgatg caagatgtca ccccggacgc cttctatacg    180

tggccggtga agctgggtga actgaccccg cgtggcggtg aactgatcgc ctatctgggt    240

cactactggc gtcagcgcct ggtggcagat ggtctgctgc cgaaaaaggg ctgcccgcag    300

agcggtcaag ttgcaattat cgctgatgtc gacgaacgta cccgcaaaac gggtgaagca    360

tttgcggccg gtctggcacc ggattgcgcc attaccgttc atacgcaggc agataccagc    420

tctccggacc cgctgttcaa cccgctgaaa accggcgtct gtcagctgga tgtcgcgcaa    480

gtgacggacg ccattctgga acgtgcaggc ggttccatcg ctgattttac cggtcactac    540

cagacggcat tccgtgaact ggaacgcgtt ctgaactttc cgcagtcaaa tctggcgctg    600

aaacgcgaaa agcaggatga aagtgcgtcc ctgacccaag ccctgccgag tgaactgaaa    660

gtctccgccg acaatgtgtc actgaccggc gcatggtcac tggcttcgat gctgacggaa    720

atttttctgc tgcagcaagc acagggtatg ccggaaccgg gttggggtcg tatcaccgat    780

tcgcatcagt ggaacacgct gctgagcctg cacaatgcgc agttcgacct gctgcaacgt    840

accccggaag tggcacgttc gcgcgccacg ccgctgctgg atctgattaa aaccgctctg    900

acgccgcatc cgccgcagaa gcaagcgtat ggcgtgaccc tgccgacgag cgttctgttt    960

atcgcgggtc acgacaccaa cctggcaaat ctgggcggtg ctctggaact gcagtggacc   1020

ctgccgggtc aaccggataa cacgccgccg ggcggtgaac tggttttcga acgttggcgt   1080

cgcctgagcg acaattctca gtggatccaa gttagcctgg tctttcagac cctgcagcaa   1140

atgcgcgata aaccccgct gttcctgaac acgccgccgg gcgaagtgaa gctgaccctg    1200

gcgggttgcg aagaacgtaa cgcccagggc atgtgttctc tggcaggttt tacccagatt   1260

gttaatgaag cacgcatccc ggcttgtagt ctggggagtg gtggcagcgg aggcgctatg   1320

gttgatacct tatcaggttt atcaagtgag caaggtcagt ccggtgatat gacaattgaa   1380

gaagatagtg ctacccatat taaattctca aaacgtgatg aggacggcaa agagttagct   1440

ggtgcaacta tggagttgcg tgattcatct ggtaaaacta ttagtacatg gatttcagat   1500

ggacaagtga aagatttcta cctgtatcca ggaaaatata catttgtcga aaccgcagca   1560

ccagacggtt atgaggtagc aactgctatt acctttacag ttaatgagca aggtcaggtt   1620

actgtaaatg gcaaagcaac taaaggtgac gctcatatt                           1659
```

<210> SEQ ID NO 119
<211> LENGTH: 553
<212> TYPE: PRT
<213> ORGANISM: Artificial Sequence
<220> FEATURE:
<223> OTHER INFORMATION: Synthetic construct, Tag:Tlinker1:Phy02:Clink1:
Catcher

<400> SEQUENCE: 119

```
Met Ala His Ile Val Met Val Asp Ala Tyr Lys Pro Thr Lys Gly Ser
1               5                   10                  15

Gly Gly Ser Gly Ala Gln Ser Glu Pro Glu Leu Lys Leu Glu Ser Val
            20                  25                  30

Val Ile Val Ser Arg His Gly Val Arg Ala Pro Thr Lys Phe Thr Gln
        35                  40                  45

Leu Met Gln Asp Val Thr Pro Asp Ala Phe Tyr Thr Trp Pro Val Lys
    50                  55                  60

Leu Gly Glu Leu Thr Pro Arg Gly Gly Glu Leu Ile Ala Tyr Leu Gly
65                  70                  75                  80

His Tyr Trp Arg Gln Arg Leu Val Ala Asp Gly Leu Leu Pro Lys Lys
                85                  90                  95

Gly Cys Pro Gln Ser Gly Gln Val Ala Ile Ile Ala Asp Val Asp Glu
            100                 105                 110

Arg Thr Arg Lys Thr Gly Glu Ala Phe Ala Ala Gly Leu Ala Pro Asp
        115                 120                 125

Cys Ala Ile Thr Val His Thr Gln Ala Asp Thr Ser Ser Pro Asp Pro
    130                 135                 140

Leu Phe Asn Pro Leu Lys Thr Gly Val Cys Gln Leu Asp Val Ala Gln
145                 150                 155                 160

Val Thr Asp Ala Ile Leu Glu Arg Ala Gly Gly Ser Ile Ala Asp Phe
                165                 170                 175

Thr Gly His Tyr Gln Thr Ala Phe Arg Glu Leu Glu Arg Val Leu Asn
            180                 185                 190

Phe Pro Gln Ser Asn Leu Ala Leu Lys Arg Glu Lys Gln Asp Glu Ser
        195                 200                 205

Ala Ser Leu Thr Gln Ala Leu Pro Ser Glu Leu Lys Val Ser Ala Asp
    210                 215                 220

Asn Val Ser Leu Thr Gly Ala Trp Ser Leu Ala Ser Met Leu Thr Glu
225                 230                 235                 240

Ile Phe Leu Leu Gln Gln Ala Gln Gly Met Pro Glu Pro Gly Trp Gly
                245                 250                 255

Arg Ile Thr Asp Ser His Gln Trp Asn Thr Leu Leu Ser Leu His Asn
            260                 265                 270

Ala Gln Phe Asp Leu Leu Gln Arg Thr Pro Glu Val Ala Arg Ser Arg
        275                 280                 285

Ala Thr Pro Leu Leu Asp Leu Ile Lys Thr Ala Leu Thr Pro His Pro
    290                 295                 300

Pro Gln Lys Gln Ala Tyr Gly Val Thr Leu Pro Thr Ser Val Leu Phe
305                 310                 315                 320

Ile Ala Gly His Asp Thr Asn Leu Ala Asn Leu Gly Gly Ala Leu Glu
                325                 330                 335

Leu Gln Trp Thr Leu Pro Gly Gln Pro Asp Asn Thr Pro Pro Gly Gly
            340                 345                 350

Glu Leu Val Phe Glu Arg Trp Arg Arg Leu Ser Asp Asn Ser Gln Trp
```

```
        355                 360                 365

Ile Gln Val Ser Leu Val Phe Gln Thr Leu Gln Gln Met Arg Asp Lys
    370                 375                 380

Thr Pro Leu Phe Leu Asn Thr Pro Pro Gly Glu Val Lys Leu Thr Leu
385                 390                 395                 400

Ala Gly Cys Glu Glu Arg Asn Ala Gln Gly Met Cys Ser Leu Ala Gly
                405                 410                 415

Phe Thr Gln Ile Val Asn Glu Ala Arg Ile Pro Ala Cys Ser Leu Gly
            420                 425                 430

Ser Gly Gly Ser Gly Gly Ala Met Val Asp Thr Leu Ser Gly Leu Ser
        435                 440                 445

Ser Glu Gln Gly Gln Ser Gly Asp Met Thr Ile Glu Glu Asp Ser Ala
    450                 455                 460

Thr His Ile Lys Phe Ser Lys Arg Asp Glu Asp Gly Lys Glu Leu Ala
465                 470                 475                 480

Gly Ala Thr Met Glu Leu Arg Asp Ser Ser Gly Lys Thr Ile Ser Thr
                485                 490                 495

Trp Ile Ser Asp Gly Gln Val Lys Asp Phe Tyr Leu Tyr Pro Gly Lys
            500                 505                 510

Tyr Thr Phe Val Glu Thr Ala Ala Pro Asp Gly Tyr Glu Val Ala Thr
        515                 520                 525

Ala Ile Thr Phe Thr Val Asn Glu Gln Gly Gln Val Thr Val Asn Gly
    530                 535                 540

Lys Ala Thr Lys Gly Asp Ala His Ile
545                 550
```

<210> SEQ ID NO 120
<211> LENGTH: 48
<212> TYPE: DNA
<213> ORGANISM: Artificial Sequence
<220> FEATURE:
<223> OTHER INFORMATION: Synthetic construct, L33-1 linker coding seq

<400> SEQUENCE: 120
agcggcggcg gcagcggcgg cggcagcacc ccgcagagcg ccttcgcc 48

<210> SEQ ID NO 121
<211> LENGTH: 33
<212> TYPE: DNA
<213> ORGANISM: Artificial Sequence
<220> FEATURE:
<223> OTHER INFORMATION: Synthetic construct, L33-2 linker coding seq

<400> SEQUENCE: 121
ggcggcggca gcggcggcgg cagcggcggc ggc 33

<210> SEQ ID NO 122
<211> LENGTH: 60
<212> TYPE: DNA
<213> ORGANISM: Artificial Sequence
<220> FEATURE:
<223> OTHER INFORMATION: Synthetic construct, L38-1 linker coding seq

<400> SEQUENCE: 122
agcggcggca gcagcggcag caccaccacc accaggatca ccccgcagag cgccttcgcc 60

<210> SEQ ID NO 123
<211> LENGTH: 36
<212> TYPE: DNA
<213> ORGANISM: Artificial Sequence

```
<220> FEATURE:
<223> OTHER INFORMATION: Synthetic construct, L38-2 linker codng seq

<400> SEQUENCE: 123

cagaacacct tcagccaggg cagcagcagc ggcagc                                36

<210> SEQ ID NO 124
<211> LENGTH: 12
<212> TYPE: DNA
<213> ORGANISM: Artificial Sequence
<220> FEATURE:
<223> OTHER INFORMATION: Synthetic construct, L46-1 linker coding seq

<400> SEQUENCE: 124

agcgccttcg cc                                                         12

<210> SEQ ID NO 125
<211> LENGTH: 108
<212> TYPE: DNA
<213> ORGANISM: Artificial Sequence
<220> FEATURE:
<223> OTHER INFORMATION: Synthetic construct, L46-2 coding seq

<400> SEQUENCE: 125

ggcgccgccc cggccgccgc cccggccaag caggaggccg ccgccccggc cccggccgcc     60

aaggccgagg ccccggccgc cgccccggcc gccaaggcca ccccgcag                 108

<210> SEQ ID NO 126
<211> LENGTH: 99
<212> TYPE: DNA
<213> ORGANISM: Artificial Sequence
<220> FEATURE:
<223> OTHER INFORMATION: Synthetic construct, L55-1 linker coding seq

<400> SEQUENCE: 126

agcgccgccg aggccgccgc caaggaggcc gccgccaagg aggccgccgc caaggaggcc     60

gccgccaagg ccctgaacac cccgcagagc gccttcgcc                            99

<210> SEQ ID NO 127
<211> LENGTH: 48
<212> TYPE: DNA
<213> ORGANISM: Artificial Sequence
<220> FEATURE:
<223> OTHER INFORMATION: Synthetic construct, L55-2 linker coding seq

<400> SEQUENCE: 127

ggcggcgccg aggccgccgc caaggaggcc gccgccaagg tgaacctg                  48

<210> SEQ ID NO 128
<211> LENGTH: 3274
<212> TYPE: DNA
<213> ORGANISM: Artificial Sequence
<220> FEATURE:
<223> OTHER INFORMATION: Synthetic construct, #1 Phy02opt

<400> SEQUENCE: 128

ggtaccaaag taatcatatt attttatgtg tgaatcttct ttactttttc atttgattat     60

gattatgaag gtatgacctt cataaccttc gtccgaaatc cattatatcc aaaggaaaat   120

aatgcttcga aggacgaagg attttgatat ttaacatttt atgttgcctt gttcttaatt   180

catagcattt gagaacaagt ccccaacacc aatctttatc tttactatat taaagcacca   240

gttcaacgat cgtctcgtgt caatattatt aaaaaactcc tacatttctt tataatcaac   300
```

-continued

```
ccgcactctt ataatctctt ctcttactac tataataaga gagtttatgt acaaaataag    360
gtgaaattat gtataagtgt tctggacctt ggttgttggc tcatattcac acaacctaat    420
caatagaaaa catatgtttt attaaaacaa aatttatcat atatatatat atatatatat    480
atatatatat atatatatat aatataaacc gtagcaatgc acaggcatat gactagtggc    540
aacttaatac catgtgtgta ttaagatgaa taagaggtat ccaaataaat aacttgttcg    600
cttacgtctg gatcgaaagg ggttggaaac gattaaatct cttcctagtc aaaattaaat    660
agaaggagat ttaatcgatt tctcccaatc cccttcgatc caggtgcaac cgaataagtc    720
cttaaatgtt gaggaacacg aaacaaccat gcattggcat gtaaagctcc aagaattcgt    780
tgtatcctta acaactcaca gaacatcaac caaaattgca cgtcaagggt attgggtaag    840
aaacaatcaa acaaatcctc tctgtgtgca aagaaacacg gtgagtcatg ccgagatcat    900
actcatctga tatacatgct tacagctcac aagacattac aaacaactca tattgcatta    960
caaagatcgt ttcatgaaaa ataaaatagg ccggaacagg acaaaaatcc ttgacgtgta   1020
aagtaaattt acaacaaaaa aaaagccata tgtcaagcta aatctaattc gttttacgta   1080
gatcaacaac ctgtagaagg caacaaaact gagccacgca gaagtacaga atgattccag   1140
atgaaccatc gacgtgctac gtaaagagag tgacgagtca tatacatttg gcaagaaacc   1200
atgaagctgc ctacagccgt ctcggtggca taagaacaca agaaattgtg ttaattaatc   1260
aaagctataa ataacgctcg catgcctgtg cacttctcca tcaccaccac tgggtcttca   1320
gaccattagc tttatctact ccagagcgca gaagaacccg atcgacaccg gatccaccat   1380
gatgctgaag aagatcctga agatcgagga gctggacgag agggagctga tcgacatcga   1440
ggtgagcggc aaccacctgt tctacgccaa cgacatcctg acccacaaca gcgcccagtc   1500
cgagccggag ctgaagctgg agtccgtggt gatcgtgtcg cgccacgggg tgcgcgcccc   1560
gaccaagttc acgcagctca tgcaggacgt gaccccggac gccttctaca cctggccggt   1620
gaagctcggc gagctgaccc cgcgcggcgg cgagctgatc gcctacctcg gccactactg   1680
gcgccagcgc ctcgtggccg acggcctcct cccgaagaag ggctgcccgc agtccggcca   1740
ggtggcgatc atcgccgacg tggacgagcg cacccgcaag acgggcgagg ccttcgccgc   1800
cggcctcgcc ccggactgcg ccatcaccgt gcacacccag gccgacacct cctccccgga   1860
cccgctcttc aacccgctca agaccggcgt gtgccagctc gacgtggccc aggtgaccga   1920
cgccatcctg gagcgcgccg gcggctccat cgccgacttc accggccact accagaccgc   1980
cttccgcgag ctggagcgcg tgctcaactt cccgcagtcg aacctcgccc tcaagcgcga   2040
gaagcaggac gagtccgcct ccctcaccca ggccctcccg tccgagctga aggtgtccgc   2100
cgacaacgtg tccctcaccg gcgcctggtc cctcgcctcc atgctcaccg aaatcttcct   2160
cctccagcag gcccagggca tgccggagcc gggctggggc cgcatcaccg actcccacca   2220
gtggaacacc ctcctctccc tccacaacgc ccagttcgac ctcctccagc gcaccccgga   2280
ggtggcccgc tcccgcgcca ccccgctcct cgacctcatc aagaccgccc tcaccccgca   2340
cccgccgcag aagcaggcct acggcgtgac cctcccgacc tcggtgctct tcatcgccgg   2400
ccacgacacc aacctcgcca acctcggcgg cgccctggag ctgcagtgga ccctcccggg   2460
ccagccggac aacaccccgc cgggcggcga gctggtgttc gagcgctggc gccgcctctc   2520
cgacaactcc cagtggattc aggtgtccct cgtgttccag accctccagc agatgcgcga   2580
caagaccccg ctcttcctca acaccccgcc gggcgaggtg aagctcaccc tggccggctg   2640
cgaggagcgc aacgcgcagg gcatgtgctc cctcgccggc ttcacccaga tcgtgaacga   2700
```

ggcccgcatc ccggcctgct ccctctgcct ggacctgaag acccaggtgc agaccccgca 2760
gggcatgaag gagatcagca acatccaggt gggcgacctg gtgctgagca acaccggcta 2820
caacgaggtg ctgaacgtgt tcccgaagag caagaagaag agctacaaga tcaccctgga 2880
ggacggcaag gagatcatct gcagcgagga gcacctgttc ccgacccaga ccggcgagat 2940
gaacatcagc ggcggcctga aggagggcat gtgcctgtac gtgaaggagt gacctaggtc 3000
cccgaatttc cccgatcgtt caaacatttg gcaataaagt ttcttaagat tgaatcctgt 3060
tgccggtctt gcgatgatta tcatataatt tctgttgaat tacgttaagc atgtaataat 3120
taacatgtaa tgcatgacgt tatttatgag atgggttttt atgattagag tcccgcaatt 3180
atacatttaa tacgcgatag aaaacaaaat atagcgcgca aactaggata aattatcgcg 3240
cgcggtgtca tctatgttac tagatcggga attg 3274

<210> SEQ ID NO 129
<211> LENGTH: 3364
<212> TYPE: DNA
<213> ORGANISM: Artificial Sequence
<220> FEATURE:
<223> OTHER INFORMATION: Synthetic construct, #2 Phy02opt

<400> SEQUENCE: 129
ggtaccaaag taatcatatt attttatgtg tgaatcttct ttactttttc atttgattat 60
gattatgaag gtatgacctt cataaccttc gtccgaaatc cattatatcc aaaggaaaat 120
aatgcttcga aggacgaagg attttgatat ttaacatttt atgttgcctt gttcttaatt 180
catagcattt gagaacaagt ccccaacacc aatctttatc tttactatat taaagcacca 240
gttcaacgat cgtctcgtgt caatattatt aaaaaactcc tacatttctt tataatcaac 300
ccgcactctt ataatctctt ctcttactac tataataaga gagtttatgt acaaaataag 360
gtgaaattat gtataagtgt tctggacctt ggttgttggc tcatattcac acaacctaat 420
caatagaaaa catatgtttt attaaaacaa aatttatcat atatatatat atatatatat 480
atatatatat atatatatat aatataaacc gtagcaatgc acaggcatat gactagtggc 540
aacttaatac catgtgtgta ttaagatgaa taagaggtat ccaaataaat aacttgttcg 600
cttacgtctg gatcgaaagg ggttggaaac gattaaatct cttcctagtc aaaattaaat 660
agaaggagat ttaatcgatt tctcccaatc cccttcgatc caggtgcaac cgaataagtc 720
cttaaatgtt gaggaacacg aaacaaccat gcattggcat gtaaagctcc aagaattcgt 780
tgtatcctta acaactcaca gaacatcaac caaaattgca cgtcaagggt attgggtaag 840
aaacaatcaa acaaatcctc tctgtgtgca aagaaacacg gtgagtcatg ccgagatcat 900
actcatctga tatacatgct tacagctcac aagacattac aaacaactca tattgcatta 960
caaagatcgt ttcatgaaaa ataaaatagg ccggaacagg acaaaaatcc ttgacgtgta 1020
aagtaaattt acaacaaaaa aaaagccata tgtcaagcta aatctaattc gttttacgta 1080
gatcaacaac ctgtagaagg caacaaaact gagccacgca gaagtacaga atgattccag 1140
atgaaccatc gacgtgctac gtaaagagag tgacgagtca tatacatttg gcaagaaacc 1200
atgaagctgc ctacagccgt ctcggtggca taagaacaca agaaattgtg ttaattaatc 1260
aaagctataa ataacgctcg catgcctgtg cacttctcca tcaccaccac tgggtcttca 1320
gaccattagc tttatctact ccagagcgca gaagaacccg atcgacaccg gatccaccat 1380
gagggtgttg ctcgttgccc tcgctctcct ggctctcgct gcgagcgcca ccagcatgat 1440

```
gctgaagaag atcctgaaga tcgaggagct ggacgagagg gagctgatcg acatcgaggt   1500

gagcggcaac cacctgttct acgccaacga catcctgacc cacaacagcg ctgcgcagtc   1560

cgagccggag ctgaagctgg agtccgtggt gatcgtgtcg cgccacgggg tgcgcgcccc   1620

gaccaagttc acgcagctca tgcaggacgt gaccccggac gccttctaca cctggccggt   1680

gaagctcggc gagctgaccc cgcgcggcgg cgagctgatc gcctacctcg gccactactg   1740

gcgccagcgc ctcgtggccg acggcctcct cccgaagaag ggctgcccgc agtccggcca   1800

ggtggcgatc atcgccgacg tggacgagcg cacccgcaag acgggcgagg ccttcgccgc   1860

cggcctcgcc ccggactgcg ccatcaccgt gcacacccag gccgacacct cctccccgga   1920

cccgctcttc aacccgctca agaccggcgt gtgccagctc gacgtggccc aggtgaccga   1980

cgccatcctg gagcgcgccg gcggctccat cgccgacttc accggccact accagaccgc   2040

cttccgcgag ctggagcgcg tgctcaactt cccgcagtcg aacctcgccc tcaagcgcga   2100

gaagcaggac gagtccgcct ccctcaccca ggccctcccg tccgagctga aggtgtccgc   2160

cgacaacgtg tccctcaccg gcgcctggtc cctcgcctcc atgctcaccg aaatcttcct   2220

cctccagcag gcccagggca tgccggagcc gggctggggc cgcatcaccg actcccacca   2280

gtggaacacc ctcctctccc tccacaacgc ccagttcgac ctcctccagc gcaccccgga   2340

ggtggcccgc tcccgcgcca ccccgctcct cgacctcatc aagaccgccc tcaccccgca   2400

cccgccgcag aagcaggcct acggcgtgac cctcccgacc tcggtgctct tcatcgccgg   2460

ccacgacacc aacctcgcca acctcggcgg cgccctggag ctgcagtgga ccctcccggg   2520

ccagccggac aacaccccgc cgggcggcga gctggtgttc gagcgctggc gccgcctctc   2580

cgacaactcc cagtggattc aggtgtccct cgtgttccag accctccagc agatgcgcga   2640

caagaccccg ctcttcctca acaccccgcc gggcgaggtg aagctcaccc tggccggctg   2700

cgaggagcgc aacgcgcagg gcatgtgctc cctcgccggc ttcacccaga tcgtgaacga   2760

ggcccgcatc ccggcctgct ccctctgcct ggacctgaag acccaggtgc agaccccgca   2820

gggcatgaag gagatcagca acatccaggt gggcgacctg gtgctgagca acaccggcta   2880

caacgaggtg ctgaacgtgt tcccgaagag caagaagaag agctacaaga tcaccctgga   2940

ggacggcaag gagatcatct gcagcgagga gcacctgttc ccgacccaga ccggcgagat   3000

gaacatcagc ggcggcctga aggagggcat gtgcctgtac gtgaaggagg acccgaacgg   3060

ctccgagaag gacgagctgt gacctaggtc cccgaatttc cccgatcgtt caaacatttg   3120

gcaataaagt ttcttaagat tgaatcctgt tgccggtctt gcgatgatta tcatataatt   3180

tctgttgaat tacgttaagc atgtaataat taacatgtaa tgcatgacgt tatttatgag   3240

atgggttttt atgattagag tcccgcaatt atacatttaa tacgcgatag aaaacaaaat   3300

atagcgcgca aactaggata aattatcgcg cgcggtgtca tctatgttac tagatcggga   3360

attg                                                                3364
```

<210> SEQ ID NO 130
<211> LENGTH: 3379
<212> TYPE: DNA
<213> ORGANISM: Artificial Sequence
<220> FEATURE:
<223> OTHER INFORMATION: Synthetic construct, #3 Phy02opt

<400> SEQUENCE: 130

```
ggtaccaaag taatcatatt attttatgtg tgaatcttct ttactttttc atttgattat     60

gattatgaag gtatgacctt cataaccttc gtccgaaatc cattatatcc aaaggaaaat    120
```

```
aatgcttcga aggacgaagg attttgatat ttaacatttt atgttgcctt gttcttaatt    180
catagcattt gagaacaagt ccccaacacc aatctttatc tttactatat taaagcacca    240
gttcaacgat cgtctcgtgt caatattatt aaaaaactcc tacatttctt tataatcaac    300
ccgcactctt ataatctctt ctcttactac tataataaga gagtttatgt acaaaataag    360
gtgaaattat gtataagtgt tctggacctt ggttgttggc tcatattcac acaacctaat    420
caatagaaaa catatgtttt attaaaacaa aatttatcat atatatatat atatatatat    480
atatatatat atatatatat aatataaacc gtagcaatgc acaggcatat gactagtggc    540
aacttaatac catgtgtgta ttaagatgaa taagaggtat ccaaataaat aacttgttcg    600
cttacgtctg gatcgaaagg ggttggaaac gattaaatct cttcctagtc aaaattaaat    660
agaaggagat ttaatcgatt tctcccaatc cccttcgatc caggtgcaac cgaataagtc    720
cttaaatgtt gaggaacacg aaacaaccat gcattggcat gtaaagctcc aagaattcgt    780
tgtatcctta acaactcaca gaacatcaac caaaattgca cgtcaagggt attgggtaag    840
aaacaatcaa acaaatcctc tctgtgtgca aagaaacacg gtgagtcatg ccgagatcat    900
actcatctga tatacatgct tacagctcac aagacattac aaacaactca tattgcatta    960
caaagatcgt ttcatgaaaa ataaaatagg ccggaacagg acaaaaatcc ttgacgtgta   1020
aagtaaattt acaacaaaaa aaaagccata tgtcaagcta aatctaattc gttttacgta   1080
gatcaacaac ctgtagaagg caacaaaact gagccacgca gaagtacaga atgattccag   1140
atgaaccatc gacgtgctac gtaaagagag tgacgagtca tatacatttg gcaagaaacc   1200
atgaagctgc ctacagccgt ctcggtggca taagaacaca agaaattgtg ttaattaatc   1260
aaagctataa ataacgctcg catgcctgtg cacttctcca tcaccaccac tgggtcttca   1320
gaccattagc tttatctact ccagagcgca gaagaacccg atcgacaccg gatccaccat   1380
ggttaaggtg attggaagac gttctcttgg tgttcaaagg atcttcgata tcggattgcc   1440
acaagaccac aactttcttc tcgctaatgg tgccatcgct gccaatagcg ctgcgcagtc   1500
cgagccggag ctgaagctgg agtccgtggt gatcgtgtcg cgccacgggg tgcgcgcccc   1560
gaccaagttc acgcagctca tgcaggacgt gaccccggac gccttctaca cctggccggt   1620
gaagctcggc gagctgaccc cgcgcggcgg cgagctgatc gcctacctcg gccactactg   1680
gcgccagcgc ctcgtggccg acggcctcct cccgaagaag ggctgcccgc agtccggcca   1740
ggtggcgatc atcgccgacg tggacgagcg cacccgcaag acgggcgagg ccttcgccgc   1800
cggcctcgcc ccggactgcg ccatcaccgt gcacacccag gccgacacct cctccccgga   1860
cccgctcttc aacccgctca agaccggcgt gtgccagctc gacgtggccc aggtgaccga   1920
cgccatcctg gagcgcgccg gcggctccat cgccgacttc accggccact accagaccgc   1980
cttccgcgag ctggagcgcg tgctcaactt cccgcagtcg aacctcgccc tcaagcgcga   2040
gaagcaggac gagtccgcct ccctcaccca ggccctcccg tccgagctga aggtgtccgc   2100
cgacaacgtg tccctcaccg gcgcctggtc cctcgcctcc atgctcaccg aaatcttcct   2160
cctccagcag gcccagggca tgccggagcc gggctggggc cgcatcaccg actcccacca   2220
gtggaacacc ctcctctccc tccacaacgc ccagttcgac ctcctccagc gcaccccgga   2280
ggtggcccgc tcccgcgcca ccccgctcct cgacctcatc aagaccgccc tcaccccgca   2340
cccgccgcag aagcaggcct acggcgtgac cctcccgacc tcggtgctct tcatcgccgg   2400
ccacgacacc aacctcgcca acctcggcgg cgccctggag ctgcagtgga ccctcccggg   2460
```

```
ccagccggac aacaccccgc cgggcggcga gctggtgttc gagcgctggc gccgcctctc   2520

cgacaactcc cagtggattc aggtgtccct cgtgttccag accctccagc agatgcgcga   2580

caagaccccg ctcttcctca acaccccgcc gggcgaggtg aagctcaccc tggccggctg   2640

cgaggagcgc aacgcgcagg gcatgtgctc cctcgccggc ttcacccaga tcgtgaacga   2700

ggcccgcatc ccggcctgct ccctctgcct ttctttcgga actgagatcc ttaccgttga   2760

gtacggacca cttcctattg gtaagatcgt ttctgaggaa attaactgct cagtgtactc   2820

tgttgatcca gaaggaagag tttacactca ggctatcgca caatggcacg ataggggtga   2880

acaagaggtt ctggagtacg agcttgaaga tggatccgtt attcgtgcta cctctgacca   2940

tagattcttg actacagatt atcagcttct cgctatcgag gaaatctttg ctaggcaact   3000

tgatctcctt actttggaga acatcaagca gacagaagag gctcttgaca accacagact   3060

tccattccct ttgctcgatg ctggaaccat caagtaacct aggtccccga atttccccga   3120

tcgttcaaac atttggcaat aaagtttctt aagattgaat cctgttgccg gtcttgcgat   3180

gattatcata taatttctgt tgaattacgt taagcatgta ataattaaca tgtaatgcat   3240

gacgttattt atgagatggg tttttatgat tagagtcccg caattataca tttaatacgc   3300

gatagaaaac aaaatatagc gcgcaaacta ggataaatta tcgcgcgcgg tgtcatctat   3360

gttactagat cgggaattg                                                3379
```

<210> SEQ ID NO 131
<211> LENGTH: 3466
<212> TYPE: DNA
<213> ORGANISM: Artificial Sequence
<220> FEATURE:
<223> OTHER INFORMATION: Synthetic construct, #4 Phy02opt

<400> SEQUENCE: 131

```
ggtaccaaag taatcatatt attttatgtg tgaatcttct ttactttttc atttgattat     60

gattatgaag gtatgacctt cataaccttc gtccgaaatc cattatatcc aaaggaaaat    120

aatgcttcga aggacgaagg attttgatat ttaacatttt atgttgcctt gttcttaatt    180

catagcattt gagaacaagt ccccaacacc aatctttatc tttactatat taaagcacca    240

gttcaacgat cgtctcgtgt caatattatt aaaaaactcc tacatttctt tataatcaac    300

ccgcactctt ataatctctt ctcttactac tataataaga gagtttatgt acaaaataag    360

gtgaaattat gtataagtgt tctggacctt ggttgttggc tcatattcac acaacctaat    420

caatagaaaa catatgtttt attaaaacaa aatttatcat atatatatat atatatatat    480

atatatatat atatatatat aatataaacc gtagcaatgc acaggcatat gactagtggc    540

aacttaatac catgtgtgta ttaagatgaa taagaggtat ccaaataaat aacttgttcg    600

cttacgtctg gatcgaaagg ggttggaaac gattaaatct cttcctagtc aaaattaaat    660

agaaggagat ttaatcgatt tctcccaatc cccttcgatc caggtgcaac cgaataagtc    720

cttaaatgtt gaggaacacg aaacaaccat gcattggcat gtaaagctcc aagaattcgt    780

tgtatcctta acaactcaca gaacatcaac caaaattgca cgtcaagggt attgggtaag    840

aaacaatcaa acaaatcctc tctgtgtgca aagaaacacg gtgagtcatg ccgagatcat    900

actcatctga tatacatgct tacagctcac aagacattac aaacaactca tattgcatta    960

caaagatcgt ttcatgaaaa ataaaatagg ccggaacagg acaaaaatcc ttgacgtgta   1020

aagtaaattt acaacaaaaa aaaagccata tgtcaagcta aatctaattc gttttacgta   1080

gatcaacaac ctgtagaagg caacaaaact gagccacgca gaagtacaga atgattccag   1140
```

```
atgaaccatc gacgtgctac gtaaagagag tgacgagtca tatacatttg gcaagaaacc   1200
atgaagctgc ctacagccgt ctcggtggca taagaacaca agaaattgtg ttaattaatc   1260
aaagctataa ataacgctcg catgcctgtg cacttctcca tcaccaccac tgggtcttca   1320
gaccattagc tttatctact ccagagcgca gaagaacccg atcgacaccg gatccaccat   1380
gagggtgttg ctcgttgccc tcgctctcct ggctctcgct gcgagcgcca ccagcatggt   1440
taaggtgatt ggaagacgtt ctcttggtgt tcaaaggatc ttcgatatcg gattgccaca   1500
agaccacaac tttcttctcg ctaatggtgc catcgctgcc aatagcgctg cgcagtccga   1560
gccggagctg aagctggagt ccgtggtgat cgtgtcgcgc cacggggtgc gcgcccccgac  1620
caagttcacg cagctcatgc aggacgtgac cccggacgcc ttctacacct ggccggtgaa   1680
gctcggcgag ctgaccccgc gcggcggcga gctgatcgcc tacctcggcc actactggcg   1740
ccagcgcctc gtggccgacg gcctcctccc gaagaagggc tgcccgcagt ccggccaggt   1800
ggcgatcatc gccgacgtgg acgagcgcac ccgcaagacg ggcgaggcct tcgccgccgg   1860
cctcgccccg gactgcgcca tcaccgtgca cacccaggcc gacacctcct ccccggaccc   1920
gctcttcaac ccgctcaaga ccggcgtgtg ccagctcgac gtggcccagg tgaccgacgc   1980
catcctggag cgcgccggcg gctccatcgc cgacttcacc ggccactacc agaccgcctt   2040
ccgcgagctg gagcgcgtgc tcaacttccc gcagtcgaac ctcgccctca agcgcgagaa   2100
gcaggacgag tccgcctccc tcacccaggc cctcccgtcc gagctgaagg tgtccgccga   2160
caacgtgtcc ctcaccggcg cctggtccct cgcctccatg ctcaccgaaa tcttcctcct   2220
ccagcaggcc cagggcatgc cggagccggg ctggggccgc atcaccgact cccaccagtg   2280
gaacaccctc ctctccctcc acaacgccca gttcgacctc ctccagcgca ccccggaggt   2340
ggcccgctcc cgcgccaccc cgctcctcga cctcatcaag accgccctca ccccgcaccc   2400
gccgcagaag caggcctacg gcgtgaccct cccgacctcg gtgctcttca tcgccggcca   2460
cgacaccaac ctcgccaacc tcggcggcgc cctggagctg cagtggaccc tcccgggcca   2520
gccggacaac accccgccgg gcggcgagct ggtgttcgag cgctggcgcc gcctctccga   2580
caactcccag tggattcagg tgtccctcgt gttccagacc ctccagcaga tgcgcgacaa   2640
gaccccgctc ttcctcaaca ccccgccggg cgaggtgaag ctcaccctgg ccggctgcga   2700
ggagcgcaac gcgcagggca tgtgctccct cgccggcttc acccagatcg tgaacgaggc   2760
ccgcatcccg gcctgctccc tctgcctttc tttcggaact gagatcctta ccgttgagta   2820
cggaccactt cctattggta agatcgtttc tgaggaaatt aactgctcag tgtactctgt   2880
tgatccagaa ggaagagttt acactcaggc tatcgcacaa tggcacgata ggggtgaaca   2940
agaggttctg gagtacgagc ttgaagatgg atccgttatt cgtgctacct ctgaccatag   3000
attcttgact acagattatc agcttctcgc tatcgaggaa atctttgcta ggcaacttga   3060
tctccttact ttggagaaca tcaagcagac agaagaggct cttgacaacc acagacttcc   3120
attccctttg ctcgatgctg gaaccatcaa ggacccgaac ggctccgaga aggacgagct   3180
gtaacctagg tccccgaatt tccccgatcg ttcaaacatt tggcaataaa gtttcttaag   3240
attgaatcct gttgccggtc ttgcgatgat tatcatataa tttctgttga attacgttaa   3300
gcatgtaata attaacatgt aatgcatgac gttatttatg agatgggttt ttatgattag   3360
agtcccgcaa ttatacattt aatacgcgat agaaaacaaa atatagcgcg caaactagga   3420
taaattatcg cgcgcggtgt catctatgtt actagatcgg gaattg                  3466
```

<210> SEQ ID NO 132
<211> LENGTH: 3457
<212> TYPE: DNA
<213> ORGANISM: Artificial Sequence
<220> FEATURE:
<223> OTHER INFORMATION: Synthetic construct, #5 Phy02opt

<400> SEQUENCE: 132
ggtaccaaag taatcatatt attttatgtg tgaatcttct ttactttttc atttgattat 60
gattatgaag gtatgacctt cataaccttc gtccgaaatc cattatatcc aaaggaaaat 120
aatgcttcga aggacgaagg attttgatat ttaacatttt atgttgcctt gttcttaatt 180
catagcattt gagaacaagt ccccaacacc aatctttatc tttactatat taaagcacca 240
gttcaacgat cgtctcgtgt caatattatt aaaaaactcc tacatttctt tataatcaac 300
ccgcactctt ataatctctt ctcttactac tataataaga gagtttatgt acaaaataag 360
gtgaaattat gtataagtgt tctggacctt ggttgttggc tcatattcac acaacctaat 420
caatagaaaa catatgtttt attaaaacaa aatttatcat atatatatat atatatatat 480
atatatatat atatatatat aatataaacc gtagcaatgc acaggcatat gactagtggc 540
aacttaatac catgtgtgta ttaagatgaa taagaggtat ccaaataaat aacttgttcg 600
cttacgtctg gatcgaaagg ggttggaaac gattaaatct cttcctagtc aaaattaaat 660
agaaggagat ttaatcgatt tctcccaatc cccttcgatc caggtgcaac cgaataagtc 720
cttaaatgtt gaggaacacg aaacaaccat gcattggcat gtaaagctcc aagaattcgt 780
tgtatcctta acaactcaca gaacatcaac caaaattgca cgtcaagggt attgggtaag 840
aaacaatcaa acaaatcctc tctgtgtgca aagaaacacg gtgagtcatg ccgagatcat 900
actcatctga tatacatgct tacagctcac aagacattac aaacaactca tattgcatta 960
caaagatcgt ttcatgaaaa ataaaatagg ccggaacagg acaaaaatcc ttgacgtgta 1020
aagtaaattt acaacaaaaa aaaagccata tgtcaagcta aatctaattc gttttacgta 1080
gatcaacaac ctgtagaagg caacaaaact gagccacgca gaagtacaga atgattccag 1140
atgaaccatc gacgtgctac gtaaagagag tgacgagtca tatacatttg gcaagaaacc 1200
atgaagctgc ctacagccgt ctcggtggca taagaacaca agaaattgtg ttaattaatc 1260
aaagctataa ataacgctcg catgcctgtg cacttctcca tcaccaccac tgggtcttca 1320
gaccattagc tttatctact ccagagcgca gaagaacccg atcgacaccg gatccaccat 1380
ggttaaggtg attggaagac gttctcttgg tgttcaaagg atcttcgata tcggattgcc 1440
acaagaccac aactttcttc tcgctaatgg tgccatcgct gccaatagcg gcggcggcag 1500
cggcggcggc agcaccccgc agagcgcctt cgccgctgcg cagtccgagc cggagctgaa 1560
gctggagtcc gtggtgatcg tgtcgcgcca cggggtgcgc gccccgacca agttcacgca 1620
gctcatgcag gacgtgaccc cggacgcctt ctacacctgg ccggtgaagc tcggcgagct 1680
gaccccgcgc ggcggcgagc tgatcgccta cctcggccac tactggcgcc agcgcctcgt 1740
ggccgacggc ctcctcccga agaagggctg cccgcagtcc ggccaggtgg cgatcatcgc 1800
cgacgtggac gagcgcaccc gcaagacggg cgaggccttc gccgccggcc tcgccccgga 1860
ctgcgccatc accgtgcaca cccaggccga cacctcctcc ccggacccgc tcttcaaccc 1920
gctcaagacc ggcgtgtgcc agctcgacgt ggcccaggtg accgacgcca tcctggagcg 1980
cgccggcggc tccatcgccg acttcaccgg ccactaccag accgccttcc gcgagctgga 2040
gcgcgtgctc aacttcccgc agtcgaacct cgccctcaag cgcgagaagc aggacgagtc 2100
cgcctccctc acccaggccc tcccgtccga gctgaaggtg tccgccgaca acgtgtccct 2160
caccggcgcc tggtccctcg cctccatgct caccgaaatc ttcctcctcc agcaggccca 2220
gggcatgccg gagccgggct ggggccgcat caccgactcc caccagtgga acaccctcct 2280
ctccctccac aacgcccagt tcgacctcct ccagcgcacc ccggaggtgg cccgctcccg 2340
cgccaccccg ctcctcgacc tcatcaagac cgccctcacc ccgcacccgc cgcagaagca 2400
ggcctacggc gtgaccctcc cgacctcggt gctcttcatc gccggccacg acaccaacct 2460
cgccaacctc ggcggcgccc tggagctgca gtggaccctc ccgggccagc cggacaacac 2520
cccgccgggc ggcgagctgg tgttcgagcg ctggcgccgc ctctccgaca actcccagtg 2580
gattcaggtg tccctcgtgt tccagaccct ccagcagatg cgcgacaaga ccccgctctt 2640
cctcaacacc ccgccgggcg aggtgaagct caccctggcc ggctgcgagg agcgcaacgc 2700
gcagggcatg tgctccctcg ccggcttcac ccagatcgtg aacgaggccc gcatcccggc 2760
ctgctccctc ggcggcggca gcggcggcgg cagcggcggc ggctgccttt ctttcggaac 2820
tgagatcctt accgttgagt acggaccact tcctattggt aagatcgttt ctgaggaaat 2880
taactgctca gtgtactctg ttgatccaga aggaagagtt tacactcagg ctatcgcaca 2940
atggcacgat aggggtgaac aagaggttct ggagtacgag cttgaagatg gatccgttat 3000
tcgtgctacc tctgaccata gattcttgac tacagattat cagcttctcg ctatcgagga 3060
aatctttgct aggcaacttg atctccttac tttggagaac atcaagcaga cagaagaggc 3120
tcttgacaac cacagacttc cattcccttt gctcgatgct ggaaccatca agtaacctag 3180
gtccccgaat ttccccgatc gttcaaacat ttggcaataa agtttcttaa gattgaatcc 3240
tgttgccggt cttgcgatga ttatcatata atttctgttg aattacgtta agcatgtaat 3300
aattaacatg taatgcatga cgttatttat gagatgggtt tttatgatta gagtcccgca 3360
attatacatt taatacgcga tagaaaacaa aatatagcgc gcaaactagg ataaattatc 3420
gcgcgcggtg tcatctatgt tactagatcg ggaattg 3457

<210> SEQ ID NO 133
<211> LENGTH: 3544
<212> TYPE: DNA
<213> ORGANISM: Artificial Sequence
<220> FEATURE:
<223> OTHER INFORMATION: Synthetic construct, #6 Phy02opt

<400> SEQUENCE: 133
ggtaccaaag taatcatatt attttatgtg tgaatcttct ttactttttc atttgattat 60
gattatgaag gtatgacctt cataaccttc gtccgaaatc cattatatcc aaaggaaaat 120
aatgcttcga aggacgaagg attttgatat ttaacatttt atgttgcctt gttcttaatt 180
catagcattt gagaacaagt ccccaacacc aatctttatc tttactatat taaagcacca 240
gttcaacgat cgtctcgtgt caatattatt aaaaaactcc tacatttctt tataatcaac 300
ccgcactctt ataatctctt ctcttactac tataataaga gagtttatgt acaaaataag 360
gtgaaattat gtataagtgt tctggacctt ggttgttggc tcatattcac acaacctaat 420
caatagaaaa catatgtttt attaaaacaa aatttatcat atatatatat atatatatat 480
atatatatat atatatatat aatataaacc gtagcaatgc acaggcatat gactagtggc 540
aacttaatac catgtgtgta ttaagatgaa taagaggtat ccaaataaat aacttgttcg 600
cttacgtctg gatcgaaagg ggttggaaac gattaaatct cttcctagtc aaaattaaat 660
agaaggagat ttaatcgatt tctcccaatc cccttcgatc caggtgcaac cgaataagtc 720
cttaaatgtt gaggaacacg aaacaaccat gcattggcat gtaaagctcc aagaattcgt 780
tgtatcctta acaactcaca gaacatcaac caaaattgca cgtcaagggt attgggtaag 840
aaacaatcaa acaaatcctc tctgtgtgca aagaaacacg gtgagtcatg ccgagatcat 900
actcatctga tatacatgct tacagctcac aagacattac aaacaactca tattgcatta 960
caaagatcgt ttcatgaaaa ataaaatagg ccggaacagg acaaaaatcc ttgacgtgta 1020
aagtaaattt acaacaaaaa aaaagccata tgtcaagcta aatctaattc gttttacgta 1080
gatcaacaac ctgtagaagg caacaaaact gagccacgca gaagtacaga atgattccag 1140
atgaaccatc gacgtgctac gtaaagagag tgacgagtca tatacatttg gcaagaaacc 1200
atgaagctgc ctacagccgt ctcggtggca taagaacaca agaaattgtg ttaattaatc 1260
aaagctataa ataacgctcg catgcctgtg cacttctcca tcaccaccac tgggtcttca 1320
gaccattagc tttatctact ccagagcgca gaagaacccg atcgacaccg gatccaccat 1380
gagggtgttg ctcgttgccc tcgctctcct ggctctcgct gcgagcgcca ccagcatggt 1440
taaggtgatt ggaagacgtt ctcttggtgt tcaaaggatc ttcgatatcg gattgccaca 1500
agaccacaac tttcttctcg ctaatggtgc catcgctgcc aatagcggcg gcggcagcgg 1560
cggcggcagc accccgcaga gcgccttcgc cgctgcgcag tccgagccgg agctgaagct 1620
ggagtccgtg gtgatcgtgt cgcgccacgg ggtgcgcgcc ccgaccaagt tcacgcagct 1680
catgcaggac gtgaccccgg acgccttcta cacctggccg gtgaagctcg gcgagctgac 1740
cccgcgcggc ggcgagctga tcgcctacct cggccactac tggcgccagc gcctcgtggc 1800
cgacggcctc ctcccgaaga agggctgccc gcagtccggc caggtggcga tcatcgccga 1860
cgtggacgag cgcacccgca agacgggcga ggccttcgcc gccggcctcg ccccggactg 1920
cgccatcacc gtgcacaccc aggccgacac ctcctccccg gacccgctct tcaacccgct 1980
caagaccggc gtgtgccagc tcgacgtggc ccaggtgacc gacgccatcc tggagcgcgc 2040
cggcggctcc atcgccgact tcaccggcca ctaccagacc gccttccgcg agctggagcg 2100
cgtgctcaac ttcccgcagt cgaacctcgc cctcaagcgc gagaagcagg acgagtccgc 2160
ctccctcacc caggccctcc cgtccgagct gaaggtgtcc gccgacaacg tgtccctcac 2220
cggcgcctgg tccctcgcct ccatgctcac cgaaatcttc ctcctccagc aggcccaggg 2280
catgccggag ccgggctggg gccgcatcac cgactcccac cagtggaaca ccctcctctc 2340
cctccacaac gcccagttcg acctcctcca gcgcaccccg gaggtggccc gctcccgcgc 2400
caccccgctc ctcgacctca tcaagaccgc cctcaccccg cacccgccgc agaagcaggc 2460
ctacggcgtg accctcccga cctcggtgct cttcatcgcc ggccacgaca ccaacctcgc 2520
caacctcggc ggcgccctgg agctgcagtg gaccctcccg ggccagccgg acaacacccc 2580
gccgggcggc gagctggtgt tcgagcgctg gcgccgcctc tccgacaact cccagtggat 2640
tcaggtgtcc ctcgtgttcc agaccctcca gcagatgcgc gacaagaccc cgctcttcct 2700
caacaccccg ccgggcgagg tgaagctcac cctggccggc tgcgaggagc gcaacgcgca 2760
gggcatgtgc tccctcgccg gcttcaccca gatcgtgaac gaggcccgca tcccggcctg 2820
ctccctcggc ggcggcagcg gcggcggcag cggcggcggc tgcctttctt tcggaactga 2880
gatccttacc gttgagtacg gaccacttcc tattggtaag atcgtttctg aggaaattaa 2940
ctgctcagtg tactctgttg atccagaagg aagagtttac actcaggcta tcgcacaatg 3000
gcacgatagg ggtgaacaag aggttctgga gtacgagctt gaagatggat ccgttattcg 3060

```
tgctacctct gaccatagat tcttgactac agattatcag cttctcgcta tcgaggaaat   3120

ctttgctagg caacttgatc tccttacttt ggagaacatc aagcagacag aagaggctct   3180

tgacaaccac agacttccat tccctttgct cgatgctgga accatcaagg acccgaacgg   3240

ctccgagaag gacgagctgt aacctaggtc cccgaatttc cccgatcgtt caaacatttg   3300

gcaataaagt ttcttaagat tgaatcctgt tgccggtctt gcgatgatta tcatataatt   3360

tctgttgaat tacgttaagc atgtaataat taacatgtaa tgcatgacgt tatttatgag   3420

atgggttttt atgattagag tcccgcaatt atacatttaa tacgcgatag aaaacaaaat   3480

atagcgcgca aactaggata aattatcgcg cgcggtgtca tctatgttac tagatcggga   3540

attg                                                                3544
```

<210> SEQ ID NO 134
<211> LENGTH: 10
<212> TYPE: PRT
<213> ORGANISM: Artificial Sequence
<220> FEATURE:
<223> OTHER INFORMATION: Synthetic construct, AQSEPELKLE

<400> SEQUENCE: 134

```
Ala Gln Ser Glu Pro Glu Leu Lys Leu Glu
1               5                   10
```

<210> SEQ ID NO 135
<211> LENGTH: 8
<212> TYPE: PRT
<213> ORGANISM: Artificial Sequence
<220> FEATURE:
<223> OTHER INFORMATION: Synthetic construct, SEPELKLE

<400> SEQUENCE: 135

```
Ser Glu Pro Glu Leu Lys Leu Glu
1               5
```

<210> SEQ ID NO 136
<211> LENGTH: 15
<212> TYPE: PRT
<213> ORGANISM: Artificial Sequence
<220> FEATURE:
<223> OTHER INFORMATION: Synthetic construct, AQSEPELKLESVVIV

<400> SEQUENCE: 136

```
Ala Gln Ser Glu Pro Glu Leu Lys Leu Glu Ser Val Val Ile Val
1               5                   10                  15
```

<210> SEQ ID NO 137
<211> LENGTH: 1363
<212> TYPE: DNA
<213> ORGANISM: Zea mays
<220> FEATURE:
<221> NAME/KEY: promoter
<222> LOCATION: (1)..(1363)
<223> OTHER INFORMATION: Maize gamma zein 27

<400> SEQUENCE: 137

```
aaagtaatca tattatttta tgtgtgaatc ttctttactt tttcatttga ttatgattat     60

gaaggtatga ccttcataac cttcgtccga aatccattat atccaaagga aaataatgct    120

tcgaaggacg aaggattttg atatttaaca ttttatgttg ccttgttctt aattcatagc    180

atttgagaac aagtccccaa caccaatctt tatctttact atattaaagc accagttcaa    240

cgatcgtctc gtgtcaatat tattaaaaaa ctcctacatt tctttataat caacccgcac    300
```

-continued

```
tcttataatc tcttctctta ctactataat aagagagttt atgtacaaaa taaggtgaaa    360

ttatgtataa gtgttctgga ccttggttgt tggctcatat tcacacaacc taatcaatag    420

aaaacatatg ttttattaaa acaaaattta tcatatatat atatatatat atatatatat    480

atatatatat atataatata aaccgtagca atgcacaggc atatgactag tggcaactta    540

ataccatgtg tgtattaaga tgaataagag gtatccaaat aaataacttg ttcgcttacg    600

tctggatcga aaggggttgg aaacgattaa atctcttcct agtcaaaatt aaatagaagg    660

agatttaatc gatttctccc aatccccttc gatccaggtg caaccgaata agtccttaaa    720

tgttgaggaa cacgaaacaa ccatgcattg gcatgtaaag ctccaagaat tcgttgtatc    780

cttaacaact cacagaacat caaccaaaat tgcacgtcaa gggtattggg taagaaacaa    840

tcaaacaaat cctctctgtg tgcaaagaaa cacggtgagt catgccgaga tcatactcat    900

ctgatataca tgcttacagc tcacaagaca ttacaaacaa ctcatattgc attacaaaga    960

tcgtttcatg aaaaataaaa taggccggaa caggacaaaa atccttgacg tgtaaagtaa   1020

atttacaaca aaaaaaaagc catatgtcaa gctaaatcta attcgtttta cgtagatcaa   1080

caacctgtag aaggcaacaa aactgagcca cgcagaagta cagaatgatt ccagatgaac   1140

catcgacgtg ctacgtaaag agagtgacga gtcatataca tttggcaaga aaccatgaag   1200

ctgcctacag ccgtctcggt ggcataagaa cacaagaaat tgtgttaatt aatcaaagct   1260

ataaataacg ctcgcatgcc tgtgcacttc tccatcacca ccactgggtc ttcagaccat   1320

tagctttatc tactccagag cgcagaagaa cccgatcgac acc                      1363
```

<210> SEQ ID NO 138
<211> LENGTH: 57
<212> TYPE: DNA
<213> ORGANISM: Zea mays

<400> SEQUENCE: 138

```
atgcgcgtgc tgctcgtggc cctggccctg ctggctcttg ctgccagcgc cacctct        57
```

<210> SEQ ID NO 139
<211> LENGTH: 18
<212> TYPE: DNA
<213> ORGANISM: Artificial Sequence
<220> FEATURE:
<223> OTHER INFORMATION: Synthetic construct, SEKDEL coding seq

<400> SEQUENCE: 139

```
agcgagaagg acgagctg                                                   18
```

<210> SEQ ID NO 140
<211> LENGTH: 6
<212> TYPE: PRT
<213> ORGANISM: Artificial Sequence
<220> FEATURE:
<223> OTHER INFORMATION: Synthetic construct, SEKDEL peptide

<400> SEQUENCE: 140

```
Ser Glu Lys Asp Glu Leu
1               5
```

<210> SEQ ID NO 141
<211> LENGTH: 276
<212> TYPE: DNA
<213> ORGANISM: Agrobacterium tumefaciens

<400> SEQUENCE: 141
tccccgaatt tccccgatcg ttcaaacatt tggcaataaa gtttcttaag attgaatcct 60
gttgccggtc ttgcgatgat tatcatataa tttctgttga attacgttaa gcatgtaata 120
attaacatgt aatgcatgac gttatttatg agatgggttt ttatgattag agtcccgcaa 180
ttatacattt aatacgcgat agaaaacaaa atatagcgcg caaactagga taaattatcg 240
cgcgcggtgt catctatgtt actagatcgg gaattg 276

<210> SEQ ID NO 142
<211> LENGTH: 282
<212> TYPE: DNA
<213> ORGANISM: Artificial Sequence
<220> FEATURE:
<223> OTHER INFORMATION: Synthetic construct, Cbu_DnaB-N (#12-N) coding seq

<400> SEQUENCE: 142
tgcgtgacag gggacactct catctgcctc gctgacgggc gccgcgttcc tattcaggat 60
ctcgtggggc attcgccgga ggttattgcg gtcgacgata agggccgcct cgtttgcgct 120
aagtcagagg tcatctggaa ggtcggcgag cggtccgttt tcgagatcaa gctggcttcc 180
gggaggagca ttaaggctac cgctgagcac aggctcctgg cgttcaaggg ctggaggcat 240
gttaaggact tcaaagtggg ggataggctc gctattgctc ac 282

<210> SEQ ID NO 143
<211> LENGTH: 120
<212> TYPE: DNA
<213> ORGANISM: Artificial Sequence
<220> FEATURE:
<223> OTHER INFORMATION: Synthetic construct, Cbu_DnaB-C (#12-C) coding seq

<400> SEQUENCE: 143
atgtcggacc tgttctggga taggatcgtg tcgattgagg agaaggggtc tgaggaggtc 60
tacgatctca cagttccaaa gtacgcttct tggctcgcgg atggggttgt ttcacataat 120

<210> SEQ ID NO 144
<211> LENGTH: 288
<212> TYPE: DNA
<213> ORGANISM: Artificial Sequence
<220> FEATURE:
<223> OTHER INFORMATION: Synthetic construct, Mja_GF6P-N (#44-N) coding seq

<400> SEQUENCE: 144
tgcctgcacc ctgacacata cgttattctc cctgacgggc gcatgaagaa gatttcggag 60
attgatgagg atgaggttct ctcagtcaac ttcgaggacc tgaagctcta caataagaag 120
atcaagaagt tcaagcacaa ggctccgaag atcctctaca agattaagac cgcgttctcc 180
gagctcatca ccacgggcga gcataagctg ttcgtggtcg agaacgggaa gatcgtcgag 240
aagtgcgtta aggacctcaa tggcagcgag ctgatcgggg ttgtgagg 288

<210> SEQ ID NO 145
<211> LENGTH: 123
<212> TYPE: DNA
<213> ORGANISM: Artificial Sequence
<220> FEATURE:
<223> OTHER INFORMATION: Synthetic construct, Mja_GF6P-C (#44-C) coding seq

<400> SEQUENCE: 145
atggcggata tcgtttggac gaagttcaag attgaggagg tggagagcga tgttgagtat 60
gtgtacgatc tggaggtgga ggactaccac aacttcattg gcaatctcat catcaaccac 120
aac 123

<210> SEQ ID NO 146
<211> LENGTH: 378
<212> TYPE: DNA
<213> ORGANISM: Artificial Sequence
<220> FEATURE:
<223> OTHER INFORMATION: Synthetic construct, Mja_Hyp1-N (#46-N) coding seq

<400> SEQUENCE: 146
tgcgttccgc ctgacactct gctcatcctg gagaatgggt tcaagcgcat cgtggacatt 60
aaggtcgggg acaaggtcct gacgcacgag aaccggttca agaaggttga gaaggtgtac 120
aagcgcaggt acatcggcga catcattaag attaaggtgc gctacttccc agaggagatc 180
attctcaccc cagagcaccc tgtctacgct atcaagacgg agaagaggtg cgatggctct 240
catgggatct gcaagttcaa ctgcctcaca cagtacacta atccttcatg caagaagcgg 300
taccgcaagt acaagaggga gtggatcatt gccaaggacc tgaaggtcgg cgatgtgatc 360
gtctacccga ttcccaac 378

<210> SEQ ID NO 147
<211> LENGTH: 123
<212> TYPE: DNA
<213> ORGANISM: Artificial Sequence
<220> FEATURE:
<223> OTHER INFORMATION: Synthetic construct, Mja_Hyp1-C (#46-C) coding seq

<400> SEQUENCE: 147
atggggaatt acctgtacgc tcccatcatt aggatcggcc gggagtacta cgacgggttc 60
gtctacaatc tggaggtgga ggatgactct tcatacgtta cagtctcagg cactctgcac 120
aac 123

<210> SEQ ID NO 148
<211> LENGTH: 330
<212> TYPE: DNA
<213> ORGANISM: Artificial Sequence
<220> FEATURE:
<223> OTHER INFORMATION: Synthetic construct, Mja_IF2-N (#47-N) coding seq

<400> SEQUENCE: 148
tgcctgatgc cgcatgagaa ggtgctgacg gagtacgggg agattaagat tgaggacctg 60
ttcaagatcg ggaaggagat cgtggagaag gacgagctca aggagatcag gaagctgaat 120
attaaggtgc acactctcaa cgagaatggc gagatcaaga tcattaacgc cccatacgtg 180
tggaagctca agcataaggg gaagatgatc aaggtcaagc tgaagaactg gcactcgatc 240
accacgacac cggagcatcc cttcctgacc aacaatggct ggatcaaggc ggagaatatt 300
aagaagggga tgtatgtggc tatccctcgc 330

<210> SEQ ID NO 149
<211> LENGTH: 117
<212> TYPE: DNA
<213> ORGANISM: Artificial Sequence
<220> FEATURE:
<223> OTHER INFORMATION: Synthetic construct, Mja_IF2-C (#47-C) coding seq

<400> SEQUENCE: 149
atgaacattg cgttcgtcga ggttgaggat gtcgagatca ttgactacga tggctacgtt 60
tacgatctca caacagagac tcataacttc attgctaatg gcatcgtggt tcataat 117

<210> SEQ ID NO 150
<211> LENGTH: 306
<212> TYPE: DNA
<213> ORGANISM: Artificial Sequence
<220> FEATURE:
<223> OTHER INFORMATION: Synthetic construct, Mja_Pol1-N (#50-N) coding seq

<400> SEQUENCE: 150
tgccatccaa aggggacaaa ggtcgtggtc aagggcaagg gcatcgtgaa tattgaggac 60
gttaaggagg ggaattacgt tctcggcatc gacggctggc agaaggttaa gaaggtctgg 120
aagtacgagt acgagggcga gctcattaac gttaatgggc tgaagtgcac accgaaccac 180
aagatccccc tccgctacaa gattaagcat aagaagatca acaagaacga ttacctggtg 240
agggacatct acgcgaagtc gctcctgacc aagttcaagg gcgaggggaa gctcatcctg 300
tgcaag 306

<210> SEQ ID NO 151
<211> LENGTH: 123
<212> TYPE: DNA
<213> ORGANISM: Artificial Sequence
<220> FEATURE:
<223> OTHER INFORMATION: Synthetic construct, Mja_Pol1-C (#50-C) coding seq

<400> SEQUENCE: 151
atgtacgggt tctacgacct cgacgatgtg tgcgtctcac tggagtccta caagggcgag 60
gtgtacgatc tcactctgga gggcaggcct tactacttcg ccaatggcat cctcactcat 120
aat 123

<210> SEQ ID NO 152
<211> LENGTH: 366
<212> TYPE: DNA
<213> ORGANISM: Artificial Sequence
<220> FEATURE:
<223> OTHER INFORMATION: Synthetic construct, Pab_CDC211-N (#79-N) coding seq

<400> SEQUENCE: 152
tgcgtggatt acgagactga ggtcgtgctg gggaatgggg agcggaagaa gatcggggag 60
atcgtggagc gggctattga ggaggctgag aagaacggca agctcgggcg ggttgacgat 120
ggcttctacg ctccgatcga cattgaggtc tactcgctcg atctggagac cctcaaggtt 180
cggaaggcgc gggcaaatat cgcgtggaag cgcacagctc caaagaagat gatgctggtg 240
aagactaggg gcgggaagcg cattagggtc accccgacgc accccttctt cgttctggag 300
gagggcaagg tggctatgag gaaggcccgg gacctggagg agggcaacaa gatcgccacg 360
attgag 366

<210> SEQ ID NO 153
<211> LENGTH: 123
<212> TYPE: DNA
<213> ORGANISM: Artificial Sequence
<220> FEATURE:
<223> OTHER INFORMATION: Synthetic construct, Pab_CDC211-C (#79-C)

coding seq

<400> SEQUENCE: 153
atgtccgtga gctgggacga ggtcgcggag atcctggagt acgagccaaa ggatccttgg 60
gtctacgatc tgcaggttcc aggctaccac aacttcctcg ctaatggcat cttcgttcat 120
aat 123

<210> SEQ ID NO 154
<211> LENGTH: 333
<212> TYPE: DNA
<213> ORGANISM: Artificial Sequence
<220> FEATURE:
<223> OTHER INFORMATION: Synthetic construct, Pab_IF2-N (#81-N) coding seq

<400> SEQUENCE: 154
tgcctcctcc ctgatgagaa ggtcgtggtt ccctcggtcg ggttcgtgac actcaaggag 60
ctgttcgaga cggcttccaa ggtcgtggag cgcgacgatg agaaggagat cagggagctc 120
gacgagcgga ttaccagcgt taacggcgat gggaagacgg gcctggtcaa ggcctcctac 180
gtgtggaagg ttaggcacaa gggcaaggtc atccgggtca agctcaagaa ttggcacggc 240
gttacagtga ctccggagca tcccttcctc accacgaagg ggtggaagag ggctgaccag 300
ctgaggccag gcgattacgt cgcggttcct agg 333

<210> SEQ ID NO 155
<211> LENGTH: 114
<212> TYPE: DNA
<213> ORGANISM: Artificial Sequence
<220> FEATURE:
<223> OTHER INFORMATION: Synthetic construct, Pab_IF2-C (#81-C) coding seq

<400> SEQUENCE: 155
acgctggtgt tcatccccgt tgagaatgtg gaggaggagg agtacgacgg ctacgtttac 60
gatctcacta cggagactca taacttcatt gctaatggca tcctcgttca taat 114

<210> SEQ ID NO 156
<211> LENGTH: 363
<212> TYPE: DNA
<213> ORGANISM: Artificial Sequence
<220> FEATURE:
<223> OTHER INFORMATION: Synthetic construct, Pab_VMA-N (#92-N) coding seq

<400> SEQUENCE: 156
tgcgtggacg gggacactct cgtgctgaca aaggagttcg ggctcatcaa gatcaaggac 60
ctctacaaga ttctggacgg caaggggaag aagacagtga acggcaatga ggagtggaca 120
gagctggaga ggccaatcac tctgtacggc tacaaggacg ggaagatcgt cgagattaag 180
gctacccacg tttacaaggg cttctccgcc gggatgatcg agattcggac ccgcacgggc 240
cgcaagatta aggtcacgcc catccataag ctcttcacag gcagggttac taagaatggg 300
ctggagatcc gggaggtcat ggccaaggac ctcaagaagg gcgatcggat cattgtggcg 360
aag 363

<210> SEQ ID NO 157
<211> LENGTH: 126
<212> TYPE: DNA
<213> ORGANISM: Artificial Sequence
<220> FEATURE:

<223> OTHER INFORMATION: Synthetic construct, Pab_VMA-C (#92-C) coding
      seq

<400> SEQUENCE: 157
atgacccatg ttctgttcga cgagatcgtg gagattcggt acatctccga gggccaggag     60
gtgtacgacg ttactacgga gactcataat ttcattgggg gcaacatgcc tactctgctc    120
cacaac                                                               126

<210> SEQ ID NO 158
<211> LENGTH: 333
<212> TYPE: DNA
<213> ORGANISM: Artificial Sequence
<220> FEATURE:
<223> OTHER INFORMATION: Synthetic construct, Pho_IF2-N (#103-N) coding
      seq

<400> SEQUENCE: 158
tgcctgctgc cggaggagcg ggttattctg cctgactacg ggcctattac tctggaggag     60
ctcttcaata tgacaaagga gacagtgttc aaggacgagg agaaggaggt ccggaagctc    120
ggcatccgca tgccagtggc tggcgtcgat gggcgggtgc gcctgctgga gggcccctac    180
gtttggaagg tgcgctacaa ggggaagatg ctcagggtca agctgaagga ctggcacagc    240
gtggctgtca caccagagca tcccttcctc accacgcggg gctgggtgcg cgctgaccag    300
ctgaagcccg gggattacgt tgccgtgcca aag                                 333

<210> SEQ ID NO 159
<211> LENGTH: 117
<212> TYPE: DNA
<213> ORGANISM: Artificial Sequence
<220> FEATURE:
<223> OTHER INFORMATION: Synthetic construct, Pho_IF2-C (#103-C) coding
      seq

<400> SEQUENCE: 159
atgaacttcg ttttcctgcc ggtggagaag atcgaggagt tcgagtacga tggctacgtc     60
tacgacgtta ctacagagac tcataatttc attgctaatg gcatcctcgt tcataat      117

<210> SEQ ID NO 160
<211> LENGTH: 363
<212> TYPE: DNA
<213> ORGANISM: Artificial Sequence
<220> FEATURE:
<223> OTHER INFORMATION: Synthetic construct, Pho_VMA-N (#110-N) coding
      seq

<400> SEQUENCE: 160
tgcgtggacg gggacacact ggtgctgaca aaggagttcg ggctcatcaa gatcaaggag     60
ctctacgaga agctggacgg caaggggcgc aagattgtgg agggcaacga ggagtggacc    120
gagctggaga agccaatcac ggtctacggc tacaaggacg ggaagatcgt tgagattaag    180
gccacccacg tttacaaggg cgtgtccagc gggatggtcg agatcaggac ccggacgggc    240
cggaagatca aggtgacgcc gattcaccgc ctgttcacag gcagggtcac taaggacggg    300
ctgatcctca aggaggtcat ggctatgcat gttaagcccg gcgataggat cgccgtggtc    360
aag                                                                  363

<210> SEQ ID NO 161
<211> LENGTH: 126
<212> TYPE: DNA
<213> ORGANISM: Artificial Sequence
<220> FEATURE:
<223> OTHER INFORMATION: Synthetic construct, Pho_VMA-C (#110-C) coding seq

<400> SEQUENCE: 161
atgcagcata tcattttcga cgaggtcatc gatgtcaggt acattccgga gccccaggag 60
gtgtacgatg ttactacaga gactcataat ttcgtggggg gcaacatgcc aactctgctc 120
cacaat 126

<210> SEQ ID NO 162
<211> LENGTH: 288
<212> TYPE: DNA
<213> ORGANISM: Artificial Sequence
<220> FEATURE:
<223> OTHER INFORMATION: Synthetic construct, Rma_DnaB-N (#116-N) coding seq

<400> SEQUENCE: 162
tgcctcgcgg gggacactct cattacactg gctgacgggc ggcgggttcc tattcgggag 60
ctggtctcgc agcagaattt ctcggtctgg gcgctgaacc cgcagacgta caggctggag 120
agggctcggg tctcccgggc cttctgcaca ggcatcaagc ccgtttacag gctgaccacg 180
aggctcggga ggagcattag ggctactgct aatcaccgct tcctgacccc acagggctgg 240
aagagggtgg acgagctcca gcctggggat tacctggctc tcccaagg 288

<210> SEQ ID NO 163
<211> LENGTH: 120
<212> TYPE: DNA
<213> ORGANISM: Artificial Sequence
<220> FEATURE:
<223> OTHER INFORMATION: Synthetic construct, Rma_DnaB-C (#116-C) coding seq

<400> SEQUENCE: 163
atgtcagacg tctactggga tccgatcgtt tccattgagc ccgacggcgt tgaggaggtg 60
ttcgatctca ctgttccagg gccacataac ttcgttgcta atgacatcat tgctcataat 120

<210> SEQ ID NO 164
<211> LENGTH: 267
<212> TYPE: DNA
<213> ORGANISM: Artificial Sequence
<220> FEATURE:
<223> OTHER INFORMATION: Synthetic construct, Sru_DnaB-N (#123-N) coding seq

<400> SEQUENCE: 164
tgcctcggga aggggacacc ggttatgatg tacgatgggc ggacaaagcc agtggagaag 60
gtggaggtcg gggacaggct catgggggac gatggcagcc caaggacggt gcagtcgctg 120
gccaggggga gggagcagat gtactgggtc cgccagaaga ggggcatgga ctacagggtt 180
aacgagagcc acatcctctc gctgaagaag tctaggaggg agggcgcccg cgacaggggg 240
tcaatcgcgg atatttccgt ccgcgac 267

<210> SEQ ID NO 165
<211> LENGTH: 114
<212> TYPE: DNA
<213> ORGANISM: Artificial Sequence
<220> FEATURE:
<223> OTHER INFORMATION: Synthetic construct, Sru_DnaB-C (#123-C) coding seq

<400> SEQUENCE: 165
atgtggcgga tgaccggcat cgatgtcgag cccgacggcg ttggggatta cttcggcttc 60
actctggatg gcaatgggcg cttcctcctc ggggatggca ctgttactca taat 114

<210> SEQ ID NO 166
<211> LENGTH: 285
<212> TYPE: DNA
<213> ORGANISM: Artificial Sequence
<220> FEATURE:
<223> OTHER INFORMATION: Synthetic construct, Tag_Pol1Tsp-TYPol1-N (#128-N) coding seq

<400> SEQUENCE: 166
tgccatcctg cggacactaa ggtcatcgtg aagggcaagg gcatcgttaa tatctcggac 60
gtgaaggagg gggactacat tctcggcatc gacggctggc agcgggtcaa gaaggtttgg 120
aagtaccact acgagggcaa gctcatcaac attaatgggc tgaagtgcac gccgaaccat 180
aaggttcccg tggtcacaga gaatgacagg cagactcgca tcagggattc cctcgccaag 240
agcttcctgt cgggcaaggt caaggggaag atcattacca cgaag 285

<210> SEQ ID NO 167
<211> LENGTH: 86
<212> TYPE: DNA
<213> ORGANISM: Artificial Sequence
<220> FEATURE:
<223> OTHER INFORMATION: Synthetic construct, Tag_Pol1Tsp-TYPol1-C (#128-C) coding seq

<400> SEQUENCE: 167
catccgagta ctacaagggc gaggtctacg atctcactct ggagggcaat ccttactact 60
tcgccaatgg catcctcaca cataat 86

<210> SEQ ID NO 168
<211> LENGTH: 321
<212> TYPE: DNA
<213> ORGANISM: Artificial Sequence
<220> FEATURE:
<223> OTHER INFORMATION: Synthetic construct, Ter_RIR14-N (#135-N) coding seq

<400> SEQUENCE: 168
tgcctggaca agacggctct gcggattttc aatcaggggc tgctctacgc ggatgaggtc 60
gtgacaccgg gctcggggga gacagtcggc ctcgggctga cggtcaggaa cggcatcggg 120
gcgtccacag ccattgcgaa tcagccgatg gagctggttg agatcaagct cgctaacggc 180
cggaagctgc gcatgacccc taatcaccgg atgtccgtga agggcaagtg gattcatgcc 240
tgcaacctca agccggggat gctcctggac tacagcatcg gcgagtacca gaagcgcgag 300
gacaccctcc tgattcctct c 321

<210> SEQ ID NO 169
<211> LENGTH: 147
<212> TYPE: DNA
<213> ORGANISM: Artificial Sequence
<220> FEATURE:
<223> OTHER INFORMATION: Synthetic construct, Ter_RIR14-C (#135-C) coding seq

<400> SEQUENCE: 169
atgtcgaagt gcgtcctcaa ctactcgccc tacaagatcg agtctgttaa tattggcgct 60
gtgtgcgact acagctacga tttcgccatc gagggcatca atgataatga ctcttggtac 120
tggcaggggg ctctcaagtc tcacaac 147

<210> SEQ ID NO 170
<211> LENGTH: 333
<212> TYPE: DNA
<213> ORGANISM: Artificial Sequence
<220> FEATURE:
<223> OTHER INFORMATION: Synthetic construct, Tko_IF2-N (#143-N) coding seq

<400> SEQUENCE: 170
tgcctgctgc cggatgagaa ggttattctc cctgagcatg ggcctattac actcaagggg 60
ctcttcgatc tcgctaagga gacagtcgtg gctgacaacg agaaggagat ccgcaagctg 120
ggcgccaagc tcaccattgt gggcgaggat gggaggctca gggtcctgga gagcccatac 180
gtttggaagg tgcggcaccg cggcaagatg ctgagggtca agctcaagaa ctggcactca 240
gtgtccgtca cgccagagca tcccttcctg accacgcggg gctgggtgcg cgctgaccag 300
ctcaagccgg gggattacgt tgcggtgccc agg 333

<210> SEQ ID NO 171
<211> LENGTH: 117
<212> TYPE: DNA
<213> ORGANISM: Artificial Sequence
<220> FEATURE:
<223> OTHER INFORMATION: Synthetic construct, Tko_IF2-C (#143-C) coding seq

<400> SEQUENCE: 171
atgaatctcg tcttcatccc ggttgaggac attgaggagt tcgagtacga gggctacgtt 60
tacgacgtta ctacagagac tcataatttc gttgctaatg gcatcctcgt tcataat 117

<210> SEQ ID NO 172
<211> LENGTH: 297
<212> TYPE: DNA
<213> ORGANISM: Artificial Sequence
<220> FEATURE:
<223> OTHER INFORMATION: Synthetic construct, Tth-HB27DnaE2-N (#150-N) coding seq

<400> SEQUENCE: 172
tgcctgcctg cgcgggctag ggtcgtggat tggtgcacag ggcgggtcgt tcgggtcggg 60
gagatcgtta ggggggaggc taagggcgtc tgggtggtct ccctggacga ggctaggctg 120
aggctcgttc caaggcctgt tgtggctgct ttcccaagcg gcaaggctca ggtgtacgct 180
ctgaggaccg ctacgggcag ggtgctggag gcgacagcta accacccagt ctacactcca 240
gagggctgga ggccactggg gaccctcgct cctggcgact acgtcgctct gccaagg 297

<210> SEQ ID NO 173
<211> LENGTH: 120
<212> TYPE: DNA
<213> ORGANISM: Artificial Sequence
<220> FEATURE:
<223> OTHER INFORMATION: Synthetic construct, Tth-HB27DnaE2-C (#150-C) coding seq

<400> SEQUENCE: 173
atggctgagg tttactggga tcgcgtcgag gcggttgagc cgctcggcga ggaggaggtc 60
ttcgatctca ctgtggaggg cactcatact ttcgttgcgg aggatgttat cgttcataat 120

<210> SEQ ID NO 174
<211> LENGTH: 42

<212> TYPE: DNA
<213> ORGANISM: Artificial Sequence
<220> FEATURE:
<223> OTHER INFORMATION: Synthetic construct, Phy_tag1-N coding seq

<400> SEQUENCE: 174
atggcccaca tcgtgatggt ggacgcctac aagccgacga ag 42

<210> SEQ ID NO 175
<211> LENGTH: 39
<212> TYPE: DNA
<213> ORGANISM: Artificial Sequence
<220> FEATURE:
<223> OTHER INFORMATION: Synthetic construct, Phy_tag1-C coding seq

<400> SEQUENCE: 175
gcccacatcg tgatggtgga cgcctacaag ccgacgaag 39

<210> SEQ ID NO 176
<211> LENGTH: 351
<212> TYPE: DNA
<213> ORGANISM: Artificial Sequence
<220> FEATURE:
<223> OTHER INFORMATION: Synthetic construct, Phy_catcher1-N coding seq

<400> SEQUENCE: 176
atgggcgcta tggttgatac cttatcaggt ttatcaagtg agcaaggtca gtccggtgat 60
atgacaattg aagaagatag tgctacccat attaaattct caaaacgtga tgaggacggc 120
aaagagttag ctggtgcaac tatggagttg cgtgattcat ctggtaaaac tattagtaca 180
tggatttcag atggacaagt gaaagatttc tacctgtatc caggaaaata tacatttgtc 240
gaaaccgcag caccagacgg ttatgaggta gcaactgcta ttacctttac agttaatgag 300
caaggtcagg ttactgtaaa tggcaaagca actaaaggtg acgctcatat t 351

<210> SEQ ID NO 177
<211> LENGTH: 348
<212> TYPE: DNA
<213> ORGANISM: Artificial Sequence
<220> FEATURE:
<223> OTHER INFORMATION: Synthetic construct, Phy_catcher1-C coding seq

<400> SEQUENCE: 177
ggcgctatgg ttgatacctt atcaggttta tcaagtgagc aaggtcagtc cggtgatatg 60
acaattgaag aagatagtgc tacccatatt aaattctcaa aacgtgatga ggacggcaaa 120
gagttagctg gtgcaactat ggagttgcgt gattcatctg gtaaaactat tagtacatgg 180
atttcagatg gacaagtgaa agatttctac ctgtatccag gaaaatatac atttgtcgaa 240
accgcagcac cagacggtta tgaggtagca actgctatta cctttacagt taatgagcaa 300
ggtcaggtta ctgtaaatgg caaagcaact aaaggtgacg ctcatatt 348

<210> SEQ ID NO 178
<211> LENGTH: 102
<212> TYPE: DNA
<213> ORGANISM: Artificial Sequence
<220> FEATURE:
<223> OTHER INFORMATION: Synthetic construct, cc17 N-terminal coil
      coding seq

<400> SEQUENCE: 178
atgagggcca agcagctgga ggacaagatt gaggagctgc tgagcaagat ctaccacctg 60
gagaacgaga tagcccgcct gaagaagctg attggcgagc gc 102

<210> SEQ ID NO 179
<211> LENGTH: 101
<212> TYPE: DNA
<213> ORGANISM: Artificial Sequence
<220> FEATURE:
<223> OTHER INFORMATION: Synthetic construct, cc17 C-terminal coil coding seq

<400> SEQUENCE: 179
cagctggagg acaagattga ggagctgctg agcaagatct accacctgga gaacgagata 60
gcgaggctga agaagctgat tggcgagcgc accaccccta a 101

<210> SEQ ID NO 180
<211> LENGTH: 102
<212> TYPE: DNA
<213> ORGANISM: Artificial Sequence
<220> FEATURE:
<223> OTHER INFORMATION: Synthetic construct, cc30 N-terminal coil coding seq

<400> SEQUENCE: 180
atgagggcca agcagctgga ggacaaggtc gaggagctgc tgagcaagaa ctaccacctg 60
gagaacgagg tcgcccgcct gaagaagctg gtgggcaccc gc 102

<210> SEQ ID NO 181
<211> LENGTH: 87
<212> TYPE: DNA
<213> ORGANISM: Artificial Sequence
<220> FEATURE:
<223> OTHER INFORMATION: Synthetic construct, cc30 C-terminal coil coding seq

<400> SEQUENCE: 181
cagctggagg acaaggtcga ggagctgctg agcaagaact accacctgga gaacgaggtc 60
gcgaggctga agaagctggt cggctaa 87

<210> SEQ ID NO 182
<211> LENGTH: 99
<212> TYPE: DNA
<213> ORGANISM: Artificial Sequence
<220> FEATURE:
<223> OTHER INFORMATION: Synthetic construct, L55-1.1 inker coding seq

<400> SEQUENCE: 182
agcgccgccg aggccgccgc caaggaggcc gccgccaagg aggccgccgc caaggaggcc 60
gccgccaagg ccgttaacac cccgcagagc gccttcgcc 99

<210> SEQ ID NO 183
<211> LENGTH: 18
<212> TYPE: DNA
<213> ORGANISM: Artificial Sequence
<220> FEATURE:
<223> OTHER INFORMATION: Synthetic construct, Phy_taglink coding seq

<400> SEQUENCE: 183
ggttcagggg gttccggt 18

<210> SEQ ID NO 184
<211> LENGTH: 18
<212> TYPE: DNA
<213> ORGANISM: Artificial Sequence
<220> FEATURE:
<223> OTHER INFORMATION: Synthetic construct, Phy_catcherlink coding seq

<400> SEQUENCE: 184
ggttcagggg gttccggt 18

<210> SEQ ID NO 185
<211> LENGTH: 1254
<212> TYPE: DNA
<213> ORGANISM: Artificial Sequence
<220> FEATURE:
<223> OTHER INFORMATION: Synthetic construct, Nov9X coding seq

<400> SEQUENCE: 185
gcgcagtccg agccggagct gaagctggag tccgtggtga tcgtgtcgcg ccacggggtg 60
cgcgccccga ccaaggccac gcagctcatg caggacgtga ccccggacgc ctggccgacc 120
tggccggtga agctcggcga gctgaccccg cgcggcggcg agctgatcgc ctacctcggc 180
cactactggc gccagcgcct cgtggccgac ggcctcctcc cgaagtgcgg ctgcccgcag 240
tccggccagg tggcgatcat cgccgacgtg gacgagcgca cccgcaagac gggcgaggcc 300
ttcgccgccg gcctcgcccc ggactgcgcc atcaccgtgc acacccaggc cgacacctcc 360
tccccggacc cgctcttcaa cccgctcaag accggcgtgt gccagctcga caacgccaac 420
gtgaccgacg ccatcctgga gcgcgccggc ggctccatcg ccgacttcac cggccactac 480
cagaccgcct tccgcgagct ggagcgcgtg ctcaacttcc cgcagtcgaa cctctgcctc 540
aagcgcgaga agcaggacga gtcctgctcc ctcacccagg ccctcccgtc cgagctgaag 600
gtgtccgccg actgcgtgtc cctcaccggc gccgtgtccc tcgcctccat gctcaccgaa 660
atcttcctcc tccagcaggc ccagggcatg ccggagccgg gctggggccg catcaccgac 720
tcccaccagt ggaacaccct cctctccctc cacaacgccc agttcgacct cctccagcgc 780
accccggagg tggcccgctc ccgcgccacc ccgctcctcg acctcatcaa gaccgccctc 840
accccgcacc cgccgcagaa gcaggcctac ggcgtgaccc tcccgacctc ggtgctcttc 900
atcgccggcc acgacaccaa cctcgccaac ctcggcggcg ccctggagct gaactggacc 960
ctcccgggcc agccggacaa caccccgccg ggcggcgagc tggtgttcga gcgctggcgc 1020
cgcctctccg acaactccca gtggattcag gtgtccctcg tgttccagac cctccagcag 1080
atgcgcgaca agaccccgct ctccctcaac accccgccgg gcgaggtgaa gctcaccctg 1140
gccggctgcg aggagcgcaa cgcgcagggc atgtgctccc tcgccggctt cacccagatc 1200
gtgaacgagg cccgcatccc ggcctgctcc ctctccgaga aggacgagct gtaa 1254

<210> SEQ ID NO 186
<211> LENGTH: 264
<212> TYPE: DNA
<213> ORGANISM: Artificial Sequence
<220> FEATURE:
<223> OTHER INFORMATION: Synthetic construct, gp41-1N coding seq

<400> SEQUENCE: 186
tgtctggacc tgaaaacgca agtgcaaacc ccgcaaggca tgaaggaaat ctcaaacatc 60
caagtcggtg acctggtgct gtcgaatacc ggctataacg aagtgctgaa tgtttttccg 120
aagagcaaaa agaaatctta caagatcacg ctggaagatg gcaaggaaat tatttgcagc 180
gaagaacatc tgttcccgac ccagacgggc gaaatgaata tctccggcgg tctgaaagaa 240
ggcatgtgtc tgtacgtcaa ggaa 264

<210> SEQ ID NO 187

<211> LENGTH: 88
<212> TYPE: PRT
<213> ORGANISM: Artificial Sequence
<220> FEATURE:
<223> OTHER INFORMATION: Synthetic construct, gp41-1N intein

<400> SEQUENCE: 187

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85

<210> SEQ ID NO 188
<211> LENGTH: 111
<212> TYPE: DNA
<213> ORGANISM: Artificial Sequence
<220> FEATURE:
<223> OTHER INFORMATION: Synthetic construct, gp41-1C coding seq

<400> SEQUENCE: 188
atgatgctga agaaaattct gaagatcgaa gaactggatg aacgtgaact gattgacatc     60
gaagttagcg gcaaccatct gttttacgcg aatgacattc tgacccacaa c             111

<210> SEQ ID NO 189
<211> LENGTH: 37
<212> TYPE: PRT
<213> ORGANISM: Artificial Sequence
<220> FEATURE:
<223> OTHER INFORMATION: Synthetic construct, gp41-1C intein

<400> SEQUENCE: 189

Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Asp
            20                  25                  30

Ile Leu Thr His Asn
        35

<210> SEQ ID NO 190
<211> LENGTH: 108
<212> TYPE: DNA
<213> ORGANISM: Artificial Sequence
<220> FEATURE:
<223> OTHER INFORMATION: Synthetic construct, gp41-1C[MTT] coding seq

<400> SEQUENCE: 190
atgacgaaga aaattacgaa gatcgaagaa ctggatgaac gtgaactgat tgacatcgaa     60
gttagcggca accatctgtt ttacgcgaat gacattggga cccacaac                 108

<210> SEQ ID NO 191
<211> LENGTH: 36
<212> TYPE: PRT
<213> ORGANISM: Artificial Sequence
<220> FEATURE:

<223> OTHER INFORMATION: Synthetic construct, gp41-1C[MTT] intein

<400> SEQUENCE: 191

```
Met Thr Lys Lys Ile Thr Lys Ile Glu Glu Leu Asp Glu Arg Glu Leu
1               5                   10                  15

Ile Asp Ile Glu Val Ser Gly Asn His Leu Phe Tyr Ala Asn Asp Ile
            20                  25                  30

Gly Thr His Asn
        35
```

<210> SEQ ID NO 192
<211> LENGTH: 369
<212> TYPE: DNA
<213> ORGANISM: Artificial Sequence
<220> FEATURE:
<223> OTHER INFORMATION: Synthetic construct, Ssp DnaE-N coding seq

<400> SEQUENCE: 192

```
tgcctttctt tcggaactga gatccttacc gttgagtacg gaccacttcc tattggtaag     60

atcgtttctg aggaaattaa ctgctcagtg tactctgttg atccagaagg aagagtttac    120

actcaggcta tcgcacaatg gcacgatagg ggtgaacaag aggttcttga gtacgagctt    180

gaagatggat ccgttattcg tgctacctct gaccatagat tcttgactac agattatcag    240

cttctcgcta tcgaggaaat ctttgctagg caacttgatc tccttacttt ggagaacatc    300

aagcagacag aagaggctct tgacaaccac agacttccat tccctttgct cgatgctgga    360

accatcaag                                                            369
```

<210> SEQ ID NO 193
<211> LENGTH: 123
<212> TYPE: PRT
<213> ORGANISM: Artificial Sequence
<220> FEATURE:
<223> OTHER INFORMATION: Synthetic construct, Ssp DnaE-N intein

<400> SEQUENCE: 193

```
Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120
```

<210> SEQ ID NO 194
<211> LENGTH: 108
<212> TYPE: DNA
<213> ORGANISM: Artificial Sequence
<220> FEATURE:
<223> OTHER INFORMATION: Synthetic construct, Ssp DnaE-C coding seq

<400> SEQUENCE: 194
atggttaagg tgattggaag acgttctctt ggtgttcaaa ggatcttcga tatcggattg 60
ccacaagacc acaactttct tctcgctaat ggtgccatcg ctgccaat 108

<210> SEQ ID NO 195
<211> LENGTH: 36
<212> TYPE: PRT
<213> ORGANISM: Artificial Sequence
<220> FEATURE:
<223> OTHER INFORMATION: Synthetic construct, Ssp DnaE-C intein

<400> SEQUENCE: 195

Met Val Lys Val Ile Gly Arg Arg Ser Leu Gly Val Gln Arg Ile Phe
1 5 10 15

Asp Ile Gly Leu Pro Gln Asp His Asn Phe Leu Leu Ala Asn Gly Ala
20 25 30

Ile Ala Ala Asn
35

<210> SEQ ID NO 196
<211> LENGTH: 255
<212> TYPE: DNA
<213> ORGANISM: Artificial Sequence
<220> FEATURE:
<223> OTHER INFORMATION: Synthetic construct, TrxH coding seq

<400> SEQUENCE: 196
atgctgattg aagtgtttag cagtccgatc tgtccgcact gcccaggcgc cgagcgtgtt 60
gtcgaagagg tcgtcgataa actgagctgc gatgatattg aagtgcgcca cattgatgtg 120
acagaagatc cgggcagtgc agagaagtac tctatcatgg cagtgcccac cattgtggta 180
gatggtgagg tggcatttgt tggcgccccg acgacgcagc aatttgagga atatctgcgt 240
aaaaagctta atcgg 255

<210> SEQ ID NO 197
<211> LENGTH: 85
<212> TYPE: PRT
<213> ORGANISM: Artificial Sequence
<220> FEATURE:
<223> OTHER INFORMATION: Synthetic construct, TrxH domain

<400> SEQUENCE: 197

Met Leu Ile Glu Val Phe Ser Ser Pro Ile Cys Pro His Cys Pro Gly
1 5 10 15

Ala Glu Arg Val Val Glu Glu Val Val Asp Lys Leu Ser Cys Asp Asp
20 25 30

Ile Glu Val Arg His Ile Asp Val Thr Glu Asp Pro Gly Ser Ala Glu
35 40 45

Lys Tyr Ser Ile Met Ala Val Pro Thr Ile Val Val Asp Gly Glu Val
50 55 60

Ala Phe Val Gly Ala Pro Thr Thr Gln Gln Phe Glu Glu Tyr Leu Arg
65 70 75 80

Lys Lys Leu Asn Arg
85

<210> SEQ ID NO 198
<211> LENGTH: 12
<212> TYPE: DNA
<213> ORGANISM: Artificial Sequence
<220> FEATURE:

<223> OTHER INFORMATION: Synthetic construct, DPNG linker coding seq

<400> SEQUENCE: 198
gatcctaatg gt 12

<210> SEQ ID NO 199
<211> LENGTH: 4
<212> TYPE: PRT
<213> ORGANISM: Artificial Sequence
<220> FEATURE:
<223> OTHER INFORMATION: Synthetic construct, DPNG linker

<400> SEQUENCE: 199

Asp Pro Asn Gly
1

<210> SEQ ID NO 200
<211> LENGTH: 1752
<212> TYPE: DNA
<213> ORGANISM: Artificial Sequence
<220> FEATURE:
<223> OTHER INFORMATION: Synthetic construct, #1 gp41-Phy02 coding seq

<400> SEQUENCE: 200
atgatgctga agaaaattct gaagatcgaa gaactggatg aacgtgaact gattgacatc 60
gaagttagcg gcaaccatct gttttacgcg aatgacattc tgacccacaa cagcgcagcc 120
gaagccgctg cgaaggaggc agctgcgaaa gaagcggctg caaaagaagc ggcagctaag 180
gctttgaata ccccgcaatc ggctttcgct caatcggaac cggaactgaa actggaaagt 240
gtggttattg tgtctcgtca tggcgttcgc gctccgacca aatttacgca gctgatgcaa 300
gatgtcaccc cggacgcctt ctatacgtgg ccggtgaagc tgggtgaact gaccccgcgt 360
ggcggtgaac tgatcgccta tctgggtcac tactggcgtc agcgcctggt ggcagatggt 420
ctgctgccga aaaagggctg cccgcagagc ggtcaagttg caattatcgc tgatgtcgac 480
gaacgtaccc gcaaaacggg tgaagcattt gcggccggtc tggcaccgga ttgcgccatt 540
accgttcata cgcaggcaga taccagctct ccggacccgc tgttcaaccc gctgaaaacc 600
ggcgtctgtc agctggatgt cgcgcaagtg acggacgcca ttctggaacg tgcaggcggt 660
tccatcgctg attttaccgg tcactaccag acggcattcc gtgaactgga acgcgttctg 720
aactttccgc agtcaaatct ggcgctgaaa cgcgaaaagc aggatgaaag tgcgtccctg 780
acccaagccc tgccgagtga actgaaagtc tccgccgaca atgtgtcact gaccggcgca 840
tggtcactgg cttcgatgct gacggaaatt tttctgctgc agcaagcaca gggtatgccg 900
gaaccgggtt ggggtcgtat caccgattcg catcagtgga acacgctgct gagcctgcac 960
aatgcgcagt tcgacctgct gcaacgtacc ccggaagtgg cacgttcgcg cgccacgccg 1020
ctgctggatc tgattaaaac cgctctgacg ccgcatccgc cgcagaagca agcgtatggc 1080
gtgaccctgc cgacgagcgt tctgtttatc gcgggtcacg acaccaacct ggcaaatctg 1140
ggcggtgctc tggaactgca gtggaccctg ccgggtcaac cggataacac gccgccgggc 1200
ggtgaactgg ttttcgaacg ttggcgtcgc ctgagcgaca attctcagtg gatccaagtt 1260
agcctggtct ttcagaccct gcagcaaatg cgcgataaaa ccccgctgtt cctgaacacg 1320
ccgccgggcg aagtgaagct gaccctggcg ggttgcgaag aacgtaacgc ccagggcatg 1380
tgttctctgg caggttttac ccagattgtt aatgaagcac gcatcccggc ttgtagtctg 1440
gggggcgcag aagcagctgc caaagaggcg gccgcaaagg tcaatctgtg tctggacctg 1500
aaaacgcaag tgcaaacccc gcaaggcatg aaggaaatct caaacatcca agtcggtgac 1560
ctggtgctgt cgaataccgg ctataacgaa gtgctgaatg tttttccgaa gagcaaaaag 1620
aaatcttaca agatcacgct ggaagatggc aaggaaatta tttgcagcga agaacatctg 1680
ttcccgaccc agacgggcga aatgaatatc tccggcggtc tgaaagaagg catgtgtctg 1740
tacgtcaagg aa 1752

<210> SEQ ID NO 201
<211> LENGTH: 583
<212> TYPE: PRT
<213> ORGANISM: Artificial Sequence
<220> FEATURE:
<223> OTHER INFORMATION: Synthetic construct, #1 gp41-Phy02

<400> SEQUENCE: 201

Met Leu Lys Lys Ile Leu Lys Ile Glu Glu Leu Asp Glu Arg Glu Leu
1 5 10 15

Ile Asp Ile Glu Val Ser Gly Asn His Leu Phe Tyr Ala Asn Asp Ile
20 25 30

Leu Thr His Asn Ser Ala Ala Glu Ala Ala Ala Lys Glu Ala Ala Ala
35 40 45

Lys Glu Ala Ala Ala Lys Glu Ala Ala Ala Lys Ala Leu Asn Thr Pro
50 55 60

Gln Ser Ala Phe Ala Gln Ser Glu Pro Glu Leu Lys Leu Glu Ser Val
65 70 75 80

Val Ile Val Ser Arg His Gly Val Arg Ala Pro Thr Lys Phe Thr Gln
85 90 95

Leu Met Gln Asp Val Thr Pro Asp Ala Phe Tyr Thr Trp Pro Val Lys
100 105 110

Leu Gly Glu Leu Thr Pro Arg Gly Gly Glu Leu Ile Ala Tyr Leu Gly
115 120 125

His Tyr Trp Arg Gln Arg Leu Val Ala Asp Gly Leu Leu Pro Lys Lys
130 135 140

Gly Cys Pro Gln Ser Gly Gln Val Ala Ile Ile Ala Asp Val Asp Glu
145 150 155 160

Arg Thr Arg Lys Thr Gly Glu Ala Phe Ala Ala Gly Leu Ala Pro Asp
165 170 175

Cys Ala Ile Thr Val His Thr Gln Ala Asp Thr Ser Ser Pro Asp Pro
180 185 190

Leu Phe Asn Pro Leu Lys Thr Gly Val Cys Gln Leu Asp Val Ala Gln
195 200 205

Val Thr Asp Ala Ile Leu Glu Arg Ala Gly Gly Ser Ile Ala Asp Phe
210 215 220

Thr Gly His Tyr Gln Thr Ala Phe Arg Glu Leu Glu Arg Val Leu Asn
225 230 235 240

Phe Pro Gln Ser Asn Leu Ala Leu Lys Arg Glu Lys Gln Asp Glu Ser
245 250 255

Ala Ser Leu Thr Gln Ala Leu Pro Ser Glu Leu Lys Val Ser Ala Asp
260 265 270

Asn Val Ser Leu Thr Gly Ala Trp Ser Leu Ala Ser Met Leu Thr Glu
275 280 285

Ile Phe Leu Leu Gln Gln Ala Gln Gly Met Pro Glu Pro Gly Trp Gly
290 295 300

Arg Ile Thr Asp Ser His Gln Trp Asn Thr Leu Leu Ser Leu His Asn
305 310 315 320

```
Ala Gln Phe Asp Leu Leu Gln Arg Thr Pro Glu Val Ala Arg Ser Arg
                325                 330                 335

Ala Thr Pro Leu Leu Asp Leu Ile Lys Thr Ala Leu Thr Pro His Pro
            340                 345                 350

Pro Gln Lys Gln Ala Tyr Gly Val Thr Leu Pro Thr Ser Val Leu Phe
        355                 360                 365

Ile Ala Gly His Asp Thr Asn Leu Ala Asn Leu Gly Gly Ala Leu Glu
    370                 375                 380

Leu Gln Trp Thr Leu Pro Gly Gln Pro Asp Asn Thr Pro Pro Gly Gly
385                 390                 395                 400

Glu Leu Val Phe Glu Arg Trp Arg Arg Leu Ser Asp Asn Ser Gln Trp
                405                 410                 415

Ile Gln Val Ser Leu Val Phe Gln Thr Leu Gln Gln Met Arg Asp Lys
            420                 425                 430

Thr Pro Leu Phe Leu Asn Thr Pro Pro Gly Glu Val Lys Leu Thr Leu
        435                 440                 445

Ala Gly Cys Glu Glu Arg Asn Ala Gln Gly Met Cys Ser Leu Ala Gly
    450                 455                 460

Phe Thr Gln Ile Val Asn Glu Ala Arg Ile Pro Ala Cys Ser Leu Gly
465                 470                 475                 480

Gly Ala Glu Ala Ala Ala Lys Glu Ala Ala Ala Lys Val Asn Leu Cys
                485                 490                 495

Leu Asp Leu Lys Thr Gln Val Gln Thr Pro Gln Gly Met Lys Glu Ile
            500                 505                 510

Ser Asn Ile Gln Val Gly Asp Leu Val Leu Ser Asn Thr Gly Tyr Asn
        515                 520                 525

Glu Val Leu Asn Val Phe Pro Lys Ser Lys Lys Lys Ser Tyr Lys Ile
    530                 535                 540

Thr Leu Glu Asp Gly Lys Glu Ile Ile Cys Ser Glu Glu His Leu Phe
545                 550                 555                 560

Pro Thr Gln Thr Gly Glu Met Asn Ile Ser Gly Gly Leu Lys Glu Gly
                565                 570                 575

Met Cys Leu Tyr Val Lys Glu
            580
```

<210> SEQ ID NO 202
<211> LENGTH: 1692
<212> TYPE: DNA
<213> ORGANISM: Artificial Sequence
<220> FEATURE:
<223> OTHER INFORMATION: Synthetic construct, #2 gp41-Phy02 coding seq

<400> SEQUENCE: 202

```
atgacgaaga aaattacgaa gatcgaagaa ctggatgaac gtgaactgat tgacatcgaa     60

gttagcggca accatctgtt ttacgcgaat gacattggga cccacaacag cgcagccgaa    120

gccgctgcga aggaggcagc tgcgaaagaa gcggctgcaa aagaagcggc agctaaggct    180

ttgaataccc cgcaatcggc tttcgctcaa tcggaaccgg aactgaaact ggaaagtgtg    240

gttattgtgt ctcgtcatgg cgttcgcgct ccgaccaaat ttacgcagct gatgcaagat    300

gtcaccccgg acgccttcta tacgtggccg gtgaagctgg gtgaactgac cccgcgtggc    360

ggtgaactga tcgcctatct gggtcactac tggcgtcagc gcctggtggc agatggtctg    420

ctgccgaaaa agggctgccc gcagagcggt caagttgcaa ttatcgctga tgtcgacgaa    480

cgtacccgca aaacgggtga agcatttgcg gccggtctgg caccggattg cgccattacc    540
```

```
gttcatacgc aggcagatac cagctctccg gacccgctgt tcaacccgct gaaaaccggc    600

gtctgtcagc tggatgtcgc gcaagtgacg gacgccattc tggaacgtgc aggcggttcc    660

atcgctgatt ttaccggtca ctaccagacg gcattccgtg aactggaacg cgttctgaac    720

tttccgcagt caaatctggc gctgaaacgc gaaaagcagg atgaaagtgc gtccctgacc    780

caagccctgc cgagtgaact gaaagtctcc gccgacaatg tgtcactgac cggcgcatgg    840

tcactggctt cgatgctgac ggaaattttt ctgctgcagc aagcacaggg tatgccggaa    900

ccgcagttcg acctgctgca acgtaccccg gaagtggcac gttcgcgcgc cacgccgctg    960

ctggatctga ttaaaaccgc tctgacgccg catccgccgc agaagcaagc gtatggcgtg   1020

accctgccga cgagcgttct gtttatcgcg ggtcacgaca ccaacctggc aaatctgggc   1080

ggtgctctgg aactgcagtg gaccctgccg ggtcaaccgg ataacacgcc gccgggcggt   1140

gaactggttt tcgaacgttg gcgtcgcctg agcgacaatt ctcagtggat ccaagttagc   1200

ctggtctttc agaccctgca gcaaatgcgc gataaaaccc cgctgttcct gaacacgccg   1260

ccgggcgaag tgaagctgac cctggcgggt tgcgaagaac gtaacgccca gggcatgtgt   1320

tctctggcag gttttaccca gattgttaat gaagcacgca tcccggcttg tagtctgggg   1380

ggcgcagaag cagctgccaa agaggcggcc gcaaaggtca atctgtgtct ggacctgaaa   1440

acgcaagtgc aaaccccgca aggcatgaag gaaatctcaa acatccaagt cggtgacctg   1500

gtgctgtcga ataccggcta taacgaagtg ctgaatgttt ttccgaagag caaaaagaaa   1560

tcttacaaga tcacgctgga agatggcaag gaaattattt gcagcgaaga acatctgttc   1620

ccgacccaga cgggcgaaat gaatatctcc ggcggtctga aagaaggcat gtgtctgtac   1680

gtcaaggaat aa                                                       1692
```

<210> SEQ ID NO 203
<211> LENGTH: 583
<212> TYPE: PRT
<213> ORGANISM: Artificial Sequence
<220> FEATURE:
<223> OTHER INFORMATION: Synthetic construct, #2 gp41-Phy02

<400> SEQUENCE: 203

```
Met Thr Lys Lys Ile Thr Lys Ile Glu Glu Leu Asp Glu Arg Glu Leu
1               5                   10                  15

Ile Asp Ile Glu Val Ser Gly Asn His Leu Phe Tyr Ala Asn Asp Ile
            20                  25                  30

Gly Thr His Asn Ser Ala Ala Glu Ala Ala Ala Lys Glu Ala Ala Ala
        35                  40                  45

Lys Glu Ala Ala Ala Lys Glu Ala Ala Ala Lys Ala Leu Asn Thr Pro
    50                  55                  60

Gln Ser Ala Phe Ala Gln Ser Glu Pro Glu Leu Lys Leu Glu Ser Val
65                  70                  75                  80

Val Ile Val Ser Arg His Gly Val Arg Ala Pro Thr Lys Phe Thr Gln
                85                  90                  95

Leu Met Gln Asp Val Thr Pro Asp Ala Phe Tyr Thr Trp Pro Val Lys
            100                 105                 110

Leu Gly Glu Leu Thr Pro Arg Gly Gly Glu Leu Ile Ala Tyr Leu Gly
        115                 120                 125

His Tyr Trp Arg Gln Arg Leu Val Ala Asp Gly Leu Leu Pro Lys Lys
    130                 135                 140

Gly Cys Pro Gln Ser Gly Gln Val Ala Ile Ile Ala Asp Val Asp Glu
```

-continued

```
145                 150                 155                 160

Arg Thr Arg Lys Thr Gly Glu Ala Phe Ala Ala Gly Leu Ala Pro Asp
                165                 170                 175

Cys Ala Ile Thr Val His Thr Gln Ala Asp Thr Ser Ser Pro Asp Pro
            180                 185                 190

Leu Phe Asn Pro Leu Lys Thr Gly Val Cys Gln Leu Asp Val Ala Gln
        195                 200                 205

Val Thr Asp Ala Ile Leu Glu Arg Ala Gly Gly Ser Ile Ala Asp Phe
    210                 215                 220

Thr Gly His Tyr Gln Thr Ala Phe Arg Glu Leu Glu Arg Val Leu Asn
225                 230                 235                 240

Phe Pro Gln Ser Asn Leu Ala Leu Lys Arg Glu Lys Gln Asp Glu Ser
                245                 250                 255

Ala Ser Leu Thr Gln Ala Leu Pro Ser Glu Leu Lys Val Ser Ala Asp
            260                 265                 270

Asn Val Ser Leu Thr Gly Ala Trp Ser Leu Ala Ser Met Leu Thr Glu
        275                 280                 285

Ile Phe Leu Leu Gln Gln Ala Gln Gly Met Pro Glu Pro Gly Trp Gly
    290                 295                 300

Arg Ile Thr Asp Ser His Gln Trp Asn Thr Leu Leu Ser Leu His Asn
305                 310                 315                 320

Ala Gln Phe Asp Leu Leu Gln Arg Thr Pro Glu Val Ala Arg Ser Arg
                325                 330                 335

Ala Thr Pro Leu Leu Asp Leu Ile Lys Thr Ala Leu Thr Pro His Pro
            340                 345                 350

Pro Gln Lys Gln Ala Tyr Gly Val Thr Leu Pro Thr Ser Val Leu Phe
        355                 360                 365

Ile Ala Gly His Asp Thr Asn Leu Ala Asn Leu Gly Gly Ala Leu Glu
    370                 375                 380

Leu Gln Trp Thr Leu Pro Gly Gln Pro Asp Asn Thr Pro Pro Gly Gly
385                 390                 395                 400

Glu Leu Val Phe Glu Arg Trp Arg Arg Leu Ser Asp Asn Ser Gln Trp
                405                 410                 415

Ile Gln Val Ser Leu Val Phe Gln Thr Leu Gln Gln Met Arg Asp Lys
            420                 425                 430

Thr Pro Leu Phe Leu Asn Thr Pro Pro Gly Glu Val Lys Leu Thr Leu
        435                 440                 445

Ala Gly Cys Glu Glu Arg Asn Ala Gln Gly Met Cys Ser Leu Ala Gly
    450                 455                 460

Phe Thr Gln Ile Val Asn Glu Ala Arg Ile Pro Ala Cys Ser Leu Gly
465                 470                 475                 480

Gly Ala Glu Ala Ala Ala Lys Glu Ala Ala Ala Lys Val Asn Leu Cys
                485                 490                 495

Leu Asp Leu Lys Thr Gln Val Gln Thr Pro Gln Gly Met Lys Glu Ile
            500                 505                 510

Ser Asn Ile Gln Val Gly Asp Leu Val Leu Ser Asn Thr Gly Tyr Asn
        515                 520                 525

Glu Val Leu Asn Val Phe Pro Lys Ser Lys Lys Lys Ser Tyr Lys Ile
    530                 535                 540

Thr Leu Glu Asp Gly Lys Glu Ile Ile Cys Ser Glu Glu His Leu Phe
545                 550                 555                 560

Pro Thr Gln Thr Gly Glu Met Asn Ile Ser Gly Gly Leu Lys Glu Gly
                565                 570                 575
```

Met Cys Leu Tyr Val Lys Glu
580

<210> SEQ ID NO 204
<211> LENGTH: 2019
<212> TYPE: DNA
<213> ORGANISM: Artificial Sequence
<220> FEATURE:
<223> OTHER INFORMATION: Synthetic construct, #1 TrxH-Phy02 cod seq

<400> SEQUENCE: 204
atgctgattg aagtgtttag cagtccgatc tgtccgcact gcccaggcgc cgagcgtgtt 60
gtcgaagagg tcgtcgataa actgagctgc gatgatattg aagtgcgcca cattgatgtg 120
acagaagatc cgggcagtgc agagaagtac tctatcatgg cagtgcccac cattgtggta 180
gatggtgagg tggcatttgt tggcgccccg acgacgcagc aatttgagga atatctgcgt 240
aaaaagctta atcgggatcc taatggtatg acgaagaaaa ttacgaagat cgaagaactg 300
gatgaacgtg aactgattga catcgaagtt agcggcaacc atctgtttta cgcgaatgac 360
attgggaccc acaacagcgc agccgaagcc gctgcgaagg aggcagctgc gaaagaagcg 420
gctgcaaaag aagcggcagc taaggctttg aataccccgc aatcggcttt cgctcaatcg 480
gaaccggaac tgaaactgga aagtgtggtt attgtgtctc gtcatggcgt tcgcgctccg 540
accaaattta cgcagctgat gcaagatgtc accccggacg ccttctatac gtggccggtg 600
aagctgggtg aactgacccc gcgtggcggt gaactgatcg cctatctggg tcactactgg 660
cgtcagcgcc tggtggcaga tggtctgctg ccgaaaaagg gctgcccgca gagcggtcaa 720
gttgcaatta tcgctgatgt cgacgaacgt acccgcaaaa cgggtgaagc atttgcggcc 780
ggtctggcac cggattgcgc cattaccgtt catacgcagg cagataccag ctctccggac 840
ccgctgttca acccgctgaa aaccggcgtc tgtcagctgg atgtcgcgca agtgacggac 900
gccattctgg aacgtgcagg cggttccatc gctgatttta ccggtcacta ccagacggca 960
ttccgtgaac tggaacgcgt tctgaacttt ccgcagtcaa atctggcgct gaaacgcgaa 1020
aagcaggatg aaagtgcgtc cctgacccaa gccctgccga gtgaactgaa agtctccgcc 1080
gacaatgtgt cactgaccgg cgcatggtca ctggcttcga tgctgacgga aatttttctg 1140
ctgcagcaag cacagggtat gccggaaccg ggttggggtc gtatcaccga ttcgcatcag 1200
tggaacacgc tgctgagcct gcacaatgcg cagttcgacc tgctgcaacg taccccggaa 1260
gtggcacgtt cgcgcgccac gccgctgctg gatctgatta aaaccgctct gacgccgcat 1320
ccgccgcaga agcaagcgta tggcgtgacc ctgccgacga gcgttctgtt tatcgcgggt 1380
cacgacacca acctggcaaa tctgggcggt gctctggaac tgcagtggac cctgccgggt 1440
caaccggata acacgccgcc gggcggtgaa ctggttttcg aacgttggcg tcgcctgagc 1500
gacaattctc agtggatcca agttagcctg gtctttcaga ccctgcagca aatgcgcgat 1560
aaaaccccgc tgttcctgaa cacgccgccg ggcgaagtga agctgaccct ggcgggttgc 1620
gaagaacgta acgcccaggg catgtgttct ctggcaggtt ttacccagat tgttaatgaa 1680
gcacgcatcc cggcttgtag tctggggggc gcagaagcag ctgccaaaga ggcggccgca 1740
aaggtcaatc tgtgtctgga cctgaaaacg caagtgcaaa ccccgcaagg catgaaggaa 1800
atctcaaaca tccaagtcgg tgacctggtg ctgtcgaata ccggctataa cgaagtgctg 1860
aatgtttttc cgaagagcaa aaagaaatct tacaagatca cgctggaaga tggcaaggaa 1920
attatttgca gcgaagaaca tctgttcccg acccagacgg gcgaaatgaa tatctccggc 1980
ggtctgaaag aaggcatgtg tctgtacgtc aaggaataa 2019

<210> SEQ ID NO 205
<211> LENGTH: 672
<212> TYPE: PRT
<213> ORGANISM: Artificial Sequence
<220> FEATURE:
<223> OTHER INFORMATION: Synthetic construct, #1 TrxH-Phy02

<400> SEQUENCE: 205

Met Leu Ile Glu Val Phe Ser Ser Pro Ile Cys Pro His Cys Pro Gly
1 5 10 15

Ala Glu Arg Val Val Glu Glu Val Val Asp Lys Leu Ser Cys Asp Asp
20 25 30

Ile Glu Val Arg His Ile Asp Val Thr Glu Asp Pro Gly Ser Ala Glu
35 40 45

Lys Tyr Ser Ile Met Ala Val Pro Thr Ile Val Val Asp Gly Glu Val
50 55 60

Ala Phe Val Gly Ala Pro Thr Thr Gln Gln Phe Glu Glu Tyr Leu Arg
65 70 75 80

Lys Lys Leu Asn Arg Asp Pro Asn Gly Met Thr Lys Lys Ile Thr Lys
85 90 95

Ile Glu Glu Leu Asp Glu Arg Glu Leu Ile Asp Ile Glu Val Ser Gly
100 105 110

Asn His Leu Phe Tyr Ala Asn Asp Ile Gly Thr His Asn Ser Ala Ala
115 120 125

Glu Ala Ala Ala Lys Glu Ala Ala Ala Lys Glu Ala Ala Ala Lys Glu
130 135 140

Ala Ala Ala Lys Ala Leu Asn Thr Pro Gln Ser Ala Phe Ala Gln Ser
145 150 155 160

Glu Pro Glu Leu Lys Leu Glu Ser Val Val Ile Val Ser Arg His Gly
165 170 175

Val Arg Ala Pro Thr Lys Phe Thr Gln Leu Met Gln Asp Val Thr Pro
180 185 190

Asp Ala Phe Tyr Thr Trp Pro Val Lys Leu Gly Glu Leu Thr Pro Arg
195 200 205

Gly Gly Glu Leu Ile Ala Tyr Leu Gly His Tyr Trp Arg Gln Arg Leu
210 215 220

Val Ala Asp Gly Leu Leu Pro Lys Lys Gly Cys Pro Gln Ser Gly Gln
225 230 235 240

Val Ala Ile Ile Ala Asp Val Asp Glu Arg Thr Arg Lys Thr Gly Glu
245 250 255

Ala Phe Ala Ala Gly Leu Ala Pro Asp Cys Ala Ile Thr Val His Thr
260 265 270

Gln Ala Asp Thr Ser Ser Pro Asp Pro Leu Phe Asn Pro Leu Lys Thr
275 280 285

Gly Val Cys Gln Leu Asp Val Ala Gln Val Thr Asp Ala Ile Leu Glu
290 295 300

Arg Ala Gly Gly Ser Ile Ala Asp Phe Thr Gly His Tyr Gln Thr Ala
305 310 315 320

Phe Arg Glu Leu Glu Arg Val Leu Asn Phe Pro Gln Ser Asn Leu Ala
325 330 335

Leu Lys Arg Glu Lys Gln Asp Glu Ser Ala Ser Leu Thr Gln Ala Leu
340 345 350

```
Pro Ser Glu Leu Lys Val Ser Ala Asp Asn Val Ser Leu Thr Gly Ala
        355                 360                 365

Trp Ser Leu Ala Ser Met Leu Thr Glu Ile Phe Leu Leu Gln Gln Ala
    370                 375                 380

Gln Gly Met Pro Glu Pro Gly Trp Gly Arg Ile Thr Asp Ser His Gln
385                 390                 395                 400

Trp Asn Thr Leu Leu Ser Leu His Asn Ala Gln Phe Asp Leu Leu Gln
                405                 410                 415

Arg Thr Pro Glu Val Ala Arg Ser Arg Ala Thr Pro Leu Leu Asp Leu
            420                 425                 430

Ile Lys Thr Ala Leu Thr Pro His Pro Pro Gln Lys Gln Ala Tyr Gly
        435                 440                 445

Val Thr Leu Pro Thr Ser Val Leu Phe Ile Ala Gly His Asp Thr Asn
    450                 455                 460

Leu Ala Asn Leu Gly Gly Ala Leu Glu Leu Gln Trp Thr Leu Pro Gly
465                 470                 475                 480

Gln Pro Asp Asn Thr Pro Pro Gly Gly Glu Leu Val Phe Glu Arg Trp
                485                 490                 495

Arg Arg Leu Ser Asp Asn Ser Gln Trp Ile Gln Val Ser Leu Val Phe
            500                 505                 510

Gln Thr Leu Gln Gln Met Arg Asp Lys Thr Pro Leu Phe Leu Asn Thr
        515                 520                 525

Pro Pro Gly Glu Val Lys Leu Thr Leu Ala Gly Cys Glu Glu Arg Asn
    530                 535                 540

Ala Gln Gly Met Cys Ser Leu Ala Gly Phe Thr Gln Ile Val Asn Glu
545                 550                 555                 560

Ala Arg Ile Pro Ala Cys Ser Leu Gly Gly Ala Glu Ala Ala Ala Lys
                565                 570                 575

Glu Ala Ala Ala Lys Val Asn Leu Cys Leu Asp Leu Lys Thr Gln Val
            580                 585                 590

Gln Thr Pro Gln Gly Met Lys Glu Ile Ser Asn Ile Gln Val Gly Asp
        595                 600                 605

Leu Val Leu Ser Asn Thr Gly Tyr Asn Glu Val Leu Asn Val Phe Pro
    610                 615                 620

Lys Ser Lys Lys Lys Ser Tyr Lys Ile Thr Leu Glu Asp Gly Lys Glu
625                 630                 635                 640

Ile Ile Cys Ser Glu Glu His Leu Phe Pro Thr Gln Thr Gly Glu Met
                645                 650                 655

Asn Ile Ser Gly Gly Leu Lys Glu Gly Met Cys Leu Tyr Val Lys Glu
            660                 665                 670
```

<210> SEQ ID NO 206
<211> LENGTH: 1992
<212> TYPE: DNA
<213> ORGANISM: Artificial Sequence
<220> FEATURE:
<223> OTHER INFORMATION: Synthetic construct, #2 TrxH-Phy02 coding seq

<400> SEQUENCE: 206

```
atgctgattg aagtgtttag cagtccgatc tgtccgcact gcccaggcgc cgagcgtgtt      60

gtcgaagagg tcgtcgataa actgagctgc gatgatattg aagtgcgcca cattgatgtg     120

acagaagatc cgggcagtgc agagaagtac tctatcatgg cagtgcccac cattgtggta     180

gatggtgagg tggcatttgt tggcgccccg acgacgcagc aatttgagga atatctgcgt     240

aaaaagctta atcgggatcc taatggtatg acgaagaaaa ttacgaagat cgaagaactg     300
```

```
gatgaacgtg aactgattga catcgaagtt agcggcaacc atctgtttta cgcgaatgac    360
attgggaccc acaacagcgc ctttgcacaa tcggaaccgg aactgaaact ggaaagtgtg    420
gttattgtgt ctcgtcatgg cgttcgcgct ccgaccaaat ttacgcagct gatgcaagat    480
gtcaccccgg acgccttcta tacgtggccg gtgaagctgg gtgaactgac cccgcgtggc    540
ggtgaactga tcgcctatct gggtcactac tggcgtcagc gcctggtggc agatggtctg    600
ctgccgaaaa agggctgccc gcagagcggt caagttgcaa ttatcgctga tgtcgacgaa    660
cgtacccgca aaacgggtga agcatttgcg gccggtctgg caccggattg cgccattacc    720
gttcatacgc aggcagatac cagctctccg gacccgctgt tcaacccgct gaaaaccggc    780
gtctgtcagc tggatgtcgc gcaagtgacg gacgccattc tggaacgtgc aggcggttcc    840
atcgctgatt ttaccggtca ctaccagacg gcattccgtg aactggaacg cgttctgaac    900
tttccgcagt caaatctggc gctgaaacgc gaaaagcagg atgaaagtgc gtccctgacc    960
caagccctgc cgagtgaact gaaagtctcc gccgacaatg tgtcactgac cggcgcatgg   1020
tcactggctt cgatgctgac ggaaattttt ctgctgcagc aagcacaggg tatgccggaa   1080
ccgggttggg gtcgtatcac cgattcgcat cagtggaaca cgctgctgag cctgcacaat   1140
gcgcagttcg acctgctgca acgtaccccg gaagtggcac gttcgcgcgc cacgccgctg   1200
ctggatctga ttaaaaccgc tctgacgccg catccgccgc agaagcaagc gtatggcgtg   1260
accctgccga cgagcgttct gtttatcgcg ggtcacgaca ccaacctggc aaatctgggc   1320
ggtgctctgg aactgcagtg gaccctgccg ggtcaaccgg ataacacgcc gccgggcggt   1380
gaactggttt tcgaacgttg gcgtcgcctg agcgacaatt ctcagtggat ccaagttagc   1440
ctggtctttc agaccctgca gcaaatgcgc gataaaaccc cgctgttcct gaacacgccg   1500
ccgggcgaag tgaagctgac cctggcgggt tgcgaagaac gtaacgccca gggcatgtgt   1560
tctctggcag gttttaccca gattgttaat gaagcacgca tcccggcttg tagtctgggt   1620
gcagctccag cggccgcacc ggctaaacag gaagcggcag ctccggctcc tgcagcgaag   1680
gcggaagcac cggccgcagc tcctgcggca aaagcgaccc cgcagtgtct ggacctgaaa   1740
acgcaagtgc aaaccccgca aggcatgaag gaaatctcaa acatccaagt cggtgacctg   1800
gtgctgtcga ataccggcta taacgaagtg ctgaatgttt ttccgaagag caaaaagaaa   1860
tcttacaaga tcacgctgga agatggcaag gaaattattt gcagcgaaga acatctgttc   1920
ccgacccaga cgggcgaaat gaatatctcc ggcggtctga aagaaggcat gtgtctgtac   1980
gtcaaggaat aa                                                       1992
```

<210> SEQ ID NO 207
<211> LENGTH: 663
<212> TYPE: PRT
<213> ORGANISM: Artificial Sequence
<220> FEATURE:
<223> OTHER INFORMATION: Synthetic construct, #2 TrxH-Phy02

<400> SEQUENCE: 207

```
Met Leu Ile Glu Val Phe Ser Ser Pro Ile Cys Pro His Cys Pro Gly
1               5                   10                  15

Ala Glu Arg Val Val Glu Glu Val Val Asp Lys Leu Ser Cys Asp Asp
            20                  25                  30

Ile Glu Val Arg His Ile Asp Val Thr Glu Asp Pro Gly Ser Ala Glu
        35                  40                  45

Lys Tyr Ser Ile Met Ala Val Pro Thr Ile Val Val Asp Gly Glu Val
```

-continued

```
    50                  55                  60

Ala Phe Val Gly Ala Pro Thr Thr Gln Gln Phe Glu Glu Tyr Leu Arg
65                  70                  75                  80

Lys Lys Leu Asn Arg Asp Pro Asn Gly Met Thr Lys Lys Ile Thr Lys
                85                  90                  95

Ile Glu Glu Leu Asp Glu Arg Glu Leu Ile Asp Ile Glu Val Ser Gly
            100                 105                 110

Asn His Leu Phe Tyr Ala Asn Asp Ile Gly Thr His Asn Ser Ala Phe
        115                 120                 125

Ala Gln Ser Glu Pro Glu Leu Lys Leu Glu Ser Val Val Ile Val Ser
    130                 135                 140

Arg His Gly Val Arg Ala Pro Thr Lys Phe Thr Gln Leu Met Gln Asp
145                 150                 155                 160

Val Thr Pro Asp Ala Phe Tyr Thr Trp Pro Val Lys Leu Gly Glu Leu
                165                 170                 175

Thr Pro Arg Gly Gly Glu Leu Ile Ala Tyr Leu Gly His Tyr Trp Arg
            180                 185                 190

Gln Arg Leu Val Ala Asp Gly Leu Leu Pro Lys Lys Gly Cys Pro Gln
        195                 200                 205

Ser Gly Gln Val Ala Ile Ile Ala Asp Val Asp Glu Arg Thr Arg Lys
    210                 215                 220

Thr Gly Glu Ala Phe Ala Ala Gly Leu Ala Pro Asp Cys Ala Ile Thr
225                 230                 235                 240

Val His Thr Gln Ala Asp Thr Ser Ser Pro Asp Pro Leu Phe Asn Pro
                245                 250                 255

Leu Lys Thr Gly Val Cys Gln Leu Asp Val Ala Gln Val Thr Asp Ala
            260                 265                 270

Ile Leu Glu Arg Ala Gly Gly Ser Ile Ala Asp Phe Thr Gly His Tyr
        275                 280                 285

Gln Thr Ala Phe Arg Glu Leu Glu Arg Val Leu Asn Phe Pro Gln Ser
    290                 295                 300

Asn Leu Ala Leu Lys Arg Glu Lys Gln Asp Glu Ser Ala Ser Leu Thr
305                 310                 315                 320

Gln Ala Leu Pro Ser Glu Leu Lys Val Ser Ala Asp Asn Val Ser Leu
                325                 330                 335

Thr Gly Ala Trp Ser Leu Ala Ser Met Leu Thr Glu Ile Phe Leu Leu
            340                 345                 350

Gln Gln Ala Gln Gly Met Pro Glu Pro Gly Trp Gly Arg Ile Thr Asp
        355                 360                 365

Ser His Gln Trp Asn Thr Leu Leu Ser Leu His Asn Ala Gln Phe Asp
    370                 375                 380

Leu Leu Gln Arg Thr Pro Glu Val Ala Arg Ser Arg Ala Thr Pro Leu
385                 390                 395                 400

Leu Asp Leu Ile Lys Thr Ala Leu Thr Pro His Pro Pro Gln Lys Gln
                405                 410                 415

Ala Tyr Gly Val Thr Leu Pro Thr Ser Val Leu Phe Ile Ala Gly His
            420                 425                 430

Asp Thr Asn Leu Ala Asn Leu Gly Gly Ala Leu Glu Leu Gln Trp Thr
        435                 440                 445

Leu Pro Gly Gln Pro Asp Asn Thr Pro Pro Gly Gly Glu Leu Val Phe
    450                 455                 460

Glu Arg Trp Arg Arg Leu Ser Asp Asn Ser Gln Trp Ile Gln Val Ser
465                 470                 475                 480
```

```
Leu Val Phe Gln Thr Leu Gln Gln Met Arg Asp Lys Thr Pro Leu Phe
                485                 490                 495

Leu Asn Thr Pro Pro Gly Glu Val Lys Leu Thr Leu Ala Gly Cys Glu
            500                 505                 510

Glu Arg Asn Ala Gln Gly Met Cys Ser Leu Ala Gly Phe Thr Gln Ile
        515                 520                 525

Val Asn Glu Ala Arg Ile Pro Ala Cys Ser Leu Gly Ala Ala Pro Ala
    530                 535                 540

Ala Ala Pro Ala Lys Gln Glu Ala Ala Ala Pro Ala Pro Ala Ala Lys
545                 550                 555                 560

Ala Glu Ala Pro Ala Ala Ala Pro Ala Ala Lys Ala Thr Pro Gln Cys
                565                 570                 575

Leu Asp Leu Lys Thr Gln Val Gln Thr Pro Gln Gly Met Lys Glu Ile
            580                 585                 590

Ser Asn Ile Gln Val Gly Asp Leu Val Leu Ser Asn Thr Gly Tyr Asn
        595                 600                 605

Glu Val Leu Asn Val Phe Pro Lys Ser Lys Lys Lys Ser Tyr Lys Ile
    610                 615                 620

Thr Leu Glu Asp Gly Lys Glu Ile Ile Cys Ser Glu Glu His Leu Phe
625                 630                 635                 640

Pro Thr Gln Thr Gly Glu Met Asn Ile Ser Gly Gly Leu Lys Glu Gly
                645                 650                 655

Met Cys Leu Tyr Val Lys Glu
            660
```

<210> SEQ ID NO 208
<211> LENGTH: 1992
<212> TYPE: DNA
<213> ORGANISM: Artificial Sequence
<220> FEATURE:
<223> OTHER INFORMATION: Synthetic construct, [N125A-1] coding seq

<400> SEQUENCE: 208

```
atgctgattg aagtgtttag cagtccgatc tgtccgcact gcccaggcgc cgagcgtgtt      60

gtcgaagagg tcgtcgataa actgagctgc gatgatattg aagtgcgcca cattgatgtg     120

acagaagatc cgggcagtgc agagaagtac tctatcatgg cagtgcccac cattgtggta     180

gatggtgagg tggcatttgt tggcgccccg acgacgcagc aatttgagga atatctgcgt     240

aaaaagctta atcgggatcc taatggtatg acgaagaaaa ttacgaagat cgaagaactg     300

gatgaacgtg aactgattga catcgaagtt agcggcaacc atctgtttta cgcgaatgac     360

attgggaccc acgccagcgc ctttgcacaa tcggaaccgg aactgaaact ggaaagtgtg     420

gttattgtgt ctcgtcatgg cgttcgcgct ccgaccaaat ttacgcagct gatgcaagat     480

gtcaccccgg acgccttcta tacgtggccg gtgaagctgg gtgaactgac cccgcgtggc     540

ggtgaactga tcgcctatct gggtcactac tggcgtcagc gcctggtggc agatggtctg     600

ctgccgaaaa agggctgccc gcagagcggt caagttgcaa ttatcgctga tgtcgacgaa     660

cgtacccgca aaacgggtga agcatttgcg gccggtctgg caccggattg cgccattacc     720

gttcatacgc aggcagatac cagctctccg gacccgctgt tcaacccgct gaaaaccggc     780

gtctgtcagc tggatgtcgc gcaagtgacg gacgccattc tggaacgtgc aggcggttcc     840

atcgctgatt ttaccggtca ctaccagacg gcattccgtg aactggaacg cgttctgaac     900

tttccgcagt caaatctggc gctgaaacgc gaaaagcagg atgaaagtgc gtccctgacc     960
```

-continued

```
caagccctgc cgagtgaact gaaagtctcc gccgacaatg tgtcactgac cggcgcatgg   1020

tcactggctt cgatgctgac ggaaattttt ctgctgcagc aagcacaggg tatgccggaa   1080

ccgggttggg gtcgtatcac cgattcgcat cagtggaaca cgctgctgag cctgcacaat   1140

gcgcagttcg acctgctgca acgtaccccg gaagtggcac gttcgcgcgc cacgccgctg   1200

ctggatctga ttaaaaccgc tctgacgccg catccgccgc agaagcaagc gtatggcgtg   1260

accctgccga cgagcgttct gtttatcgcg ggtcacgaca ccaacctggc aaatctgggc   1320

ggtgctctgg aactgcagtg gaccctgccg ggtcaaccgg ataacacgcc gccgggcggt   1380

gaactggttt tcgaacgttg gcgtcgcctg agcgacaatt ctcagtggat ccaagttagc   1440

ctggtctttc agaccctgca gcaaatgcgc gataaaaccc cgctgttcct gaacacgccg   1500

ccgggcgaag tgaagctgac cctggcgggt tgcgaagaac gtaacgccca gggcatgtgt   1560

tctctggcag gttttaccca gattgttaat gaagcacgca tcccggcttg tagtctgggt   1620

gcagctccag cggccgcacc ggctaaacag gaagcggcag ctccggctcc tgcagcgaag   1680

gcggaagcac cggccgcagc tcctgcggca aaagcgaccc cgcagtgtct ggacctgaaa   1740

acgcaagtgc aaaccccgca aggcatgaag gaaatctcaa acatccaagt cggtgacctg   1800

gtgctgtcga ataccggcta taacgaagtg ctgaatgttt ttccgaagag caaaaagaaa   1860

tcttacaaga tcacgctgga agatggcaag gaaattattt gcagcgaaga acatctgttc   1920

ccgacccaga cgggcgaaat gaatatctcc ggcggtctga aagaaggcat gtgtctgtac   1980

gtcaaggaat aa                                                        1992
```

<210> SEQ ID NO 209
<211> LENGTH: 663
<212> TYPE: PRT
<213> ORGANISM: Artificial Sequence
<220> FEATURE:
<223> OTHER INFORMATION: Synthetic construct, [N125A-1]

<400> SEQUENCE: 209

```
Met Leu Ile Glu Val Phe Ser Ser Pro Ile Cys Pro His Cys Pro Gly
1               5                   10                  15

Ala Glu Arg Val Val Glu Glu Val Val Asp Lys Leu Ser Cys Asp Asp
            20                  25                  30

Ile Glu Val Arg His Ile Asp Val Thr Glu Asp Pro Gly Ser Ala Glu
        35                  40                  45

Lys Tyr Ser Ile Met Ala Val Pro Thr Ile Val Val Asp Gly Glu Val
    50                  55                  60

Ala Phe Val Gly Ala Pro Thr Thr Gln Gln Phe Glu Glu Tyr Leu Arg
65                  70                  75                  80

Lys Lys Leu Asn Arg Asp Pro Asn Gly Met Thr Lys Lys Ile Thr Lys
                85                  90                  95

Ile Glu Glu Leu Asp Glu Arg Glu Leu Ile Asp Ile Glu Val Ser Gly
            100                 105                 110

Asn His Leu Phe Tyr Ala Asn Asp Ile Gly Thr His Ala Ser Ala Phe
        115                 120                 125

Ala Gln Ser Glu Pro Glu Leu Lys Leu Glu Ser Val Val Ile Val Ser
    130                 135                 140

Arg His Gly Val Arg Ala Pro Thr Lys Phe Thr Gln Leu Met Gln Asp
145                 150                 155                 160

Val Thr Pro Asp Ala Phe Tyr Thr Trp Pro Val Lys Leu Gly Glu Leu
                165                 170                 175
```

-continued

```
Thr Pro Arg Gly Gly Glu Leu Ile Ala Tyr Leu Gly His Tyr Trp Arg
            180                 185                 190

Gln Arg Leu Val Ala Asp Gly Leu Leu Pro Lys Lys Gly Cys Pro Gln
        195                 200                 205

Ser Gly Gln Val Ala Ile Ile Ala Asp Val Asp Glu Arg Thr Arg Lys
    210                 215                 220

Thr Gly Glu Ala Phe Ala Ala Gly Leu Ala Pro Asp Cys Ala Ile Thr
225                 230                 235                 240

Val His Thr Gln Ala Asp Thr Ser Ser Pro Asp Pro Leu Phe Asn Pro
                245                 250                 255

Leu Lys Thr Gly Val Cys Gln Leu Asp Val Ala Gln Val Thr Asp Ala
            260                 265                 270

Ile Leu Glu Arg Ala Gly Gly Ser Ile Ala Asp Phe Thr Gly His Tyr
        275                 280                 285

Gln Thr Ala Phe Arg Glu Leu Glu Arg Val Leu Asn Phe Pro Gln Ser
    290                 295                 300

Asn Leu Ala Leu Lys Arg Glu Lys Gln Asp Glu Ser Ala Ser Leu Thr
305                 310                 315                 320

Gln Ala Leu Pro Ser Glu Leu Lys Val Ser Ala Asp Asn Val Ser Leu
                325                 330                 335

Thr Gly Ala Trp Ser Leu Ala Ser Met Leu Thr Glu Ile Phe Leu Leu
            340                 345                 350

Gln Gln Ala Gln Gly Met Pro Glu Pro Gly Trp Gly Arg Ile Thr Asp
        355                 360                 365

Ser His Gln Trp Asn Thr Leu Leu Ser Leu His Asn Ala Gln Phe Asp
    370                 375                 380

Leu Leu Gln Arg Thr Pro Glu Val Ala Arg Ser Arg Ala Thr Pro Leu
385                 390                 395                 400

Leu Asp Leu Ile Lys Thr Ala Leu Thr Pro His Pro Pro Gln Lys Gln
                405                 410                 415

Ala Tyr Gly Val Thr Leu Pro Thr Ser Val Leu Phe Ile Ala Gly His
            420                 425                 430

Asp Thr Asn Leu Ala Asn Leu Gly Gly Ala Leu Glu Leu Gln Trp Thr
        435                 440                 445

Leu Pro Gly Gln Pro Asp Asn Thr Pro Pro Gly Gly Glu Leu Val Phe
    450                 455                 460

Glu Arg Trp Arg Arg Leu Ser Asp Asn Ser Gln Trp Ile Gln Val Ser
465                 470                 475                 480

Leu Val Phe Gln Thr Leu Gln Gln Met Arg Asp Lys Thr Pro Leu Phe
                485                 490                 495

Leu Asn Thr Pro Pro Gly Glu Val Lys Leu Thr Leu Ala Gly Cys Glu
            500                 505                 510

Glu Arg Asn Ala Gln Gly Met Cys Ser Leu Ala Gly Phe Thr Gln Ile
        515                 520                 525

Val Asn Glu Ala Arg Ile Pro Ala Cys Ser Leu Gly Ala Ala Pro Ala
    530                 535                 540

Ala Ala Pro Ala Lys Gln Glu Ala Ala Ala Pro Ala Pro Ala Ala Lys
545                 550                 555                 560

Ala Glu Ala Pro Ala Ala Ala Pro Ala Ala Lys Ala Thr Pro Gln Cys
                565                 570                 575

Leu Asp Leu Lys Thr Gln Val Gln Thr Pro Gln Gly Met Lys Glu Ile
            580                 585                 590

Ser Asn Ile Gln Val Gly Asp Leu Val Leu Ser Asn Thr Gly Tyr Asn
```

```
        595                 600                 605

Glu Val Leu Asn Val Phe Pro Lys Ser Lys Lys Lys Ser Tyr Lys Ile
    610                 615                 620

Thr Leu Glu Asp Gly Lys Glu Ile Ile Cys Ser Glu Glu His Leu Phe
625                 630                 635                 640

Pro Thr Gln Thr Gly Glu Met Asn Ile Ser Gly Gly Leu Lys Glu Gly
                645                 650                 655

Met Cys Leu Tyr Val Lys Glu
            660
```

<210> SEQ ID NO 210
<211> LENGTH: 1992
<212> TYPE: DNA
<213> ORGANISM: Artificial Sequence
<220> FEATURE:
<223> OTHER INFORMATION: Synthetic construct, [S1A-1] coding seq

<400> SEQUENCE: 210

```
atgctgattg aagtgtttag cagtccgatc tgtccgcact gcccaggcgc cgagcgtgtt     60

gtcgaagagg tcgtcgataa actgagctgc gatgatattg aagtgcgcca cattgatgtg    120

acagaagatc cgggcagtgc agagaagtac tctatcatgg cagtgcccac cattgtggta    180

gatggtgagg tggcatttgt tggcgccccg acgacgcagc aatttgagga atatctgcgt    240

aaaaagctta atcgggatcc taatggtatg acgaagaaaa ttacgaagat cgaagaactg    300

gatgaacgtg aactgattga catcgaagtt agcggcaacc atctgtttta cgcgaatgac    360

attgggaccc acaacgccgc ctttgcacaa tcggaaccgg aactgaaact ggaaagtgtg    420

gttattgtgt ctcgtcatgg cgttcgcgct ccgaccaaat ttacgcagct gatgcaagat    480

gtcaccccgg acgccttcta tacgtggccg gtgaagctgg gtgaactgac cccgcgtggc    540

ggtgaactga tcgcctatct gggtcactac tggcgtcagc gcctggtggc agatggtctg    600

ctgccgaaaa agggctgccc gcagagcggt caagttgcaa ttatcgctga tgtcgacgaa    660

cgtacccgca aaacgggtga agcatttgcg gccggtctgg caccggattg cgccattacc    720

gttcatacgc aggcagatac cagctctccg gacccgctgt tcaacccgct gaaaaccggc    780

gtctgtcagc tggatgtcgc gcaagtgacg gacgccattc tggaacgtgc aggcggttcc    840

atcgctgatt ttaccggtca ctaccagacg gcattccgtg aactggaacg cgttctgaac    900

tttccgcagt caaatctggc gctgaaacgc gaaaagcagg atgaaagtgc gtccctgacc    960

caagccctgc cgagtgaact gaaagtctcc gccgacaatg tgtcactgac cggcgcatgg   1020

tcactggctt cgatgctgac ggaaattttt ctgctgcagc aagcacaggg tatgccggaa   1080

ccgggttggg gtcgtatcac cgattcgcat cagtggaaca cgctgctgag cctgcacaat   1140

gcgcagttcg acctgctgca acgtaccccg gaagtggcac gttcgcgcgc cacgccgctg   1200

ctggatctga ttaaaaccgc tctgacgccg catccgccgc agaagcaagc gtatggcgtg   1260

accctgccga cgagcgttct gtttatcgcg ggtcacgaca ccaacctggc aaatctgggc   1320

ggtgctctgg aactgcagtg gaccctgccg ggtcaaccgg ataacacgcc gccgggcggt   1380

gaactggttt tcgaacgttg gcgtcgcctg agcgacaatt ctcagtggat ccaagttagc   1440

ctggtctttc agaccctgca gcaaatgcgc gataaaaccc cgctgttcct gaacacgccg   1500

ccgggcgaag tgaagctgac cctggcgggt tgcgaagaac gtaacgccca gggcatgtgt   1560

tctctggcag gttttaccca gattgttaat gaagcacgca tcccggcttg tagtctgggt   1620

gcagctccag cggccgcacc ggctaaacag gaagcggcag ctccggctcc tgcagcgaag   1680
```

gcggaagcac cggccgcagc tcctgcggca aaagcgaccc cgcagtgtct ggacctgaaa 1740
acgcaagtgc aaaccccgca aggcatgaag gaaatctcaa acatccaagt cggtgacctg 1800
gtgctgtcga ataccggcta taacgaagtg ctgaatgttt ttccgaagag caaaaagaaa 1860
tcttacaaga tcacgctgga agatggcaag gaaattattt gcagcgaaga acatctgttc 1920
ccgacccaga cgggcgaaat gaatatctcc ggcggtctga aagaaggcat gtgtctgtac 1980
gtcaaggaat aa 1992

<210> SEQ ID NO 211
<211> LENGTH: 663
<212> TYPE: PRT
<213> ORGANISM: Artificial Sequence
<220> FEATURE:
<223> OTHER INFORMATION: Synthetic construct, [S1A-1]

<400> SEQUENCE: 211

Met Leu Ile Glu Val Phe Ser Ser Pro Ile Cys Pro His Cys Pro Gly
1 5 10 15

Ala Glu Arg Val Val Glu Glu Val Val Asp Lys Leu Ser Cys Asp Asp
20 25 30

Ile Glu Val Arg His Ile Asp Val Thr Glu Asp Pro Gly Ser Ala Glu
35 40 45

Lys Tyr Ser Ile Met Ala Val Pro Thr Ile Val Val Asp Gly Glu Val
50 55 60

Ala Phe Val Gly Ala Pro Thr Thr Gln Gln Phe Glu Glu Tyr Leu Arg
65 70 75 80

Lys Lys Leu Asn Arg Asp Pro Asn Gly Met Thr Lys Lys Ile Thr Lys
85 90 95

Ile Glu Glu Leu Asp Glu Arg Glu Leu Ile Asp Ile Glu Val Ser Gly
100 105 110

Asn His Leu Phe Tyr Ala Asn Asp Ile Gly Thr His Asn Ala Ala Phe
115 120 125

Ala Gln Ser Glu Pro Glu Leu Lys Leu Glu Ser Val Val Ile Val Ser
130 135 140

Arg His Gly Val Arg Ala Pro Thr Lys Phe Thr Gln Leu Met Gln Asp
145 150 155 160

Val Thr Pro Asp Ala Phe Tyr Thr Trp Pro Val Lys Leu Gly Glu Leu
165 170 175

Thr Pro Arg Gly Gly Glu Leu Ile Ala Tyr Leu Gly His Tyr Trp Arg
180 185 190

Gln Arg Leu Val Ala Asp Gly Leu Leu Pro Lys Lys Gly Cys Pro Gln
195 200 205

Ser Gly Gln Val Ala Ile Ile Ala Asp Val Asp Glu Arg Thr Arg Lys
210 215 220

Thr Gly Glu Ala Phe Ala Ala Gly Leu Ala Pro Asp Cys Ala Ile Thr
225 230 235 240

Val His Thr Gln Ala Asp Thr Ser Ser Pro Asp Pro Leu Phe Asn Pro
245 250 255

Leu Lys Thr Gly Val Cys Gln Leu Asp Val Ala Gln Val Thr Asp Ala
260 265 270

Ile Leu Glu Arg Ala Gly Gly Ser Ile Ala Asp Phe Thr Gly His Tyr
275 280 285

Gln Thr Ala Phe Arg Glu Leu Glu Arg Val Leu Asn Phe Pro Gln Ser
290 295 300

Asn Leu Ala Leu Lys Arg Glu Lys Gln Asp Glu Ser Ala Ser Leu Thr
305 310 315 320

Gln Ala Leu Pro Ser Glu Leu Lys Val Ser Ala Asp Asn Val Ser Leu
325 330 335

Thr Gly Ala Trp Ser Leu Ala Ser Met Leu Thr Glu Ile Phe Leu Leu
340 345 350

Gln Gln Ala Gln Gly Met Pro Glu Pro Gly Trp Gly Arg Ile Thr Asp
355 360 365

Ser His Gln Trp Asn Thr Leu Leu Ser Leu His Asn Ala Gln Phe Asp
370 375 380

Leu Leu Gln Arg Thr Pro Glu Val Ala Arg Ser Arg Ala Thr Pro Leu
385 390 395 400

Leu Asp Leu Ile Lys Thr Ala Leu Thr Pro His Pro Pro Gln Lys Gln
405 410 415

Ala Tyr Gly Val Thr Leu Pro Thr Ser Val Leu Phe Ile Ala Gly His
420 425 430

Asp Thr Asn Leu Ala Asn Leu Gly Gly Ala Leu Glu Leu Gln Trp Thr
435 440 445

Leu Pro Gly Gln Pro Asp Asn Thr Pro Pro Gly Gly Glu Leu Val Phe
450 455 460

Glu Arg Trp Arg Arg Leu Ser Asp Asn Ser Gln Trp Ile Gln Val Ser
465 470 475 480

Leu Val Phe Gln Thr Leu Gln Gln Met Arg Asp Lys Thr Pro Leu Phe
485 490 495

Leu Asn Thr Pro Pro Gly Glu Val Lys Leu Thr Leu Ala Gly Cys Glu
500 505 510

Glu Arg Asn Ala Gln Gly Met Cys Ser Leu Ala Gly Phe Thr Gln Ile
515 520 525

Val Asn Glu Ala Arg Ile Pro Ala Cys Ser Leu Gly Ala Ala Pro Ala
530 535 540

Ala Ala Pro Ala Lys Gln Glu Ala Ala Ala Pro Ala Pro Ala Ala Lys
545 550 555 560

Ala Glu Ala Pro Ala Ala Ala Pro Ala Ala Lys Ala Thr Pro Gln Cys
565 570 575

Leu Asp Leu Lys Thr Gln Val Gln Thr Pro Gln Gly Met Lys Glu Ile
580 585 590

Ser Asn Ile Gln Val Gly Asp Leu Val Leu Ser Asn Thr Gly Tyr Asn
595 600 605

Glu Val Leu Asn Val Phe Pro Lys Ser Lys Lys Lys Ser Tyr Lys Ile
610 615 620

Thr Leu Glu Asp Gly Lys Glu Ile Ile Cys Ser Glu Glu His Leu Phe
625 630 635 640

Pro Thr Gln Thr Gly Glu Met Asn Ile Ser Gly Gly Leu Lys Glu Gly
645 650 655

Met Cys Leu Tyr Val Lys Glu
660

<210> SEQ ID NO 212
<211> LENGTH: 1692
<212> TYPE: DNA
<213> ORGANISM: Artificial Sequence
<220> FEATURE:
<223> OTHER INFORMATION: Synthetic construct, [N125A-2] coding seq

<400> SEQUENCE: 212

```
atgacgaaga aaattacgaa gatcgaagaa ctggatgaac gtgaactgat tgacatcgaa     60

gttagcggca accatctgtt ttacgcgaat gacattggga cccacgccag cgcagccgaa    120

gccgctgcga aggaggcagc tgcgaaagaa gcggctgcaa aagaagcggc agctaaggct    180

ttgaataccc cgcaatcggc tttcgctcaa tcggaaccgg aactgaaact ggaaagtgtg    240

gttattgtgt ctcgtcatgg cgttcgcgct ccgaccaaat ttacgcagct gatgcaagat    300

gtcaccccgg acgccttcta tacgtggccg gtgaagctgg gtgaactgac cccgcgtggc    360

ggtgaactga tcgcctatct gggtcactac tggcgtcagc gcctggtggc agatggtctg    420

ctgccgaaaa agggctgccc gcagagcggt caagttgcaa ttatcgctga tgtcgacgaa    480

cgtacccgca aaacgggtga agcatttgcg gccggtctgg caccggattg cgccattacc    540

gttcatacgc aggcagatac cagctctccg gacccgctgt tcaacccgct gaaaaccggc    600

gtctgtcagc tggatgtcgc gcaagtgacg gacgccattc tggaacgtgc aggcggttcc    660

atcgctgatt ttaccggtca ctaccagacg gcattccgtg aactggaacg cgttctgaac    720

tttccgcagt caaatctggc gctgaaacgc gaaaagcagg atgaaagtgc gtccctgacc    780

caagccctgc cgagtgaact gaaagtctcc gccgacaatg tgtcactgac cggcgcatgg    840

tcactggctt cgatgctgac ggaaattttt ctgctgcagc aagcacaggg tatgccggaa    900

ccgcagttcg acctgctgca acgtaccccg gaagtggcac gttcgcgcgc cacgccgctg    960

ctggatctga ttaaaaccgc tctgacgccg catccgccgc agaagcaagc gtatggcgtg   1020

accctgccga cgagcgttct gtttatcgcg ggtcacgaca ccaacctggc aaatctgggc   1080

ggtgctctgg aactgcagtg gaccctgccg ggtcaaccgg ataacacgcc gccgggcggt   1140

gaactggttt tcgaacgttg gcgtcgcctg agcgacaatt ctcagtggat ccaagttagc   1200

ctggtctttc agaccctgca gcaaatgcgc gataaaaccc cgctgttcct gaacacgccg   1260

ccgggcgaag tgaagctgac cctggcgggt tgcgaagaac gtaacgccca gggcatgtgt   1320

tctctggcag gttttaccca gattgttaat gaagcacgca tcccggcttg tagtctgggg   1380

ggcgcagaag cagctgccaa agaggcggcc gcaaaggtca atctgtgtct ggacctgaaa   1440

acgcaagtgc aaaccccgca aggcatgaag gaaatctcaa acatccaagt cggtgacctg   1500

gtgctgtcga ataccggcta taacgaagtg ctgaatgttt ttccgaagag caaaaagaaa   1560

tcttacaaga tcacgctgga agatggcaag gaaattattt gcagcgaaga acatctgttc   1620

ccgacccaga cgggcgaaat gaatatctcc ggcggtctga aagaaggcat gtgtctgtac   1680

gtcaaggaat aa                                                       1692
```

<210> SEQ ID NO 213
<211> LENGTH: 583
<212> TYPE: PRT
<213> ORGANISM: Artificial Sequence
<220> FEATURE:
<223> OTHER INFORMATION: Synthetic construct, [N125A-2]

<400> SEQUENCE: 213

```
Met Thr Lys Lys Ile Thr Lys Ile Glu Glu Leu Asp Glu Arg Glu Leu
1               5                   10                  15

Ile Asp Ile Glu Val Ser Gly Asn His Leu Phe Tyr Ala Asn Asp Ile
            20                  25                  30

Gly Thr His Ala Ser Ala Ala Glu Ala Ala Ala Lys Glu Ala Ala Ala
        35                  40                  45

Lys Glu Ala Ala Ala Lys Glu Ala Ala Ala Lys Ala Leu Asn Thr Pro
```

```
    50                  55                  60

Gln Ser Ala Phe Ala Gln Ser Glu Pro Glu Leu Lys Leu Glu Ser Val
65                  70                  75                  80

Val Ile Val Ser Arg His Gly Val Arg Ala Pro Thr Lys Phe Thr Gln
                85                  90                  95

Leu Met Gln Asp Val Thr Pro Asp Ala Phe Tyr Thr Trp Pro Val Lys
            100                 105                 110

Leu Gly Glu Leu Thr Pro Arg Gly Gly Glu Leu Ile Ala Tyr Leu Gly
        115                 120                 125

His Tyr Trp Arg Gln Arg Leu Val Ala Asp Gly Leu Leu Pro Lys Lys
    130                 135                 140

Gly Cys Pro Gln Ser Gly Gln Val Ala Ile Ile Ala Asp Val Asp Glu
145                 150                 155                 160

Arg Thr Arg Lys Thr Gly Glu Ala Phe Ala Ala Gly Leu Ala Pro Asp
                165                 170                 175

Cys Ala Ile Thr Val His Thr Gln Ala Asp Thr Ser Ser Pro Asp Pro
            180                 185                 190

Leu Phe Asn Pro Leu Lys Thr Gly Val Cys Gln Leu Asp Val Ala Gln
        195                 200                 205

Val Thr Asp Ala Ile Leu Glu Arg Ala Gly Gly Ser Ile Ala Asp Phe
    210                 215                 220

Thr Gly His Tyr Gln Thr Ala Phe Arg Glu Leu Glu Arg Val Leu Asn
225                 230                 235                 240

Phe Pro Gln Ser Asn Leu Ala Leu Lys Arg Glu Lys Gln Asp Glu Ser
                245                 250                 255

Ala Ser Leu Thr Gln Ala Leu Pro Ser Glu Leu Lys Val Ser Ala Asp
            260                 265                 270

Asn Val Ser Leu Thr Gly Ala Trp Ser Leu Ala Ser Met Leu Thr Glu
        275                 280                 285

Ile Phe Leu Leu Gln Gln Ala Gln Gly Met Pro Glu Pro Gly Trp Gly
    290                 295                 300

Arg Ile Thr Asp Ser His Gln Trp Asn Thr Leu Leu Ser Leu His Asn
305                 310                 315                 320

Ala Gln Phe Asp Leu Leu Gln Arg Thr Pro Glu Val Ala Arg Ser Arg
                325                 330                 335

Ala Thr Pro Leu Leu Asp Leu Ile Lys Thr Ala Leu Thr Pro His Pro
            340                 345                 350

Pro Gln Lys Gln Ala Tyr Gly Val Thr Leu Pro Thr Ser Val Leu Phe
        355                 360                 365

Ile Ala Gly His Asp Thr Asn Leu Ala Asn Leu Gly Gly Ala Leu Glu
    370                 375                 380

Leu Gln Trp Thr Leu Pro Gly Gln Pro Asp Asn Thr Pro Pro Gly Gly
385                 390                 395                 400

Glu Leu Val Phe Glu Arg Trp Arg Arg Leu Ser Asp Asn Ser Gln Trp
                405                 410                 415

Ile Gln Val Ser Leu Val Phe Gln Thr Leu Gln Gln Met Arg Asp Lys
            420                 425                 430

Thr Pro Leu Phe Leu Asn Thr Pro Pro Gly Glu Val Lys Leu Thr Leu
        435                 440                 445

Ala Gly Cys Glu Glu Arg Asn Ala Gln Gly Met Cys Ser Leu Ala Gly
    450                 455                 460

Phe Thr Gln Ile Val Asn Glu Ala Arg Ile Pro Ala Cys Ser Leu Gly
465                 470                 475                 480
```

```
Gly Ala Glu Ala Ala Ala Lys Glu Ala Ala Ala Lys Val Asn Leu Cys
                485                 490                 495

Leu Asp Leu Lys Thr Gln Val Gln Thr Pro Gln Gly Met Lys Glu Ile
            500                 505                 510

Ser Asn Ile Gln Val Gly Asp Leu Val Leu Ser Asn Thr Gly Tyr Asn
        515                 520                 525

Glu Val Leu Asn Val Phe Pro Lys Ser Lys Lys Lys Ser Tyr Lys Ile
    530                 535                 540

Thr Leu Glu Asp Gly Lys Glu Ile Ile Cys Ser Glu Glu His Leu Phe
545                 550                 555                 560

Pro Thr Gln Thr Gly Glu Met Asn Ile Ser Gly Gly Leu Lys Glu Gly
                565                 570                 575

Met Cys Leu Tyr Val Lys Glu
            580


<210> SEQ ID NO 214
<211> LENGTH: 1692
<212> TYPE: DNA
<213> ORGANISM: Artificial Sequence
<220> FEATURE:
<223> OTHER INFORMATION: Synthetic construct, [S1A-2] coding seq

<400> SEQUENCE: 214

atgacgaaga aaattacgaa gatcgaagaa ctggatgaac gtgaactgat tgacatcgaa      60

gttagcggca accatctgtt ttacgcgaat gacattggga cccacaacgc cgcagccgaa     120

gccgctgcga aggaggcagc tgcgaaagaa gcggctgcaa aagaagcggc agctaaggct     180

ttgaataccc cgcaatcggc tttcgctcaa tcggaaccgg aactgaaact ggaaagtgtg     240

gttattgtgt ctcgtcatgg cgttcgcgct ccgaccaaat ttacgcagct gatgcaagat     300

gtcaccccgg acgccttcta tacgtggccg gtgaagctgg gtgaactgac cccgcgtggc     360

ggtgaactga tcgcctatct gggtcactac tggcgtcagc gcctggtggc agatggtctg     420

ctgccgaaaa agggctgccc gcagagcggt caagttgcaa ttatcgctga tgtcgacgaa     480

cgtacccgca aaacgggtga agcatttgcg gccggtctgg caccggattg cgccattacc     540

gttcatacgc aggcagatac cagctctccg gacccgctgt tcaacccgct gaaaaccggc     600

gtctgtcagc tggatgtcgc gcaagtgacg gacgccattc tggaacgtgc aggcggttcc     660

atcgctgatt ttaccggtca ctaccagacg gcattccgtg aactggaacg cgttctgaac     720

tttccgcagt caaatctggc gctgaaacgc gaaaagcagg atgaaagtgc gtccctgacc     780

caagccctgc cgagtgaact gaaagtctcc gccgacaatg tgtcactgac cggcgcatgg     840

tcactggctt cgatgctgac ggaaattttt ctgctgcagc aagcacaggg tatgccggaa     900

ccgcagttcg acctgctgca acgtaccccg gaagtggcac gttcgcgcgc cacgccgctg     960

ctggatctga ttaaaaccgc tctgacgccg catccgccgc agaagcaagc gtatggcgtg    1020

accctgccga cgagcgttct gtttatcgcg ggtcacgaca ccaacctggc aaatctgggc    1080

ggtgctctgg aactgcagtg gaccctgccg ggtcaaccgg ataacacgcc gccgggcggt    1140

gaactggttt tcgaacgttg gcgtcgcctg agcgacaatt ctcagtggat ccaagttagc    1200

ctggtctttc agaccctgca gcaaatgcgc gataaaaccc cgctgttcct gaacacgccg    1260

ccgggcgaag tgaagctgac cctggcgggt tgcgaagaac gtaacgccca gggcatgtgt    1320

tctctggcag gttttaccca gattgttaat gaagcacgca tcccggcttg tagtctgggg    1380

ggcgcagaag cagctgccaa agaggcggcc gcaaaggtca atctgtgtct ggacctgaaa    1440
```

-continued

```
acgcaagtgc aaaccccgca aggcatgaag gaaatctcaa acatccaagt cggtgacctg   1500

gtgctgtcga ataccggcta taacgaagtg ctgaatgttt ttccgaagag caaaaagaaa   1560

tcttacaaga tcacgctgga agatggcaag gaaattattt gcagcgaaga acatctgttc   1620

ccgacccaga cgggcgaaat gaatatctcc ggcggtctga aagaaggcat gtgtctgtac   1680

gtcaaggaat aa                                                         1692


<210> SEQ ID NO 215
<211> LENGTH: 583
<212> TYPE: PRT
<213> ORGANISM: Artificial Sequence
<220> FEATURE:
<223> OTHER INFORMATION: Synthetic construct, [S1A-2]

<400> SEQUENCE: 215

Met Thr Lys Lys Ile Thr Lys Ile Glu Glu Leu Asp Glu Arg Glu Leu
1               5                   10                  15

Ile Asp Ile Glu Val Ser Gly Asn His Leu Phe Tyr Ala Asn Asp Ile
            20                  25                  30

Gly Thr His Asn Ala Ala Ala Glu Ala Ala Ala Lys Glu Ala Ala Ala
        35                  40                  45

Lys Glu Ala Ala Ala Lys Glu Ala Ala Ala Lys Ala Leu Asn Thr Pro
    50                  55                  60

Gln Ser Ala Phe Ala Gln Ser Glu Pro Glu Leu Lys Leu Glu Ser Val
65                  70                  75                  80

Val Ile Val Ser Arg His Gly Val Arg Ala Pro Thr Lys Phe Thr Gln
                85                  90                  95

Leu Met Gln Asp Val Thr Pro Asp Ala Phe Tyr Thr Trp Pro Val Lys
            100                 105                 110

Leu Gly Glu Leu Thr Pro Arg Gly Gly Glu Leu Ile Ala Tyr Leu Gly
        115                 120                 125

His Tyr Trp Arg Gln Arg Leu Val Ala Asp Gly Leu Leu Pro Lys Lys
    130                 135                 140

Gly Cys Pro Gln Ser Gly Gln Val Ala Ile Ile Ala Asp Val Asp Glu
145                 150                 155                 160

Arg Thr Arg Lys Thr Gly Glu Ala Phe Ala Ala Gly Leu Ala Pro Asp
                165                 170                 175

Cys Ala Ile Thr Val His Thr Gln Ala Asp Thr Ser Ser Pro Asp Pro
            180                 185                 190

Leu Phe Asn Pro Leu Lys Thr Gly Val Cys Gln Leu Asp Val Ala Gln
        195                 200                 205

Val Thr Asp Ala Ile Leu Glu Arg Ala Gly Gly Ser Ile Ala Asp Phe
    210                 215                 220

Thr Gly His Tyr Gln Thr Ala Phe Arg Glu Leu Glu Arg Val Leu Asn
225                 230                 235                 240

Phe Pro Gln Ser Asn Leu Ala Leu Lys Arg Glu Lys Gln Asp Glu Ser
                245                 250                 255

Ala Ser Leu Thr Gln Ala Leu Pro Ser Glu Leu Lys Val Ser Ala Asp
            260                 265                 270

Asn Val Ser Leu Thr Gly Ala Trp Ser Leu Ala Ser Met Leu Thr Glu
        275                 280                 285

Ile Phe Leu Leu Gln Gln Ala Gln Gly Met Pro Glu Pro Gly Trp Gly
    290                 295                 300

Arg Ile Thr Asp Ser His Gln Trp Asn Thr Leu Leu Ser Leu His Asn
```

305 310 315 320

Ala Gln Phe Asp Leu Leu Gln Arg Thr Pro Glu Val Ala Arg Ser Arg
325 330 335

Ala Thr Pro Leu Leu Asp Leu Ile Lys Thr Ala Leu Thr Pro His Pro
340 345 350

Pro Gln Lys Gln Ala Tyr Gly Val Thr Leu Pro Thr Ser Val Leu Phe
355 360 365

Ile Ala Gly His Asp Thr Asn Leu Ala Asn Leu Gly Gly Ala Leu Glu
370 375 380

Leu Gln Trp Thr Leu Pro Gly Gln Pro Asp Asn Thr Pro Pro Gly Gly
385 390 395 400

Glu Leu Val Phe Glu Arg Trp Arg Arg Leu Ser Asp Asn Ser Gln Trp
405 410 415

Ile Gln Val Ser Leu Val Phe Gln Thr Leu Gln Gln Met Arg Asp Lys
420 425 430

Thr Pro Leu Phe Leu Asn Thr Pro Pro Gly Glu Val Lys Leu Thr Leu
435 440 445

Ala Gly Cys Glu Glu Arg Asn Ala Gln Gly Met Cys Ser Leu Ala Gly
450 455 460

Phe Thr Gln Ile Val Asn Glu Ala Arg Ile Pro Ala Cys Ser Leu Gly
465 470 475 480

Gly Ala Glu Ala Ala Ala Lys Glu Ala Ala Ala Lys Val Asn Leu Cys
485 490 495

Leu Asp Leu Lys Thr Gln Val Gln Thr Pro Gln Gly Met Lys Glu Ile
500 505 510

Ser Asn Ile Gln Val Gly Asp Leu Val Leu Ser Asn Thr Gly Tyr Asn
515 520 525

Glu Val Leu Asn Val Phe Pro Lys Ser Lys Lys Lys Ser Tyr Lys Ile
530 535 540

Thr Leu Glu Asp Gly Lys Glu Ile Ile Cys Ser Glu Glu His Leu Phe
545 550 555 560

Pro Thr Gln Thr Gly Glu Met Asn Ile Ser Gly Gly Leu Lys Glu Gly
565 570 575

Met Cys Leu Tyr Val Lys Glu
580

<210> SEQ ID NO 216
<211> LENGTH: 13
<212> TYPE: PRT
<213> ORGANISM: Artificial Sequence
<220> FEATURE:
<223> OTHER INFORMATION: Synthetic construct, SpyTag for wild type

<400> SEQUENCE: 216

Ala His Ile Val Met Val Asp Ala Tyr Lys Pro Thr Lys
1 5 10

<210> SEQ ID NO 217
<211> LENGTH: 13
<212> TYPE: PRT
<213> ORGANISM: Artificial Sequence
<220> FEATURE:
<223> OTHER INFORMATION: Syntehtic construct, Spy Tag for mutant

<400> SEQUENCE: 217

Ala His Ile Val Met Val Ala Ala Tyr Lys Pro Thr Lys
1 5 10

<210> SEQ ID NO 218
<211> LENGTH: 1236
<212> TYPE: DNA
<213> ORGANISM: Artificial Sequence
<220> FEATURE:
<223> OTHER INFORMATION: Synthetic construct, Phy02opt coding seq

<400> SEQUENCE: 218

```
gctgcgcagt ccgagccgga gctgaagctg gagtccgtgg tgatcgtgtc gcgccacggg     60

gtgcgcgccc cgaccaagtt cacgcagctc atgcaggacg tgaccccgga cgccttctac    120

acctggccgg tgaagctcgg cgagctgacc ccgcgcggcg gcgagctgat cgcctacctc    180

ggccactact ggcgccagcg cctcgtggcc gacggcctcc tcccgaagaa gggctgcccg    240

cagtccggcc aggtggcgat catcgccgac gtggacgagc gcacccgcaa gacgggcgag    300

gccttcgccg ccggcctcgc cccggactgc gccatcaccg tgcacaccca ggccgacacc    360

tcctccccgg acccgctctt caacccgctc aagaccggcg tgtgccagct cgacgtggcc    420

caggtgaccg acgccatcct ggagcgcgcc ggcggctcca tcgccgactt caccggccac    480

taccagaccg ccttccgcga gctggagcgc gtgctcaact tcccgcagtc gaacctcgcc    540

ctcaagcgcg agaagcagga cgagtccgcc tccctcaccc aggccctccc gtccgagctg    600

aaggtgtccg ccgacaacgt gtccctcacc ggcgcctggt ccctcgcctc catgctcacc    660

gaaatcttcc tcctccagca ggcccagggc atgccggagc cgggctgggg ccgcatcacc    720

gactcccacc agtggaacac cctcctctcc ctccacaacg cccagttcga cctcctccag    780

cgcaccccgg aggtggcccg ctcccgcgcc accccgctcc tcgacctcat caagaccgcc    840

ctcaccccgc acccgccgca gaagcaggcc tacggcgtga ccctcccgac ctcggtgctc    900

ttcatcgccg gccacgacac caacctcgcc aacctcggcg gcgccctgga gctgcagtgg    960

accctcccgg gccagccgga caacaccccg ccgggcggcg agctggtgtt cgagcgctgg   1020

cgccgcctct ccgacaactc ccagtggatt caggtgtccc tcgtgttcca gaccctccag   1080

cagatgcgcg acaagacccc gctcttcctc aacaccccgc cgggcgaggt gaagctcacc   1140

ctggccggct gcgaggagcg caacgcgcag ggcatgtgct ccctcgccgg cttcacccag   1200

atcgtgaacg aggcccgcat cccggcctgc tccctc                             1236
```

<210> SEQ ID NO 219
<211> LENGTH: 412
<212> TYPE: PRT
<213> ORGANISM: Artificial Sequence
<220> FEATURE:
<223> OTHER INFORMATION: Synthetic construct, Phy02opt

<400> SEQUENCE: 219

```
Ala Ala Gln Ser Glu Pro Glu Leu Lys Leu Glu Ser Val Val Ile Val
1               5                   10                  15

Ser Arg His Gly Val Arg Ala Pro Thr Lys Phe Thr Gln Leu Met Gln
            20                  25                  30

Asp Val Thr Pro Asp Ala Phe Tyr Thr Trp Pro Val Lys Leu Gly Glu
        35                  40                  45

Leu Thr Pro Arg Gly Gly Glu Leu Ile Ala Tyr Leu Gly His Tyr Trp
    50                  55                  60

Arg Gln Arg Leu Val Ala Asp Gly Leu Leu Pro Lys Lys Gly Cys Pro
65                  70                  75                  80

Gln Ser Gly Gln Val Ala Ile Ile Ala Asp Val Asp Glu Arg Thr Arg
                85                  90                  95
```

-continued

```
Lys Thr Gly Glu Ala Phe Ala Ala Gly Leu Ala Pro Asp Cys Ala Ile
            100                 105                 110

Thr Val His Thr Gln Ala Asp Thr Ser Ser Pro Asp Pro Leu Phe Asn
        115                 120                 125

Pro Leu Lys Thr Gly Val Cys Gln Leu Asp Val Ala Gln Val Thr Asp
    130                 135                 140

Ala Ile Leu Glu Arg Ala Gly Gly Ser Ile Ala Asp Phe Thr Gly His
145                 150                 155                 160

Tyr Gln Thr Ala Phe Arg Glu Leu Glu Arg Val Leu Asn Phe Pro Gln
                165                 170                 175

Ser Asn Leu Ala Leu Lys Arg Glu Lys Gln Asp Glu Ser Ala Ser Leu
            180                 185                 190

Thr Gln Ala Leu Pro Ser Glu Leu Lys Val Ser Ala Asp Asn Val Ser
        195                 200                 205

Leu Thr Gly Ala Trp Ser Leu Ala Ser Met Leu Thr Glu Ile Phe Leu
    210                 215                 220

Leu Gln Gln Ala Gln Gly Met Pro Glu Pro Gly Trp Gly Arg Ile Thr
225                 230                 235                 240

Asp Ser His Gln Trp Asn Thr Leu Leu Ser Leu His Asn Ala Gln Phe
                245                 250                 255

Asp Leu Leu Gln Arg Thr Pro Glu Val Ala Arg Ser Arg Ala Thr Pro
            260                 265                 270

Leu Leu Asp Leu Ile Lys Thr Ala Leu Thr Pro His Pro Pro Gln Lys
        275                 280                 285

Gln Ala Tyr Gly Val Thr Leu Pro Thr Ser Val Leu Phe Ile Ala Gly
    290                 295                 300

His Asp Thr Asn Leu Ala Asn Leu Gly Gly Ala Leu Glu Leu Gln Trp
305                 310                 315                 320

Thr Leu Pro Gly Gln Pro Asp Asn Thr Pro Pro Gly Gly Glu Leu Val
                325                 330                 335

Phe Glu Arg Trp Arg Arg Leu Ser Asp Asn Ser Gln Trp Ile Gln Val
            340                 345                 350

Ser Leu Val Phe Gln Thr Leu Gln Gln Met Arg Asp Lys Thr Pro Leu
        355                 360                 365

Phe Leu Asn Thr Pro Pro Gly Glu Val Lys Leu Thr Leu Ala Gly Cys
    370                 375                 380

Glu Glu Arg Asn Ala Gln Gly Met Cys Ser Leu Ala Gly Phe Thr Gln
385                 390                 395                 400

Ile Val Asn Glu Ala Arg Ile Pro Ala Cys Ser Leu
                405                 410
```

ENGINEERED PHYTASES AND METHODS OF USING THE SAME

CROSS REFERENCE TO RELATED APPLICATION

This application claims the benefit of U.S. provisional application No. 62/220,688 filed Sep. 18, 2015, which is incorporated herein by reference as if fully set forth.

The sequence listing electronically filed with this application titled "Sequence Listing," created on Sep. 18, 2016, and having a file size of 399,733 bytes is incorporated herein by reference as if fully set forth.

FIELD OF INVENTION

This disclosure relates to engineered phytase molecules that have improved thermal stability, improved or reduced gastric stability, the nucleic acids encoding the same, methods of making the same, as well as methods of using the same in industrial processing or animal feed.

This disclosure relates to transgenic plants expressing the phytases with improved thermal stability, the nucleic acids encoding the same, as well as methods of processing the transgenic plants and tissues, and producing and utilizing animal feed. The disclosure also relates to feed additives, grain and fiber processing additives that include phytases.

This disclosure relates to forms of an engineered *E. coli*-derived phytase that have been modified to improve their performance as components of feed for monogastric and ruminant animals. These modified phytases can be expressed directly in feed components such as corn grain and incorporated into animal diets, for example in mash or pelleted feeds for monogastric animals, or in silage or grain for ruminants. Diets containing these plant-expressed phytases support efficient animal growth using less phosphate than would otherwise be necessary in the absence of engineered phytase.

BACKGROUND

Phytases are a class of acid phosphatase enzymes that hydrolyze phosphates from phytate to produce free phosphate and inositol. Phytic acid (inositol hexakisphosphate), or its deprotonated form, phytate, is common in many animal feed components such as grains and legumes, and can represent a significant portion of the total phosphate content in these feeds. However, many livestock animals cannot efficiently digest phytic acid and are therefore unable to absorb the phosphate.

As a result, other forms of phosphate, such as rock phosphate or calcium phosphate, must be added to animal diets to provide this critical nutrient. Furthermore, phytic acid acts as an antinutrient in the diet, binding to proteins and chelating minerals such as iron, calcium and magnesium, which prevents their absorption. Since undigested phytic acid and excess inorganic phosphate can be excreted in the feces, they can act as a significant source of phosphate pollution in agricultural run-off. Phytase is commonly used in industrial processing and animal production. Inclusion of phytases in animal diets can alleviate the need to add inorganic phosphate, increasing the absorption of phosphate, proteins and minerals by the animal, and decreasing phosphate pollution from agricultural run-offs. When combined these effects can significantly increase the efficiency of animal growth and overall nutrition obtained from the feed they consume.

In industrial process, particularly fermentation processes, phytase is often used to hydrolyze phytate, releasing minerals and other nutrients into the fermentation, as well as enhancing starch degradation by enzymes that require cofactors sequestered by phytate (E. Khullar, J. K. Shetty, M. E. Tumbleson, V. Singh, "Use of Phytases in Ethanol Production from E-Mill Corn Processing," Cereal Chem., 88(3): 223-227, 2011, which is incorporated herein by reference as if fully set forth). It is also used industrially to reduce scaling that may be associated with phytate or phosphate build-up (sometimes referred to as "beer stone"), which often occurs in fermentation or related processes. In animal production and nutrition, one strategy for making phosphorus from phytate nutritionally available to monogastric animals is the addition of phytase to animal feeds (Jongbloed and Lenis, 1998; Onyango et al., 2005, both of which are incorporated herein by reference as if fully set forth). The use of phytase in the diets of poultry and swine has been shown to improve performance and phosphorus utilization (Baker, 2002; Nyannor et al., 2007 and 2009, both of which are incorporated herein by reference as if fully set forth). A number of phytase products are currently marketed for this use and include Natuphos™ (BASF), a phytase derived from *Aspergillus niger*, Ronozyme™ (DSM) a phytase derived from *Peniophora lycii*, and Quantum and Quantum Blue (AB Vista) phytases derived from *Escherichia coli*. The use of phytase in animal feeds allows a reduction in the amount of inorganic phosphorus added to animal feeds and has been reported to result in reductions in fecal phosphorus as high as 56% (Nahm, 2002; Sharpley et al., 1994; Wodzinski and Ullah, 1996, all of which are incorporated herein by reference as if fully set forth). While phytase use in animal feed and industrial processing is beneficial, one common challenge for using microbially or plant-produced phytases in animal feed diets is their inability to maintain full activity through the conditioning, extrusion, or pelleting processes commonly used to make feed pellets. Although some enzymes have been engineered to improve their thermal stability, most lose activity during pelleting, increasing their relative costs and decreasing the efficacy of the enzyme. Therefore, enzymes with further improvements in thermal stability are needed, particularly as feed manufacturers prefer to use higher-temperature pelleting processes.

It is well known in the art that many biomolecules can be rendered inactive through exposure to high temperatures. Because proteins are ubiquitous in nature, occurring in all kingdoms of life and being present in organisms as diverse as mesophiles to extreme thermophiles, they have an enormous range of thermal stabilities. Proteins that are characterized to have low thermal stability often progress through a molecular pathway wherein their structures increase in energy, increasing molecular vibration and movement, which overcomes intramolecular bonding forces and cause the protein to unfold. As unfolding occurs, structures within the protein are disordered, simultaneously exposing hydrophilic and hydrophobic regions and amino acids in the protein structure, and often leading to aggregation of the protein. For proteins that have low thermal stability, the unfolding process is often considerably faster than the refolding process, and in some cases may essentially be irreversible. Conversely, proteins that possess high degrees of thermal stability often have a greater degree of intramolecular bonding, which helps hold their structure together in the presence of increasing levels of thermal energy, as well as rapid rates of refolding, which can enhance a protein's ability to recover its activity when confronted by destabilizing thermal exposure. Given the broad range of thermal stabilities observed among different proteins, an opportunity exists to engineer less stable proteins to be more thermally stable. This is specifically relevant to phytases, which are often derived from mesophilic or less thermophilic organisms, and commonly struggle to maintain high levels of activity in animal feed pelleting processes, or industrial processes.

Another common challenge with producing heterologous proteins in plants, microbial cells, or other cellular production systems, is the risk that the heterologous protein poses as an allergen to humans. Any heterologously-expressed enzyme presents an allergenicity risk to those exposed to the protein through inhalation or ingestion. In order to reduce the allergenicity risk of the protein, particularly a plant-expressed protein that could be inadvertently consumed, it is desirable to engineer the phytase so that it has reduced stability when exposed to a gastric environment, an intestinal environment, or when exposed to pepsin. Reduced pepsin stability makes the protein safer as it would be readily digested in the human digestive tract if the plant material containing the engineered phytase was inadvertently ingested.

SUMMARY

In an aspect, the invention relates to an engineered phytase. The engineered phytase comprises a target phytase, a first binding element and a second binding element. The first binding element is fused to the target phytase, and the second binding element is fused the target phytase. The first binding element interacts with the second binding element to cause cyclization of the engineered phytase and enhance thermal stability of the target phytase. The first binding element is selected from the group consisting of: an intein or part thereof, a coiled-coil dimerization domain or part thereof, a tag domain, and a catcher domain. The second binding element is selected from the group consisting of: a tag domain, a catcher domain, an intein or part thereof, and a coiled-coil dimerization domain or part thereof.

In an aspect, the invention relates to an engineered nucleic acid encoding any one of the engineered phytases described herein.

In an aspect, the invention relates to an engineered nucleic acid encoding an engineered phytase. The engineered phytase comprises a target phytase, a first binding element and a second binding element. Each of the first binding element and the second binding is fused to the target phytase. The first binding element interacts with the second binding element to cause cyclization of the engineered phytase, and enhance thermal stability of the target phytase. The first binding element or the second binding element is selected from the group consisting of: a tag domain, a catcher domain, an intein or part thereof, and a coiled-coil dimerization domain or part thereof.

In an aspect, the invention relates to a vector that comprises any one of the engineered nucleic acids described herein.

In an aspect, the invention relates to a host comprising any one of the engineered phytases described herein. The host is selected from the group consisting of: a microorganism, a plant cell, a phage, a virus, a mammalian cell, and an insect cell.

In an aspect, the invention relates to a method of enhancing thermal stability of a target phytase. The method includes producing any one of the engineered phytase described herein.

In an aspect, the invention relates to a method of preparing an animal feed comprising adding any one of the engineered phytases described herein to the animal feed.

In an aspect, the invention relates to an animal feed comprising any one of the engineered phytases described herein.

BRIEF DESCRIPTION OF THE DRAWINGS

The following detailed description of preferred embodiments of the present invention will be better understood when read in conjunction with the appended drawings. For the purpose of illustrating the invention, particular embodiments are shown in the drawings. It is understood, however, that the invention is not limited to the precise arrangements and instrumentalities shown. In the drawings:

FIG. 9A illustrates ZmZ27P:xGZein27ss:Gp41-1C:Phy02opt:Gp41-1N:DPNGSEKDEL:NosT. FIG. 9B illustrates ZmZ27P:Ssp DnaE-C:Phy02opt:Ssp DnaE-N:NosT. FIG. 9C illustrates ZmZ27P:xGZein27ss:Ssp DnaE-C:Phy02opt:Ssp DnaE-N: DPNGSEKDEL: NosT.

FIG. 10A illustrates ZmZ27P:Ssp DnaE-C:L33-1:Phy02opt:L33-2:Ssp DnaE-N:NosT. FIG. 10B illustrates ZmZ27P:xGZein27ss:Ssp DnaE-C:L33-1:Phy02opt:L33-2:Ssp DnaE-N:DPNG (SEQ IDNO: 199) SEKDEL (SEQ ID NO: 140):NosT. FIG. 10C illustrates ZmZ27P:Ssp DnaE-C:L38-1:Phy02opt:L38-2:Ssp DnaE-N:NosT. FIG. 10D illustrates ZmZ27P:xGZein27ss:Ssp DnaE-C:L38-1:Phy02opt:L38-2:Ssp DnaE-N:DPNG (SEQ ID NO: 199) SEKDEL (SEQ ID NO: 140):NosT. FIG. 10E illustrates ZmZ27P:Ssp DnaE-C:L46-1:Phy02opt:L46-2:Ssp DnaE-N:NosT. FIG. 10F illustrates ZmZ27P:xGZein27ss:Ssp DnaE-C:L46-1:Phy02opt:L46-2:Ssp DnaE-N:DPNG (SEQ ID NO: 199) SEKDEL (SEQ ID NO: 140):NosT. FIG. 10G illustrates ZmZ27P:Ssp DnaE-C:L55-1:Phy02opt:L55-2:Ssp DnaE-N:NosT. FIG. 10H illustrates ZmZ27P:xGZein27ss:Ssp DnaE-C:L55-1:Phy02opt:L55-2:Ssp DnaE-N:DPNG (SEQ ID NO: 199) SEKDEL (SEQ ID NO: 140):NosT.

FIG. 13A shows enzyme activity of untreated (37° C.) and heat treated (75° C./60 sec) samples. FIG. 13B shows residual phytase activity in heat pretreated samples as percentage of activity of their respective untreated control (37° C.).

FIG. 15A illustrates phytase activity of heat pretreated samples. FIG. 15B illustrates retention of phytase activity of heat pretreated samples.

DETAILED DESCRIPTION OF EMBODIMENTS

Figure 1:
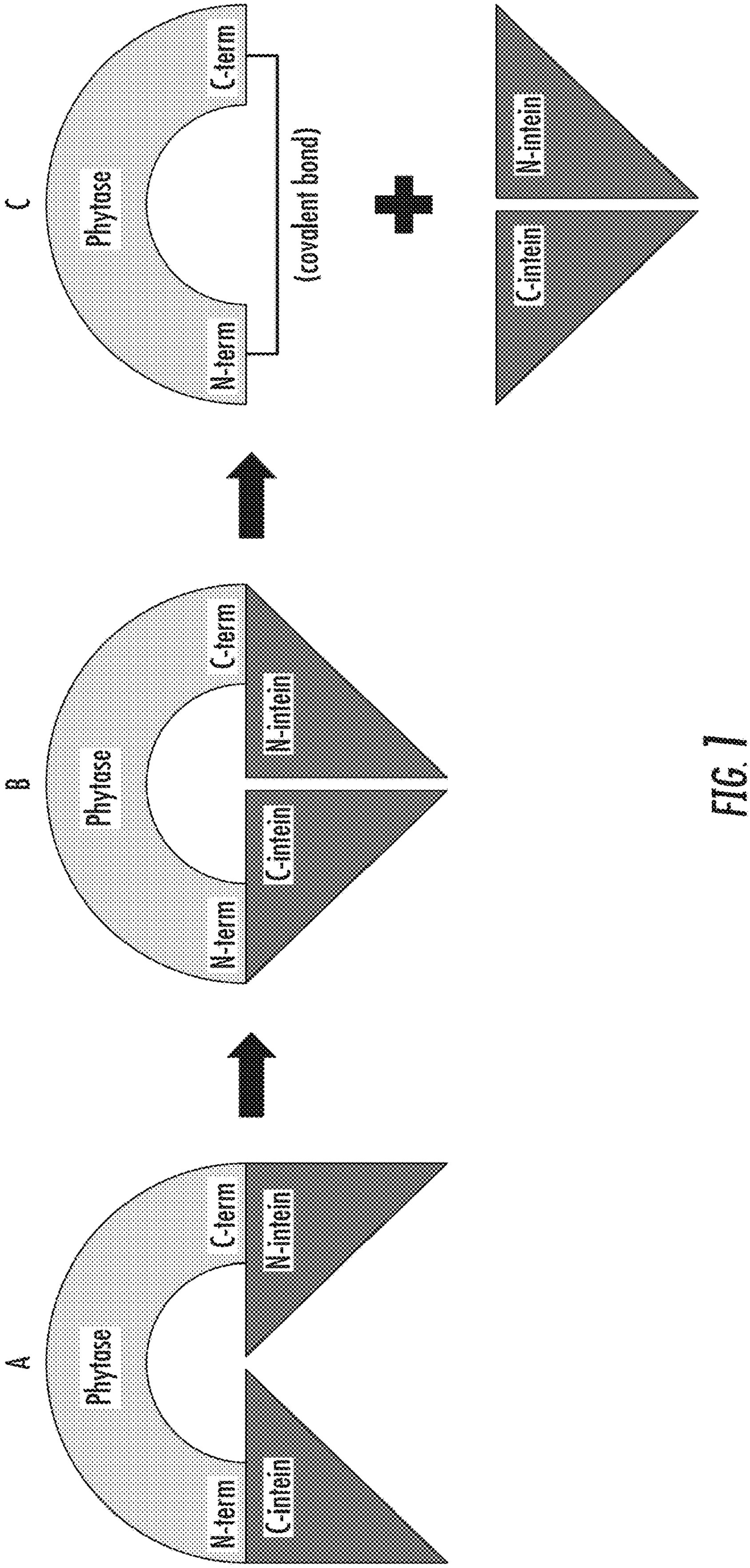
FIG. 1 is a schematic diagram illustrating an engineered phytase with a split intein attached to the ends of the phytase coding sequence (A), binding of the split intein to cyclize the phytase using non-covalent binding (B), and the form of the cyclized phytase that results following splicing of the intein and formation of a covalent bond (C).

Certain terminology is used in the following description for convenience only and is not limiting.

As used herein, "variant" refers to a molecule that retains a biological activity that is the same or substantially similar to that of the original sequence. The variant may be from the same or different species or be a synthetic sequence based on a natural or prior molecule.

An embodiment includes an engineered phytase comprising a target phytase, a first binding element and a second binding element. The first binding element may be fused to the target phytase, and the second binding element may be fused to the target phytase. The first binding element may interact with the second binding element to cause cyclization of the engineered phytase, and alter thermal stability of the target phytase.

Each of the first binding element and the second binding element may be capable of being released from the engineered phytase. The first binding element and the second binding element may be capable of being released from the engineered phytase spontaneously. The first binding element and the second binding element may be capable of being released from the engineered phytase upon exposure to a triggering condition. The triggering condition may be, but is not limited to, a triggering temperature, a triggering pH, a triggering ligand binding, a triggering light, a triggering ion, a triggering concentration of an ion, a triggering sound, a triggering compound, or a triggering concentration of a compound.

In an embodiment, the target phytase may be any phytase. As used herein, "phytase" is an enzyme capable of catalyzing the hydrolysis of phytic acid. The target phytase may be a phytase derived from a mesophilic, thermophilic, or hyperthermophilic organism. The target phytase may be a phytase derived from an eukaryotic or prokaryotic organism. The target phytase may be, but is not limited to, a phytase derived from *Escherichia coli, Aspergillus niger, Peniophora lycii, Neurospora crassa*, or *Schwaniomyces accidentalis*. The phytase may be modified for improved thermal stability. The thermally stable phytase may have activity when heated to a temperature of 70° C. to 90° C. The thermally stable phytase may be active following exposure of a temperature of 70° C. to 90° C. The target phytase may be a phytase stable to pepsin digestion, may have an increased stability in the animal digestive tract, and may be produced by a microbial host. The target phytase may be a phytase that is readily degradable by pepsin. The readily degradable phytase may completely degrade in a time period from 45 minutes to 40 minutes, from 40 minutes to 35 minutes, from 35 minutes to 30 minutes, from 30 minutes to 25 minutes, from 25 minutes to 20 minutes, from 20 minutes to 15 minutes, from 15 minutes to 10 minutes, from 10 minutes to 8 minutes, from 8 minutes to 6 minutes, from 6 minutes to 4 minutes, from 4 minutes to 2 minutes of the pepsin treatment. The time period for degradation may be in a range between any two integer value between 2 minutes and 45 minutes. The complete degradation of the phytase by pepsin may occur in 10 minutes. The target phytase may be any phytase that is sold commercially for use in animal feed.

In an embodiment, the target phytase may be the Phy02 phytase derived from *E. coli*. The Phy02 phytase may be a variant optimized for expression in plants. The variant may be a phytase having an amino acid sequence of SEQ ID NO: 53 and encoded by a codon optimized nucleic acid sequence of SEQ ID NO: 52. The variant may be a phytase having an amino acid sequence of SEQ ID NO: 219 and encoded by a codon optimized nucleic acid sequence of SEQ ID NO: 218. The target phytase may be the Nov9X phytase having an amino acid sequence of SEQ ID NO: 54. The target phytase may be the CQBscks phytase having an amino acid sequence of SEQ ID NO: 56. The target phytase may comprise, consist essentially of, or consist of an amino acid sequence with at least 70, 72, 75, 80, 85, 90, 91, 92, 93, 94, 95, 96, 97, 98, 99 or 100% identity to a reference sequence selected from the group consisting of SEQ ID NOS: 53, 54, and 56.

In an embodiment, a phytase of the composition may be a variant. Variants may include conservative amino acid substitutions: i.e., substitutions with amino acids having similar properties. Conservative substitutions may be a polar for polar amino acid (Glycine (G, Gly), Serine (S, Ser), Threonine (T, Thr), Tyrosine (Y, Tyr), Cysteine (C, Cys), Asparagine (N, Asn) and Glutamine (Q, Gln)); a non-polar for non-polar amino acid (Alanine (A, Ala), Valine (V, Val), Thyptophan (W, Trp), Leucine (L, Leu), Proline (P, Pro), Methionine (M, Met), Phenilalanine (F, Phe)); acidic for acidic amino acid Aspartic acid (D, Asp), Glutamic acid (E, Glu)); basic for basic amino acid (Arginine (R, Arg), Histidine (H, His), Lysine (K, Lys)); charged for charged amino acids (Aspartic acid (D, Asp), Glutamic acid (E, Glu), Histidine (H, His), Lysine (K, Lys) and Arginine (R, Arg)); and a hydrophobic for hydrophobic amino acid (Alanine (A, Ala), Leucine (L, Leu), Isoleucine (I, Ile), Valine (V, Val), Proline (P, Pro), Phenylalanine (F, Phe), Tryptophan (W, Trp) and Methionine (M, Met)). Conservative nucleotide substitutions may be made in a nucleic acid sequence by substituting a codon for an amino acid with a different codon for the same amino acid. Variants may include non-conservative substitutions. A variant may have 40% phytase activity in comparison to the unchanged phytase. A variant may have at least 40%, 45%, 50%, 55%, 60%, 65%, 70%, 75%, 80%, 85%, 90%, 91%, 92%, 93%, 94%, 95%, 96%, 97%, 98%, 99%, or 100% activity, or an integer between any of the two values herein, in comparison to the unchanged phytase. The phytase activity may be determined by a colorimetric enzymatic assay described in Example 6 herein.

In an embodiment, the one or more proteins having less than 100% identity to its corresponding amino acid sequence of SEQ ID NO: 53 [Phy02], SEQ ID NO: 54 [Nov9X], SEQ ID NO: 56 [CQBscks], and SEQ ID NO: 219 [Phy02opt] is a variant of the referenced protein or amino acid. In an embodiment, an isolated protein, polypeptide, oligopeptide, or peptide having a sequence with at least 70, 75, 80, 85, 90, 91, 92, 93, 94, 95, 96, 97, 98, 99, or 100% identity to a protein having the sequence of any one of SEQ ID NO: 53 [Phy02], SEQ ID NO: 54 [Nov9X], SEQ ID NO: 56 [CQBscks], and SEQ ID NO: 219 [Phy02opt] along 10 to 50, 10 to 100, 10 to 150, 10 to 300, 10 to 400, 10 to 500, 10 to 600, 10 to 700, 10 to 800, 10 to 900, or 10 to all amino acids of a protein having the sequence of any of one any one of SEQ ID NO: 53 [Phy02], SEQ ID NO: 54 [Nov9X], SEQ ID NO: 56 [CQBscks] and SEQ ID NO: 219 [Phy02opt] is provided. This list of sequence lengths encompasses every full length protein in SEQ ID NO: 53 [Phy02], SEQ ID NO: 54 [Nov9X], SEQ ID NO: 56 [CQBscks], and SEQ ID NO: 219 [Phy02opt] and every smaller length within the list, even for proteins that do not include over 450 amino acids. For example, the lengths of 10 to 50, 10 to 100, 10 to 150, 10 to 300, 10 to 400, and 10 to all amino acids would apply to a sequence with 400 amino acids. A range of amino acid sequence lengths recited herein includes every length of amino sequence within the range, endpoints inclusive. The recited length of amino acids may start at any single position within a reference sequence where enough amino acids follow the single position to accommodate the recited length. The range of sequence lengths can be extended by increments of 10 to 100N amino acids, where N=an integer of ten or greater, for sequences of 1000 amino acids or larger. The fragment of the phytase may be a subsequence of the polypeptides herein that retain at least 40% activity of the phytase. The fragment may have 400, 405, or 410 amino acids. The fragments may include 20, 30, 40, 50, 100, 150, 200, 300, 400 or 410 contiguous amino acids. Embodiments also include nucleic acids encoding said amino acid sequences, and antibodies recognizing epitopes on said amino acid sequences. A less than full length amino acid sequence may be selected from any portion of one of the sequences of SEQ ID NO: 53 [Phy02], SEQ ID NO: 54 [Nov9X], SEQ ID NO: 56 [CQBscks], and SEQ ID NO: 219 [Phy02opt] corresponding to the recited length of amino acids. A less than full length amino acid sequence may be selected from a portion of any one of SEQ ID NO: 53 [Phy02], SEQ ID NO: 54 [Nov9X], SEQ ID NO: 55 [CQBscks], and SEQ ID NO: 219 [Phy02opt].

In an embodiment, the first binding element and the second binding element may be selected from the group consisting of: inteins or parts thereof, coiled-coil dimerization domains or parts thereof, and tag and catcher domains.

In an embodiment, the first binding element or the second binding element may be an intein or part thereof. The intein may be split into intein parts. The parts of the split inteins may derive from thermophilic, cis-splicing inteins. The parts of the split inteins may derive from trans-splicing inteins. The parts of the split intein may be used to bind a phytase's termini and thereby improve its thermal stability. As used herein, the term "split inteins" refers to cis-splicing inteins derived from the thermophilic organisms that can be split into trans-splicing intein pairs or parts of trans-splicing inteins. The split inteins may be identified by screening cis-splicing inteins selected from INbase based upon their sequence divergence between molecules. For INbase see Perler, F. B. (2002). InBase: the intein database. *Nucleic acids research,* 30(1), 383-384, which is incorporated herein by reference as if fully set forth. These artificially split trans-splicing intein pairs may have canonical splicing residues at the N- and C-termini, where each new subdomain would have a net charge of at least 3.5. The artificially split trans-splicing intein pairs may include N-inteins and C-inteins. The N-inteins may be positively charged and the C-inteins may be negatively charged. The N-inteins and the C-inteins may be selected with the goal of not incorporating the internal endonuclease domain into either split intein component when an endonuclease domain was present in the cis-splicing intein precursor from which these split inteins were selected. The division points may be selected based upon sequence alignments to a miniaturized Tth intein (mTth) and the GP41-1 intein. These division points may be modified, and variants of these inteins may be used in the invention. N-inteins and C-inteins may be truncated, extended or modified for optimum performance in binding the termini of the phytase and improving thermal stability, expression, solubility, specific activity, or gastric stability of digestion of the phytase. A methionine residue may be added to the amino terminus of the C-inteins.

In an embodiment, the first binding element may be C-intein of an intein and that the second binding element may be an N-intein of an intein. FIG. 1 illustrates that a C-intein may be connected to the N-terminus of the phytase sequence and that an N-intein may be connected to the C-terminus of the phytase sequence. The C-intein may be but is not limited to Cbu_DnaB-C, Mja_GF6P-C, Mja_Hyp1-C, Mja_IF2-C, Mja_Pol1-C, Pab_CDC211-C, Pab_IF2-C, Pab_VMA-C, Pho_IF2-C, Pho-VMA-C, Rma_DnaB-C, Sru_DnaB-C, Tag_Pol1Tsp-TYPol1-C, Ter_RIR14-C, Tko_IF2-C, Tth-HB27DnaE2-C, Gp41-1C, Gp41-1C[MTT], and Ssp DnaE-C. The N-intein may be but is not limited to Cbu_DnaB-N, Mja_GF6P-N, Mja_Hyp1-N, Mja_IF2-N, Mja_Pol1-N, Pab_CDC211-N, Pab_IF2-N, Pab_VMA-N, Pho_IF2-N, Pho-VMA-N, Rma_DnaB-N, Sru_DnaB-N, Tag_Pol1Tsp-TYPol1-N, Ter_RIR14-N, Tko_IF2-N, Tth-HB27DnaE2-N, Gp41-1N, and Ssp DnaE-N. The C-intein may comprise, consist essentially of, or consist of an amino acid sequence with at least 70, 72, 75, 80, 85, 90, 91, 92, 93, 94, 95, 96, 97, 98, 99 or 100% identity to a reference sequence selected from the group consisting of: SEQ ID NOS: 2, 4, 6, 8, 10, 12, 14, 16, 18, 20, 22, 24, 26, 28, 30, 32, 189, 191, and 195, and the N-intein may comprise, consist essentially of, or consist of an amino acid sequence with at least 70, 72, 75, 80, 85, 90, 91, 92, 93, 94, 95, 96, 97, 98, 99 or 100% identity to a reference sequence selected from the group consisting of: SEQ ID NOS: 1, 3, 5, 7, 9, 11, 13, 15, 17, 19, 21, 23, 25, 27, 29, 31, 187, and 193. The first binding element may be Cbu_DnaB-C(SEQ ID NO: 2) and the second binding element may be Cbu_DnaB-N(SEQ ID NO: 1). The first binding element may be Mja_GF6P-C(SEQ ID NO: 4) and the second binding element may be Mja_GF6P-N(SEQ ID NO: 3). The first binding element may be Mja_Hyp1-C(SEQ ID NO: 6) and the second binding element may be Mja_Hyp1-N(SEQ ID NO: 5). The first binding element may be Mja_IF2-C (SEQ ID NO: 8) and the second binding element may be Mja_IF2-N(SEQ ID NO: 7). The first binding element may be Mja_Pol1-C(SEQ ID NO: 10) and the second binding element may be Mja_Pol1-N(SEQ ID NO: 9). The first binding element may be Pab_CDC211-C(SEQ ID NO: 12) and the second binding element may be Pab_CDC211-N(SEQ ID NO: 11). The first binding element may be Pab_IF2-C(SEQ ID NO: 14) and the second binding element may be Pab_IF2-N(SEQ ID NO: 13). The first binding element may be Pab_VMA-C(SEQ ID NO: 16) and the second binding element may be Pab_VMA-N(SEQ ID NO: 15). The first binding element may be Pho_IF2-C (SEQ ID NO: 18) and the second binding element may be Pho_IF2-N(SEQ ID NO: 17). The first binding element may be Pho_VMA-C(SEQ ID NO: 20) and the second binding element may be Pho_VMA-N(SEQ ID NO: 19). The first binding element may be Rma_DnaB-C(SEQ ID NO: 22) and the second binding element may be Rma_DnaB-N(SEQ ID NO: 21). The first binding element may be Sru_DnaB-C(SEQ ID NO: 24) and the second binding element may be Sru_DnaB-N(SEQ ID NO: 23). The first binding element may be Tag_Pol1Tsp-TYPol1-C(SEQ ID NO: 26) and the second binding element may be Tag_Pol1Tsp-TYPol1-N(SEQ ID NO: 25). The first binding element may be Ter_RIR14-C(SEQ ID NO: 28) and the second binding element may be Ter_RIR14-N(SEQ ID NO: 27). The first binding element may be Tko_IF2-C(SEQ ID NO: 30) and the second binding element may be Tko_IF2-N(SEQ ID NO: 29). The first binding element may be Tth-HB27DnaE2-C(SEQ ID NO: 32) and the second binding element may be Tth-HB27DnaE2-C(SEQ ID NO: 31). The first binding element may be Gp41-1C (SEQ ID NO: 189) and the second binding element may be Gp41-1N (SEQ ID NO: 187). The first binding element may be Gp41-1C[MTT] (SEQ ID NO: 191) and the second binding element may be Gp41-1N (SEQ ID NO: 187). The first binding element may be Ssp DnaE-C(SEQ ID NO: 195) and the second binding element may be Ssp DnaE-N(SEQ ID NO: 193).

In an embodiment, the first binding element and the second binding element may be coiled-coil dimerization domains. The coiled-coil dimerization domains may bind a target phytase's termini non-covalently. The coiled-coil domains may form stable dimers to bind the phytase's termini. The coiled-coil domains may vary in length and sequence identity, and may be optimized to improve the engineered phytase's thermal stability, specific activity, gastric stability, gastric digestion, or heterologous expression level in a given expression host. Any coiled-coil domains may be used as the first binding element or the second binding element to bind a phytase's termini and thereby improve its thermal stability.

Figure 3:
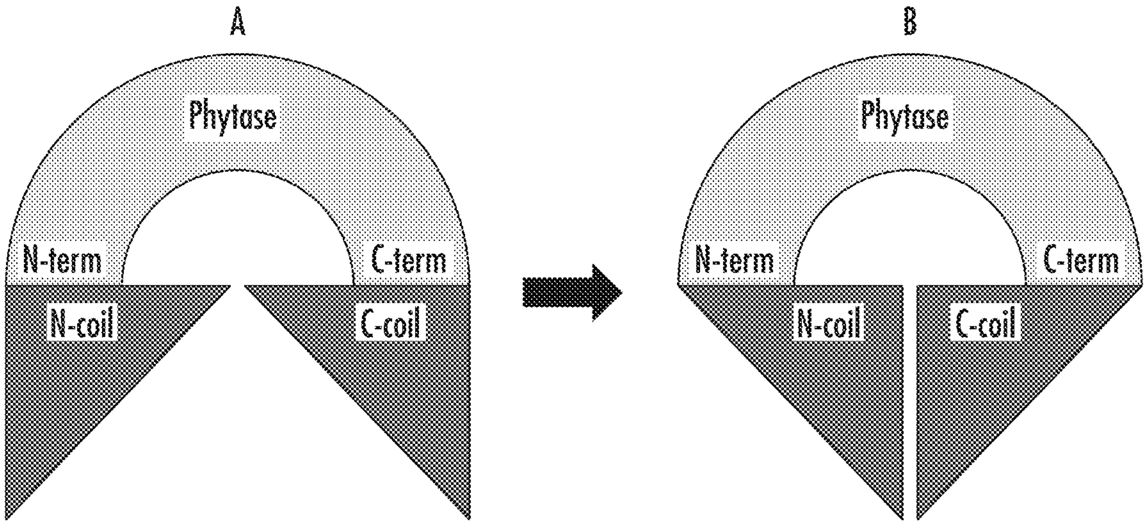
FIG. 3 is a schematic diagram illustrating an engineered phytase with a coiled coil domain that connects to the ends of the phytase coding sequence (A) and binding of the coiled coil domain to cyclize the phytase using non-covalent binding (B).

In an embodiment, the first binding element may be an N-coil of the coiled-coil dimerization domain and the second binding element may be a C-coil of a coiled-coil dimerization domain. FIG. 3 illustrates that an N-coil may be connected to the N-terminus of the phytase sequence and that a C-coil may be connected to the C-terminus of the phytase sequence. The N-coil may comprise, consist essentially of, or consist of an amino acid sequence with at least 70, 72, 75, 80, 85, 90, 91, 92, 93, 94, 95, 96, 97, 98, 99 or 100% identity to a reference sequence of SEQ ID NOS: 37 or 39, and the C-coil may comprise, consist essentially of, or consist of an amino acid sequence with at least 70, 72, 75, 80, 85, 90, 91, 92, 93, 94, 95, 96, 97, 98, 99 or 100% identity to a reference sequence of SEQ ID NOS: 38 or 40. The first binding element may be the cc17 N-terminal coil (SEQ ID NO: 37) and the second binding element may be the cc17 C-terminal coil (SEQ ID NO: 38). The first binding element may be the cc30 N-terminal coil (SEQ ID NO: 39) and the second binding element may be the cc30 C-terminal coil (SEQ ID NO: 40).

In an embodiment, the first binding element or the second binding element may be a tag-domain or a catcher domain. The tag- and catcher domains may bind the target phytase's termini and may create covalent bonds between the termini. The tag- and catcher domains may help in refolding of the target phytase following exposure to high temperatures, and improving phytase thermal stability. The tag- and catcher-domains may be applied to either a C-terminus or an N-terminus of the target phytase (and newly created termini if the protein sequence is rearranged to facilitate binding of the termini) and generally form a stable isopeptide bond when they react.

Figure 4:
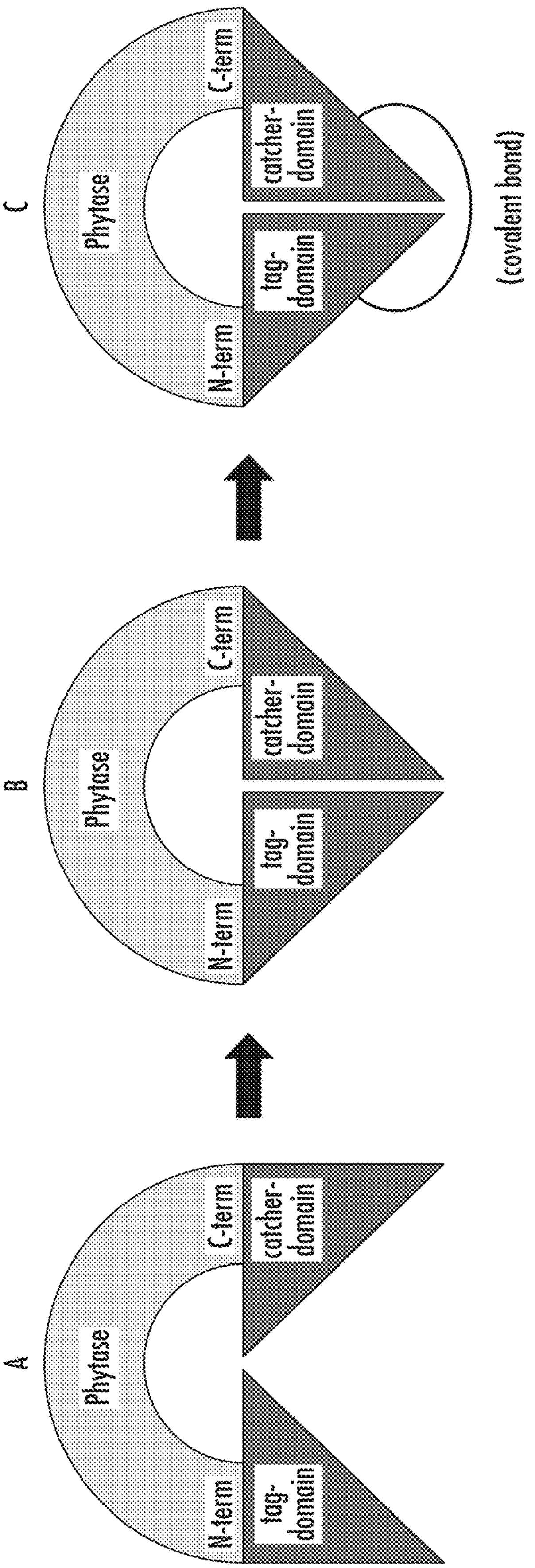
FIG. 4 is a schematic diagram illustrating an engineered phytase with a tag and catcher domain attached to the amino- and carboxy-termini, respectively, of the phytase coding sequence (A) and binding of the tag and catcher domains to cyclize the phytase using non-covalent binding (B), and the form of the cyclized phytase that results following reaction of the tag-catcher domains to form a covalent bond (C).
Figure 5:
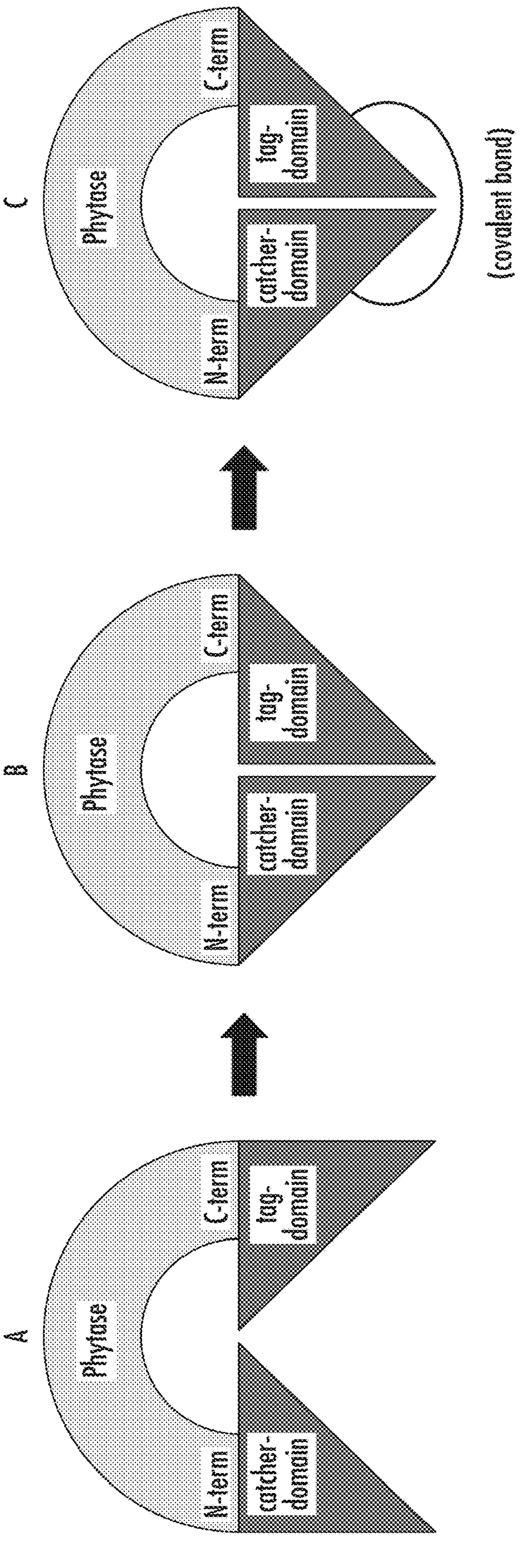
FIG. 5 is a schematic diagram illustrating an engineered phytase with a tag and catcher domain attached to the carboxy- and amino-termini, respectively, of the phytase coding sequence (A) and binding of the tag and catcher domains to cyclize the phytase using non-covalent binding (B), and the form of the cyclized phytase that results following reaction of the tag-catcher domains to form a covalent bond (C).

In an embodiment, the first binding element may be a tag domain or a catcher domain. The second binding element may be a tag domain or a catcher domain. The domain selected as the first binding element may differ from the domain selected as the second binding element. FIG. 4 illustrates that a tag-domain may be connected to the N-terminus of the phytase sequence and that a catcher domain may be connected to the C-terminus of the phytase sequence. FIG. 5 illustrates that a catcher domain may be connected to the N-terminus of the phytase sequence and that a tag domain may be connected to the C-terminus of the phytase sequence. The tag domain may comprise, consist essentially of, or consist of an amino acid sequence with at least 70, 72, 75, 80, 85, 90, 91, 92, 93, 94, 95, 96, 97, 98, 99 or 100% identity to a reference sequence of SEQ ID NOS: 33 or 34. The catcher domain may comprise, consist essentially of, or consist of an amino acid sequence with at least 70, 72, 75, 80, 85, 90, 91, 92, 93, 94, 95, 96, 97, 98, 99 or 100% identity to a reference sequence of SEQ ID NOS: 35 or 36. The first binding element may be Phy_catcher1-C (SEQ ID NO: 36) and the second binding element may be Phy_tag1-N(SEQ ID NO: 33). The first binding element may be Phy_tag1-C(SEQ ID NO: 34) and the second binding element may be Phy_catcher1-N(SEQ ID NO: 35).

To further facilitate binding of the phytase termini using a first binding element or the second binding element, an embodiment provides the engineered phytase that comprises one or more linkers. The one or more linkers may be a first linker and a second linker. The engineered phytase may comprise a first linker. The engineered phytase may comprise a second linker. The engineered phytase may comprise a first linker and a second linker. The first linker may be contiguous with and between the first binding element and the target phytase. The second linker may be contiguous with and between the target phytase and the second binding element. The first linker or the second linker may be a peptide sequence placed contiguously between the target phytase and the first binding element or the second binding element. When using a split intein, either, or both, of the amino-intein (N-intein) and carboxy-intein (C-intein) portions of the split intein may be connected to the first linker or the second linker and to the termini of the target phytase. In naming the linkers, the convention of proceeding an N-linker with a prefix of "N-" was adopted, which denotes that an N-linker would attach to the C-terminus of a desired binding element and the N-terminus of the phytase. Likewise, the convention of appending the suffix "-C" to the end of the names of the C-linkers was used, which denotes that a C-linker attaches to the C-terminus of the phytase and the N-terminus of a desired binding element.

Figure 2:
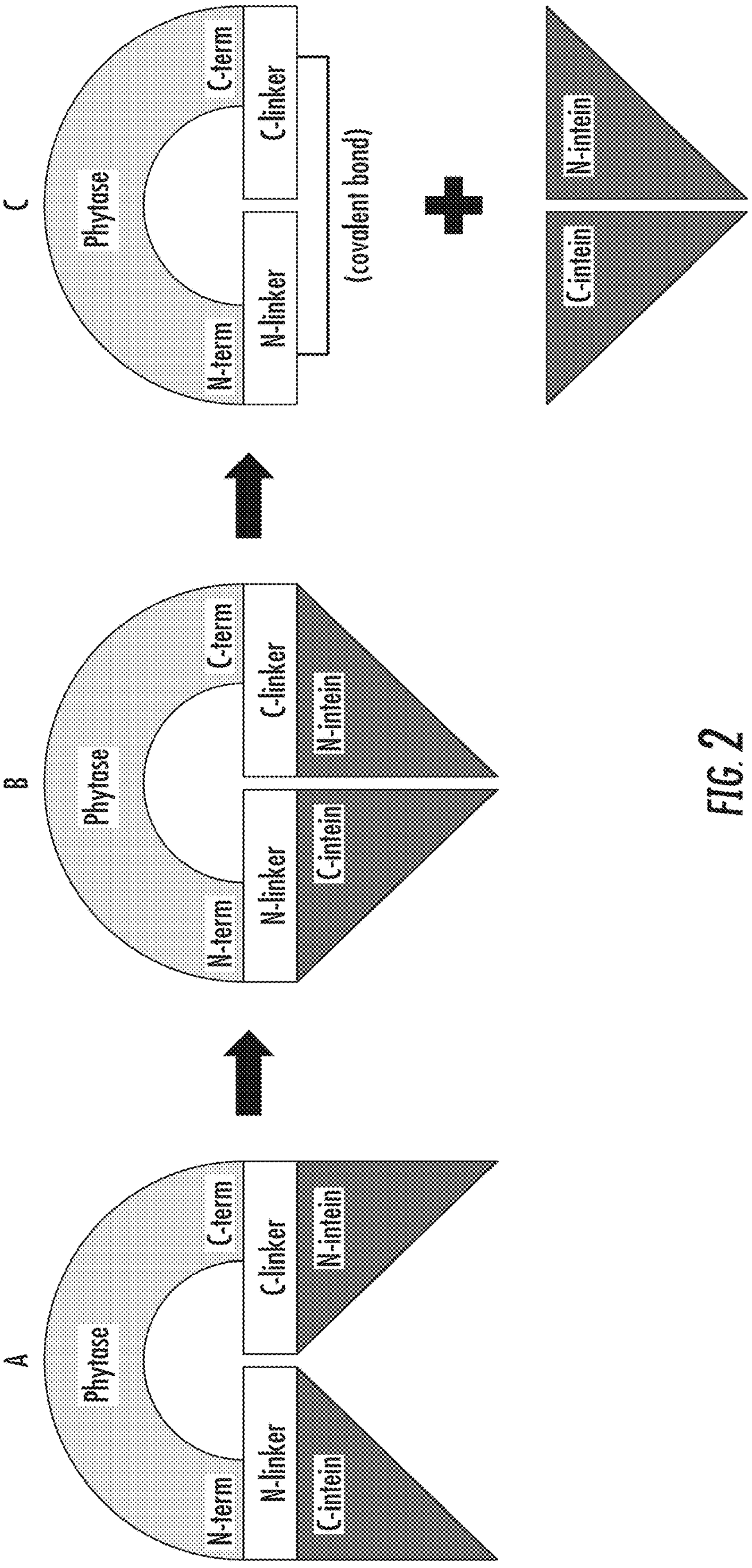
FIG. 2 is a schematic diagram illustrating an engineered phytase with a split intein attached to a linker that connects to the ends of the phytase coding sequence (A), binding of the split intein to cyclize the phytase using non-covalent binding (B), and the form of the cyclized phytase that results following splicing of the intein and formation of a covalent bond (C).
Figure 6:
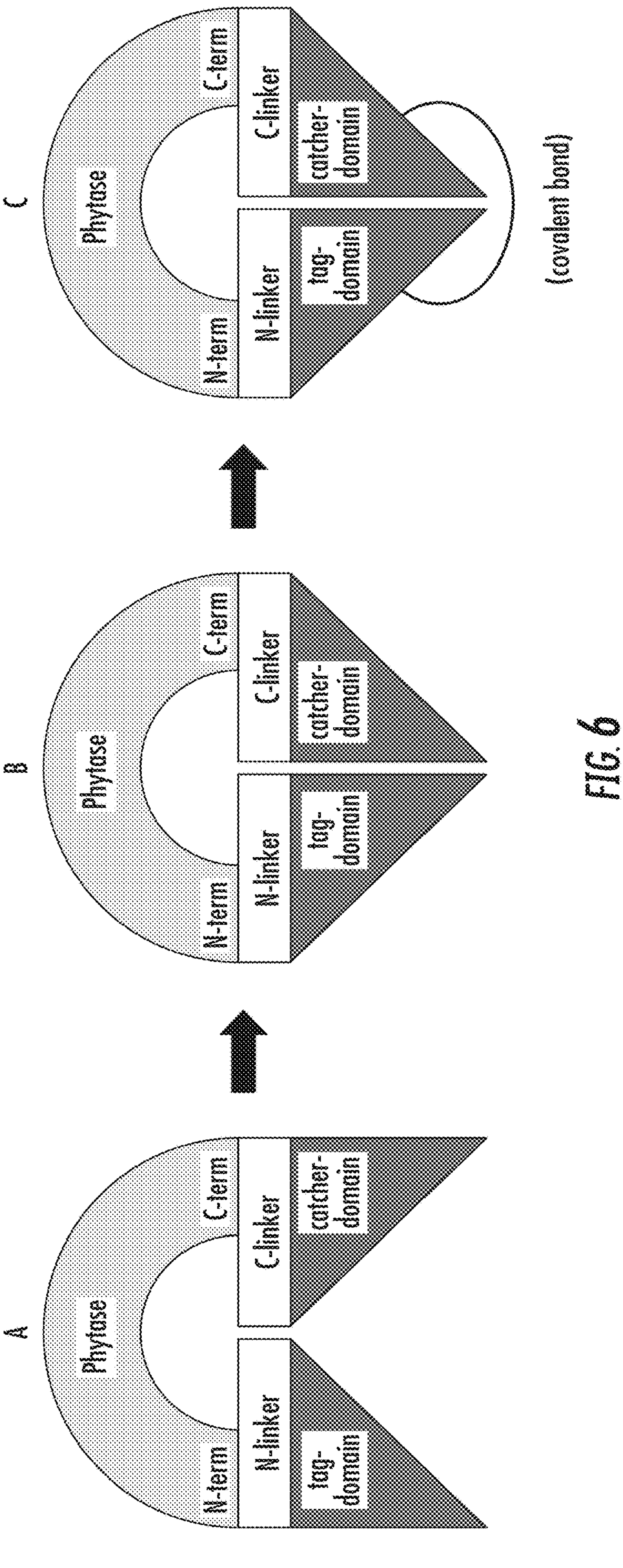
FIG. 6 is a schematic diagram illustrating an engineered phytase with a tag and catcher domain attached to a linker that connects to the amino- and carboxy-termini, respectively, of the phytase coding sequence (A), and binding of the tag and catcher domains to cyclize the phytase using non-covalent binding (B), and the form of the cyclized phytase that results following reaction of the tag-catcher domains to form a covalent bond (C).
Figure 7:
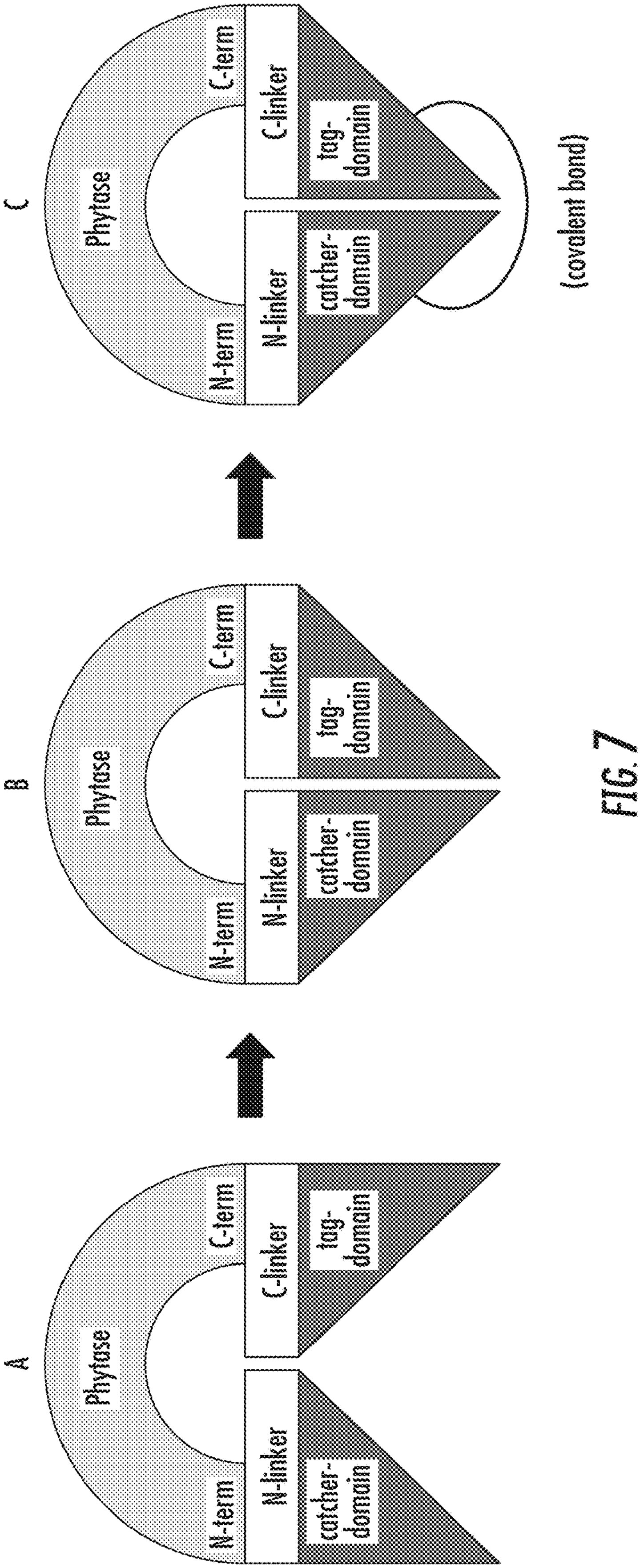
FIG. 7 is a schematic diagram illustrating an engineered phytase with a tag and catcher domain attached to a linker that connects to the carboxy- and amino-termini, respectively, of the phytase coding sequence (A), and binding of the tag and catcher domains to cyclize the phytase using non-covalent binding (B), and the form of the cyclized phytase that results following reaction of the tag-catcher domains to form a covalent bond (C).

In an embodiment, the first linker may be an N-linker and the second linker may be a C-linker. For example, FIG. 2 illustrates that a C-intein may be connected to an N-linker that connects to the N-terminus of the phytase sequence and that an N-intein may be connected to a C-linker that connects to the C-terminus of the phytase sequence. FIGS. 6 and 7 illustrate examples where a tag-domain and catcher-domain may be connected to the phytase using either a linker to the amino- or carboxy-terminus of the phytase. FIG. 6 illustrates that a tag domain may be connected to an N-linker that connects to the N-terminus of the phytase sequence and that a catcher domain may be connected to a C-linker that connects to the C-terminus of the phytase sequence. FIG. 7 illustrates that a catcher domain may be connected to an N-linker that connects to the N-terminus of the phytase sequence and that a tag domain may be connected to a C-linker that connects to the C-terminus of the phytase sequence. The first linker or the second linker may be useful in positioning the first binding element or the second binding element to enhance their binding and thereby enhance overall thermal stability of the resulting engineered phytase. The length (defined as at least one amino acid long), flexibility or rigidity, isoelectric point, structure, hydrophobicity, and sequence of the first linker or the second linker may vary depending upon the target phytase and the binding elements used to engineer the target phytase. The first linker or the second linker, or both, may be used for improving the thermal stability, expression level, pepsin digestibility, pepsin stability, or specific activity of the engineered phytase relative to the engineered phytase using identical binding elements but lacking the first linker or the second linker.

Variants of the first linker or the second linker may also be used. The first linker or the second linker may be initially used in the engineered phytase, and subsequently amino acids may be substituted to improve the thermal stability, expression level, specific activity, pepsin stability, or pepsin digestibility of the engineered phytase. The first linker or the second linker may be highly flexible and largely unstructured peptide sequences. The first linker or the second linker may be rigid. The first linker or the second linker may form ordered structures. The ordered structures may be but are not limited to helices or coils, beta-sheets, or other domains. The first linker or the second linker may include a domain that slows down the rate of unfolding of the enzyme or improves the rate of refolding following exposure of the enzyme to higher temperatures. The first linker or the second linker may include a domain or structure that increases the thermal stability of the engineered phytase. The first linker or the second linker may contain another enzyme, or peptide sequence possessing enzymatic activity.

The first linker or the second linker may be easily modified and optimized for performance with any particular target phytase and molecular structure through mutagenesis techniques including site directed mutagenesis, deletion, insertion, or other methods. The variations of the first linker or the second linker may be constructed by moving an amino acid in the sequence from the N-terminus of an N-linker to the C-terminus of a C-linker, or from the C-terminus of a C-Linker to the N-terminus of an N-linker. The first linker or the second linker may be used to attach an intein molecular structure to the phytase. If intein splicing is desired, the N-terminus of the N-linker must be either a serine, threonine, or cysteine amino acid residue in most cases in order to facilitate intein splicing. Furthermore, it is known that some inteins have preferred insertion site motifs, and when using these linkers with a given intein, it may be beneficial to incorporate either the native insertion site motif, or a preferred insertion site motif, into the linker. See Apgar et al., 2012, A predictive model of intein insertion site for use in the engineering of molecular switches, *PloS one,* 7(5), e37355, which is incorporated herein by reference as if fully set forth.

In an embodiment, the first linker may comprise, consist essentially of, or consist of a sequence with at least 70, 72, 75, 80, 85, 90, 91, 92, 93, 94, 95, 96, 97, 98, 99 or 100% identity to a sequence selected from the group consisting of: SEQ ID NOS: 41, 43, 45, 47, 48, 50, and 51 and the second linker may comprise, consist essentially of, or consist of a sequence with at least 70, 72, 75, 80, 85, 90, 91, 92, 93, 94, 95, 96, 97, 98, 99 or 100% identity to a sequence selected from the group consisting of: SEQ ID NOS: 42, 44, 46, 49, 50, and 51. The first linker may be L33-1 linker (N-linker) (SEQ ID NO: 41) and the second linker may be L33-2 linker (C-linker) (SEQ ID NO: 42). The first linker may be L38-1 linker (N-linker) (SEQ ID NO: 43) and the second linker may be L38-2 linker (C-linker) (SEQ ID NO: 44). The first linker may be L46-1 linker (N-linker) (SEQ ID NO: 45) and the second linker may be L46-2 linker (C-linker) (SEQ ID NO: 46). The first linker may be L55-1.1 linker (N-linker) (SEQ ID NO: 47) and the second linker may be L55-2 linker (C-linker) (SEQ ID NO: 49). The first linker may be L55-1 linker (N-linker) (SEQ ID NO: 48) and the second linker may be L55-2 linker (C-linker) (SEQ ID NO: 49). The first linker may be Phy_taglink (N-linker) (SEQ ID NO: 50) and the second linker may be Phy_catcher1ink (C-linker) (SEQ ID NO: 51). The first linker may be Phy_catcher1ink (N-linker) (SEQ ID NO: 51) and the second linker may be Phy_taglink (C-linker) (SEQ ID NO: 50). The thermal stability of the engineered phytase may be enhanced. The phytase activity may be stable at a temperature in a range from 70° C. to 90° C. The temperature may be 70° C., 75° C., 80° C., 85° C., 90° C., 70° C. to 75° C., 70° C. to 80° C., 70° C. to 85° C., 70° C. to 90° C., or less than 90° C. The engineered phytase modified for thermal stability may be produced by standard molecular biological techniques and then screened. The engineered phytase may be subjected to mutation and then screened for thermal stability. Screening systems that can be utilized may include lambda phage, yeast, or other expression systems that allow production of the protein and/or testing of its physical and/or functional characteristics. From a population of engineered proteins, candidates may be isolated and may be further analyzed. Further analysis may include DNA sequencing, functional assays, structural assays, enzyme activity assays, and monitoring changes in thermal stability, or structure in response to elevated temperature conditions.

In an embodiment, the engineered phytase may comprise, consist essentially of or consist of an amino acid sequence having at least 70, 72, 75, 80, 85, 90, 91, 92, 93, 94, 95, 96, 97, 98, 99 or 100% identity to a reference sequence selected from the group consisting of: SEQ ID NO: 58 [Cbu_DnaB-C:Phy02:Cbu_DnaB-N (#12 Phy02C)], SEQ ID NO: 60 [Mja_GF6P-C:Phy02:Mja_GF6P-N (#44 Phy02C)], SEQ ID NO: 62 [Mja_Hyp1S-N:Phy02:Mja_Hyp1S-C (#46 Phy02C)], SEQ ID NO: 64 [Mja_IF2-N:Phy002:Mja_IF2-C (#47 Phy02C)], SEQ ID NO: 66 [Mja_Pol1-C:Phy02: Mja_Pol1-N (#50 Phy02C)], SEQ ID NO: 68 [Pab_CDC211-C:Phy02: Pab_CDC211-N (#79 Phy02C)], SEQ ID NO: 70 [Pab_IF2-C:Phy02:Pab_IF2-N (#81 Phy02C)], SEQ ID NO: 72 [Pab_VMA-C:Phy02: Pab_VMA-N (#92 Phy02C)], SEQ ID NO: 74 [Pho_IF2-C: Phy02:Pho_IF2-N (#103 Phy02C)], SEQ ID NO: 76 [Pho_VMA-C:Phy02:Pho_VMA-N (#110 Phy02C)], SEQ ID NO: 78 [Rma_DnaB-C:Phy02:Rma_DnaB-N (#116 Phy02C)], SEQ ID NO: 80 [Sru_DnaB-C:Phy02: Sru_DnaB-N (#123 Phy02C)], SEQ ID NO: 82 [Tag_Pol1_TspTYPol1-C:Phy02:Tag_Pol1_TspTYPol1-N (#128 Phy02C)], SEQ ID NO: 84 [Ter_RIR14-C:Phy02: Ter_RIR4-N (#135 Phy02C)], SEQ ID NO: 86 [Tko_IF2-C:Phy02:Tko_IF-N (#143 Phy02C)], SEQ ID NO: 88 [Tth-HB27_DnaE2-C:Phy02:Tth-HB27_DnaE2-N (#150 Phy02C)], SEQ ID NO: 90 [Ssp_DnaE-C:Phy02:Ssp_DnaE-N (#225 Phy02C)], SEQ ID NO: 92 [Gp411-C:Phy02:Gp411-N (#230 Phy02C)], SEQ ID NO: 93 [Gp411-C:Phy02r14:Gp411-N], SEQ ID NO: 95 [Phy02C-27: SspDnaE (SSp_DnaE-C:L33-1: Phy02: L33-2: Ssp_DnaE-N)], SEQ ID NO: 97 [Phy02C-32:SspDnaE (SSp_DnaE-C: L38-1: Phy02: L38-2: Ssp_DnaE-N)], SEQ ID NO: 99 [Phy02C-40: SspDnaE (SSp_DnaE-C:L46-1: Phy02:L46-2: Ssp_DnaE-N)], SEQ ID NO: 101 [Phy02C-49:SspDnaE (SSp_DnaE-C:L55-1: Phy02: L55-2: Ssp DnaE-N)], SEQ ID NO: 103 [Phy02-33:cc17 (cc17-N: L33-1-Phy02-L33-2: cc17-C)], SEQ ID NO: 105 [Phy02-38: cc17 (cc17-N: L38-1-Phy02-L38-2:cc17-C)], SEQ ID NO: 107 [Phy02-46: cc17 (cc17-N: L46-1-Phy02-L46-2:cc17-C)], SEQ ID NO: 109 [Phy02-55: cc17 (cc17-N: L55-1-Phy02-L55-2:cc17-C)], SEQ ID NO: 111 [Phy02-33:cc30 (cc30-N: L33-1-Phy02-L33-2:cc30-C)], SEQ ID NO: 113 [Phy02-38: cc30 (cc30-N: L38-1-Phy02-L38-2:cc30-C)], SEQ ID NO: 115 [Phy02-46: cc30 (cc30-N: L46-1-Phy02-L46-2:cc30-C)], SEQ ID NO: 117 [Phy02-55: cc30 (cc30-N: L55-1-Phy02-L55-2:cc30-C)], SEQ ID NO: 119 [Tag-Domain:Taglink1: Phy02:Catcherlink1: Catcher], SEQ ID NO: 201 [gp41-1C: L55-1:Phy02:L55-2:gp41-1N (#1 gp41-Phy02)], SEQ ID NO: 203 [gp41-1C[MTT]:L55-1:Phy02:L55-2:gp41-1N (#2 gp41-Phy02)], SEQ ID NO: 205 [TrxH:DPNG:gp41-1C [MTT]:L55-1:Phy02:L55-2:gp41-1N (#1 TrxH-Phy02)], and SEQ ID NO: 207 [TrxH:DPNG:gp41-1C[MTT]:L46-1: Phy02:L46-2:gp41-1N (#2 TrxH-Phy02)].

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity can be measured by the Smith Waterman algorithm (Smith T F, Waterman MS 1981 "Identification of Common Molecular Subsequences," *Journal of Molecular Biology* 147: 195-197, which is incorporated by reference in its entirety as if fully set forth).

In an embodiment, an engineered nucleic acid encoding any one of the engineered phytases described herein is provided. The sequence encoding the target phytase may have at least 70, 72, 75, 80, 85, 90, 91, 92, 93, 94, 95, 96, 97, 98, 99 or 100% identity to a reference sequence selected from the group consisting of: SEQ ID NO: 52 [Phy02], SEQ ID NO: 55 [CQBscks], SEQ ID NO: 185 [Nov9X], and SEQ ID NO: 218[Phy02opt].

In an embodiment, the engineered nucleic acid may include a sequence that encodes the first binding element, or the second binding element. The engineered nucleic acid may comprise a sequence encoding a C-intein of an intein. The engineered nucleic acid may comprise, consist essentially of, or consist of a sequence having at least 70, 72, 75, 80, 85, 90, 91, 92, 93, 94, 95, 96, 97, 98, 99, or 100% identity to SEQ ID NO: 143 [Cbu_DnaB-C], SEQ ID NO: 145 [Mja_GF6P-C], SEQ ID NO: 147 [Mja_Hyp1-C], SEQ ID NO: 149 [Mja_IF2-C], SEQ ID NO: 151 [Mja_Pol1-C], SEQ ID NO: 153 [Pab_CDC211-C], SEQ ID NO: 155 [Pab_IF2-C], SEQ ID NO: 157 [Pab_VMA-C], SEQ ID NO: 159 [Pho_IF2-C], SEQ ID NO: 161 [Pho-VMA-C], SEQ ID NO: 163 [Rma_DnaB-C], SEQ ID NO: 165 [Sru_DnaB-C], SEQ ID NO: 167 [Tag_Pol1Tsp-TYPol1-C], SEQ ID NO: 169 [Ter_RIR14-C] SEQ ID NO: 171 [Tko_IF2-C], SEQ ID NO: 173 [Tth-HB27DnaE2-C], SEQ ID NO: 188 [Gp41-1C], SEQ ID NO: 190 [Gp41-1C[MTT]], and SEQ ID NO: 194 [Ssp DnaE-C]. The engineered nucleic acid may comprise a sequence encoding an N-intein of an intein. The engineered nucleic acid may comprise, consist essentially of, or consist of a sequence having at least 70, 72, 75, 80, 85, 90, 91, 92, 93, 94, 95, 96, 97, 98, 99, or 100% identity to a sequence selected from the group consisting of: SEQ ID NO: 142 [Cbu_DnaB-N], SEQ ID NO: 144 [Mja_GF6P-N], SEQ ID NO: 146 [Mja_Hyp1l-N], SEQ ID NO: 148 [Mja_IF2-N], SEQ ID NO: 150 [Mja_Pol1-N], SEQ ID NO: 152 [Pab_CDC211-N], SEQ ID NO: 154 [Pab_IF2-N], SEQ ID NO: 156 [Pab_VMA-N], SEQ ID NO: 158 [Pho_IF2-N], SEQ ID NO: 160 [Pho-VMA-N], SEQ ID NO: 162 [Rma_DnaB-N], SEQ ID NO: 164 [Sru_DnaB-N], SEQ ID NO: 166 [Tag_Pol1Tsp-TYPol1-N], SEQ ID NO: 168 [Ter_RIR14-N], SEQ ID NO: 170 [Tko_IF2-N], SEQ ID NO: 172 [Tth-HB27DnaE2-N], SEQ ID NO: 186 [Gp41-1N], and SEQ ID NO: 192 [Ssp DnaE-N].

The engineered nucleic acid may comprise a sequence encoding an N-coil of the coiled-coil dimerization domain. The engineered nucleic acid may comprise, consist essentially of, or consist of a sequence having at least 70, 72, 75, 80, 85, 90, 91, 92, 93, 94, 95, 96, 97, 98, 99, or 100% identity to a sequence of SEQ ID NO: 178 [cc17 N-terminal coil] or SEQ ID NO: 180 [cc30 N-terminal coil]. The engineered nucleic acid may comprise a sequence encoding a C-coil of the coiled-coil dimerization domain. The engineered nucleic acid may comprise, consist essentially of, or consist of a sequence having at least 70, 72, 75, 80, 85, 90, 91, 92, 93, 94, 95, 96, 97, 98, 99, or 100% identity to SEQ ID NO: 179 [cc17 N-terminal coil] or SEQ ID NO: 181 [cc30 N-terminal coil].

The engineered nucleic acid may comprise a sequence encoding a tag domain. The engineered nucleic acid may comprise, consist essentially of, or consist of a sequence having at least 70, 72, 75, 80, 85, 90, 91, 92, 93, 94, 95, 96, 97, 98, 99, or 100% identity to a sequence of SEQ ID NO: 174 [Phy_tag1-N] or SEQ ID NO: 176 [Phy_tag1-C]. The engineered nucleic acid may comprise a sequence encoding a catcher domain. The engineered nucleic acid may comprise, consist essentially of, or consist of a sequence having at least 70, 72, 75, 80, 85, 90, 91, 92, 93, 94, 95, 96, 97, 98, 99, or 100% identity to a sequence of SEQ ID NO: 176 [Phy_catcher1-N] or SEQ ID NO: 177 [Phy_catcher1-C].

In an embodiment, the engineered nucleic acid may include a sequence that encodes an N-linker or a C-linker. The engineered nucleic acid may comprise a sequence having at least 70, 72, 75, 80, 85, 90, 91, 92, 93, 94, 95, 96, 97, 98, 99 or 100% identity to a reference sequence selected from the group consisting of: SEQ ID NO: 120 [L33-1 linker; N-linker], SEQ ID NO: 122 [L38-1 linker; N-linker], SEQ ID NO: 124 [L46-1 linker; N-linker], SEQ ID NO: 126 [L55-1 linker; N-linker] and SEQ ID NO: 188 [L55-1.1 linker; N-linker]. The engineered nucleic acid may comprise a sequence having at least 70, 72, 75, 80, 85, 90, 91, 92, 93, 94, 95, 96, 97, 98, 99 or 100% identity to a reference sequence selected from the group consisting of: SEQ ID NO: 121 [L33-2 linker; C-linker], SEQ ID NO: 123 [L38-2 linker; C-linker], SEQ ID NO: 125 [L46-2 linker; C-linker], and SEQ ID NO: 127: [L55-2 linker; C-linker]. The engineered nucleic acid may include sequences of other linkers. The engineered nucleic acid may include sequences of a taglinker or a catcherlinker, or both. The engineered nucleic acid may comprise a sequence having at least 70, 72, 75, 80, 85, 90, 91, 92, 93, 94, 95, 96, 97, 98, 99 or 100% identity to a reference sequence of: SEQ ID NO: 183 [Phy_taglink1] or SEQ ID NO: 184 [Phy_catcherlink1].

In an embodiment, the engineered nucleic acid may comprise a sequence having at least 70, 72, 75, 80, 85, 90, 91, 92, 93, 94, 95, 96, 97, 98, 99 or 100% identity to a reference sequence selected from the group consisting of: SEQ ID NO: 57 [Cbu_DnaB-C:Phy02:Cbu_DnaB-N (#12 Phy02C)], SEQ ID NO: 59 [Mja_GF6P-C:Phy02: Mja_GF6P-N (#44 Phy02C)], SEQ ID NO: 61 [Mja_Hyp1S-N:Phy02:Mja_Hyp1S-C (#46 Phy02C)], SEQ ID NO: 63 [Mja_IF2-N:Phy02:Mja_IF2-C (#47 Phy02C)], SEQ ID NO: 65 [Mja_Pol1-C:Phy02:Mja_Pol1-N (#50 Phy02C)], SEQ ID NO: 67 [Pab_CDC211-C:Phy02: Pab_CDC211-N (#79 Phy02C)], SEQ ID NO: 69 [Pab_IF2-C:Phy02:Pab_IF2-N (#81 Phy02C)], SEQ ID NO: 71 Pab_VMA-C:Phy02:Pab_VMA-N (#92 Phy02C)], SEQ ID NO: 73 [Pho_IF2-C:Phy02:Pho_IF2-N (#103 Phy02C)], SEQ ID NO: 75 [Pho_VMA-C:Phy02:Pho_VMA-N (#110 Phy02C)], SEQ ID NO: 77 [Rma_DnaB-C:Phy02: Rma_DnaB-N (#116 Phy02C)], SEQ ID NO: 79 [Sru_DnaB-C:Phy02:Sru_DnaB-N (#123 Phy02C)], SEQ ID NO: 81 [Tag_Pol1_TspTYPol1-C:Phy02: Tag_Pol1_TspTYPol1-N (#128 Phy02C)], SEQ ID NO: 83 [Ter_RIR14-C:Phy02:Ter_RIR4-N (#135 Phy02C)], SEQ ID NO: 85 [Tko_IF2-C:Phy02:Tko_IF-N (#143 Phy02C)], SEQ ID NO: 87 [Tth-HB27_DnaE2-C:Phy02:Tth-HB27_DnaE2-N (#150 Phy02C)], SEQ ID NO: 89 [Ssp_DnaE-C:Phy02:Ssp_DnaE-N (#225 Phy02C)], SEQ ID NO: 91 [Gp411-C:Phy02:Gp411-N (#230 Phy02C)], SEQ ID NO: 94 [Phy02C-27:SspDnaE (SSp_DnaE-C:L33-1: Phy02: L33-2:Ssp_DnaE-N)], SEQ ID NO: 96 [Phy02C-32:SspDnaE (SSp_DnaE-C: L38-1: Phy02: L38-2: Ssp_DnaE-N)], SEQ ID NO: 98 [Phy02C-40: SspDnaE (SSp_DnaE-C:L46-1: Phy02: L46-2:Ssp_DnaE-N)], SEQ ID NO: 100 Phy02C-49:SspDnaE (SSp_DnaE-C: L55-1: Phy02: L55-2: Ssp DnaE-N)], SEQ ID NO: 102 [Phy02-33:cc17 (cc17-N: L33-1-Phy02-L33-2:cc17-C)], SEQ ID NO: 104 [Phy02-38: cc17 (cc17-N: L38-1-Phy02-L38-2:cc17-C)], SEQ ID NO: 106 Phy02-46: cc17 (cc17-N: L46-1-Phy02-L46-2:cc17-C)], SEQ ID NO: 108 [Phy02-55: cc17 (cc17-N: L55-1-Phy02-L55-2:cc17-C)], SEQ ID NO: 110 [Phy02-33:cc30 (cc30-N: L33-1-Phy02-L33-2:cc30-C)], SEQ ID NO: 112 [Phy02-38: cc30 (cc30-N: L38-1-Phy02-L38-2:cc30-C)], SEQ ID NO: 114 [Phy02-46: cc30 (cc30-N: L46-1-Phy02-L46-2:cc30-C)], SEQ ID NO: 116 Phy02-55: cc30 (cc30-N: L55-1-Phy02-L55-2:cc30-C)], SEQ ID NO: 118 [Tag-Domain: Taglink1:Phy02:Catcherlink1:Catcher], SEQ ID NO: 128 [ZmZ27P:Gp411C:Phy02opt:Gp411N:NosT (#1Phy02opt)], SEQ ID NO:129 [Z27P:xGZein27ss:Gp411-C:Phy02opt:Gp411-N:DPNGSEKDEL:NosT (#2Phy02opt)], SEQ ID NO:130 [ZmZ27P:Ssp_DnaE-C: Phy02opt Ssp_DnaE-N:NosT (#3Phy02op)t], SEQ ID NO:131 [mZ27P:xGZein27ss: Ssp_DnaE-C:Phy02opt: Ssp_DnaE-N:DPNGSEKDEL:NosT (#4Phy02op)t], SEQ ID NO:132 [ZmZ27P:Ssp_DnaE:L33-1:Phy02opt:L33-2: NosT (SSp_DnaE-C:L33-1:Phy02opt:L33-2:Ssp_DnaE-N) #5Phy02opt, SEQ ID NO:133 [ZmZ27P:xGZein27ss: Ssp_DnaE:L33-1:Phy02opt:L33-2 DPNGSEKDEL:NosT (#6Phy02opt]), SEQ ID NO:200 [gp41-1C:L55-1 Phy02: L55-2:gp41-1N (#1 gp41-Phy02)], SEQ ID NO:202 [gp41-1C[MTT]L55-1:Phy02:L55-2:gp41-1N (#2 gp41-Phy02)], SEQ ID NO:204 [TrxH:DPNG:gp41-1C[MTT]:L55-1: Phy02:L55-2:gp41-1N (#1 TrxH-Phy02)], and SEQ ID NO:206 [TrxH:DPNG:gp41-1C [MTT]:L46-1:Phy02: L46-2: gp41-1N (#2 TrxH-Phy02)].

The engineered nucleic acid may be included in the expression cassette. The expression cassette may include at least one regulatory element. The regulatory element may be operably connected to the engineered nucleic acid. In this context, operably linked means that the regulatory element imparts its function on the nucleic acid. The regulatory element may be selected from the group consisting of: a promoter, a signal peptide, a C-terminal extension and a terminator. For example, a regulatory element may be a promoter, and the operably linked promoter would control expression of the engineered nucleic acid.

The expression of an engineered nucleic acid encoding an engineered phytase from the expression cassette may be under the control of a promoter which provides for transcription of the nucleic acid in a plant. The promoter may be a constitutive promoter or, tissue specific, or an inducible promoter. A constitutive promoter may provide transcription of the nucleic acid throughout most cells and tissues of the plant and during many stages of development but not necessarily all stages. An inducible promoter may initiate transcription of the nucleic acid sequence only when exposed to a particular chemical or environmental stimulus. A tissue specific promoter may be capable of initiating transcription in a particular plant tissue. Plant tissue may be, but is not limited to, a stem, leaves, trichomes, anthers, cob, seed, endosperm, or embryo. The constitutive promoter may be, but is not limited to the Cauliflower Mosaic Virus (CAMV) 35S promoter, the Cestrum Yellow Leaf Curling Virus promoter (CMP), the actin promoter, or the Rubisco small subunit promoter. The tissue specific promoter may be the maize globulin promoter (ZmGlb1), the rice glutelin promoter (prGTL), the maize gamma zein promoter (ZmZ27), or the maize oleosin promoter (ZmOle). The signal peptide may be but is not limited to a maize gamma zein 27 signal peptide or a rice glutelin B4 signal peptide. The C-terminal extension may be buts is not limited to HvVSD (from the *Hordeum vulgare* vacuolar sorting determinant (Cervelli et al., 2004)) or SEKDEL (SEQ ID NO: 140; Endoplasmic reticulum retention signal; (Arakawa, Chong, & Langridge, 1998; Haq, Mason, Clements, & Arntzen, 1995; Korban, 2002; Munro & Pelham, 1987)). The terminator may be but is not limited to a NOS (from the *Agrobacterium tumefaciens* nopaline synthase gene) terminator or a maize globulin 1 terminator.

The promoter may be a maize zein 27 promoter. The maize zein 27 promoter (ZmZ27P) may be encoded by a sequence with at least 70, 72, 75, 80, 85, 90, 91, 92, 93, 94, 95, 96, 97, 98, 99 or 100% identity to a reference sequence of: SEQ ID NO: 137. The signal peptide may be a maize zein 27 signal peptide. The maize zein 27 signal peptide (xGZein27ss) may be encoded by a sequence with at least 70, 72, 75, 80, 85, 90, 91, 92, 93, 94, 95, 96, 97, 98, 99 or 100% identity to a reference sequence of: SEQ ID NO: 138. The C-terminal extension may be SEKDEL (SEQ ID NO: 140). The SEKDEL (SEQ ID NO: 140) may be encoded by a sequence with at least 70, 72, 75, 80, 85, 90, 91, 92, 93, 94, 95, 96, 97, 98, 99 or 100% identity to a sequence of SEQ ID NO: 139. The terminator may be a NOS terminator. The NOS terminator (NosT) may be encoded by a sequence with at least 70, 72, 75, 80, 85, 90, 91, 92, 93, 94, 95, 96, 97, 98, 99 or 100% identity to a reference sequence of: SEQ ID NOS: 141.

In an embodiment, a vector comprising any one the engineered nucleic acids or expression cassettes described herein is provided.

Any one of the engineered phytase described herein may be expressed in a host. The host may be but is not limited to a microorganism, a plant cell, a phage, a virus, a mammalian cell, or an insect cell. In an embodiment, any one of the engineered phytases may be produced in a plant or plant tissue. The engineered phytases may be produced upon introduction into the plant genome of any one more of the engineered nucleic acids described herein. The engineered nucleic acid may encode the engineered phytase enzyme or fragment thereof. The engineered nucleic acid may be an expression cassette that directs the plant to express one or more engineered phytases. The methods of introduction of engineered nucleic acids into the plants are known in the art. The method may be transformation of the plant with a vector that includes engineered nucleic acids encoding the one or more of the engineered phytases. The one or more engineered phytases may be isolated from the plant or plant tissue. The one or more engineered phytases expressed in a transgenic plant herein may have activity when exposed to a temperature in the range of 70° C. to 90° C., endpoints inclusive. The temperature may be 70° C., 75° C., 80° C., 85° C., 90° C., 70° C. to 75° C., 70° C. to 80° C., 70° C. to 85° C., 70° C. to 90° C., or less than 90° C. The one or more engineered phytases may be produced in any transgenic plant.

In an embodiment, a host comprising any one of the engineered nucleic acids described herein is provided. The host may be but is not limited to a microorganism, a plant cell, a phage, a virus, a mammalian cell, or an insect cell.

The host may be a transgenic plant or part thereof including an engineered nucleic acid encoding any one or more of the engineered phytases described herein is provided. As used herein, the transgenic plant may refer to a whole transgenic plant or a part thereof. The part may be but is not limited to one or more of leaves, stems, flowers, buds, petals, ovaries, fruits, or seeds. The part may be callus from a transgenic plant. A transgenic plant may be regenerated from parts of a transgenic plant. A transgenic plant may be a product of sexual crossing of a first transgenic plant and a second transgenic plant or a non-transgenic plant where the product plant retains an engineered nucleic acid introduced to the first transgenic plant. An embodiment provides a progeny of any one of the transgenic plants described herein.

In an embodiment a method of enhancing thermal stability of the target phytase is provided. One mechanism to improve the thermal stability of a target phytase may be to bind its N- and C-termini together in a way that restricts movement of the termini. Restricting movement of the termini may increase the energy necessary for unfolding of the target phytase, as well as facilitate refolding of the target phytase. Binding of the ends of the target phytase may occur through both intramolecular covalent and non-convalent bonds. It is understood that binding the N- and C-termini of the target phytase may occur specifically in a reaction between the first amino acid of the target phytase and the last amino acid of the target phytase, or between any amino acid in between, such that the reaction between the amino acids improves thermal stability of the target phytase. Likewise, more than two amino acids may be involved in the binding of the termini, especially when the binding either completely or partially uses non-covalent bonds. A variety of intramolecular bonds may be useful for binding the termini of the target phytase including cysteine bonds, peptide bonds, isopeptide bonds, amide bonds, hydrogen bonds, and others. Thus, the method may include producing an engineered phytase by fusing a first binding element, and a second binding element to a target phytase. Within the engineered phytase, the first binding element may interact with the second binding element. The first binding element may interact with the second binding element to cause cyclization of the engineered phytase. The cyclization of the engineered phytase may alter thermal stability of the target phytase. The first binding element or the second binding element may be any one of the inteins or parts thereof, coiled-coil dimerization domains or parts thereof, tags and catcher domains described herein.

The step of engineering may include making an expression construct that includes a nucleic acid encoding the engineered phytase.

The step of making the expression construct may include analyzing the molecular structures that are useful for binding a target phytase's termini and, or, catalyzing a reaction to create a covalent bond between a target phytase's termini. A variety of intramolecular bonds may be useful for binding the termini of the protein including cysteine bonds, peptide bonds, isopeptide bonds, amide bonds, hydrogen bonds, and others. The step of engineering may include selecting molecular structures that can be used to facilitate either, or both, the formation of covalent or non-covalent bonds within the phytase molecule to improve its thermal stability. These structures may include inteins, tag and catcher domains, coiled coil domains, and other affinity domains. See Perler et al., 1994, Protein splicing elements: inteins and exteins—a definition of terms and recommended nomenclature. Nucleic acids research, 22(7), 1125; Gogarten et al., 2002, Inteins: structure, function, and evolution. Annual Reviews in Microbiology, 56(1), 263-287; Perler, 2002, InBase: the intein database. Nucleic acids research, 30(1), 383-384; Schoene et al., 2014, SpyTag/SpyCatcher cyclization confers resilience to boiling on a mesophilic enzyme. Angewandte Chemie International Edition, 53(24), 6101-6104.; Zakeri et al., 2012, Peptide tag forming a rapid covalent bond to a protein, through engineering a bacterial adhesin. Proceedings of the National Academy of Sciences, 109(12), E690-E69; U.S. application Ser. No. 14/774,954, "Use of Dimerization Domains for Temperature Regulation of Enzyme Activity," all of which are incorporated herein by reference as if fully set forth. The molecular structures may be assessed for their ability to bind the phytases termini and form covalent or non-covalent bonds along the phytases termini or at point near the termini. The molecular structures may be used as a first binding element or the second binding element in the method described herein. The molecular structures may be a split intein attached to the termini of a target phytase that may bind its amino-intein and carboxy-intein components together, effectively binding the termini of the phytase, but may not react to form either an isopeptide or peptide bond. Likewise, in some cases, the intein may react to form an isopeptide or peptide bond, in the latter case, releasing the intein segments that were bond to the phytase and leaving a fully cyclized phytase. In each of these cases, the engineered phytase may be tested for improvements in thermal stability relative to the form of the phytase prior to engineering.

The step of making the expression construct may include making variations of the sequences encoding engineered phytases. The variants of the engineered phytases may be created, screened, and developed further. There are many techniques known in the art for modifying DNA sequences and the corresponding protein sequences they encode. Mutagenesis techniques that may be useful in this regard include site directed mutagenesis, saturating mutagenesis (where each amino acid is individually substituted at each position in the protein sequence, and improved variants are selected and combined), random mutagenesis, domain swapping or exchange, and others. Additionally, small deletions, or insertions, may be beneficial when optimizing the sequences for thermal stability, specific activity, host expression, gastric stability or gastric digestibility.

The method may further include linking a nucleic acid that encodes the first binding element, or the second binding element to the nucleic acid encoding the terminus of the target phytase in such a position that effects interaction of the binding elements and causes cyclization of the target phytase. The binding elements may be portions of a split inteins. The first binding element may be a C-intein of an intein. The second binding element may be an N-intein of an intein. FIG. 1 shows that when the C-intein is fused to the N-terminus of the phytase, and the N-intein is fused to the C-terminus of the phytase (A structure), the C-intein associates with the N-intein (B structure). FIG. 1 also shows that following the association, the inteins splice and the termini of the phytase get connected by the covalent bond (C structure), and that the phytase is cyclized. The cyclized phytase shown in structure C may have an enhanced thermal stability compared to the phytases shown in structures A or B. The structure B shown in FIG. 1 is an intermediate structure having association of the C- and N-inteins. The association without splicing may stabilize the engineered phytase. However, this stabilization may not be permanent and may be lost at the dissociation temperature. On the other hand, when association of the C- and N-inteins progresses to splicing, a stable covalent bond may link the termini of the engineered phytase and a permanent structure (C) may be produced that has high thermal stability.

FIG. 2 shows that the C-intein and the N-intein may be connected to the phytase termini via linkers. As shown in FIG. 2, the N-linker is placed between the C-intein and the N-terminus of the phytase and the C-linker is placed between the N-intein and the C-terminus of the phytase (A structure). When the C-intein associates with the N-intein (B structure), the inteins splice, and the N-linker gets connected to the C-linker by the covalent bond causing cyclization of the phytase (C structure). The cyclized phytase shown in structure C may have an enhanced thermal stability compared to the phytase shown in structures A or B of FIG. 2.

The binding elements may be coiled-coil dimerization domains. The first binding element may be an N-coil. The second binding element may be a C-coil. Referring to FIG. 3, the N-coil and C-coil dimerization domains may be fused to the N-terminus and C-terminus of the target protein (A structure). When domains associate, the phytase together with the associated domains form cyclic structure (B structure) which has an enhanced thermal stability compared to the A structure shown in FIG. 3. Coiled coil dimerization domains may be tailored to dissociate at a specific temperature or remain stably associated at high temperature. The stability of coiled coils is proportional with the number of heptad repeats and the correct pairing of the hydrophobic and ionic residues (Lau et al, 1984; Woolfson D N, 2005; Parry at al. 2008, all of which are incorporated herein by reference as if fully set forth). The larger coil interface may increase the strength of dimerization of the coiled coil and may be used to stabilize target proteins above their melting point without covalent linkage.

The binding elements may be tag- and catcher domains. The first binding element may be a tag domain. The second binding element may be a catcher domain. FIG. 4 shows the tag-domain may be fused to the N-terminus of the target phytase, and the catcher-domain may be fused to the C-terminus of the target phytase (A structure). When domains associate (B structure), they get linked by a covalent bond and form a cyclic structure together with the target phytase (C structure) which has an enhanced thermal stability compared to the phytase shown in A structure of FIG. 4. FIG. 5 shows that tag- and catcher domains are interchangeable and that the catcher-domain may be fused to the N-terminus of the target phytase, and the tag-domain may be fused to the C-terminus of the target phytase. FIGS. 6 and 7 show that tag- and catcher domains may be connected to the phytase termini via linkers. The cyclic structures (C structures) shown in FIGS. 4-7 may have enhanced thermal stability compared to non-cyclized target phytases shown in these figures.

The step of engineering may further include contacting a host with an expression construct. The expression construct may include any one of the engineered nucleic acids described herein. The expression construct may be inserted in a transformation vector. The transformation vector may be used to transform the host. The transformation may be but is not limited to an *Agrobacterium*-mediated transformation, electroporation with a plasmid DNA, a DNA uptake, a biolistic transformation, a virus-mediated transformation, or a protoplast transformation. The transformation may be any other transformation procedure suitable for a particular host. The method may include selecting the host cell that includes the engineered nucleic acid and expresses the chimeric protein. The method may include regenerating the host cell into a multicellular organism. The method may include multiplying the host cell to obtain a plurality of the host cells that include the engineered nucleic acid and expresses the engineered phytase. The thermal stability of the target phytase may be enhanced.

In an embodiment, an animal feed that includes any one of the engineered phytases described herein is provided. The term "animal feed" refers to any food, feed, feed composition, preparation, additive, supplement, or mixture suitable and intended for intake by animals for their nourishment and growth. The engineered phytases include in the animal feed may be active in the gastrointestinal or rumen environment of animals. The engineered phytases included the animal feed may be a phytase that is stable to pepsin digestion. The animal may be a monogastric animal. The animal may be a ruminant animal. The monogastric animal may be but is not limited to a chicken, a turkey, a duck, a swine, a fish, a cat, or a dog. The ruminant animal may be but is not limited to cattle, a cow, a sheep, a horse, or a goat. The engineered phytases may be active after preparation of the animal feed. The temperatures which feeds are exposed to during ensiling may be within range of 20° C. to 70° C. The temperatures which feeds are exposed to during pelleting may be within range of 70° C. to 130° C. The engineered phytases may have improved thermal stability and may retain activity after being exposed to high temperatures during feed pelleting.

In an embodiment, the animal feed may further include a feed supplement. The feed supplement may be any plant material. The plant material may be a non-transgenic plant or an engineered plant. The plant material may include an engineered plant or a mutant plant. The plant material may be a grain that contains starch. The plant material may be a grain that contains fiber. The plant material may be a chemically treated forage. The feed supplement may be a mineral. The mineral may be a trace mineral. The mineral may be a macro mineral. The mineral may be rock phosphate or a phosphate salt. The mineral may be calcium phosphate. The feed supplement may be at least one vitamin. The at least one vitamin may be a fat-soluble vitamin. The feed supplement may be an amino acid. The feed supplement may include one or more exogenous enzymes. The one or more exogenous enzymes may include a hydrolytic enzyme. The hydrolytic enzyme may be an enzyme classified under EC3.4 as hydrolase. The hydrolytic enzymes may be but are not limited to xylanases, mannanases, carbohydrases, proteases, peptidases, glucanases, cellulases, lipases, phospholipases, pectinases, galactosidases, laccases, amylases, hemicellulases, or cellobiohydrolases. The hydrolytic enzymes may be expressed in the engineered plants or parts thereof included in the feed supplement. The feed supplement may include purified hydrolytic enzymes. The feed supplements may be but are not limited to growth improving additives, coloring agents, flavorings, stabilizers, limestone, stearine, starch, saccharides, fatty acids, or a gum. The coloring agents may be carotenoids. The carotenoids may be but are not limited to cantaxanthin, beta-carotene, astaxanthin, or lutein. The fatty acids may be polyunsaturated fatty acids. The polyunsaturated fatty acids may include but are not limited to arachidonic acid, docosohexaenoic acid (DHA), eicosapentaenoic acid (EPA) or gamma-linoleic acid. The plant material may be a non-transgenic plant or part thereof. The plant material may include at least one component selected from the group consisting of: barley, wheat, rye, oat, corn, rice, triticale, beet, sugar beet, spinach, cabbage, quinoa, corn meal, corn pellets, corn oil, distillers grains, forage, wheat meal, wheat pellets, wheat grain, barley grain, barley pellets, soybean meal, soybean oilcake, lupin meal, rapeseed meal, sorghum grain, sorghum pellets, rapeseed, sunflower seed, and cotton seed.

The feed supplement may include at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix. The feed supplement may include fish meal, fish oil, bone meal, feather meal and animal fat. The feed supplement may include yeast or yeast extract.

In an embodiment, a method of preparing an animal feed is provided. The method may include producing any one of the engineered phytases described herein by any one of the methods described herein.

An embodiment provides a method of producing an animal feed. The method may include mixing any one of the transgenic plants or parts thereof described herein, or the progeny thereof with plant material. The transgenic plant may be a progeny of the transgenic plant. The engineered nucleic acid(s) may be included in a genetic construct(s) or an expression cassette(s). The method may comprise making any transgenic plant herein. The transgenic plant or its progeny may be the plant, in which phytase levels may be increased by the method herein. The method may further include pelletizing the mixture. The method may further include adding a feed supplement to the mixture. The feed supplement may include at least one exogenous enzyme. The at least one exogenous enzyme may be a hydrolase selected from the group consisting of: xylanase, mannanase, protease, glucanase, and cellulase. Preparing the animal feed may include combining one or more transgenic plant herein with any other feed supplement.

An expression cassette having an engineered nucleic acid encoding an engineered phytase in a plant in may be expressed at any point in the methods. The engineered nucleic acid may be expressed prior to the step of step of mixing the plant. The engineered nucleic acid may be expressed during the step of pelletizing the plant. The expression may be induced. Upon the expression of the nucleic acid(s), the transgenic plant may have an increased level of an engineered phytase compared to the level of a phytase in a non-genetically engineered plant of the same genetic background but lacking the one or more expression cassettes.

The engineered phytase may be isolated, purified and added to the animal feed as a pure phytase. The engineered phytase may be isolated from the intact host organism and added to the animal feed as a phytase composition. The engineered phytase may be added to the animal feed in admixture with other feed supplements. The transgenic plant including the engineered phytase or the purified engineered phytase may be combined with other feed supplements to form premixes.

An animal feed may be produced as mash feed. The animal feed may be produced as pellets. The milled feed stuffs may be mixed with the premix that includes any one of the transgenic plants that include an engineered phytase. The engineered phytase may be a phytase stable to pepsin digestion. The milled stuffs may include the plant material and the feed supplements described herein. The feed supplements may include one or more exogenous enzymes described herein. Enzymes may be added as liquid or solid formulations. For mash feed, a solid or liquid enzyme formulation may be added before or during the mixing step. For pelleted feed, the enzyme preparation may be added before or after the pelleting step. The phytase may be included in premix. The premix may also include vitamins and trace minerals. Macro minerals may be added separately to animal feedstock.

In an embodiment, a method of enhancing thermal stability of a target phytase is provided. The method may include producing a transgenic plant that includes an engineered nucleic acid encoding the phytase. The engineered nucleic acid may include any one the sequences described herein. The phytase may be thermally stable upon exposure to temperatures in the range of 70° C. to 90° C., endpoints inclusive. The phytase may be thermally stable upon exposure to temperatures in the range of 70° C. to 90° C., endpoints inclusive. The phytase may be thermally stable upon exposure to temperatures in the range from 70° C., 75° C., 80° C., 85° C., 90° C., 70° C. to 75° C., 70° C. to 80° C., 70° C. to 85° C., 70° C. to 90° C., or less than 90° C. The thermally stable phytase may be a phytase that is stable to pepsin digestion.

The following list includes particular embodiments. The list, however, is not limiting and does not exclude the embodiments otherwise described herein or alternate embodiments.

EMBODIMENTS

1. An engineered phytase comprising a target phytase, a first binding element and a second binding element, wherein each of the first binding element and the second binding is fused to the target phytase, the first binding element interacts with the second binding element to cause cyclization of the engineered phytase, and enhance thermal stability of the target phytase, wherein each of the first binding element and the second binding element is selected from the group consisting of: a tag domain, a catcher domain, an intein or part thereof, and a coiled-coil dimerization domain or part thereof.

2. The engineered phytase of embodiment 1, wherein upon the interaction, each of the first binding element and the second binding element is capable of being released from the engineered phytase spontaneously.

3. The engineered phytase of any one or both of embodiments 1 or 2, wherein upon the interaction, each of the first binding element and the second binding element is capable of being released from the engineered phytase upon exposure to a triggering condition.

4. The engineered phytase of embodiment 3, wherein the triggering condition is selected from the group consisting of triggering temperature, a triggering pH, a triggering ligand binding, a triggering light, a triggering ion, a triggering concentration of an ion, a triggering sound, a triggering compound, or a triggering concentration of a compound.

5. The engineered phytase of any one or more of the preceding embodiments, wherein the first binding element or the second binding element is fused to the N-terminus or the C-terminus of the target phytase.

6. The engineered phytase of any one or more of the preceding embodiments, wherein the N-terminus of the second binding element is linked to and contiguous with the C-terminus of the target phytase.

7. The engineered phytase of any one or more of the preceding embodiments, wherein the C-terminus of the first binding element is linked to and contiguous with the N-terminus of the target phytase, and the N-terminus of the second binding element is linked to and contiguous with the C-terminus of the target phytase.

8. The engineered phytase of any one or more of the preceding embodiments, wherein the target phytase is selected from the group consisting of phytases derived from *Escherichia coli, Aspergillus niger, Peniophora lycii, Neurospora crassa*, and *Schwaniomyces accidentalis*.

9. The engineered phytase of any one or more of the preceding embodiments, wherein the target phytase comprises an amino acid sequence with at least 70, 72, 75, 80, 85, 90, 91, 92, 93, 94, 95, 96, 97, 98, 99 or 100% identity to a reference sequence selected from the group consisting of SEQ ID NOS: 53-54, 56, and 219.

10. The engineered phytase of any one or more of the preceding embodiments, wherein the first binding element is a C-intein of an intein and the second binding element is an N-intein of an intein.

11. The engineered phytase of any one or more of the preceding embodiments, wherein the C-intein comprises an amino acid sequence with at least 70, 72, 75, 80, 85, 90, 91, 92, 93, 94, 95, 96, 97, 98, 99 or 100% identity to a reference sequence selected from the group consisting of: SEQ ID NOS: 2, 4, 6, 8, 10, 12, 14, 16, 18, 20, 22, 24, 26, 28, 30, 32, 189, 191, and 195, and the N-intein comprises an amino acid sequence with at least 70, 72, 75, 80, 85, 90, 91, 92, 93, 94, 95, 96, 97, 98, 99 or 100% identity to a reference sequence selected from the group consisting of: SEQ ID NOS: 1, 3, 5, 7, 9, 11, 13, 15, 17, 19, 21, 23, 25, 27, 29, 31, 187, and 193.

12. The engineered phytase of any one or more of embodiments 1-9, wherein the first binding element is a C-coil of the coiled-coil dimerization domain and the second binding element is an N-coil of a coiled-coil dimerization domain.

13. The engineered phytase of embodiment 12, wherein the C-coil comprises an amino acid sequence with at least 70, 72, 75, 80, 85, 90, 91, 92, 93, 94, 95, 96, 97, 98, 99 or 100% identity to a reference sequence of SEQ ID NOS: 38 or 40, and the N-coil comprises an amino acid sequence with at least 70, 72, 75, 80, 85, 90, 91, 92, 93, 94, 95, 96, 97, 98, 99 or 100% identity to a reference sequence of SEQ ID NOS: 37 or 39.

14. The engineered phytase of any one or more of embodiments 1-9, wherein each of the first binding element and the second biding element comprises a tag domain or a catcher domain, wherein the domain selected as the first binding element differs from the domain selected as the second binding element.

15. The engineered phytase of embodiment 14, wherein the tag domain comprises an amino acid sequence with at least 70, 72, 75, 80, 85, 90, 91, 92, 93, 94, 95, 96, 97, 98, 99 or 100% identity to a reference sequence of SEQ ID NOS: 33 or 34.

16. The engineered phytase of embodiment 14, wherein and the catcher domain comprises an amino acid sequence with at least 70, 72, 75, 80, 85, 90, 91, 92, 93, 94, 95, 96, 97, 98, 99 or 100% identity to a reference sequence of SEQ ID NOS: 35 or 36.

17. The engineered phytase of any one or more of preceding embodiments further comprising a first linker and a second linker, wherein the first linker is contiguous with and between the first binding element and the target phytase and the second linker is contiguous with and between the target phytase and the second binding element.

18. The engineered phytase of embodiment 17, wherein the first linker comprises a sequence with at least 70, 72, 75, 80, 85, 90, 91, 92, 93, 94, 95, 96, 97, 98, 99 or 100% identity to a sequence selected from the group consisting of: SEQ ID NOS: 41, 43, 45, 47, 48, 50, and 51, and the second linker comprises a sequence with at least 70, 72, 75, 80, 85, 90, 91, 92, 93, 94, 95, 96, 97, 98, 99 or 100% identity to a sequence selected from the group consisting of: SEQ ID NOS: 42, 44, 46, 49, 50, and 51.

19. The engineered phytase of any one or more of the preceding embodiments comprising an amino acid sequence having at least 70, 72, 75, 80, 85, 90, 91, 92, 93, 94, 95, 96, 97, 98, 99 or 100% identity to a reference sequence selected from the group consisting of: SEQ ID NOS: 58, 60, 62, 64, 66, 68, 70, 72, 74, 76, 78, 80, 82, 84, 86, 88, 90, 92, 93, 95, 97, 99, 101, 103, 105, 107, 109, 111, 113, 115, 117, 119, 201, 203, 205, and 207.

20. The engineered phytase of any one or more of the preceding embodiments, wherein the phytase activity is stable at a temperature in a range from 70° C. to 90° C.

21. The engineered phytase of any one or more of the preceding embodiments, wherein the engineered phytase is expressed in a host selected form the group consisting of a microorganism, a plant cell, a phage, a virus, a mammalian cell, and an insect cell.

22. An engineered nucleic acid encoding the engineered phytase of any one or more of the preceding embodiments.

23. An engineered nucleic acid encoding an engineered phytase comprising a target phytase, a first binding element and a second binding element, wherein each of the first binding element and the second binding is fused to the target phytase, the first binding element interacts with the second binding element to cause cyclization of the engineered phytase, and enhance thermal stability of the target phytase, and each of the first binding element and the second binding element is selected from the group consisting of: a tag domain, a catcher domain, an intein or part thereof, and a coiled-coil dimerization domain or part thereof.

24. The engineered nucleic acid of embodiment 23, wherein upon the interaction, each of the first binding element and the second binding element is capable of being released from the engineered phytase spontaneously.

25. The engineered nucleic acid of any one or both of embodiments 23 or 24, wherein upon the interaction, each of the first binding element and the second binding element is capable of being released from the engineered phytase upon exposure to a triggering condition.

26. The engineered nucleic acid of embodiment 25, wherein the triggering condition is selected from the group consisting of triggering temperature, a triggering pH, a triggering ligand binding, a triggering light, a triggering ion, a triggering concentration of an ion, a triggering sound, a triggering compound, or a triggering concentration of a compound.

27. The engineered nucleic acid of any one or more of embodiments 23-26, wherein the first binding element or the second binding element is fused to the N-terminus or the C-terminus of the target phytase.

28. The engineered nucleic acid of any one or more of embodiments 23-27, wherein the N-terminus of the second binding element is linked to and contiguous with the C-terminus of the target phytase.

29. The engineered nucleic acid of any one or more of embodiments 23-28, wherein the C-terminus of the first binding element is linked to and contiguous with the N-terminus of the target phytase, and the N-terminus of the second binding element is linked to and contiguous with the C-terminus of the target phytase.

30. The engineered nucleic acid of any one or more of embodiments 23-29 comprising a sequence encoding the target phytase selected from the group consisting of phytases derived from *Escherichia coli, Aspergillus niger, Peniophora lycii, Neurospora crassa*, and *Schwaniomyces accidentalis*.

31. The engineered nucleic acid of any one or more embodiments 23-30 comprising a sequence encoding the target phytase and having at least 70, 72, 75, 80, 85, 90, 91, 92, 93, 94, 95, 96, 97, 98, 99 or 100% identity to a reference sequence selected from the group consisting of SEQ ID NOS: 52, 55, 185, and 218.

32. The engineered nucleic acid of any one or more of embodiments 23-31 comprising the sequence encoding the first binding element, wherein the first binding element is a C-intein of an intein.

33. The engineered nucleic acid of any one or more of embodiments 23-32 comprising the sequence encoding the second binding element, wherein the second binding element is an N-intein of an intein.

34. The engineered nucleic acid of embodiment 32 comprising the sequence with at least 70, 72, 75, 80, 85, 90, 91, 92, 93, 94, 95, 96, 97, 98, 99 or 100% identity to a reference sequence selected from the group consisting of: SEQ ID NOS: 143, 145, 147, 149, 151, 153, 155, 157, 159, 161, 163, 165, 167, 169, 171, 173, 188, 190, and 194.

35. The engineered nucleic acid of embodiment 33 comprising the sequence with at least 70, 72, 75, 80, 85, 90, 91, 92, 93, 94, 95, 96, 97, 98, 99 or 100% identity to a reference sequence selected from the group consisting of: SEQ ID NOS: 142, 144, 146, 148, 150, 152, 154, 156, 158, 160, 162, 164, 166, 168, 170, 172, 186, and 192.

36. The engineered nucleic acid of any one or more of embodiments 23-31 comprising the sequence encoding the first binding element, wherein the first binding element is a C-coil of the coiled-coil dimerization domain.

37. The engineered nucleic acid of any one or more of embodiments 23-31 and 36 comprising the sequence encoding the second binding element, wherein the second binding element is an N-coil of a coiled-coil dimerization domain.

38. The engineered nucleic acid of embodiment 36 comprising the sequence with at least 70, 72, 75, 80, 85, 90, 91, 92, 93, 94, 95, 96, 97, 98, 99 or 100% identity to a reference sequence of SEQ ID NOS: 179 or 181.

39. The engineered nucleic acid of embodiment 37 comprising the sequence with at least 70, 72, 75, 80, 85, 90, 91, 92, 93, 94, 95, 96, 97, 98, 99 or 100% identity to a reference sequence of SEQ ID NOS: 178 or 180.

40. The engineered nucleic acid of any one or more of embodiments 23-31 comprising the sequence encoding the first binding element, wherein the first binding element is a tag domain or a catcher domain.

41. The engineered nucleic acid of any one or more of embodiments 23-31 and 40 comprising the sequence encoding the second binding element, wherein the second binding element is a tag domain or a catcher domain, and wherein the sequence selected as the second binding element differs from the sequence selected as the first binding element.

42. The engineered nucleic acid of any one or both of embodiments 40 and 41 comprising a sequence encoding the tag domain and having at least 70, 72, 75, 80, 85, 90, 91, 92, 93, 94, 95, 96, 97, 98, 99 or 100% identity to a reference sequence of SEQ ID NOS: 174 or 175.

43. The engineered nucleic acid of any one or more of embodiments 40-42 comprising a sequence encoding the catcher domain and having at least 70, 72, 75, 80, 85, 90, 91, 92, 93, 94, 95, 96, 97, 98, 99 or 100% identity to a reference sequence of SEQ ID NOS: 176 or 177.

44. The engineered nucleic acid of any one or more of embodiments 23-43 further comprising a sequence encoding a first linker and a sequence encoding a second linker, wherein the first linker is contiguous with and between the first binding element and the target phytase and the second linker is contiguous with and between the target phytase and the second binding element.

45. The engineered nucleic acid of embodiment 44 comprising a sequence encoding the first linker and having at least 70, 72, 75, 80, 85, 90, 91, 92, 93, 94, 95, 96, 97, 98, 99 or 100% identity to a sequence selected from the group consisting of: SEQ ID NOS: 120, 122, 124, 126, 182, 183, and 184, and a sequence encoding the second linker and having at least 70, 72, 75, 80, 85, 90, 91, 92, 93, 94, 95, 96, 97, 98, 99 or 100% identity to a sequence selected from the group consisting of: SEQ ID NOS: 121, 123, 125, 127, 183 and 184.

46. The engineered nucleic acid of any one or more of embodiments 23-45 comprising a sequence having at least 70, 72, 75, 80, 85, 90, 91, 92, 93, 94, 95, 96, 97, 98, 99 or 100% identity to a reference sequence selected from the group consisting of: SEQ ID NOS: 57, 59, 61, 63, 65, 67, 69, 71, 73, 75, 77, 79, 81, 83, 85, 87, 89, 91, 94, 96, 98, 100, 102, 104, 106, 108, 110, 112, 114, 116, 118, 128-133, 200, 202, 204 and 206.

47. The engineered nucleic acid of any one or more of embodiments 23-46 comprising a sequence encoding the engineered phytase having stable phytase activity at a temperature in a range from 70° C. to 90° C.

48. The engineered nucleic acid of any one or more of embodiments 23-47 expressed in a host is selected form the group consisting of a microorganism, a plant cell, a phage, a virus, a mammalian cell, and an insect cell.

49. The engineered nucleic acid of embodiment 48, wherein the host is the plant cell.

50. A vector comprising the engineered nucleic acid encoding the engineered phytase of any one or more of embodiments 1-21.

51. A vector comprising the engineered nucleic acid of any one or more of embodiments 23-48.

52. A host comprising the engineered phytase of any one or more of embodiments 1-21 or the engineered nucleic acid of any one or more of embodiments 23-48, wherein the host is selected from the group consisting of: a microorganism, a plant cell, a phage, a virus, a mammalian cell, and an insect cell.

53. A method of enhancing thermal stability of a target phytase comprising producing the engineered phytase of any one or more of embodiments 1-21.

54. An animal feed comprising an engineered phytase of any one or more of embodiments 1-21.

55. The animal feeds of embodiment 54 further comprising a feed supplement.

56. The animal feed of embodiment 55, wherein the feed supplement is plant material.

57. The animal feed of embodiment 56, wherein the plant material is a non-transgenic plant or an engineered plant.

58. The animal feed of any one or more of embodiments 54-57, wherein the feed supplement includes one or more exogenous enzymes.

59. The animal feed of embodiment 58, wherein the one or more exogenous enzymes includes a hydrolytic enzyme selected from the group consisting of: xylanase, endoglucanase, cellulase, protease, glucanase, amylase and mannanase.

60. The animal feed of any one or more of embodiments 54-59, wherein the plant material includes at least one component selected from the group consisting of: corn meal, corn pellets, wheat meal, wheat pellets, wheat grain, barley grain, barley pellets, soybean meal, soybean oilcake, sorghum grain and sorghum pellets.

61. The animal feed of any one or more of embodiments 55-60, wherein the feed supplement includes at least one component selected from the group consisting of: soluble solids, fat and vermiculite, limestone, plain salt, DL-methionine, L-lysine, L-threonine, COBAN®, vitamin premix, dicalcium phosphate, selenium premix, choline chloride, sodium chloride, and mineral premix.

62. A method of preparing an animal feed comprising adding the engineered phytase of any one or more of embodiments 1-21 to the animal feed.

63. The method of embodiment 62 further comprising pelletizing the mixture.

64. The method of any one or both of embodiments 62 or 63 further comprising adding a feed supplement to the mixture.

65. The method of embodiment 64, wherein the feed supplement includes at least one exogenous enzyme.

66. The method of embodiment 65, wherein the at least one exogenous enzyme is a hydrolase selected from the group consisting of: xylanase, mannanase, protease, glucanase, and cellulase.

67. A method of promoting the release of inorganic phosphate from a phytic acid or phytate in an animal comprising feeding an animal with an animal feed comprising the engineered phytase of any one or more of embodiments 1-22.

68. The method of embodiment 31 further comprising preparing the animal feed according to a method of any one or more of embodiments 62-66.

69. The method of any one or both of embodiments 67 or 68, wherein the animal is a monogastric animal or a ruminant animal.

70. A cyclized phytase comprising the engineered phytase of any one or more of embodiments 1, 5-9, and 12-21, wherein the first binding element is bound to the second binding element.

71. A cyclized phytase comprising the engineered phytase of any one or more of embodiments 1-10, and 13-21, wherein upon interaction, the first binding element and the second binding element are released from the engineered phytase, and the N-terminus of the target phytase and the C-terminus of the target phytase are linked.

Further embodiments herein may be formed by supplementing an embodiment with one or more elements from any one or more other embodiments herein, and/or substituting one or more elements from one embodiment with one or more elements from one or more other embodiments herein.

EXAMPLES

The following non-limiting examples are provided to illustrate particular embodiments. The embodiments throughout may be supplemented with one or more details from one or more examples below, and/or one or more elements from an embodiment may be substituted with one or more details from one or more examples below.

Example 1. Descriptions of Genetic Elements for Improving Phytase Thermal Stability Molecular Structures or Domains for Improving Phytase Thermal Stability.

Among the molecular structures that are useful for binding a protein's termini and, or, catalyzing a reaction to create a covalent bond between a protein's termini, are inteins, and tag- and catcher-domains.

Inteins.

While any split intein may be used in this invention to bind a phytase's termini and thereby improve its thermal stability, a set of inteins derived from thermophilic, cis-splicing inteins was used. This set was assembled by screening a set of 157 cis-splicing inteins selected from INbase based upon their sequence divergence between molecules. For INbase see Perler, F. B. (2002). InBase: the intein database. *Nucleic acids research,* 30(1). 383-384, which is incorporated herein by reference as if fully set forth. Cis-splicing inteins from thermophilic organisms were selected and divided into trans-splicing intein pairs. These artificially split inteins were required to have canonical splicing residues at the N- and C-termini, where each new subdomain would have a net charge of at least 3.5. This resulted in 18 split inteins, of which all N-inteins are positively charged and C-inteins are negatively charged. N- and C-terminal domains were selected with the goal of not incorporating the internal endonuclease domain into either split intein component (that is, either the N-intein or the C-intein) when an endonuclease domain was present in the cis-splicing intein precursor from which these split inteins were selected. Division points were then selected based upon sequence alignments to a miniaturized Tth intein (mTth) and the GP41-1 intein. A methionine residue was added to the amino terminus of the C-inteins in the set below. The sequences of trans-splicing inteins are shown in Table 1 as follows:

TABLE 1

Sequences of the Trans-splicing Inteins

| SEQ ID Amino Acid | NO Nucleic Acid | SEQ_ID NO SEQUENCE DESCRIPTION |
|---|---|---|
| 1 | 142 | Cbu_DnaB—N (#12-N) |
| 2 | 143 | Cbu_DnaB—C (#12-C) |
| 3 | 144 | Mja_GF6P—N (#44-N) |
| 4 | 145 | Mja_GF6P—C (#44-C) |
| 5 | 146 | Mja_Hyp1—N (#46-N) |
| 6 | 147 | Mja_Hyp1—C (#46-C) |
| 7 | 148 | Mja_IF2—N (#47-N) |
| 8 | 149 | Mja_IF2—C (#47-C) |
| 9 | 150 | Mja_Pol1—N (#50-N) |
| 10 | 151 | Mja_Pol1-C (#50-C) |
| 11 | 152 | Pab_CDC211—N (#79-N) |
| 12 | 153 | Pab_CDC211—C (#79-C) |
| 13 | 154 | Pab_IF2—N (#81-N) |
| 14 | 155 | Pab_IF2—C (#81-C) |
| 15 | 156 | Pab_VMA-N (#92-N) |
| 16 | 157 | Pab_VMA-C (#92-C) |
| 17 | 158 | Pho_IF2—N (#103-N) |
| 18 | 159 | Pho_IF2-C (#103-C) |
| 19 | 160 | Pho_VMA-N (#110-N) |
| 20 | 161 | Pho_VMA-C (#110-C) |
| 21 | 162 | Rma_DnaB—N (#116-N) |
| 22 | 163 | Rma_DnaB—C (#116-C) |
| 23 | 164 | Sru_DnaB-N (#123-N) |
| 24 | 165 | Sru_DnaB-C (#123-C) |
| 25 | 166 | Tag_Pol1Tsp-TYPol1—N (#128-N) |
| 26 | 167 | Tag_Pol1Tsp-TYPol1—C (#128-C) |
| 27 | 168 | Ter_RIR14—N (#135-N) |
| 28 | 169 | Ter_RIR14—C (#135-C) |
| 29 | 170 | Tko_IF2—N (#143-N) |
| 30 | 171 | Tko_IF2—C (#143-C) |
| 31 | 172 | Tth-HB27DnaE2—N (#150-N) |
| 32 | 173 | Tth-HB27DnaE2—C (#150-C) |
| 187 | 186 | gp41-1N |
| 189 | 188 | gp41-1C |
| 191 | 190 | gp41-C[MTT] |
| 193 | 192 | Ssp DnaE-N |
| 195 | 194 | Ssp DnaE-C |

Tag- and Catcher Domains.

Tag- and catcher-domain can create covalent bonds between the protein's termini and are used to help in refolding of the protein following exposure to high temperatures. The sequences of the tag- and catcher domains are shown in Table 2 as follows.

TABLE 2

Sequences of the Tag-Catcher Domains

| SEQ ID NO Amino Acid | SEQ ID NO Nucleic Acid | SEQUENCE DESCRIPTION |
|---|---|---|
| 33 | 174 | Phy_tag1-N |
| 34 | 175 | Phy_tag1-C |
| 35 | 176 | Phy_catcher1-N |
| 36 | 177 | Phy_catcher1-C |

Coiled-Coil Dimerization Domains.

A set of coiled-coil domains may be used as described in Table 3 and illustrated in FIG. 3. The sequences of coiled coil domains are shown in Table 3.

TABLE 3

Sequences of the Coiled-Coil Domains

| SEQ ID NO Amino Acid | SEQ ID NO Nucleic Acid | SEQUENCE DESCRIPTION |
|---|---|---|
| 37 | 178 | cc17 N-terminal coil |
| 38 | 179 | cc17 C-terminal coil |
| 39 | 180 | cc30 N-terminal coil |
| 40 | 181 | cc30 C-terminal coil |

The coiled-coil cc17 was designed for heat stability, forms dimers at elevated temperatures, which are stable up to at least 60° C. Conversely, the coiled-coil cc30 forms dimers at temperatures <30° C. and begins to dissociate at temperatures around 50° C.

Linkers.

Linkers vary in both sequence composition and length. The sequences of the linkers are shown in Table 4.

TABLE 4

Sequences of the Linkers

| SEQ ID NO Amino Acid | SEQ ID NO Nucleic Acid | SEQUENCE DESCRIPTION |
|---|---|---|
| 41 | 120 | L33-1 linker (N-linker) |
| 42 | 121 | L33-2 linker (C-linker) |
| 43 | 122 | L38-1 linker (N-linker) |
| 44 | 123 | L38-2 linker (C-linker) |
| 45 | 124 | L46-1 linker (N-linker) |
| 46 | 125 | L46-2 linker (C-linker) |
| 47 | 182 | L55-1.1 linker (N-linker) |
| 48 | 126 | L55-1 linker (N-linker) |
| 49 | 127 | L55-2 linker (C-linker) |
| 50 | 183 | Phy_taglink |
| 51 | 184 | Phy_catcherlink |
| 199 | 198 | DPNG linker |

An engineered phytase constructed with a selection of molecular structures and with any desired linker, if necessary, that possesses increased thermal stability may be stable to pepsin digestion, as might be used in a microbial product to increase its stability in the animal, or it may be readily degraded (in less than 30 minutes, or less than 10 minutes) by pepsin to decrease its potential allergenicity.

Target Phytases.

Although any phytase can be used as the target phytase of the invention, one target phytase for expression in plants is the Phy02 phytase variant derived from *E. coli*. The *E. coli* codon optimized sequence (Phy02opt) of the enzyme, without a signal sequence, leader, or first methionine is given below.

The sequences of the target phytases are shown in Table 5.

TABLE 5

Sequences of the Target Phytases

| SEQ ID NO Amino Acid | SEQ ID NO Nucleic Acid | SEQUENCE DESCRIPTION |
|---|---|---|
| 53 | 52 | Phy02 |
| 219 | 218 | Phy02opt |

TABLE 5-continued

| Sequences of the Target Phytases | | |
|---|---|---|
| SEQ ID NO Amino Acid | SEQ ID NO Nucleic Acid | SEQUENCE DESCRIPTION |
| 54 | 185 | Nov9X |
| 56 | 55 | CQBscks |

Example 2. Creating an Engineered Phytase Using Inteins Directly Attached to the Phytase Genes encoding engineered, or cyclized, phytase molecules are constructed using standard recombinant DNA and molecular biology techniques (Ausubel, Current Methods in Molecular Biology) that are known in the art. Alternatively, fully synthetic genes can be ordered and obtained directly from the design of a specified enzyme sequence. Such synthetic DNA sequences can be obtained from a vendor, codon optimized for expression in any particular organism (microbial, plant, mammalian, et cetera), and comprising any desirable restriction sites that may facilitate cloning and expression.

The DNA sequence of the phytase (Phy02, SEQ ID NO. 52, was used as the target phytase in this example, but could be substituted by other phytases) without the signal sequence, was fused to DNA sequences encoding the trans-splicing intein portions to create a linear molecule encoding the C-intein at the amino terminus of the molecule, whose carboxy terminus was fused directly to the amino terminus of the Phy02 phytase, and with the N-intein's amino terminus fused directly to the carboxy terminus of the Phy02 phytase (C-intein:Phy02:N-intein) as described in FIG. 1. FIG. 1 illustrates an engineered phytase with a split intein attached to the ends of the phytase coding sequence (A), binding of the split intein to cyclize the phytase using non-covalent binding (B), and the form of the cyclized phytase that results following splicing of the intein and formation of a covalent bond (C). Constructs were cloned between the EcoRI and XhoI sites of the pETDuet I expression vector and transformed into the Shuffle T7 *E. coli* host (NEB). One skilled in the art would be knowledgeable of the requirements for intein splicing and would understand that an appropriate amino acid is necessary at the junction between the C-intein and amino-terminus of the target phytase to facilitate intein splicing. See Apgar et al., 2012, A predictive model of intein insertion site for use in the engineering of molecular switches. *PloS one,* 7(5), e37355; Xu, M. Q., & Perler, F. B., 1996, The mechanism of protein splicing and its modulation by mutation. *The EMBO journal,* 15(19), 5146, both of which are incorporated herein by reference as if fully set forth. Whether this single amino acid is considered a linker or as part of the target phytase, is not a critical point of differentiation in this example. In this example, the addition of the single serine amino acid at the N-terminus of the Phy02 phytase, could be considered a linker between the C-intein and target phytase with a length of one amino acid. This single amino acid serine linker can be substituted by a threonine or a cysteine. Nucleotide sequences of the constructs are listed below. Nucleotide sequences of trans-splicing C-intein and N-intein are capitalized, a splicing essential serine (agc) has been added to the N-terminus of the phytase sequences are in bold character, sequences of the Phy02 phytase are in lower case underlined characters.

> The nucleotide sequence encoding Cbu_DnaB-C:Phy02:Cbu_DnaB-N (#12 Phy02C) [Amino Acid (AA)_SEQ ID NO: 58] is as follows:

(SEQ ID NO: 57)

ATGTCGGACCTGTTCTGGGATAGGATCGTGTCGATTGAGGAGAAGGGGTC

TGAGGAGGTCTACGATCTCACAGTTCCAAAGTACGCTTCTTGGCTCGCGG

ATGGGGTTGTTTCACATAATagcgcccaatcggaaccggaactgaaactg gaaagtgtggttattgtgtctcgtcatggcgttcgcgctccgaccaaatt tacgcagctgatgcaagatgtcaccccggacgccttctatacgtggccgg tgaagctgggtgaactgaccccgcgtggcggtgaactgatcgcctatctg ggtcactactggcgtcagcgcctggtggcagatggtctgctgccgaaaaa gggctgcccgcagagcggtcaagttgcaattatcgctgatgtcgacgaac gtacccgcaaaacgggtgaagcatttgcggccggtctggcaccggattgc gccattaccgttcatacgcaggcagataccagctctccggacccgctgtt caacccgctgaaaaccggcgtctgtcagctggatgtcgcgcaagtgacgg acgccattctggaacgtgcaggcggttccatcgctgattttaccggtcac taccagacggcattccgtgaactggaacgcgttctgaactttccgcagtc aaatctggcgctgaaacgcgaaaagcaggatgaaagtgcgtccctgaccc aagccctgccgagtgaactgaaagtctccgccgacaatgtgtcactgacc ggcgcatggtcactggcttcgatgctgacggaaatttttctgctgcagca agcacagggtatgccggaaccgggttggggtcgtatcaccgattcgcatc agtggaacacgctgctgagcctgcacaatgcgcagttcgacctgctgcaa cgtaccccggaagtggcacgttcgcgcgccacgccgctgctggatctgat taaaaccgctctgacgccgcatccgccgcagaagcaagcgtatggcgtga ccctgccgacgagcgttctgtttatcgcgggtcacgacaccaacctggca aatctgggcggtgctctggaactgcagtggaccctgccgggtcaaccgga taacacgccgccgggcggtgaactggttttcgaacgttggcgtcgcctga gcgacaattctcagtggatccaagttagcctggtctttcagaccctgcag caaatgcgcgataaaaccccgctgttcctgaacacgccgccgggcgaagt gaagctgaccctggcgggttgcgaagaacgtaacgcccagggcatgtgtt ctctggcaggttttacccagattgttaatgaagcacgcatcccggcttgt agtctgTGCGTGACAGGGGACACTCTCATCTGCCTCGCTGACGGGCGCCG

CGTTCCTATTCAGGATCTCGTGGGGCATTCGCCGGAGGTTATTGCGGTCG

ACGATAAGGGCCGCCTCGTTTGCGCTAAGTCAGAGGTCATCTGGAAGGTC

GGCGAGCGGTCCGTTTTCGAGATCAAGCTGGCTTCCGGGAGGAGCATTAA

GGCTACCGCTGAGCACAGGCTCCTGGCGTTCAAGGGCTGGAGGCATGTTA

AGGACTTCAAAGTGGGGGATAGGCTCGCTATTGCTCACTAA

> The nucleotide sequence encoding Mja_GF6P-C:Phy02: Mja_GF6P-N (#44 Phy02C) [AA_SEQ ID NO: 60] is as follows:

(SEQ ID NO: 59)
ATGGCGGATATCGTTTGGACGAAGTTCAAGATTGAGGAGGTGGAGAGCGA
TGTTGAGTATGTGTACGATCTGGAGGTGGAGGACTACCACAACTTCATTG
GCAATCTCATCATCAACCACAACagcgcccaatcggaaccggaactgaaa
ctggaaagtgtggttattgtgtctcgtcatggcgttcgcgctccgaccaa
atttacgcagctgatgcaagatgtcaccccggacgccttctatacgtggc
cggtgaagctgggtgaactgaccccgcgtggcggtgaactgatcgcctat
ctgggtcactactggcgtcagcgcctggtggcagatggtctgctgccgaa
aaagggctgcccgcagagcggtcaagttgcaattatcgctgatgtcgacg
aacgtacccgcaaaacgggtgaagcatttgcggccggtctggcaccggat
tgcgccattaccgttcatacgcaggcagataccagctctccggacccgct
gttcaacccgctgaaaaccggcgtctgtcagctggatgtcgcgcaagtga
cggacgccattctggaacgtgcaggcggttccatcgctgattttaccggt
cactaccagacggcattccgtgaactggaacgcgttctgaactttccgca
gtcaaatctggcgctgaaacgcgaaaagcaggatgaaagtgcgtccctga
cccaagccctgccgagtgaactgaaagtctccgccgacaatgtgtcactg
accggcgcatggtcactggcttcgatgctgacggaaatttttctgctgca
gcaagcacagggtatgccggaaccgggttggggtcgtatcaccgattcgc
atcagtggaacacgctgctgagcctgcacaatgcgcagttcgacctgctg
caacgtaccccggaagtggcacgttcgcgcgccacgccgctgctggatct
gattaaaaccgctctgacgccgcatccgccgcagaagcaagcgtatggcg
tgaccctgccgacgagcgttctgtttatcgcgggtcacgacaccaacctg
gcaaatctgggcggtgctctggaactgcagtggaccctgccgggtcaacc
ggataacacgccgccgggcggtgaactggttttcgaacgttggcgtcgcc
tgagcgacaattctcagtggatccaagttagcctggtctttcagaccctg
cagcaaatgcgcgataaaaccccgctgttcctgaacacgccgccgggcga
agtgaagctgaccctggcgggttgcgaagaacgtaacgcccagggcatgt
gttctctggcaggttttacccagattgttaatgaagcacgcatcccggct
tgtagtctgTGCCTGCACCCTGACACATACGTTATTCTCCCTGACGGGCG
CATGAAGAAGATTTCGGAGATTGATGAGGATGAGGTTCTCTCAGTCAACT
TCGAGGACCTGAAGCTCTACAATAAGAAGATCAAGAAGTTCAAGCACAAG
GCTCCGAAGATCCTCTACAAGATTAAGACCGCGTTCTCCGAGCTCATCAC
CACGGGCGAGCATAAGCTGTTCGTGGTCGAGAACGGGAAGATCGTCGAGA
AGTGCGTTAAGGACCTCAATGGCAGCGAGCTGATCGGGGTTGTGAGGTAA > The nucleotide sequence encoding Mja_Hyp1S-N:Phy02: Mja_Hyp1S-C (#46 Phy02C) [AA_SEQ ID NO: 62] is as follows:

(SEQ ID NO: 61)
ATGGGGAATTACCTGTACGCTCCCATCATTAGGATCGGCCGGGAGTACTA
CGACGGGTTCGTCTACAATCTGGAGGTGGAGGATGACTCTTCATACGTTA
CAGTCTCAGGCACTCTGCACAACagcgcccaatcggaaccggaactgaaa
ctggaaagtgtggttattgtgtctcgtcatggcgttcgcgctccgaccaa
atttacgcagctgatgcaagatgtcaccccggacgccttctatacgtggc
cggtgaagctgggtgaactgaccccgcgtggcggtgaactgatcgcctat
ctgggtcactactggcgtcagcgcctggtggcagatggtctgctgccgaa
aaagggctgcccgcagagcggtcaagttgcaattatcgctgatgtcgacg
aacgtacccgcaaaacgggtgaagcatttgcggccggtctggcaccggat
tgcgccattaccgttcatacgcaggcagataccagctctccggacccgct
gttcaacccgctgaaaaccggcgtctgtcagctggatgtcgcgcaagtga
cggacgccattctggaacgtgcaggcggttccatcgctgattttaccggt
cactaccagacggcattccgtgaactggaacgcgttctgaactttccgca
gtcaaatctggcgctgaaacgcgaaaagcaggatgaaagtgcgtccctga
cccaagccctgccgagtgaactgaaagtctccgccgacaatgtgtcactg
accggcgcatggtcactggcttcgatgctgacggaaatttttctgctgca
gcaagcacagggtatgccggaaccgggttggggtcgtatcaccgattcgc
atcagtggaacacgctgctgagcctgcacaatgcgcagttcgacctgctg
caacgtaccccggaagtggcacgttcgcgcgccacgccgctgctggatct
gattaaaaccgctctgacgccgcatccgccgcagaagcaagcgtatggcg
tgaccctgccgacgagcgttctgtttatcgcgggtcacgacaccaacctg
gcaaatctgggcggtgctctggaactgcagtggaccctgccgggtcaacc
ggataacacgccgccgggcggtgaactggttttcgaacgttggcgtcgcc
tgagcgacaattctcagtggatccaagttagcctggtctttcagaccctg
cagcaaatgcgcgataaaaccccgctgttcctgaacacgccgccgggcga
agtgaagctgaccctggcgggttgcgaagaacgtaacgcccagggcatgt
gttctctggcaggttttacccagattgttaatgaagcacgcatcccggct
tgtagtctgTGCGTTCCGCCTGACACTCTGCTCATCCTGGAGAATGGGTT
CAAGCGCATCGTGGACATTAAGGTCGGGGACAAGGTCCTGACGCACGAGA
ACCGGTTCAAGAAGGTTGAGAAGGTGTACAAGCGCAGGTACATCGGCGAC
ATCATTAAGATTAAGGTGCGCTACTTCCCAGAGGAGATCATTCTCACCCC
AGAGCACCCTGTCTACGCTATCAAGACGGAGAAGAGGTGCGATGGCTCTC
ATGGGATCTGCAAGTTCAACTGCCTCACACAGTACACTAATCCTTCATGC
AAGAAGCGGTACCGCAAGTACAAGAGGGAGTGGATCATTGCCAAGGACCT
GAAGGTCGGCGATGTGATCGTCTACCCGATTCCCAACTAA > The nucleotide sequence encoding Mja_IF2-N:Phy02: Mja_IF2-C (#47 Phy02C) [AA_SEQ ID NO: 64] is as follows:

(SEQ ID NO: 63)
ATGAACATTGCGTTCGTCGAGGTTGAGGATGTCGAGATCATTGACTACGA
TGGCTACGTTTACGATCTCACAACAGAGACTCATAACTTCATTGCTAATG

-continued

GCATCGTGGTTCATAATagcgcccaatcggaaccggaactgaaactggaaagtgtggttattgtgtctcgtcatggcgttcgcgctccgaccaaatttacgcagctgatgcaagatgtcaccccggacgccttctatacgtggcggtgaagctgggtgaactgaccccgcgtggcggtgaactgatcgcctatctgggtcactactggcgtcagcgcctggtggcagatggtctgctgccgaaaaagggctgcccgcagagcggtcaagttgcaattatcgctgatgtcgacgaacgtacccgcaaaacgggtgaagcatttgcggccggtctggcaccggattgcgccattaccgttcatacgcaggcagataccagctctccggacccgctgttcaacccgctgaaaaccggcgtctgtcagctggatgtcgcgcaagtgacggacgccattctggaacgtgcaggcggttccatcgctgattttaccggtcactaccagacggcattccgtgaactggaacgcgttctgaactttccgcagtcaaatctggcgctgaaacgcgaaaagcaggatgaaagtgcgtccctgacccaagccctgccgagtgaactgaaagtctccgccgacaatgtgtcactgaccggcgcatggtcactggcttcgatgctgacggaaatttttctgctgcagcaagcacagggtatgccggaaccgggttggggtcgtatcaccgattcgcatcagtggaacacgctgctgagcctgcacaatgcgcagttcgacctgctgcaacgtaccccggaagtggcacgttcgcgcgccacgccgctgctggatctgattaaaaccgctctgacgccgcatccgccgcagaagcaagcgtatggcgtgaccctgccgacgagcgttctgtttatcgcgggtcacgacaccaacctggcaaatctgggcggtgctctggaactgcagtggaccctgccgggtcaaccggataacacgccgccgggcggtgaactggttttcgaacgttggcgtcgcctgagcgacaattctcagtggatccaagttagcctggtctttcagaccctgcagcaaatgcgcgataaaaccccgctgttcctgaacacgccgccgggcgaagtgaagctgaccctggcgggttgcgaagaacgtaacgcccagggcatgtgttctctggcaggttttacccagattgttaatgaagcacgcatcccggcttgtagtctgTGCCTGATGCCGCATGAGAAGGTGCTGACGGAGTACGGGGAGATTAAGATTGAGGACCTGTTCAAGATCGGGAAGGAGATCGTGGAGAAGGACGAGCTCAAGGAGATCAGGAAGCTGAATATTAAGGTGCACACTCTCAACGAGAATGGCGAGATCAAGATCATTAACGCCCCATACGTGTGGAAGCTCAAGCATAAGGGGAAGATGATCAAGGTCAAGCTGAAGAACTGGCACTCGATCACCACGACACCGGAGCATCCCTTCCTGACCAACAATGGCTGGATCAAGGCGGAGAATATTAAGAAGGGGATGTATGTGGCTATCCCTCGCTAA > The nucleotide sequence encoding Mja_Pol1-C:Phy02:Mja_Pol1-N (#50 Phy02C)[AA_SE ID NO: 66] is as follows:

(SEQ ID NO: 65)

ATGTACGGGTTCTACGACCTCGACGATGTGTGCGTCTCACTGGAGTCCTACAAGGGCGAGGTGTACGATCTCACTCTGGAGGGCAGGCCTTACTACTTCGCCAATGGCATCCTCACTCATAATagcgcccaatcggaaccggaactgaaactggaaagtgtggttattgtgtctcgtcatggcgttcgcgctccgaccaaatttacgcagctgatgcaagatgtcaccccggacgccttctatacgtggccggtgaagctgggtgaactgaccccgcgtggcggtgaactgatcgcctatctgggtcactactggcgtcagcgcctggtggcagatggtctgctgccgaaaaagggctgcccgcagagcggtcaagttgcaattatcgctgatgtcgacgaacgtacccgcaaaacgggtgaagcatttgcggccggtctggcaccggattgcgccattaccgttcatacgcaggcagataccagctctccggacccgctgttcaacccgctgaaaaccggcgtctgtcagctggatgtcgcgcaagtgacggacgccattctggaacgtgcaggcggttccatcgctgattttaccggtcactaccagacggcattccgtgaactggaacgcgttctgaactttccgcagtcaaatctggcgctgaaacgcgaaaagcaggatgaaagtgcgtccctgacccaagccctgccgagtgaactgaaagtctccgccgacaatgtgtcactgaccggcgcatggtcactggcttcgatgctgacggaaatttttctgctgcagcaagcacagggtatgccggaaccgggttggggtcgtatcaccgattcgcatcagtggaacacgctgctgagcctgcacaatgcgcagttcgacctgctgcaacgtaccccggaagtggcacgttcgcgcgccacgccgctgctggatctgattaaaaccgctctgacgccgcatccgccgcagaagcaagcgtatggcgtgaccctgccgacgagcgttctgtttatcgcgggtcacgacaccaacctggcaaatctgggcggtgctctggaactgcagtggaccctgccgggtcaaccggataacacgccgccgggcggtgaactggttttcgaacgttggcgtcgcctgagcgacaattctcagtggatccaagttagcctggtctttcagaccctgcagcaaatgcgcgataaaaccccgctgttcctgaacacgccgccgggcgaagtgaagctgaccctggcgggttgcgaagaacgtaacgcccagggcatgtgttctctggcaggttttacccagattgttaatgaagcacgcatcccggcttgtagtctgTGCCATCCAAAGGGGACAAAGGTCGTGGTCAAGGGCAAGGGCATCGTGAATATTGAGGACGTTAAGGAGGGGAATTACGTTCTCGGCATCGACGGCTGGCAGAAGGTTAAGAAGGTCTGGAAGTACGAGTACGAGGGCGAGCTCATTAACGTTAATGGGCTGAAGTGCACACCGAACCACAAGATCCCCCTCCGCTACAAGATTAAGCATAAGAAGATCAACAAGAACGATTACCTGGTGAGGGACATCTACGCGAAGTCGCTCCTGACCAAGTTCAAGGGCGAGGGGAAGCTCATCCTGTGCAAGTAA > The nucleotide sequence encoding Pab_CDC211-C:Phy02:Pab_CDC211-N (#79 Phy02C) [AA_SEQ ID NO: 68] is as follows:

(SEQ ID NO: 67)

ATGTCCGTGAGCTGGGACGAGGTCGCGGAGATCCTGGAGTACGAGCCAAAGGATCCTTGGGTCTACGATCTGCAGGTTCCAGGCTACCACAACTTCCTCGCTAATGGCATCTTCGTTCATAATagcgcccaatcggaaccggaactgaaactggaaagtgtggttattgtgtctcgtcatggcgttcgcgctccgaccaaatttacgcagctgatgcaagatgtcaccccggacgccttctatacgtggccggtgaagctgggtgaactgaccccgcgtggcggtgaactgatcgcctatctgggtcactactggcgtcagcgcctggtggcagatggtctgctgccgaaaaagggctgcccgcagagcggtcaagttgcaattatcgctgatgtcgacg -continued

```
aacgtacccgcaaaacgggtgaagcatttgcggccggtctggcaccggat
tgcgccattaccgttcatacgcaggcagataccagctctccggacccgct
gttcaacccgctgaaaaccggcgtctgtcagctggatgtcgcgcaagtga
cggacgccattctggaacgtgcaggcggttccatcgctgattttaccggt
cactaccagacggcattccgtgaactggaacgcgttctgaactttccgca
gtcaaatctggcgctgaaacgcgaaaagcaggatgaaagtgcgtccctga
cccaagccctgccgagtgaactgaaagtctccgccgacaatgtgtcactg
accggcgcatggtcactggcttcgatgctgacggaaatttttctgctgca
gcaagcacagggtatgccggaaccgggttggggtcgtatcaccgattcgc
atcagtggaacacgctgctgagcctgcacaatgcgcagttcgacctgctg
caacgtaccccggaagtggcacgttcgcgcgccacgccgctgctggatct
gattaaaaccgctctgacgccgcatccgccgcagaagcaagcgtatggcg
tgaccctgccgacgagcgttctgtttatcgcgggtcacgacaccaacctg
gcaaatctgggcggtgctctggaactgcagtggaccctgccgggtcaacc
ggataacacgccgccgggcggtgaactggttttcgaacgttggcgtcgcc
tgagcgacaattctcagtggatccaagttagcctggtctttcagaccctg
cagcaaatgcgcgataaaaccccgctgttcctgaacacgccgccgggcga
agtgaagctgaccctggcgggttgcgaagaacgtaacgcccagggcatgt
gttctctggcaggttttacccagattgttaatgaagcacgcatcccggct
tgtagtctgTGCGTGGATTACGAGACTGAGGTCGTGCTGGGGAATGGGGA
GCGGAAGAAGATCGGGGAGATCGTGGAGCGGGCTATTGAGGAGGCTGAGA
AGAACGGCAAGCTCGGGCGGGTTGACGATGGCTTCTACGCTCCGATCGAC
ATTGAGGTCTACTCGCTCGATCTGGAGACCCTCAAGGTTCGGAAGGCGCG
GGCAAATATCGCGTGGAAGCGCACAGCTCCAAAGAAGATGATGCTGGTGA
AGACTAGGGGCGGGAAGCGCATTAGGGTCACCCCGACGCACCCCTTCTTC
GTTCTGGAGGAGGGCAAGGTGGCTATGAGGAAGGCCCGGGACCTGGAGGA
GGGCAACAAGATCGCCACGATTGAGTAA
```

> The nucleotide sequence encoding Pab_IF2-C:Phy02: Pab_IF2-N (#81 Phy02C) [AA_SEQ ID NO: 70] is as follows:

(SEQ ID NO: 69)

ATGACGCTGGTGTTCATCCCCGTTGAGAATGTGGAGGAGGAGGAGTACGA
CGGCTACGTTTACGATCTCACTACGGAGACTCATAACTTCATTGCTAATG
GCATCCTCGTTCATAATagcgcccaatcggaaccggaactgaaactggaa
agtgtggttattgtgtctcgtcatggcgttcgcgctccgaccaaatttac
gcagctgatgcaagatgtcaccccggacgccttctatacgtggccggtga
agctgggtgaactgaccccgcgtggcggtgaactgatcgcctatctgggt
cactactggcgtcagcgcctggtggcagatggtctgctgccgaaaaaggg
ctgcccgcagagcggtcaagttgcaattatcgctgatgtcgacgaacgta
cccgcaaaacgggtgaagcatttgcggccggtctggcaccggattgcgcc
attaccgttcatacgcaggcagataccagctctccggacccgctgttcaa

```
cccgctgaaaaccggcgtctgtcagctggatgtcgcgcaagtgacggacg
ccattctggaacgtgcaggcggttccatcgctgattttaccggtcactac
cagacggcattccgtgaactggaacgcgttctgaactttccgcagtcaaa
tctggcgctgaaacgcgaaaagcaggatgaaagtgcgtccctgacccaag
ccctgccgagtgaactgaaagtctccgccgacaatgtgtcactgaccggc
gcatggtcactggcttcgatgctgacggaaatttttctgctgcagcaagc
acagggtatgccggaaccgggttggggtcgtatcaccgattcgcatcagt
ggaacacgctgctgagcctgcacaatgcgcagttcgacctgctgcaacgt
accccggaagtggcacgttcgcgcgccacgccgctgctggatctgattaa
aaccgctctgacgccgcatccgccgcagaagcaagcgtatggcgtgaccc
tgccgacgagcgttctgtttatcgcgggtcacgacaccaacctggcaaat
ctgggcggtgctctggaactgcagtggaccctgccgggtcaaccggataa
cacgccgccgggcggtgaactggttttcgaacgttggcgtcgcctgagcg
acaattctcagtggatccaagttagcctggtctttcagaccctgcagcaa
atgcgcgataaaaccccgctgttcctgaacacgccgccgggcgaagtgaa
gctgaccctggcgggttgcgaagaacgtaacgcccagggcatgtgttctc
tggcaggttttacccagattgttaatgaagcacgcatcccggcttgtagt
ctgTGCCTCCTCCCTGATGAGAAGGTCGTGGTTCCCTCGGTCGGGTTCGT
GACACTCAAGGAGCTGTTCGAGACGGCTTCCAAGGTCGTGGAGCGCGACG
ATGAGAAGGAGATCAGGGAGCTCGACGAGCGGATTACCAGCGTTAACGGC
GATGGGAAGACGGGCCTGGTCAAGGCCTCCTACGTGTGGAAGGTTAGGCA
CAAGGGCAAGGTCATCCGGGTCAAGCTCAAGAATTGGCACGGCGTTACAG
TGACTCCGGAGCATCCCTTCCTCACCACGAAGGGGTGGAAGAGGGCTGAC
CAGCTGAGGCCAGGCGATTACGTCGCGGTTCCTAGGTAA
```

> The nucleotide sequence encoding Pab_VMVA-C:Phy02: Pab_VMVA-N (#92 Phy02C) [AA_SEQ ID NO:72] is as follows:

(SEQ ID NO: 71)

ATGACCCATGTTCTGTTCGACGAGATCGTGGAGATTCGGTACATCTCCGA
GGGCCAGGAGGTGTACGACGTTACTACGGAGACTCATAATTTCATTGGGG
GCAACATGCCTACTCTGCTCCACAACagcgcccaatcggaaccggaactg
aaactggaaagtgtggttattgtgtctcgtcatggcgttcgcgctccgac
caaatttacgcagctgatgcaagatgtcaccccggacgccttctatacgt
ggccggtgaagctgggtgaactgaccccgcgtggcggtgaactgatcgcc
tatctgggtcactactggcgtcagcgcctggtggcagatggtctgctgcc
gaaaaagggctgcccgcagagcggtcaagttgcaattatcgctgatgtcg
acgaacgtacccgcaaaacgggtgaagcatttgcggccggtctggcaccg
gattgcgccattaccgttcatacgcaggcagataccagctctccggaccc
gctgttcaacccgctgaaaaccggcgtctgtcagctggatgtcgcgcaag
tgacggacgccattctggaacgtgcaggcggttccatcgctgattttacc
ggtcactaccagacggcattccgtgaactggaacgcgttctgaactttcc -continued gcagtcaaatctggcgctgaaacgcgaaaagcaggatgaaagtgcgtccc tgacccaagccctgccgagtgaactgaaagtctccgccgacaatgtgtca ctgaccggcgcatggtcactggcttcgatgctgacggaaatttttctgct gcagcaagcacagggtatgccggaaccgggttggggtcgtatcaccgatt cgcatcagtggaacacgctgctgagcctgcacaatgcgcagttcgacctg ctgcaacgtaccccggaagtggcacgttcgcgcgccacgccgctgctgga tctgattaaaaccgctctgacgccgcatccgccgcagaagcaagcgtatg gcgtgaccctgccgacgagcgttctgtttatcgcgggtcacgacaccaac ctggcaaatctgggcggtgctctggaactgcagtggaccctgccgggtca accggataacacgccgccgggcggtgaactggttttcgaacgttggcgtc gcctgagcgacaattctcagtggatccaagttagcctggtctttcagacc ctgcagcaaatgcgcgataaaaccccgctgttcctgaacacgccgccggg cgaagtgaagctgaccctggcgggttgcgaagaacgtaacgcccagggca tgtgttctctggcaggttttacccagattgttaatgaagcacgcatcccg gcttgtagtctgTGCGTGGACGGGGACACTCTCGTGCTGACAAAGGAGTT

CGGGCTCATCAAGATCAAGGACCTCTACAAGATTCTGGACGGCAAGGGGA

AGAAGACAGTGAACGGCAATGAGGAGTGGACAGAGCTGGAGAGGCCAATC

ACTCTGTACGGCTACAAGGACGGGAAGATCGTCGAGATTAAGGCTACCCA

CGTTTACAAGGGCTTCTCCGCCGGGATGATCGAGATTCGGACCCGCACGG

GCCGCAAGATTAAGGTCACGCCCATCCATAAGCTCTTCACAGGCAGGGTT

ACTAAGAATGGGCTGGAGATCCGGGAGGTCATGGCCAAGGACCTCAAGAA

GGGCGATCGGATCATTGTGGCGAAGTAA

> The nucleotide sequence encoding Pho_IF2-C:Phy02: Pho_IF2-N (#103 Phy02C)[AA_SEQ ID NO: 74] is as follows:

(SEQ ID NO: 73)

ATGAACTTCGTTTTCCTGCCGGTGGAGAAGATCGAGGAGTTCGAGTACGA

TGGCTACGTCTACGACGTTACTACAGAGACTCATAATTTCATTGCTAATG

GCATCCTCGTTCATAATagcgcccaatcggaaccggaactgaaactggaa agtgtggttattgtgtctcgtcatggcgttcgcgctccgaccaaatttac gcagctgatgcaagatgtcaccccggacgccttctatacgtggccggtga agctgggtgaactgaccccgcgtggcggtgaactgatcgcctatctgggt cactactggcgtcagcgcctggtggcagatggtctgctgccgaaaaaggg ctgcccgcagagcggtcaagttgcaattatcgctgatgtcgacgaacgta cccgcaaaacgggtgaagcatttgcggccggtctggcaccggattgcgcc attaccgttcatacgcaggcagataccagctctccggacccgctgttcaa cccgctgaaaaccggcgtctgtcagctggatgtcgcgcaagtgacggacg ccattctggaacgtgcaggcggttccatcgctgattttaccggtcactac cagacggcattccgtgaactggaacgcgttctgaactttccgcagtcaaa tctggcgctgaaacgcgaaaagcaggatgaaagtgcgtccctgacccaag ccctgccgagtgaactgaaagtctccgccgacaatgtgtcactgaccggc -continued gcatggtcactggcttcgatgctgacggaaatttttctgctgcagcaagc acagggtatgccggaaccgggttggggtcgtatcaccgattcgcatcagt ggaacacgctgctgagcctgcacaatgcgcagttcgacctgctgcaacgt accccggaagtggcacgttcgcgcgccacgccgctgctggatctgattaa aaccgctctgacgccgcatccgccgcagaagcaagcgtatggcgtgaccc tgccgacgagcgttctgtttatcgcgggtcacgacaccaacctggcaaat ctgggcggtgctctggaactgcagtggaccctgccgggtcaaccggataa cacgccgccgggcggtgaactggttttcgaacgttggcgtcgcctgagcg acaattctcagtggatccaagttagcctggtctttcagaccctgcagcaa atgcgcgataaaaccccgctgttcctgaacacgccgccgggcgaagtgaa gctgaccctggcgggttgcgaagaacgtaacgcccagggcatgtgttctc tggcaggttttacccagattgttaatgaagcacgcatcccggcttgtagt ctgTGCCTGCTGCCGGAGGAGCGGGTTATTCTGCCTGACTACGGGCCTAT

TACTCTGGAGGAGCTCTTCAATATGACAAAGGAGACAGTGTTCAAGGACG

AGGAGAAGGAGGTCCGGAAGCTCGGCATCCGCATGCCAGTGGCTGGCGTC

GATGGGCGGGTGCGCCTGCTGGAGGGCCCCTACGTTTGGAAGGTGCGCTA

CAAGGGGAAGATGCTCAGGGTCAAGCTGAAGGACTGGCACAGCGTGGCTG

TCACACCAGAGCATCCCTTCCTCACCACGCGGGGCTGGGTGCGCGCTGAC

CAGCTGAAGCCCGGGGATTACGTTGCCGTGCCAAAGTAA

> The nucleotide sequence encoding Pho_VMVA-C:Phy02: Pho_VMVA-N (#110 Phy02C) [AA_SEQ ID NO: 76] is as follows:

(SEQ ID NO: 75)

ATGCAGCATATCATTTTCGACGAGGTCATCGATGTCAGGTACATTCCGGA

GCCCCAGGAGGTGTACGATGTTACTACAGAGACTCATAATTTCGTGGGGG

GCAACATGCCAACTCTGCTCCACAATagcgcccaatcggaaccggaactg aaactggaaagtgtggttattgtgtctcgtcatggcgttcgcgctccgac caaatttacgcagctgatgcaagatgtcaccccggacgccttctatacgt ggccggtgaagctgggtgaactgaccccgcgtggcggtgaactgatcgcc tatctgggtcactactggcgtcagcgcctggtggcagatggtctgctgcc gaaaaagggctgcccgcagagcggtcaagttgcaattatcgctgatgtcg acgaacgtacccgcaaaacgggtgaagcatttgcggccggtctggcaccg gattgcgccattaccgttcatacgcaggcagataccagctctccggaccc gctgttcaacccgctgaaaaccggcgtctgtcagctggatgtcgcgcaag tgacggacgccattctggaacgtgcaggcggttccatcgctgattttacc ggtcactaccagacggcattccgtgaactggaacgcgttctgaactttcc gcagtcaaatctggcgctgaaacgcgaaaagcaggatgaaagtgcgtccc tgacccaagccctgccgagtgaactgaaagtctccgccgacaatgtgtca ctgaccggcgcatggtcactggcttcgatgctgacggaaatttttctgct gcagcaagcacagggtatgccggaaccgggttggggtcgtatcaccgatt cgcatcagtggaacacgctgctgagcctgcacaatgcgcagttcgacctg -continued ctgcaacgtaccccggaagtggcacgttcgcgcgccacgccgctgctgga
tctgattaaaaccgctctgacgccgcatccgccgcagaagcaagcgtatg
gcgtgaccctgccgacgagcgttctgtttatcgcgggtcacgacaccaac
ctggcaaatctgggcggtgctctggaactgcagtggaccctgccgggtca
accggataacacgccgccgggcggtgaactggttttcgaacgttggcgtc
gcctgagcgacaattctcagtggatccaagttagcctggtctttcagacc
ctgcagcaaatgcgcgataaaaccccgctgttcctgaacacgccgccggg
cgaagtgaagctgaccctggcgggttgcgaagaacgtaacgcccagggca
tgtgttctctggcaggttttacccagattgttaatgaagcacgcatcccg
gcttgtagtctgTGCGTGGACGGGGACACACTGGTGCTGACAAAGGAGTT
CGGGCTCATCAAGATCAAGGAGCTCTACGAGAAGCTGGACGGCAAGGGGC
GCAAGATTGTGGAGGGCAACGAGGAGTGGACCGAGCTGGAGAAGCCAATC
ACGGTCTACGGCTACAAGGACGGGAAGATCGTTGAGATTAAGGCCACCCA
CGTTTACAAGGGCGTGTCCAGCGGGATGGTCGAGATCAGGACCCGGACGG
GCCGGAAGATCAAGGTGACGCCGATTCACCGCCTGTTCACAGGCAGGGTC
ACTAAGGACGGGCTGATCCTCAAGGAGGTCATGGCTATGCATGTTAAGCC
CGGCGATAGGATCGCCGTGGTCAAGTAA > The nucleotide sequence encoding Rma_DnaB-C:Phy02: Rma_DnaB-N (#116 Phy02C) [AA_SEQ ID NO:78] is as follows:

(SEQ ID NO: 77)

ATGTCAGACGTCTACTGGGATCCGATCGTTTCCATTGAGCCCGACGGCGT
TGAGGAGGTGTTCGATCTCACTGTTCCAGGGCCACATAACTTCGTTGCTA
ATGACATCATTGCTCATAATagcgcccaatcggaaccggaactgaaactg
gaaagtgtggttattgtgtctcgtcatggcgttcgcgctccgaccaaatt
tacgcagctgatgcaagatgtcaccccggacgccttctatacgtggccgg
tgaagctgggtgaactgaccccgcgtggcggtgaactgatcgcctatctg
ggtcactactggcgtcagcgcctggtggcagatggtctgctgccgaaaaa
gggctgcccgcagagcggtcaagttgcaattatcgctgatgtcgacgaac
gtacccgcaaaacgggtgaagcatttgcggccggtctggcaccggattgc
gccattaccgttcatacgcaggcagataccagctctccggacccgctgtt
caacccgctgaaaaccggcgtctgtcagctggatgtcgcgcaagtgacgg
acgccattctggaacgtgcaggcggttccatcgctgattttaccggtcac
taccagacggcattccgtgaactggaacgcgttctgaactttccgcagtc
aaatctggcgctgaaacgcgaaaagcaggatgaaagtgcgtccctgaccc
aagccctgccgagtgaactgaaagtctccgccgacaatgtgtcactgacc
ggcgcatggtcactggcttcgatgctgacggaaatttttctgctgcagca
agcacagggtatgccggaaccgggttggggtcgtatcaccgattcgcatc
agtggaacacgctgctgagcctgcacaatgcgcagttcgacctgctgcaa
cgtaccccggaagtggcacgttcgcgcgccacgccgctgctggatctgat
taaaaccgctctgacgccgcatccgccgcagaagcaagcgtatggcgtga
ccctgccgacgagcgttctgtttatcgcgggtcacgacaccaacctggca
aatctgggcggtgctctggaactgcagtggaccctgccgggtcaaccgga
taacacgccgccgggcggtgaactggttttcgaacgttggcgtcgcctga
gcgacaattctcagtggatccaagttagcctggtctttcagaccctgcag
caaatgcgcgataaaaccccgctgttcctgaacacgccgccgggcgaagt
gaagctgaccctggcgggttgcgaagaacgtaacgcccagggcatgtgtt
ctctggcaggttttacccagattgttaatgaagcacgcatcccggcttgt
agtctgTGCCTCGCGGGGGACACTCTCATTACACTGGCTGACGGGCGGCG
GGTTCCTATTCGGGAGCTGGTCTCGCAGCAGAATTTCTCGGTCTGGGCGC
TGAACCCGCAGACGTACAGGCTGGAGAGGGCTCGGGTCTCCCGGGCCTTC
TGCACAGGCATCAAGCCCGTTTACAGGCTGACCACGAGGCTCGGGAGGAG
CATTAGGGCTACTGCTAATCACCGCTTCCTGACCCCACAGGGCTGGAAGA
GGGTGGACGAGCTCCAGCCTGGGGATTACCTGGCTCTCCCAAGGTAA > The nucleotide sequence encoding Sru_DnaB-C:Phy02: Sru_DnaB-N (#123 Phy02C) [AA_SEQ ID NO: 80] is as follows:

(SEQ ID NO: 79)

ATGTGGCGGATGACCGGCATCGATGTCGAGCCCGACGGCGTTGGGGATTA
CTTCGGCTTCACTCTGGATGGCAATGGGCGCTTCCTCCTCGGGGATGGCA
CTGTTACTCATAATagcgcccaatcggaaccggaactgaaactggaaagt
gtggttattgtgtctcgtcatggcgttcgcgctccgaccaaatttacgca
gctgatgcaagatgtcaccccggacgccttctatacgtggccggtgaagc
tgggtgaactgaccccgcgtggcggtgaactgatcgcctatctgggtcac
tactggcgtcagcgcctggtggcagatggtctgctgccgaaaaagggctg
cccgcagagcggtcaagttgcaattatcgctgatgtcgacgaacgtaccc
gcaaaacgggtgaagcatttgcggccggtctggcaccggattgcgccatt
accgttcatacgcaggcagataccagctctccggacccgctgttcaaccc
gctgaaaaccggcgtctgtcagctggatgtcgcgcaagtgacggacgcca
ttctggaacgtgcaggcggttccatcgctgattttaccggtcactaccag
acggcattccgtgaactggaacgcgttctgaactttccgcagtcaaatct
ggcgctgaaacgcgaaaagcaggatgaaagtgcgtccctgacccaagccc
tgccgagtgaactgaaagtctccgccgacaatgtgtcactgaccggcgca
tggtcactggcttcgatgctgacggaaatttttctgctgcagcaagcaca
gggtatgccggaaccgggttggggtcgtatcaccgattcgcatcagtgga
acacgctgctgagcctgcacaatgcgcagttcgacctgctgcaacgtacc
ccggaagtggcacgttcgcgcgccacgccgctgctggatctgattaaaac
cgctctgacgccgcatccgccgcagaagcaagcgtatggcgtgaccctgc
cgacgagcgttctgtttatcgcgggtcacgacaccaacctggcaaatctg
ggcggtgctctggaactgcagtggaccctgccgggtcaaccggataacac
gccgccgggcggtgaactggttttcgaacgttggcgtcgcctgagcgaca
attctcagtggatccaagttagcctggtctttcagaccctgcagcaaatg -continued cgcgataaaaccccgctgttcctgaacacgccgccgggcgaagtgaagct gaccctggcgggttgcgaagaacgtaacgcccagggcatgtgttctctgg caggttttacccagattgttaatgaagcacgcatcccggcttgtagtctg

TGCCTCGGGAAGGGGACACCGGTTATGATGTACGATGGGCGGACAAAGCC

AGTGGAGAAGGTGGAGGTCGGGGACAGGCTCATGGGGGACGATGGCAGCC

CAAGGACGGTGCAGTCGCTGGCCAGGGGGAGGGAGCAGATGTACTGGGTC

CGCCAGAAGAGGGGCATGGACTACAGGGTTAACGAGAGCCACATCCTCTC

GCTGAAGAAGTCTAGGAGGGAGGGCGCCCGCGACAGGGGGTCAATCGCGG

ATATTTCCGTCCGCGACTAA

> The nucleotide sequence encodingTag_Pol1_TspTYPol1-C:Phy02: Tag_Pol1_TspTYPol1-N (#128 Phy02C) [AA_SEQ ID NO: 82] is as follows:

(SEQ ID NO: 81)

ATGAATTCTTTCTACAATCTGTCAACCTTCGAGGTGTCATCCGAGTACTA

CAAGGGCGAGGTCTACGATCTCACTCTGGAGGGCAATCCTTACTACTTCG

CCAATGGCATCCTCACACATAATagcgcccaatcggaaccggaactgaaa ctggaaagtgtggttattgtgtctcgtcatggcgttcgcgctccgaccaa atttacgcagctgatgcaagatgtcaccccggacgccttctatacgtggc cggtgaagctgggtgaactgaccccgcgtggcggtgaactgatcgcctat ctgggtcactactggcgtcagcgcctggtggcagatggtctgctgccgaa aaagggctgcccgcagagcggtcaagttgcaattatcgctgatgtcgacg aacgtacccgcaaaacgggtgaagcatttgcggccggtctggcaccggat tgcgccattaccgttcatacgcaggcagataccagctctccggacccgct gttcaacccgctgaaaaccggcgtctgtcagctggatgtcgcgcaagtga cggacgccattctggaacgtgcaggcggttccatcgctgattttaccggt cactaccagacggcattccgtgaactggaacgcgttctgaactttccgca gtcaaatctggcgctgaaacgcgaaaagcaggatgaaagtgcgtccctga cccaagccctgccgagtgaactgaaagtctccgccgacaatgtgtcactg accggcgcatggtcactggcttcgatgctgacggaaatttttctgctgca gcaagcacagggtatgccggaaccgggttggggtcgtatcaccgattcgc atcagtggaacacgctgctgagcctgcacaatgcgcagttcgacctgctg caacgtaccccggaagtggcacgttcgcgcgccacgccgctgctggatct gattaaaaccgctctgacgccgcatccgccgcagaagcaagcgtatggcg tgaccctgccgacgagcgttctgtttatcgcgggtcacgacaccaacctg gcaaatctgggcggtgctctggaactgcagtggaccctgccgggtcaacc ggataacacgccgccgggcggtgaactggttttcgaacgttggcgtcgcc tgagcgacaattctcagtggatccaagttagcctggtctttcagaccctg cagcaaatgcgcgataaaaccccgctgttcctgaacacgccgccgggcga agtgaagctgaccctggcgggttgcgaagaacgtaacgcccagggcatgt gttctctggcaggttttacccagattgttaatgaagcacgcatcccggct tgtagtctgTGCCATCCTGCGGACACTAAGGTCATCGTGAAGGGCAAGGG -continued

CATCGTTAATATCTCGGACGTGAAGGAGGGGGACTACATTCTCGGCATCG

ACGGCTGGCAGCGGGTCAAGAAGGTTTGGAAGTACCACTACGAGGGCAAG

CTCATCAACATTAATGGGCTGAAGTGCACGCCGAACCATAAGGTTCCCGT

GGTCACAGAGAATGACAGGCAGACTCGCATCAGGGATTCCCTCGCCAAGA

GCTTCCTGTCGGGCAAGGTCAAGGGGAAGATCATTACCACGAAGTAA

> The nucleotide sequence encoding Ter_RIR14-C:Phy02: Ter_RIR4-N (#135 Phy02C) [AA_SEQ ID NO: 84] is as follows:

(SEQ ID NO: 83)

ATGTCGAAGTGCGTCCTCAACTACTCGCCCTACAAGATCGAGTCTGTTAA

TATTGGCGCTGTGTGCGACTACAGCTACGATTTCGCCATCGAGGGCATCA

ATGATAATGACTCTTGGTACTGGCAGGGGGCTCTCAAGTCTCACAACagc gcccaatcggaaccggaactgaaactggaaagtgtggttattgtgtctcg tcatggcgttcgcgctccgaccaaatttacgcagctgatgcaagatgtca ccccggacgccttctatacgtggccggtgaagctgggtgaactgaccccg cgtggcggtgaactgatcgcctatctgggtcactactggcgtcagcgcct ggtggcagatggtctgctgccgaaaaagggctgcccgcagagcggtcaag ttgcaattatcgctgatgtcgacgaacgtacccgcaaaacgggtgaagca tttgcggccggtctggcaccggattgcgccattaccgttcatacgcaggc agataccagctctccggacccgctgttcaacccgctgaaaaccggcgtct gtcagctggatgtcgcgcaagtgacggacgccattctggaacgtgcaggc ggttccatcgctgattttaccggtcactaccagacggcattccgtgaact ggaacgcgttctgaactttccgcagtcaaatctggcgctgaaacgcgaaa agcaggatgaaagtgcgtccctgacccaagccctgccgagtgaactgaaa gtctccgccgacaatgtgtcactgaccggcgcatggtcactggcttcgat gctgacggaaatttttctgctgcagcaagcacagggtatgccggaaccgg gttggggtcgtatcaccgattcgcatcagtggaacacgctgctgagcctg cacaatgcgcagttcgacctgctgcaacgtaccccggaagtggcacgttc gcgcgccacgccgctgctggatctgattaaaaccgctctgacgccgcatc cgccgcagaagcaagcgtatggcgtgaccctgccgacgagcgttctgttt atcgcgggtcacgacaccaacctggcaaatctgggcggtgctctggaact gcagtggaccctgccgggtcaaccggataacacgccgccgggcggtgaac tggttttcgaacgttggcgtcgcctgagcgacaattctcagtggatccaa gttagcctggtctttcagaccctgcagcaaatgcgcgataaaaccccgct gttcctgaacacgccgccgggcgaagtgaagctgaccctggcgggttgcg aagaacgtaacgcccagggcatgtgttctctggcaggttttacccagatt gttaatgaagcacgcatcccggcttgtagtctgTGCCTGGACAAGACGGC

TCTGCGGATTTTCAATCAGGGGCTGCTCTACGCGGATGAGGTCGTGACAC

CGGGCTCGGGGGAGACAGTCGGCCTCGGGCTGACGGTCAGGAACGGCATC

GGGGCGTCCACAGCCATTGCGAATCAGCCGATGGAGCTGGTTGAGATCAA

GCTCGCTAACGGCCGGAAGCTGCGCATGACCCCTAATCACCGGATGTCCG

-continued

TGAAGGGCAAGTGGATTCATGCCTGCAACCTCAAGCCGGGGATGCTCCTG

GACTACAGCATCGGCGAGTACCAGAAGCGCGAGGACACCCTCCTGATTCC

TCTCTAA

> The nucleotide sequence encoding Tko_IF2-C:Phy02: Tko_IF-N (#143 Phy02C) [AA_SEQID NO: 86] is as follows:

(SEQ ID NO: 85)

ATGAATCTCGTCTTCATCCCGGTTGAGGACATTGAGGAGTTCGAGTACGA

GGGCTACGTTTACGACGTTACTACAGAGACTCATAATTTCGTTGCTAATG

GCATCCTCGTTCATAATagcgcccaatcggaaccggaactgaaactggaa agtgtggttattgtgtctcgtcatggcgttcgcgctccgaccaaatttac gcagctgatgcaagatgtcaccccggacgccttctatacgtggccggtga agctgggtgaactgaccccgcgtggcggtgaactgatcgcctatctgggt cactactggcgtcagcgcctggtggcagatggtctgctgccgaaaaaggg ctgcccgcagagcggtcaagttgcaattatcgctgatgtcgacgaacgta cccgcaaaacgggtgaagcatttgcggccggtctggcaccggattgcgcc attaccgttcatacgcaggcagataccagctctccggacccgctgttcaa cccgctgaaaaccggcgtctgtcagctggatgtcgcgcaagtgacggacg ccattctggaacgtgcaggcggttccatcgctgattttaccggtcactac cagacggcattccgtgaactggaacgcgttctgaactttccgcagtcaaa tctggcgctgaaacgcgaaaagcaggatgaaagtgcgtccctgacccaag ccctgccgagtgaactgaaagtctcgccgacaatgtgtcactgaccggcg catggtcactggcttcgatgctgacggaaatttttctgctgcagcaagca cagggtatgccggaaccgggttggggtcgtatcaccgattcgcatcagtg gaacacgctgctgagcctgcacaatgcgcagttcgacctgctgcaacgta ccccggaagtggcacgttcgcgcgccacgccgctgctggatctgattaaa accgctctgacgccgcatccgccgcagaagcaagcgttggcgtgaccctg ccgacgagcgttctgtttatcgcgggtcacgacaccaacctggcaaatct gggcggtgctctggaactgcagtggaccctgccgggtcaaccggataaca cgccgccgggcggtgaactggttttcgaacgttggcgtcgcctgagcgac aattctcagtggatccaagttagcctggtctttcagaccctgcagcaaat gcgcgataaaaccccgctgttcctgaacacgccgccgggcgaagtgaagc tgaccctggcgggttgcgaagaacgtaacgcccagggcatgtgttctctg gcaggttttacccagattgttaatgaagcacgcatcccggcttgtagtct gTGCCTGCTGCCGGATGAGAAGGTTATTCTCCCTGAGCATGGGCCTATTA

CACTCAAGGGGCTCTTCGATCTCGCTAAGGAGACAGTCGTGGCTGACAAC

GAGAAGGAGATCCGCAAGCTGGGCGCCAAGCTCACCATTGTGGGCGAGGA

TGGGAGGCTCAGGGTCCTGGAGAGCCCATACGTTTGGAAGGTGCGGCACC

GCGGCAAGATGCTGAGGGTCAAGCTCAAGAACTGGCACTCAGTGTCCGTC

ACGCCAGAGCATCCCTTCCTGACCACGCGGGGCTGGGTGCGCGCTGACCA

GCTCAAGCCGGGGGATTACGTTGCGGTGCCCAGGTAA

> The nucleotide sequence encoding Tth-HB27_DnaE2-C: Phy02:Tth-HB27_DnaE2-N (#150 Phy02C) [AA_SEQ ID NO: 88] is as follows:

(SEQ ID NO: 87)

ATGGCTGAGGTTTACTGGGATCGCGTCGAGGCGGTTGAGCCGCTCGGCGA

GGAGGAGGTCTTCGATCTCACTGTGGAGGGCACTCATACTTTCGTTGCGG

AGGATGTTATCGTTCATAATagcgcccaatcggaaccggaactgaaactg gaaagtgtggttattgtgtctcgtcatggcgttcgcgctccgaccaaatt tacgcagctgatgcaagatgtcaccccggacgccttctatacgtggccgg tgaagctgggtgaactgaccccgcgtggcggtgaactgatcgcctatctg ggtcactactggcgtcagcgcctggtggcagatggtctgctgccgaaaaa gggctgcccgcagagcggtcaagttgcaattatcgctgatgtcgacgaac gtacccgcaaaacgggtgaagcatttgcggccggtctggcaccggattgc gccattaccgttcatacgcaggcagataccagctctccggacccgctgtt caacccgctgaaaaccggcgtctgtcagctggatgtcgcgcaagtgacgg acgccattctggaacgtgcaggcggttccatcgctgattttaccggtcac taccagacggcattccgtgaactggaacgcgttctgaactttccgcagtc aaatctggcgctgaaacgcgaaaagcaggatgaaagtgcgtccctgaccc aagccctgccgagtgaactgaaagctccgccgacaatgtgtcactgaccg gcgcatggtcactggcttcgatgctgacggaaatttttctgctgcagcaa gcacagggtatgccggaaccgggttggggtcgtatcaccgattcgcatca gtggaacacgctgctgagcctgcacaatgcgcagttcgacctgctgcaac gtaccccggaagtggcacgttcgcgcgccacgccgctgctggatctgatt aaaaccgctctgacgccgcatccgccgcagaagcaagcgtatggcgtgac cctgccgacgagcgttctgtttatcgcgggtcacgacaccaacctggcaa atctgggcggtgctctggaactgcagtggaccctgccgggtcaaccggat aacacgccgccgggcggtgaactggttttcgaacgttggcgtcgcctgag cgacaattctcagtggatccaagttagcctggtctttcagaccctgcagc aaatgcgcgataaaaccccgctgttcctgaacacgccgccgggcgaagtg aagctgaccctggcgggttgcgaagaacgtaacgcccagggcatgtgttc tctggcaggttttacccgattgttaatgaagcacgcatcccggcttgtag tctgTGCCTGCCTGCGCGGGCTAGGGTCGTGGATTGGTGCACAGGGCGGG

TCGTTCGGGTCGGGGAGATCGTTAGGGGGGAGGCTAAGGGCGTCTGGGTG

GTCTCCCTGGACGAGGCTAGGCTGAGGCTCGTTCCAAGGCCTGTTGTGGC

TGCTTTCCCAAGCGGCAAGGCTCAGGTGTACGCTCTGAGGACCGCTACGG

GCAGGGTGCTGGAGGCGACAGCTAACCACCCAGTCTACACTCCAGAGGGC

TGGAGGCCACTGGGGACCCTCGCTCCTGGCGACTACGTCGCTCTGCCAAG

GTAA

> The nucleotide sequence encoding Ssp_DnaE-C:Phy02: Ssp_DnaE-N (#225 Phy02C) [AA_SEQ ID NO: 90] is as follow:

(SEQ ID NO: 89)

ATGGTTAAGGTGATTGGAAGACGTTCTCTTGGTGTTCAAAGGATCTTCGA
TATCGGATTGCCACAAGACCACAACTTTCTTCTCGCTAATGGTGCCATCG
CTGCCAATagcgcccaatcggaaccggaactgaaactggaaagtgtggtt
attgtgtctcgtcatggcgttcgcgctccgaccaaatttacgcagctgat
gcaagatgtcaccccggacgccttctatacgtggccggtgaagctgggtg
aactgaccccgcgtggcggtgaactgatcgcctatctgggtcactactgg
cgtcagcgcctggtggcagatggtctgcgccgaaaaagggctgcccgcag
agcggtcaagttgcaattatcgctgatgtcgacgaacgtacccgcaaaac
gggtgaagcatttgcggccggtctggcaccggattgcgccattaccgttc
atacgcaggcagataccagctctccggacccgctgttcaacccgctgaaa
accggcgtctgtcagctggatgtcgcgcaagtgacggacgccattctgga
acgtgcaggcggttccatcgctgattttaccggtcactaccagacggcat
tccgtgaactggaacgcgttctgaactttccgcagtcaaatctggcgctg
aaacgcgaaaagcaggatgaaagtgcgtccctgacccaagccctgccgag
tgaactgaaagtctccgccgacatgtgtcactgaccggcgcatggtcact
ggcttcgatgctgacggaaatttttctgctgcagcaagcacagggtatgc
cggaaccgggttggggtcgtatcaccgattcgcatcagtggaacacgctg
ctgacctgcacaatgcgcagttcgacctgctgcaacgtaccccggaagtg
gcacgttcgcgcgccacgccgctgctggatctgattaaaaccgctctgac
gccgcatccgccgcagaagcaagcgtatggcgtgaccctgccgacgagcg
ttctgtttatcgcgggtcacgacaccaacctggcaaatctgggcggtgct
ctggaactgcagtggaccctgccgggtcaaccggataacacgccgccggg
cggtgaactggttttcgaacgttggcgtcgcctgagcgacaattctcagt
ggatccaagttagcctggtctttcagaccctgcagcaaatgcgcgataaa
accccgctgttcctgaacacgccgccgggcgaagtgaagctgaccctggc
gggttgcgaagaacgtaacgcccagggcatgtgttctctggcaggtttta
cccagattgttaatgaagcacgcatcccggcttgtagtctgTGCCTTTCT
TTCGGAACTGAGATCCTTACCGTTGAGTACGGACCACTTCCTATTGGTAA
GATCGTTTCTGAGGAAATTAACTGCTCAGTGTACTCTGTTGATCCAGAAG
GAAGAGTTTACACTCAGGCTATCGCACAATGGCACGATAGGGGTGAACAA
GAGGTTCTGGAGTACGAGCTTGAAGATGGATCCGTTATTCGTGCTACCTC
TGACCATAGATTCTTGACTACAGATTATCAGCTTCTCGCTATCGAGGAAA
TCTTTGCTAGGCAACTTGATCTCCTTACTTTGGAGAACATCAAGCAGACA
GAAGAGGCTCTTGACAACCACAGACTTCCATTCCCTTTGCTCGATGCTGG
AACCATCAAGTAA > The nucleotide sequence encoding Gp411-C:Phy02:Gp411-N (#230 Phy02C) [AA_SEQ ID NO: 92] is as follows:

(SEQ ID NO: 91)

ATGATGCTGAAGAAAATTCTGAAGATCGAAGAACTGGATGAACGTGAACT
GATTGACATCGAAGTTAGCGGCAACCATCTGTTTTACGCGAATGACATTC

-continued

TGACCCACAACagcgcccaatcggaaccggaactgaaactggaaagtgtg
gttattgtgtctcgtcatggcgttcgcgctccgaccaaatttacgcagct
gatgcaagatgtcaccccggacgccttctatacgtggccggtgaagctgg
gtgaactgaccccgcgtggcggtgaactgatcgcctatctgggtcactac
tggcgtcagcgcctggtggcagatggtctgctgccgaaaaagggctgccc
gcagagcggtcaagttgcaattatcgctgatgtcgacgaacgtacccgca
aaacgggtgaagcatttgcggccggtctggcaccggattgcgccattacc
gttcatacgcaggcagataccagctctccggacccgctgttcaacccgct
gaaaaccggcgtctgtcagctggatgtcgcgcaagtgacggacgccattc
tggaacgtgcaggcggttccatcgctgattttaccggtcactaccagacg
gcattccgtgaactggaacgcgttctgaactttccgcagtcaaatctggc
gctgaaacgcgaaaagcaggatgaaagtgcgtccctgacccaagccctgc
cgagtgaactgaaagtctccgccgacaatgtgtcactgaccggcgcatgg
tcactggcttcgatgctgacggaaatttttctgctgcagcaagcacaggg
tatgccggaaccgggttggggtcgtatcaccgattcgcatcagtggaaca
cgctgctgagcctgcacaatgcgcagttcgacctgctgcaacgtaccccg
gaagtggcacgttcgcgcgccacgccgctgctggatctgattaaaaccgc
tctgacgccgcatccgccgcagaagcaagcgtatggcgtgaccctgccga
cgagcgttctgtttatcgcgggtcacgacaccaacctggcaaatctgggc
ggtgctctggaactgcagtggaccctgccgggtcaaccggataacacgcc
gccgggcggtgaactggttttcgaacgttggcgtcgcctgagcgacaatt
ctcagtggatccaagttagcctggtctttcagaccctgcagcaaatgcgc
gataaaaccccgctgttcctgaacacgccgccgggcgaagtgaagctgac
cctggcgggttgcgaagaacgtaacgcccagggcatgtgttctctggcag
gttttacccagattgttaatgaagcacgcatcccggcttgtagtctgTGT
CTGGACCTGAAAACGCAAGTGCAAACCCCGCAAGGCATGAAGGAAATCTC
AAACATCCAAGTCGGTGACCTGGTGCTGTCGAATACCGGCTATAACGAAG
TGCTGAATGTTTTTCCGAAGAGCAAAAAGAAATCTTACAAGATCACGCTG
GAAGATGGCAAGGAAATTATTTGCAGCGAAGAACATCTGTTCCCGACCCA
GACGGGCGAAATGAATATCTCCGGCGGTCTGAAAGAAGGCATGTGTCTGT
ACGTCAAGGAATAA One skilled in the art will appreciate that many variations on these sequences can be created, screened, and developed further. There are many techniques known in the art for modifying DNA sequences and the corresponding protein sequences they encode. Mutagenesis techniques that would be useful in this regard include site directed mutagenesis, saturating mutagenesis (where each amino acid is individually substituted at each position in the protein sequence, and improved variants are selected and combined), random mutagenesis, domain swapping or exchange, and others. Additionally, small deletions, or insertions, may be beneficial when optimizing the sequences for thermal stability, specific activity, host expression, gastric stability or gastric digestibility.

In this particular example, when it is desired to fuse the inteins directly to the termini of the target phytase without adding another serine amino acid, because the target phytase sequence, Phy02 (SEQ ID NO: 53), begins with AQSEPELKLE . . . (SEQ ID NO: 134), it is readily apparent that in each of the sequences provided in this example, the added serine amino acid ( . . . S . . . ) between the carboxy terminus of the C-intein ( . . . HN), and the amino terminus of the phytase (AQSEPELKLE . . . (SEQ ID NO: 134)), would not be necessary if the first two amino acids alanine and glutamine (AQ) of the phytase sequence was deleted (resulting in SEPELKLE . . . (SEQ ID NO: 135), and the first serine at the resulting amino terminus of the phytase sequence (SEPELKLE . . . (SEQ ID NO: 135)) was used as the serine to facilitate intein splicing. If it is desired to reassemble the entire target phytase sequence (including the deleted alanine and glutamine) during binding of the termini, the alanine and glutamine removed from the amino terminus of the phytase sequence, can be added to the carboxy terminus of the phytase sequence, right at the junction with the N-intein. In this way, the entire native sequence of the phytase will be reassembled following the intein splicing reaction, with no apparent rearrangement of the target phytase sequence. Likewise, even if the inteins bind to cyclize the protein, but do not splice, the added alanine and glutamine will be in a position spatially similar to where it would have been had it been left at the amino terminus of the phytase following binding of the termini.

This technique, of removing amino-terminal amino acid residues from the phytase and adding them in sequence to the carboxy terminus, can be extended and applied to any desired intein insertion point in the target phytase. This provides a general algorithm and technique for facilitating intein-based binding and, or, cyclization of the target phytase. For example, if the termini of the target phytase are spatially too distant to enable effective binding of the termini using inteins, tag-catcher domains, coiled coil domains, or other molecular structures, then a new set of termini can be selected by moving amino acids from the amino terminus and adding them in sequence to the carboxy terminus of the target phytase, and adding the molecular structures to the newly selected termini.

To illustrate the rearrangement technique described above, the final protein sequence of Gp411-C:Phy02:Gp411-N (#230 Phy02C) could be rearranged as follows (Phy02 (in bold) amino acid string AQSEPELKLESVVIV (SEQ ID NO: 136) is moved from its N-terminal to its C-terminal). The amino acid sequence of Gp411-C:Phy02r14:Gp411-N is as follows:

```
                                                          (SEQ ID NO: 93)
MMLKKILKIEELDERELIDIEVSGNHLFYANDILTHNSRHGVRAPTKFTQ         50

LMQDVTPDAFYTWPVKLGELTPRGGELIAYLGHYWRQRLVADGLLPKKGC         100

PQSGQVAIIADVDERTRKTGEAFAAGLAPDCAITVHTQADTSSPDPLFNP         150

LKTGVCQLDVAQVTDAILERAGGSIADFTGHYQTAFRELERVLNFPQSNL         200

ALKREKQDESASLTQALPSELKVSADNVSLTGAWSLASMLTEIFLLQQAQ         250

GMPEPGWGRITDSHQWNTLLSLHNAQFDLLQRTPEVARSRATPLLDLIKT         300

ALTPHPPQKQAYGVTLPTSVLFIAGHDTNLANLGGALELQWTLPGQPDNT         350

PPGGELVFERWRRLSDNSQWIQVSLVFQTLQQMRDKTPLFLNTPPGEVKL         400

TLAGCEERNAQGMCSLAGFTQIVNEARIPACSIAQSEPELKLESVVIV           450

DLKTQVQTPQGMKEISNIQVGDLVLSNTGYNEVLNVFPKSKKKSYKITLE         500

DGKETICSEEHLEPTQTGEMNISGGLKEGMCLYVKE*
```

Example 3. Creating an Engineered Phytase Using Inteins Linked to the Phytase

Similar to Example 2, engineered, or cyclized, phytases can be constructed using linker sequences as illustrated in FIG. 2. FIG. 2 illustrates an engineered phytase with a split intein attached to a linker that connects to the ends of the phytase coding sequence (A), binding of the split intein to cyclize the phytase using non-covalent binding (B), and the form of the cyclized phytase that results following splicing of the intein and formation of a covalent bond (C). Such molecules can be made as described in Example 2, using known recombinant DNA and molecular biology methods, or by directly ordering the DNA sequences that encode these engineered phytases. Sample linker sequences are listed in Example 1 and were used to construct the following engineered phytases, where the intein sequences are capitalized, the linker sequences are italicized underlined lower case font, and the phytase sequence is lower case and not italicized.

> The amino acid and nucleotide sequence encoding Phy02C-27:SspDnaE (SSp_DnaE-C: L33-1: Phy02: L33-2: Ssp_DnaE-N) are as follows:

(SEQ ID NO: 94)

ATGGTTAAGGTGATTGGAAGACGTTCTCTTGGTGTTCAAAGGATCTTCGATAT

CGGATTGCCACAAGACCACAACTTTCTTCTCGCTAATGGTGCCATCGCTGCCA

AT*agcgggggtggcagtggaggcggttcgaccccgcagtccgcatttgcc* gcccaatcggaaccggaactgaaactggaaagtgtggttattgtgtctcgtca tggcgttcgcgctccgaccaaatttacgcagctgatgcaagatgtcaccccgg acgccttctatacgtggccggtgaagctgggtgaactgaccccgcgtggcggt gaactgatcgcctatctgggtcactactggcgtcagcgcctggtggcagatgg tctgctgccgaaaaagggctpccgcagagcggtcaagttgcaattatcgctga tgtcgacgaacgtacccgcaaaacgggtgaagratttgcggccggtaggcacc ggattgcgccattaccgttcatacgcaggcagataccagctctccggacccpt gttcaacccptgaaaaccggcgtctgtcagctggatgtcgcgcaagtgacgga cgccattctggaacgtgcaggcggttccatcgctgattttaccggtcactacc agacggcattccgtgaactggaacgcgttctgaactttccgcagtcaaatagg cgrtgaaacgcgaaaagcaggatgaaagtgcgtccctgacccaagccctgccg agtgaactgaaagtctccgccgacaatgtgtcactgaccggcgcatggtcact ggcttcgatgctgacggaaatttttctgctpagcaagcacagggtatgccgga accgggttggggtcgtatcaccgattcgcatcagtggaacacgctgctgagcc tgcacaatgcgcagttcgacctgctgcaacgtaccccggaagtggtacgttcg cgcgccacgccgctgctggatctgattaaaaccgctctgacgccgcatccgcc gcagaagcaagcgtatggcgtgaccctgccgacgagcgttctgtttatcgcgg gtcacgacaccaacctggcaaatctgggcggtgctctggaactgcagtggacc ctgccgggtcaaccggataacacgccgccgggcggtgaactggttttcgaacg ttggcgtcgtctgagcgacaattctcagtggatccaagttagcctggtctttc agaccctaagcaaatgcgcgataaaaccccgctgttcctgaacacgccgccgg gcgaagtgaagctgaccctggcgggttgcgaagaacgtaacgcccagggcatg tgttctctggcaggttttacccagattgttaatgaagtacgcatcccggcttg tagtct*gggtggcgggagcggtggagggagtggggcggt*TGCCTTTCTT

TCGGAACTGAGATCCTTACCGTTGAGTACGGACCACTTCCTATTGGTAAGATC

GTTTCTGAGGAAATTAACTGCTCAGTGTACTCTGTTGATCCAGAAGGAAGAGT

TTACACTCAGGCTATCGCACAATGGCACGATAGGGGTGAACAAGAGGTTCTGG

AGTACGAGCTTGAAGATGGATCCGTTATTCGTGCTACCTCTGACCATAGATTC

TTGACTACAGATTATCAGCTTCTCGCTATCGAGGAAATCTTTGCTAGGCAACT

TGATCTCCTTACTTTGGAGAACATCAAGCAGACAGAAGAGGCTCTTGACAACC

ACAGACTTCCATTCCCTTTGCTCGATGCTGGAACCATCAAGTAA

SEQ ID NO: 95)

MVKVIGRRSLGVQRIFDIGLPQDHNFLLANGAIAANSGGGSGGGSTPQSA 50

FAAQSEPELKLESVVIVSRHGVRAPTKFTQLMQDVTPDAFYTWPVKLGEL 100

TPRGGELIAYLGHYWRQRLVADGLLPKKGCPQSGQVAIIADVDERTRKTG 150

EAFAAGLAPDCAITVHTQADTSSPDPLFNPLKTGVCQLDVAQVTDAILER 200

AGGSIADFTGHYQTAFRELERVLNFPQSNLALKREKQDESASLTQALPSE 250

LKVSADNVSLTGAWSLASMLTEIFLLQQAQGMPEPGWGRITDSHQWNTLL 300

-continued

SLHNAQFDLLQRTPEVARSRATPLLDLIKTALTPHPPQKQAYGVTLPTSV 350

LFIAGHDTNLANLGGALELQWTLPGQPDNTPPGGELVFERWRRLSDNSQW 400

IQVSLVFQTLQQMRDKTPLFLNTPPGEVKLTLAGCEERNAQGMCSLAGFT 450

QIVNEARIPACSLGGGSGGGSGGGCLSFGTEILTVEYGPLPIGKIVSEEI 500

NCSVYSVDPEGRVYTQATAQWHDRGEQEVLEYELEDGSVIRATSDHRFLT 550

TDYQLLAIEEIFARQLDLLTLENIKQTEEALDNHRLPFPLLDAGTIK*

> The amino acid and nucleotide sequence encoding Phy02C-32:SspDnaE (SSp_DnaE-C:L38-1: Phy02:L38-2: Ssp_DnaE-N) are as follows:

(SEQ ID NO: 96)

>ATGGTTAAGGTGATTGGAAGACGTTCTCTTGGTGTTCAAAGGATCTTCGATATCGGATTGCCACA

AGACCACAACTTTCTTCTCGCTAATGGTGCCATCGCTGCCAAT*agcggtggctcgtcagggagtac*

*gacaaccacgcgtatcaccccgcaatctgcgttcgct*gcccaatcggaaccggaactgaaactgga aagtgtggttattgtgtctcgtcatggcgttcgcgctccgaccaaatttacgcagctgatgcaaga tgtcaccccggacgccttctatacgtggccggtgaagctgggtgaactgaccccgcgtggcggtga actgatcgcctatctgggtcactactggcgtcagcgcctggtggcagatggtctgctgccgaaaaa gggctgcccgcagagcggtcaagttgcaattatcgctgatgtcgacgaacgtacccgcaaaacggg tgaagcatttgcggccggtctggcaccggattgcgccattaccgttcatacgcaggcagataccag ctctccggacccgctgttcaacccgctgaaaaccggcgtctgtcagctggatgtcgcgcaagtgac ggacgccattctggaacgtgcaggcggttccatcgctgattttaccggtcactaccagacggcatt ccgtgaactggaacgcgttctgaactttccgcagtcaaatctggcgctgaaacgcgaaaagcagga tgaaagtgcgtccctgacccaagccctgccgagtgaactgaaagtctccgccgacaatgtgtcact gaccggcgcatggtcactggcttcgatgctgacggaaatttttctgctgcagcaagcacagggtat gccggaaccgggttggggtcgtatcaccgattcgcatcagtggaacacgctgctgagcctgcacaa tgcgcagttcgacctgctgcaacgtaccccggaagtggcacgttcgcgcgccacgccgctgctgga tctgattaaaaccgctctgacgccgcatccgccgcagaagcaagcgtatggcgtgaccctgccgac gagcgttctgtttatcgcgggtcacgacaccaacctggcaaatctgggcggtgctctggaactgca gtggaccctgccgggtcaaccggataacacgccgccgggcggtgaactggttttcgaacgttggcg tcgcctgagcgacaattctcagtggatccaagttagcctggtctttcagaccctgcagcaaatgcg cgataaaaccccgctgttcctgaacacgccgccgggcgaagtgaagctgaccctggcgggttgcga agaacgtaacgcccagggcatgtgttctctggcaggttttacccagattgttaatgaagcacgcat ccggcttgtagtctg*caaaacacgtttagccaggggagtagctcgggatcc*TGCCTTTCTTTCGG

AACTGAGATCCTTACCGTTGAGTACGGACCACTTCCTATTGGTAAGATCGTTTCTGAGGAAATTAA

CTGCTCAGTGTACTCTGTTGATCCAGAAGGAAGAGTTTACACTCAGGCTATCGCACAATGGCACGA

TAGGGGTGAACAAGAGGTTCTGGAGTACGAGCTTGAAGATGGATCCGTTATTCGTGCTACCTCTGA

CCATAGATTCTTGACTACAGATTATCAGCTTCTCGCTATCGAGGAAATCTTTGCTAGGCAACTTGA

TCTCCTTACTTTGGAGAACATCAAGCAGACAGAAGAGGCTCTTGACAACCACAGACTTCCATTCCC

TTTGCTCGATGCTGGAACCATCAAGTAA (SEQ ID NO: 97)

MVKVIGRRSLGVQRIFDIGLPQDHNELLANGAIAANSGGSSGSTITTRIT 50

PQSAFAAQSEPELKLESVVIVSRHGVRAPTKFTQLMQDVTPDAFYTWPVK 100

-continued

```
LGELTPRGGELIAYLGHYWRQRLVADGLLPKKGCPQSGQVAIIADVDERT 150

RKTGEAFAAGLAPDCAITVHTQADTSSPDPLFNPLKTGVCQLDVAQVTDA 200

ILERAGGSIADFTGHYQTAFRELERVLNFPQSNLALKREKQDESASLTQA 250

LPSELKVSADNVSLTGAWSLASMLTEIFLLQQAQGMPEPGWGRITDSHQW 300

NTLLSLHNAQFDLLQRTPEVARSRATPLLDLIKTALTPHPPQKQAYGVTL 350

PTSVLFIAGHDTNLANLGGALELQWTLPGQPDNTPPGGELVFERWRRLSD 400

NSQWIQVSLVFQTLQQMRDKTPLFLNTPPGEVKLTLAGCEERNAQGMCSL 450
```

AGFTQIVNEARIPACSL*QNTFSQGSSSGS*CLSEGTEILTVEYGPLPIGKI 500

```
VSEEINCSVYSVDPEGRVYTQATAQWHDRGEQEVLEYELEDGSVIRATSD 550

HRFLTTDYQLLAIEEIFARQLDLLTLENIKQTEEALDNHRLPFPLLDAGT 600

IK*
```

> The amino acid and nucleotide sequence encoding Phy02C-40: SspDnaE (SSp_DnaE-C:L46-1: Phy02: L46-2: Ssp_DnaE-N) are as follows:

(SEQ ID NO: 98)

>ATGGTTAAGGTGATTGGAAGACGTTCTCTTGGTGTTCAAAGGATCTTCGATATCGGATTGCCACA

AGACCACAACTTTCTTCTCGCTAATGGTGCCATCGCTGCCAAT*agcgcctttgca*gcccaatcgga accggaactgaaactggaaagtgtggttattgtgtctcgtcatggcgttcgcgctccgaccaaatt tacgcagctgatgcaagatgtcaccccggacgccttctatacgtggccggtgaagctgggtgaact gaccccgcgtggcggtgaactgatcgcctatctgggtcactactggcgtcagcgcctggtggcaga tggtctgctgccgaaaaagggctgcccgcagagcggtcaagttgcaattatcgctgatgtcgacga acgtacccgcaaaacgggtgaagcatttgcggccggtctggcaccggattgcgccattaccgttca tacgcaggcagataccagctctccggacccgctgttcaacccgctgaaaaccggcgtctgtcagct ggatgtcgcgcaagtgacggacgccattctggaacgtgcaggcggttccatcgctgattttaccgg tcactaccagacggcattccgtgaactggaacgcgttctgaactttccgcagtcaaatctggcgct gaaacgcgaaaagcaggatgaaagtgcgtccctgacccaagccctgccgagtgaactgaaagtctc cgccgacaatgtgtcactgaccggcgcatggtcactggcttcgatgctgacggaaatttttctgct gcagcaagcacagggtatgccggaaccgggttggggtcgtatcaccgattcgcatcagtggaacac gctgctgagcctgcacaatgcgcagttcgacctgctgcaacgtaccccggaagtggcacgttcgcg cgccacgccgctgctggatctgattaaaaccgctctgacgccgcatccgccgcagaagcaagcgta tggcgtgaccctgccgacgagcgttctgtttatcgcgggtcacgacaccaacctggcaaatctggg cggtgctctggaactgcagtggaccctgccgggtcaaccggataacacgccgccgggcggtgaact ggttttcgaacgttggcgtcgcctgagcgacaattctcagtggatccaagttagcctggtctttca gaccctgcagcaaatgcgcgataaaaccccgctgttcctgaacacgccgccgggcgaagtgaagct gaccctggcgggttgcgaagaacgtaacgcccagggcatgtgttctctggcaggttttacccagat tgttaatgaagcacgcatcccggcttgtagtctg*ggtgcagctccagcggccgcaccggctaaaca*

*ggaagcggcagctccggctcctgcagcgaaggcggaagcaccggccgcagctcctgcggcaaaagc*

*gaccccgcag*TGCCTTTCTTTCGGAACTGAGATCCTTACCGTTGAGTACGGACCACTTCCTATTGG

TAAGATCGTTTCTGAGGAAATTAACTGCTCAGTGTACTCTGTTGATCCAGAAGGAAGAGTTTACAC

TCAGGCTATCGCACAATGGCACGATAGGGGTGAACAAGAGGTTCTGGAGTACGAGCTTGAAGATGG

-continued

ATCCGTTATTCGTGCTACCTCTGACCATAGATTCTTGACTACAGATTATCAGCTTCTCGCTATCGA

GGAAATCTTTGCTAGGCAACTTGATCTCCTTACTTTGGAGAACATCAAGCAGACAGAAGAGGCTCT

TGACAACCACAGACTTCCATTCCCTTTGCTCGATGCTGGAACCATCAAGTAA (SEQ ID NO: 99)

MVKVIGRRSLGVQRIFDIGLPQDHNELLANGAIAAN<u>SAFA</u>AQSEPELKLE 50

SVVIVSRHGVRAPTKFTQLMQDVTPDAFYIWPVKLGELTPRGGELIAYLG 100

HYWRQRLVADGLLPKKGCPQSGQVAIIADVDERTRKTGEAFAAGLAPDCA 150

ITVHTQADTSSPDPLFNPLKTGVCQLDVAQVTDAILERAGGSIADFTGHY 200

QTAFRELERVLNFPQSNLALKREKQDESASLTQALPSELKVSADNVSLTG 250

AWSLASMLTEIFLLQQAQGMPEPGWGRITDSHQWNTLLSLHNAQFDLLQR 300

TPEVARSRATPLLDLIKTALTPHPPQKQAYGVILPTSVLFIAGHDINLAN 350

LGGALELQWTLPGQPDNTPPGGELVFERWRRLSDNSQWIQVSLVFQTLQQ 400

MRDKTPLFLNTPPGEVKLTLAGCEERNAQGMCSLAGFTQIVNEARIPACS 450

<u>LGAAPAAAPAKQEAAAPAPAAKAEAPAAAPAAKATPQ</u>CLSEGTEILTVEY 500

GPLPIGKIVSEEINCSVYSVDPEGRVYTQATAQWHDRGEQEVLEYELEDG 550

SVIRATSDHRFLTTDYQLLAIEEIFARQLDLLTLENIKQTEEALDNHRLP 600

FPLLDAGTIK*

> The amino acid and nucleotide sequence encoding Phy02C-49:SspDnaE (SSp_DnaE-C:L55-1:Phy02: L55-2: Ssp DnaE-N) are as follows:

(SEQ ID NO: 100)

ATGGTTAAGGTGATTGGAAGACGTTCTCTTGGTGTTCAAAGGATCTTCGATATCGGATTGCCACAA

GACCACAACTTTCTTCTCGCTAATGGTGCCATCGCTGCCAAT<u>*agcgcagccgaagccgctgcgaag*</u>

<u>*gaggcagctgcgaaagaagcggctgcaaaagaagcggcagctaaggctttgaataccccgcaatcg*</u>

<u>*gctttcgct*</u>gcccaatcggaaccggaactgaaactggaaagtgtggttattgtgtctcgtcatggc gttcgcgctccgaccaaatttacgcagctgatgcaagatgtcaccccggacgccttctatacgtgg ccggtgaagctgggtgaactgaccccgcgtggcggtgaactgatcgcctatctgggtcactactgg cgtcagcgcctggtggcagatggtctgctgccgaaaaagggctgcccgcagagcggtcaagttgca attatcgctgatgtcgacgaacgtacccgcaaaacgggtgaagcatttgcggccggtctggcaccg gattgcgccattaccgttcatacgcaggcagataccagctctccggacccgctgttcaacccgctg aaaaccggcgtctgtcagctggatgtcgcgcaagtgacggacgccattctggaacgtgcaggcggt tccatcgctgattttaccggtcactaccagacggcattccgtgaactggaacgcgttctgaacttt ccgcagtcaaatctggcgctgaaacgcgaaaagcaggatgaaagtgcgtccctgacccaagccctg ccgagtgaactgaaagtctccgccgacaatgtgtcactgaccggcgcatggtcactggcttcgatg ctgacggaaatttttctgctgcagcaagcacagggtatgccggaaccgggttggggtcgtatcacc gattcgcatcagtggaacacgctgctgagcctgcacaatgcgcagttcgacctgctgcaacgtacc ccggaagtggcacgttcgcgcgccacgccgctgctggatctgattaaaaccgctctgacgccgcat ccgccgcagaagcaagcgtatggcgtgaccctgccgacgagcgttctgtttatcgcgggtcacgac accaacctggcaaatctgggcggtgctctggaactgcagtggaccctgccgggtcaaccggataac acgccgccgggcggtgaactggttttcgaacgttggcgtcgcctgagcgacaattctcagtggatc caagttagcctggtctttcagaccctgcagcaaatgcgcgataaaaccccgctgttcctgaacacg -continued ccgccgggcgaagtgaagctgaccctggcgggttgcgaagaacgtaacgcccagggcatgtgttct ctggcaggttttacccagattgttaatgaagcacgcatccggcttgtagtctg*gggggcgcagaa*

*gcagctgccaaagaggcggccgcaaaggtcaatctg*TGCCTTTCTTTCGGAACTGAGATCCTTACC

GTTGAGTACGGACCACTTCCTATTGGTAAGATCGTTTCTGAGGAAATTAACTGCTCAGTGTACTCT

GTTGATCCAGAAGGAAGAGTTTACACTCAGGCTATCGCACAATGGCACGATAGGGGTGAACAAGAG

GTTCTGGAGTACGAGCTTGAAGATGGATCCGTTATTCGTGCTACCTCTGACCATAGATTCTTGACT

ACAGATTATCAGCTTCTCGCTATCGAGGAAATCTTTGCTAGGCAACTTGATCTCCTTACTTTGGAG

AACATCAAGCAGACAGAAGAGGCTCTTGACAACCACAGACTTCCATTCCCTTTGCTCGATGCTGGA

ACCATCAAGTAA (SEQ ID NO: 101)

MVKVIGRRSLGVQRIFDIGLPQDHNFLLANGAIAANSAAEAAAKEAAAKE 50

AAAKEAAAKALNTPQSAFAAQSEPELKLESVVIVSRHGVRAPTKFTQLMQ 100

DVTPDAFYTWPVKLGELTPRGGELIAYLGHYWRQRLVADGLLPKKGCPQS 150

GQVAIIADVDERTRKTGEAFAAGLAPDCAITVHTQADTSSPDPLFNPLKT 200

GVCQLDVAQVIDAILERAGGSIADFIGHYQTAFRELERVLNFPQSNLALK 250

REKQDESASLTQALPSELKVSADNVSLTGAWSLASMLTEIFLLQQAQGMP 300

EPGWGRITDSHQWNILLSLHNAQFDLLQRTPEVARSRATPLLDLIKTALT 350

PHPPQKQAYGVTLPTSVLFIAGHDTNLANLGGALELQWTLPGQPDNTPPG 400

GELVFERWRRLSDNSQWIQVSLVFQTLQQMRDKTPLFLNTPPGEVKLTLA 450

GCEERNAQGMCSLAGFTQIVNEARIPACSLGGAEAAAKEAAAKVNLCLSF 500

GTEILTVEYGPLPIGKIVSEEINCSVYSVDPEGRVYTQATAQWHDRGEQE 550

VLEYELEDGSVIRATSDHRFLTIDYQLLAIEEIFARQLDLLTLENIKQTE 600

EALDNHRLPFPLLDAGTIK*

These engineered phytases can be evaluated the same as other molecules for thermal stability, heterologous expression levels from any desirable host (microbial, plant, or otherwise), specific activity, gastric stability or gastric digestion using known techniques (Thomas, K., et al., 2004, A multi-laboratory evaluation of a common in vitro pepsin digestion assay protocol used in assessing the safety of novel proteins. *Regulatory Toxicology and Pharmacology,* 39(2), 87-98.; FU, T. J. (2002). Digestion stability as a criterion for protein allergenicity assessment. *Annals of the New York Academy of Sciences,* 964(1), 99-110, all of which are incorporated herein by reference as if fully set forth).

Example 4. Creating an Engineered Phytase Using Coiled Coil Domains

The following molecules were design based on the engineered phytases from Example 3. These molecules contain linkers but the trans-splicing C- and N-inteins are substituted with N- and C-terminal coils, respectively. The four prototype designs differ in the linker length and composition.

Nucleotide and amino acid sequences of the four prototype coiled coil stabilized phytase are below. Coil sequences at the N- and C-terminus are capitalized, linker sequences are lower case italics, phytase sequences are lower case. The nucleotide sequence encoding Phy02-33:cc17 (cc17-N: L33-1-Phy02-L33-2: cc17-C) [AA_SEQ ID NO: 103] is as follows:

(SEQ ID NO: 102)

ATGAGGGCCAAGCAGCTGGAGGACAAGATTGAGGAGCTGCTGAGCAAGAT

CTACCACCTGGAGAACGAGATAGCCCGCCTGAAGAAGCTGATTGGCGAGC

GC*agcgggggtggcagtggaggcggttcgaccccgcagtccgcatttgcc* gcccaatcggaaccggaactgaaactggaaagtgtggttattgtgtctcg tcatggcgttcgcgctccgaccaaatttacgcagctgatgcaagatgtca ccccggacgccttctatacgtggccggtgaagctgggtgaactgaccccg cgtggcggtgaactgatcgcctatctgggtcactactggcgtcagcgcct ggtggcagatggtctgctgccgaaaaagggctgcccgcagagcggtcaag ttgcaattatcgctgatgtcgacgaacgtacccgcaaaacgggtgaagca tttgcggccggtctggcaccggattgcgccattaccgttcatacgcaggc agataccagctctccggacccgctgttcaacccgctgaaaaccggcgtct gtcagctggatgtcgcgcaagtgacggacgccattctggaacgtgcaggc ggttccatcgctgattttaccggtcactaccagacggcattccgtgaact ggaacgcgttctgaactttccgcagtcaaatctggcgctgaaacgcgaaa agcaggatgaaagtgcgtccctgacccaagccctgccgagtgaactgaaa gtctccgccgacaatgtgtcactgaccggcgcatggtcactggcttcgat -continued gctgacggaaatttttctgctgcagcaagcacagggtatgccggaaccgg
gttggggtcgtatcaccgattcgcatcagtggaacacgctgctgagcctg
cacaatgcgcagttcgacctgctgcaacgtaccccggaagtggcacgttc
gcgcgccacgccgctgctggatctgattaaaaccgctctgacgccgcatc
cgccgcagaagcaagcgtatggcgtgaccctgccgacgagcgttctgttt
atcgcgggtcacgacaccaacctggcaaatctgggcggtgctctggaact
gcagtggaccctgccgggtcaaccggataacacgccgccgggcggtgaac
tggttttcgaacgttggcgtcgcctgagcgacaattctcagtggatccaa
gttagcctggtctttcagaccctgcagcaaatgcgcgataaaaccccgct
gttcctgaacacgccgccgggcgaagtgaagctgaccctggcgggttgcg
aagaacgtaacgcccagggcatgtgttctctggcaggttttacccagatt
gttaatgaagcacgcatcccggcttgtagtctg*ggtggcgggagcggtgg*
*agggagtgggggcggt*CAGCTGGAGGACAAGATTGAGGAGCTGCTGAGCA
AGATCTACCACCTGGAGAACGAGATAGCGAGGCTGAAGAAGCTGATTGGC
TAA The nucleotide sequence encoding Phy02-38: cc17 (cc17-N: L38-1-Phy02-L38-2: cc17-C) [AA_SEQ ID NO: 105] is as follows:

(SEQ ID NO: 104)
ATGAGGGCCAAGCAGCTGGAGGACAAGATTGAGGAGCTGCTGAGCAAGAT
CTACCACCTGGAGAACGAGATAGCCCGCCTGAAGAAGCTGATTGGCGAGC
GC*agcggtggctcgtcagggagtacgacaaccacgcgtatcaccccgcaa*
*tctgcgttcgct*gcccaatcggaaccggaactgaaactggaaagtgtggt
tattgtgtctcgtcatggcgttcgcgctccgaccaaatttacgcagctga
tgcaagatgtcaccccggacgccttctatacgtggccggtgaagctgggt
gaactgaccccgcgtggcggtgaactgatcgcctatctgggtcactactg
gcgtcagcgcctggtggcagatggtctgctgccgaaaaagggctgcccgc
agagcggtcaagttgcaattatcgctgatgtcgacgaacgtacccgcaaa
acgggtgaagcatttgcggccggtctggcaccggattgcgccattaccgt
tcatacgcaggcagataccagctctccggacccgctgttcaacccgctga
aaaccggcgtctgtcagctggatgtcgcgcaagtgacggacgccattctg
gaacgtgcaggcggttccatcgctgattttaccggtcactaccagacggc
attccgtgaactggaacgcgttctgaactttccgcagtcaaatctggcgc
tgaaacgcgaaaagcaggatgaaagtgcgtccctgacccaagccctgccg
agtgaactgaaagtctccgccgacaatgtgtcactgaccggcgcatggtc
actggcttcgatgctgacggaaatttttctgctgcagcaagcacagggta
tgccggaaccgggttggggtcgtatcaccgattcgcatcagtggaacacg
ctgctgagcctgcacaatgcgcagttcgacctgctgcaacgtaccccgga
agtggcacgttcgcgcgccacgccgctgctggatctgattaaaaccgctc
tgacgccgcatccgccgcagaagcaagcgtatggcgtgaccctgccgacg
agcgttctgtttatcgcgggtcacgacaccaacctggcaaatctgggcgg
tgctctggaactgcagtggaccctgccgggtcaaccggataacacgccgc
cgggcggtgaactggttttcgaacgttggcgtcgcctgagcgacaattct
cagtggatccaagttagcctggtctttcagaccctgcagcaaatgcgcga
taaaaccccgctgttcctgaacacgccgccgggcgaagtgaagctgaccc
tggcgggttgcgaagaacgtaacgcccagggcatgtgttctctggcaggt
tttacccagattgttaatgaagcacgcatcccggcttgtagtctg*caaaa*
*cacgtttagccaggggagtagctcgggatcc*CAGCTGGAGGACAAGATTG
AGGAGCTGCTGAGCAAGATCTACCACCTGGAGAACGAGATAGCGAGGCTG
AAGAAGCTGATTGGCTAA The nucleotide sequence encoding Phy02-46: cc17 (cc17-N: L46-1-Phy02-L46-2: cc17-C) [AA_SEQ ID NO: 107] is as follows:

(SEQ ID NO: 106)
ATGAGGGCCAAGCAGCTGGAGGACAAGATTGAGGAGCTGCTGAGCAAGAT
CTACCACCTGGAGAACGAGATAGCCCGCCTGAAGAAGCTGATTGGCGAGC
GC*agcgcctttgca*gcccaatcggaaccggaactgaaactggaaagtgtg
gttattgtgtctcgtcatggcgttcgcgctccgaccaaatttacgcagct
gatgcaagatgtcaccccggacgccttctatacgtggccggtgaagctgg
gtgaactgaccccgcgtggcggtgaactgatcgcctatctgggtcactac
tggcgtcagcgcctggtggcagatggtctgctgccgaaaaagggctgccc
gcagagcggtcaagttgcaattatcgctgatgtcgacgaacgtacccgca
aaacgggtgaagcatttgcggccggtctggcaccggattgcgccattacc
gttcatacgcaggcagataccagctctccggacccgctgttcaacccgct
gaaaaccggcgtctgtcagctggatgtcgcgcaagtgacggacgccattc
tggaacgtgcaggcggttccatcgctgattttaccggtcactaccagacg
gcattccgtgaactggaacgcgttctgaactttccgcagtcaaatctggc
gctgaaacgcgaaaagcaggatgaaagtgcgtccctgacccaagccctgc
cgagtgaactgaaagtctccgccgacaatgtgtcactgaccggcgcatgg
tcactggcttcgatgctgacggaaatttttctgctgcagcaagcacaggg
tatgccggaaccgggttggggtcgtatcaccgattcgcatcagtggaaca
cgctgctgagcctgcacaatgcgcagttcgacctgctgcaacgtaccccg
gaagtggcacgttcgcgcgccacgccgctgctggatctgattaaaaccgc
tctgacgccgcatccgccgcagaagcaagcgtatggcgtgaccctgccga
cgagcgttctgtttatcgcgggtcacgacaccaacctggcaaatctgggc
ggtgctctggaactgcagtggaccctgccgggtcaaccggataacacgcc
gccgggcggtgaactggttttcgaacgttggcgtcgcctgagcgacaatt
ctcagtggatccaagttagcctggtctttcagaccctgcagcaaatgcgc
gataaaaccccgctgttcctgaacacgccgccgggcgaagtgaagctgac
cctggcgggttgcgaagaacgtaacgcccagggcatgtgttctctggcag
gttttacccagattgttaatgaagcacgcatcccggcttgtagtctg*ggt*
*gcagctccagcggccgcaccggctaaacaggaagcggcagctccggctcc*

-continued tgcagcgaaggcggaagcaccggccgcagctcctgcggcaaaagcgaccc cgcagCAGCTGGAGGACAAGATTGAGGAGCTGCTGAGCAAGATCTACCAC

CTGGAGAACGAGATAGCGAGGCTGAAGAAGCTGATTGGCTAA

The nucleotide sequence encoding Phy02-55: cc17 (cc17-N: L55-1-Phy02-L55-2:cc17-C)[AA_SEQ ID NO: 109] is as follows:

(SEQ ID NO: 108)
ATGAGGGCCAAGCAGCTGGAGGACAAGATTGAGGAGCTGCTGAGCAAGATCTACCACCTGGAGAAC

GAGATAGCCCGCCTGAAGAAGCTGATTGGCGAGCGCagcgcagccgaagccgctgcgaaggaggca gctgcgaaagaagcggctgcaaaagaagcggcagctaaggctttgaatacccgcaatcggctttc gctgcccaatcggaaccggaactgaaactggaaagtgtggttattgtgtctcgtcatggcgttcgc gctccgaccaaatttacgcagctgatgcaagatgtcaccccggacgccttctatacgtggccggtg aagctgggtgaactgaccccgcgtggcggtgaactgatcgcctatctgggtcactactggcgtcag cgcctggtggcagatggtctgctgccgaaaaagggctgcccgcagagcggtcaagttgcaattatc gctgatgtcgacgaacgtacccgcaaaacgggtgaagcatttgcggccggtctggcaccggattgc gccattaccgttcatacgcaggcagataccagctctccggacccgctgttcaacccgctgaaaacc ggcgtctgtcagctggatgtcgcgcaagtgacggacgccattctggaacgtgcaggcggttccatc gctgattttaccggtcactaccagacggcattccgtgaactggaacgcgttctgaactttccgcag tcaaatctggcgctgaaacgcgaaaagcaggatgaaagtgcgtccctgacccaagccctgccgagt gaactgaaagtctccgccgacaatgtgtcactgaccggcgcatggtcactggcttcgatgctgacg gaaatttttctgctgcagcaagcacagggtatgccggaaccgggttggggtcgtatcaccgattcg catcagtggaacacgctgctgagcctgcacaatgcgcagttcgacctgctgcaacgtaccccggaa gtggcacgttcgcgcgccacgccgctgctggatctgattaaaaccgctctgacgccgcatccgccg cagaagcaagcgtatggcgtgaccctgccgacgagcgttctgtttatcgcgggtcacgacaccaac ctggcaaatctgggcggtgctctggaactgcagtggaccctgccgggtcaaccggataacacgccg ccgggcggtgaactggttttcgaacgttggcgtcgcctgagcgacaattctcagtggatccaagtt agcctggtctttcagaccctgcagcaaatgcgcgataaaaccccgctgttcctgaacacgccgccg ggcgaagtgaagctgaccctggcgggttgcgaagaacgtaacgcccagggcatgtgttctctggca ggttttacccagattgttaatgaagcacgcatccoggcttgtagtotgggggcgcagaagcagct gccaaagaggcggccgcaaaggtcaatctgCAGCTGGAGGACAAGATTGAGGAGCTGCTGAGCAAG

ATCTACCACCTGGAGAACGAGATAGCGAGGCTGAAGAAGCTGATTGGCTAA

Heat unstable coiled-coil modified phytase (controls; cc30 with the four prototype linkers).
The nucleotide sequence encoding Phy02-33:cc30 (cc30-N: L33-1-Phy02-L33-2: cc30-C) [AA_SEQ ID NO: 111] is as follows:

(SEQ ID NO: 110)
ATGAGGGCCAAGCAGCTGGAGGACAAGGTCGAGGAGCTGCTGAGCAAGAA

CTACCACCTGGAGAACGAGGTCGCCCGCCTGAAGAAGCTGGTGGGCACCC

GCagcgggggtggcagtggaggcggttcgaccccgcagtccgcatttgcc gcccaatcggaaccggaactgaaactggaaagtgtggttattgtgtctcg -continued tcatggcgttcgcgctccgaccaaatttacgcagctgatgcaagatgtca ccccggacgccttctatacgtggccggtgaagctgggtgaactgaccccg cgtggcggtgaactgatcgcctatctgggtcactactggcgtcagcgcct ggtggcagatggtctgctgccgaaaaagggctgcccgcagagcggtcaag -continued ttgcaattatcgctgatgtcgacgaacgtacccgcaaaacgggtgaagca tttgcggccggtctggcaccggattgcgccattaccgttcatacgcaggc agataccagctctccggacccgctgttcaacccgctgaaaaccggcgtct gtcagctggatgtcgcgcaagtgacggacgccattctggaacgtgcaggc ggttccatcgctgattttaccggtcactaccagacggcattccgtgaact ggaacgcgttctgaactttccgcagtcaaatctggcgctgaaacgcgaaa agcaggatgaaagtgcgtccctgacccaagccctgccgagtgaactgaaa -continued gtctccgccgacaatgtgtcactgaccggcgcatggtcactggcttcgat
gctgacggaaatttttctgctgcagcaagcacagggtatgccggaaccgg
gttggggtcgtatcaccgattcgcatcagtggaacacgctgctgagcctg
cacaatgcgcagttcgacctgctgcaacgtaccccggaagtggcacgttc
gcgcgccacgccgctgctggatctgattaaaaccgctctgacgccgcatc
cgccgcagaagcaagcgtatggcgtgaccctgccgacgagcgttctgttt
atcgcgggtcacgacaccaacctggcaaatctgggcggtgctctggaact
gcagtggaccctgccgggtcaaccggataacacgccgccgggcggtgaac
tggttttcgaacgttggcgtcgcctgagcgacaattctcagtggatccaa
gttagcctggtctttcagaccctgcagcaaatgcgcgataaaaccccgct
gttcctgaacacgccgccgggcgaagtgaagctgaccctggcgggttgcg
aagaacgtaacgcccagggcatgtgttctctggcaggttttacccagatt
gttaatgaagcacgcatcccggcttgtagtct*gggtggcgggagcggtgg*
*agggagtgggggcggt*CAATTGGAAGATAAAGTGGAAGAGCTCCTGTCCA
AAAATTATCATCTGGAAAATGAGGTGGCCCGCTTGAAGAAACTCGTGGGA
TAA The nucleotide sequence encoding Phy02-38: cc30 (cc30-N: L38-1-Phy02-L38-2:cc30-C) [AA_SEQ ID NO: 113] is as follows:

(SEQ ID NO: 112)
ATGAGGGCCAAGCAGCTGGAGGACAAGGTCGAGGAGCTGCTGAGCAAGAA
CTACCACCTGGAGAACGAGGTCGCCCGCCTGAAGAAGCTGGTGGGCACCC
GC*agcggtggctcgtcagggagtacgacaaccacgcgtatcaccccgcaa*
*tctgcgttcgct*gcccaatcggaaccggaactgaaactggaaagtgtggt
tattgtgtctcgtcatggcgttcgcgctccgaccaaatttacgcagctga
tgcaagatgtcaccccggacgccttctatacgtggccggtgaagctgggt
gaactgaccccgcgtggcggtgaactgatcgcctatctgggtcactactg
gcgtcagcgcctggtggcagatggtctgctgccgaaaaagggctgcccgc
agagcggtcaagttgcaattatcgctgatgtcgacgaacgtacccgcaaa
acgggtgaagcatttgcggccggtctggcaccggattgcgccattaccgt
tcatacgcaggcagataccagctctccggacccgctgttcaacccgctga
aaaccggcgtctgtcagctggatgtcgcgcaagtgacggacgccattctg
gaacgtgcaggcggttccatcgctgattttaccggtcactaccagacggc
attccgtgaactggaacgcgttctgaactttccgcagtcaaatctggcgc
tgaaacgcgaaaagcaggatgaaagtgcgtccctgacccaagccctgccg
agtgaactgaaagtctccgccgacaatgtgtcactgaccggcgcatggtc
actggcttcgatgctgacggaaatttttctgctgcagcaagcacagggta
tgccggaaccgggttggggtcgtatcaccgattcgcatcagtggaacacg
ctgctgagcctgcacaatgcgcagttcgacctgctgcaacgtaccccgga
agtggcacgttcgcgcgccacgccgctgctggatctgattaaaaccgctc
tgacgccgcatccgccgcagaagcaagcgtatggcgtgaccctgccgacg -continued agcgttctgtttatcgcgggtcacgacaccaacctggcaaatctgggcgg
tgctctggaactgcagtggaccctgccgggtcaaccggataacacgccgc
cgggcggtgaactggttttcgaacgttggcgtcgcctgagcgacaattct
cagtggatccaagttagcctggtctttcagaccctgcagcaaatgcgcga
taaaaccccgctgttcctgaacacgccgccgggcgaagtgaagctgaccc
tggcgggttgcgaagaacgtaacgcccagggcatgtgttctctggcaggt
tttacccagattgttaatgaagcacgcatcccggcttgtagtctg*caaaa*
*cacgtttagccaggggagtagctcgggatcc*CAATTGGAAGATAAAGTGG
AAGAGCTCCTGTCCAAAAATTATCATCTGGAAAATGAGGTGGCCCGCTTG
AAGAAACTCGTGGGATAA The nucleotide sequence encoding Phy02-46: cc30 (cc30-N: L46-1-Phy02-L46-2:cc30-C) [AA_SEQ ID NO: 115] is as follows:

(SEQ ID NO: 114)
ATGAGGGCCAAGCAGCTGGAGGACAAGGTCGAGGAGCTGCTGAGCAAGAA
CTACCACCTGGAGAACGAGGTCGCCCGCCTGAAGAAGCTGGTGGGCACCC
GC*agcgcctttgcag*cccaatcggaaccggaactgaaactggaaagtgtg
gttattgtgtctcgtcatggcgttcgcgctccgaccaaatttacgcagct
gatgcaagatgtcaccccggacgccttctatacgtggccggtgaagctgg
gtgaactgaccccgcgtggcggtgaactgatcgcctatctgggtcactac
tggcgtcagcgcctggtggcagatggtctgctgccgaaaaagggctgccc
gcagagcggtcaagttgcaattatcgctgatgtcgacgaacgtacccgca
aaacgggtgaagcatttgcggccggtctggcaccggattgcgccattacc
gttcatacgcaggcagataccagctctccggacccgctgttcaacccgct
gaaaaccggcgtctgtcagctggatgtcgcgcaagtgacggacgccattc
tggaacgtgcaggcggttccatcgctgattttaccggtcactaccagacg
gcattccgtgaactggaacgcgttctgaactttccgcagtcaaatctggc
gctgaaacgcgaaaagcaggatgaaagtgcgtccctgacccaagccctgc
cgagtgaactgaaagtctccgccgacaatgtgtcactgaccggcgcatgg
tcactggcttcgatgctgacggaaatttttctgctgcagcaagcacaggg
tatgccggaaccgggttggggtcgtatcaccgattcgcatcagtggaaca
cgctgctgagcctgcacaatgcgcagttcgacctgctgcaacgtaccccg
gaagtggcacgttcgcgcgccacgccgctgctggatctgattaaaaccgc
tctgacgccgcatccgccgcagaagcaagcgtatggcgtgaccctgccga
cgagcgttctgtttatcgcgggtcacgacaccaacctggcaaatctgggc
ggtgctctggaactgcagtggaccctgccgggtcaaccggataacacgcc
gccgggcggtgaactggttttcgaacgttggcgtcgcctgagcgacaatt
ctcagtggatccaagttagcctggtctttcagaccctgcagcaaatgcgc
gataaaaccccgctgttcctgaacacgccgccgggcgaagtgaagctgac
cctggcgggttgcgaagaacgtaacgcccagggcatgtgttctctggcag
gttttacccagattgttaatgaagcacgcatcccggcttgtagtctg*ggt*

-continued

*gcagctccagcggccgcaccggctaaacaggaagcggcagctccggctcc*

*tgcagcgaaggcggaagcaccggccgcagctcctgcggcaaaagcgaccc*

*cgcag*CAATTGGAAGATAAAGTGGAAGAGCTCCTGTCCAAAAATTATCAT

CTGGAAAATGAGGTGGCCCGCTTGAAGAAACTCGTGGGATAA

The nucleotide sequence encoding Phy02-55: cc30 (cc30-N: L55-1-Phy02-L55-2:cc30-C) [AA_SEQ ID NO: 117] is as follows:

(SEQ ID NO: 116)

ATGAGGGCCAAGCAGCTGGAGGACAAGGTCGAGGAGCTGCTGAGCAAGAA

CTACCACCTGGAGAACGAGGTCGCCCGCCTGAAGAAGCTGGTGGGCACCC

GC*agcgcagccgaagccgctgcgaaggaggcagctgcgaaagaagcggct*

*gcaaaagaagcggcagctaaggctttgaataccccgcaatcggctttcgc* tgcccaatcggaaccggaactgaaactggaaagtgtggttattgtgtctc gtcatggcgttcgcgctccgaccaaatttacgcagctgatgcaagatgtc accccggacgccttctatacgtggccggtgaagctgggtgaactgacccc gcgtggcggtgaactgatcgcctatctgggtcactactggcgtcagcgcc tggtggcagatggtctgctgccgaaaaagggctgcccgcagagcggtcaa gttgcaattatcgctgatgtcgacgaacgtacccgcaaaacgggtgaagc atttgcggccggtctggcaccggattgcgccattaccgttcatacgcagg cagataccagctctccggacccgctgttcaacccgctgaaaaccggcgtc tgtcagctggatgtcgcgcaagtgacggacgccattctggaacgtgcagg cggttccatcgctgattttaccggtcactaccagacggcattccgtgaac tggaacgcgttctgaactttccgcagtcaaatctggcgctgaaacgcgaa aagcaggatgaaagtgcgtccctgacccaagccctgccgagtgaactgaa agtctccgccgacaatgtgtcactgaccggcgcatggtcactggcttcga tgctgacggaaatttttctgctgcagcaagcacagggtatgccggaaccg ggttggggtcgtatcaccgattcgcatcagtggaacacgctgctgagcct gcacaatgcgcagttcgacctgctgcaacgtaccccggaagtggcacgtt cgcgcgccacgccgctgctggatctgattaaaaccgctctgacgccgcat ccgccgcagaagcaagcgtatggcgtgaccctgccgacgagcgttctgtt tatcgcgggtcacgacaccaacctggcaaatctgggcggtgctctggaac tgcagtggaccctgccgggtcaaccggataacacgccgccgggcggtgaa ctggttttcgaacgttggcgtcgcctgagcgacaattctcagtggatcca agttagcctggtctttcagaccctgcagcaaatgcgcgataaaaccccgc tgttcctgaacacgccgccgggcgaagtgaagctgaccctggcgggttgc gaagaacgtaacgcccagggcatgtgttctctggcaggttttacccagat tgttaatgaagcacgcatcccggcttgtagtctg*gggggcgcagaagcag*

*ctgccaaagaggcggccgcaaaggtcaatctg*CAATTGGAAGATAAAGTG

GAAGAGCTCCTGTCCAAAAATTATCATCTGGAAAATGAGGTGGCCCGCTT

GAAGAAACTCGTGGGATAA

Example 5. Creating an Engineered Phytase Using a Tag-Catcher Domain Set

Using the methods described in Example 1, engineered phytases can be constructed using tag- and catcher-domains as described in FIGS. 4-7. FIG. 4 illustrates an engineered phytase with a tag- and catcher-domain attached to the amino- and carboxy-termini, respectively, of the phytase coding sequence (A) and binding of the tag- and catcher-domains to cyclize the phytase using non-covalent binding (B), and the form of the cyclized phytase that results following reaction of the tag-catcher domains to form a covalent bond (C). FIG. 5 illustrates an engineered phytase with a tag- and catcher-domain attached to the carboxy- and amino-termini, respectively, of the phytase coding sequence (A) and binding of the tag- and catcher-domains to cyclize the phytase using non-covalent binding (B), and the form of the cyclized phytase that results following reaction of the tag-catcher domains to form a covalent bond (C). FIG. 6 illustrates an engineered phytase with a tag- and catcher-domains attached to linkers that connect to the amino- and carboxy-termini, respectively, of the phytase coding sequence (A), and binding of the tag- and catcher domains to cyclize the phytase using non-covalent binding (B), and the form of the cyclized phytase that results following reaction of the tag-catcher domains to form a covalent bond (C). FIG. 7 illustrates an engineered phytase with a tag- and catcher-domains attached to linkers that connect to the carboxy- and amino-termini, respectively, of the phytase coding sequence (A), and binding of the tag- and catcher-domains to cyclize the phytase using non-covalent binding (B), and the form of the cyclized phytase that results following reaction of the tag-catcher domains to form a covalent bond (C).

The tag- and catcher-domains can be directly connected to the phytase's termini, or connected to the termini using linkers. Unlike split inteins, which generally have a preferred termini to which each part of the intein attaches, tag- and catcher-domains can be used at either termini. For example, one engineered phytase may have the tag-domain connected to the target phytase's amino terminus without a linker (FIG. 4), or with a linker (FIG. 6), and have the catcher-domain connected to the target phytase's carboxy terminus without a linker (FIG. 4), or with a linker (FIG. 6). Similarly, one engineered phytase may have the tag-domain connected to the target phytase's carboxy terminus without a linker (FIG. 5), or with a linker (FIG. 7), and have the catcher-domain connected to the target phytase's amino terminus without a linker (FIG. 5), or with a linker (FIG. 7). The tag- and catcher-domains are capable of binding the termini of the target phytase in both configurations and forming a cyclic phytase through formation of a covalent bond. The following sequences illustrate how an engineered Phy02 phytase is constructed:

Tag-Domain:Tlinker1:Phy02:Clinker1:Catcher (linker is in bold and underlined):

(SEQ ID NO: 118)

atggcccacatcgtgatggtggacgcctacaagccgacgaag<u>ggttcagg</u>

<u>gggttccggt</u>gcccaatcggaaccggaactgaaactggaaagtgtggtta ttgtgtctcgtcatggcgttcgcgctccgaccaaatttacgcagctgatg -continued caagatgtcaccccggacgccttctatacgtggccggtgaagctgggtga actgaccccgcgtggcggtgaactgatcgcctatctgggtcactactggc gtcagcgcctggtggcagatggtctgctgccgaaaaagggctgcccgcag agcggtcaagttgcaattatcgctgatgtcgacgaacgtacccgcaaaac gggtgaagcatttgcggccggtctggcaccggattgcgccattaccgttc atacgcaggcagataccagctctccggacccgctgttcaacccgctgaaa accggcgtctgtcagctggatgtcgcgcaagtgacggacgccattctgga acgtgcaggcggttccatcgctgattttaccggtcactaccagacggcat tccgtgaactggaacgcgttctgaactttccgcagtcaaatctggcgctg aaacgcgaaaagcaggatgaaagtgcgtccctgacccaagccctgccgag tgaactgaaagtctccgccgacaatgtgtcactgaccggcgcatggtcac tggcttcgatgctgacggaaattttctgctgcagcaagcacagggtatg ccggaaccgggttggggtcgtatcaccgattcgcatcagtggaacacgct gctgagcctgcacaatgcgcagttcgacctgctgcaacgtaccccggaag tggcacgttcgcgcgccacgccgctgctggatctgattaaaaccgctctg acgccgcatccgccgcagaagcaagcgtatggcgtgaccctgccgacgag cgttctgtttatcgcgggtcacgacaccaacctggcaaatctgggcggtg ctctggaactgcagtggaccctgccgggtcaaccggataacacgccgccg ggcggtgaactggttttcgaacgttggcgtcgcctgagcgacaattctca gtggatccaagttagcctggtctttcagaccctgcagcaaatgcgcgata aaaccccgctgttcctgaacacgccgccgggcgaagtgaagctgaccctg gcgggttgcgaagaacgtaacgcccagggcatgtgttctctggcaggttt tacccagattgttaatgaagcacgcatcccggcttgtagtctggggagtg gtggcagcggaggcgctatggttgataccttatcaggtttatcaagtgag caaggtcagtccggtgatatgacaattgaagaagatagtgctacccatat taaattctcaaaacgtgatgaggacggcaaagagttagctggtgcaacta tggagttgcgtgattcatctggtaaaactattagtacatggatttcagat ggacaagtgaaagatttctacctgtatccaggaaaatatacatttgtcga aaccgcagcaccagacggttatgaggtagcaactgctattacctttacag ttaatgagcaaggtcaggttactgtaaatggcaaagcaactaaaggtgac gctcatatt (SEQ ID NO: 119)
AHIVMVDAYKPIKGSGGSGAQSEPELKLESVVIVSRHGVRAPTKFTQLMQ

DVTPDAFYIWPVKLGELTPRGGELIAYLGHYWRQRLVADGLLPKKGCPQS

GQVAIIADVDERTRKTGEAFAAGLAPDCAITVHTQADTSSPDPLFNPLKT

GVCQLDVAQVTDAILERAGGSIADFTGHYQTAFRELERVLNFPQSNLALK

REKQDESASLTQALPSELKVSADNVSLTGAWSLASMLTEIFLLQQAQGMP

EPGWGRITDSHQWNILLSLHNAQFDLLQRTPEVARSRATPLLDLIKTALT

PHPPQKQAYGVILPTSVLFIAGHDINLANLGGALELQWTLPGQPDNTPPG

GELVFERWRRLSDNSQWIQVSLVFQTLQQMRDKTPLFLNTPPGEVKLTLA

GCEERNAQGMCSLAGFTQIVNEARIPACSLGSGGSGGAMVDTLSGLSSEQ

-continued

GQSGDMTIEEDSATHIKFSKRDEDGKELAGATMELRDSSGKTISTWISDG

QVKDFYLYPGKYTFVETAAPDGYEVATAITFTVNEQGQVTVNGKATKGDA

HI

As with the other engineered molecules described herein, optimization of the molecules and variants of the molecules and processes described herein can be used. Many different methods of optimization and mutagenesis may be employed, as described in Examples 2 and 3, and elsewhere in this specification.

One skilled in the art would also recognize that any of the target phytases could be used in any of the examples described above with different molecular structures and binding domains. For example, the tag- and catcher-domains can be attached to the CQBscks phytase, with or without linkers, to create a version of the phytase with improved thermal stability. Likewise any other structures, including inteins and coiled coils, could be used with CQBscks or any other target phytase to improve the target phytase's thermal stability.

Example 6. Assaying for Phytase Activity

Phytase assays are necessary for engineering phytases for improved thermal stability as described herein. See Engelen et al., 2001, Determination of phytase activity in feed by a colorimetric enzymatic method: collaborative interlaboratory study. *Journal of AOAC International,* 84(3), 629-633; and U.S. Pat. No. 7,629,139, issued Dec. 8, 2009, all of which are incorporated herein by reference as if fully set forth. These assays often rely on comparing the amount of phosphate released from sodium phytate over time with a phosphate standard curve and adjusting for background phosphate levels and enzyme levels. Measurements are commonly reported in phytase units (FTUs), which are defined as a mass of phosphate (commonly a micromole of inorganic phosphate) released per unit time (commonly one minute) under a given set of assay conditions (commonly 37° C., pH 5.5 under an excess of sodium phosphate, but other conditions are also reported and used in research and industry). These methods can be used with microbially produced phytases and engineered phytases, as well as those produced from other host expression systems, including plant expression systems.

To conduct the assay, enzyme extracts must be prepared from the expression host. Many different protein preparation methods exist and are known in the art. In each, case cells are disrupted using a method such as mechanical disruption (e.g., using a French press), liquid homogenization, sonication, repetitive freezing and thawing cycles, a detergent and chemical lysis, or manual grinding. Following lysis of the cells, the lysate may be used directly, or may be further fractionated to enrich for the desired protein, or even purified to a nearly pure protein substance (see "Current Protocols in Molecular Biology," 10.0.1-10.0.23, April, 2010, John Wiley & Sons, Inc., which is incorporated herein by reference as if fully set forth). Cellular lysis and protein extraction can even be automated to a large extent, facilitating the processing of many samples simultaneously. For protein extraction from plants, or seeds, generally larger tissue samples must first be disrupted, often through milling or grinding, and sometimes including freezing of the sample or repetitive freezing and thawing cycles, and then the protein can be extracted in a method similar to those described and referred to above.

Phytase activity was measured starting with up to 1 mL of cellular lysate, protein extracts are diluted 100-fold in assay buffer (250 mM sodium acetate, pH 5.5, 1 mM calcium chloride, 0.01% TWEEN® 20 (polyethylene glycol sorbitan monolaurate)). Seventy-five (75) microliters of the diluted extracts or 75 µl of buffer-only controls were dispensed into individual wells of a round-bottom 96-well plate. One-hundred fifty (150) microliters of freshly-prepared phytic acid (9.1 mM dodecasodium salt from Biosynth International, Staad, Switzerland, prepared in assay buffer) were added to each well. Plates were sealed and incubated for 60 minutes at 37° C. One-hundred fifty (150) microliters of stop solution (20 mM ammonium molybdate, 5 mM ammonium vanadate, 4% nitric acid) was added to each well, mixed thoroughly via pipetting, and allowed to incubate at room temperature for 10 minutes. Plates were centrifuged at 3000×G for 10 minutes, and 100 µL of the clarified supernatants were transferred to the wells of a flat-bottom 96-well plate. Absorbance at 415 nm from each sample was compared to that of negative controls (buffer-only, no enzyme) and potassium phosphate standards. The standard curve was prepared by mixing 50 µl of potassium phosphate standards (0-1.44 mM, prepared in assay buffer) with 100 µL of freshly-prepared phytic acid, followed by 100 µL of stop solution.

Example 7. Testing the Thermal Stability of Cyclized Phytases

In order to determine the thermal stability of an engineered phytase, the activity of the engineered phytase must be measured following different temperature treatments. Measurement of phytase activity can be conducted using a phytase assay as known in the art. Phytase assays that may be used to measure phytase activity are also described in Example 6 herein. While many different procedures could be used to investigate the thermal stability of an engineered phytase, one method was used herein as an example, recognizing that other procedures, experimental designs, and assay methods may be used in this analysis. Furthermore, the exact experimental conditions may vary dramatically depending on the breadth and depth of the analysis. Preferred procedures use a microbial expression system to rapidly produce the engineered phytase to be tested, and other control molecules that may be included in the evaluation, regardless of the final production system used to produce the engineered phytase at a greater scale. Microbial expression systems that may be used in this evaluation include *E. coli, Saccharomyces cerevisiae, Pichia pastoris, Bacillus, Aspergillus niger*, and *Trichoderma reesei* expression systems, although other systems may also be used. Following evaluation from a microbial expression system, it would be beneficial to repeat the evaluation using materials produced by the final production system whenever those materials are available.

To evaluate the thermal stability of an engineered phytase, it is desirable to test the engineered phytase and corresponding target phytase (without any molecular structures attached to the target phytase), at different temperatures, and for different lengths of time, under desirable conditions. Ideally, the experimental design for these tests would use a known molar quantity of engineered phytase and target phytase, incubating the molecules separately in a desired buffer for a length of time ranging from zero seconds (an untreated negative control) up to 30 minutes or more. Measurements can be taken at any desired time interval, but shorter time intervals will be necessary if activity values above the background of the assay are to be measured at higher temperatures. A constant temperature and pH of the buffer are used in each incubation. Temperatures in the range of 60° C. up to 90° C. or more would be of interest in determining the thermal stability of the engineered phytase relative to its corresponding target phytase. Likewise, pH values in the range from 2 up to 7 or more would be relevant for determining the thermal stability of the phytases at physiologically relevant levels of acidity. Following incubation, a sample of the incubation mixture is taken and the enzymatic activity is measured at a standard temperature (preferably between 25° C. and 37° C.) and pH (preferably between 5 and 7). The measured activities of the engineered phytase can then be compared against the target phytase and the improvement in thermal stability can be determined. Target phytases Phy02, Nov9X, and CQBscks were incubated individually along with the engineered Phy02 phytases described herein. Incubations were conducted at pH 5.5 in a water bath set at 65° C., 70° C., 75° C., 80° C., 85° C., and 90° C. For each incubation, samples were removed at 15 seconds, 40 seconds, 1 minute, 1.5 minutes, 2 minutes, 3 minutes, 5 minutes, 10 minutes, and 15 minutes. Prior to each incubation, a sample was taken to represent the zero time point, where no elevated temperature exposure occurred. The activity measured at the zero time point was within the experimental variation of the maximum activity observed in the experiment. From the zero time point and each incubation sample, the activity was measured in triplicate as described in Example 6, at 37° C. and pH 5.5. The activity of the engineered Phy02 phytases were then compared with the activity of the target phytases Phy02, Nov9X, and CQBscks. Nov9X showed the lowest activity across the treatments, with Phy02 and CQBscks showing greater activity at the different treatments. Engineered Phy02 phytases were selected that had elevated activity relative to the target enzymes in the different treatments.

Often times, experimental conditions are less than ideal and variations on the procedures described in this example are used. It is desirable to make activity measurements in at least triplicate, to be able to determine the variation in the activity measurement under a given set of conditions, but in some case only duplicate or single measurements may be feasible. In many cases, it's not feasible to purify each engineered enzyme or target enzyme in order to use equimolar concentrations. Often times, this is also not necessary given that expression levels for the different phytase enzymes from a given expression system may be similar. In these cases, enzyme loading into the incubations may be based upon culture volume, lysate volume, amount of total protein, or a similar variable. It's also not necessary to use purified enzyme in these evaluations, as the relative change in thermal stability can be used to compare enzymes and evaluate improvements in thermal stability. To evaluate the relative changes in thermal stability, the activity levels measured across time points at a given temperature are normalized to the zero time point by dividing the activity measured at all subsequent time points by the activity measured at the zero time point and multiplying by 100 percent. Thus, if for example an engineered Phy02 enzyme was measured to have 1000 FTU at the zero time point, and the following measurements were made at a given temperature (for example 90° C.) 950 FTU at 15 seconds, 902 FTU at 40 seconds, 857 FTU at one minute, 797 FTU at 1.5 minutes, 741 FTU at two minutes, 669 FTU at three minutes, 545 FTU at five minutes, 400 FTU at 10 minutes, and 238

FTU at 15 minutes, then the percent activity measurements would be calculated to give 100% (0 s), 95% (15s), 90.2% (40s), 85.7% (1 m), 79.7% (1.5m), 74.1% (2m), 66.9% (3m), 54.5% (5m), 40.0% (10m), and 23.8% (15m). If the corresponding values for the target enzyme were determined to be 100% (0 s), 85% (15s), 60.2% (40s), 25.7% (1m), 5.1% (1.5m), 1.3% (2m), 1.5% (3m), 0.9% (5m), 0.0% (10m), and 0.0% (15m), then it would be clear to one skilled in the art that the engineered Phy02 phytase had improved thermal stability relative to the target phytase. This procedure may be repeated at multiple temperatures and other pH values to define the differences in thermal stability between the engineered phytase and target phytase in greater detail and more precision. Using relative measurements and readily available automation, many engineered phytase variants can be readily screened and evaluated, and the most improved enzymes selected for commercial use.

Furthermore, other methods exist to determine thermal stability. Differential scanning calorimetry is a method known in the art, which can provide very accurate measurements of thermal stability.

Example 8. Thermal Stability Optimization of Engineered Phytases

Any of the molecules or procedures described in the previous examples can be continued to develop further improvements in the engineered phytase's thermal stability or other properties. Properties of particular commercial and scientific interest include the specific activity of the engineered phytase, expression level of the engineered phytase in a variety of heterologous expression systems (including microbial expression systems, plant expression systems, and mammalian expression systems), gastric and pepsin stability of the engineered phytase, and pepsin digestibility of the engineered phytase. Many methods exist for further optimizing the engineered phytase to have improved thermal stability or other properties. These methods include site directed mutagenesis, saturation mutagenesis, random mutagenesis, sequence shuffling, modeling, and others. In addition, these methods can easily be employed using automated screening systems, enabling the evaluation of millions of variants within reasonable time frames.

For optimization of engineered phytases whose coding sequences comprise an intein sequence, several methods can be particularly useful, including saturating mutagenesis and site directed mutagenesis. It is known in the art that mutations which occur near the intein-extein junction can have a significant impact on intein splicing, thus enabling the development of molecules that bind but don't splice, bind and create an isopeptide, bind and selectively cleave one portion of the split intein, or bind and fully splice to form a covalent bond at the insertion site (Xu, M. Q., & Perler, F. B. (1996). The mechanism of protein splicing and its modulation by mutation. *The EMBO journal,* 15(19), 5146, which is incorporated herein by reference as if fully set forth). Thus mutations at the −3 to −1 position in the target phytase at the intein junction, as well as mutations at the +1 to +3 positions relative to the intein insertion site commonly have a significant effect on the extent of the binding and splicing reactions, as well as the rate of reaction under different conditions. Mutations at these sites may improve the rate of splicing, thereby improving the rate of cyclization of the phytase and in some cases the observed thermal stability of the enzyme (as evaluated in Example 7). Because preferred insertion cassettes have been identified for many inteins, these cassettes may be successfully used in a target phytase backbone to improve intein splicing and therefore the thermal stability of the resulting engineered phytase or in linkers for the same purpose and effect. Similarly, other mutations in the protein coding sequence, including the molecular structures, may be used to improve thermal stability. For insertion cassettes for inteins, see Apgar et al. 2012, which is incorporated herein by reference as if fully set forth.

Specific activity, heterologous expression levels, gastric stability, and pepsin digestion may also be improved by further mutagenesis studies on an engineered phytase constructed in this study. The procedures used to optimize these properties would be carried out in an analogous way to thermal stability optimization, but in each case a different property would be considered in the evaluations program.

Example 9. Descriptions of Expression Cassettes for Engineered Phytases

Cyclic Phytase Sequences and Maps for Plant Expression.

Figure 8:
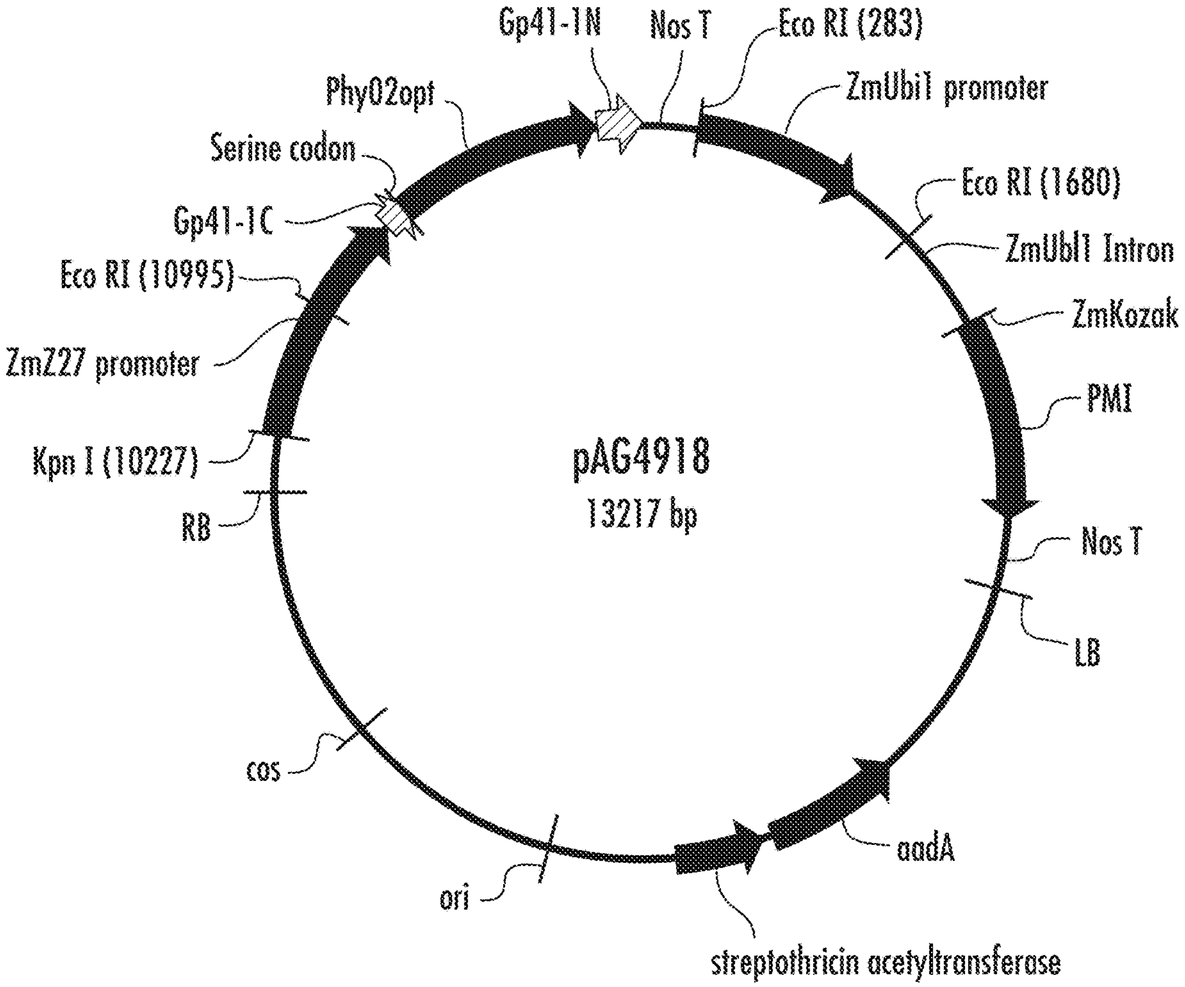
FIG. 8 is a schematic diagram illustrating an expression vector pAG4918.

Sequences containing different variants of cyclic phytases for plant expression have been assembled as expression cassettes with KpnI restriction site at 5' and EcoRI restriction site at 3' ends. All sequences for individual genetic elements were codon optimized for expression in maize. Two cassettes per each individual sequence were designed with one for cytoplasmic and the other for endoplasmic reticulum (ER) targeted protein expression. To generate final plant expression constructs, each expression cassette can be cloned into KpnI-EcoRI digested vector such as pAG4500. A representative map of resulting construct pAG4918 which contains expression cassette ZmZ27:Gp41-1C:Phy02opt: Gp41-1N:NosT (the Phy02opt cassette) cloned in this way is illustrated on FIG. 8. As shown in FIG. 8, the Phy02opt expression cassette including polynucleotides encoding the ZmZ27 promoter, Gp41-1C intein, Phy02opt phytase, Gp41-1N intein, and NosT terminator can be introduced into pAG4918 at the KpnI site (position 10227) and the EcoRI site (position 283). pAG4918 also carries a plant selectable marker comprised of a *Zea mays* ubiquitin (ZmUbi1) promoter, a *Zea mays* ubiquitin (ZmUbi1) intron, a *Zea mays* (Zm) Kozak, the phosphomannose isomerase coding sequence, and NosT terminator a phosphomannose isomerase (PMI) gene, and the NosT terminator. Both the Phy02 opt and the plant selectable marker cassettes are integrated into pAG4918 between the right border (RT) and the left border (LB). pAG4918 includes the spectinomycin adenylyltransferase gene (aadA), the streptothricin adenyltransferase gene, the cohesive site (cos) of bacteriophage λ and the Ori origin of replication. pAG4918 or similar vectors can be transferred from *E. coli* to *Agrobacterium tumefaciens* LBA4404 via conjugal transfer, during which the plasmid will integrate into pSB1 (a resident Ti plasmid) via homologous recombination. Co-culture of the resulting recombinant *Agrobacterium* strain with plant cells can result in the transfer of the pAG4918-derived DNA to the plant genome. Embodiments herein include a transformation vector having any one of engineered phytases.

Plant transformation vectors were assembled by inserting the expression cassettes or constructs described herein between the *Agrobacterium* T-DNA right border (RB) and left border (LB) sequences of pAG4500 or any suitable plasmid.

Figure 9A:
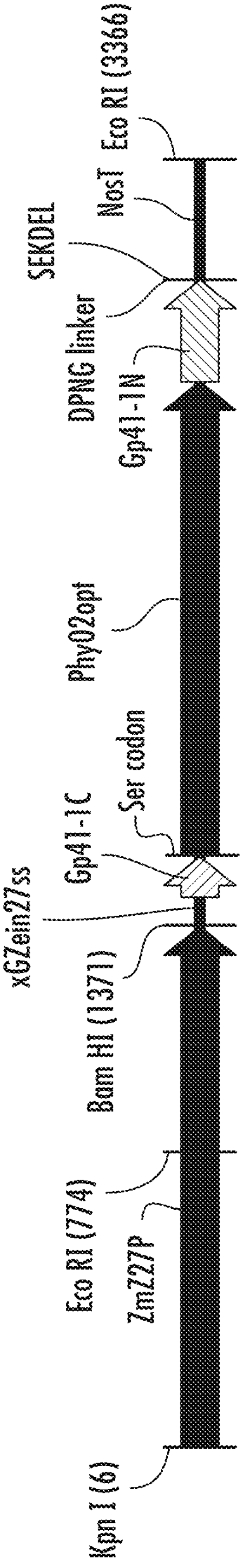
FIGS. 9A-9C are schematic diagrams illustrating expression cassettes for selected engineered phytases with split inteins attached to the ends of the phytase coding sequences.
Figure 9B:
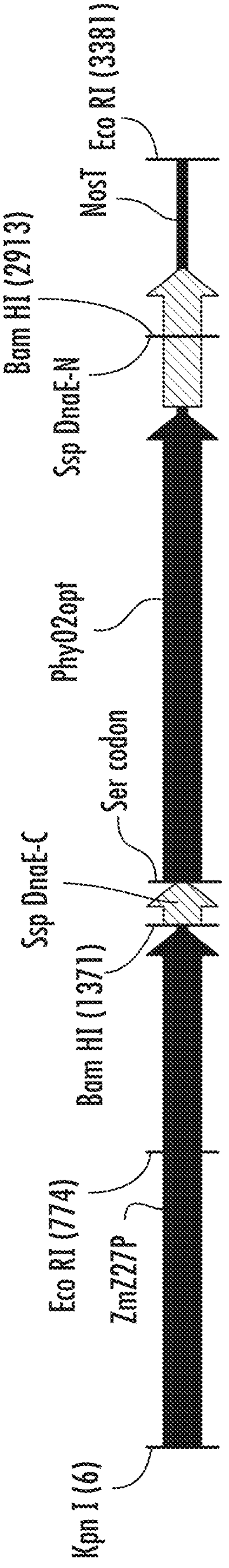
Figure 9C:
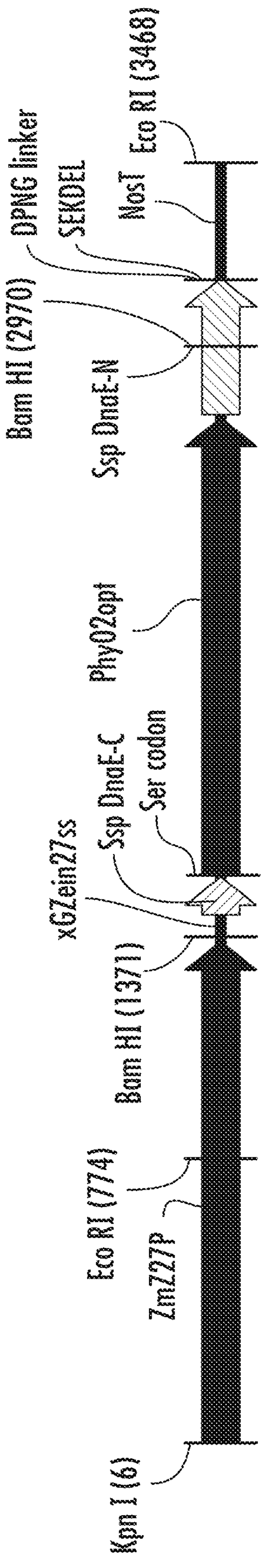

FIGS. 9A-9C illustrate examples of expression cassettes for selected engineered phytases with split inteins attached to the ends of the phytase coding sequences. FIG. 9A illustrates the Phy02opt expression cassette the ZmZ27P: xGZein27ss: Gp41-1C: Phy02opt: Gp41-1N: DPNG (SEQ ID NO: 199) SEKDEL (SEQ ID NO: 140): NosT including polynucleotides encoding the ZmZ27 promoter, GZein27ss signal sequence, Gp41-1C intein, Phy02opt phytase, Gp41-1N intein, DPNG linker, SEKDEL (SEQ ID NO: 140) terminal extension sequence, and NosT terminator that can be introduced into pAG4918 at the KpnI site (position 10227) and the EcoR1 site (position 283). pAG4918 also carries a plant selectable marker comprised of a *Zea mays* ubiquitin (ZmUbi1) promoter, a *Zea mays* ubiquitin (ZmUbi1) intron, a *Zea mays* (Zm) Kozak, the phosphomannose isomerase (PMI) coding sequence, and NosT terminator. FIG. 9B illustrates the ZmZ27P:Ssp DnaE-C: Phy02opt:Ssp DnaE-N:NosT expression cassette. Referring to FIG. 9B, the expression cassette includes the ZmZ27 promoter, Ssp DnaE-C intein, Phy02opt phytase, Ssp DnaE-N intein, and NosT terminator. FIG. 9C illustrates the ZmZ27P:xGZein27ss:Ssp DnaE-C:Phy02opt:Ssp DnaE-N: DPNG (SEQ ID NO: 199) SEKDEL (SEQ ID NO: 140): NosT expression cassette. Referring to FIG. 9C, the expression cassette includes the ZmZ27 promoter, GZein27ss signal sequence, Ssp DnaE-C intein, Phy02opt phytase, Ssp DnaE-N intein, DPNG (SEQ ID NO: 199) linker, SEKDEL (SEQ ID NO: 140) terminal extension sequence, and NosT terminator.

FIGS. 10A-10H are schematic diagrams illustrating expression cassettes for selected engineered phytases with split intein attached to linkers that connect to the ends of the phytase coding sequences.

Figure 10A:
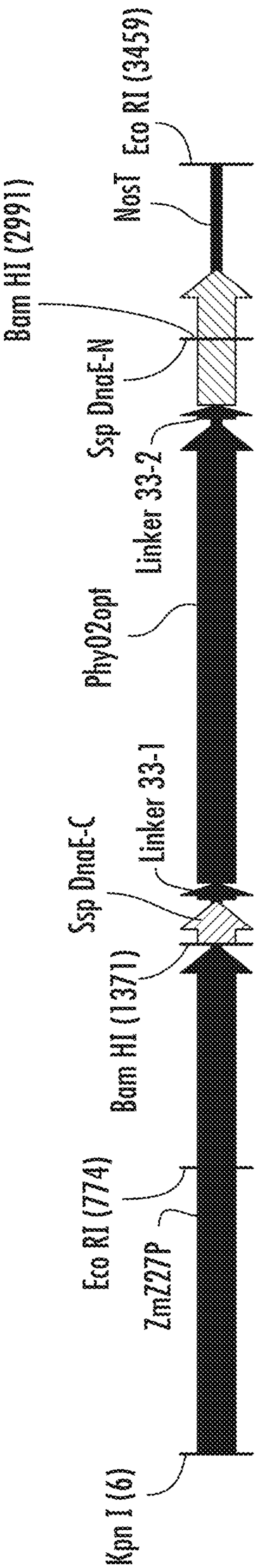
FIGS. 10A-10H are schematic diagrams illustrating expression cassettes for selected engineered phytases with split intein attached to linkers that connect to the ends of the phytase coding sequences.
Figure 10B:
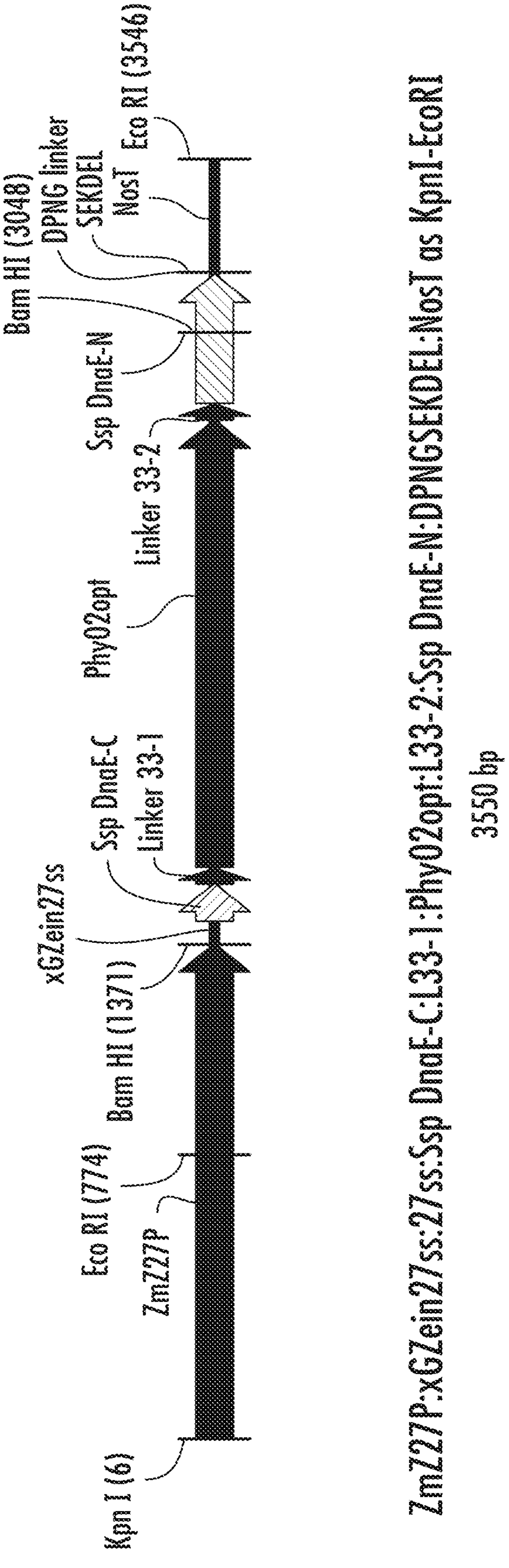
Figure 10C:
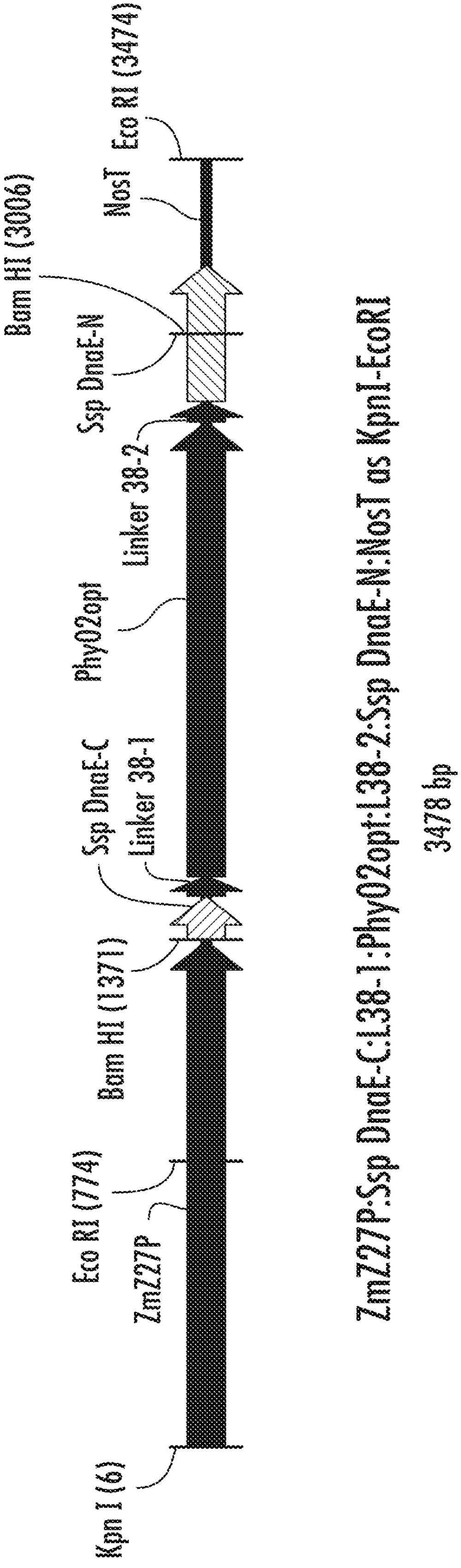
Figure 10D:
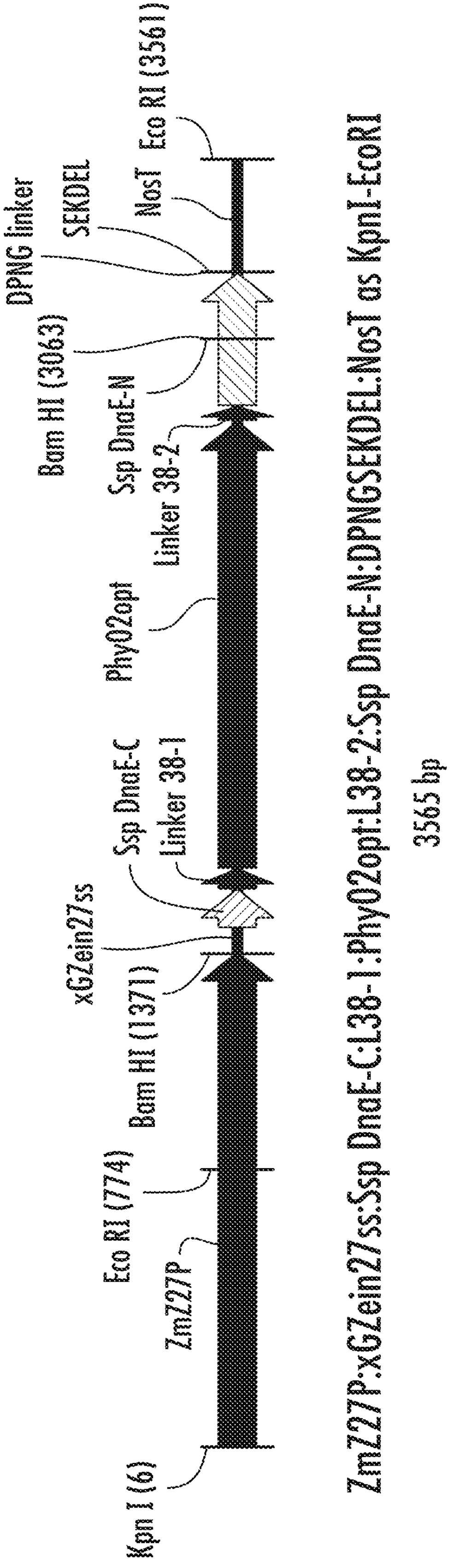
Figure 10E:
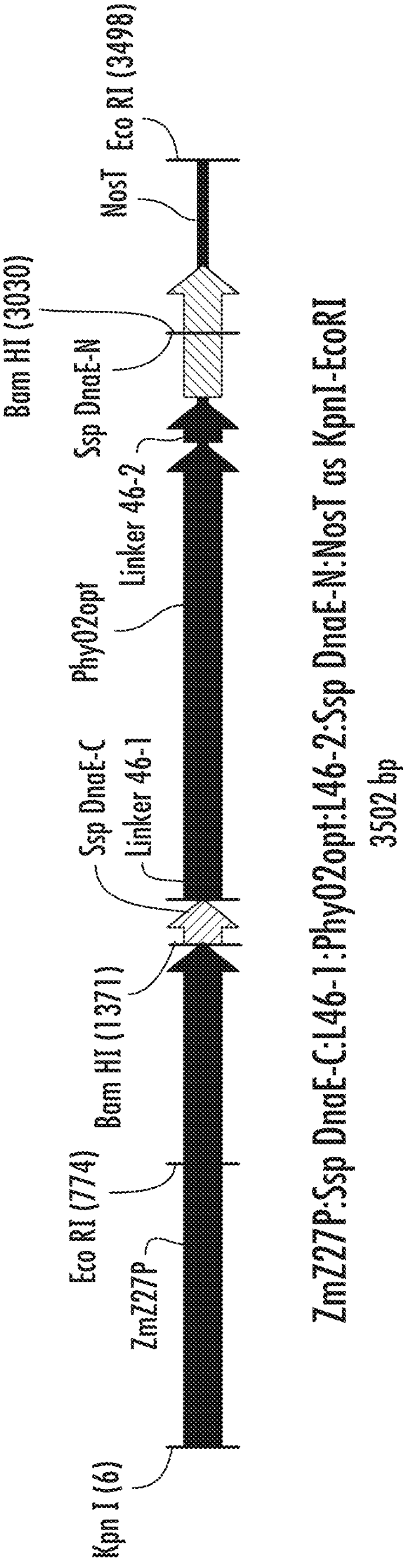
Figure 10F:
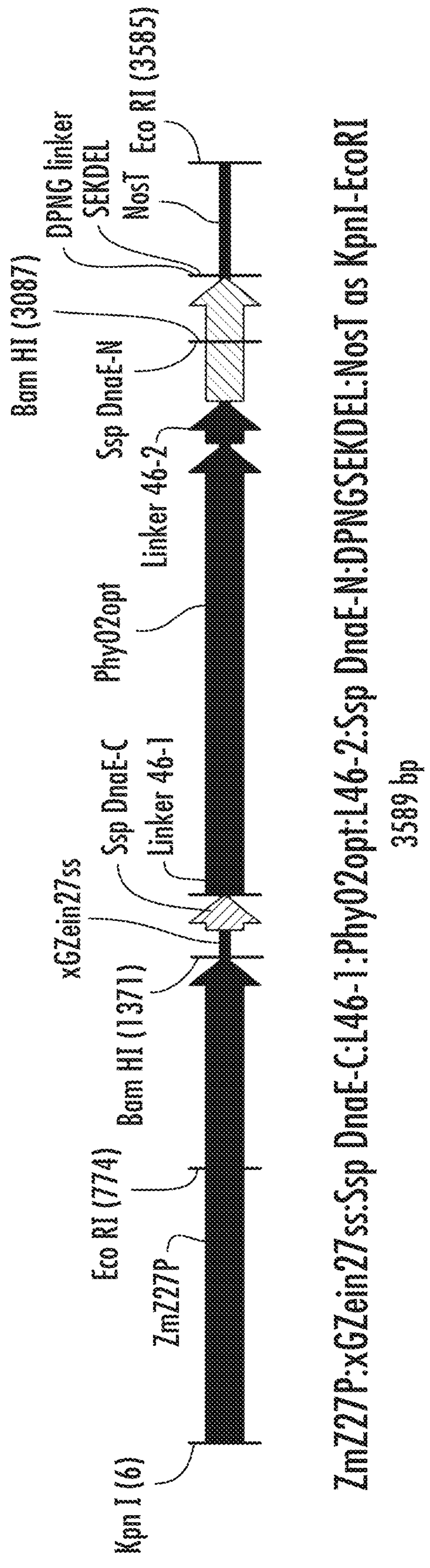
Figure 10G:
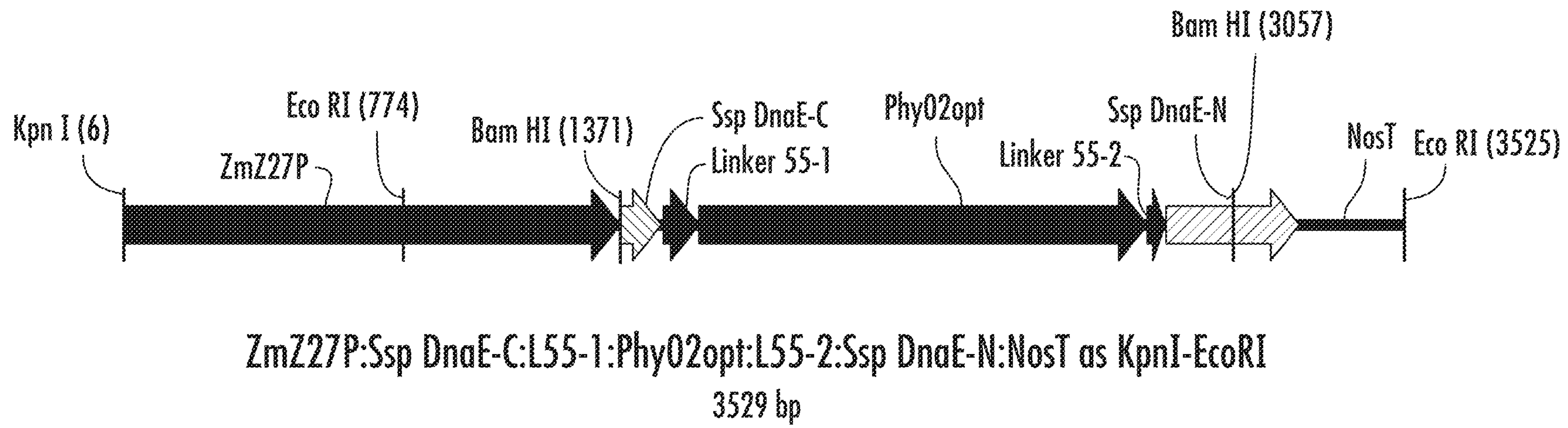
Figure 10H:
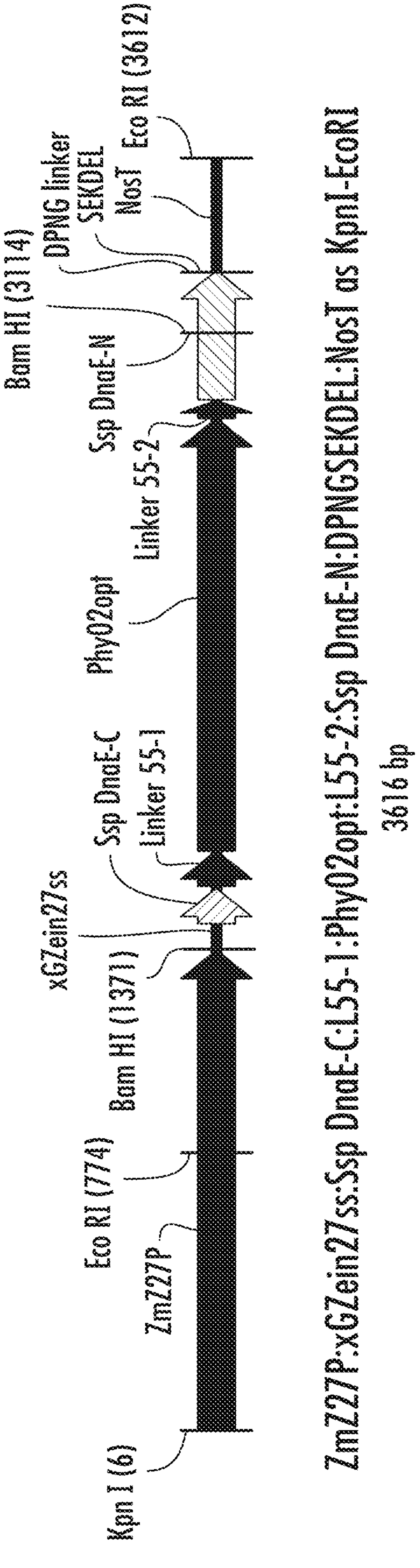

FIG. 10A illustrates the ZmZ27P:Ssp DnaE-C:L33-1: Phy02opt:L33-2:Ssp DnaE-N:NosT expression cassette. Referring to FIG. 10A the expression cassette includes the ZmZ27 promoter, Ssp DnaE-C intein, L33-1 linker (L33-1), Phy02opt phytase, L33-2 linker (L33-2), Ssp DnaE-N intein, and NosT terminator. FIG. 10B illustrates the ZmZ27P: xGZein27ss:Ssp DnaE-C:L33-1:Phy02opt:L33-2:Ssp DnaE-N:DPNG (SEQ ID NO: 199) SEKDEL (SEQ ID NO: 140): NosT expression cassette. Referring to FIG. 10B the expression cassette includes the ZmZ27 promoter, GZein27ss signal sequence, Ssp DnaE-C intein, L33-1 linker (L33-1), Phy02opt phytase, L33-2 linker (L33-2), Ssp DnaE-N intein, DPNG (SEQ ID NO: 199) linker, SEKDEL (SEQ ID NO: 140) terminal extension sequence, and NosT terminator. FIG. 10C illustrates the ZmZ27P:Ssp DnaE-C: L38-1:Phy02opt:L38-2:Ssp DnaE-N:NosT expression cassette. Referring to FIG. 10C the expression cassette includes the ZmZ27 promoter, Ssp DnaE-C intein, L38-1 linker (L38-1), Phy02opt phytase, L38-2 linker (L38-2), Ssp DnaE-N intein, and NosT terminator. FIG. 10D illustrates the ZmZ27P:xGZein27ss: Ssp DnaE-C:L38-1:Phy02opt: L38-2:Ssp DnaE-N:DPNG (SEQ ID NO: 199) SEKDEL (SEQ ID NO: 140):NosT expression cassette. Referring to FIG. 10D the expression cassette includes the ZmZ27 promoter, GZein27ss signal sequence, Ssp DnaE-C intein, L38-1 linker (L38-1), Phy02opt phytase, L38-2 linker (L38-2), Ssp DnaE-N intein, DPNG (SEQ ID NO: 199) linker, SEKDEL (SEQ ID NO: 140) terminal extension sequence and NosT terminator. FIG. 10E illustrates the ZmZ27P:Ssp DnaE-C:L46-1:Phy02opt:L46-2:Ssp DnaE-N:NosT expression cassette. Referring to FIG. 10E the expression cassette includes the ZmZ27 promoter, Ssp DnaE-C intein, L46-1 linker (L46-1), Phy02opt phytase, L46-2 linker (L46-2), Ssp DnaE-N intein, and NosT terminator. FIG. 10F illustrates the ZmZ27P:xGZein27ss:Ssp DnaE-C: L46-1:Phy02opt:L46-2: Ssp DnaE-N: DPNG (SEQ ID NO: 199) SEKDEL (SEQ ID NO: 140): NosT expression cassette. Referring to FIG. 10F the expression cassette includes the ZmZ27 promoter, GZein27ss signal sequence, Ssp DnaE-C intein, L46-1 linker (L46-1), Phy02opt phytase, L46-2 linker (L46-2), Ssp DnaE-N intein, DPNG (SEQ ID NO: 199) linker, SEKDEL (SEQ ID NO: 140) terminal extension sequence and NosT terminator. FIG. 10G illustrates the ZmZ27P:Ssp DnaE-C: L55-1:Phy02opt:L55-2:Ssp DnaE-N:NosT expression cassette. Referring to FIG. 10G the expression cassette includes the ZmZ27 promoter, GZein27ss signal sequence, Ssp DnaE-C intein, L55-1 linker (L55-1), Phy02opt phytase, L55-2 linker (L55-2), Ssp DnaE-N intein, DPNG (SEQ ID NO: 199) linker, SEKDEL (SEQ ID NO: 140) terminal extension sequence and NosT terminator. FIG. 10H illustrates the ZmZ27P:xGZein27ss:Ssp DnaE-C:L55-1: Phy02opt:L55-2:Ssp DnaE-N: DPNG (SEQ ID NO: 199) SEKDEL (SEQ ID NO: 140): NosT expression cassette. Referring to FIG. 10H the expression cassette includes the ZmZ27 promoter, GZein27ss signal sequence, Ssp DnaE-C intein, L55-1 linker (L55-1), Phy02opt phytase, L55-2 linker (L55-2), Ssp DnaE-N intein, DPNG (SEQ ID NO: 199) linker, SEKDEL (SEQ ID NO: 140) terminal extension sequence and NosT terminator. Each one of the cassettes shown in FIGS. 10A-10H has KpnI, EcoRI, and BamHI restriction sites, and can be cloned as a KpnI-EcoRI fragment into the T-DNA of the transformation vector.

TABLE 6

Construct list

| Vector | Expression cassette |
|---|---|
| pAG4918 | ZmZ27P:Gp41-1C:Phy02opt:Gp41-1N:NosT |
| pAG4919 | ZmZ27P:xGZein27ss:Gp41-1C:Phy02opt:Gp41-1N:DPNG (SEQ ID NO: 199) SEKDEL (SEQ ID NO: 140):NosT |
| pAG4920 | ZmZ27P:Ssp_DnaE—C:Phy02opt:Ssp_DnaE—N:NosT |
| pAG4921 | ZmZ27P:xGZein27ss:Ssp_DnaE—C:Phy02opt: Ssp_DnaE—N:DPNG (SEQ ID NO: 199) SEKDEL (SEQ ID NO: 140):NosT |
| pAG4922 | ZmZ27P:Ssp_DnaE:L33-1:Phy02opt:L33-2:NosT |
| pAG4923 | ZmZ27P:xGZein27ss:Ssp_DnaE:L33-1:Phy02opt:L33-2:DPNG (SEQ ID NO: 199) SEKDEL (SEQ ID NO: 140):NosT |
| pAG4924 | ZmZ27P:Ssp_DnaE:L38-1:Phy02opt:L38-2:NosT |
| pAG4925 | ZmZ27P:xGZein27ss:Ssp_DnaE:L38-1:Phy02opt:L38-2:DPNG (SEQ ID NO: 199) SEKDEL (SEQ ID NO: 140):NosT |
| pAG4926 | ZmZ27P:Ssp_DnaE:L46-1:Phy02opt:L46-2:NosT |
| pAG4927 | ZmZ27P:xGZein27ss:Ssp_DnaE:L46-1:Phy02opt:L46-2:DPNG (SEQ ID NO: 199) SEKDEL (SEQ ID NO: 140):NosT |
| pAG4928 | ZmZ27P:Ssp_DnaE:L55-1:Phy02opt:L55-2:NosT |
| pAG4929 | ZmZ27P:xGZein27ss:Ssp_DnaE:L55-1:Phy02opt:L55-2:DPNG (SEQ ID NO: 199) SEKDEL (SEQ ID NO: 140):NosT |

Nucleotide sequences in vectors pAG4924, pAG4926, and pAG4928 are identical to those in pAG4922 with the exception of two linker sequences. Similarly, all nucleotide sequences in constructs pAG4925, pAG4927 and pAG4929 are the same as in pAG4923 except for two linker sequences. The linker sequences that are specified on provided maps of expression cassettes pAG4918-pAG4929 include L33-1, L33-2, L38-1, L38-2, L46-1, L46-2, L55-1 and L55-2 and are shown in Table 4.

Relevant sequences of plant expression cassettes for cyclic phytases

>ZmZ27P:Gp411C:Phy02opt:Gp411N:NosT

ZmZ27P is shown in bold upper case font and italicized, gp411 is underlined, NosT is italicized (SEQ TD NO: 128)

ggtaccAAAGTAATCATATTATTTTATGTGTGAATCTTCTTTACTTTTTCATTTGATTATGATTAT

GAAGGTATGACCTTCATAACCTTCGTCCGAAATCCATTATATCCAAAGGAAAATAATGCTTCGAAG

GACGAAGGATTTTGATATTTAACATTTTATGTTGCCTTGTTCTTAATTCATAGCATTTGAGAACAA

GTCCCCAACACCAATCTTTATCTTTACTATATTAAAGCACCAGTTCAACGATCGTCTCGTGTCAAT

ATTATTAAAAAACTCCTACATTTCTTTATAATCAACCCGCACTCTTATAATCTCTTCTCTTACTAC

TATAATAAGAGAGTTTATGTACAAAATAAGGTGAAATTATGTATAAGTGTTCTGGACCTTGGTTGT

TGGCTCATATTCACACAACCTAATCAATAGAAAACATATGTTTTATTAAAACAAAATTTATCATAT

ATATATATATATATATATATATATATATATATATATATAATATAAACCGTAGCAATGCACAGGCAT

ATGACTAGTGGCAACTTAATACCATGTGTGTATTAAGATGAATAAGAGGTATCCAAATAAATAACT

TGTTCGCTTACGTCTGGATCGAAAGGGGTTGGAAACGATTAAATCTCTTCCTAGTCAAAATTAAAT

AGAAGGAGATTTAATCGATTTCTCCCAATCCCCTTCGATCCAGGTGCAACCGAATAAGTCCTTAAA

TGTTGAGGAACACGAAACAACCATGCATTGGCATGTAAAGCTCCAAGAATTCGTTGTATCCTTAAC

AACTCACAGAACATCAACCAAAATTGCACGTCAAGGGTATTGGGTAAGAAACAATCAAACAAATCC

TCTCTGTGTGCAAAGAAACACGGTGAGTCATGCCGAGATCATACTCATCTGATATACATGCTTACA

GCTCACAAGACATTACAAACAACTCATATTGCATTACAAAGATCGTTTCATGAAAAATAAAATAGG

CCGGAACAGGACAAAAATCCTTGACGTGTAAAGTAAATTTACAACAAAAAAAAAGCCATATGTCAA

GCTAAATCTAATTCGTTTTACGTAGATCAACAACCTGTAGAAGGCAACAAAACTGAGCCACGCAGA

AGTACAGAATGATTCCAGATGAACCATCGACGTGCTACGTAAAGAGAGTGACGAGTCATATACATT

TGGCAAGAAACCATGAAGCTGCCTACAGCCGTCTCGGTGGCATAAGAACACAAGAAATTGTGTTAA

TTAATCAAAGCTATAAATAACGCTCGCATGCCTGTGCACTTCTCCATCACCACCACTGGGTCTTCA

GACCATTAGCTTTATCTACTCCAGAGCGCAGAAGAACCCGATCGACACCggatccaccATGATGCT

GAAGAAGATCCTGAAGATCGAGGAGCTGGACGAGAGGGAGCTGATCGACATCGAGGTGAGCGGCAA

CCACCTGTTCTACGCCAACGACATCCTGACCCACAACAGCGCCCAGTCCGAGCCGGAGCTGAAGCT

GGAGTCCGTGGTGATCGTGTCGCGCCACGGGGTGCGCGCCCCGACCAAGTTCACGCAGCTCATGCA

GGACGTGACCCCGGACGCCTTCTACACCTGGCCGGTGAAGCTCGGCGAGCTGACCCCGCGCGGCGG

CGAGCTGATCGCCTACCTCGGCCACTACTGGCGCCAGCGCCTCGTGGCCGACGGCCTCCTCCCGAA

GAAGGGCTGCCCGCAGTCCGGCCAGGTGGCGATCATCGCCGACGTGGACGAGCGCACCCGCAAGAC

GGGCGAGGCCTTCGCCGCCGGCCTCGCCCCGGACTGCGCCATCACCGTGCACACCCAGGCCGACAC

CTCCTCCCCGGACCCGCTCTTCAACCCGCTCAAGACCGGCGTGTGCCAGCTCGACGTGGCCCAGGT

GACCGACGCCATCCTGGAGCGCGCCGGCGGCTCCATCGCCGACTTCACCGGCCACTACCAGACCGC

CTTCCGCGAGCTGGAGCGCGTGCTCAACTTCCCGCAGTCGAACCTCGCCCTCAAGCGCGAGAAGCA

GGACGAGTCCGCCTCCCTCACCCAGGCCCTCCCGTCCGAGCTGAAGGTGTCCGCCGACAACGTGTC

CCTCACCGGCGCCTGGTCCCTCGCCTCCATGCTCACCGAAATCTTCCTCCTCCAGCAGGCCCAGGG

CATGCCGGAGCCGGGCTGGGGCCGCATCACCGACTCCCACCAGTGGAACACCCTCCTCTCCCTCCA

CAACGCCCAGTTCGACCTCCTCCAGCGCACCCCGGAGGTGGCCCGCTCCCGCGCCACCCCGCTCCT

CGACCTCATCAAGACCGCCCTCACCCCGCACCCGCCGCAGAAGCAGGCCTACGGCGTGACCCTCCC

GACCTCGGTGCTCTTCATCGCCGGCCACGACACCAACCTCGCCAACCTCGGCGGCGCCCTGGAGCT

GCAGTGGACCCTCCCGGGCCAGCCGGACAACACCCCGCCGGGCGGCGAGCTGGTGTTCGAGCGCTG

GCGCCGCCTCTCCGACAACTCCCAGTGGATTCAGGTGTCCCTCGTGTTCCAGACCCTCCAGCAGAT

GCGCGACAAGACCCCGCTCTTCCTCAACACCCCGCCGGGCGAGGTGAAGCTCACCCTGGCCGGCTG

-continued

CGAGGAGCGCAACGCGCAGGGCATGTGCTCCCTCGCCGGCTTCACCCAGATCGTGAACGAGGCCCG

CATCCCGGCCTGCTCCCTCTGCCTGGACCTGAAGACCCAGGTGCAGACCCCGCAGGGCATGAAGGA

GATCAGCAACATCCAGGTGGGCGACCTGGTGCTGAGCAACACCGGCTACAACGAGGTGCTGAACGT

GTTCCCGAAGAGCAAGAAGAAGAGCTACAAGATCACCCTGGAGGACGGCAAGGAGATCATCTGCAG

CGAGGAGCACCTGTTCCCGACCCAGACCGGCGAGATGAACATCAGCGGCGGCCTGAAGGAGGGCAT

GTGCCTGTACGTGAAGGAGTGAcctagg*tccccgaatttccccgatcgttcaaacatttggcaata*

*aagtttcttaagattgaatcctgttgccggtcttgcgatgattatcatataatttctgttgaatta*

*cgttaagcatgtaataattaacatgtaatgcatgacgttatttatgagatgggtttttatgattag*

*agtcccgcaattatacatttaatacgcgatagaaaacaaaatatagcgcgcaaactaggataaatt*

*atcgcgcgcggtgtcatctatgttactagatcgggaattg*

>ZmZ27P:xGZein27ss:Gp411-C:Phy02opt:Gp411-N: DPNG (SEQ ID NO: 199) SEKDEL (SEQ ID NO: 140): NosT ZmZ27P is shown in bold upper case font and italicized, gp411 is underlined, DPNG (SEQ ID NO: 199) is in upper case and italicized, SEKDEL (SEQ ID NO: 140) is in bold upper case, NosT is italicized.

(SEQ TD NO: 129)

ggtaccAAAGTAATCATATTATTTTATGTGTGAATCTTCTTTACTTTTTCATTTGATTATGATTATGAAG

GTATGACCTTCATAACCTTCGTCCGAAATCCATTATATCCAAAGGAAAATAATGCTTCGAAGGACGAAGG

ATTTTGATATTTAACATTTTATGTTGCCTTGTTCTTAATTCATAGCATTTGAGAACAAGTCCCCAACACC

AATCTTTATCTTTACTATATTAAAGCACCAGTTCAACGATCGTCTCGTGTCAATATTATTAAAAAACTCC

TACATTTCTTTATAATCAACCCGCACTCTTATAATCTCTTCTCTTACTACTATAATAAGAGAGTTTATGT

ACAAAATAAGGTGAAATTATGTATAAGTGTTCTGGACCTTGGTTGTTGGCTCATATTCACACAACCTAAT

CAATAGAAAACATATGTTTTATTAAAACAAAATTTATCATATATATATATATATATATATATATATATAT

ATATATATATAATATAAACCGTAGCAATGCACAGGCATATGACTAGTGGCAACTTAATACCATGTGTGTA

TTAAGATGAATAAGAGGTATCCAAATAAATAACTTGTTCGCTTACGTCTGGATCGAAAGGGGTTGGAAAC

GATTAAATCTCTTCCTAGTCAAAATTAAATAGAAGGAGATTTAATCGATTTCTCCCAATCCCCTTCGATC

CAGGTGCAACCGAATAAGTCCTTAAATGTTGAGGAACACGAAACAACCATGCATTGGCATGTAAAGCTCC

AAGAATTCGTTGTATCCTTAACAACTCACAGAACATCAACCAAAATTGCACGTCAAGGGTATTGGGTAAG

AAACAATCAAACAAATCCTCTCTGTGTGCAAAGAAACACGGTGAGTCATGCCGAGATCATACTCATCTGA

TATACATGCTTACAGCTCACAAGACATTACAAACAACTCATATTGCATTACAAAGATCGTTTCATGAAAA

ATAAAATAGGCCGGAACAGGACAAAAATCCTTGACGTGTAAAGTAAATTTACAACAAAAAAAAAGCCATA

TGTCAAGCTAAATCTAATTCGTTTTACGTAGATCAACAACCTGTAGAAGGCAACAAAACTGAGCCACGCA

GAAGTACAGAATGATTCCAGATGAACCATCGACGTGCTACGTAAAGAGAGTGACGAGTCATATACATTTG

GCAAGAAACCATGAAGCTGCCTACAGCCGTCTCGGTGGCATAAGAACACAAGAAATTGTGTTAATTAATC

AAAGCTATAAATAACGCTCGCATGCCTGTGCACTTCTCCATCACCACCACTGGGTCTTCAGACCATTAGC

TTTATCTACTCCAGAGCGCAGAAGAACCCGATCGACACCggatccaccATGAGGGTGTTGCTCGTTGCCC

TCGCTCTCCTGGCTCTCGCTGCGAGCGCCACCAGCATGATGCTGAAGAAGATCCTGAAGATCGAGGAGCT

GGACGAGAGGGAGCTGATCGACATCGAGGTGAGCGGCAACCACCTGTTCTACGCCAACGACATCCTGACC

CACAACAGCGCTGCGCAGTCCGAGCCGGAGCTGAAGCTGGAGTCCGTGGTGATCGTGTCGCGCCACGGGG

TGCGCGCCCCGACCAAGTTCACGCAGCTCATGCAGGACGTGACCCCGGACGCCTTCTACACCTGGCCGGT

-continued

GAAGCTCGGCGAGCTGACCCCGCGCGGCGGCGAGCTGATCGCCTACCTCGGCCACTACTGGCGCCAGCGC

CTCGTGGCCGACGGCCTCCTCCCGAAGAAGGGCTGCCCGCAGTCCGGCCAGGTGGCGATCATCGCCGACG

TGGACGAGCGCACCCGCAAGACGGGCGAGGCCTTCGCCGCCGGCCTCGCCCCGGACTGCGCCATCACCGT

GCACACCCAGGCCGACACCTCCTCCCCGGACCCGCTCTTCAACCCGCTCAAGACCGGCGTGTGCCAGCTC

GACGTGGCCCAGGTGACCGACGCCATCCTGGAGCGCGCCGGCGGCTCCATCGCCGACTTCACCGGCCACT

ACCAGACCGCCTTCCGCGAGCTGGAGCGCGTGCTCAACTTCCCGCAGTCGAACCTCGCCCTCAAGCGCGA

GAAGCAGGACGAGTCCGCCTCCCTCACCCAGGCCCTCCCGTCCGAGCTGAAGGTGTCCGCCGACAACGTG

TCCCTCACCGGCGCCTGGTCCCTCGCCTCCATGCTCACCGAAATCTTCCTCCTCCAGCAGGCCCAGGGCA

TGCCGGAGCCGGGCTGGGGCCGCATCACCGACTCCCACCAGTGGAACACCCTCCTCTCCCTCCACAACGC

CCAGTTCGACCTCCTCCAGCGCACCCCGGAGGTGGCCCGCTCCCGCGCCACCCCGCTCCTCGACCTCATC

AAGACCGCCCTCACCCCGCACCCGCCGCAGAAGCAGGCCTACGGCGTGACCCTCCCGACCTCGGTGCTCT

TCATCGCCGGCCACGACACCAACCTCGCCAACCTCGGCGGCGCCCTGGAGCTGCAGTGGACCCTCCCGGG

CCAGCCGGACAACACCCCGCCGGGCGGCGAGCTGGTGTTCGAGCGCTGGCGCCGCCTCTCCGACAACTCC

CAGTGGATTCAGGTGTCCCTCGTGTTCCAGACCCTCCAGCAGATGCGCGACAAGACCCCGCTCTTCCTCA

ACACCCCGCCGGGCGAGGTGAAGCTCACCCTGGCCGGCTGCGAGGAGCGCAACGCGCAGGGCATGTGCTC

CCTCGCCGGCTTCACCCAGATCGTGAACGAGGCCCGCATCCCGGCCTGCTCCCTCTGCCTGGACCTGAAG

ACCCAGGTGCAGACCCCGCAGGGCATGAAGGAGATCAGCAACATCCAGGTGGGCGACCTGGTGCTGAGCA

ACACCGGCTACAACGAGGTGCTGAACGTGTTCCCGAAGAGCAAGAAGAAGAGCTACAAGATCACCCTGGA

GGACGGCAAGGAGATCATCTGCAGCGAGGAGCACCTGTTCCCGACCCAGACCGGCGAGATGAACATCAGC

GGCGGCCTGAAGGAGGGCATGTGCCTGTACGTGAAGGAG*GACCCGAACGGC*TCCGAGAAGGACGAGCTGT

GAcctagg*tccccgaatttccccgatcgttcaaacatttggcaataaagtttcttaagattgaatcctgt*

*tgccggtcttgcgatgattatcatataatttctgttgaattacgttaagcatgtaataattaacatgtaa*

*tgcatgacgttatttatgagatgggtttttatgattagagtcccgcaattatacatttaatacgcgatag*

*aaaacaaaatatagcgcgcaaactaggataaattatcgcgcgcggtgtcatctatgttactagatcggga*

*attg*

>ZmZ27P:Ssp DnaE-C:Phy02opt:SsD DnaE-N:NosT

ZmZ27P is shown in bold upper case font and italicized, SSp_DnaE is underlined, NosT is italicized.

(SEQ TD NO: 130)

ggtaccAAAGTAATCATATTATTTTATGTGTGAATCTTCTTTACTTTTTCATTTGATTATGATTAT

GAAGGTATGACCTTCATAACCTTCGTCCGAAATCCATTATATCCAAAGGAAAATAATGCTTCGAAG

GACGAAGGATTTTGATATTTAACATTTTATGTTGCCTTGTTCTTAATTCATAGCATTTGAGAACAA

GTCCCCAACACCAATCTTTATCTTTACTATATTAAAGCACCAGTTCAACGATCGTCTCGTGTCAAT

ATTATTAAAAAACTCCTACATTTCTTTATAATCAACCCGCACTCTTATAATCTCTTCTCTTACTAC

TATAATAAGAGAGTTTATGTACAAAATAAGGTGAAATTATGTATAAGTGTTCTGGACCTTGGTTGT

TGGCTCATATTCACACAACCTAATCAATAGAAAACATATGTTTTATTAAAACAAAATTTATCATAT

ATATATATATATATATATATATATATATATATATATATAATATAAACCGTAGCAATGCACAGGCAT

ATGACTAGTGGCAACTTAATACCATGTGTGTATTAAGATGAATAAGAGGTATCCAAATAAATAACT

TGTTCGCTTACGTCTGGATCGAAAGGGGTTGGAAACGATTAAATCTCTTCCTAGTCAAAATTAAAT

AGAAGGAGATTTAATCGATTTCTCCCAATCCCCTTCGATCCAGGTGCAACCGAATAAGTCCTTAAA

TGTTGAGGAACACGAAACAACCATGCATTGGCATGTAAAGCTCCAAGAATTCGTTGTATCCTTAAC

-continued

AACTCACAGAACATCAACCAAAATTGCACGTCAAGGGTATTGGGTAAGAAACAATCAAACAAATCC

TCTCTGTGTGCAAAGAAACACGGTGAGTCATGCCGAGATCATACTCATCTGATATACATGCTTACA

GCTCACAAGACATTACAAACAACTCATATTGCATTACAAAGATCGTTTCATGAAAAATAAAATAGG

CCGGAACAGGACAAAAATCCTTGACGTGTAAAGTAAATTTACAACAAAAAAAAAGCCATATGTCAA

GCTAAATCTAATTCGTTTTACGTAGATCAACAACCTGTAGAAGGCAACAAAACTGAGCCACGCAGA

AGTACAGAATGATTCCAGATGAACCATCGACGTGCTACGTAAAGAGAGTGACGAGTCATATACATT

TGGCAAGAAACCATGAAGCTGCCTACAGCCGTCTCGGTGGCATAAGAACACAAGAAATTGTGTTAA

TTAATCAAAGCTATAAATAACGCTCGCATGCCTGTGCACTTCTCCATCACCACCACTGGGTCTTCA

GACCATTAGCTTTATCTACTCCAGAGCGCAGAAGAACCCGATCGACACCggatccaccATGGTTAA

GGTGATTGGAAGACGTTCTCTTGGTGTTCAAAGGATCTTCGATATCGGATTGCCACAAGACCACAA

CTTTCTTCTCGCTAATGGTGCCATCGCTGCCAATAGCGCTGCGCAGTCCGAGCCGGAGCTGAAGCT

GGAGTCCGTGGTGATCGTGTCGCGCCACGGGGTGCGCGCCCCGACCAAGTTCACGCAGCTCATGCA

GGACGTGACCCCGGACGCCTTCTACACCTGGCCGGTGAAGCTCGGCGAGCTGACCCCGCGCGGCGG

CGAGCTGATCGCCTACCTCGGCCACTACTGGCGCCAGCGCCTCGTGGCCGACGGCCTCCTCCCGAA

GAAGGGCTGCCCGCAGTCCGGCCAGGTGGCGATCATCGCCGACGTGGACGAGCGCACCCGCAAGAC

GGGCGAGGCCTTCGCCGCCGGCCTCGCCCCGGACTGCGCCATCACCGTGCACACCCAGGCCGACAC

CTCCTCCCCGGACCCGCTCTTCAACCCGCTCAAGACCGGCGTGTGCCAGCTCGACGTGGCCCAGGT

GACCGACGCCATCCTGGAGCGCGCCGGCGGCTCCATCGCCGACTTCACCGGCCACTACCAGACCGC

CTTCCGCGAGCTGGAGCGCGTGCTCAACTTCCCGCAGTCGAACCTCGCCCTCAAGCGCGAGAAGCA

GGACGAGTCCGCCTCCCTCACCCAGGCCCTCCCGTCCGAGCTGAAGGTGTCCGCCGACAACGTGTC

CCTCACCGGCGCCTGGTCCCTCGCCTCCATGCTCACCGAAATCTTCCTCCTCCAGCAGGCCCAGGG

CATGCCGGAGCCGGGCTGGGGCCGCATCACCGACTCCCACCAGTGGAACACCCTCCTCTCCCTCCA

CAACGCCCAGTTCGACCTCCTCCAGCGCACCCCGGAGGTGGCCCGCTCCCGCGCCACCCCGCTCCT

CGACCTCATCAAGACCGCCCTCACCCCGCACCCGCCGCAGAAGCAGGCCTACGGCGTGACCCTCCC

GACCTCGGTGCTCTTCATCGCCGGCCACGACACCAACCTCGCCAACCTCGGCGGCGCCCTGGAGCT

GCAGTGGACCCTCCCGGGCCAGCCGGACAACACCCCGCCGGGCGGCGAGCTGGTGTTCGAGCGCTG

GCGCCGCCTCTCCGACAACTCCCAGTGGATTCAGGTGTCCCTCGTGTTCCAGACCCTCCAGCAGAT

GCGCGACAAGACCCCGCTCTTCCTCAACACCCCGCCGGGCGAGGTGAAGCTCACCCTGGCCGGCTG

CGAGGAGCGCAACGCGCAGGGCATGTGCTCCCTCGCCGGCTTCACCCAGATCGTGAACGAGGCCCG

CATCCCGGCCTGCTCCCTCTGCCTTTCTTTCGGAACTGAGATCCTTACCGTTGAGTACGGACCACT

TCCTATTGGTAAGATCGTTTCTGAGGAAATTAACTGCTCAGTGTACTCTGTTGATCCAGAAGGAAG

AGTTTACACTCAGGCTATCGCACAATGGCACGATAGGGGTGAACAAGAGGTTCTGGAGTACGAGCT

TGAAGATGGATCCGTTATTCGTGCTACCTCTGACCATAGATTCTTGACTACAGATTATCAGCTTCT

CGCTATCGAGGAAATCTTTGCTAGGCAACTTGATCTCCTTACTTTGGAGAACATCAAGCAGACAGA

AGAGGCTCTTGACAACCACAGACTTCCATTCCCTTTGCTCGATGCTGGAACCATCAAGTAAcctag

*gtccccgaatttccccgatcgttcaaacatttggcaataaagtttcttaagattgaatcctgttgc*

*cggtcttgcgatgattatcatataatttctgttgaattacgttaagcatgtaataattaacatgta*

*atgcatgacgttatttatgagatgggtttttatgattagagtcccgcaattatacatttaatacgc*

*gatagaaaacaaaatatagcgcgcaaactaggataaattatcgcgcgcggtgtcatctatgttact*

*agatcgggaattg*

>ZmZ27P:xGZein27ss:Ssp DnaE-C:Phy02opt:Ssp DnaE-N:DPNG (SEQ ID NO: 199) SEKDEL (SEQ ID NO: 140):NosT ZmZ27P is shown in bold upper case font and italicized, Ssp_DnaE is underlined, DPNG (SEQ ID NO: 199) is in upper case and italicized, SEKDEL (SEQ ID NO: 140) is in bold upper case, NosT is italicized.

(SEQ TD NO: 131)

ggtaccAAAGTAATCATATTATTTTATGTGTGAATCTTCTTTACTTTTTCATTTGATTATGATTATGAAG

GTATGACCTTCATAACCTTCGTCCGAAATCCATTATATCCAAAGGAAAATAATGCTTCGAAGGACGAAGG

ATTTTGATATTTAACATTTTATGTTGCCTTGTTCTTAATTCATAGCATTTGAGAACAAGTCCCCAACACC

AATCTTTATCTTTACTATATTAAAGCACCAGTTCAACGATCGTCTCGTGTCAATATTATTAAAAAACTCC

TACATTTCTTTATAATCAACCCGCACTCTTATAATCTCTTCTCTTACTACTATAATAAGAGAGTTTATGT

ACAAAATAAGGTGAAATTATGTATAAGTGTTCTGGACCTTGGTTGTTGGCTCATATTCACACAACCTAAT

CAATAGAAAACATATGTTTTATTAAAACAAAATTTATCATATATATATATATATATATATATATATATAT

ATATATATATAATATAAACCGTAGCAATGCACAGGCATATGACTAGTGGCAACTTAATACCATGTGTGTA

TTAAGATGAATAAGAGGTATCCAAATAAATAACTTGTTCGCTTACGTCTGGATCGAAAGGGGTTGGAAAC

GATTAAATCTCTTCCTAGTCAAAATTAAATAGAAGGAGATTTAATCGATTTCTCCCAATCCCCTTCGATC

CAGGTGCAACCGAATAAGTCCTTAAATGTTGAGGAACACGAAACAACCATGCATTGGCATGTAAAGCTCC

AAGAATTCGTTGTATCCTTAACAACTCACAGAACATCAACCAAAATTGCACGTCAAGGGTATTGGGTAAG

AAACAATCAAACAAATCCTCTCTGTGTGCAAAGAAACACGGTGAGTCATGCCGAGATCATACTCATCTGA

TATACATGCTTACAGCTCACAAGACATTACAAACAACTCATATTGCATTACAAAGATCGTTTCATGAAAA

ATAAAATAGGCCGGAACAGGACAAAAATCCTTGACGTGTAAAGTAAATTTACAACAAAAAAAAAGCCATA

TGTCAAGCTAAATCTAATTCGTTTTACGTAGATCAACAACCTGTAGAAGGCAACAAAACTGAGCCACGCA

GAAGTACAGAATGATTCCAGATGAACCATCGACGTGCTACGTAAAGAGAGTGACGAGTCATATACATTTG

GCAAGAAACCATGAAGCTGCCTACAGCCGTCTCGGTGGCATAAGAACACAAGAAATTGTGTTAATTAATC

AAAGCTATAAATAACGCTCGCATGCCTGTGCACTTCTCCATCACCACCACTGGGTCTTCAGACCATTAGC

TTTATCTACTCCAGAGCGCAGAAGAACCCGATCGACACCggatccaccATGAGGGTGTTGCTCGTTGCCC

TCGCTCTCCTGGCTCTCGCTGCGAGCGCCACCAGCATGGTTAAGGTGATTGGAAGACGTTCTCTTGGTGT

TCAAAGGATCTTCGATATCGGATTGCCACAAGACCACAACTTTCTTCTCGCTAATGGTGCCATCGCTGCC

AATAGCGCTGCGCAGTCCGAGCCGGAGCTGAAGCTGGAGTCCGTGGTGATCGTGTCGCGCCACGGGGTGC

GCGCCCCGACCAAGTTCACGCAGCTCATGCAGGACGTGACCCCGGACGCCTTCTACACCTGGCCGGTGAA

GCTCGGCGAGCTGACCCCGCGCGGCGGCGAGCTGATCGCCTACCTCGGCCACTACTGGCGCCAGCGCCTC

GTGGCCGACGGCCTCCTCCCGAAGAAGGGCTGCCCGCAGTCCGGCCAGGTGGCGATCATCGCCGACGTGG

ACGAGCGCACCCGCAAGACGGGCGAGGCCTTCGCCGCCGGCCTCGCCCCGGACTGCGCCATCACCGTGCA

CACCCAGGCCGACACCTCCTCCCCGGACCCGCTCTTCAACCCGCTCAAGACCGGCGTGTGCCAGCTCGAC

GTGGCCCAGGTGACCGACGCCATCCTGGAGCGCGCCGGCGGCTCCATCGCCGACTTCACCGGCCACTACC

AGACCGCCTTCCGCGAGCTGGAGCGCGTGCTCAACTTCCCGCAGTCGAACCTCGCCCTCAAGCGCGAGAA

GCAGGACGAGTCCGCCTCCCTCACCCAGGCCCTCCCGTCCGAGCTGAAGGTGTCCGCCGACAACGTGTCC

CTCACCGGCGCCTGGTCCCTCGCCTCCATGCTCACCGAAATCTTCCTCCTCCAGCAGGCCCAGGGCATGC

CGGAGCCGGGCTGGGGCCGCATCACCGACTCCCACCAGTGGAACACCCTCCTCTCCCTCCACAACGCCCA

GTTCGACCTCCTCCAGCGCACCCCGGAGGTGGCCCGCTCCCGCGCCACCCCGCTCCTCGACCTCATCAAG

ACCGCCCTCACCCCGCACCCGCCGCAGAAGCAGGCCTACGGCGTGACCCTCCCGACCTCGGTGCTCTTCA

TCGCCGGCCACGACACCAACCTCGCCAACCTCGGCGGCGCCCTGGAGCTGCAGTGGACCCTCCCGGGCCA

-continued

GCCGGACAACACCCCGCCGGGCGGCGAGCTGGTGTTCGAGCGCTGGCGCCGCCTCTCCGACAACTCCCAG

TGGATTCAGGTGTCCCTCGTGTTCCAGACCCTCCAGCAGATGCGCGACAAGACCCCGCTCTTCCTCAACA

CCCCGCCGGGCGAGGTGAAGCTCACCCTGGCCGGCTGCGAGGAGCGCAACGCGCAGGGCATGTGCTCCCT

CGCCGGCTTCACCCAGATCGTGAACGAGGCCCGCATCCCGGCCTGCTCCCTCTGCCTTTCTTTCGGAACT

GAGATCCTTACCGTTGAGTACGGACCACTTCCTATTGGTAAGATCGTTTCTGAGGAAATTAACTGCTCAG

TGTACTCTGTTGATCCAGAAGGAAGAGTTTACACTCAGGCTATCGCACAATGGCACGATAGGGGTGAACA

AGAGGTTCTGGAGTACGAGCTTGAAGATGGATCCGTTATTCGTGCTACCTCTGACCATAGATTCTTGACT

ACAGATTATCAGCTTCTCGCTATCGAGGAAATCTTTGCTAGGCAACTTGATCTCCTTACTTTGGAGAACA

TCAAGCAGACAGAAGAGGCTCTTGACAACCACAGACTTCCATTCCTTTGCTCGATGCTGGAACCATCAA

G*GACCCGAACGGC*TCCGAGAAGGACGAGCTGTAAcctagg*tccccgaatttccccgatcgttcaaacatt*

*tggcaataaagtttcttaagattgaatcctgttgccggtcttgcgatgattatcatataatttctgttga*

*attacgttaagcatgtaataattaacatgtaatgcatgacgttatttatgagatgggtttttatgattag*

*agtcccgcaattatacatttaatacgcgatagaaaacaaaatatagcgcgcaaactaggataaattatcg*

*cgcgcggtgtcatctatgttactagatcgggaattg*

>ZmZ27P:Ssp_DnaE:L33-1:Phy02opt: L33-3:NosT (SSp_DnaE-C:L33-1:Phy02opt:L33-2:Ssp_DnaE-N)

ZmZ27P is shown in bold upper case font and italicized, Ssp_DnaE is underlined, linker is in bold, DPNG (SEQ ID NO: 199) is in upper case and italicized, SEKDEL (SEQ ID NO: 140) is in bold upper case, and NosT is italicized.

(SEQ TD NO: 132)

ggtaccAAAGTAATCATATTATTTTATGTGTGAATCTTCTTTACTTTTTCATTTGATTATGATTATGAAG

GTATGACCTTCATAACCTTCGTCCGAAATCCATTATATCCAAAGGAAAATAATGCTTCGAAGGACGAAGG

ATTTTGATATTTAACATTTTATGTTGCCTTGTTCTTAATTCATAGCATTTGAGAACAAGTCCCCAACACC

AATCTTTATCTTTACTATATTAAAGCACCAGTTCAACGATCGTCTCGTGTCAATATTATTAAAAAACTCC

TACATTTCTTTATAATCAACCCGCACTCTTATAATCTCTTCTCTTACTACTATAATAAGAGAGTTTATGT

ACAAAATAAGGTGAAATTATGTATAAGTGTTCTGGACCTTGGTTGTTGGCTCATATTCACACAACCTAAT

CAATAGAAAACATATGTTTTATTAAAACAAAATTTATCATATATATATATATATATATATATATATATAT

ATATATATATAATATAAACCGTAGCAATGCACAGGCATATGACTAGTGGCAACTTAATACCATGTGTGTA

TTAAGATGAATAAGAGGTATCCAAATAAATAACTTGTTCGCTTACGTCTGGATCGAAAGGGGTTGGAAAC

GATTAAATCTCTTCCTAGTCAAAATTAAATAGAAGGAGATTTAATCGATTTCTCCCAATCCCCTTCGATC

CAGGTGCAACCGAATAAGTCCTTAAATGTTGAGGAACACGAAACAACCATGCATTGGCATGTAAAGCTCC

AAGAATTCGTTGTATCCTTAACAACTCACAGAACATCAACCAAAATTGCACGTCAAGGGTATTGGGTAAG

AAACAATCAAACAAATCCTCTCTGTGTGCAAAGAAACACGGTGAGTCATGCCGAGATCATACTCATCTGA

TATACATGCTTACAGCTCACAAGACATTACAAACAACTCATATTGCATTACAAAGATCGTTTCATGAAAA

ATAAAATAGGCCGGAACAGGACAAAAATCCTTGACGTGTAAAGTAAATTTACAACAAAAAAAAAGCCATA

TGTCAAGCTAAATCTAATTCGTTTTACGTAGATCAACAACCTGTAGAAGGCAACAAAACTGAGCCACGCA

GAAGTACAGAATGATTCCAGATGAACCATCGACGTGCTACGTAAAGAGAGTGACGAGTCATATACATTTG

GCAAGAAACCATGAAGCTGCCTACAGCCGTCTCGGTGGCATAAGAACACAAGAAATTGTGTTAATTAATC

AAAGCTATAAATAACGCTCGCATGCCTGTGCACTTCTCCATCACCACCACTGGGTCTTCAGACCATTAGC

TTTATCTACTCCAGAGCGCAGAAGAACCCGATCGACACCggatccaccATGGTTAAGGTGATTGGAAGAC

GTTCTCTTGGTGTTCAAAGGATCTTCGATATCGGATTGCCACAAGACCACAACTTTCTTCTCGCTAATGG

-continued

TGCCATCGCTGCCAATagcggcggcggcagcggcggcggcagcaccccgcagagcgccttcgccGCTGCG
CAGTCCGAGCCGGAGCTGAAGCTGGAGTCCGTGGTGATCGTGTCGCGCCACGGGGTGCGCGCCCCGACCA
AGTTCACGCAGCTCATGCAGGACGTGACCCCGGACGCCTTCTACACCTGGCCGGTGAAGCTCGGCGAGCT
GACCCCGCGCGGCGGCGAGCTGATCGCCTACCTCGGCCACTACTGGCGCCAGCGCCTCGTGGCCGACGGC
CTCCTCCCGAAGAAGGGCTGCCCGCAGTCCGGCCAGGTGGCGATCATCGCCGACGTGGACGAGCGCACCC
GCAAGACGGGCGAGGCCTTCGCCGCCGGCCTCGCCCCGGACTGCGCCATCACCGTGCACACCCAGGCCGA
CACCTCCTCCCCGGACCCGCTCTTCAACCCGCTCAAGACCGGCGTGTGCCAGCTCGACGTGGCCCAGGTG
ACCGACGCCATCCTGGAGCGCGCCGGCGGCTCCATCGCCGACTTCACCGGCCACTACCAGACCGCCTTCC
GCGAGCTGGAGCGCGTGCTCAACTTCCCGCAGTCGAACCTCGCCCTCAAGCGCGAGAAGCAGGACGAGTC
CGCCTCCCTCACCCAGGCCCTCCCGTCCGAGCTGAAGGTGTCCGCCGACAACGTGTCCCTCACCGGCGCC
TGGTCCCTCGCCTCCATGCTCACCGAAATCTTCCTCCTCCAGCAGGCCCAGGGCATGCCGGAGCCGGGCT
GGGGCCGCATCACCGACTCCCACCAGTGGAACACCCTCCTCTCCCTCCACAACGCCCAGTTCGACCTCCT
CCAGCGCACCCCGGAGGTGGCCCGCTCCCGCGCCACCCCGCTCCTCGACCTCATCAAGACCGCCCTCACC
CCGCACCCGCCGCAGAAGCAGGCCTACGGCGTGACCCTCCCGACCTCGGTGCTCTTCATCGCCGGCCACG
ACACCAACCTCGCCAACCTCGGCGGCGCCCTGGAGCTGCAGTGGACCCTCCCGGGCCAGCCGGACAACAC
CCCGCCGGGCGGCGAGCTGGTGTTCGAGCGCTGGCGCCGCCTCTCCGACAACTCCCAGTGGATTCAGGTG
TCCCTCGTGTTCCAGACCCTCCAGCAGATGCGCGACAAGACCCCGCTCTTCCTCAACACCCCGCCGGGCG
AGGTGAAGCTCACCCTGGCCGGCTGCGAGGAGCGCAACGCGCAGGGCATGTGCTCCCTCGCCGGCTTCAC
CCAGATCGTGAACGAGGCCCGCATCCCGGCCTGCTCCCTCggcggcggcagcggcggcggcagcggcggc
ggcTGCCTTTCTTTCGGAACTGAGATCCTTACCGTTGAGTACGGACCACTTCCTATTGGTAAGATCGTTT
CTGAGGAAATTAACTGCTCAGTGTACTCTGTTGATCCAGAAGGAAGAGTTTACACTCAGGCTATCGCACA
ATGGCACGATAGGGGTGAACAAGAGGTTCTGGAGTACGAGCTTGAAGATGGATCCGTTATTCGTGCTACC
TCTGACCATAGATTCTTGACTACAGATTATCAGCTTCTCGCTATCGAGGAAATCTTTGCTAGGCAACTTG
ATCTCCTTACTTTGGAGAACATCAAGCAGACAGAAGAGGCTCTTGACAACCACAGACTTCCATTCCCTTT
GCTCGATGCTGGAACCATCAAGTAAcctagg*tccccgaatttccccgatcgttcaaacatttggcaataa*
*agtttcttaagattgaatcctgttgccggtcttgcgatgattatcatataatttctgttgaattacgtta*
*agcatgtaataattaacatgtaatgcatgacgttatttatgagatgggtttttatgattagagtcccgca*
*attatacatttaatacgcgatagaaaacaaaatatagcgcgcaaactaggataaattatcgcgcgcggtg*
*tcatctatgttactagatcgggaattg*

>ZmZ27P:xGZein27ss:Ssp DnaE:L33-1:Phy02opt:L33-2:DPNG (SEQ ID NO: 199) SEKDEL (SEQ ID NO: 140): NosT ZmZ27P is shown in bold upper case font and italicized, Ssp_DnaE is underlined, L33 linker is in bold upper case, DPNG (SEQ ID NO: 199) is in upper case and italicized, SEKDEL (SEQ ID NO: 140) is in bold upper case, and NosT is italicized.

(SEQ TD NO: 133)

ggtaccAAAGTAATCATATTATTTTATGTGTGAATCTTCTTTACTTTTTCATTTGATTATGATTATGAAG
GTATGACCTTCATAACCTTCGTCCGAAATCCATTATATCCAAAGGAAAATAATGCTTCGAAGGACGAAGG
ATTTTGATATTTAACATTTTATGTTGCCTTGTTCTTAATTCATAGCATTTGAGAACAAGTCCCCAACACC
AATCTTTATCTTTACTATATTAAAGCACCAGTTCAACGATCGTCTCGTGTCAATATTATTAAAAAACTCC

-continued

TACATTTCTTTATAATCAACCCGCACTCTTATAATCTCTTCTCTTACTACTATAATAAGAGAGTTTATGT

ACAAAATAAGGTGAAATTATGTATAAGTGTTCTGGACCTTGGTTGTTGGCTCATATTCACACAACCTAAT

CAATAGAAAACATATGTTTTATTAAAACAAAATTTATCATATATATATATATATATATATATATATATAT

ATATATATATAATATAAACCGTAGCAATGCACAGGCATATGACTAGTGGCAACTTAATACCATGTGTGTA

TTAAGATGAATAAGAGGTATCCAAATAAATAACTTGTTCGCTTACGTCTGGATCGAAAGGGGTTGGAAAC

GATTAAATCTCTTCCTAGTCAAAATTAAATAGAAGGAGATTTAATCGATTTCTCCCAATCCCCTTCGATC

CAGGTGCAACCGAATAAGTCCTTAAATGTTGAGGAACACGAAACAACCATGCATTGGCATGTAAAGCTCC

AAGAATTCGTTGTATCCTTAACAACTCACAGAACATCAACCAAAATTGCACGTCAAGGGTATTGGGTAAG

AAACAATCAAACAAATCCTCTCTGTGTGCAAAGAAACACGGTGAGTCATGCCGAGATCATACTCATCTGA

TATACATGCTTACAGCTCACAAGACATTACAAACAACTCATATTGCATTACAAAGATCGTTTCATGAAAA

ATAAAATAGGCCGGAACAGGACAAAAATCCTTGACGTGTAAAGTAAATTTACAACAAAAAAAAAGCCATA

TGTCAAGCTAAATCTAATTCGTTTTACGTAGATCAACAACCTGTAGAAGGCAACAAAACTGAGCCACGCA

GAAGTACAGAATGATTCCAGATGAACCATCGACGTGCTACGTAAAGAGAGTGACGAGTCATATACATTTG

GCAAGAAACCATGAAGCTGCCTACAGCCGTCTCGGTGGCATAAGAACACAAGAAATTGTGTTAATTAATC

AAAGCTATAAATAACGCTCGCATGCCTGTGCACTTCTCCATCACCACCACTGGGTCTTCAGACCATTAGC

TTTATCTACTCCAGAGCGCAGAAGAACCCGATCGACACCggatccaccATGAGGGTGTTGCTCGTTGCCC

TCGCTCTCCTGGCTCTCGCTGCGAGCGCCACCAGCATGGTTAAGGTGATTGGAAGACGTTCTCTTGGTGT

TCAAAGGATCTTCGATATCGGATTGCCACAAGACCACAACTTTCTTCTCGCTAATGGTGCCATCGCTGCC

AATagcggcggcggcagcggcggcggcagcaccccgcagagcgccttcgccGCTGCGCAGTCCGAGCCGG

AGCTGAAGCTGGAGTCCGTGGTGATCGTGTCGCGCCACGGGGTGCGCGCCCCGACCAAGTTCACGCAGCT

CATGCAGGACGTGACCCCGGACGCCTTCTACACCTGGCCGGTGAAGCTCGGCGAGCTGACCCCGCGCGGC

GGCGAGCTGATCGCCTACCTCGGCCACTACTGGCGCCAGCGCCTCGTGGCCGACGGCCTCCTCCCGAAGA

AGGGCTGCCCGCAGTCCGGCCAGGTGGCGATCATCGCCGACGTGGACGAGCGCACCCGCAAGACGGGCGA

GGCCTTCGCCGCCGGCCTCGCCCCGGACTGCGCCATCACCGTGCACACCCAGGCCGACACCTCCTCCCCG

GACCCGCTCTTCAACCCGCTCAAGACCGGCGTGTGCCAGCTCGACGTGGCCCAGGTGACCGACGCCATCC

TGGAGCGCGCCGGCGGCTCCATCGCCGACTTCACCGGCCACTACCAGACCGCCTTCCGCGAGCTGGAGCG

CGTGCTCAACTTCCCGCAGTCGAACCTCGCCCTCAAGCGCGAGAAGCAGGACGAGTCCGCCTCCCTCACC

CAGGCCCTCCCGTCCGAGCTGAAGGTGTCCGCCGACAACGTGTCCCTCACCGGCGCCTGGTCCCTCGCCT

CCATGCTCACCGAAATCTTCCTCCTCCAGCAGGCCCAGGGCATGCCGGAGCCGGGCTGGGGCCGCATCAC

CGACTCCCACCAGTGGAACACCCTCCTCTCCCTCCACAACGCCCAGTTCGACCTCCTCCAGCGCACCCCG

GAGGTGGCCCGCTCCCGCGCCACCCCGCTCCTCGACCTCATCAAGACCGCCCTCACCCCGCACCCGCCGC

AGAAGCAGGCCTACGGCGTGACCCTCCCGACCTCGGTGCTCTTCATCGCCGGCCACGACACCAACCTCGC

CAACCTCGGCGGCGCCCTGGAGCTGCAGTGGACCCTCCCGGGCCAGCCGGACAACACCCCGCCGGGCGGC

GAGCTGGTGTTCGAGCGCTGGCGCCGCCTCTCCGACAACTCCCAGTGGATTCAGGTGTCCCTCGTGTTCC

AGACCCTCCAGCAGATGCGCGACAAGACCCCGCTCTTCCTCAACACCCCGCCGGGCGAGGTGAAGCTCAC

CCTGGCCGGCTGCGAGGAGCGCAACGCGCAGGGCATGTGCTCCCTCGCCGGCTTCACCCAGATCGTGAAC

GAGGCCCGCATCCCGGCCTGCTCCCTCggcggcggcagcggcggcggcagcggcggcggcTGCCTTTCTT

TCGGAACTGAGATCCTTACCGTTGAGTACGGACCACTTCCTATTGGTAAGATCGTTTCTGAGGAAATTAA

CTGCTCAGTGTACTCTGTTGATCCAGAAGGAAGAGTTTACACTCAGGCTATCGCACAATGGCACGATAGG

GGTGAACAAGAGGTTCTGGAGTACGAGCTTGAAGATGGATCCGTTATTCGTGCTACCTCTGACCATAGAT

TCTTGACTACAGATTATCAGCTTCTCGCTATCGAGGAAATCTTTGCTAGGCAACTTGATCTCCTTACTTT

-continued

```
GGAGAACATCAAGCAGACAGAAGAGGCTCTTGACAACCACAGACTTCCATTCCTTTGCTCGATGCTGGA

ACCATCAAGGACCCGAACGGCTCCGAGAAGGACGAGCTGTAAcctaggtccccgaatttccccgatcgtt

caaacatttggcaataaagtttcttaagattgaatcctgttgccggtcttgcgatgattatcatataatt

tctgttgaattacgttaagcatgtaataattaacatgtaatgcatgacgttatttatgagatgggttttt

atgattagagtcccgcaattatacatttaatacgcgatagaaaacaaaatatagcgcgcaaactaggata

aattatcgcgcgcggtgtcatctatgttactagatcgggaattg
```

Example 11. Expression of Cyclized Phytases in Transgenic Plants

Independently transgenic maize plants that had been transformed with vectors as described above were grown to maturity, and cross-pollinated with wild-type (untransformed) maize plants. Approximately 20 seeds were harvested from each of these plants. Seed was milled through a 0.5 mm screen to produce a fine powder. Enzyme was then extracted and assayed for phytase activity as described below.

Phytase assay from seed, brief description of the protocol. Enzyme extracts were prepared by incubating 15 mg milled seed flour for 1 hour at room temperature in 1.5 ml of 25 mM sodium borate, pH10, 0.01% TWEEN® 20 (polyethylene glycol sorbitan monolaurate). Extracts were then diluted 100-fold in assay buffer (250 mM sodium acetate, pH15.5, 1 mM calcium chloride, 0.01% TWEEN® 20 (polyethylene glycol sorbitan monolaurate)). Seventy-five (75) microliters of the diluted extracts or 75 μl of buffer-only controls were dispensed into individual wells of a round-bottom 96-well plate. One-hundred fifty (150) microliters of freshly-prepared phytic acid (9.1 mM dodecasodium salt from Biosynth International, Staad, Switzerland, prepared in assay buffer) were added to each well. Plates were sealed and incubated for 60 min at 37° C. 150 μL of stop solution (20 mM ammonium molybdate, 5 mM ammonium vanadate, 4% nitric acid) was added to each well, mixed thoroughly via pipetting, and allowed to incubate at room temperature for 10 min. Plates were centrifuged at 3000×G for 10 minutes, and 100 μL of the clarified supernatants were transferred to the wells of a flat-bottom 96-well plate. Absorbance at 415 nm from each sample was compared to that of negative controls (buffer-only, no enzyme) and potassium phosphate standards. The standard curve was prepared by mixing 50 μl of potassium phosphate standards (0-1.44 mM, prepared in assay buffer) with 100 μL of freshly-prepared phytic acid, followed by 100 μL of stop solution.

Phytase activity varied significantly in seed from independent transgenic plants, as expected.

Example 12. Thermal Stability of Cyclic Phytases in Pelleting Processes

To determine the thermal stability of an engineered phytase, feed must be mixed containing a specified level of the engineered phytase, the corresponding target phytase, and any control phytases that it is desired to compare the thermal stability with and include in the evaluation. For testing thermal stability in feed, it is beneficial to mix several diets at a few different dosing levels, and then evaluate each in a series of pelleting processes conducted at different temperatures. Doses used in the evaluation may include 500 FTU/kg, 1000FTU/kg, or 3000 FTU/kg. Temperatures used in the evaluation may include 60° C., 65° C., 70° C., 75° C., 80° C., 85° C., 90° C., and 95° C., or any other desired temperatures. The residence time in the pelleting process may range from 15 seconds or less, up to one minute or more. For each formulated diet, for each enzyme (and the negative control diets containing no enzyme), a pre-pelleting sample is taken in addition to samples taken after pelleting. From these samples, the activity is measured and compared. Pelleted samples are compared with the corresponding mash samples in each treatment, and also compared with the identical treatments with other enzymes included in the trial. Engineered enzymes that maintain the highest percentage of activity post-pelleting at the highest temperatures demonstrate the greatest degree of thermal stability. Engineered phytases that demonstrate higher thermal stability than the corresponding target phytase have improved thermal performance and are candidates for commercial development.

Example 13. Performance of Cyclic Phytases in Broilers and Pigs

A basal corn-soy diet was prepared with a low content of inorganic phosphate. Replicate diets were prepared from this basal diet by adding enzyme in the form of Quantum Blue (AB Enzymes) or milled corn grain expressing either Phy02, Nov9X, engineered cyclic Phy02, or engineered cyclic Nov9X, varying the total amount of enzyme incorporated into each diet. For Phy02 and Nov9X, a small amount of corn was omitted from the basal diet to account for the transgenic grain that was being added back to supply the enzyme. Control diets were prepared in which the amount of inorganic phosphate was increased relative to the basal diet.

Male broiler chicks were distributed among various feed treatments in pens with about 12 birds per pen, and 6 replicate pens per treatment. The feed was provided to one set of birds in mash form, and pelleted feeds was provided to another set of birds. After 14, 21, 28, 35, and 42 days, birds are weighed and compared to determine the effect of the various enzyme treatments on broiler production.

Similarly, pigs were distributed among various feed treatments in pens with about 7 pigs per pen, and 5 replicate pens per treatment. The pelleted feed was provided the pigs. After 21, 35, and 49 days, pigs are weighed and compared to determine the effect of the various enzyme treatments on broiler production.

Example 14. Heat Stability of Modified Phytases

Figure 11:
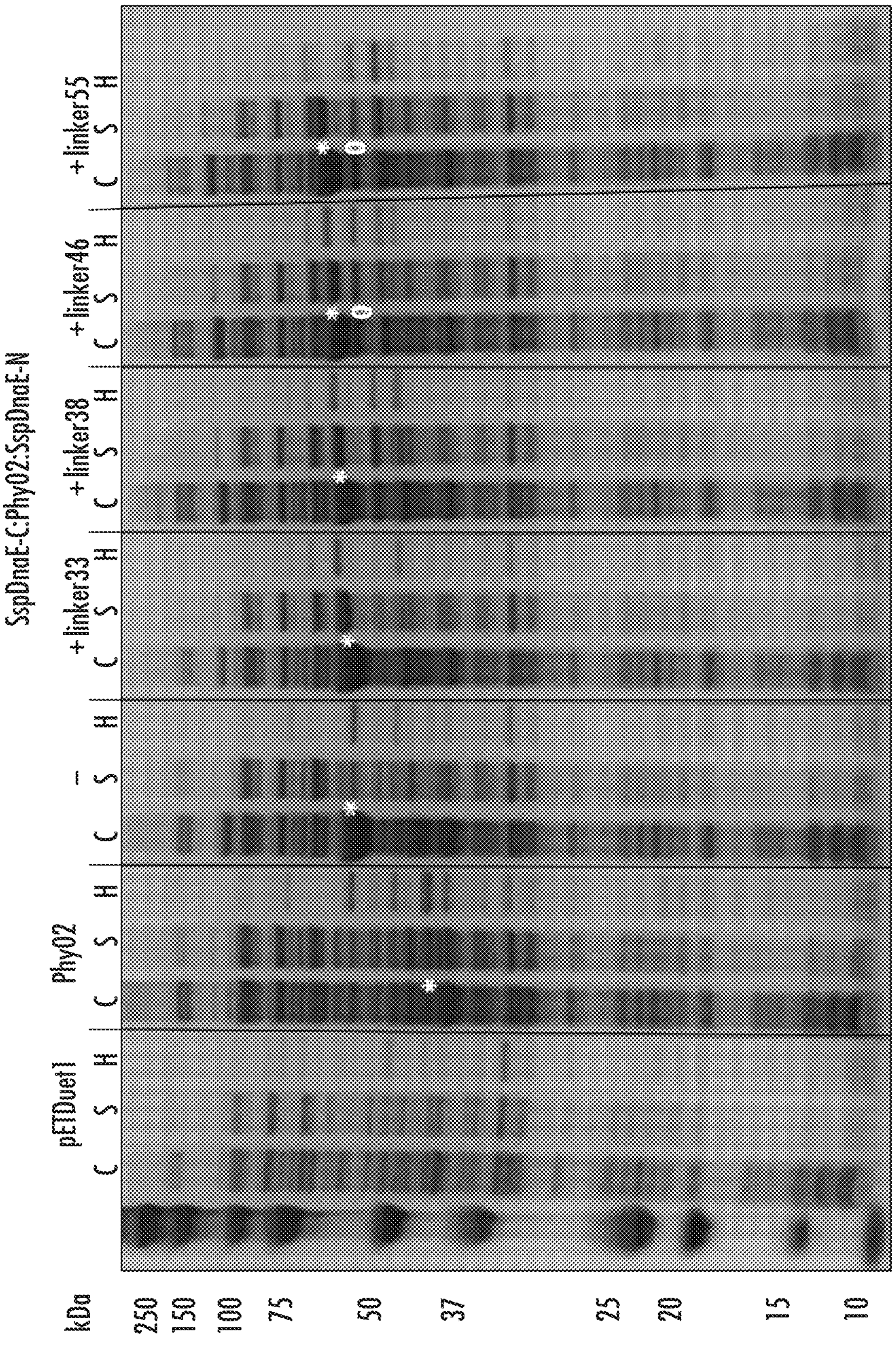
FIG. 11 is a photograph of a gel showing expression profiles of SspDnaE-C:Phy02:SspDnaE-N constructs.

FIG. 11 illustrates expression profiles of SspDnaE-C: Phy02:SspDnaE-N constructs. Referring to this figure, "C" represents the crude extract, "S" represents the soluble fraction, "*" marks the position of the target protein in the crude extract and "○" marks the position of cyclic Phy02 in the crude extract. Coomassie gel of IPTG induced expression cultures. Constructs were cloned between the EcoRI and XhoI sites of pETDuetI (Novagen) and transformed into Shuffle T7 (NEB) *E. coli* expression host. To analyze expression profiles, overnight starter cultures in LB+ Carbenicillin (100 mg/L) were 40-fold diluted to fresh medium and grown at 30° C., 250 rpm to $OD_{600}$=0.6, then IPTG was added to 0.5 mM final concentration and the cultures were grown for another 3 hours. Cells were harvested at 3000 g for 10 minutes, washed with one culture volume of phytase wash buffer (250 mM NaOAc pH=5.5 and 1 mM $CaCl_2$) and cells were pelleted as before. Cell pellet was lysed (30° C., 250 rpm, 1 hr) in phytase lysis buffer that contains 1× Fastbreak (Promega) with Benzonase (50U/mL, Novagen). Sample preparation for the Coomassie gel was as follows: Crude extract (C) was made by mixing equal volumes of lysate with 2× Laemmli sample buffer (Bio-Rad) containing 5% beta-mercaptoethanol. To prepare the soluble fraction (S) lysates were centrifuged at 5000 g for 10 min and the supernatants were mixed with equal volumes of loading dye as before. The heat soluble fraction (H) was made by incubating the lysates at 55° C. for 15 min followed by centrifugation at 5000 g for 10 minutes and supernatants were mixed with equal volumes of loading dye. Before loading, SDS/PAGE samples were heated at 95° C. for 5 min and 5 μL aliquots were loaded to Criterion XT 12% Bis-Tris gels together with 10 μL of the Mw marker (Precision Plus Protein Kaleidoscope, Bio-Rad). After separation of the proteins, gel was stained with SimplyBlue Safe Stain (Novex by Life Technologies).

Referring to FIG. 11, it was observed that Phy02 represented comparably in the crude (C), soluble (S) and heat soluble (H) fraction. Expression levels of SspDnaE-C: phy02:SspDnaE-N fusion proteins were comparable but showed significant difference in solubility: without linker (-) the protein was primarily non-soluble, while the linker containing constructs primarily expressed to the soluble fraction and were well represented in the heat soluble fractions as well. Phy02 and its intein-modified versions were resolved at the expected size of the linear molecules (marked "*", around 58KD), except two constructs with the longest linkers (linker 46 and 55), that in addition to the linear proteins showed faster moving new protein species (marked "○") at comparable levels in the crude (C), soluble (S) and heat soluble (H) fractions. Higher mobility is a hallmark of cyclic Phy02 as established by comparing mobility of cyclization competent SpyTag:Phy02:SpyCatcher with the cyclization deficient mutant (see FIG. 12).

Figure 12:
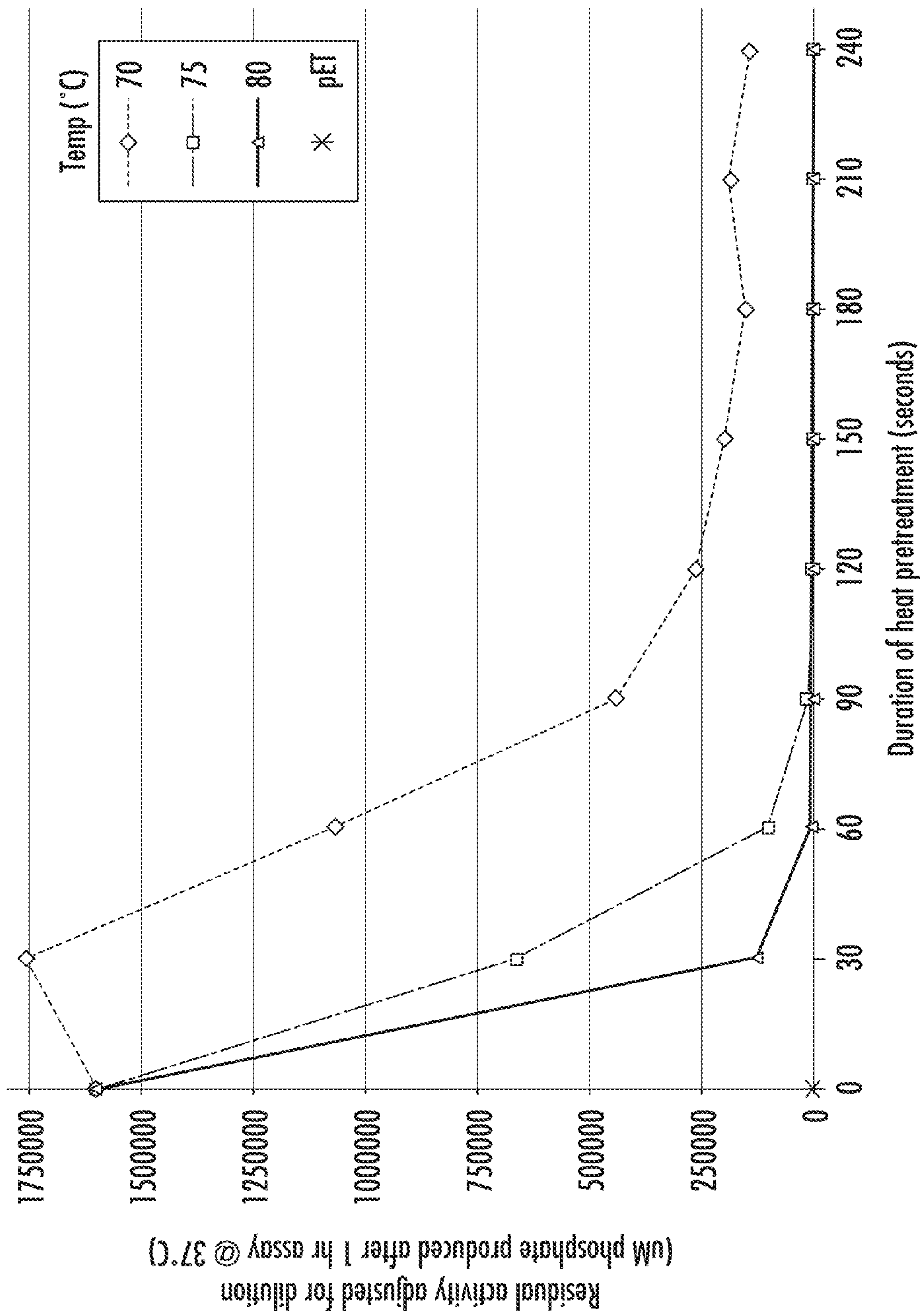
FIG. 12 is a graph illustrating the heat stability assay of Phy02.

FIG. 12 illustrates the heat stability assay of Phy02. Referring to FIG. 12, the crude extract was prepared as described in FIG. 11 and diluted 50× in phytase wash buffer. 150 μL aliquots in PCR tubes were heat treated in a PCR block programmed to for identical block a lid temperature. Tubes were withdrawn at specified time points and incubated at room temp for 1 hour to allow for refolding. Each sample was diluted to 250-, 1000-, 5000- and 20000-fold and phytase activity was assayed based on established protocol.

The graph illustrates heat stability of the unmodified Phy02 in crude cell lysates pretreated at 70° C., 75° C. and 80° C. over 4 min in samples taken in 30 sec intervals. Full activity was retained only in the 70° C./30 sec sample. Increasing either heat exposure time and/or temperature quickly diminished phytase activity. One minute exposure to 75° C. or 80° C. reduced the unmodified Phy02 phytase activity to levels borderline detectable or undetectable, respectively.

Figures 13A, 13B:
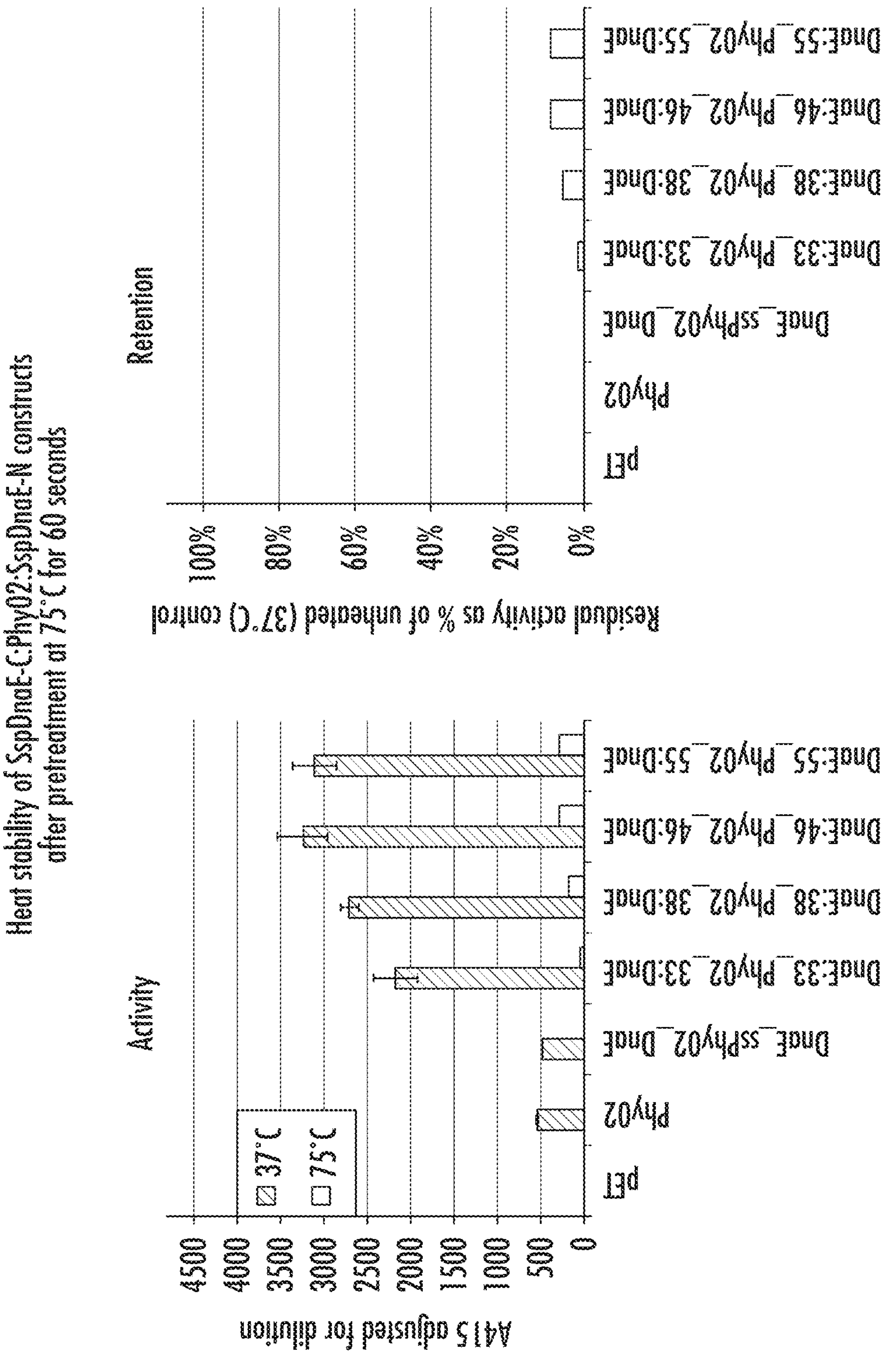
FIGS. 13A-13B are bar graphs illustrating heat stability of SspDnaE-C:Phy02:SspDnaE-N constructs.

FIGS. 13A-13B illustrate heat stability of SspDnaE-C: Phy02:SspDnaE-N constructs. Expression culture and preparation of crude extract was as in FIG. 11. Heat pretreatment was performed at 75° C. for 60 sec and phytase activity was assayed as in FIG. 12. FIG. 13A shows enzyme activity of untreated (37° C.) and heat treated (75° C./60 sec) samples. FIG. 13B shows residual phytase activity in heat pretreated samples as percentage of activity of their respective untreated control (37° C.).

Each linker modified trans-splicing Phy02 retained some activity after a heat pretreatment that completely abolished phytase activity of the unmodified Phy02 control. The two clones with the longest linkers (linker 46 and 55) showed the highest heat tolerance at retained ~10% activity in the heat pretreated samples. Intein fusion without linker (DnaE-sPhy02_DnaE) did not improve heat stability.

Figure 14:
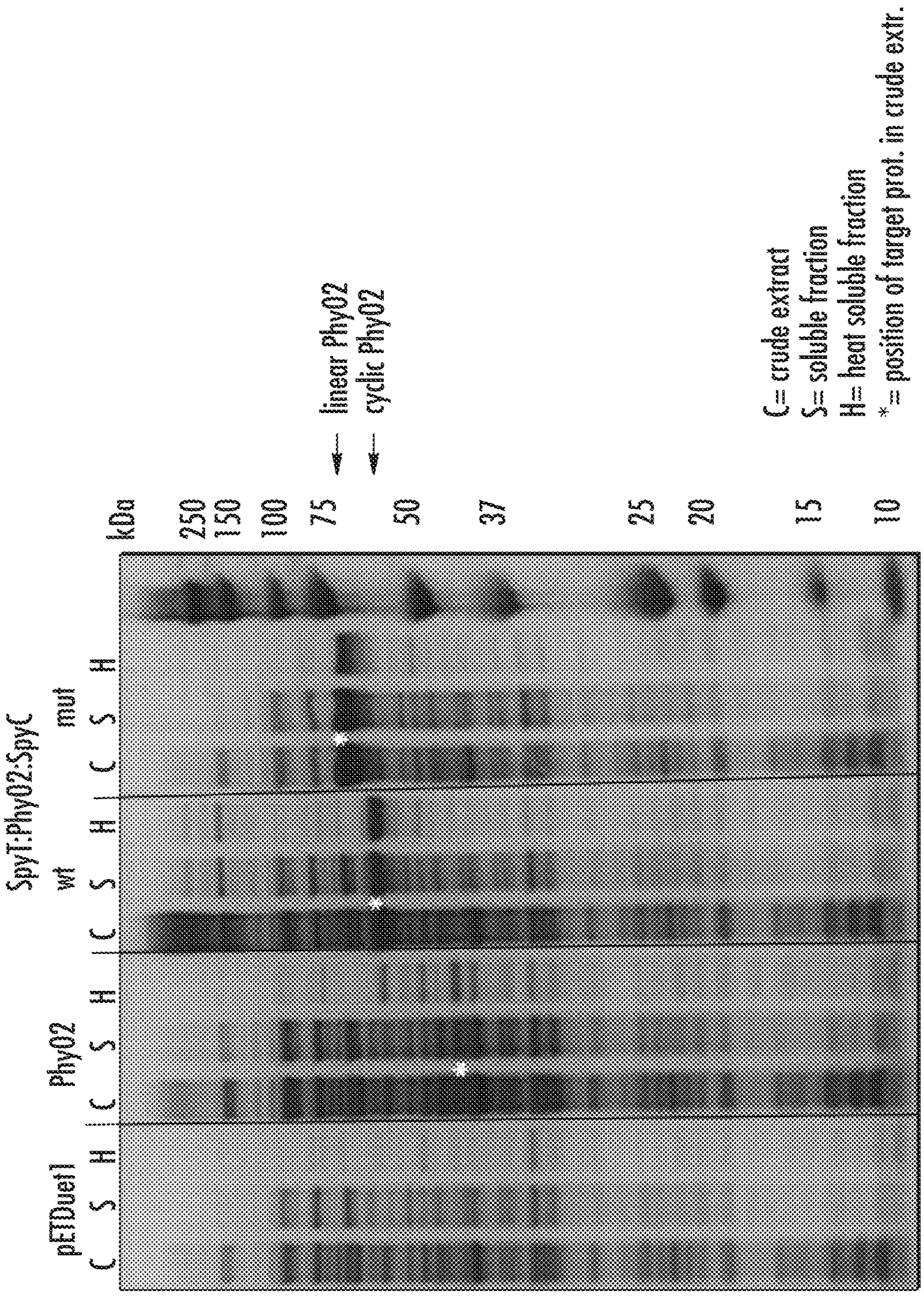
FIG. 14 is a photograph of the gel showing expression profiles of SpyTag:Phy02:SpyCatcher wild type and mutated forms.

FIG. 14 illustrates expression profiles of SpyTag:Phy02:SpyCatcher wild type and mutated forms. Coomassie gel of IPTG induced expression cultures.

Constructs were cloned between the NcoI and XhoI sites of pETDuetI (Novagen) and transformed into Shuffle T7 (NEB) *E. coli* expression host. The cyclization deficient mutant carried an alanine mutation in the SpyTag (AHIVMVDAYKPTK [SEQ ID NO: 216] for wild type and AHIVMVAAYKPTK [SEQ ID NO: 217] for mutant). Induction cultures, preparation of the crude (C), soluble (S) and heat soluble (H) fraction and SDS/PAGE were the same as in FIG. 11. Position of the target proteins are marked by asterisk in the crude extracts.

Both the wild type and the mutated SpyTag:Phy02:SpyCatcher expressed to the soluble fraction and were equally represented in the heat soluble (H), soluble (S) fractions as well as in the crude (C). While the cyclization competent version (wt) separated at the expected size for the linear molecule at 63 kD (552 amino acids), the cyclization deficient mutant (mut) moved fast on the gel. This observation is consistent with the interpretation that intramolecular interaction between SpyTag and SpyCatcher leads to intramolecular cyclization of the cyclization competent molecule. Mutation in the SpyTag prevented cyclization. Cyclic Phy02 has higher mobility than the cyclization deficient linear molecule. The cyclization competent wild type SpyTag: Phy02:SpyCatcher dominantly express the high mobility Phy02 form indicating that cyclization is highly efficient.

Figure 15A:
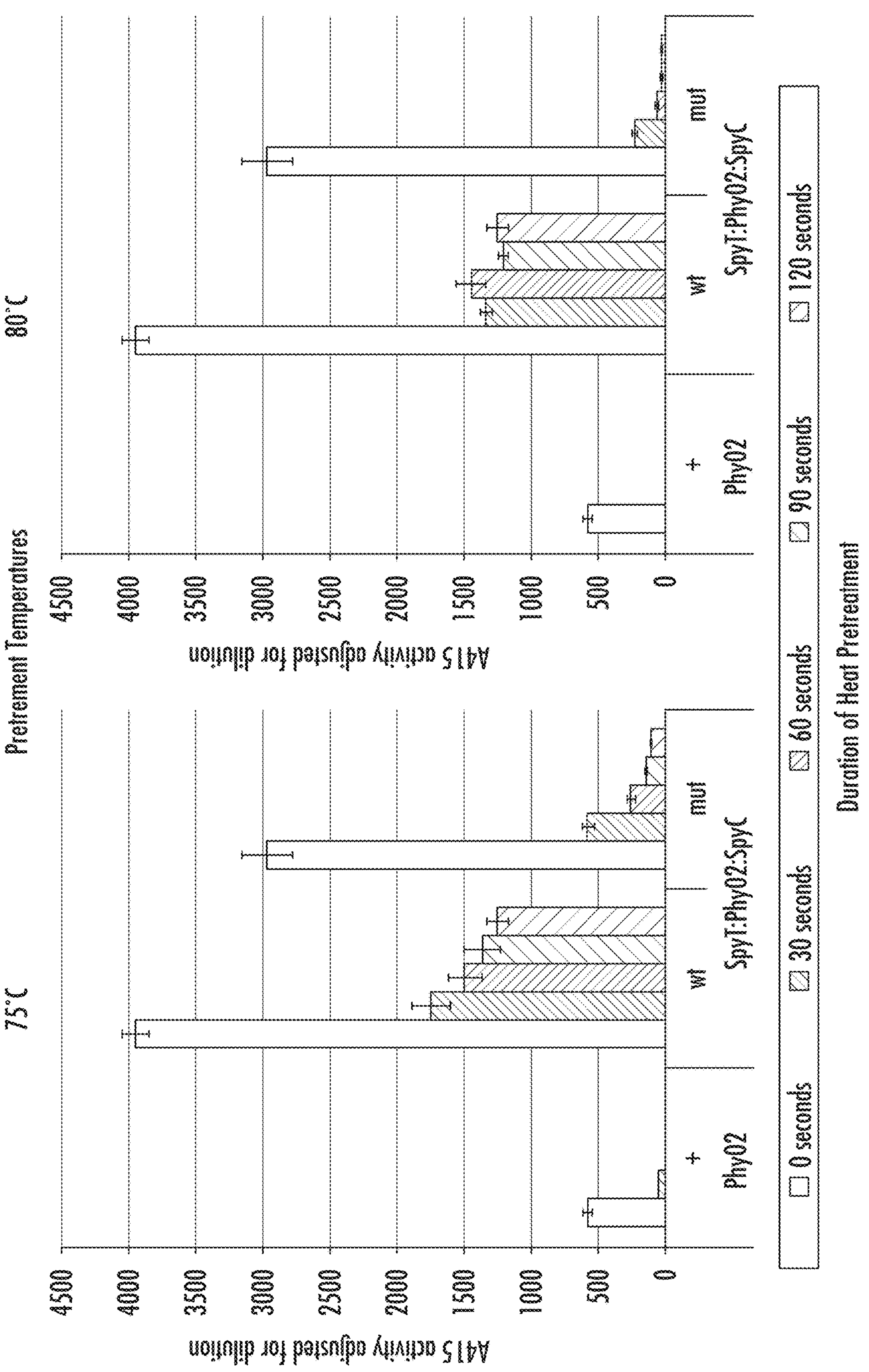
FIGS. 15A-15B are bar graphs illustrating that SpyTag:Phy02:SpyCatcher improves heat tolerance of phytase.

FIG. 15A illustrates SpyTag:Phy02:SpyCatcher improves heat tolerance of phytase. Phytase activity of heat pretreated samples. Expression of recombinant proteins was as described in FIG. 14, heat pretreatment and enzyme assay was performed as in FIG. 12 at 75° C. and 80° C. and aliquots were taken at 30 sec intervals over 120 sec. Left panel show enzyme activity after heat treatment at 75° C., right panel after heat treatment at 80° C., respectively. The cyclization competent wild type SpyTag:Phy02:SpyCatcher (wt) showed dramatically improved heat stability and remained stable at 80° C. over the entire length of heat pretreatment tested. The cyclization deficient mutant SpyTag:Phy02:SpyCatcher (mut) also displayed improved heat stability compared to the unmodified Phy02.

Figure 15B:
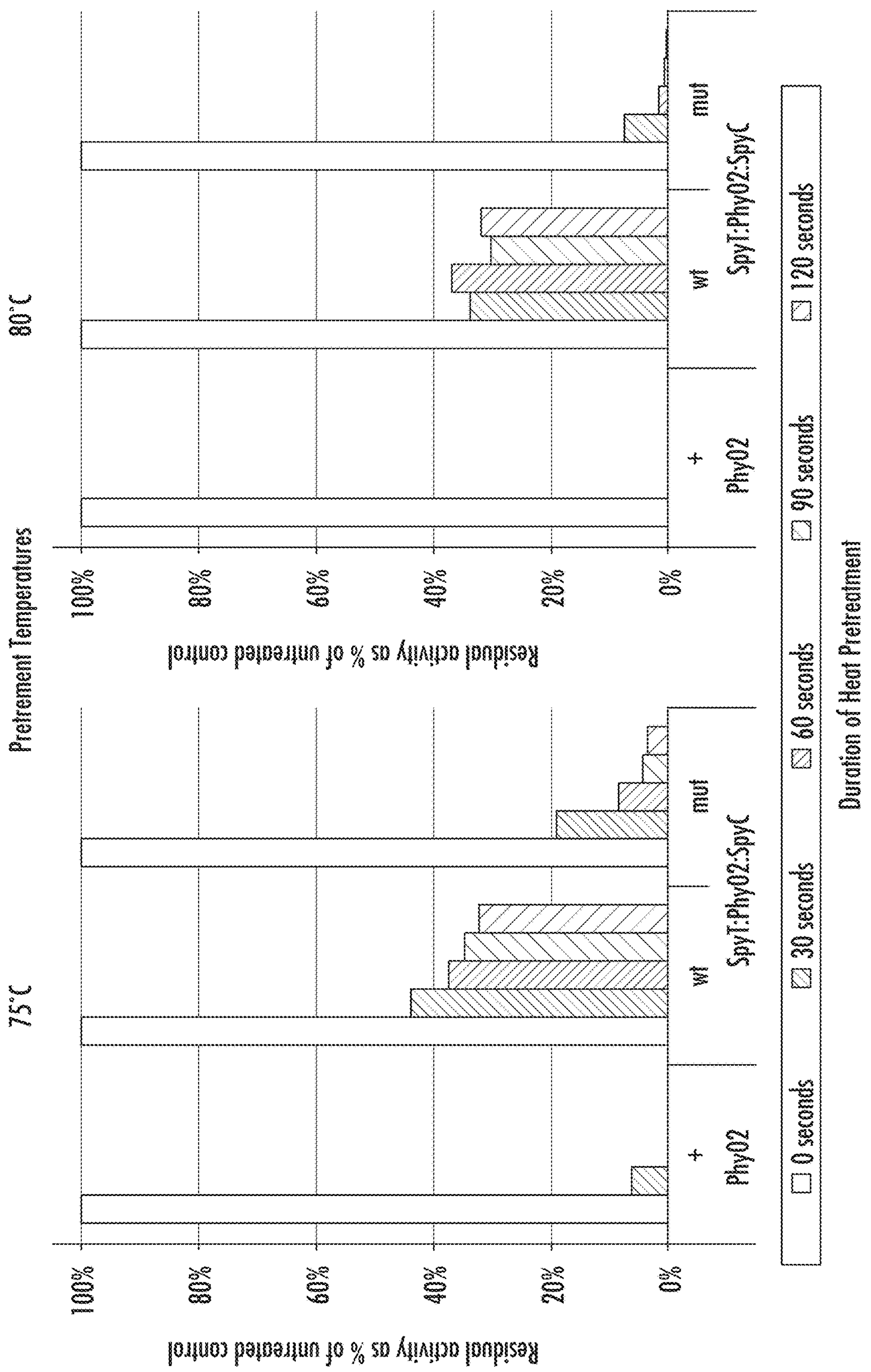

FIG. 15B illustrates SpyTag:Phy02:SpyCatcher improves heat tolerance of phytase. Retention of phytase activity of heat pretreated samples. Phytase activities of heat pretreated samples of FIG. 17A are graphed as percentage of their respective untreated control. The cyclization competent phytase (wt) retained more than 35% activity at 80° C. that remained stable over the entire heat treatment period of 2 minutes. In contrast, the cyclization disabled linear form (mut) quickly lost activity at 80° C., but thermo-tolerance exceeded heat stability of the unmodified Phy02. This beneficial effect possibly due to retention of the refolding functionality of the SpyCatcher in the cyclization disabled mutated SpyTag construct. Possibly, the differences between heat tolerance of phytase activity of the cyclic and linear molecules could indicate the extent to which cyclization and refolding impact on heat stability.

Example 15. Intein Splicing is Required for Attaining Elevated Heat Tolerance of the Cyclic Phytase Constructs The prototype cyclic phytase was constructed by using the rigid linker 55-1 and 55-2 and the trans-splicing intein gp41-1 and created the gp41-1C:L55-1:Phy02:L55-2:gp41-1N [Amino acid (AA)_SEQ ID NO: 201 and nucleic acid (NA)_SEQ ID NO: 200]. In addition, a solubility optimized version of the construct that have a solubility enhancer thioredoxin domain (TrxH) [AA_SEQ ID NO: 197 and NA_Seq ID NO: 196] at the N-terminus attached with an Asp-Pro-Asn-Gly linker (DPNG) [AA_SEQ ID NO: 199 and NA_SEQ ID NO: 198] to a mutated version of the gp41-1C (MTT) encoding the construct of TrxH:DPNG: gp41-1C[MTT]:L55-1:Phy02:L55-2:gp41-1N [AA_205 and NA_204] was created.

Figure 16:
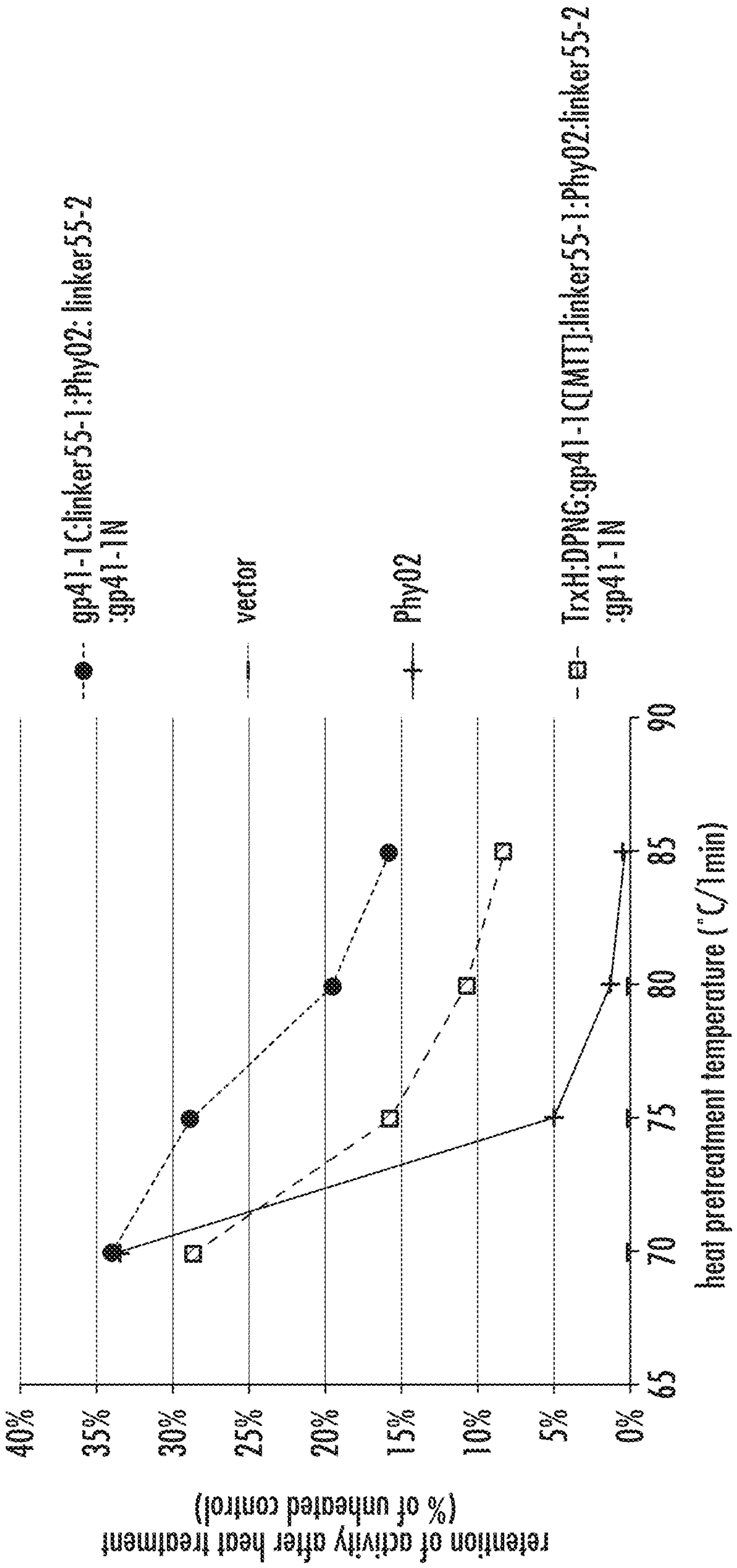
FIG. 16 is a graph illustrating heat pretreatment of cyclic phytases gp41-1C:linker55-1:Phy02:linker55-2:gp41-1N (closed circle) and TrxH:DPNG:gp41-1C[MTT]:linker55-1:Phy02:linker55-2:gp41-1N (closed square) compared to the wild type enzyme Phy02 (vertical mark) and an empty vector (horizontal mark).

Constructs were cloned between the EcoRI and XhoI sites of pETDuetI, expressed from the Shuffle T7 *E. coli* host and were tested for phytase heat stability. Induction cultures and preparation of crude lysates were as described for FIG. 11. For heat treatments, 150 μL of the crude lysates in PCR tubes were heated for 1 min at the specified temperatures in PCR blocks, then tubes were incubated at room temp for 1 hr to allow for refolding. Each sample was diluted to 250-, 1000-, 5000- and 2000-fold and phytase activity was assayed as in FIG. 12. FIG. 16 illustrates heat pretreatment of cyclic phytases gp41-1C:L55-1:Phy02:L55-2: 41-1N (closed circle) and TrxH:DPNG: 41-1C[MTT]:L55-1: Phy02:L55-2: 41-1N (closed square) compared to the wild type enzyme Phy02 (vertical line) and an empty vector (horizontal line). Referring to FIG. 16, it was observed the wild type phytase (Phy02) quickly lost activity above 75° C. while both cyclic phytase constructs retained activity at 85° C., showing 16% versus 8% activity in the prototype vs. solubility optimized phytase, respectively.

To evaluate whether protein cyclization is required for acquisition of heat tolerance, splicing was disabled by mutating splicing essential amino acid residues in two cyclic phytase constructs with different linkers, in the TrxH: DPNG:gp41-1C [MTT]:L46-1:Phy02:L46-2:gp41-1N [AA_SEQ ID NO: 207 and NA_SEQ ID NO: 206] and the gp41-1C[MTT]:L55-1:Phy02:L55-2:gp41-1N [AA_SEQ ID NO: 205 and NA_SEQ ID NO: 204]. Splicing disabling mutations were either the gp41-1C intein C-terminal Asn residue to Ala [N125A] or the gp41-1C C-terminal flanking Ser residue to Ala [S1A] in +1 position of the linkers. The following mutants were created: [N125A-1] splicing disabled TrxH:DPNG:gp41-1C[MTT]:L46-1:Phy02:L46-2: gp41-1N [AA_SEQ ID NO: 209 and NA_SEQ ID NO: 208], [N125A-2]splicing disabled gp41-1C[MTT]:L55-1:Phy02: L55-2:gp41-1N [AA_SEQ ID NO: 213 and NA_SEQ ID NO: 212], [S1A-1] splicing disabled TrxH:DPNG:gp41-1C [MTT]:L46-1:Phy002:L46-2:gp41-1N [AA_SEQ ID NO: 211 and NA_SEQ ID NO: 210], and [S1A-2] splicing disabled gp41-1C[MTT]:L55-1:Phy02:L55-2:gp41-1N [AA_SEQ ID NO: 215 and NA_SEQ ID NO: 214].

Figure 17:
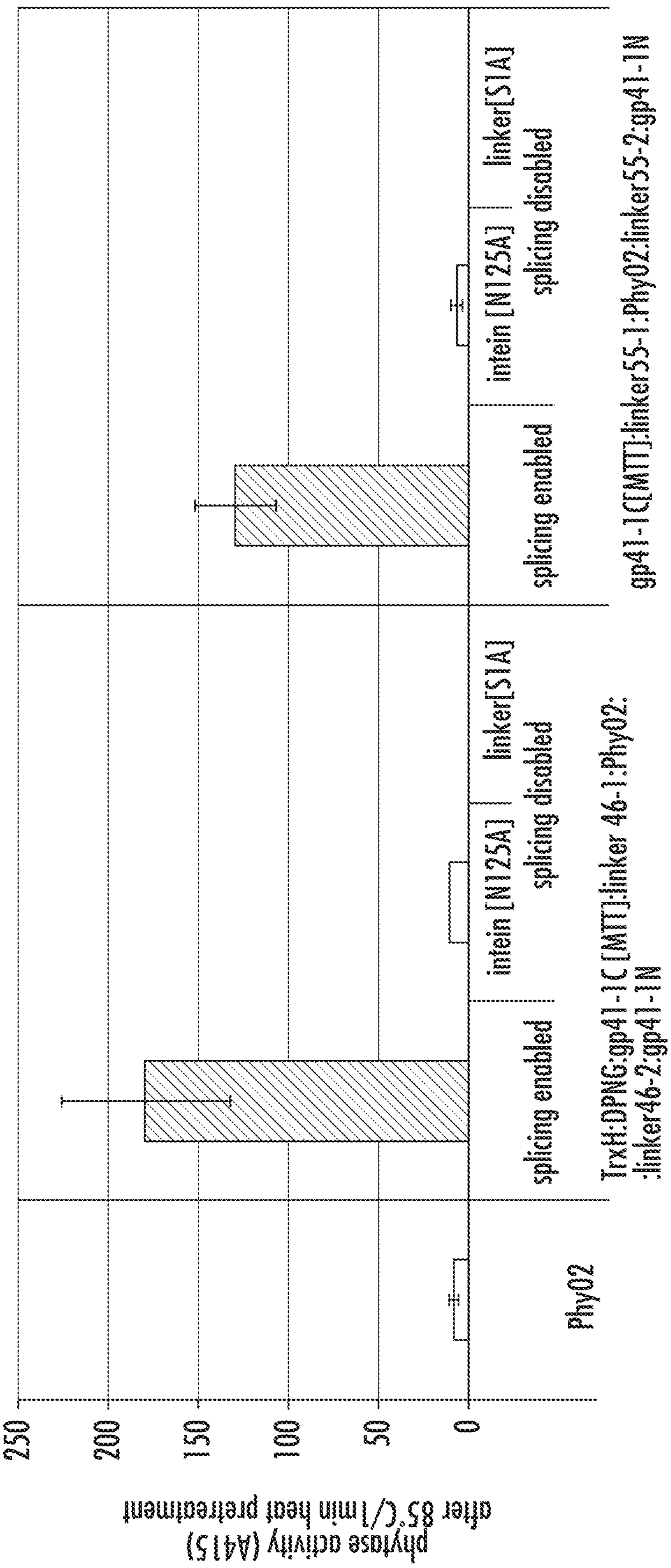
FIG. 17 is a bar graph illustrating phytase activity of the splicing enabled and splicing disabled (intein N125A and linker S1A) cyclic phytases gp41-1C:linker55-1:Phy02:linker55-2:gp41-1N and TrxH:DPNG gp41-1C[MTT]:linker55-1:Phy02:linker55-2:gp41-1N and wild type Phy02 phytase following pretreatment at 85° C. for 1 minute.

Constructs were cloned between the EcoRI and XhoI sites of pETDuetI, expressed from Shuffle T7 *E. coli* host and heat tolerance of splicing enabled and disabled constructs were tested after heat pretreatment at 85° C./1 min. FIG. 17 illustrates phytase activity of the splicing enabled and the splicing disabled (intein N125A and linker S1A) cyclic phytases gp41-1C:L55-1:Phy02:L55-2:gp41-1N and TrxH: DPNG:gp41-1C[MTT]:L55-1:Phy02:L55-2:gp41-1N and wild type Phy02 phytase following pretreatment at 85° C. for 1 minute. Referring to FIG. 17, it was observed that at 37° C., all constructs showed phytase activity. After 1 min exposure to 85° C. however, only the splicing enabled constructs retained activity. The splicing disabled mutants all displayed heat sensitivity similar to the intein unmodified wild type phytase. These results are consistent with the interpretation that acquisition of heat tolerance depends from intein splicing mediated protein cyclization.

REFERENCES

Apgar, J., Ross, M., Zuo, X., Dohle, S., Sturtevant, D., Shen, B., . . . & Raab, R. M. (2012). A predictive model of intein insertion site for use in the engineering of molecular switches. *PloS one,* 7(5), e37355.

Arakawa, T., Chong, D. K., & Langridge, W. H. (1998). Efficacy of a food plant-based oral cholera toxin B subunit vaccine. *Nature Biotechnology,* 16(3), 292-297. doi: 10.1038/nbt0398-292.

Basu, S. S., Winslow, S., Nelson, A., Ono, M., & Betts, S. (2009). EXTRACTION METHODS AND ASSAYS FOR FEED ENZYMES.

Cervelli, M., Di Caro, O., Di Penta, A., Angelini, R., Federico, R., Vitale, A., & Mariottini, P. (2004). A novel C-terminal sequence from barley polyamine oxidase is a vacuolar sorting signal. *Plant Journal,* 40(3), 410-418. doi: 10.1111/j.1365-313X.2004.02221.X.

"*Current Protocols in Molecular Biology,*" 10.0.1-10.0.23, April, 2010, John Wiley & Sons, Inc.

Engelen, A. J., Heeft, F. C., Randsdorp, P. H., Somers, W. A., Schaefer, J., & van der Vat, B. J. (2001). Determination of phytase activity in feed by a colorimetric enzymatic method: collaborative interlaboratory study. *Journal of AOAC International,* 84(3), 629-633.

FU, T. J. (2002). Digestion stability as a criterion for protein allergenicity assessment. *Annals of the New York Academy of Sciences,* 964(1), 99-110.

Gogarten, J. P., Senejani, A. G., Zhaxybayeva, O., Olendzenski, L., & Hilario, E. (2002). Inteins: structure, function, and evolution. *Annual Reviews in Microbiology,* 56(1), 263-287.

Haq, T. a, Mason, H. S., Clements, J. D., & Arntzen, C. J. (1995). Oral immunization with a recombinant bacterial antigen produced in transgenic plants. *Science* (New York, N.Y.), 268(5211), 714-716. doi: 10.1126/science.7732379.

Lau S Y M, Taneja A K and Hodges R S (1984) Synthesis of a model protein of defined secondary and quaternary structure. Effect of chain length on the stabilization and formation of two-stranded a-helical coiled-coils. J. Biol. Chem. 259 (21), 13253-61.

Korban, S. S. (2002). Targeting and expression of antigenic proteins in transgenic plants for production of edible oral vaccines. In *Vitro Cellular & Developmental Biology—Plant,* 38(3), 231-236. doi: 10.1079/IVP2002292.

Munro, S., & Pelham, H. R. (1987). A C-terminal signal prevents secretion of luminal ER proteins. *Cell,* 48(5), 899-907. doi: 10.1016/0092-8674(87)90086-9.

Parry D A, Fraser R D and Squire J M (2008) Fifty years of coiled-coils and alpha-helical bundles: a close relationship between sequence and structure. *J Struct Biol.* 163 (3), 258-69.

Perler, F. B. (2002). InBase: the intein database. *Nucleic acids research,* 30(1), 383-384.

Perler, F. B., Davis, E. O., Dean, G. E., Gimble, F. S., Jack, W. E., Neff, N., . . . & Belfort, M. (1994). Protein splicing elements: inteins and exteins—a definition of terms and recommended nomenclature. *Nucleic acids research,* 22(7), 1125.

Schoene, C., Fierer, J. O., Bennett, S. P., & Howarth, M. (2014). SpyTag/SpyCatcher cyclization confers resilience to boiling on a mesophilic enzyme. *Angewandte Chemie International Edition,* 53(24), 6101-6104.

Thomas, K., Aalbers, M., Bannon, G. A., Bartels, M., Dearman, R. J., Esdaile, D. J., . . . & Zawodny, J. (2004). A multi-laboratory evaluation of a common in vitro pepsin digestion assay protocol used in assessing the safety of novel proteins. *Regulatory Toxicology and Pharmacology,* 39(2), 87-98.

U.S. Pat. No. 7,629,139, issued Dec. 8, 2009.

Woolfson D N (2005) The design of coiled-coil structures and assemblies. Adv. Protein Chem. 70, 79-f112

Xu, M. Q., & Perler, F. B. (1996). The mechanism of protein splicing and its modulation by mutation. *The EMBO journal,* 15(19), 5146.

Zakeri, B., Fierer, J. O., Celik, E., Chittock, E. C., Schwarz-Linek, U., Moy, V. T., & Howarth, M. (2012). Peptide tag forming a rapid. covalent bond to a protein, through engineering a bacterial adhesin. *Proceedings of the National Academy of Sciences,* 109(12), E690-E697.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. An engineered phytase comprising a target phytase, a first binding element and a second binding element, wherein the C-terminus of the first binding element is fused to the N-terminus of the target phytase and the N-terminus of the second binding element is fused to the C-terminus of the target phytase, wherein the first binding element interacts with the second binding element to cause cyclization of the engineered phytase, and enhance thermal stability of the target phytase, wherein the first binding element comprises a C-intein of an intein, and the second binding element comprises an N-intein of an intein, and wherein the engineered phytase comprises an amino acid sequence having at least 90% sequence identity to the amino acid sequence set forth in SEQ ID NO: 201.

2. The engineered phytase of claim 1, wherein the engineered phytase has stable activity at a temperature in a range from 70° C. to 90° C.

3. The engineered phytase of claim 1 comprising the amino acid sequence set forth in SEQ ID NO: 201.

* * * * *